(12) United States Patent
Hammerman et al.

(10) Patent No.: US 10,702,527 B2
(45) Date of Patent: Jul. 7, 2020

(54) COMBINATION THERAPY OF TRANSCRIPTION INHIBITORS AND KINASE INHIBITORS

(71) Applicant: Dana-Farber Cancer Institute, Inc., Boston, MA (US)

(72) Inventors: Peter Hammerman, Newton, MA (US); Kwok-kin Wong, Arlington, MA (US); Nathanael S. Gray, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/735,532

(22) PCT Filed: Jun. 10, 2016

(86) PCT No.: PCT/US2016/037086
§ 371 (c)(1),
(2) Date: Dec. 11, 2017

(87) PCT Pub. No.: WO2016/201370
PCT Pub. Date: Dec. 15, 2016

(65) Prior Publication Data
US 2018/0169097 A1    Jun. 21, 2018
US 2019/0015411 A9    Jan. 17, 2019

Related U.S. Application Data

(60) Provisional application No. 62/175,077, filed on Jun. 12, 2015, provisional application No. 62/175,035, filed on Jun. 12, 2015.

(51) Int. Cl.
| | | |
|---|---|---|
| *A61K 31/506* | (2006.01) | |
| *A61K 31/52* | (2006.01) | |
| *A61K 31/551* | (2006.01) | |
| *A61K 31/5517* | (2006.01) | |
| *A61K 31/69* | (2006.01) | |
| *A61P 35/00* | (2006.01) | |
| *A61K 31/4162* | (2006.01) | |
| *A61K 31/519* | (2006.01) | |
| *A61K 31/53* | (2006.01) | |
| *A61K 45/06* | (2006.01) | |

(52) U.S. Cl.
CPC ........ *A61K 31/506* (2013.01); *A61K 31/4162* (2013.01); *A61K 31/519* (2013.01); *A61K 31/52* (2013.01); *A61K 31/53* (2013.01); *A61K 31/551* (2013.01); *A61K 31/5517* (2013.01); *A61K 31/69* (2013.01); *A61K 45/06* (2013.01); *A61P 35/00* (2018.01)

(58) Field of Classification Search
CPC .... A61K 31/506; A61K 45/06; A61K 31/519; A61K 31/4162; A61K 31/53; A61K 31/52; A61K 31/551; A61K 31/5517; A61K 31/69; A61P 35/00
See application file for complete search history.

(56) References Cited

U.S. PATENT DOCUMENTS

| | | |
|---|---|---|
| 3,681,343 A | 8/1972 | Hester, Jr. |
| 3,709,898 A | 1/1973 | Hester, Jr. |
| 3,812,259 A | 5/1974 | Collins |
| 4,231,938 A | 11/1980 | Monaghan et al. |
| 4,270,537 A | 6/1981 | Romaine et al. |
| 4,596,556 A | 6/1986 | Morrow et al. |
| 4,621,083 A | 11/1986 | Casals-Stenzel et al. |
| 4,782,084 A | 11/1988 | Vyas et al. |
| 4,790,824 A | 12/1988 | Morrow et al. |
| 4,885,314 A | 12/1989 | Vyas et al. |
| 4,886,499 A | 12/1989 | Cirelli et al. |
| 4,940,460 A | 7/1990 | Casey et al. |
| 4,941,880 A | 7/1990 | Burns et al. |
| 5,015,235 A | 5/1991 | Crossman et al. |
| 5,064,413 A | 11/1991 | McKinnon et al. |
| 5,104,543 A | 4/1992 | Brandt et al. |
| 5,141,496 A | 8/1992 | Dalto et al. |
| 5,190,521 A | 3/1993 | Hubbard et al. |
| 5,312,335 A | 5/1994 | McKinnon et al. |
| 5,328,483 A | 7/1994 | Jacoby et al. |
| 5,334,144 A | 8/1994 | Alchas et al. |
| 5,339,163 A | 8/1994 | Homma et al. |

(Continued)

FOREIGN PATENT DOCUMENTS

| | | |
|---|---|---|
| CA | 2020806 A1 | 1/1991 |
| CA | 2486101 A1 | 11/2003 |

(Continued)

OTHER PUBLICATIONS

Zhang et al,, Chemistry & Biology, 19, 140-154 (Year: 2012).*

(Continued)

*Primary Examiner* — Sudhakar Katakam

(74) *Attorney, Agent, or Firm* — Wolf, Greenfield & Sacks, P.C.

(57) ABSTRACT

The present disclosure provides combination therapy of a transcription inhibitor and a kinase inhibitor. The combination of the transcription inhibitor and the kinase inhibitor may be useful in treating and/or preventing in a subject a proliferative disease, such as proliferative a disease that is resistant to the transcription inhibitor alone or the kinase inhibitor alone. In certain embodiments, the proliferative disease is a cancer. The combination of the transcription inhibitor and the kinase inhibitor is expected to be synergistic.

26 Claims, 108 Drawing Sheets
Specification includes a Sequence Listing.

(56) References Cited

U.S. PATENT DOCUMENTS

| | | |
|---|---|---|
| 5,383,851 A | 1/1995 | McKinnon et al. |
| 5,417,662 A | 5/1995 | Hjertman et al. |
| 5,420,245 A | 5/1995 | Brown et al. |
| 5,466,220 A | 11/1995 | Brenneman et al. |
| 5,480,381 A | 1/1996 | Weston et al. |
| 5,484,596 A | 1/1996 | Hanna et al. |
| 5,503,627 A | 4/1996 | McKinnon et al. |
| 5,510,510 A | 4/1996 | Patel et al. |
| 5,520,639 A | 5/1996 | Peterson et al. |
| 5,523,430 A | 6/1996 | Patel et al. |
| 5,527,288 A | 6/1996 | Gross et al. |
| 5,532,359 A | 7/1996 | Marsters et al. |
| 5,569,189 A | 10/1996 | Parsons et al. |
| 5,571,792 A | 11/1996 | Bolton et al. |
| 5,589,485 A | 12/1996 | Hocolowski et al. |
| 5,593,988 A | 1/1997 | Tahara et al. |
| 5,599,302 A | 2/1997 | Lilley et al. |
| 5,602,098 A | 2/1997 | Sebti et al. |
| 5,643,958 A | 7/1997 | Iwasawa et al. |
| 5,649,912 A | 7/1997 | Peterson et al. |
| 5,661,152 A | 8/1997 | Bishop et al. |
| 5,704,911 A | 1/1998 | Parsons et al. |
| 5,712,274 A | 1/1998 | Sueoka et al. |
| 5,721,231 A | 2/1998 | Moriwaki et al. |
| 5,750,567 A | 5/1998 | Baudoin et al. |
| 5,753,649 A | 5/1998 | Tahaw et al. |
| 5,760,032 A | 6/1998 | Kitajima et al. |
| 5,846,972 A | 12/1998 | Buckman et al. |
| 5,854,238 A | 12/1998 | Kempen |
| 5,856,439 A | 1/1999 | Clerc et al. |
| 5,889,053 A | 3/1999 | Baudoin et al. |
| 5,893,397 A | 4/1999 | Peterson et al. |
| 5,925,641 A | 7/1999 | Kanda et al. |
| 5,936,097 A | 8/1999 | Commercon et al. |
| 5,993,412 A | 11/1999 | Deily et al. |
| 6,069,134 A | 5/2000 | Roth et al. |
| 6,214,852 B1 | 4/2001 | Kim et al. |
| 6,444,664 B1 | 9/2002 | Princen et al. |
| 6,806,272 B2 | 10/2004 | Bauer et al. |
| 6,861,422 B2 | 3/2005 | Hoffmann et al. |
| 6,921,763 B2 | 7/2005 | Hirst et al. |
| 6,939,874 B2 | 9/2005 | Harmange et al. |
| 7,015,213 B1 | 3/2006 | Bigg et al. |
| 7,115,617 B2 | 10/2006 | Buchanan et al. |
| 7,312,225 B2 | 12/2007 | Luecking et al. |
| 7,371,753 B2 | 5/2008 | Stadtmueller et al. |
| 7,528,143 B2 | 5/2009 | Noronha et al. |
| 7,528,153 B2 | 5/2009 | Noronha et al. |
| 7,589,167 B2 | 9/2009 | Zhou et al. |
| 7,750,152 B2 | 7/2010 | Hoffman et al. |
| 7,786,299 B2 | 8/2010 | Hoffman et al. |
| 7,816,530 B2 | 10/2010 | Grauert |
| 7,825,246 B2 | 11/2010 | Noronha et al. |
| 7,884,117 B2 | 2/2011 | Zhang et al. |
| 7,928,140 B2 | 4/2011 | Booker et al. |
| 8,003,786 B2 | 8/2011 | Hoffman et al. |
| 8,044,042 B2 | 10/2011 | Adachi et al. |
| 8,133,900 B2 | 3/2012 | Hood et al. |
| 8,138,199 B2 | 3/2012 | Noronha et al. |
| 8,273,765 B2 | 9/2012 | Fancelli et al. |
| 8,338,464 B2 | 12/2012 | Melnick et al. |
| 8,394,818 B2 | 3/2013 | Gray et al. |
| 8,476,260 B2 | 7/2013 | Miyoshi et al. |
| 8,604,042 B2 | 12/2013 | Noronha et al. |
| 8,765,747 B2 | 7/2014 | Choi et al. |
| 8,889,706 B2 | 11/2014 | Gray et al. |
| 8,981,083 B2 | 3/2015 | Bradner et al. |
| 8,987,275 B2 | 3/2015 | Gray et al. |
| 9,180,127 B2 | 11/2015 | Gray et al. |
| 9,301,962 B2 | 4/2016 | Bradner et al. |
| 9,320,741 B2 | 4/2016 | Bradner et al. |
| 9,358,231 B2 | 6/2016 | Gray et al. |
| 9,382,239 B2 | 7/2016 | Gray et al. |
| 9,505,784 B2 | 11/2016 | Choi et al. |
| 9,670,165 B2 | 6/2017 | Cohen et al. |
| 9,695,172 B2 | 7/2017 | Bradner et al. |
| 9,714,946 B2 | 7/2017 | Bradner et al. |
| 9,758,522 B2 | 9/2017 | Gray et al. |
| 9,789,120 B2 | 10/2017 | Bradner et al. |
| 9,862,688 B2 | 1/2018 | Gray et al. |
| 10,000,483 B2 | 6/2018 | Gray et al. |
| 10,017,477 B2 | 7/2018 | Gray et al. |
| 10,112,927 B2 | 10/2018 | Gray et al. |
| 10,144,730 B2 | 12/2018 | Gray et al. |
| 10,150,756 B2 | 12/2018 | Bradner et al. |
| 2002/0032200 A1 | 3/2002 | Cai et al. |
| 2002/0169158 A1 | 11/2002 | Hunt, III et al. |
| 2003/0130268 A1 | 7/2003 | Sagawa et al. |
| 2003/0139416 A1 | 7/2003 | Buchanan et al. |
| 2003/0216758 A1 | 11/2003 | Signore |
| 2004/0106634 A1 | 6/2004 | Satoh et al. |
| 2004/0176380 A1 | 9/2004 | Hoffmann et al. |
| 2004/0209878 A1 | 10/2004 | Guzi et al. |
| 2005/0026914 A1 | 2/2005 | Buchanan et al. |
| 2005/0250837 A1 | 11/2005 | D'Mello et al. |
| 2006/0035902 A1 | 2/2006 | Linz et al. |
| 2006/0074088 A1 | 4/2006 | Munzert et al. |
| 2006/0106083 A1 | 5/2006 | Martina et al. |
| 2006/0142257 A1 | 6/2006 | Nieschlag et al. |
| 2006/0189627 A1 | 8/2006 | Laird et al. |
| 2006/0223055 A1 | 10/2006 | Howley et al. |
| 2007/0093537 A1 | 4/2007 | Hynes et al. |
| 2007/0105839 A1 | 5/2007 | Imbach et al. |
| 2007/0179178 A1 | 8/2007 | Buettelmann et al. |
| 2007/0185171 A1 | 8/2007 | Germain et al. |
| 2007/0218135 A1 | 9/2007 | Mukharya et al. |
| 2007/0225286 A1 | 9/2007 | Ren et al. |
| 2007/0275963 A1 | 11/2007 | Guzi et al. |
| 2007/0281907 A1 | 12/2007 | Watkins |
| 2008/0004308 A1 | 1/2008 | Dhanak et al. |
| 2008/0039629 A1 | 2/2008 | Ramesh et al. |
| 2008/0081781 A1 | 4/2008 | Lippa et al. |
| 2008/0090849 A1 | 4/2008 | Bordon-Pallier et al. |
| 2008/0103167 A1 | 5/2008 | Bebernitz et al. |
| 2008/0214501 A1 | 9/2008 | Pan et al. |
| 2008/0249079 A1 | 10/2008 | Chen et al. |
| 2008/0300267 A1 | 12/2008 | Okram et al. |
| 2008/0305113 A1 | 12/2008 | Kwon et al. |
| 2009/0012064 A1 | 1/2009 | Sagara et al. |
| 2009/0054392 A1 | 2/2009 | Pelletier et al. |
| 2009/0054405 A1 | 2/2009 | Booker et al. |
| 2009/0082346 A1 | 3/2009 | Brasca et al. |
| 2009/0105250 A1 | 4/2009 | Sim et al. |
| 2009/0238828 A1 | 9/2009 | Munzert et al. |
| 2009/0280115 A1 | 11/2009 | Maier et al. |
| 2009/0281191 A1 | 11/2009 | Rangwala et al. |
| 2009/0318408 A1 | 12/2009 | Cai et al. |
| 2010/0041643 A1 | 2/2010 | Adachi et al. |
| 2010/0056524 A1 | 3/2010 | Mciver et al. |
| 2010/0197688 A1 | 8/2010 | Nantermet et al. |
| 2010/0249412 A1 | 9/2010 | Linz et al. |
| 2010/0254905 A1 | 10/2010 | Honigberg et al. |
| 2010/0286127 A1 | 11/2010 | Miyoshi et al. |
| 2011/0028405 A1 | 2/2011 | Harrison et al. |
| 2011/0086858 A1 | 4/2011 | Wang et al. |
| 2011/0098280 A1 | 4/2011 | Garcia-Echeverria et al. |
| 2011/0098288 A1 | 4/2011 | Major et al. |
| 2011/0172231 A1 | 7/2011 | Baenteli et al. |
| 2011/0178070 A1 | 7/2011 | Gong et al. |
| 2011/0201606 A1 | 8/2011 | Garcia-Echeverria et al. |
| 2011/0207711 A1 | 8/2011 | Katz et al. |
| 2011/0212053 A1 | 9/2011 | Qian et al. |
| 2011/0212077 A1 | 9/2011 | Noronha et al. |
| 2011/0230460 A1 | 9/2011 | Kempen et al. |
| 2011/0245245 A1 | 10/2011 | Mortensen et al. |
| 2012/0014979 A1 | 1/2012 | Dent |
| 2012/0040961 A1 | 2/2012 | Gray et al. |
| 2012/0088766 A1 | 4/2012 | Choi et al. |
| 2012/0094999 A1 | 4/2012 | Gray et al. |
| 2012/0165309 A1 | 6/2012 | Takahashi et al. |
| 2012/0202798 A1 | 8/2012 | Sagara |
| 2012/0202809 A1 | 8/2012 | Li et al. |
| 2012/0277248 A1 | 11/2012 | Caruso et al. |
| 2012/0329771 A1 | 12/2012 | Treu et al. |

(56) References Cited

U.S. PATENT DOCUMENTS

| | | | |
|---|---|---|---|
| 2012/0329803 A1 | 12/2012 | Guenter et al. | |
| 2013/0040949 A1 | 2/2013 | Gray et al. | |
| 2013/0184264 A1 | 7/2013 | Bradner et al. | |
| 2013/0210813 A1 | 8/2013 | Bradner et al. | |
| 2013/0252331 A1 | 9/2013 | Bradner et al. | |
| 2013/0274239 A1 | 10/2013 | Arnold et al. | |
| 2013/0280332 A1 | 10/2013 | Moss et al. | |
| 2014/0011862 A1 | 1/2014 | Bradner et al. | |
| 2014/0243322 A1 | 8/2014 | Arnold et al. | |
| 2014/0303112 A1 | 10/2014 | Chen et al. | |
| 2014/0309249 A1* | 10/2014 | Gray | A61K 31/437 514/275 |
| 2015/0094315 A1 | 4/2015 | Choi et al. | |
| 2015/0157629 A1 | 6/2015 | Gray et al. | |
| 2015/0166532 A1 | 6/2015 | Gray et al. | |
| 2015/0246913 A1 | 9/2015 | Gray et al. | |
| 2015/0274728 A1 | 10/2015 | Gray et al. | |
| 2016/0033519 A1 | 2/2016 | Bradner et al. | |
| 2016/0046636 A1 | 2/2016 | Gray et al. | |
| 2016/0122323 A1* | 5/2016 | Gray | A61K 31/506 |
| 2016/0168154 A1 | 6/2016 | Bradner et al. | |
| 2016/0231314 A1 | 8/2016 | Bradner et al. | |
| 2016/0317547 A1 | 11/2016 | Bradner et al. | |
| 2016/0332993 A1 | 11/2016 | Bradner et al. | |
| 2016/0347749 A1 | 12/2016 | Bradner et al. | |
| 2016/0368910 A1 | 12/2016 | Gray et al. | |
| 2017/0008895 A1 | 1/2017 | Bradner et al. | |
| 2017/0044111 A1 | 2/2017 | Gray et al. | |
| 2017/0044112 A1 | 2/2017 | Gray et al. | |
| 2017/0145013 A1 | 5/2017 | Bradner et al. | |
| 2017/0145023 A1 | 5/2017 | Bradner et al. | |
| 2018/0093990 A1 | 4/2018 | Gray et al. | |
| 2018/0319801 A1 | 11/2018 | Gray et al. | |
| 2018/0362483 A1 | 12/2018 | Gray et al. | |
| 2019/0055248 A1 | 2/2019 | Gray et al. | |
| 2019/0100511 A1 | 4/2019 | Gray et al. | |
| 2019/0112305 A1 | 4/2019 | Gray et al. | |
| 2019/0248778 A1 | 8/2019 | Gray et al. | |

FOREIGN PATENT DOCUMENTS

| | | |
|---|---|---|
| CA | 2503646 A1 | 5/2004 |
| CA | 2526430 A1 | 12/2004 |
| CA | 2550128 A1 | 6/2005 |
| CA | 2563212 A1 | 10/2005 |
| CA | 2710740 A1 | 7/2009 |
| CH | 622019 A5 | 3/1981 |
| CN | 1227555 A | 9/1999 |
| CN | 1745081 A | 3/2006 |
| CN | 101022809 A | 8/2007 |
| CN | 101023070 A | 8/2007 |
| CN | 101420955 A | 4/2009 |
| CN | 102341394 A | 2/2012 |
| CN | 103037865 A | 4/2013 |
| DE | 3724164 A1 | 2/1988 |
| EA | 8778 B1 | 8/2007 |
| EA | 201070395 A1 | 10/2010 |
| EP | 0 087 850 A1 | 9/1983 |
| EP | 0 368 175 A1 | 5/1990 |
| EP | 0 387 613 A1 | 9/1990 |
| EP | 0604181 A1 | 12/1993 |
| EP | 0618221 A2 | 3/1994 |
| EP | 0675112 A1 | 3/1995 |
| EP | 0696593 A2 | 8/1995 |
| EP | 0 934 940 A1 | 8/1999 |
| EP | 0 989 131 B1 | 11/2002 |
| EP | 1 297 836 A1 | 4/2003 |
| EP | 1 935 890 A1 | 6/2008 |
| EP | 2 112 152 A1 | 10/2009 |
| EP | 2 239 264 A1 | 10/2010 |
| EP | 2 311 842 A2 | 4/2011 |
| EP | 2 481 739 A1 | 8/2012 |
| ES | 2 351 367 T3 | 2/2011 |
| FR | 2329668 A1 | 5/1977 |
| GB | 796524 A | 6/1958 |
| JP | 61-87684 A | 5/1986 |
| JP | 1-299231 | 12/1989 |
| JP | 6-157316 A | 6/1994 |
| JP | H10500998 A | 1/1998 |
| JP | 11-228576 | 8/1999 |
| JP | 11-512107 A | 10/1999 |
| JP | 3001979 | 11/1999 |
| JP | 3096299 | 8/2000 |
| JP | 2003-503481 A | 1/2003 |
| JP | 2004-529140 A | 9/2004 |
| JP | 2005-501860 A | 1/2005 |
| JP | 2005-505535 A | 2/2005 |
| JP | 2005-527529 | 9/2005 |
| JP | 2005-530711 A | 10/2005 |
| JP | 2005-534635 A | 11/2005 |
| JP | 2005-538100 A | 12/2005 |
| JP | 2006-520354 | 9/2006 |
| JP | 2006-521394 A | 9/2006 |
| JP | 2007-500226 A | 1/2007 |
| JP | 2007-500725 A | 1/2007 |
| JP | 2008-500320 A | 1/2008 |
| JP | 2008-501669 A | 1/2008 |
| JP | 2008-502610 A | 1/2008 |
| JP | 2008-509948 A | 4/2008 |
| JP | 2008-509953 A | 4/2008 |
| JP | 2008-510763 | 4/2008 |
| JP | 2008-510771 A | 4/2008 |
| JP | 2008-156311 A | 7/2008 |
| JP | 2008-543778 | 12/2008 |
| JP | 2009-510110 A | 3/2009 |
| JP | 2010-511655 A | 4/2010 |
| JP | 2010-521487 A | 6/2010 |
| JP | 2011-513457 A | 4/2011 |
| JP | 2011-515383 A | 5/2011 |
| JP | 2011-516533 A | 5/2011 |
| JP | 2012-530071 A | 11/2012 |
| JP | 2013-543879 A | 12/2013 |
| JP | 5913292 B2 | 4/2016 |
| JP | 2016-533379 A | 10/2016 |
| JP | 2017-504651 A | 2/2017 |
| MX | 2016-009974 A | 10/2016 |
| MX | 2016-009975 A | 10/2016 |
| MX | 2016-009976 A | 11/2016 |
| PT | 2 139 892 E | 11/2011 |
| RU | 2278117 C2 | 9/2003 |
| RU | 2475488 C2 | 3/2010 |
| WO | WO 84/02131 A1 | 6/1984 |
| WO | WO 94/19357 A1 | 9/1994 |
| WO | WO 95/08542 A1 | 3/1995 |
| WO | WO 95/10514 A1 | 4/1995 |
| WO | WO 95/10515 A1 | 4/1995 |
| WO | WO 95/10516 A1 | 4/1995 |
| WO | WO 95/11917 A1 | 5/1995 |
| WO | WO 95/12572 A1 | 5/1995 |
| WO | WO 95/12612 A1 | 5/1995 |
| WO | WO 95/25086 A1 | 9/1995 |
| WO | WO 95/32987 A1 | 12/1995 |
| WO | WO 95/34535 A1 | 12/1995 |
| WO | WO 96/00736 A1 | 1/1996 |
| WO | WO 96/05168 A1 | 2/1996 |
| WO | WO 96/05169 A1 | 2/1996 |
| WO | WO 96/17861 A1 | 6/1996 |
| WO | WO 96/21456 A1 | 7/1996 |
| WO | WO 96/22278 A1 | 7/1996 |
| WO | WO 96/24611 A1 | 8/1996 |
| WO | WO 96/24612 A1 | 8/1996 |
| WO | WO 96/30017 A1 | 10/1996 |
| WO | WO 96/30018 A1 | 10/1996 |
| WO | WO 96/30343 A1 | 10/1996 |
| WO | WO 96/30362 A1 | 10/1996 |
| WO | WO 96/30363 A1 | 10/1996 |
| WO | WO 96/31111 A1 | 10/1996 |
| WO | WO 96/31477 A1 | 10/1996 |
| WO | WO 96/31478 A1 | 10/1996 |
| WO | WO 96/31501 A1 | 10/1996 |
| WO | WO 96/33159 A1 | 10/1996 |
| WO | WO 96/34850 A1 | 11/1996 |
| WO | WO 96/34851 A1 | 11/1996 |

(56) References Cited

FOREIGN PATENT DOCUMENTS

| | | |
|---|---|---|
| WO | WO 97/00252 A1 | 1/1997 |
| WO | WO 97/03047 A1 | 1/1997 |
| WO | WO 97/03050 A1 | 1/1997 |
| WO | WO 97/04785 A1 | 2/1997 |
| WO | WO 97/17070 A1 | 5/1997 |
| WO | WO 97/18813 A1 | 5/1997 |
| WO | WO 97/21701 A1 | 6/1997 |
| WO | WO 97/23478 A1 | 7/1997 |
| WO | WO 97/26246 A1 | 7/1997 |
| WO | WO 97/30053 A1 | 8/1997 |
| WO | WO 97/38665 A2 | 10/1997 |
| WO | WO 97/44350 A1 | 11/1997 |
| WO | WO 97/47622 A1 | 12/1997 |
| WO | WO 98/02436 A1 | 1/1998 |
| WO | WO 98/11111 A1 | 3/1998 |
| WO | WO 98/28980 A1 | 7/1998 |
| WO | WO 98/29119 A1 | 7/1998 |
| WO | WO 2000/44777 A1 | 8/2000 |
| WO | WO 2000/50032 A1 | 8/2000 |
| WO | WO 2000/61186 A1 | 10/2000 |
| WO | WO 2001/02369 A2 | 1/2001 |
| WO | WO 2001/019829 A2 | 3/2001 |
| WO | WO 2001/95912 A1 | 12/2001 |
| WO | WO 2002/076986 A1 | 10/2002 |
| WO | WO 2002/079197 A1 | 10/2002 |
| WO | WO 2002/080926 A1 | 10/2002 |
| WO | WO 2002/083653 A1 | 10/2002 |
| WO | WO 2002/096905 A1 | 12/2002 |
| WO | WO 2002/102800 A1 | 12/2002 |
| WO | WO 2003/007983 A1 | 1/2003 |
| WO | WO 2003/018021 A1 | 3/2003 |
| WO | WO 2003/018022 A1 | 3/2003 |
| WO | WO 2003/020722 A1 | 3/2003 |
| WO | WO 2003/026664 A1 | 4/2003 |
| WO | WO 2003/051847 A1 | 6/2003 |
| WO | WO 2003/078403 A2 | 9/2003 |
| WO | WO 2003/097610 A1 | 11/2003 |
| WO | WO 2004/005283 A1 | 1/2004 |
| WO | WO 2004/009601 A1 | 1/2004 |
| WO | WO 2004/010995 A1 | 2/2004 |
| WO | WO 2004/022561 A1 | 3/2004 |
| WO | WO 2004/026229 A2 | 4/2004 |
| WO | WO 2004/039796 A1 | 5/2004 |
| WO | WO 2004/074283 A1 | 9/2004 |
| WO | WO 2004/076458 A1 | 9/2004 |
| WO | WO 2004/078757 A2 | 9/2004 |
| WO | WO 2004/081013 A1 | 9/2004 |
| WO | WO 2004/087699 A2 | 10/2004 |
| WO | WO 2004/087707 A1 | 10/2004 |
| WO | WO 2004/100868 A2 | 11/2004 |
| WO | WO 2004/113303 A1 | 12/2004 |
| WO | WO 2004/113304 A1 | 12/2004 |
| WO | WO 2005/011597 A2 | 2/2005 |
| WO | WO 2005/058891 A1 | 6/2005 |
| WO | WO 2005/097790 A1 | 10/2005 |
| WO | WO 2005/108397 A1 | 11/2005 |
| WO | WO 2005/116025 A2 | 12/2005 |
| WO | WO 2006/003276 A1 | 1/2006 |
| WO | WO 2006/018185 A2 | 2/2006 |
| WO | WO 2006/024834 A1 | 3/2006 |
| WO | WO 2006/031806 A2 | 3/2006 |
| WO | WO 2006/034341 A2 | 3/2006 |
| WO | WO 2006/040568 A1 | 4/2006 |
| WO | WO 2006/133426 A2 | 12/2006 |
| WO | WO 2007/002325 A1 | 1/2007 |
| WO | WO 2007/002433 A1 | 1/2007 |
| WO | WO 2007/024680 A1 | 3/2007 |
| WO | WO 2007/035428 A1 | 3/2007 |
| WO | WO 2007/042786 A2 | 4/2007 |
| WO | WO 2007/044420 A1 | 4/2007 |
| WO | WO 2007/048070 A2 | 4/2007 |
| WO | WO 2007/053452 | 5/2007 |
| WO | WO 2007/075869 A2 | 7/2007 |
| WO | WO 2007/095188 A2 | 8/2007 |
| WO | WO 2007/129195 A2 | 11/2007 |
| WO | WO 2007/138277 A1 | 12/2007 |
| WO | WO 2008/009909 A1 | 1/2008 |
| WO | WO 2008/049856 A1 | 5/2008 |
| WO | WO 2008/063888 A2 | 5/2008 |
| WO | WO 2008/068171 A1 | 6/2008 |
| WO | WO 2008/074749 A1 | 6/2008 |
| WO | WO 2008/079907 A1 | 7/2008 |
| WO | WO 2008/080015 A2 | 7/2008 |
| WO | WO 2008/083056 A2 | 7/2008 |
| WO | WO 2008/112913 A1 | 9/2008 |
| WO | WO 2008/113711 A1 | 9/2008 |
| WO | WO 2008/124393 A1 | 10/2008 |
| WO | WO 2008/137081 A1 | 11/2008 |
| WO | WO 2008/144253 A1 | 11/2008 |
| WO | WO 2008/151183 A1 | 12/2008 |
| WO | WO 2008/151304 A1 | 12/2008 |
| WO | WO 2009/017822 A2 | 2/2009 |
| WO | WO 2009/023269 A3 | 2/2009 |
| WO | WO 2009/028655 A1 | 3/2009 |
| WO | WO 2009/032694 A1 | 3/2009 |
| WO | WO 2009/040556 A1 | 4/2009 |
| WO | WO 2009/067547 A1 | 5/2009 |
| WO | WO 2009/084693 A1 | 7/2009 |
| WO | WO 2009/145360 A1 | 12/2009 |
| WO | WO 2009/152027 A1 | 12/2009 |
| WO | WO 2009/153197 A1 | 12/2009 |
| WO | WO 2009/155017 A2 | 12/2009 |
| WO | WO 2010/008847 A2 | 1/2010 |
| WO | WO 2010/015387 A1 | 2/2010 |
| WO | WO 2010/032195 A1 | 3/2010 |
| WO | WO 2010/049466 A1 | 5/2010 |
| WO | WO 2010/051781 A1 | 5/2010 |
| WO | WO 2010/080712 A1 | 7/2010 |
| WO | WO 2010/125799 A1 | 11/2010 |
| WO | WO 2010/144909 A1 | 12/2010 |
| WO | WO 2011/036566 A1 | 3/2011 |
| WO | WO 2011/054553 A1 | 5/2011 |
| WO | WO 2011/054841 A1 | 5/2011 |
| WO | WO 2011/054843 A1 | 5/2011 |
| WO | WO 2011/054844 A1 | 5/2011 |
| WO | WO 2011/054845 A1 | 5/2011 |
| WO | WO 2011/054846 A1 | 5/2011 |
| WO | WO 2011/054848 A1 | 5/2011 |
| WO | WO 2011/101369 A1 | 8/2011 |
| WO | WO 2011/115725 A2 | 9/2011 |
| WO | WO 2011/143651 A1 | 11/2011 |
| WO | WO 2011/143657 A1 | 11/2011 |
| WO | WO 2011/143660 A2 | 11/2011 |
| WO | WO 2011/143669 A2 | 11/2011 |
| WO | WO 2011/161031 A1 | 12/2011 |
| WO | WO 2012/072505 A1 | 6/2012 |
| WO | WO 2012/075383 A2 | 6/2012 |
| WO | WO 2012/075456 A1 | 6/2012 |
| WO | WO 2012/116170 A1 | 8/2012 |
| WO | WO 2012/118812 A2 | 9/2012 |
| WO | WO 2012/120048 A1 | 9/2012 |
| WO | WO 2012/143416 A2 | 10/2012 |
| WO | WO 2013/014162 A1 | 1/2013 |
| WO | WO 2013/033268 A2 | 3/2013 |
| WO | WO 2013/033269 A1 | 3/2013 |
| WO | WO 2013/033270 A2 | 3/2013 |
| WO | WO 2013/040436 A2 | 3/2013 |
| WO | WO 2013/074986 A1 | 5/2013 |
| WO | WO 2013/097601 A1 | 7/2013 |
| WO | WO 2013/136070 A1 | 9/2013 |
| WO | WO 2013/148197 A1 | 10/2013 |
| WO | WO 2013/154778 A1 | 10/2013 |
| WO | WO 2014/063061 A1 | 4/2014 |
| WO | WO 2014/063068 A1 | 4/2014 |
| WO | WO 2014/071247 A1 | 5/2014 |
| WO | WO 2014/095774 A1 | 6/2014 |
| WO | WO 2014/139324 A1 | 9/2014 |
| WO | WO 2014/159392 A1 | 10/2014 |
| WO | WO 2015/013635 A2 | 1/2015 |
| WO | WO 2015/058126 A1 | 4/2015 |
| WO | WO 2015/058140 A1 | 4/2015 |
| WO | WO 2015/081284 A1 | 6/2015 |
| WO | WO 2015/117053 A1 | 8/2015 |
| WO | WO 2015/117055 A1 | 8/2015 |

(56) References Cited

FOREIGN PATENT DOCUMENTS

| | | |
|---|---|---|
| WO | WO 2015/117083 A1 | 8/2015 |
| WO | WO 2015/117087 A1 | 8/2015 |
| WO | WO 2015/154022 A1 | 10/2015 |
| WO | WO 2015/164604 A1 | 10/2015 |
| WO | WO 2015/164614 A1 | 10/2015 |
| WO | WO 2016/014542 A1 | 1/2016 |
| WO | WO 2016/014551 A1 | 1/2016 |
| WO | WO 2016/022902 A1 | 2/2016 |
| WO | WO 2016/105528 A2 | 6/2016 |
| WO | WO 2016/201370 A1 | 12/2016 |
| WO | WO 2017/037576 A1 | 3/2017 |
| WO | WO 2017/044792 A1 | 3/2017 |

OTHER PUBLICATIONS

Katt et al (Trends Cancer, Jan. 2018, 4(1), 20-37) (Year: 2018).*
Tian et al (Int J Mol Sci, Feb. 2019, 20(3), 755 (Year: 2019).*
McAuley et al (Front Immonol, Aug. 2018, 9, 1887) (Year: 2018).*
Sidow et al (Trends Genet, Apr. 2015, 31(4), 208-214) (Year: 2015).*
Partial European Search Report for EP 16773870.7, dated Jul. 12, 2018.
International Preliminary Report on Patentability for PCT/US2016/051017, dated Mar. 22, 2018.
International Preliminary Report on Patentability for PCT/US2016051107, dated Mar. 22, 2018.
International Preliminary Report on Patentability for PCT/US2016/63502, dated Jun. 7, 2018.
Peifer et al., Small-molecule inhibitors of PDK1. ChemMedChem. Dec. 2008;3(12):1810-38. doi: 10.1002/cmdc.200800195.
Williamson et al., Structure-guided design of pyrazolo[1,5-a]pyrimidines as inhibitors of human cyclin-dependent kinase 2. Bioorg Med Chem Lett. Feb. 15, 2005;15(4):863-7.
International Search Report and Written Opinion for PCT/US2012/065618, dated Mar. 19, 2013.
International Preliminary Report on Patentability for PCT/US2012/065618, dated May 30, 2014.
International Search Report and Written Opinion for PCT/US2014/023386, dated Jul. 9, 2014.
International Preliminary Report on Patentability for PCT/US2014/023386, dated Sep. 24, 2015.
International Search Report and Written Opinion for PCT/US2013/065708, dated Feb. 4, 2014.
International Preliminary Report on Patentability for PCT/US2013/065708, dated Apr. 30, 2015.
International Search Report and Written Opinion for PCT/US2013/065689, dated Mar. 4, 2014.
International Preliminary Report on Patentability for PCT/US2013/065689, dated Apr. 30, 2015.
International Search Report and Written Opinion for PCT/US2013/065698, dated Feb. 20, 2014.
International Preliminary Report on Patentability for PCT/US2013/065698, dated Apr. 30, 2015.
Extended European Search Report for EP 14828728, dated Jan. 31, 2017.
Invitation to Pay Additional Fees for PCT/US2014/48230, dated Nov. 17, 2014.
International Search Report and Written Opinion for PCT/US2014/48230, dated Jan. 30, 2015.
International Preliminary Report on Patentability for PCT/US2014/48230, dated Feb. 4, 2016.
International Search Report and Written Opinion for PCT/US2014/061232, dated Dec. 23, 2014.
International Search Report and Written Opinion for PCT/US2015/027312, dated Jul. 10, 2015.
International Preliminary Report on Patentability for PCT/US2015/027312, dated Nov. 3, 2016.
Extended European Search Report for EP 15744026.4, dated Jun. 7, 2017.
Invitation to Pay Additional Fees for PCT/US2015/14109, dated Apr. 20, 2015.
International Search Report and Written Opinion for PCT/US2015/14109, dated Jul. 6, 2015.
International Preliminary Report on Patentability for PCT/US2015/14109, dated Aug. 11, 2016.
Extended European Search Report for EP 15743171.9, dated Jul. 10, 2017.
International Search Report and Written Opinion for PCT/US2015/14044, dated Apr. 23, 2015.
International Preliminary Report on Patentability for PCT/US2015/14044, dated Aug. 11, 2016.
Extended European Search Report for EP 15742537, dated Jun. 22, 2017.
International Search Report and Written Opinion for PCT/US2015/14039, dated Apr. 23, 2015.
International Preliminary Report on Patentability for PCT/US2015/14039, dated Aug. 11, 2016.
Extended European Search Report for EP 15743564.5, dated Jul. 13, 2017.
International Search Report and Written Opinion for PCT/US2015/14120, dated Apr. 23, 2015.
International Preliminary Report on Patentability for PCT/US2015/14120, dated Aug. 11, 2016.
International Search Report and Written Opinion for PCT/US2015/027294, dated Jul. 10, 2015.
Extended European Search Report for EP 10786967.9, dated Oct. 23, 2012.
International Search Report and Written Opinion for PCT/US2010/038518, dated Aug. 6, 2010.
International Preliminary Report on Patentability for PCT/US2010/038518, dated Dec. 22, 2011.
Extended European Search Report for EP 10844280.7, dated Apr. 17, 2013.
Partial European Search Report for EP 15160591.2, dated Jul. 14, 2015.
Extended European Search Report for EP 15160591.2, dated Nov. 2, 2015.
International Search Report and Written Opinion for PCT/US2010/062310, dated Oct. 4, 2011.
International Preliminary Report on Patentability for PCT/US2010/062310, dated Jul. 12, 2012.
Extended European Search Report for EP 15830298.4, dated Nov. 24, 2017.
International Search Report and Written Opinion for PCT/US2015/044180, dated Nov. 5, 2015.
International Preliminary Report on Patentability for PCT/US2015/044180, dated Feb. 23, 2017.
Extended European Search Report for EP 15829064.3, dated Dec. 21, 2017.
Invitation to Pay Additional Fees for PCT/US2015/044303, dated Oct. 21, 2015.
International Search Report and Written Opinion for PCT/US2015/044303, dated Dec. 31, 2015.
International Preliminary Report on Patentability for PCT/US2015/044303, dated Feb. 23, 2017.
International Search Report and Written Opinion for PCT/US2015/000297, dated Mar. 4, 2016.
International Preliminary Report on Patentability PCT/US2015/000297, dated Jul. 6, 2017.
International Search Report and Written Opinion for PCT/US2016/037086, dated Sep. 2, 2016.
International Preliminary Report on Patentability for PCT/US/2016/037086, dated Dec. 21, 2017.
Invitation to Pay Additional Fees for PCT/US2016/024345, dated Aug. 9, 2016.
International Search Report and Written Opinion for PCT/US2016/024345, dated Oct. 6, 2016.
International Preliminary Report on Patentability for PCT/US2016/024345, dated Oct. 12, 2017.
Invitation to Pay Additional Fees for PCT/US2016/051017, dated Oct. 31, 2016.

(56) References Cited

OTHER PUBLICATIONS

International Search Report and Written Opinion for PCT/US2016/051017, dated Jan. 10, 2017.
[No Author Listed], PubChem SID 235048169. Feb. 13, 2015. Retrieved on Oct. 24, 2016. Available at https://pubchem.ncbi.nlm.nih.gov/substance/235048169.
[No Author Listed], PubChem SID 235671906. Feb. 13, 2015. Retrieved on Oct. 24, 2016. Available at https://pubchem.ncbi.nlm.nih.gov/substance/235671906#section=Top>.
CAS Registry No. 1334419-59-8, STN Entry Date Dec. 30, 2013.
CAS Registry No. 769961-59-3, STN Entry Date Oct. 27, 2004.
CAS Registry No. 916173-61-0, STN Entry Date Dec. 21, 2006.
CAS Registry No. 769961-42-4, STN Entry Date Oct. 27, 2004.
CAPLUS Database Result for Deng et al., Structural determinants for ERK5 (MAPK7) and leucine rich repeat kinase 2 activities of benzo[e]pyrimido-[5,4-b]diazepine-6(11H)-ones. Eur J Med Chem. 2013;70:758-67. doi: 10.1016/j.ejmech.2013.10.052. Epub Oct. 29, 2013. Accession No. 2013:1979798. Abstract Only.
CAPLUS Database Result for Hoffman et al., WO 2003/020722 A1 (Mar. 13, 2003). Caplus Accession No. 2003:202640.
Genbank Accession No. M80629. Lapidot-Lifson et al., Dec. 31, 1994. 2 pages.
Genbank Accession No. NP_001790. Yang et al., Oct. 6, 2016. 4 pages.
Genbank Submission; NH/NCBI, Accession No. H86170. Hillier et al., Nov. 21, 1995. 2 pages.
Genbank Submission; NH/NCBI, Accession No. NP_001003694. Lubula et al., Oct. 6, 2016. 4 pages.
Genbank Submission; NH/NCBI, Accession No. NP_001420. Ledsaak et al., Sep. 15, 2016. 8 pages.
Genbank Submission; NH/NCBI, Accession No. NP_001717. Barda et al., Feb. 2, 2014. 2 pages.
Genbank Submission; NH/NCBI, Accession No. NP_003061. Agaimy et al., Dec. 10, 2016. 5 pages.
Genbank Submission; NH/NCBI, Accession No. NP_003063. Liao et al., May 2, 2016. 5 pages.
Genbank Submission; NH/NCBI, Accession No. NP_003875. Li et al., Oct. 7, 2016. 3 pages.
Genbank Submission; NH/NCBI, Accession No. NP_004371. Liu et al., Dec. 10, 2006. 3 pages.
Genbank Submission; NH/NCBI, Accession No. NP_004597. Herzfeld et al., Aug. 26, 2016. 5 pages.
Genbank Submission; NH/NCBI, Accession No. NP_005095. Xiao et al., Oct. 6, 2016. 4 pages.
Genbank Submission; NH/NCBI, Accession No. NP_005753. Dalgaard et al., Oct. 6, 2016. 6 pages.
Genbank Submission; NH/NCBI, Accession No. NP_009168. DiBernardo et al., Sep. 28, 2008. 2 pages.
Genbank Submission; NH/NCBI, Accession No. NP_031397. Shao et al., Jan. 4, 2017. 4 pages.
Genbank Submission; NH/NCBI, Accession No. NP_038478. Jones et al., Sep. 23, 2005. 2 pages.
Genbank Submission; NH/NCBI, Accession No. NP_054828. Hou et al., Sep. 15, 2016. 5 pages.
Genbank Submission; NH/NCBI, Accession No. NP_055392. Aberg et al., Mar. 22, 2014. 3 pages.
Genbank Submission; NH/NCBI, Accession No. NP_060404. Bezrookove et al., Oct. 7, 2016. 5 pages.
Genbank Submission; NH/NCBI, Accession No. NP_060635. Varela et al., Dec. 18, 2011. 3 pages.
Genbank Submission; NH/NCBI, Accession No. NP_060959. Kuryshev et al., Mar. 26, 2006. 2 pages.
Genbank Submission; NH/NCBI, Accession No. NP_061836. Perry et al., Feb. 21, 2016. 7 pages.
Genbank Submission; NH/NCBI, Accession No. NP_066564. Wiper-Bergeron et al., Jun. 3, 2007. 3 pages.
Genbank Submission; NH/NCBI, Accession No. NP_076413. Clark et al., Jun. 27, 2007. 2 pages.
Genbank Submission; NH/NCBI, Accession No. NP_113601. Knijnenburg et al., Jan. 17, 2014. 3 pages.
Genbank Submission; NH/NCBI, Accession No. NP_490597. Duan et al., Oct. 6, 2016. 5 pages.
Genbank Submission; NH/NCBI, Accession No. NP_612411. Saare et al., Aug. 25, 2016. 2 pages.
Genbank Submission; NH/NCBI, Accession No. NP_722516. Xia et al., Nov. 22, 2015. 3 pages.
Genbank Submission; NH/NCBI, Accession No. NP_872579. Lee et al., Oct. 6, 2016. 4 pages.
Genbank Submission; NH/NCBI, Accession No. XP_039676. [No Author Listed], Aug. 19, 2004. 3 pages.
Uniprot No. Q9NYV4. Last modified Mar. 15, 2017. 14 pages.
Abbate et al., Structure of the papillomavirus DNA-tethering complex E2:Brd4 and a peptide that ablates HPV chromosomal association. Mol Cell. Dec. 28, 2006;24(6):877-89.
Akhtar et al., TFIIH kinase places bivalent marks on the carboxy-terminal domain of RNA polymerase II. Mol Cell. May 15, 2009;34(3):387-93. doi: 10.1016/j.molcel.2009.04.016.
Akira et al., Toll-like receptor signalling. Nat Rev Immunol. Jul. 2004;4(7):499-511.
Al-Lazikani et al., Combinatorial drug therapy for cancer in the post-genomic era. Nature Biotechnology 2012;30:679-692.
Anders et al., Genome-wide localization of small molecules. Nat Biotechnol. Jan. 2014;32(1):92-6. doi: 10.1038/nbt.2776. Epub Dec. 15, 2013.
Arango et al., Reversible azoospermia in a patient treated with triazolam. Eur J Contracept Reprod Health Care. Se. 1996;1(3):293-4.
Attoub et al., The c-kit tyrosine kinase inhibitor STI571 for colorectal cancer therapy. Cancer Res. Sep. 1, 2002;62(17):4879-83.
Bajrami et al., Genome-wide profiling of genetic synthetic lethality identifies CDK12 as a novel determinant of PARP1/2 inhibitor sensitivity. Cancer Res. Jan. 1, 2014;74(1):287-97. doi: 10.1158/0008-5472.CAN-13-2541. Epub Nov. 15, 2013.
Baranwal et al., Molecular characterization of the tumor-suppressive function of nischarin in breast cancer. Journal of the National Cancer Institute 2011;103:1513-1528.
Bartholomeeusen et al., Bromodomain and extra-terminal (BET) bromodomain inhibition activate transcription via transient release of positive transcription elongation factor b (P-TEFb) from 7SK small nuclear ribonucleoprotein. J Biol Chem. Oct. 19, 2012;287(43):36609-16. doi: 10.1074/jbc.M112.410746. Epub Sep. 5, 2012.
Bartkowiak et al., CDK12 is a transcription elongation-associated CTD kinase, the metazoan ortholog of yeast Ctk1. Genes Dev. Oct. 15, 2010;24(20):2303-16. doi: 10.1101/gad.1968210.
Baud et al., Chemical biology. A bump-and-hole approach to engineer controlled selectivity of BET bromodomain chemical probes. Science. Oct. 31, 2014;346(6209):638-41. doi: 10.1126/science.1249830. Epub Oct. 16, 2014.
Beeler et al., Role of the JNK-interacting protein 1/islet brain 1 in cell degeneration in Alzheimer disease and diabetes. Brain Res Bull. Oct. 28, 2009;80(4-5):274-81. doi: 10.1016/j.brainresbull.2009.07.006. Epub Jul. 16, 2009.
Bell et al., Integrated genomic analyses of ovarian carcinoma. Nature. Jun. 29, 2011;474(7353):609-15. doi: 10.1038/nature10166.
Ben-Av et al., Induction of vascular endothelial growth factor expression in synovial fibroblasts by prostaglandin E and interleukin-1: a potential mechanism for inflammatory angiogenesis. FEBS Letters 1995;372:83-7.
Benezra et al., In vivo angiogenic activity of interleukins. Archives of Opthamology 1990;108:573.
Berkovits et al., "The Role of the Double Bromodomain-Containing BET Genes During Mammalian Spermatogenesis," Current Topics in Developmental Biology, 102: 293-326 (2013).
Berkovits et al., The first bromodomain of the testis-specific double bromodomain protein Brdt is required for chromocenter organization that is modulated by genetic background. Dev Biol. Dec. 15, 2011;360(2):358-68. doi: 10.1016/j.ydbio.2011.10.005. Epub Oct. 12, 2011.
Blakely et al., NF-kappaB-activating complex engaged in response to EGFR oncogene inhibition drives tumor cell survival and residual disease in lung cancer. Cell Reports 2015;11:98-110.

(56) References Cited

OTHER PUBLICATIONS

Blazek et al., The Cyclin K/Cdk12 complex maintains genomic stability via regulation of expression of DNA damage response genes. Genes Dev. Oct. 15, 2011;25(20):2158-72. doi: 10.1101/gad.16962311.
Blazek et al., The cyclin K/Cdk12 complex: an emerging new player in the maintenance of genome stability. Cell Cycle. Mar. 15, 2012;11(6):1049-50. doi: 10.4161/cc.11.6.19678. Epub Mar. 15, 2012.
Bloom et al., The requirement for Phr1 in CNS axon tract formation reveals the corticostriatal boundary as a choice point for cortical axons. Genes Dev. Oct. 15, 2007;21(20):2593-606. Epub Sep. 27, 2007.
Bosken et al., The structure and substrate specificity of human Cdk12/Cyclin K. Nat Commun. Mar. 24, 2014;5:3505. doi: 10.1038/ncomms4505.
Brower et al., Tumor Angiogenesis: New drugs on the block. Nature Biotechnology 1999;17:963-8.
Brunton et al., eds., Chemotherapy of Neoplastic Diseases. In Goodman & Gilman's The Pharmacological Basis of Therapeutics. 2008; 11th edition:853-908.
Buchdunger et al., Selective inhibition of the platelet-derived growth factor signal transduction pathway by a protein-tyrosine kinase inhibitor of the 2-phenylaminopyrimidine class. Proc Natl Acad Sci U S A. Mar. 28, 1995;92(7):2558-62.
Buchdunger et al.,"Inhibition of the Ab1 Protein-Tyrosine Kinase In Vitro and In Vivo by a 2-Phenylaminopyrimidine Derivative," Cancer Res, 56:100-104 (1996).
Bullock et al., Structural basis of inhibitor specificity of the human protooncogene proviral insertion site in moloney murine leukemia virus (PIM-1) kinase. J Med Chem. Dec. 1, 2005;48(24):7604-14.
Cai et al., Discovery of orally active pyrrolopyridine- and aminopyridine-based Met kinase inhibitors. Bioorg Med Chem Lett. Jun. 1, 2008;18(11):3224-9. doi: 10.1016/j.bmcl.2008.04.047. Epub Apr. 25, 2008.
Cappuzzo et al., Increased MET gene copy number negatively affects survival of surgically resected non-small-cell lung cancer patients. J Clin Oncol. Apr. 1, 2009;27(10):1667-74. doi: 10.1200/JCO.2008.19.1635. Epub Mar. 2, 2009.
Carvajal et al., KIT as a therapeutic target in metastatic melanoma. JAMA. Jun. 8, 2011;305(22):2327-34. doi: 10.1001/jama.2011.746.
Castillo et al., suzuki reaction on pyridinium N-haloheteroarylaminides: regioselective synthesis of 3,5-disubstituted 2-aminopyrazines. Available Online Nov. 22, 2007; 2008; 64(7);1351-1370.
Cellai et al., Mechanistic Insight Into WEB-2170-induced Apoptosis in Human Acute Myelogenous Leukemia Cells: the Crucial Role of PTEN, Exp Hematol, 37(10):1176-1185 (2009).
Cellai et al., Specific PAF Antagonist WEB-2086 Induces Terminal Differentiation of Murine and Human Leukemia Cells. FASEB, 2002;16:733-735.
Chaidos et al., Potent antimyeloma activity of the novel bromodomain inhibitors I-BET151 and I-BET762. Blood. Jan. 30, 2014;123(5):697-705. doi: 10.1182/blood-2013-01-478420. Epub Dec. 13, 2013.
Chakraborty et al., Developmental expression of the cyclo-oxygenase-1 and cyclo-oxygenase-2 genes in the peri-implantation mouse uterus and their differential regulation by the blastocyst and ovarian steroids. Journal of Molecular Endocrinology 1996;16:107-122.
Chell et al., Tumour cell responses to new fibroblast growth factor receptor tyrosine kinase inhibitors and identification of a gatekeeper mutation in FGFR3 as a mechanism of acquired resistance. Oncogene 2013;32:3059-3070.
Chen et al., Antiapoptotic and trophic effects of dominant-negative forms of dual leucine zipper kinase in dopamine neurons of the substantia nigra in vivo. J Neurosci. Jan. 16, 2008;28(3):672-80. doi: 10.1523/JNEUROSCI.2132-07.2008.
Chen et al., CCL18 from tumor-associated macrophages promotes breast cancer metastasis via PITPNM3. Cancer Cell 2011;19:541-555.
Chen et al., Cdk12 and Cdk13 regulate axonal elongation through a common signaling pathway that modulates Cdk5 expression. Exp Neurol. Nov. 2014;261:10-21. doi: 10.1016/j.expneurol.2014.06.024. Epub Jul. 3, 2014.
Cheng et al., Adjudin disrupts spermatogenesis via the action of some unlikely partners: Eps8, Arp2/3 complex, drebrin E, PAR6 and 14-3-3. Spermatogenesis. Oct. 2011;1(4):291-297. Epub Oct. 1, 2011.
Chiarugi et al., Cox-2, iNOS and p53 as play-makers of tumor angiogenesis. International Journal of Molecular Medicine 1998;2:715-9.
Chipumuro et al., CDK7 inhibition suppresses super-enhancer-linked oncogenic transcription in MYCN-driven cancer. Cell 2014;159:1126-1139. doi:10.1016/j.cell.2014.10.024.
Cho et al., An unnatural biopolymer. Science. Sep. 3, 1993;261(5126):1303-5.
Choi et al., Brain Penetrant LRRK2 Inhibitor. ACS Med Chem Lett. Aug. 9, 2012;3(8):658-662.
Choi et al., Development of 'DFG-out' inhibitors of gatekeeper mutant kinases. Bioorg Med Chem Lett. Aug. 15, 2012;22(16):5297-302. doi: 10.1016/j.bmcl.2012.06.036. Epub Jun. 23, 2012.
Choi et al., Discovery and structural analysis of Eph receptor tyrosine kinase inhibitors. Bioorg Med Chem Lett. Aug. 1, 2009;19(15):4467-70. doi: 10.1016/j.bmcl.2009.05.029. Epub May 13, 2009. Supplementary Materials.
Chong et al., Positive and negative regulation of Raf kinase activity and function by phosphorylation EMBO J. Jul. 16, 2001;20(14):3716-27.
Christensen et al., Cytoreductive antitumor activity of PF-2341066, a novel inhibitor of anaplastic lymphoma kinase and c-Met, in experimental models of anaplastic large-cell lymphoma. Mol Cancer Ther. Dec. 2007;6(12 Pt 1):3314-22.
Christensen et al., Targeting transcriptional addictions in small cell lung cancer with a covalent CDK7 inhibitor. Cancer Cell. Dec. 8, 2014;26(6):909-22.
Christian et al., Flavopiridol in chronic lymphocytic leukemia: a concise review. Clin Lymphoma Myeloma. 2009;9 Suppl 3:S179-85. doi: 10.3816/CLM.2009.s.009.
Cole, Chemical probes for histone-modifying enzymes. Nat Chem Biol 2008;4:590-597.
Congiu et al., Synthesis and biological evaluation of novel acylhydrazone derivatives as potential antitumor agents. Bioorganic & Medicinal Chemistry Aug. 22, 2013;21(21):6592-9. DOI: 10.1016/j.bmc.2013.08.026.
Crawford et al., Bromodomain 4 activation predicts breast cancer survival. Proc Natl Acad Sci, 2008;105:6380-6385.
Creyghton et al., Histone H3K27Ac separates active from poised enhancers and predicts developmental state. Proceedings of the National Academy of Sciences of the United States of America 2010;107:21931-21936. doi:10.1073/pnas.1016071107.
Crystal et al., Patient-derived models of acquired resistance can identify effective drug combinations for cancer. Science 2014;346:1480-1486. doi:10.1126/science.1254721.
Davies et al., Mutations of the BRAF gene in human cancer Nature. Jun. 27, 2002;417(6892):949-54. Epub Jun. 9, 2002.
Davis et al., Comprehensive analysis of kinase inhibitor selectivity. Nat Biotechnol. Oct. 30, 2011;29(11):1046-51. doi: 10.1038/nbt.1990.
Dawson et al., Inhibition of BET recruitment to chromatin as an effective treatment for MLL-fusion leukaemia. Nature. Oct. 2, 2011;478(7370):529-33. doi: 10.1038/nature10509.
Delbroek et al., Development of an enzyme-linked immunosorbent assay for detection of cellular and in vivo LRRK2 S935 phosphorylation. J Pharm Biomed Anal. Mar. 25, 2013;76:49-58.
Della Corte et al., SMO gene amplification and activation of the hedgehog pathway as novel mechanisms of resistance to anti-epidermal growth factor receptor drugs in human lung cancer. Clin Cancer Res. Oct. 15, 2015;21(20):4686-97. doi: 10.1158/1078-0432.CCR-14/3319. Epub Jun. 29, 2015.
Delmore et al., BET bromodomain inhibition as a therapeutic strategy to target c-Myc. Cell. Sep. 16, 2011;146(6):904-17. doi: 10.1016/j.cell.2011.08.017. Epub Sep. 1, 2011.

(56) References Cited

OTHER PUBLICATIONS

Deng et al., Characterization of a selective inhibitor of the Parkinson's disease kinase LRRK2. Nat Chem Biol. Apr. 2011;7(4):203-5.

Deng et al., Discovery of a benzo[e]pyrimido-[5,4-b][1,4]diazepin-6(11H)-one as a Potent and Selective Inhibitor of Big MAP Kinase 1. ACS Med Chem Lett. Mar. 10, 2011;2(3):195-200.

Deng et al., Structural determinants for ERK5 (MAPK7) and leucine rich repeat kinase 2 activities of benzo[e]pyrimido-[5,4-b]diazepine-6(11H)-ones. Eur J Med Chem. 2013;70:758-67.

Denis et al., An Emerging Role for Bromodomain-Containing Proteins in Chromatin Regulation and Transcriptional Control of Adipogenesis. FEBS Lett., 2010;584(15):3260-3268.

Desai et al., Effects of phosphorylation by CAK on cyclin binding by CDC2 and CDK2. Mol Cell Biol. Jan. 1995;15(1):345-50.

Dey et al., "Brd4 Marks Select Genes of Mitotic Chromatin and Directs Postmitotic Transcription," Molecular Biology of the Cell, 20:4899-4909 (2009).

Diaz-Flores et al., Intense vascular sprouting from rat femoral vein induced by prostaglandins E1 and E2. Anatomical Record 1994;238:68-76.

Downward, Targeting RAS signalling pathways in cancer therapy Nat Rev Cancer. Jan. 2003;3(1):11-22.

Drapkin et al., Human cyclin-dependent kinase-activating kinase exists in three distinct complexes. Proc Natl Acad Sci U S A. Jun. 25, 1996;93(13):6488-93.

Druker et al, "Effects of a selective inhibitor of the Abl Tyrosine kinase on the Growth of Bcr-Abl positive cells," Nat Med, 2:561-566 (1996).

Druker et al., "Efficacy and safety of a specific inhibitor of the BCR-ABL tyrosine kinase in chronic myeloid leukemia," N Engl J Med 344, 1031-1037 (2001).

Dupage et al., Conditional mouse lung cancer models using adenoviral or lentiviral delivery of Cre recombinase. Nature Protocols 2009;4:1064-1072.

Elkins et al., X-ray crystal structure of ERK5 (MAPK7) in complex with a specific inhibitor. J Med Chem. Jun. 13, 2013;56(11):4413-21.

Ember et al., Acetyl-lysine binding site of bromodomain-containing protein 4 (BRD4) interacts with diverse kinase inhibitors. ACS Chem Biol. May 16, 2014;9(5):1160-71. doi: 10.1021/cb500072z. Epub Mar. 13, 2014.

Ercan et al., Reactivation of ERK signaling causes resistance to EGFR kinase inhibitors. Cancer Discov. Oct. 2012;2(10):934-47.

Even et al., CDC2L5, a Cdk-like kinase with RS domain, interacts with the ASF/SF2-associated protein p32 and affects splicing in vivo. J Cell Biochem. Oct. 15, 2006;99(3):890-904.

Fan et al., Dual leucine zipper-bearing kinase (DLK) activates p46SAPK and p38mapk but not ERK2. J Biol Chem. Oct. 4, 1996;271(40):24788-93.

Fedorov et al., A Systematic Interaction Map of Validated Kinase Inhibitors with Ser/Thr kinases.Proc Natl Acad Sci., 2007;104(51):20523-20528.

Fernandes et al., JNK2 and JNK3 are major regulators of axonal injury-induced retinal ganglion cell death. Neurobiol Dis. May 2012;46(2):393-401. doi: 10.1016/j.nbd.2012.02.003. Epub Feb. 14, 2012.

Fernandez et al., Neovascularization produced by angiotensin I.Journal of Laboratory and Clinical Medicine 1985;105(2):141-5.

Filippakopoulos et al., Selective inhibition of BET bromodomains. Nature. Dec. 23, 2010;468(7327):1067-73.

Filippakopoulos et al., Targeting bromodomains: epigenetic readers of lysine acetylation. Nat Rev Drug Discov. May 2014;13(5):337-56. doi: 10.1038/nrd4286. Epub Apr. 22, 2014.

Finn et al., Dasatinib, an orally active small molecule inhibitor of both the src and abl kinases, selectively inhibits growth of basal-type/"triple-negative" breast cancer cell lines growing in vitro. Breast Cancer Res Treat. Nov. 2007;105(3):319-26. Epub Feb. 1, 2007.

Fisher et al., A novel cyclin associates with MO15/CDK7 to form the CDK-activating kinase. Cell 1994;78:713-724.

Fizazi, The role of Src in prostate cancer. Ann Oncol. Nov. 2007;18(11):1765-73. Epub Apr. 10, 2007.

Fraser et al., Dasatinib inhibits the secretion of TNF-alpha following TLR stimulation in vitro and in vivo. Exp Hematol. Dec. 2009;37(12):1435-44. doi: 10.1016/j.exphem.2009.09.007. Epub Sep. 26, 2009.

French et al., "BRD4 Bromodomain Gene Rearrangement in Aggressive Carcinoma with Translocation t(15;19)," A AT J Pathol, 159(6):1987-1992 (2001).

French et al., BRD4-NUT fusion oncogene: a novel mechanism in aggressive carcinoma. Cancer Res. Jan. 15, 2003;63(2):304-7.

French et al., BRD-NUT oncoproteins: a family of closely related nuclear proteins that block epithelial differentiation and maintain the growth of carcinoma cells. Oncogene. Apr. 3, 2008;27(15):2237-42. Epub Oct. 15, 2007.

French, Demystified Molecular pathology of NUT Midline Carcinomas. J Clin Pathol, 2010;63:492-496.

Fry et al., Specific inhibition of cyclin-dependent kinase 4/6 by PD 0332991 and associated antitumor activity in human tumor xenografts. Mol Cancer Ther. Nov. 2004;3(11):1427-38.

Gallenkamp et al., Bromodomains and their pharmacological inhibitors. ChemMedChem. Mar. 2014;9(3):438-64. doi: 10.1002/cmdc.201300434. Epub Feb. 4, 2014.

Garnett et al., Guilty as charged: B-RAF is a human oncogene Cancer Cell. Oct. 2004;6(4):313-9.

Glover-Cutter et al., TFIIH-associated Cdk7 kinase functions in phosphorylation of C-terminal domain Ser7 residues, promoter-proximal pausing, and termination by RNA polymerase II. Mol Cell Biol. Oct. 2009;29(20):5455-64. doi: 10.1128/MCB.00637-09. Epub Aug. 10, 2009.

Gojo et al., The cyclin-dependent kinase inhibitor flavopiridol induces apoptosis in multiple myeloma cells through transcriptional repression and down-regulation of Mcl-1. Clin Cancer Res. Nov. 2002;8(11):3527-38.

Greenwald et al., "E.u-BRD2 Transgenic Mice Develop B-Cell Lymphoma and Leukemia," Blood, 103(4):1475-1484 (2004).

Gu et al., Effect of novel CAAX peptidomimetic farnesyltransferase inhibitor on angiogenesis in vitro and in vivo. European Journal of Cancer 1999;35(9):1394-1401.

Haack et al., Diagnosis of NUT Midline Carcinoma Using a NUT-specific Monoclonal Antibody. A AT J Surg Pathol, 2009;33:984-991.

Harada et al., Expression and regulation of vascular endothelial growth factor in osteoblasts. Clinical Orthopedics 1995;313:76-80.

Hart et al., SB1518, a novel macrocyclic pyrimidine-based JAK2 inhibitor for the treatment of myeloid and lymphoid malignancies. Leukemia. Nov. 2011;25(11):1751-9. doi: 10.1038/leu.2011.148. Epub Jun. 21, 2011.

He et al., The histone methyltransferase Ezh2 is a crucial epigenetic regulator of allogeneic T-cell responses mediating graft-versus-host disease. Blood. Dec. 12, 2013;122(25):4119-28. Doi: 10.1182/blood-2013-05-505180. Epub Oct. 18, 2013.

Hirai et al., The c-Jun N-terminal kinase activator dual leucine zipper kinase regulates axon growth and neuronal migration in the developing cerebral cortex. J Neurosci. Nov. 15, 2006;26(46):11992-2002.

Hla et al., Human cyclooxygenase-2 cDNA. Proceedings of the National Academy of Sciences 1992;89(16):7384-8.

Hnisz et al., Convergence of Developmental and Oncogenic Signaling Pathways at Transcriptional Super-Enhancers. Molecular Cell 2015;58(2):362-370.

Hnisz et al., Super-enhancers in the control of cell identity and disease. Cell 2013;155(4): 934-947.

Holohan et al., Cancer drug resistance: an evolving paradigm. Nature Reviews: Cancer 2013;13:714-726.

Housman et al., Drug resistance in cancer: an overview. Cancers 2014;6:1769-1792.

Houzelstein et al., Growth and early postimplantation defects in mice deficient for the bromodomain-containing protein Brd4. Mol Cell Biol. Jun. 2002;22(11):3794-802.

(56) References Cited

OTHER PUBLICATIONS

Hu et al., Adjudin targeting rabbit germ cell adhesion as a male contraceptive: a pharmacokinetics study. J Androl. Jan.-Feb. 2009;30(1):87-93. doi: 10.2164/jandrol.108.004994. Epub Sep. 18, 2008.
Huang et al., "Brd4 Coactivates Transcriptional Activation of NF-κB via Specific Binding to Acetylated RelA," Mol Cell Biol, 2009;29(5):1375-1387.
Hur et al., Clinical stage EGFR inhibitors irreversibly alkylate Bmx kinase. Bioorg Med Chem Lett. Nov. 15, 2008;18(22):5916-9. doi: 10.1016/j.bmcl.2008.07.062. Epub Jul. 18, 2008.
Iorns et al., CRK7 modifies the MAPK pathway and influences the response to endocrine therapy. Carcinogenesis. Oct. 2009;30(10):1696-701. doi: 10.1093/carcin/bgp187. Epub Aug. 3, 2009.
Itoh et al., Impaired regenerative response of primary sensory neurons in ZPK/DLK gene-trap mice. Biochem Biophys Res Commun. May 29, 2009;383(2):258-62. doi: 10.1016/j.bbrc.2009.04.009. Epub Apr. 7, 2009.
Janne et al., Factors underlying sensitivity of cancers to small-molecule kinase inhibitors. Nat Rev Drug Discov. Sep. 2009;8(9):709-23. doi: 10.1038/nrd2871. Epub Jul. 24, 2009.
Joh et al., Ginsenoside Rb1 and its metabolite compound K inhibit IRAK-1 activation—the key step of inflammation. Biochem Pharmacol. Aug. 1, 2011;82(3):278-86. doi: 10.1016/j.bcp.2011.05.003. Epub May 12, 2011.
Johannessen et al., A melanocyte lineage program confers resistance to MAP kinase pathway inhibition. Nature 2013;504:138-142.
Joshi et al., Ovarian cancer-associated mutations disable catalytic activity of CDK12, a kinase that promotes homologous recombination repair and resistance to cisplatin and poly(ADP-ribose) polymerase inhibitors. J Biol Chem. Mar. 28, 2014;289(13):9247-53. doi: 10.1074/jbc.M114.551143. Epub Feb. 19, 2014.
Jouve et al., Oxidative cyclization of n-methyl- and n-benzoylpyridylthioureas. Preparation of new thiazolo[4,5-b] and [5,4-b]pyridine derivatives. J Heterocyclic Chemistry. 2003;40(2):261-68.
Kadota et al., Identification of Novel Gene Amplifications in Breast Cancer and Coexistence of Gene Amplification With an Activating Mutation of PIK3CA. Cancer Res, 2009;69:7357-7365.
Kaldis et al., Analysis of CAK activities from human cells. Eur J Biochem. Jul. 2000;267(13):4213-21.
Kanakaraj et al., Interleukin (IL)-1 receptor-associated kinase (IRAK) requirement for optimal induction of multiple IL-1 signaling pathways and IL-6 production. J Exp Med. Jun. 15, 1998;187(12):2073-9.
Kantarjian et al., Dasatinib versus imatinib in newly diagnosed chronic-phase chronic myeloid leukemia. N Engl J Med. Jun. 17, 2010;362(24):2260-70.
Kauraniemi et al., New amplified and highly expressed genes discovered in the ERBB2 amplicon in breast cancer by cDNA microarrays. Cancer Res. Nov. 15, 2001;61(22):8235-40.
Kavanagh et al., The development of CNS-active LRRK2 inhibitors using property-directed optimisation.Bioorg Med Chem Lett. Jul. 1, 2013;23(13):3690-6.
Kelso et al., Cyclin-dependent kinase 7 controls mRNA synthesis by affecting stability of preinitiation complexes, leading to altered gene expression, cell cycle progression, and survival of tumor cells. Molecular and Cellular Biology 2014;34:3675-3688.
Kim et al., "Berberine Improves Lipid Dysregulation in Obesity by Controlling Central and Peripheral AMPK Activity," AAT. J. Physiol. Endocrinol. Metab., 2009;296:E812-E819.
Kim et al., Discovery of pyrrolopyridine-pyridone based inhibitors of Met kinase: synthesis, X-ray crystallographic analysis, and biological activities. J Med Chem. Sep. 11, 2008;51(17):5330-41. doi: 10.1021/jm800476q. Epub Aug. 9, 2008.
Kim et al., Inhibition of vascular endothelial growth factor-induced angiogenesis suppresses tumour growth in vivo. Nature 1993;362:841.

King et al., Demonstration of a genetic therapeutic index for tumors expressing oncogenic BRAF by the kinase inhibitor SB-590885. Cancer Res. Dec. 1, 2006;66(23):11100-5.
Knapp et al., Selective Targeting of Protein Interactions. Mediated by Epigenetic Effector Domains. SGC Sep. 5, 2013;1-35.
Ko et al., CrkRS: a novel conserved Cdc2-related protein kinase that colocalises with SC35 speckles. J Cell Sci. Jul. 2001;114(Pt 14):2591-603.
Koivunen et al., EML4-ALK fusion gene and efficacy of an ALK kinase inhibitor in lung cancer. Clin Cancer Res. Jul. 1, 2008;14(13):4275-83. doi: 10.1158/1078-0432.CCR-08-0168.
Konig et al., The novel cyclin-dependent kinase inhibitor flavopiridol downregulates Bcl-2 and induces growth arrest and apoptosis in chronic B-cell leukemia lines. Blood. Dec. 1, 1997;90(11):4307-12.
Konze et al., An orally bioavailable chemical probe of the Lysine Methyltransferases EZH2 and EZH1. ACS Chem Biol. 2013;8(6):1324-34. Doi: 10.1021/cb400133j. Epub Apr. 24, 2013.
Krueger et al., The mechanism of release of P-TEFb and HEXIM1 from the 7SK snRNP by viral and cellular activators includes a conformational change in 7SK. PLoS One. Aug. 23, 2010;5(8):e12335. doi: 10.1371/journal.pone.0012335.
Kwiatkowski et al., Targeting transcription regulation in cancer with a covalent CDK7 inhibitor. Nature. Jul. 31, 2014;511(7511):616-20.
Kwong et al., Targeted therapy for melanoma: rational combinatorial approaches. Oncogene. Jan. 2, 2014;33(1):1-9. doi: 10.1038/onc.2013.34. Epub Feb. 18, 2013.
Larochelle et al., Cyclin-dependent kinase control of the initiation-to-elongation switch of RNA polymerase II. Nature Structural & Molecular Biology 2012;19:1108-1115.
Larochelle et al., Requirements for Cdk7 in the assembly of Cdk1/cyclin B and activation of Cdk2 revealed by chemical genetics in human cells. Mol Cell. Mar. 23, 2007;25(6):839-50.
Lavis et al., Bright ideas for chemical biology. ACS Chem Biol. Mar. 20, 2008;3(3):142-55. doi: 10.1021/cb700248m.
Lawless et al., Histone Deacetylase Inhibitors Target Diabetes Via Chromatin Remodeling or as Chemical Chaperones? Curr Diabetes Rev, 5(3):201-209 (2009).
Le Coutre et al., In vivo eradication of human BCR/ABL-positive leukemia cells with an ABL kinase inhibitor. J Natl Cancer Inst, 91:163-168 (1999).
Lee et al., Berberine, a Natural Plant Product, Activates AMP-Activated Protein Kinase with Beneficial Metabolic Effects in Diabetic and Insulin-Resistant States. Diabetes 2006;55:2256-2264.
Lee et al., BRAF mutations in non-Hodgkin's lymphoma. Br J Cancer. Nov. 17, 2003;89(10):1958-60.
Lee et al., Drug resistance via feedback activation of Stat3 in oncogene addicted cancer cells. Cancer Cell 2014;26:207-221.
Lin et al., Phase II study of flavopiridol in relapsed chronic lymphocytic leukemia demonstrating high response rates in genetically high-risk disease. J Clin Oncol. Dec. 10, 2009;27(35):6012-8.
Lin et al., Transcriptional amplification in tumor cells with elevated c-Myc. Cell 2012;151:56-67.
Liu et al., Discovery and optimization of potent and selective benzonaphthyridinone analogs as small molecule mTOR inhibitors with improved mouse microsome stability. Bioorg Med Chem Lett. Jul. 1, 2011;21(13):4036-40. doi: 10.1016/j.bmcl.2011.04.129. Epub May 7, 2011.
Liu et al., Discovery of 1-(4-(4-propionylpiperazin-1-yl)-3-(trifluoromethyl)phenyl)-9-(quinolin-3-yl)benzo[h][1,6]naphthyridin-2(1H)-one as a highly potent, selective mammalian target of rapamycin (mTOR) inhibitor for the treatment of cancer. J Med Chem. Oct. 14, 2010;53(19):7146-55. doi: 10.1021/jm101144f.
Liu et al., Salt-inducible kinase is involved in the regulation of corticotropin-releasing hormone transcription in hypothalamic neurons in rats. Endocrinology. Jan. 2012;153(1):223-33. doi: 10.1210/en.2011-1404. Epub Nov. 22, 2011.
Liu et al., Two cyclin-dependent kinases promote RNA polymerase II transcription and formation of the scaffold complex. Mol Cell Biol. Feb. 2004;24(4):1721-35.
Llambi et al., Apoptosis and oncogenesis: give and take in the BCL-2 family. Curr Opin Genet Dev. Feb. 2011;21(1):12-20. doi: 10.1016/j.gde.2010.12.001. Epub Jan. 13, 2011.

(56) References Cited

OTHER PUBLICATIONS

Lorenzo et al., Expression of proto-oncogene c-kit in high risk prostate cancer. Eur J Surg Oncol. Nov. 2004;30(9):987-92.
Lotti et al., Ultrasound of the male genital tract in relation to male reproductive health. Hum Reprod Update. Jan.-Feb. 2015;21(1):56-83. doi: 10.1093/humupd/dmu042. Epub Jul. 19, 2014.
Lyne et al., Identification of amidoheteroaryls as potent inhibitors of mutant (V600E) B-Raf kinase with in vivo activity. Bioorg Med Chem Lett. Feb. 1, 2009;19(3):1026-9. doi: 10.1016/j.bmcl.2008.10.053. Epub Oct. 15, 2008.
Majima et al., Significant Roles of Inducible Cyclooxygenase (COX)-2 in Angiogenesis in Rat Sponge Implants. Japanese Journal of Pharmacology 1997;75;105-14.
Mallinson et al., Macrocycles in new drug discovery. Future Med Chem. Jul. 2012;4(11):1409-38. doi: 10.4155/fmc.12.93.
Mansour et al., Oncogene regulation. An oncogenic super-enhancer formed through somatic mutation of a noncoding intergenic element. Science 2014;346:1373-1377.
Marelli et al., Tumor targeting via integrin ligands. Front. Oncol., Aug. 30, 2013. https://doi.org/10.3389/fonc.2013.00222.
Marques et al., A new subfamily of high molecular mass CDC2-related kinases with PITAI/VRE motifs. Biochem Biophys Res Commun. Dec. 29, 2000;279(3):832-7.
Marushige, Activation of Chromatin by Acetylation of Histone Side Chains. Proc. Nat. Acad. Sci., 1976;73(11):3937-3941.
Matsuyama et al., Activation of Discoidin Domain Receptor 1 Isoform b with Collagen Up-Regulates Chemokine Production in Human Macrophages: Role of p38 Mitogen-Activated Protein Kinase and NF-κB. J Immunol Feb. 15, 2004, 172 (4) 2332-2340; DOI: https://doi.org/10.4049/jimmunol.172.4.2332.
Matzuk, Small-Molecule Inhibition of BRDT for Male Contraception. Cell 2012;150:673-684.
Mckeown et al., Biased multicomponent reactions to develop novel bromodomain inhibitors. J Med Chem. Nov. 13, 2014;57(21):9019-27. doi: 10.1021/jm501120z. Epub Oct. 31, 2014.
Meguro et al., Heterocycles. VI. Synthesis of 4H-s-Triazolo[4,3-a][1,4]benzodiazepines, Novel Tricyclic Psychosedatives. Chem. Pharm. Bull. 1973;21(11):2382-2390.
Meng-Er et al., Use of All-Trans Retinoic Acid in the Treatment of Acute Promyelocytic Leukemia. Blood, 1988;72(2):567-572.
Mochizuki et al., The Bromodomain Protein Brd4 Stimulates G1 Gene Transcription and Promotes Progression to S Phase. J Biol Chem, 2008;283(14):9040-9048.
Mukaiyama et al., The unexpected and the unpredictable in organic synthesis. Tetrahedron Jul. 1999;55(29):8609-70.
Neklesa et al., Small-molecule hydrophobic tagging-induced degradation of HaloTag fusion proteins. Nat Chem Biol. Jul. 3, 2011;7(8):538-43. doi: 10.1038/nchembio.597.
Nicodeme et al., Suppression of inflammation by a synthetic histone mimic. Nature. Dec. 23, 2010;468(7327):1119-23.
Nishimura et al., Fertility and Reproduction Studies of Apafant (WEB 2086 BS) in Rats Dosed Orally. Oyo Yakuri/Pharmacometrics. Oct. 1, 1996. 52(3/4):185-200.
Obenauf et al., Therapy-induced tumour secretomes promote resistance and tumour progression. Nature. Apr. 16, 2015;520(7547):368-72. doi: 10.1038/nature14336. Epub Mar. 25, 2015.
Odingo et al., Synthesis and evaluation of the 2,4-diaminoquinazoline series as anti-tubercular agents. Bioorg Med Chem. Dec. 15, 2014;22(24):6965-79. doi: 10.1016/j.bmc.2014.10.007. Epub Oct. 22, 2014.
Ou et al., Activity of crizotinib (PF02341066), a dual mesenchymal-epithelial transition (MET) and anaplastic lymphoma kinase (ALK) inhibitor, in a non-small cell lung cancer patient with de novo MET amplification. J Thorac Oncol. May 2011;6(5):942-6. doi: 10.1097/JTO.0b013e31821528d3.
Owen et al., "The Structural Basis for the Recognition of Acetylated Histone R4 by the Bromodomain of Histone Acetyltransferase Gcn5p," The EMBO Journal, 19(22):6141-6149 (2000).
Patani et al., "Bioisosterism: A Rational Approach in Drug Design," Chem. Rev., 1996;96:3147-3176.

Pettazzoni et al., Genetic events that limit the efficacy of MEK and RTK inhibitor therapies in a mouse model of KRAS-driven pancreatic cancer. Cancer research 2015;75:1091-1101.
Phelps et al., "Clinical Response and Pharmacokinetics :from a Phase 1 Study of an Active Dosing Schedule ofFlavopiridol in Relapsed Chronic Lymphocytic Leukemia," Blood, 113(12):2637-2645 (2009).
Powers et al., Discovery and initial SAR of inhibitors of interleukin-1 receptor-associated kinase-4. Bioorg Med Chem Lett. Jun. 1, 2006;16(11):2842-5. Epub Mar. 24, 2006.
Presiler et al., Assessment of c-myc Expression in Individual Leukemic Cells. Leuk Res, 1988;12(6):507-516.
Ptashne, Binding Reactions: Epigenetic Switches, Signal Transduction and Cancer. Current Biology 2009;19(6):R234-R241.
Quinn et al., A homogeneous method for investigation of methylation-dependent protein-protein interactions in epigenetics. Nucleic Acids Res. Jan. 2010;38(2):e11. doi: 10.1093/nar/gkp899.
Rahl et al., "c-Myc Regulates Transcriptional Pause Release," Cell, 141 :432-445 (2010).
Ramos et al., Mechanism-based cancer therapy: resistance to therapy, therapy for resistance. Oncogene 2014;34:3617-3626.
Ramsdale et al., The transcription cofactor c-JUN mediates phenotype switching and BRAF inhibitor resistance in melanoma. Sci Signal. Aug. 18, 2015;8(390):ra82. doi: 10.1126/scisignal.aab1111.
Roberts et al., A Bead-Based Proximity Assay for BRD4 Ligand Discovery. Curr Protoc Chem Biol. Dec. 2, 2015;7(4):263-78. doi: 10.1002/9780470559277.ch150024.
Roberts et al., Antiangiogenic and antitumor activity of a selective PDGFR tyrosine kinase inhibitor, CP-673,451. Cancer Res. Feb. 1, 2005;65(3):957-66.
Robinson et al., Discovery of the hemifumarate and (alpha-L-alanyloxy)methyl ether as prod rugs of an anti rheumatic oxindole: prod rugs for the enolic OH group. J. Med. Chem. 1996;39:10-8.
Rubin et al., KIT activation is a ubiquitous feature of gastrointestinal stromal tumors. Cancer Res. Nov. 15, 2001;61(22):8118-21.
Santillan et al., Bromodomain and Histone Acetyltransferase Domain Specificities Control Mixed Lineage Leukemia Phenotype. Cancer Res 2006;66(20):10032-10039.
Schachter et al., A Cdk7-Cdk4 T-loop phosphorylation cascade promotes G1 progression. Molecular Cell 2013;50:250-260.
Schindler et al., Structural mechanism for STI-571 Inhibition of Abelson Tyrosine kinase. Science 2000;289:1938-1942.
Schreiber et al., Signaling Network Model of Chromatin. Cell 2002;111:771-778.
Schroder et al., Two-pronged binding with bromodomain-containing protein 4 liberates positive transcription elongation factor b from inactive ribonucleoprotein complexes. J Biol Chem. Jan. 6, 2012;287(2):1090-9. doi: 10.1074/jbc.M111.282855. Epub Nov. 14, 2011.
Schroeder et al., Discovery of N-(4-(2-amino-3-chloropyridin-4-yloxy)-3-fluorophenyl)-4-ethoxy-1-(4-fluorophenyl)-2-oxo-1,2-dihydropyridine-3-carboxamide (BMS-777607), a selective and orally efficacious inhibitor of the Met kinase superfamily. J Med Chem. Mar. 12, 2009;52(5):1251-4. doi: 10.1021/jm801586s.
Seed et al., The Inhibition of colon-26 Adenocarcinoma Development and Angiogenesis by Topical Diclofenac in 2.5% Hyaluronan. Cancer Research 1997;57:1625-9.
Sengupta et al., DLK induces developmental neuronal degeneration via selective regulation of proapoptotic JNK activity. Journal of Cell Biology 2011;194(5):751-764. DOI https://doi.org/10.1083/jcb.201103153.
Serizawa et al., Association of Cdk-activating kinase subunits with transcription factor TFIIH. Nature. Mar. 16, 1995;374(6519):280-2.
Seyrig et al., Effects of a Chronic Administration of Two Benzodiazepines on Food Intake in Rats Given a Highly Palatable Diet. Pharmacology Biochemistly & Behavior 1986;25:913-918.
Shang et al., The First Bromodomain of Brdt, a Testis-Specific Member of the BET Sub-Family of Double-Bromodomain-Containing Proteins, is Essential for Male Germ Cell Differentiation. Development, 2007;134:3507-3515.
Sharma et al., A chromatin-mediated reversible drug-tolerant state in cancer cell subpopulations. Cell. Apr. 2, 2010;141(1):69-80.

(56) References Cited

OTHER PUBLICATIONS

Shiekhattar et al., Cdk-activating kinase complex is a component of human transcription factor TFIIH. Nature. Mar. 16,1995;374(6519):283-7.

Shin et al., Dual leucine zipper kinase is required for retrograde injury signaling and axonal regeneration. Neuron. Jun. 21, 2012;74(6):1015-22. doi: 10.1016/j.neuron.2012.04.028.

Singh et al., EMT, cancer stem cells and drug resistance: an emerging axis of evil in the war on cancer. Oncogene 2010;29:4741-4751.

Smith et al., Recent advances in the research and development of RAF kinase inhibitors. Curr. Top Med. Chem. 2006; 6(11):1071-89.

Smith et al., The Bromodomain: A New Target in Emerging Epigenetic Medicine. ACS Chem Biol. Mar. 18, 2016;11(3):598-608. doi: 10.1021/acschembio.5b00831. Epub Dec. 3, 2015.

Smith et al., The effect of the nature of the amine leaving group on the nature of the E2 transition state for the reaction of 1-phenylethylammonium ions sodium ethoxide in ethanol. Can J Chem. Mar. 28, 1989;67:1457-67.

Srivastava et al., Augmentation of therapeutic responses in melanoma by inhibition of IRAK-1,-4. Cancer Res. Dec. 1, 2012;72(23):6209-16. doi: 10.1158/0008-5472.CAN-12-0337. Epub Oct. 4, 2012.

Stuhlmiller et al., Inhibition of Lapatinib-Induced Kinome Reprogramming in ERBB2-Positive Breast Cancer by Targeting BET Family Bromodomains. Cell Rep. Apr. 21, 2015;11(3):390-404.

Takemori et al., Inactivation of HDAC5 by SIK1 in AICAR-treated C2C12 myoblasts. Endocr J. 2009;56(1):121-30. Epub Oct. 22, 2008.

Tanaka et al., Inhibitors of emerging epigenetic targets for cancer therapy: a patent review (2010-2014). Pharm Pat Anal. 2015;4(4):261-84. doi: 10.4155/ppa.15.16.

Taskinen et al., "A High Tumor-Associated Macrophage Content Predicts Favorable Outcome in Follicular Lymphoma Patients Treated with Rituximab and Cyclophosphamide-Doxorubicin-Vincristine-Prednisone," Clin Cancer Res, 13(19): 5784-5785 (2007).

Terai et al., Activation of the FGF2-FGFR1 autocrine pathway: a novel mechanism of acquired resistance to gefitinib in NSCLC. Mol Cancer Res. Jul. 2013;11(7):759-67.

Tsai et al., Discovery of a selective inhibitor of oncogenic B-Raf kinase with potent antimelanoma activity. Proc Natl Acad Sci U S A. Feb. 26, 2008;105(8):3041-6. doi: 10.1073/pnas.0711741105. Epub Feb. 19, 2008.

Tsujii et al., Cyclooxygenase regulates angiogenesis induced by colon cancer cells. Cell. May 29, 1998;93(5):705-16.

Verma et al., Identification of Potent, Selective, Cell-Active Inhibitors of the Histone Lysine Methyltransferase EZH2. ACS Med Chem Lett. Oct. 19, 2012;3(12):1091-6. Doi: 10.1021/ml3003346. eCollection 2012.

Vollmuth et al., Structures of the dual bromodomains of the P-TEFb-activating protein Brd4 at atomic resolution. J Biol Chem, 2009;284:36547-36556.

Von Voigtlander et al., "Alprazolam: Review of Pharmacological, Pharmacokinetic and Clinical Data," Drug Development Research, 6:1-12 (1985).

Wang et al., A seamless trespass: germ cell migration across the seminiferous epithelium during spermatogenesis. J Cell Biol. Aug. 13, 2007;178(4):549-56.

Wang et al., Brd2 Disruption in Mice Causes Severe Obesity Without Type 2 Diabetes. Biochem. J. 2010;425:71-83.

Wang et al., IRAK-4 inhibitors for inflammation. Curr Top Med Chem. 2009;9(8):724-37.

Wang et al., Ligand-associated ERBB2/3 activation confers acquired resistance to FGFR inhibition in FGFR3-dependent cancer cells. Oncogene. Apr. 23, 2015;34(17):2167-77. doi: 10.1038/onc.2014.161. Epub Jun. 9, 2014.

Wang et al., Mathematical modeling in cancer drug discovery. Drug Discov Today. Feb. 2014;19(2):145-50. doi: 10.1016/j.drudis.2013.06.015. Epub Jul. 4, 2013.

Wang et al., Pharmacophore and structure-activity relationships of integrase inhibition within a dual inhibitor scaffold of HIV reverse transcriptase and integrase. Bioorg Med Chem. Jun. 15, 2010;18(12):4202-11. doi: 10.1016/j.bmc.2010.05.004. Epub May 7, 2010.

Wehner et al., Effects of natalizumab, an alpha4 integrin inhibitor, on fertility in male and female guinea pigs. Birth Defects Res B Dev Reprod Toxicol. Apr. 2009;86(2):108-16. doi: 10.1002/bdrb.20191.

Wellbrock et al., The RAF proteins take centre stage Nat Rev Mol Cell Biol. Nov. 2004;5(11):875-85.

Whyte et al., Master transcription factors and mediator establish super enhancers at key cell identity genes. Cell 2013;153:307-319. doi:10.1016/j.cell.2013.03.035.

Wietek et al., IRAK-4: a new drug target in inflammation, sepsis, and autoimmunity. Mol Interv. Jul. 2002;2(4):212-5.

Wilson et al., A functional landscape of resistance to ALK inhibition in lung cancer. Cancer Cell 2015;27:397-408.

Wilson et al., Widespread potential for growth-factor-driven resistance to anticancer kinase inhibitors. Nature 2012;487(7408):505-509.

Xin et al., Peroxisome proliferator-activated receptor gamma ligands are potent inhibitors of angiogenesis in vitro and in vivo. Journal of Biological Chemistry 1996;274(13):9116-21.

Yalpani, Cholesterol Lowering Drugs. Chemistry and Industry Feb. 1996;3:85-89.

Yamaguchi et al., Analysis of EGFR, KRAS and P53 mutations in lung cancer using cells in the curette lavage fluid obtained by bronchoscopy. Lung Cancer 2012;78:201-206.

Yang et al., Brd4 recruits P-TEFb to chromosomes at late mitosis to promote G1 gene expression and cell cycle progression. Mol Cell Biol 2008;28(3):967-976.

Yang et al., Multisite Protein Modification and Intramolecular Signaling. Oncogene, 2005;24:1653-1662.

Yang et al., Recruitment of P-TEFb for stimulation of transcriptional elongation by the bromodomain protein Brd4. Mol Cell. Aug. 19, 2005;19(4):535-45.

Yasuda et al., The stem cell factor/c-kit receptor pathway enhances proliferation and invasion of pancreatic cancer cells. Mol Cancer. Oct. 18, 2006;5:46.

You et al., Kaposi's sarcoma-associated herpesvirus latency-associated nuclear antigen interacts with bromodomain protein Brd4 on host mitotic chromosomes. J Virol 2006;80:8909-8919.

You et al., "Regulation of Aurora B Expression by the Bromodomain Protein Brd4," Mol Cell Biol, 2009;29:5094-5103.

Yun et al., The T790M mutation in EGFR kinase causes drug resistance by increasing the affinity for ATP. Proceedings of the National Academy of Sciences of the United States of America 2008;105:2070-2075.

Zambon et al., Small molecule inhibitors of BRAF in clinical trials. Bioorg Med Chem Lett. Jan. 15, 2012;22(2):789-92. doi: 10.1016/j.bmcl.2011.11.060. Epub Dec. 3, 2011.

Zang et al., Genetic and structural variation in the gastric cancer kinome revealed through targeted deep sequencing. Cancer Res. Jan. 1, 2011;71(1):29-39. doi: 10.1158/0008-5472.CAN-10-1749. Epub Nov. 19, 2010.

Zebisch et al., Back to the roots: the remarkable RAF oncogene story Cell Mol Life Sci. Jun. 2006;63(11):1314-30.

Zeng et al., Bromodomain: an acetyl-lysine binding domain. FEBS Lett. Feb. 20, 2002;513(1):124-8.

Zhang et al., Discovery of potent and selective covalent inhibitors of JNK. Chem Biol. Jan. 27, 2012;19(1):140-54. doi: 10.1016/j.chembiol.2011.11.010.

Zhang et al., Down-Regulation of NF-κB Transcriptional Activity in HIV-Associated Kidney Disease by BRD4 Inhibition. J. Biol Chem, 2012;287(34):28840-28851.

Zhang et al., Down-Regulation of NF-κB Transcriptional Activity in HIV-Associated Kidney Disease by BRD4 Inhibition. J. Biol Chem, 2012;287(46):38956.

Zhao et al., "Research Development on Fusion Protein Transcription Factor siRNA Specifically Targeting Leukemia," Sciencepaper• Online: 1-6 and J. J Med Res., 39(2):6-9 (Feb. 2010) (English-

(56) References Cited

OTHER PUBLICATIONS language translation entitled "Progiess of Research on siRNA that Targets Leukemia Specific Transcription Regulation Factor Fusion Proteins," pp. 1-10).
Zhou et al., Novel mutant-selective EGFR kinase inhibitors against EGFR T790M. Nature. Dec. 24, 2009;462(7276):1070-4.
Ziche et al., Role of prostaglandin E1 and copper in angiogenesis. Journal of the National Cancer Institute 1982;69(2):475.
Zuber et al., RNAi Screen Identifies Brd4 as a Therapeutic Target in Acute Myeloid Leukaemia. Nature 2011;478:524-528. With Supplementary Information.
Zuercher et al., Identification and structure-activity relationship of phenolic acyl hydrazones as selective agonists for the estrogen-related orphan nuclear receptors ERRbeta and ERRgamma.. J Med Chem. May 5, 2005;48(9):3107-9.
Extended European Search Report for EP 15773870.7, dated Oct. 17, 2018.
[No Author Listed] CAS Registry STN No. 1241725-90-5; Sep. 16, 2010.
[No Author Listed] STN Database Registry No. 1245644-45-4; Jun. 10, 2010.
[No Author Listed] STN Database Registry No. 1245645-74-2; Jun. 10, 2010.
[No Author Listed] STN Database Registry No. 1245645-85-5; Jun. 10, 2010.
Filippakopoulos et al., Selective inhibition of BET bromodomains. Nature. Dec. 23, 2010;468(7327):1067-73. doi: 10.1038/nature09504. Epub Sep. 24, 2010.
Hsu et al., Effects of flavonoids and phenolic acids on the inhibition of adipogenesis in 3T3-L1 adipocytes. J Agric Food Chem. Oct. 17, 2007;55(21):8404-10. Epub Sep. 20, 2007.
Illendula et al., Chemical biology. A small-molecule inhibitor of the aberrant transcription factor CBFβ-SMMHC delays leukemia in mice. Science. Feb. 13, 2015;347(6223):779-84. doi: 10.1126/science.aaa0314.
Kim et al., Substrate and functional diversity of lysine acetylation revealed by a proteomics survey. Mol Cell. Aug. 2006;23(4):607-18.
Picaud et al., RVX-208, an inhibitor of BET transcriptional regulators with selectivity for the second bromodomain. Proc Natl Acad Sci U S A. Dec. 3, 2013;110(49):19754-9. doi: 10.1073/pnas.1310658110. Epub Nov. 18, 2013.
Sterner et al., Acetylation of histones and transcription-related factors. Microbiol Mol Biol Rev. Jun. 2000;64(2):435-59.
Partial Supplementary Search Report for EP 16808476.2, dated Mar. 7, 2019.

Extended European Search Report for EP 16808476.2, dated Jun. 14, 2019.
Extended European Search Report for EP 16845194.6, dated Mar. 1, 2019.
Extended European Search Report for EP19168422.4, dated Aug. 13, 2019.
Bai et al., Design, synthesis and anticancer activity of 1-acyl-3-amino-1,4,5,6-tetrahydropyrrolo[3,4-c]pyrazole derivatives. Bioorg Med Chem Lett. Nov. 15, 2012;22(22):6947-51. Suppl. Info, 46 pages. doi: 10.1016/j.bmcl.2012.08.117. Epub Sep. 8, 2012.
Blachly et al., Emerging drug profile: cyclin-dependent kinase inhibitors. Leuk Lymphoma. Oct. 2013;54(10):2133-43. doi: 10.3109/10428194.2013.783911. Epub Jul. 29, 2013. Author manuscript.
Dent et al. Synergistic combinations of signaling pathway inhibitors: mechanisms for improved cancer therapy. Drug Resist Updat. Jun. 2009;12(3):65-73. doi: 10.1016/j.drup.2009.03.001.
Fancelli et al., Potent and selective Aurora inhibitors identified by the expansion of a novel scaffold for protein kinase inhibition. J Med Chem. Apr. 21, 2005;48(8):3080-4.
Fiskus et al., BET protein antagonist JQ1 is synergistically lethal with FLT3 tyrosine kinase inhibitor (TKI) and overcomes resistance to FLT3-TKI in AML cells expressing FLT-ITD. Mol Cancer Ther. Oct. 2014; 13(10): 2315-2327. Published online Jul. 22, 2014. doi: 10.1158/1535-7163.MCT-14-0258.
Fleming et al., Synergistic inhibition of ErbB signaling by combined treatment with seliciclib and ErbB-targeting agents. Clin Cancer Res. Jul. 1, 2008;14(13):4326-35. doi: 10.1158/1078-0432.CCR-07-4633.
Girotti et al., No longer an untreatable disease: How targeted and immunotherapies have changed the management of melanoma patients. Mol Oncol. Sep. 2014; 8(6): 1140-1158. Published online Aug. 15, 2014. doi: 10.1016/j.molonc.2014.07.027.
Ochiana et al., The human Aurora kinase inhibitor danusertib is a lead compound for anti-trypanosomal drug discovery via target repurposing. Eur J Med Chem. Apr. 2013;62:777-84. doi: 10.1016/j.ejmech.2012.07.038. Epub Jul. 31, 2012.
Orzaez et al., Intrinsic caspase-8 activation mediates sensitization of erlotinib-resistant tumor cells to erlotinib/cell-cycle inhibitors combination treatment. Cell Death Dis. Oct. 25, 2012;3:e415. doi: 10.1038/cddis.2012.155.
Pevarello et al., 3-Amino-1,4,5,6-tetrahydropyrrolo[3,4-c]pyrazoles: A new class of CDK2 inhibitors. Bioorg Med Chem Lett. Feb. 15, 2006;16(4):1084-90.
Vora et al., CDK 4/6 inhibitors sensitize PIK3CA Mutant Breast Cancer to PI3K inhibitors. Cancer Cell. Jul. 14, 2014;26(1):136-149. Published online Jul. 4, 2014. doi: 10.1016/j.ccr.2014.05.020.

\* cited by examiner

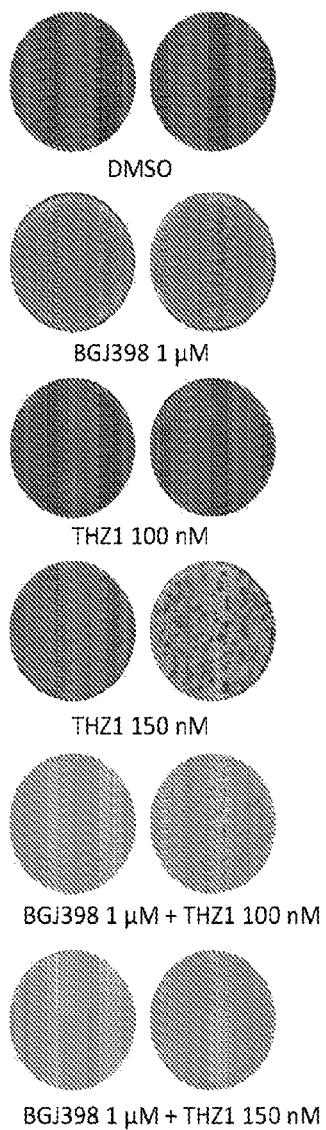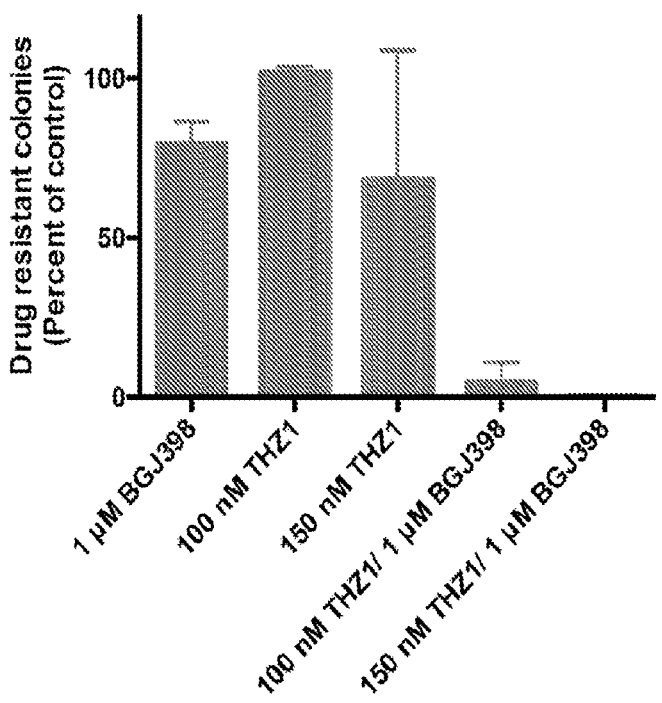
Figure 5A
Figure 5B

Note: GSK1120212 kept constant at 1 μM

A — GSK1120212 ($IC_{50}$ = 0.04 μM)

B — THZ1 ($IC_{50}$ = 0.24 μM)

C — THZ1 + GSK ($IC_{50}$ = 0.21 μM)
(normalized to GSK alone)

D — THZ1 + GSK ($IC_{50}$ = .057 pM)
(normalized to untreated)

HSC4

YD8

Detroit526

BHY

CDK7 + BEZ235 (PI3K/mTOR)
GSK1120212 (MEK)
TKIs (EGFR/FGFR)

Figure 25 (continued)

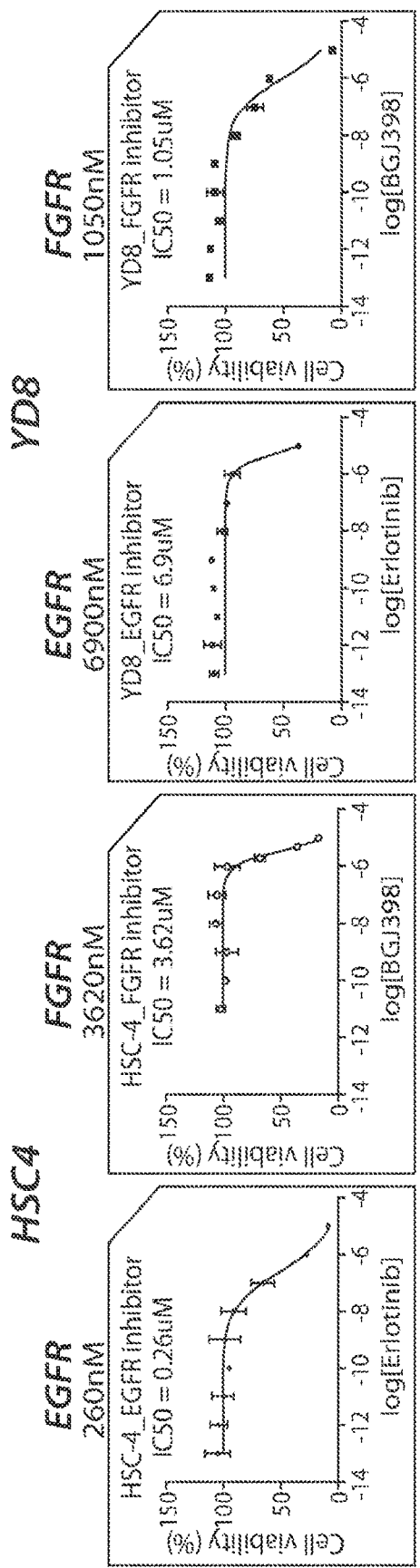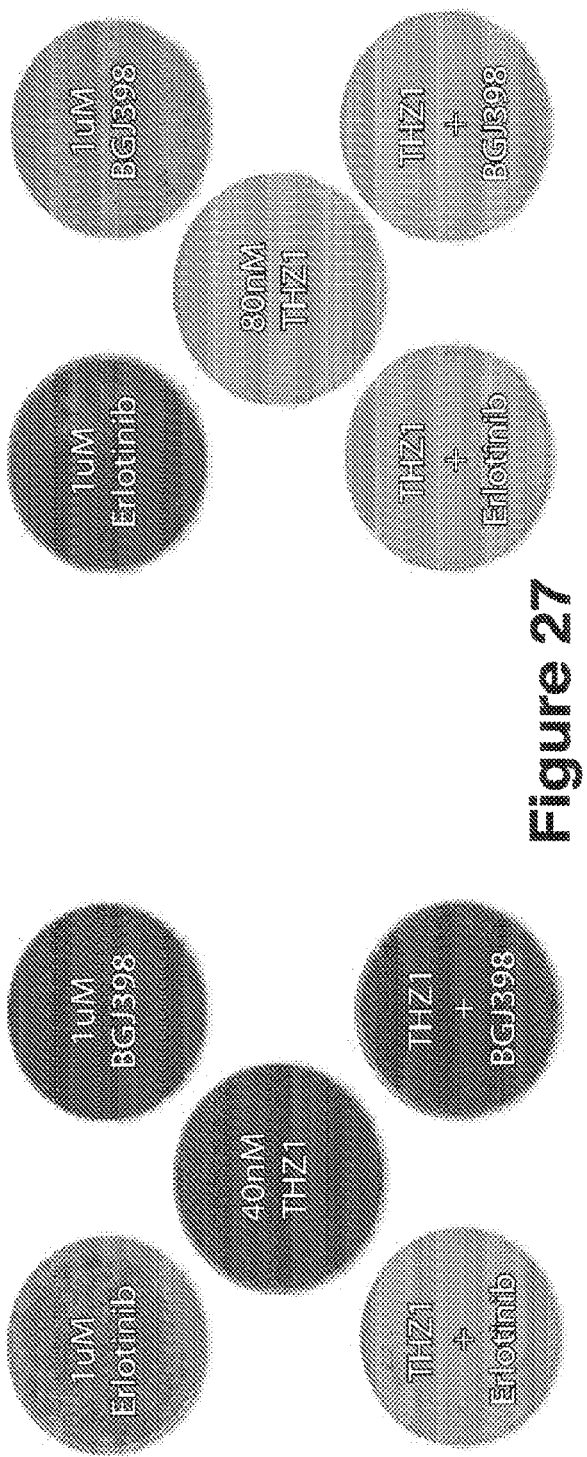
Figure 27

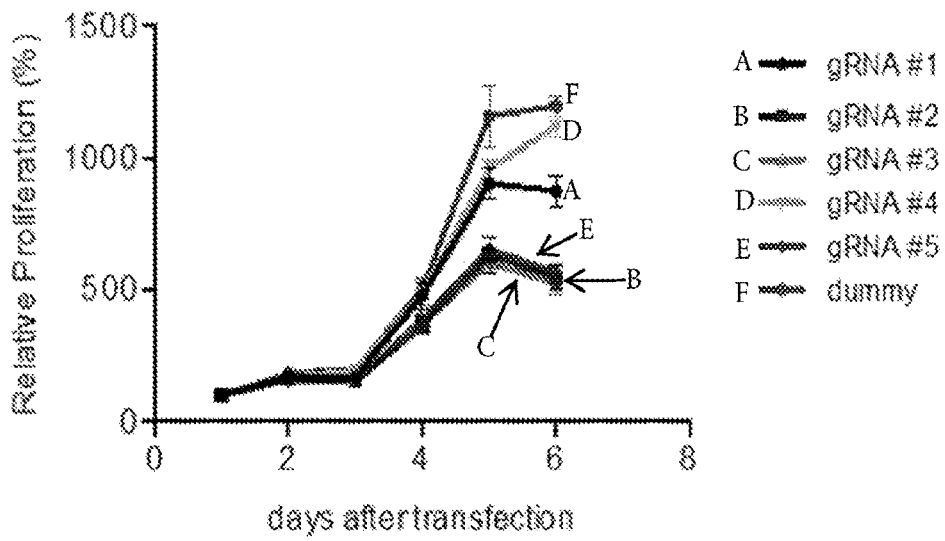
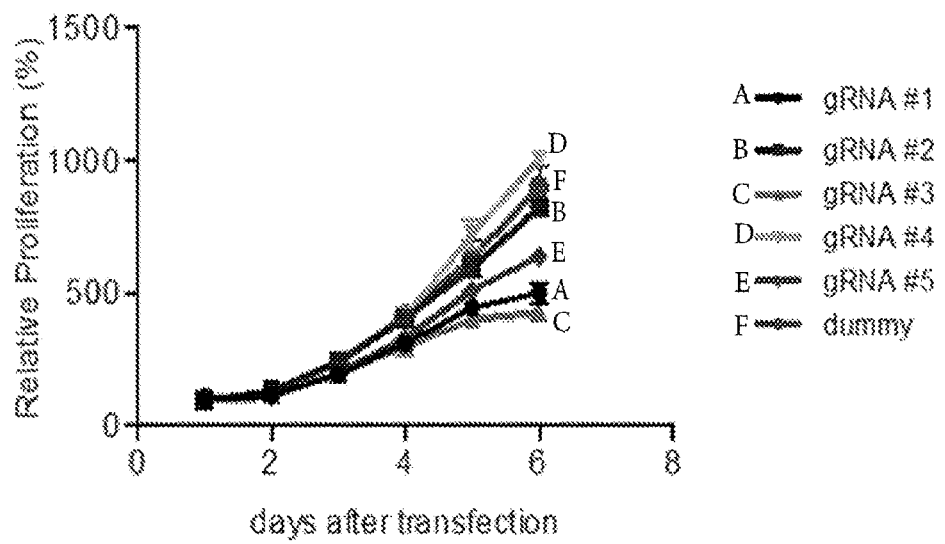
Figure 40

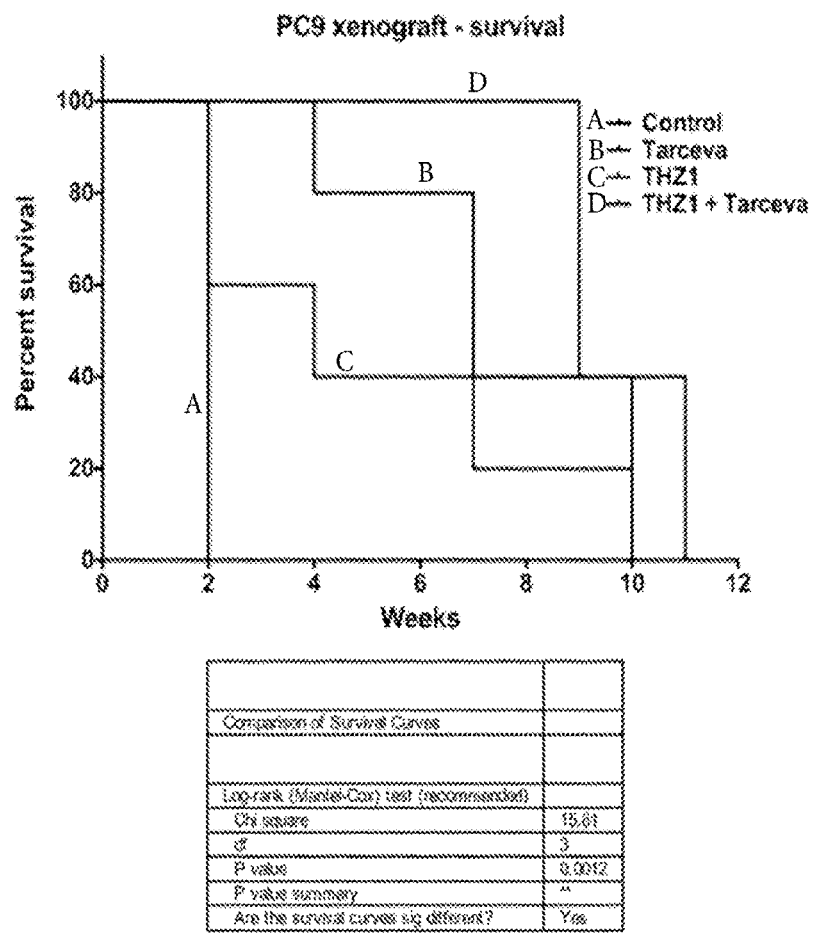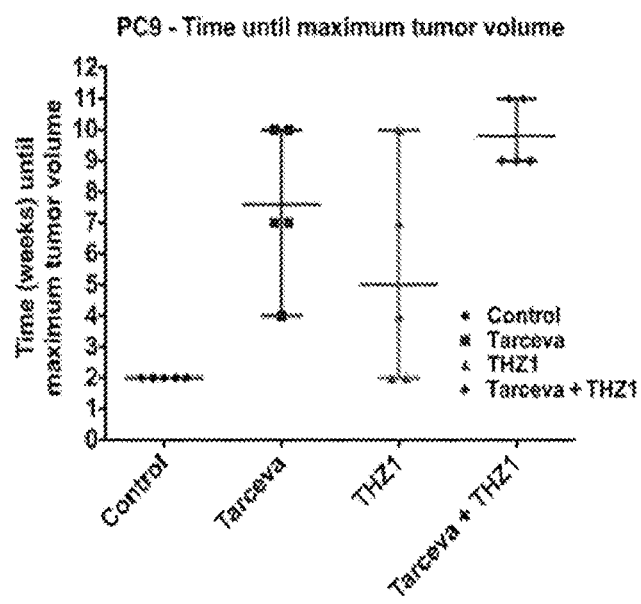
Figure 42

THZ1 + WZ4002: Tumor volume change in percent

| Mouse ID | Week 0 | Week 2 | Week 4 | Week 6 | Week 8 | Week 10 | Week 12 | Week 14 | Week 16 | |
|---|---|---|---|---|---|---|---|---|---|---|
| TLPc1_34 | 0 | -43.83515 | -20.85039 | -3.2556829 | -34.3789 | -5.9340231 | -15.923402 | -34.2388278 | -36.72830197 | ONGOING |
| TLPc1_21 | 0 | -70.494665 | -70.72758 | | | | | | | ALIVE |
| TLPc3_61 | 0 | -74.39091 | -82.31973 | | | | | | | ALIVE |
| TLPc7_81 | 0 | -36.860915 | -65.508697 | | | | | | | ALIVE |
| TLPc4_66 | 0 | -34.91678 | -0.108754 | | | | | | | DEAD |
| TLPc8_97 | 0 | -28.20298 | | | | | | | | ALIVE |

THZ1: Tumor volume change in percent

| Mouse ID | Week 0 | Week 2 | Week 4 | Week 6 | Week 8 | Week 10 | Week 12 | Week 14 | Week 16 | |
|---|---|---|---|---|---|---|---|---|---|---|
| TLPc2_91 | 0 | 32.48111 | 61.889261 | | | | | | | DEAD |
| TLPc7_92 | 0 | 81.078809 | 97.078335 | | | | | | | DEAD |

WZ4002: Tumor volume change in percent

| Mouse ID | Week 0 | Week 2 | Week 4 | Week 6 | Week 8 | Week 10 | Week 12 | Week 14 | Week 16 | |
|---|---|---|---|---|---|---|---|---|---|---|
| TLPc7_91 | 0 | 15.76705 | 92.889997 | | | | | | | DEAD |
| TLPc7_92 | 0 | 38.0258 | 74.344373 | | | | | | | DEAD |

Figure 43B

Affected upstream regulators by Ingenuity

| Upstream Regulator | Log Ratio | Molecule Type | Predicted State | z-score | p-value |
|---|---|---|---|---|---|
| NUPR1 | 5.74 | transcription regulator | Activated | 3.713 | 2.00E-15 |
| ATF3 | 3.46 | transcription regulator | Activated | 2.401 | 1.43E-04 |
| NOS3 | 2.67 | enzyme | Activated | 2.348 | 2.16E-02 |
| DOCK8 | 2.18 | other | Activated | 2.309 | 9.66E-04 |
| TNFSF10 | 1.95 | cytokine | Activated | 2.38 | 1.79E-02 |
| TOB1 | 1.91 | transcription regulator | Activated | 3.162 | 4.09E-04 |
| KLF4 | 1.74 | transcription regulator | Activated | 2.212 | 2.70E-06 |
| MYD88 | 1.5 | other | Activated | 2.943 | 6.62E-03 |
| FOXM1 | -1.42 | transcription regulator | Inhibited | -4.871 | 2.32E-11 |
| CCND1 | -1.43 | transcription regulator | Inhibited | -3.544 | 1.21E-31 |
| E2F1 | -1.51 | transcription regulator | Inhibited | -3.595 | 5.66E-29 |
| E2F2 | -1.67 | transcription regulator | Inhibited | -2.53 | 1.16E-13 |
| CCNE1 | -1.75 | transcription regulator | Inhibited | -2.219 | 5.83E-05 |
| HOXA10 | -1.94 | transcription regulator | Inhibited | -2.232 | 5.00E-05 |
| SOX7 | -2.27 | transcription regulator | Inhibited | -2.236 | 3.85E-02 |

Figure 45C

Affected upstream regulators by Ingenuity

| Upstream Regulator | Log Ratio | Molecule Type | Predicted State | z-score | pvalue |
|---|---|---|---|---|---|
| TNFSF10 | 3.949 | cytokine | Activated | 2.62 | 6.66E-04 |
| IRF5 | 2.161 | transcription regulator | Activated | 2.34 | 3.04E-03 |
| STAT2 | 2.371 | transcription regulator | Activated | 2.17 | 2.73E-05 |
| MET | -1.682 | kinase | Inhibited | -2.11 | 3.35E-06 |
| IL1B | -1.609 | cytokine | Inhibited | -2.17 | 7.30E-13 |
| PLAUR | -1.852 | transmembrane receptor | Inhibited | -2.40 | 8.34E-03 |
| MYC | -4.578 | transcription regulator | Inhibited | -4.23 | 3.52E-14 |
| CCND1 | -2.443 | transcription regulator | Inhibited | -4.63 | 1.54E-27 |

Figure 45E

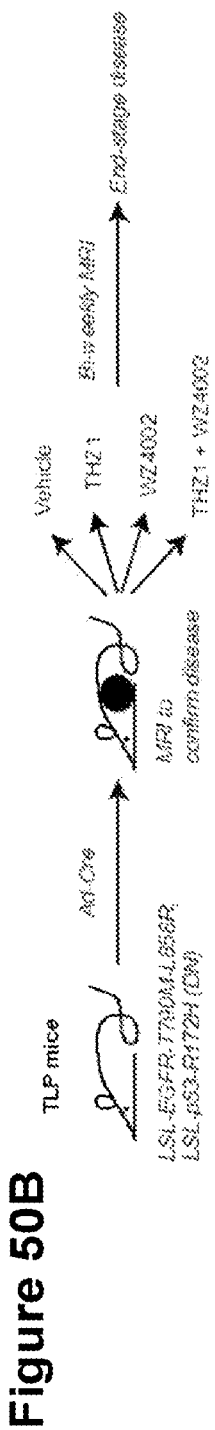
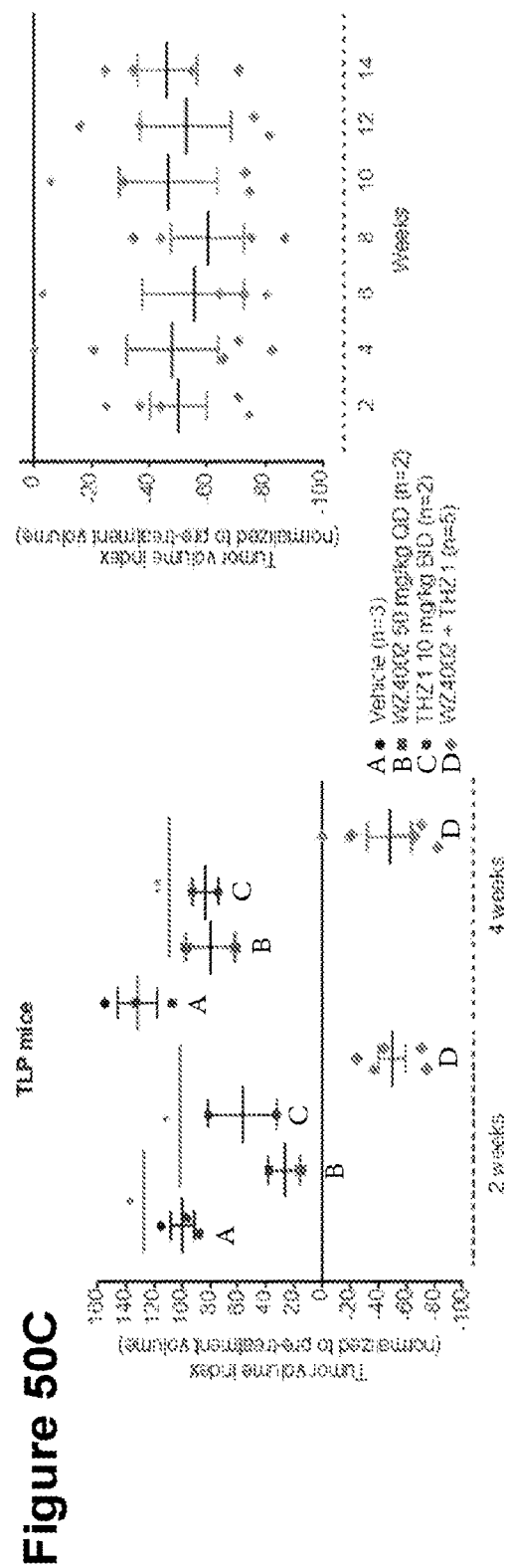
Figure 50B
Figure 50C

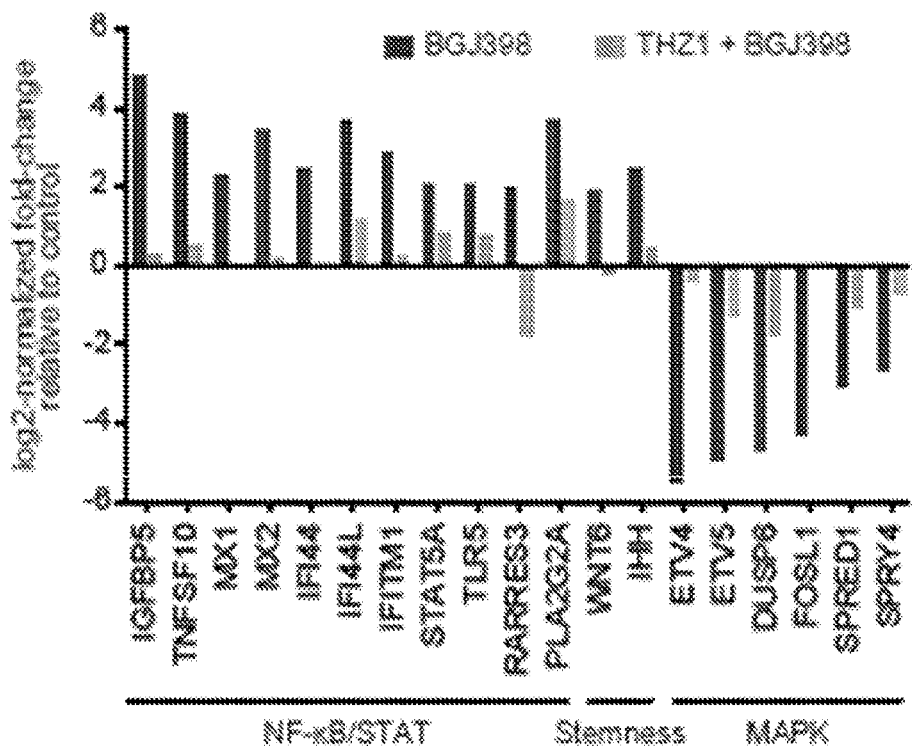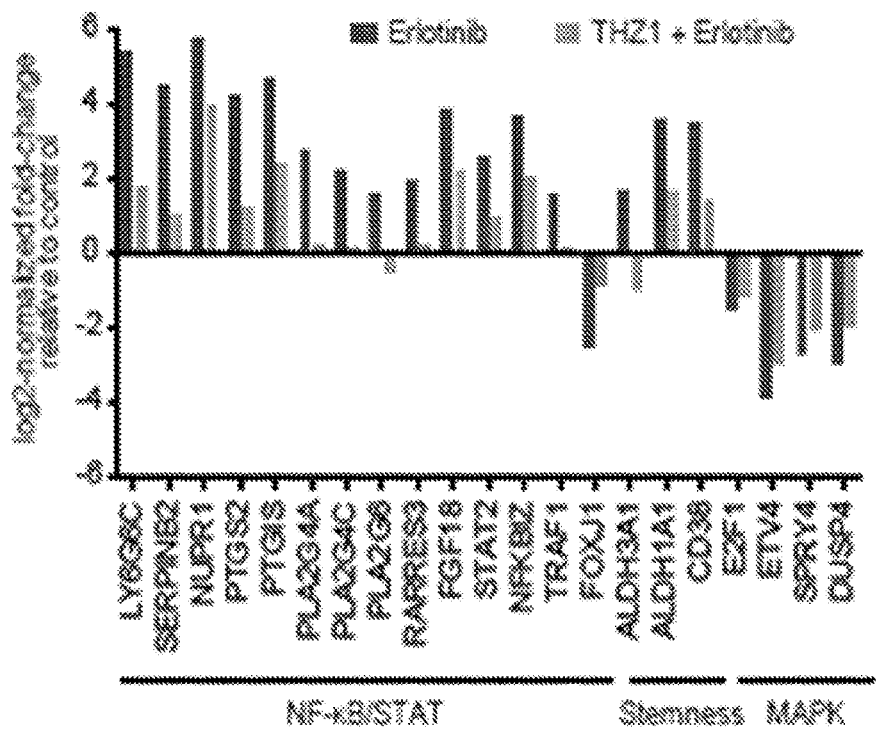
Figure 51E

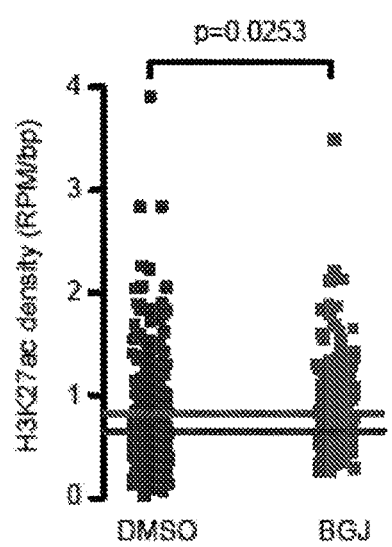
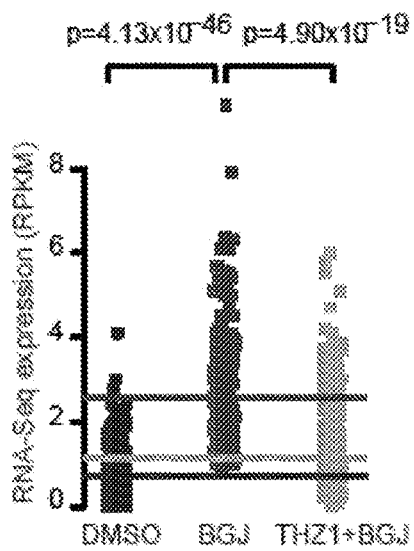
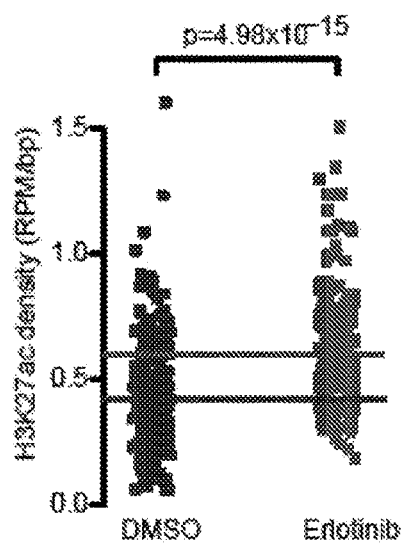
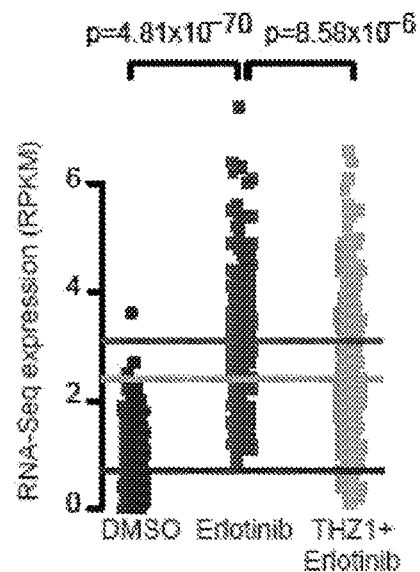
Figure 51F  Figure 51G

| GoTerm Biological Process | Benjamini |
|---|---|
| RT112: Up with BGJ398, 7 days | |
| immune response | 3.40E-01 |
| response to virus | 4.30E-01 |
| Wnt receptor signaling pathway | 4.80E-01 |
| RT112: Down with BGJ398, 7 days | |
| M-phase | 1.30E-45 |
| cell cycle | 1.60E-41 |
| nuclear division | 1.10E-38 |
| DNA replication | 1.30E-37 |
| cell division | 3.60E-37 |
| cell cycle checkpoint | 1.10E-07 |
| DNA repair | 7.60E-07 |

| GoTerm Biological Process | Benjamini |
|---|---|
| PC9: Up with Erlotinib, 7 days | |
| negative regulation of cell proliferation | 6.60E-04 |
| inflammatory response | 2.00E-02 |
| response to hypoxia | 2.40E-02 |
| positive regulation of secretion | 2.70E-02 |
| acute inflammatory response | 3.10E-02 |
| complement activation | 3.60E-02 |
| PC9: Down with Erlotinib, 7 days | |
| M-phase | 6.60E-38 |
| cell cycle | 9.60E-37 |
| nuclear division | 7.90E-36 |
| cell division | 8.40E-26 |
| DNA replication | 6.70E-21 |
| DNA repair | 4.10E-08 |
| cell cycle checkpoint | 6.00E-07 |

| Upstream Regulator | Log Ratio | Molecule Type | Predicted State | z-score | p-value |
|---|---|---|---|---|---|
| TNFSF10 | 3.949 | cytokine | Activated | 2.817 | 6.66E-04 |
| STAT2 | 2.371 | transcription regulator | Activated | 2.109 | 2.73E-05 |
| IRF5 | 2.191 | transcription regulator | Activated | 2.205 | 3.04E-03 |
| FOXM1 | -1.494 | transcription regulator | Inhibited | -4.679 | 4.04E-11 |
| IL18 | -1.609 | cytokine | Inhibited | -2.169 | 7.20E-10 |
| MET | -1.882 | kinase | Inhibited | -2.109 | 3.26E-08 |
| PLAUR | -1.882 | transmembrane receptor | Inhibited | -2.395 | 8.34E-03 |
| CCND1 | -2.489 | transcription regulator | Inhibited | -2.224 | 7.22E-11 |
| MYC | -4.579 | transcription regulator | Inhibited | -4.333 | 3.60E-14 |

PC9

| Upstream Regulator | Log Ratio | Molecule Type | Predicted State | z-score | p-value |
|---|---|---|---|---|---|
| NUPR1 | 5.74 | transcription regulator | Activated | 3.713 | 2.00E-18 |
| ATF3 | 3.46 | transcription regulator | Activated | 2.401 | 1.43E-04 |
| NOS3 | 2.67 | enzyme | Activated | 2.349 | 2.16E-02 |
| DOCK8 | 2.19 | other | Activated | 2.309 | 6.66E-04 |
| TNFSF10 | 1.95 | cytokine | Activated | 2.39 | 1.70E-02 |
| TOB1 | 1.91 | transcription regulator | Activated | 3.162 | 4.09E-04 |
| KLF4 | 1.74 | transcription regulator | Activated | 2.212 | 2.70E-06 |
| MYD88 | 1.5 | other | Activated | 2.943 | 6.62E-03 |
| FOXM1 | -1.42 | transcription regulator | Inhibited | -4.871 | 2.32E-11 |
| CCND1 | -1.43 | transcription regulator | Inhibited | -3.544 | 1.21E-31 |

Figure 57B

THZ5-31
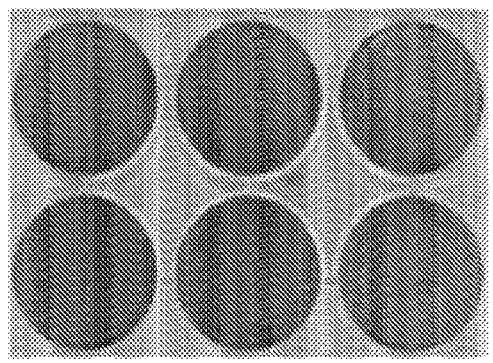
DMSO
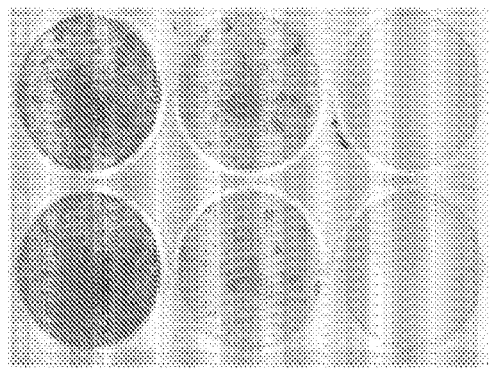
1uM Erlotinib
Figure 61

SEQUENCE LISTING

```
<160> NUMBER OF SEQ ID NOS: 17

<210> SEQ ID NO 1
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 1
atcgtttcgc ttaacggcg                                                19

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 2
tgtgatgcaa aggtattcca                                               20

<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 3
atacacatca ggttgtaacc                                               20

<210> SEQ ID NO 4
<211> LENGTH: 20
```

```
<212> TYPE: DNA
<213> ORGANISM: Artificial Sequence
<220> FEATURE:
<223> OTHER INFORMATION: Synthetic Polynucleotide

<400> SEQUENCE: 4
tgagaagctg gacttccttg                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 5
gcttgtgctt cgataccaag                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 6
gctcccagac tggaattaag                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 7
gtaggagtca taattgctcg                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 8
tattccttag aagttccacc                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 9 tcaccccccag atcagcccgg                                             20

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 10
```

```
gggacagttt gccaccgttt                                                    20

<210> SEQ ID NO 11
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 11
atgtccaaaa gcatcaagga gac                                                23

<210> SEQ ID NO 12
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 12
gaggaggcag cagagaagag                                                    20

<210> SEQ ID NO 13
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 13
taaaagttgc agcaaggcgg                                                    20

<210> SEQ ID NO 14
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 14
aataaccacc cctgacccaa c                                                  21

<210> SEQ ID NO 15
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 15
acatttgccg aagagccct                                                     19

<210> SEQ ID NO 16
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 16
ttaggaaagc ctgccggtga ctaa                                               24

<210> SEQ ID NO 17
<211> LENGTH: 24
<212> TYPE: DNA
<213> ORGANISM: Artificial Sequence
```

```
<220> FEATURE:
<223> OTHER INFORMATION: Synthetic Polynucleotide

<400> SEQUENCE: 17
aaagcatcac ccggaggaga aatc                                      24
```

COMBINATION THERAPY OF TRANSCRIPTION INHIBITORS AND KINASE INHIBITORS

RELATED APPLICATIONS

The present application is a national stage filing under 35 U.S.C. § 371 of international PCT application, PCT/US2016/037086, filed Jun. 10, 2016, which claims priority under 35 U.S.C. § 119(e) to U.S. provisional applications, U.S. Ser. No. 62/175,077, filed Jun. 12, 2015, and U.S. Ser. No. 62/175,035, filed Jun. 12, 2015, each of which is incorporated herein by reference.

GOVERNMENT SUPPORT

This invention was made with government support under grant number CA179483 awarded by The National Institutes of Health. The government has certain rights in the invention.

BACKGROUND

Kinase inhibitor therapy against genomically selected cancer cell lines can result in death of a substantial proportion of cells, but in nearly all cases resistance to targeted cancer therapies is observed. This resistance can be observed with different kinetics and can be due to a variety of cellular mechanisms but ultimately results in treatment failure. This phenomenon is observed both in pre-clinical cellular and animal models and in patients treated with these classes of drugs. Prior work has shown that cancer cell lines dependent on Fibroblast Growth Factor Receptor (FGFR) amplifications, mutations, and fusions readily acquire resistance when treated with selective FGFR inhibitors, such as BGJ398 and AZD4547, and less selective FGFR inhibitors, such as ponatinib and pazopanib (Wang et al., *Oncogene*, 2015, 34(17):2167-77). There is a need to find new treatments for proliferative diseases that are or may become resistant to kinase inhibitors.

SUMMARY

The present disclosure provides combination therapies for the treatment of proliferative diseases using combinations of transcription inhibitors and kinase inhibitors. It has been found that a combination of a transcription inhibitor and a kinase inhibitor may be useful in treating and/or preventing proliferative diseases in a subject, and in particular proliferative diseases that are resistant to transcription inhibition alone or kinase inhibition alone. In certain embodiments, the combination of a transcription inhibitor and a kinase inhibitor is synergistic in treating a proliferative disease (e.g., cancer).

Without wishing to be bound by any particular theory, the ability of a cell, in particular a cancer cell, to persist in the presence of kinase inhibition is thought to require new gene transcription, specifically the transcription of ligands that activate parallel kinase pathways. Therefore, blunting new gene transcription in the context of kinase inhibition is expected to delay and/or prevent the resistance to kinase inhibitors.

In one aspect, the present disclosure provides pharmaceutical compositions that comprise a transcription inhibitor and a kinase inhibitor, wherein the transcription inhibitor and kinase inhibitor are not the same, and optionally a pharmaceutically acceptable excipient.

The transcription inhibitor useful in the present disclosure may be any transcription inhibitor known in the art or developed in the future. In certain embodiments, the transcription inhibitor is a cyclin-dependent kinase (CDK) inhibitor (e.g., CDK1, CDK2, CDK3, CDK4, CDK5, CDK6, CDK7, CDK8, CDK9, CDK10, CDK11, or CDK12 inhibitor). In certain embodiments, the CDK inhibitor is THZ1, E9, YKL-01-116, THZ5-31-1, dinaciclib, DCA, or palbociclib. In certain embodiments, the transcription inhibitor is a bromodomain-containing protein inhibitor (e.g., bromodomain-containing protein 2 (BRD2) inhibitor, bromodomain-containing protein 3 (BRD3) inhibitor, bromodomain-containing protein 4 (BRD4) inhibitor, TBP (TATA box binding protein)-associated factor protein (TAF) inhibitor, CREB-binding protein (CBP) inhibitor, or E1A binding protein p300 (EP300) inhibitor). In certain embodiments, the bromodomain-containing protein inhibitor is JQ1.

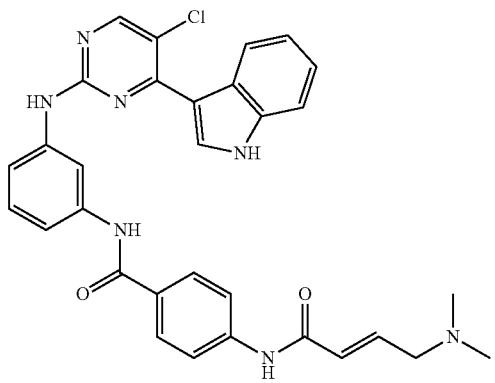

THZ1

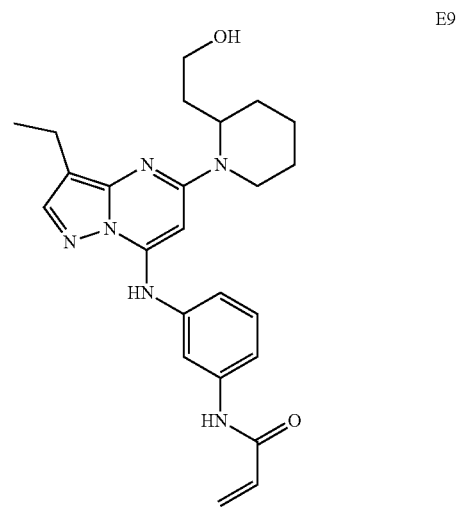

E9

3
-continued
YKL-01-116
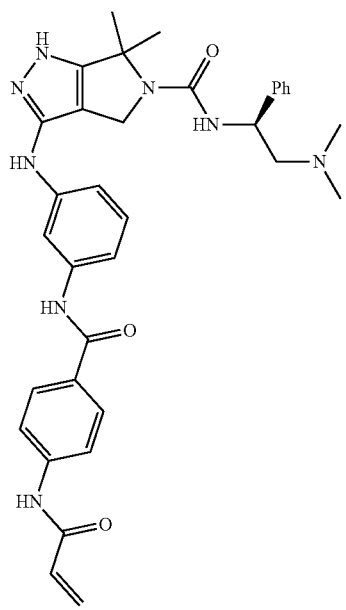
THZ5-31-1
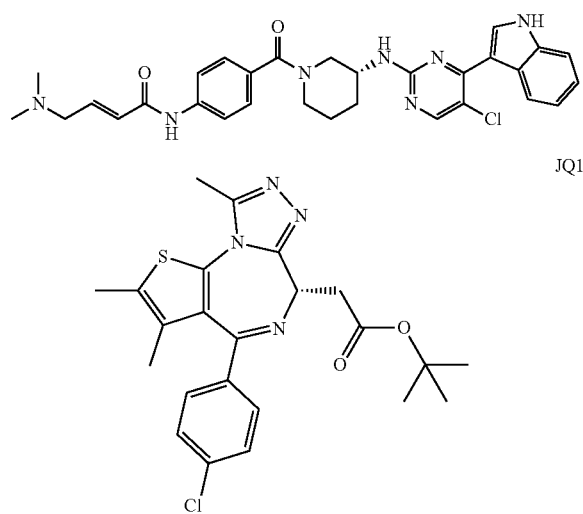
JQ1
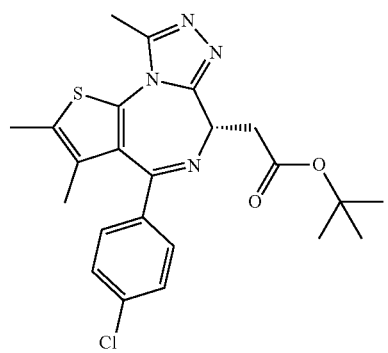
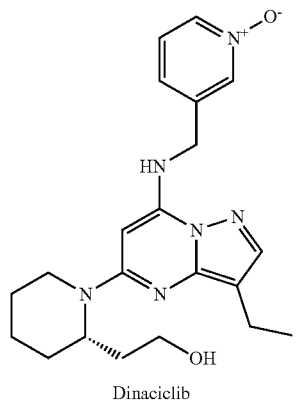
Dinaciclib
4
-continued
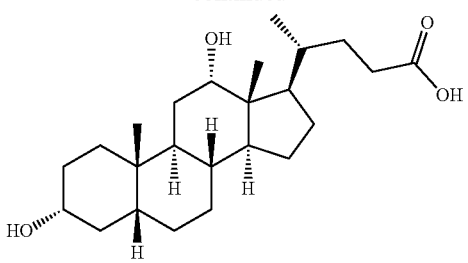
DCA
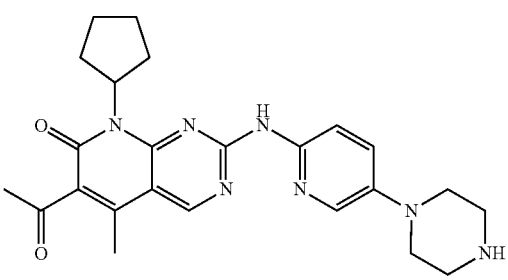
Palbociclib
In certain embodiments, the transcription inhibitor is a compound of the formula:
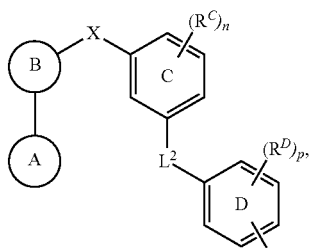 (I)
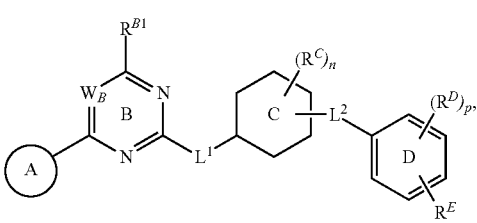 (II)
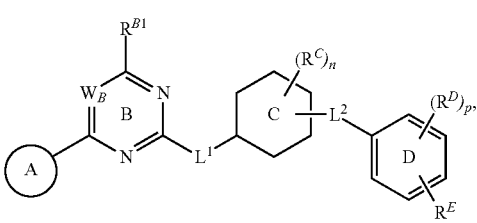 (III)
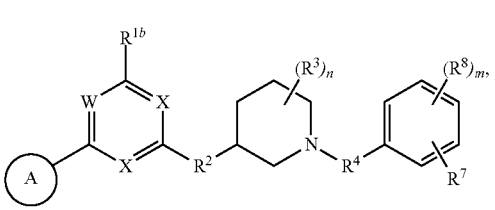 (IV)

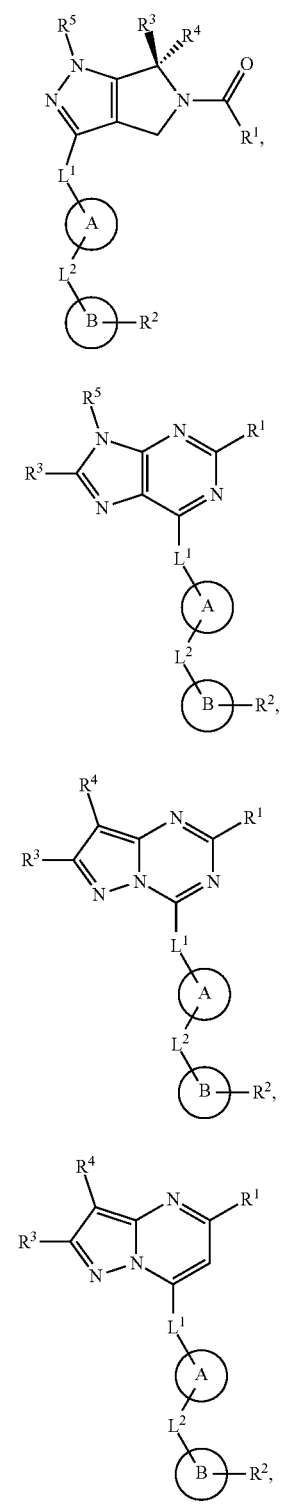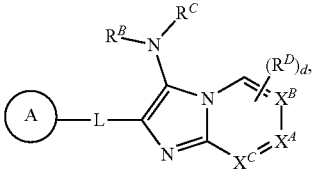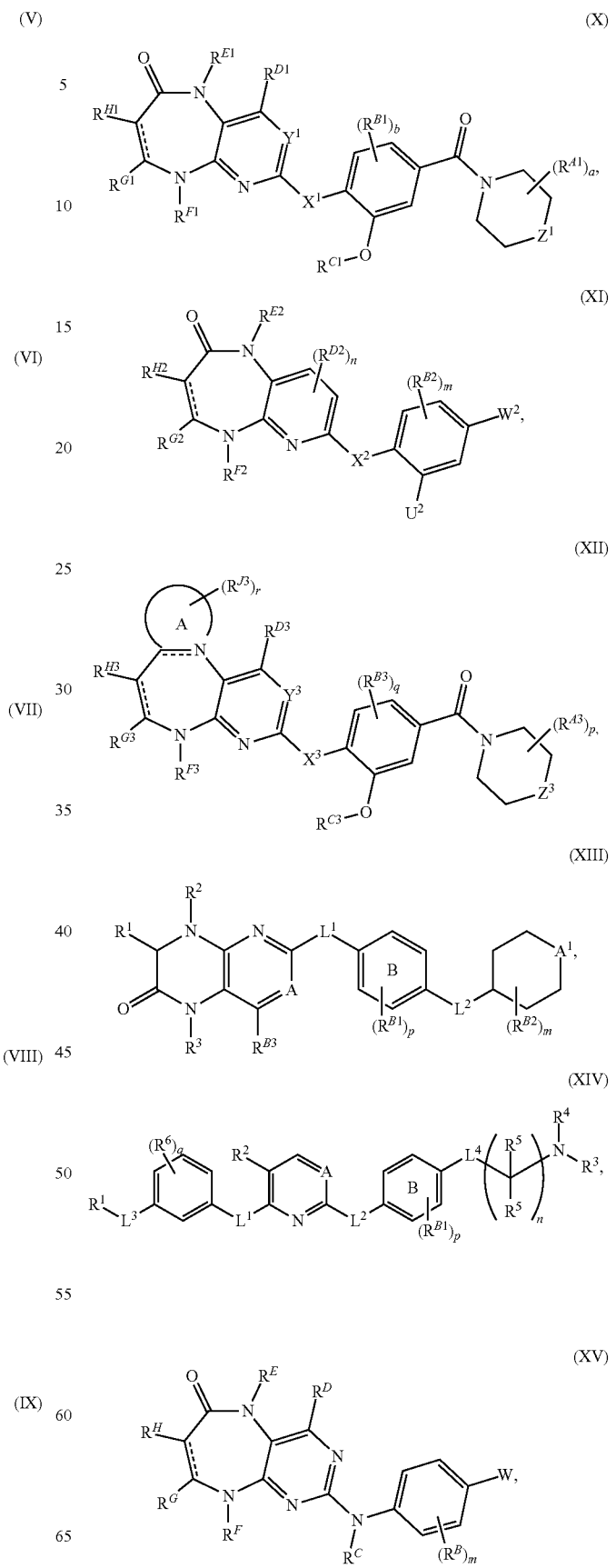

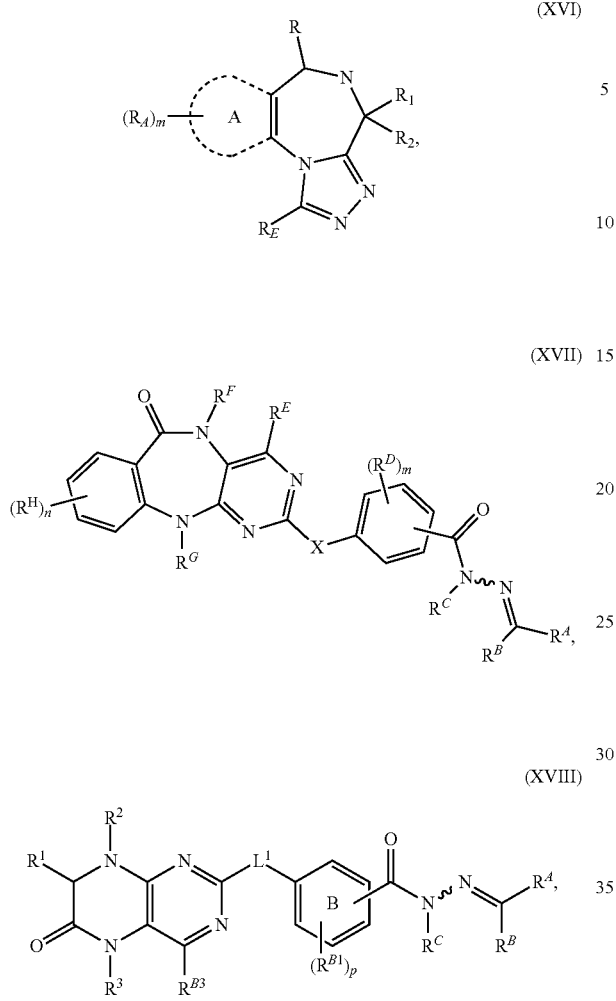

or a pharmaceutically acceptable salt, solvate, hydrate, polymorph, co-crystal, tautomer, stereoisomer, isotopically labeled derivative, or prodrug thereof.

A pharmaceutical composition of the present disclosure further includes a kinase inhibitor, in combination with a transcription inhibitor. Any kinase inhibitor known in the art or developed in the future may be used in the present disclosure. In certain embodiments, the kinase inhibitor is not a CDK inhibitor. In certain embodiments, the kinase inhibitor is a receptor tyrosine kinase (RTK) inhibitor, fibroblast growth factor receptor (FGFR) inhibitor (e.g., BGJ398), epidermal growth factor receptor (EGFR) inhibitor (e.g., erlotinib (Tarceva), AZD8931, or WZ4002), mitogen-activated protein kinase (MEK) inhibitor (e.g., trametinib), phosphatidylinositol-4,5-bisphosphate 3-kinase (PI3K) inhibitor (e.g., BKM120 (buparlisib) or BEZ235 (dactolisib)), receptor tyrosine-protein kinase erbB-2 (HER-2) inhibitor (e.g., lapatinib), mammalian target of rapamycin (mTOR) inhibitor (e.g., Torin2), or anaplastic lymphoma kinase (ALK) inhibitor (e.g., crizotinib).

In certain embodiments, the kinase inhibitor is a platelet-derived growth factor receptor (PDGFR) inhibitor (e.g., imatinib). In certain embodiments the kinase inhibitor is a or B-Raf enzyme inhibitor or MEK inhibitor (e.g., vemurafenib).

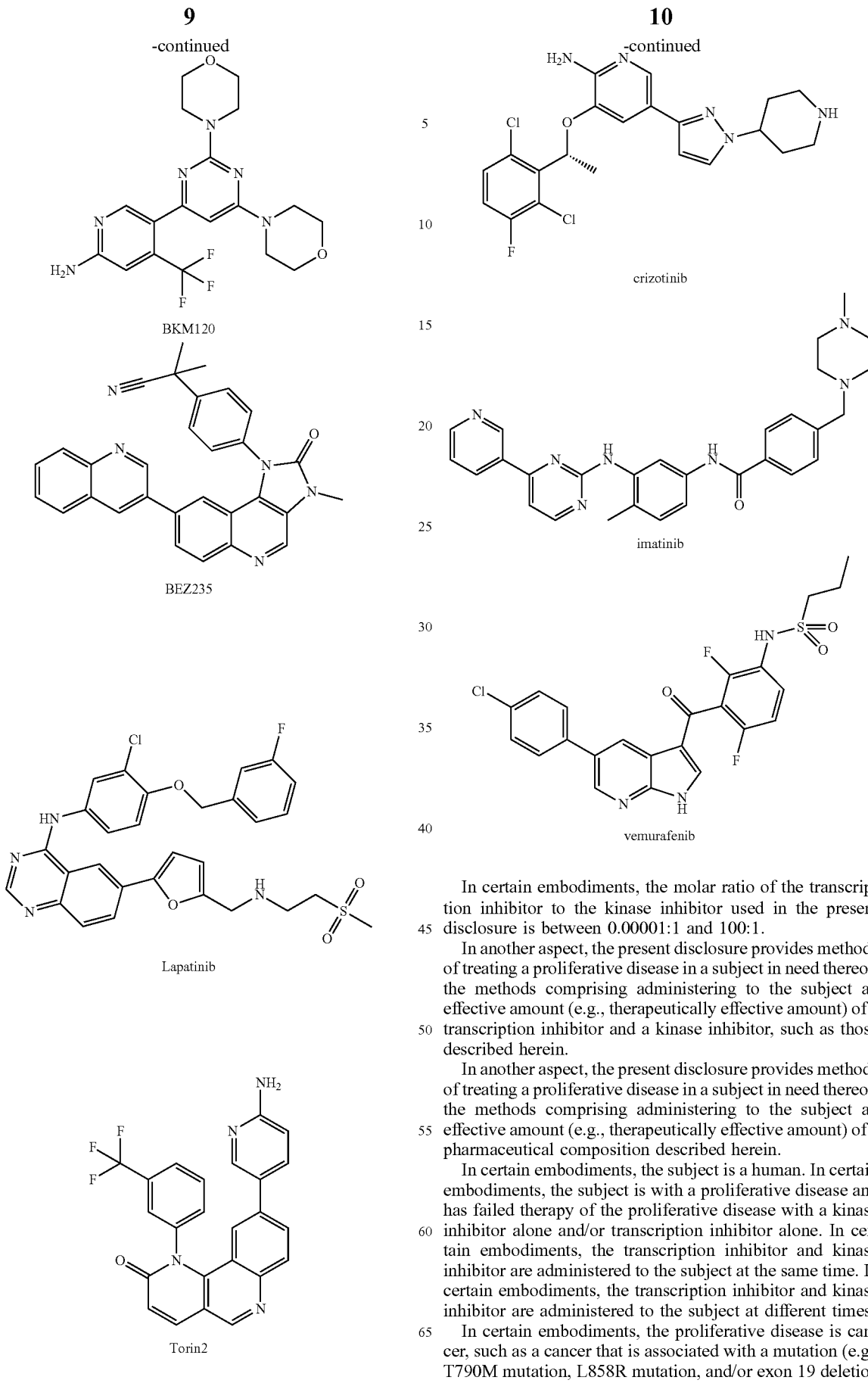

In certain embodiments, the molar ratio of the transcription inhibitor to the kinase inhibitor used in the present disclosure is between 0.00001:1 and 100:1.

In another aspect, the present disclosure provides methods of treating a proliferative disease in a subject in need thereof, the methods comprising administering to the subject an effective amount (e.g., therapeutically effective amount) of a transcription inhibitor and a kinase inhibitor, such as those described herein.

In another aspect, the present disclosure provides methods of treating a proliferative disease in a subject in need thereof, the methods comprising administering to the subject an effective amount (e.g., therapeutically effective amount) of a pharmaceutical composition described herein.

In certain embodiments, the subject is a human. In certain embodiments, the subject is with a proliferative disease and has failed therapy of the proliferative disease with a kinase inhibitor alone and/or transcription inhibitor alone. In certain embodiments, the transcription inhibitor and kinase inhibitor are administered to the subject at the same time. In certain embodiments, the transcription inhibitor and kinase inhibitor are administered to the subject at different times.

In certain embodiments, the proliferative disease is cancer, such as a cancer that is associated with a mutation (e.g., T790M mutation, L858R mutation, and/or exon 19 deletion mutation) in an epidermal growth factor receptor (EGFR) gene, a cancer that is associated with fibroblast growth factor-2 (FGF2)-fibroblast growth factor receptor (FGFR, e.g., FGFR1) activation through amplification, FGFR3-TACC3 fusion, EML4-ALK fusion, HER2 amplification, or KRAS codons 12, 13 or 61 mutations, a cancer that is associated with a mutation (e.g., Q61R mutation) in neuroblastoma RAS viral oncogene homolog (NRAS), a cancer that is associated with mesenchymal-epithelial transition (MET) amplification, or a cancer that is associated with feedback activation of signal transducer and activator of transcription 3 (STAT3).

In another aspect, the present disclosure provides methods of preventing a proliferative disease in a subject in need thereof, the methods comprising administering to the subject an effective amount (e.g., prophylactically effective amount) of a transcription inhibitor and a kinase inhibitor described herein.

In another aspect, the present disclosure provides methods of preventing a proliferative disease in a subject in need thereof, the methods comprising administering to the subject an effective amount (e.g., prophylactically effective amount) of a pharmaceutical composition described herein.

In another aspect, the present disclosure provides methods of reducing, delaying, and/or preventing in a subject in need thereof the resistance of a proliferative disease to a transcription inhibitor or kinase inhibitor, the methods comprising administering to the subject an effective amount of (1) a transcription inhibitor and a kinase inhibitor described herein, or (2) a pharmaceutical composition described herein.

In another aspect, the present disclosure provides methods of inhibiting the proliferation of a cell, the methods comprising contacting the cell with an effective amount of (1) a transcription inhibitor and a kinase inhibitor described herein, or (2) a pharmaceutical composition described herein.

In another aspect, the present disclosure provides methods of reducing, delaying, and/or preventing the resistance of a cell to a transcription inhibitor or kinase inhibitor, the methods comprising contacting the cell with an effective amount of (1) a transcription inhibitor and a kinase inhibitor described herein, or (2) a pharmaceutical composition described herein.

In certain embodiments, the cell is in vitro. In certain embodiments, the cell is in vivo. In certain embodiments, the transcription inhibitor and kinase inhibitor are contacted with the cell at the same time. In certain embodiments, the transcription inhibitor and kinase inhibitor are contacted with the cell at different times.

In another aspect, the present disclosure provides the transcription inhibitors and kinase inhibitors described herein for use in a method described herein.

In still another aspect, the present disclosure provides the pharmaceutical compositions described herein for use in a method described herein.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described Compounds (e.g., transcription inhibitors and kinase inhibitors) described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_1$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —CH₂-cyclopropyl, vinyl, allyl, n-butyl, sec-butyl, isobutyl, tert-butyl, cyclobutyl, —CH₂-cyclobutyl, n-pentyl, sec-pentyl, isopentyl, tert-pentyl, cyclopentyl, —CH₂-cyclopentyl, n-hexyl, sec-hexyl, cyclohexyl, —CH₂-cyclohexyl moieties and the like, which again, may bear one or more substituents. Alkenyl groups include, but are not limited to, for example, ethenyl, propenyl, butenyl, 1-methyl-2-buten-1- and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —CH₃ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —CF₃, Bn).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=CHCH₃ or

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_5\ 10$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_3$-cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and arylene. An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion.

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$_2$), —NR$^{ff}$C(=O)R$^{ee}$, —NR$^{ff}$CO$_2$R$^{ee}$, —NR$^{ff}$C(=O)N(R)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ -C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HCO$_3$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4$$^-$, PF$_4$$^-$, PF$_6$$^-$, AsF$_6$$^-$, SbF$_6$$^-$, B[3,5-(CF$_3$)$_2$C$_6$H$_3$]$_4$$^-$, B(C$_6$F$_5$)$_4$$^-$, BPh$_4$$^-$, Al(OC(CF$_3$)$_3$)$_4$$^-$, and carborane anions (e.g., CB$_{11}$H$_{12}$$^-$ or (HCB$_{11}$Me$_5$Br$_6$)$^-$). Exemplary counterions which may be multivalent include CO$_3$$^{2-}$, HPO$_4$$^{2-}$, PO$_4$$^{3-}$, B$_4$O$_7$$^{2-}$, SO$_4$$^{2-}$, S$_2$O$_3$$^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(=O)(R$^{aa}$)$_2$, —OP(=O)(OR$^{cc}$)$_2$, and —OP(=O)(N(R$^{bb}$))$_2$, wherein X$^-$, R$^{aa}$, R$^{bb}$, and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(N(R$^{bb}$)$_2$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R—, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(N(R$^{bb}$)$_2$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^-$, wherein R$^{bb}$ and X$^-$ are as defined herein.

The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

"Acyl" refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

The term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$, C(=NR$^{bb}$)N(R$^{bb}$)$_2$), wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4- methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3{}^+X^-$, —$P(OR^{cc})_2$, —$P(OR^{cc})_3{}^+X^-$, —$P(=O)(R^{aa})_2$, —$P(=O)(OR^{cc})_2$, and —$P(=O)(N(R^{bb})_2)_2$, wherein $X^-$, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference.

Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, o-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3{}^+X^-$, —$P(OR^{cc})_2$, —$P(OR^{cc})_3{}^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference.

A "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March Advanced Organic Chemistry 6th ed. (501-502). Exemplary leaving groups include, but are not limited to, halo (e.g., chloro, bromo, iodo) and activated substituted hydroxyl groups (e.g., —$OC(=O)SR^{aa}$, —$OC(=O)R^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$ wherein R$^{aa}$, R$^{bb}$, and R$^{cc}$ are as defined herein).

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —C$^A$H(C$^B$H$_2$C$^C$H$_3$)— includes one chain atom C$^A$, one hydrogen atom on C$^A$, and non-chain substituent —(C$^B$H$_2$C$^C$H$_3$). The term "C$_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —CH(C$_2$H$_5$)— is a C$_1$ hydrocarbon chain, and

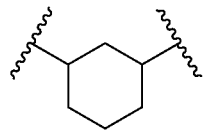 [SMILES: *C1CCCC(*)C1]

is a C$_3$ hydrocarbon chain. When a range of values is used, the meaning of the range is as described herein. For example, a C$_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —(CH$_2$)$_4$—). A hydrocarbon chain may also be unsaturated and include one or more C=C and/or C≡C bonds anywhere in the hydrocarbon chain. For instance, —CH=CH—(CH$_2$)$_2$—, —CH$_2$—C≡C—CH$_2$—, and —C≡C—CH=CH— are all examples of a unsubstituted and unsaturated hydrocarbon chain. In certain embodiments, the hydrocarbon chain is unsubstituted (e.g., —C≡C— or —(CH$_2$)$_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

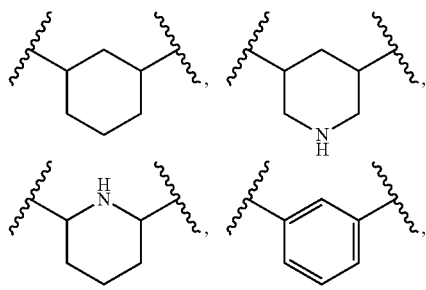

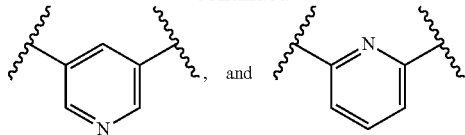

are all examples of a hydrocarbon chain. In contrast, in certain embodiments,

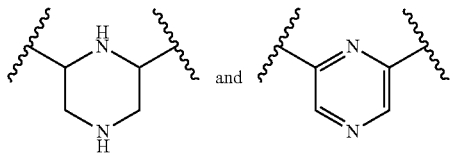 [SMILES: *C1CNCC(*)N1 ; *c1cncc(*)n1]

are not within the scope of the hydrocarbon chains described herein. When a chain atom of a C$_x$ hydrocarbon chain is replaced with a heteroatom, the resulting group is referred to as a C$_x$ hydrocarbon chain wherein a chain atom is replaced with a heteroatom, as opposed to a C$_{x-1}$ hydrocarbon chain. For example,

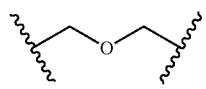 [SMILES: *COC*]

is a C$_3$ hydrocarbon chain wherein one chain atom is replaced with an oxygen atom.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R.x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R.0.5\ H_2O$)), and polyhydrates (x is a number greater than 1, e.g., dihydrates ($R.2\ H_2O$) and hexahydrates ($R.6\ H_2O$)).

The term "tautomers" or "tautomeric" refers to two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction interconverting a tautomeric pair) may be catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

"Transcription" is the first step of gene expression, in which a particular segment of DNA is copied into RNA by an RNA polymerase. During transcription, a DNA sequence is read by an RNA polymerase, which produces a complementary, antiparallel RNA strand called a primary transcript. Transcription may proceed in the following steps:

One or more sigma factor protein binds to the RNA polymerase holoenzyme, allowing it to bind to promoter DNA.

RNA polymerase creates a transcription bubble, which separates the two strands of the DNA helix. This is done by breaking the hydrogen bonds between complementary DNA nucleotides.

RNA polymerase adds matching RNA nucleotides to the complementary nucleotides of one DNA strand.

RNA sugar-phosphate backbone forms with assistance from RNA polymerase to form an RNA strand.

Hydrogen bonds of the untwisted RNA-DNA helix break, freeing the newly synthesized RNA strand.

If the cell has a nucleus, the RNA may be further processed. This may include polyadenylation, capping, and splicing.

The RNA may remain in the nucleus or exit to the cytoplasm through the nuclear pore complex.

A "transcription inhibitor" is a substance (e.g., a compound) that inhibits one or more of the steps of transcription.

The term "inhibition", "inhibiting", "inhibit," or "inhibitor" refer to the ability of a compound to reduce, slow, halt, and/or prevent activity of a particular biological process in a cell relative to vehicle.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The terms "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay and/or prevent recurrence.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount effective to prevent a condition, or one or more symptoms associated with the condition and/or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF).

"Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, hematological malignancies. The term "hematological malignancy" refers to tumors that affect blood, bone marrow, and/or lymph nodes. Exemplary hematological malignancies include, but are not limited to, leukemia, such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma, such as Hodgkin lymphoma (HL) (e.g., B-cell HL, T-cell HL) and non-Hodgkin lymphoma (NHL) (e.g., B-cell NHL, such as diffuse large cell lymphoma (DLCL) (e.g., diffuse large B-cell lymphoma (DLBCL, e.g., activated B-cell (ABC) DLBCL (ABC-DLBCL))), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt lymphoma, Waldenstrim's macroglobulinemia (WM, lymphoplasmacytic lymphoma), hairy cell leukemia (HCL), immunoblastic large cell lymphoma, precursor B-lymphoblastic lymphoma, central nervous system (CNS) lymphoma (e.g., primary CNS lymphoma and secondary CNS lymphoma); and T-cell NHL, such as precursor T-lymphoblastic lymphomalleukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); lymphoma of an immune privileged site (e.g., cerebral lymphoma, ocular lymphoma, lymphoma of the placenta, lymphoma of the fetus, testicular lymphoma); a mixture of one or more leukemiallymphoma as described above; myelodysplasia; and multiple myeloma (MM). Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

BRIEF DESCRIPTION OF THE DRAWINGS

FIG. 5A shows images of stained RT112 cell colonies after treating RT112 cells for four weeks with DMSO (control), THZ1, BGJ398, and a combination of THZ1 and BGJ398. FIG. 5B shows the drug resistant colonies expressed as a percentage of the control, according to the results in FIG. 5A.

In FIGS. 20A to 20C, GSK: GSK1120212.

FIG. 27 shows stained cells after the specified treatments in the HCS4 and YD8 cell lines.

FIG. 40 shows the relative proliferation for the various guides. For CDK7, guides 2, 3, and 5 had the greatest effect, and for CDK12, guides 1, 3, and 5 had the greatest effect.

FIG. 42 shows in vivo xenograft studies in PC9, an EGFR-dependent cell line. A significant increase in survival with the combination treatment was observed. The time until the maximum tumor volume was reached was significantly higher in the combined treatment group compared with the control and each treatment alone. The increase in survival between the MEK inhibitor and the combination treatment did not become apparent until after week 7.

FIG. 43B shows the percent tumor volume change at the indicated time points (represented graphically after transformation to the tumor volume index in FIG. 43A). One mouse under the combination treatment has survived for at least 16 weeks.

FIGS. 45B and 45C show the drug tolerant state for PC9 cells treated with erlotinib using RNAseq at 7 days of treatment (with 1 µM erlotinib). FIG. 45B: the data are log 2 values for three replicates for each condition. The data also show the log 2-fold change between erlotinib vs. control (DMSO). It was found that, not surprisingly, the drug tolerant cells were transcriptionally distinct from the parental population. There were changes in STAT3 pathway members, for example, NFKBIZ and IGFBP5 were upregulated, which is interesting given the work reported in Sharma et al., Cell, 2010, 141(1):69-80, which suggested that acute STAT3 activation in response to erlotinib was important to the establishment of resitsance. FOSL1 is downregulated, which is consistent with the findings from the Massague group on the importance of FRA-1 downregulation in the tumor secretome and establishment of resistance. See, e.g., Obenauf et al., Nature. 2015, 520, 368-72. There were a number of stress response proteins that were highly upregulated, such as NUPR1. A number of repressors of the MAPK pathway were down regulated for example DUSPS and SPRYs. Multiple autophagy related genes were upregulated, as were several TGF-beta pathway members, and a number of stemness-associated factors. Lastly, a number of cell cycle genes were downregulated, and some senescence-associated genes were upregulated, which suggests that these tolerant cells are switching to a senescent phenotype. This shows transcriptional regulators that were either upregulated or downregulated in the data described herein, and for which a large number of downstream genes were also significantly activated or inhibited. FIG. 45C: the analysis was done using INGENUITY. A number of stress response programs, stemness regulators, and cell cycle regulators were seen to come up on the list.

FIGS. 45D and 45E show the data for RT112 cells treated for 7 days with BGJ398 at 1 µM. FIG. 45D: the drug tolerant cells are transcriptionally distinct from the parental population. Some important differences were upregulation of innate immunity genes, in the interferon/NFKB family. This could be analogous to the STAT3 signature that was seen in the PC9 cells, with STAT2 and STAT5A activation in this cell line instead. What was also seen includes a number of autophagy genes being upregulated and stemness factors. There were a number of WNT/hedgehog family members that were upregulated in this cell line. What was also seen includes cell cycle genes being downregulated, as well of the MAP kinase repressors as seen in PC9 as well. As in the papers from the Massague group, e.g., Obenauf et al., Nature. 2015, 520, 368-72, FOSL1 downregulation was observed. What was also seen includes drug metabolism genes being upregulated in the BGJ398-treated cells. This shows various regulators in the data described herein that were either upregulated with BGJ398 or downregulated and shows that many of their downstream targets were also either activated or inhibited. Multiple interferon family genes come up here, and in the inhibited group a number of cell cycle regulators. FIG. 45E: the analysis was done using INGENUITY.

Figure 49A:
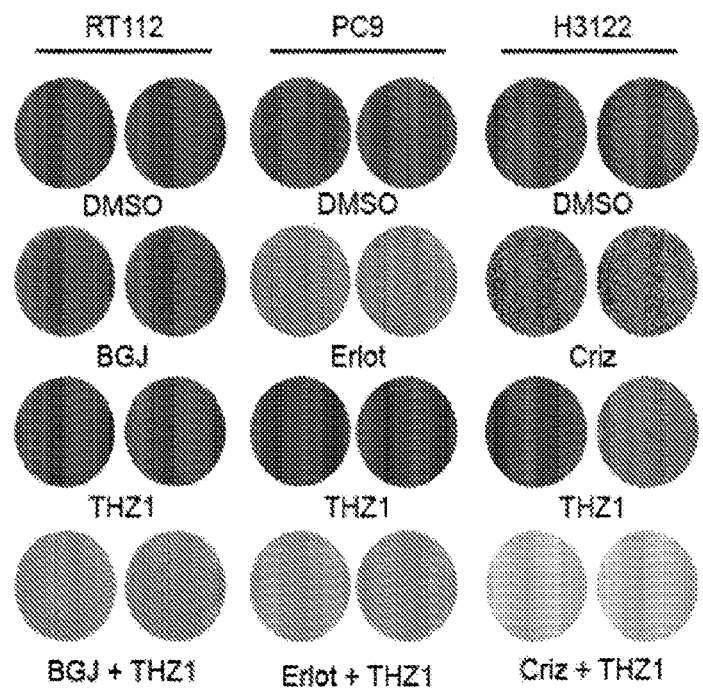
FIG. 49A shows the results of colony formation assays for receptor tyrosine kinase-dependent cell lines, RT112 (FGFR), PC9 (EGFR), and H3122 (ALK) that were treated with DMSO, the corresponding tyrosine kinase inhibitor (TKI: BGJ398 (BGJ), erlotinib (Erlot), or crizotinib (Criz)), THZ1, or THZ1 in combination with the corresponding TKI. Colony formation was assayed by crystal violet staining at 4 weeks. Two representative wells from a minimum of three biological replicates are shown per condition. (RT 112: BGJ398 1 µM, THZ1 100 nM, PC9: erlotinib 1 µM, THZ1 100 nM, H3122: crizotinib 250 nM, THZ1 50 nM).
Figure 49B:
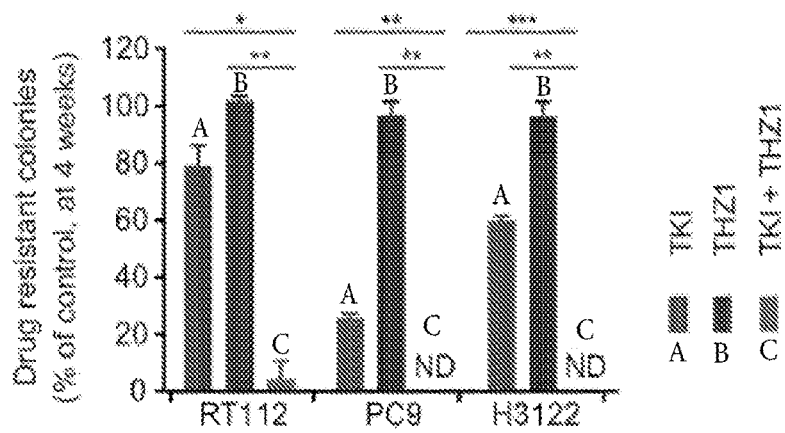
FIG. 49B shows a graph of the quantification of the colony formation described in FIG. 49A as percentage of the control. Mean (2 biological replicates)+/−standard deviation (SD) shown (*p-value<0.05, <0.005, *<0.0005, two-sided t-test). ND=not detectable.
Figure 49C:
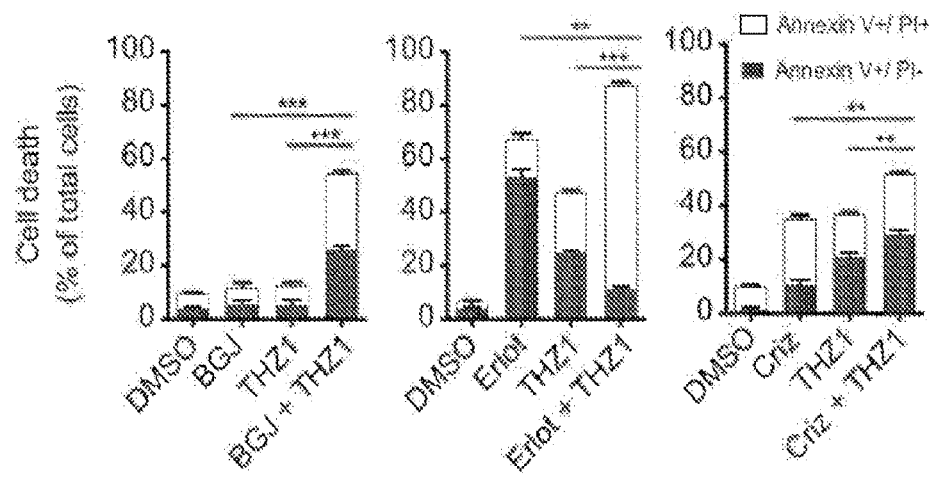
FIG. 49C shows the results of a cell death analysis of cells treated as in FIG. 49A by flow cytometry with Annexin V/PI staining, following 48 hours of treatment. Mean (3 biological replicates)+/−SD shown (*p-value<0.05, <0.005, *<0.0005, two-sided t-test). Left panel: RT112, middle panel: PC9, right panel: H3122.
Figure 49D:
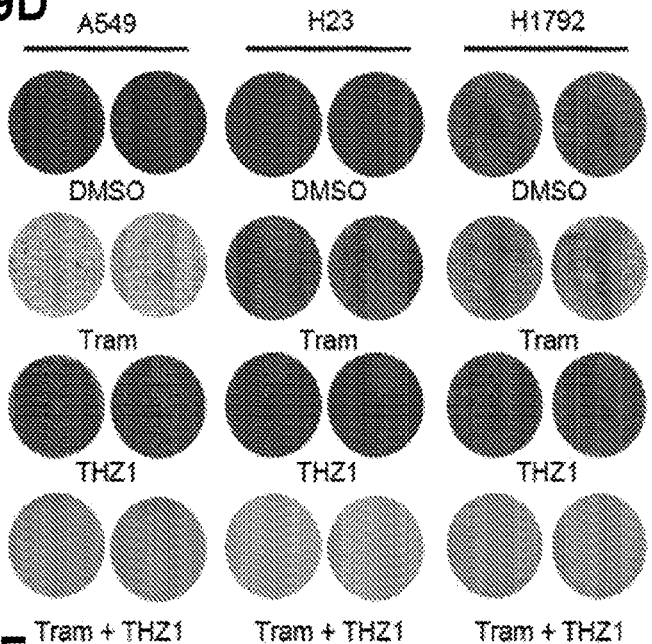
FIG. 49D shows the results of colony formation assays for KRAS-mutant cell lines, A549, H23, H1792 that were treated with DMSO, trametinib (Tram), THZ1, or a combination of THZ1 and trametinib. Colony formation was assayed by crystal violet staining at 4 weeks. Two representative wells from a minimum of three independent biological replicates are shown per condition. (A549: trametinib 200 nM, THZ1 150 nM, H23: trametinib 500 nM, THZ1 100 nM, H1792: trametinib 500 nM, THZ1 500 nM).
Figure 49E:
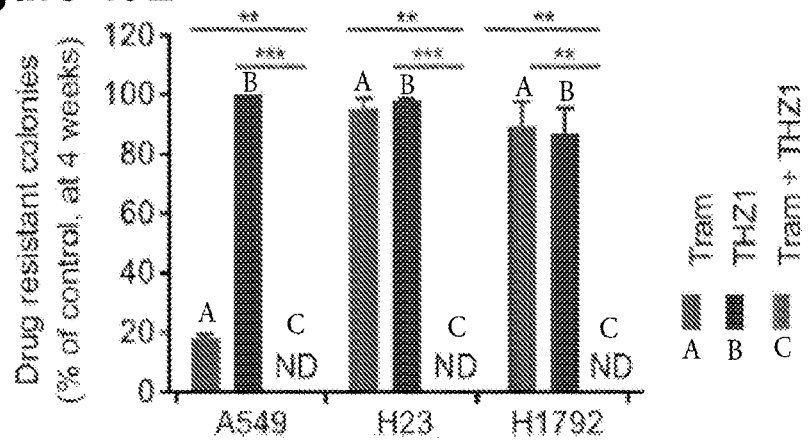

FIG. 49E shows a graph of the quantification of the colony formation described in FIG. 49D as a percentage of the control. Mean (2 biological replicates)+/−SD shown (*p-value<0.05, <0.005, *<0.0005, two-sided t-test). ND=not detectable.

Figure 49F:
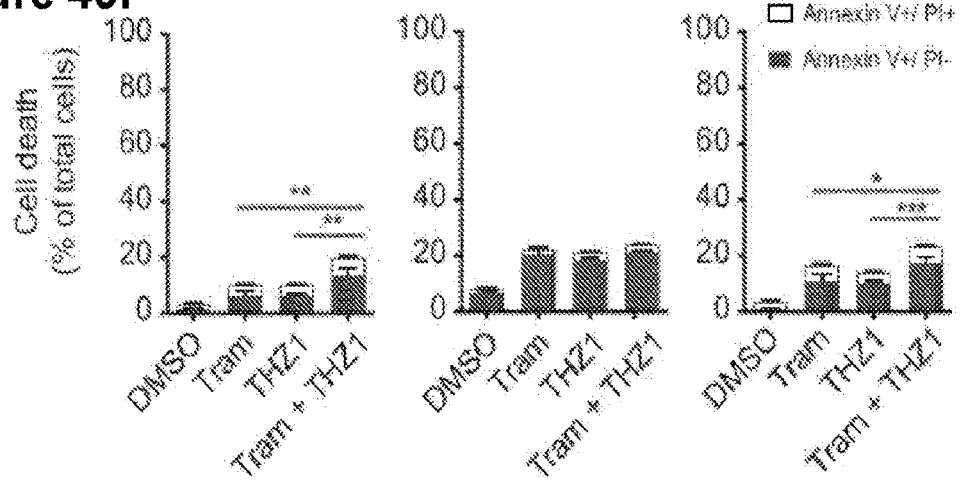

FIG. 49F shows the results of a cell death analysis of cells treated as in FIG. 49D by flow cytometry with Annexin V/PI staining, following 48 hours of treatment. Mean (3 biological replicates)+/−SD shown (*p-value<0.05, <0.005, *<0.0005, two-sided t-test). Left panel: A549, middle panel: H23, right panel: H1792.

Figure 50A:
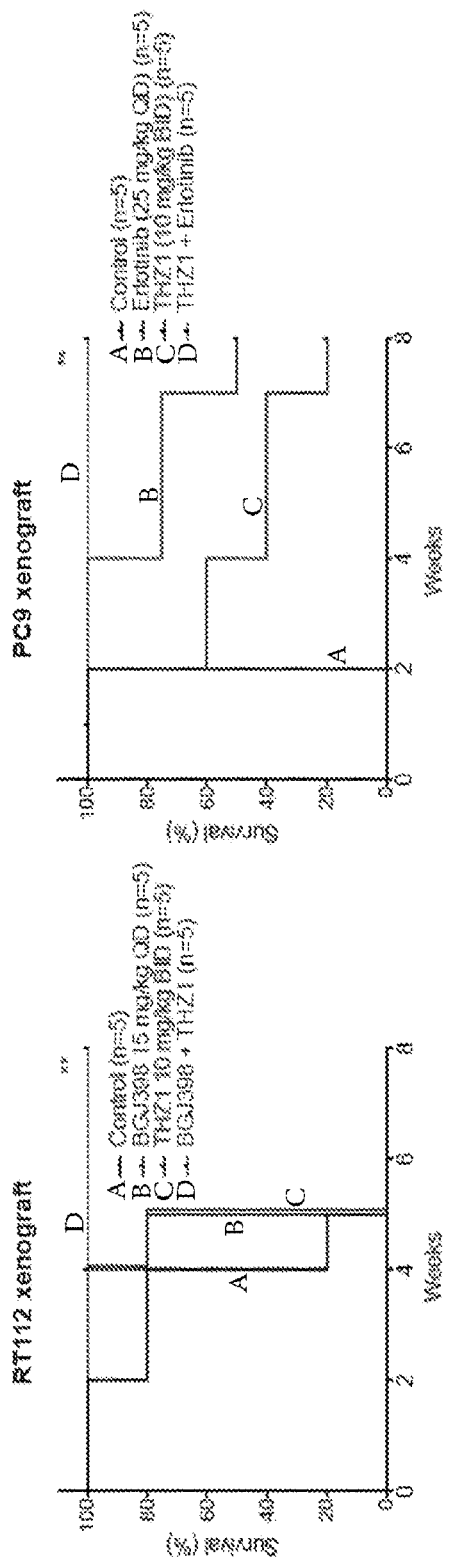

FIG. 50A shows the results of xenograft studies on RT112 and PC9 tumors that were treated with the indicated drugs for eight weeks (n=5 mice in each treatment group, equivalent to 10 tumours in each group). Survival over time is shown as a percentage for each treatment group. P-values are based on log-rank (Mantel-Cox) test analysis (*p-value<0.05, <0.005, *<0.0005).

FIG. 50B shows a schematic of a novel non-small cell lung cancer genetically-engineered mouse model (GEMM) containing lox-stop-lox (LSL) EGFR-T790M-L858R and LSL p53-R172H dominant negative (DN) alleles (TLP mice). Mice were induced by intranasal administration at 6 weeks of age with Adenovirus-Cre recombinase. Upon determination of lung tumor growth by MRI, mice were randomized into treatment groups and imaged biweekly until end-stage disease to determine tumor response.

FIG. 50C shows a tumor volume index, normalized to pre-treatment volume, for TLP mice treated with the indicated drugs at 2 and 4 weeks (left panel). Mean (n=3 for vehicle, 2 for WZ4002, 2 for THZ1, 5 for WZ4002+ THZ1)+/−standard error of the mean is shown (*p-value<0.05, <0.005, *<0.0005, two-sided t-test)). Combination treated mice had long term tumor-regression (right panel). Tumor volume index for combination-treated mice is shown up to 14 weeks.

Figure 50D:
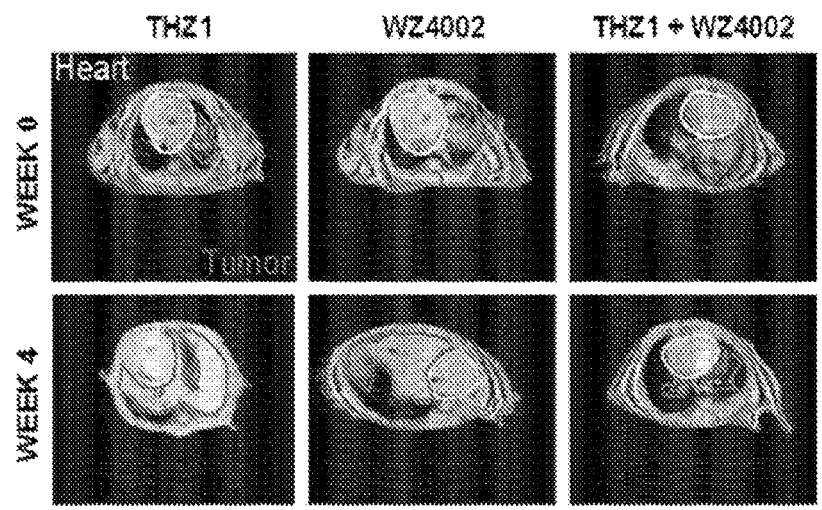

FIG. 50D shows representative MRI images for mice treated with THZ1, WZ4002 or the combination of the two, pre-treatment and at week 4, showing significant tumor regression with combination treatment. Heart and tumor areas are drawn up and marked with yellow and red lines respectively.

Figure 50E:
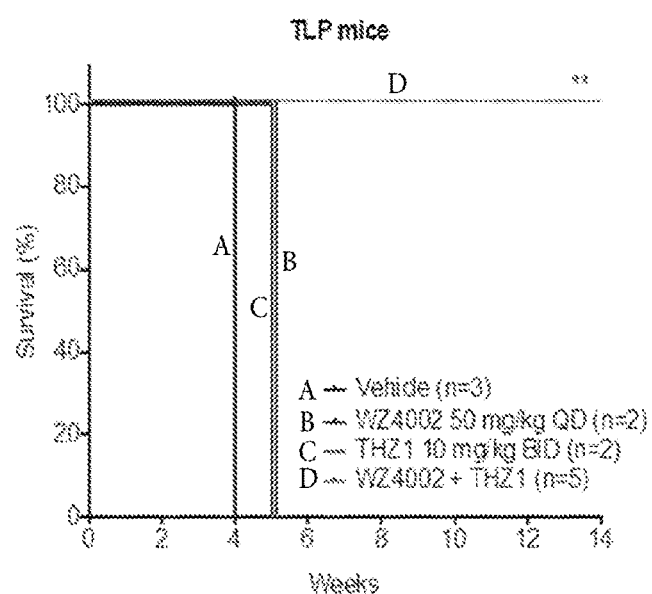

FIG. 50E shows survival curves for TLP mice treated with the indicated drugs. P-value determined by log-rank (Mantel-Cox) test analysis (*p-value<0.05, <0.005, *<0.0005).

Figure 51A:
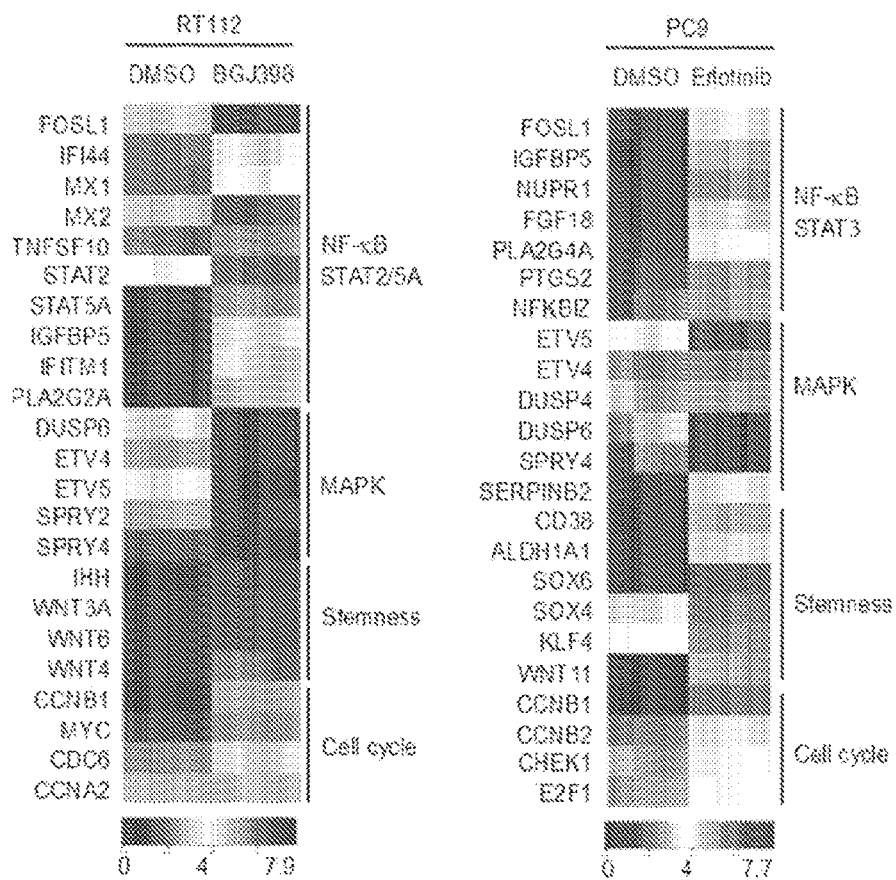

FIG. 51A shows heat maps of gene expression in BGJ398-tolerant RT112 cells and erlotinib-tolerant PC9 cells following 7 days of drug treatment (1 μM) compared to control. Heat maps display log 2-normalized fragments per kilobase of transcript per million mapped reads (FPKM) (3 biological replicates included per condition).

Figure 51B:
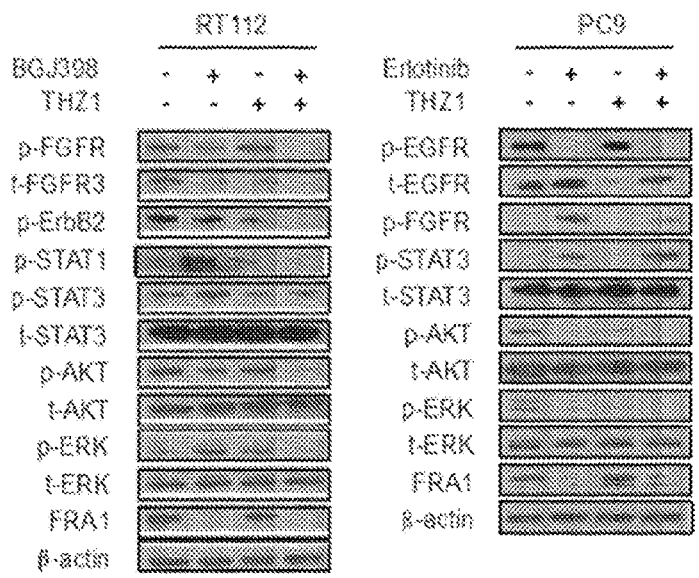

FIG. 51B shows the results of an immunoblot analysis in RT112 and PC9 at 24 hours treated with BGJ398 or erlotinib (1 μM), respectively, THZ1 (100 nM), or these in combination as indicated.

Figure 51C:
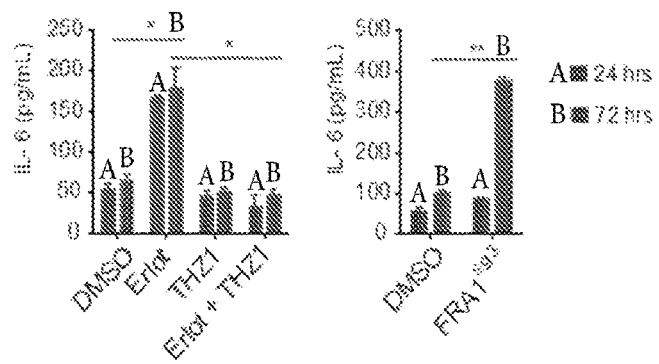

FIG. 51C shows graphs of IL-6 levels. Left panel: IL-6 levels in PC9-derived cell culture supernatants with control, erlotinib (Erlot), THZ1, or erlotinib+THZ1 (Erlot+THZ1), at the doses used in FIG. 51B, at 24 and 72 hours as determined by ELISA. Mean+/−SD from three biological replicates is shown. Right panel: IL-6 levels in FRA1-deficient PC9 cells at 24 and 72 hours as determined by ELISA. Mean+/−SD from three biological replicates is shown.

Figure 51D:
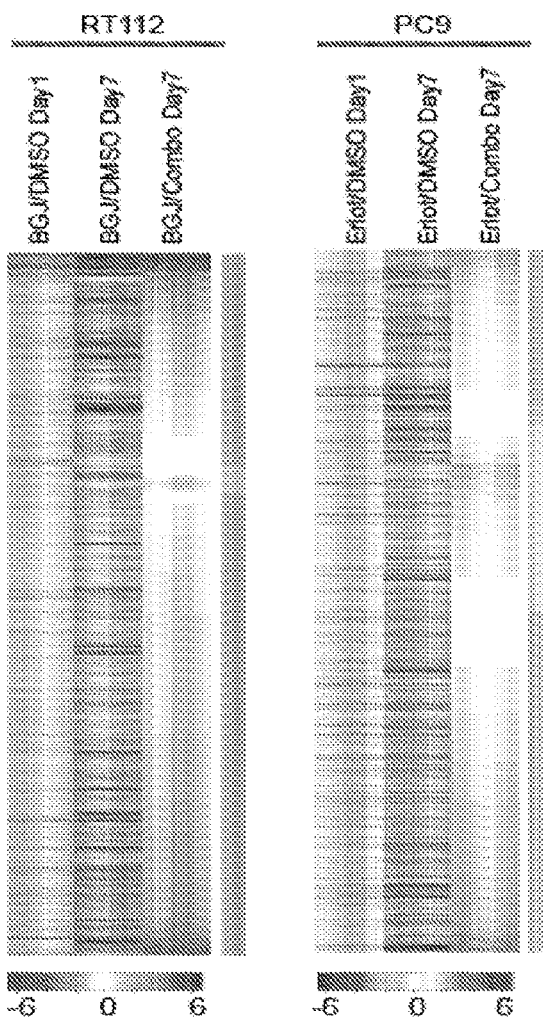

FIG. 51D shows heat maps of gene expression in RT112 and PC9 following treatment with BGJ398 (BGJ) or erlotinib (Erlot) compared to control (at day 1 and day 7). The third column compares gene expression in cells treated with targeted therapy alone versus THZ1 in combination with targeted therapy (Combo) at day 7. Log 2-normalized fold-changes are shown (mean of 3 biological replicates). The green-orange bar to the right of the heat map indicates whether combination treatment repressed or enhanced the effects of targeted therapy (green=repressed, orange=enhanced).

FIG. 51E shows a graph of select transcripts that were differentially expressed between targeted therapy and combination treatment with THZ1. Log 2-normalized fold-change is shown for RT112 (top panel) and PC9 cells (bottom panel) treated with the indicated drugs, relative to control-treated cells (mean of 3 biological replicates for each treatment group).

FIG. 51F shows the H3K27Ac ChIP-Seq signal in control and targeted therapy-treated cells. Color-coded horizontal lines denote the median enhancer signal in the distributions. Groups are compared by two-tailed t-test. Top panel: BGJ398 induces a significant increase in H3K27Ac signal at enhancers associated with genes that correspondingly have increased expression upon BGJ398 treatment in RT112 cells. H3K27Ac signal is shown for the top 200 most up-regulated genes for DMSO and BGJ398-treated RT112 cells. Bottom panel: Erlotinib induces a significant increase in H3K27Ac signal at enhancers associated with genes that correspondingly have increased expression upon erlotinib treatment in PC9 cells. H3K27Ac signal is shown for the top 200 most up-regulated genes for DMSO and erlotinib-treated PC9 cells.

FIG. 51G shows the RNA-Seq expression in control, targeted therapy-treated, and combination therapy-treated cells. Genes whose expression is induced by targeted therapy are significantly less induced by targeted therapy in combination with THZ1. Color-coded horizontal lines denote the median log 2-normalized FPKM values (3 biological replicates per treatment group). Top panel: Gene expression of the top 200 up-regulated genes with BGJ398 treatment in RT112 cells treated with DMSO, BGJ398, or combined THZ1+BGJ398 treatment is shown. Treatment with BGJ398 induces a significant increase in gene expression (two tailed t-test, p=4.13×10-46), but combined THZ1 and BGJ398 treatment significantly reduces this increase (two-tailed t-test, p=4.90×10-19). Bottom panel: Similarly, gene expression of the top 200 up-regulated genes with erlotinib treatment in PC9 cells treated with DMSO, erlotinib, and combined THZ1+erlotinib treatment. Treatment with erlotinib induces a significant increase in gene expression (two-tailed t-test, p=4.81×10-70), but combined THZ1 and erlotinib treatment significantly reduces this increase (two-tailed t-test, p=8.58×10-6).

Figure 51H:
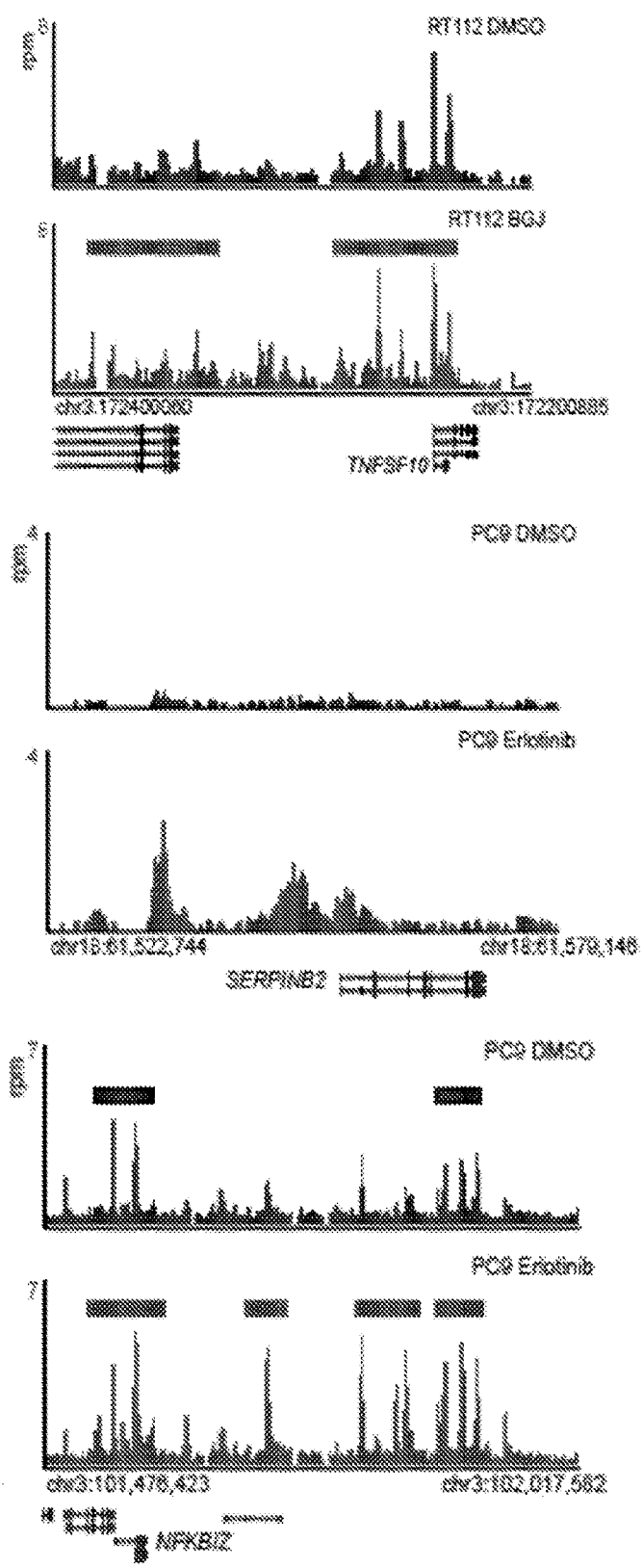

FIG. 51H shows H3K27Ac gene tracks in control and targeted therapy-treated cells for TNFSF10 (RT112), SERPINB2 (PC9), and NFKBIZ (PC9). Signal of ChIP-seq occupancy is in units of reads per million (rpm). Solid bars indicate super-enhancers.

Figure 52:
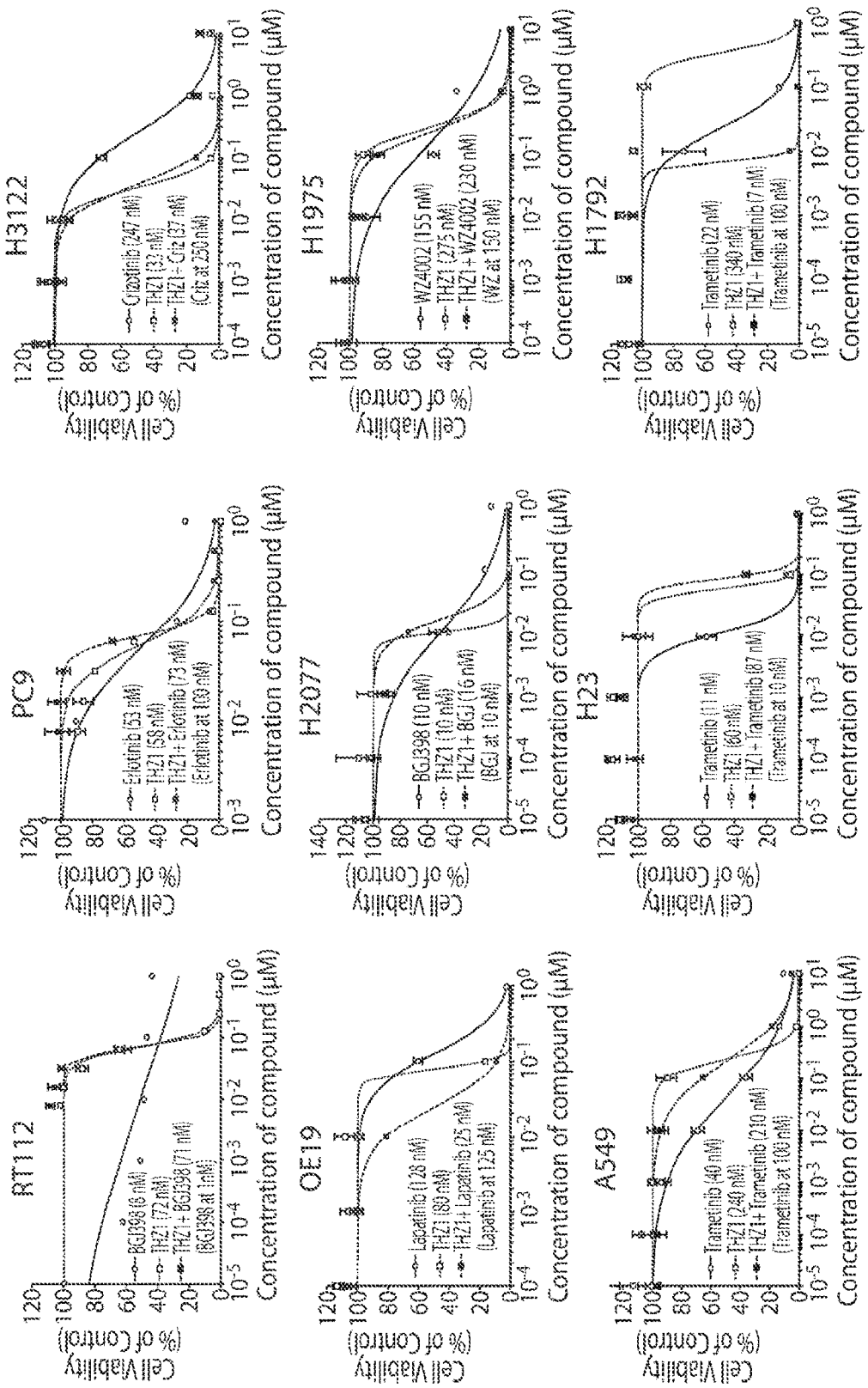

FIG. 52 shows the cell viability with Cell TiterGlo (96 hours) for the indicated oncogene-addicted cellular models used in colony formation assays (FIGS. 49A, 49D, and 53A) with targeted therapy, THZ1 or the combination of the two. Mean (3 biological replicates)+/−SD shown. Dose response curves for combination treatment were normalized to targeted therapy alone at the indicated dose. IC50 values are shown in parentheses.

Figure 53A:
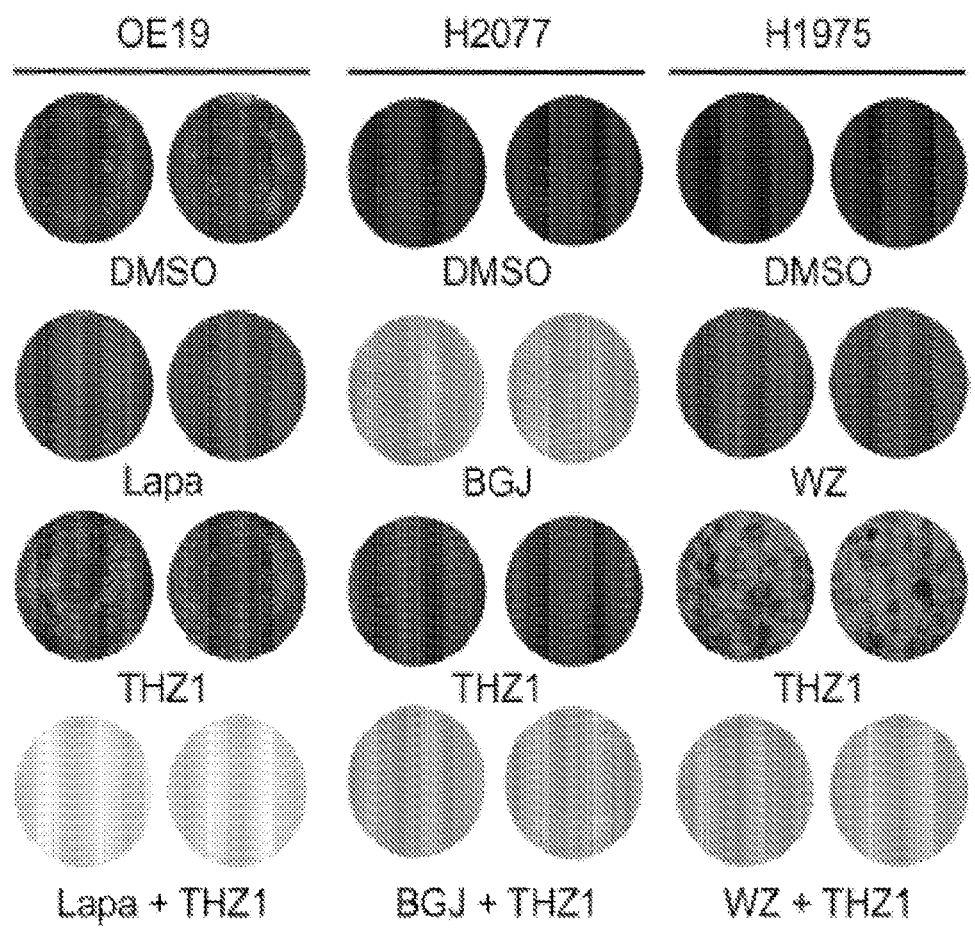

FIG. 53A shows the results of colony formation assays for receptor tyrosine kinase-dependent cell lines, OE19 (HER2), H2077 (FGFR1), and H1975 (EGFR) were treated with DMSO, THZ1, the corresponding TKI (lapatinib, BGJ398, or WZ4002), or a combination of THZ1 with TKI. Colony formation was assayed by crystal violet staining at 4 weeks. Two representative wells from a minimum of three biological replicates are shown per condition. (OE19: lapatinib 150 nM, THZ1 125 nM; H2077: BGJ398 1 µM, THZ1 10 nM; H1975: WZ4002 1 µM, THZ1 500 nM).

Figure 53B:
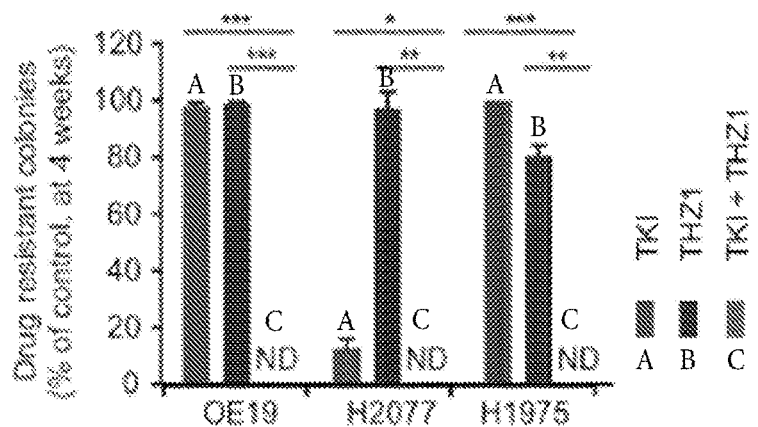

FIG. 53B shows a graph of the quantification of colony formation described in FIG. 53A shown as a percentage of the control. Mean (2 biological replicates)+/−standard deviation (SD) shown (*p-value<0.05, <0.005, *<0.0005, two-sided t-test). ND=not detectable.

Figure 53C:
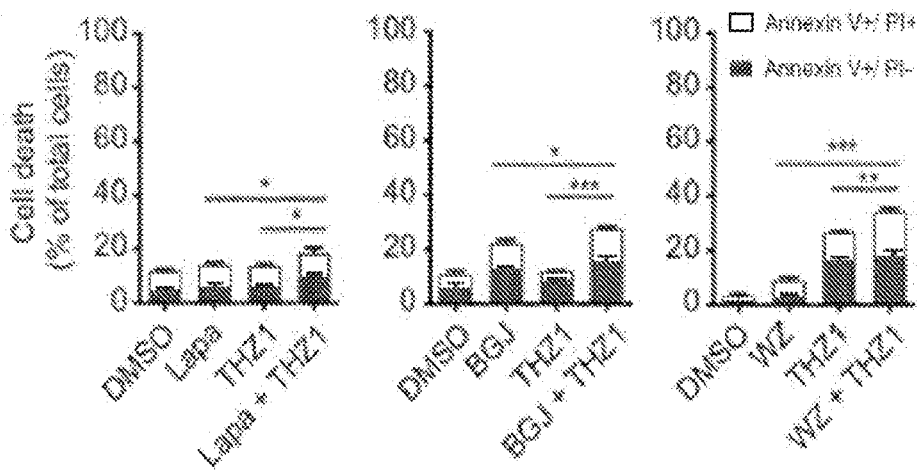

FIG. 53C shows the results of a cell death analysis with cells treated as in FIG. 53A by flow cytometry with Annexin V/PIstaining, following 48 hours of treatment (H2077 shown at 24 hours, due to differences in response to drug time-course). Mean (3 biological replicates)+/−SD shown (*p-value<0.05, <0.005, *<0.0005, two-tailed t-test). Left panel: OE19, middle panel: H2077, right panel: H1975.

Figure 53D:
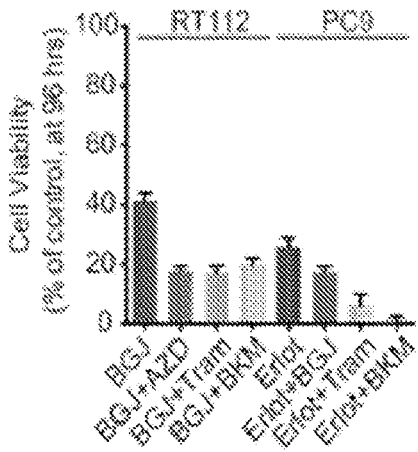

FIG. 53D shows the cell viability with Cell TiterGlo (96 hours), for drug tolerant populations that remain with dual kinase inhibition targeting known resistance mechanisms in RT112 and PC9 (BGJ=BGJ398 (FGFR inhibitor), Erlot=erlotinib (EGFR inhibitor), Tram=trametinib/GSK1120212 (MEK1/2 inhibitor), BKM=BKM120 (pan-PI3K inhibitor), AZD=AZD8931 (pan-ERBB inhibitor), all at 1 µM). Mean (3 biological replicates)+/−SD shown.

Figure 53E:
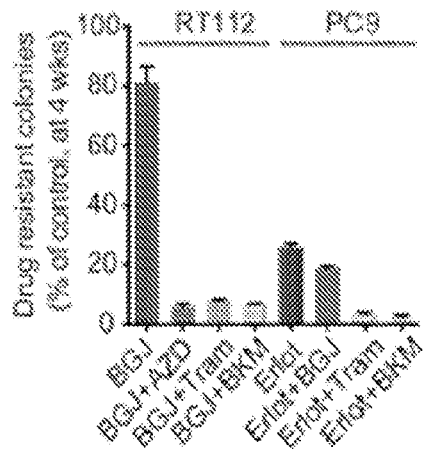

FIG. 53E shows a graph of the quantification of colony formation at 4 weeks with single or rational dual kinase inhibition in RT112 and PC9. Mean (2 biological replicates)+/−SD shown.

Figure 54A:
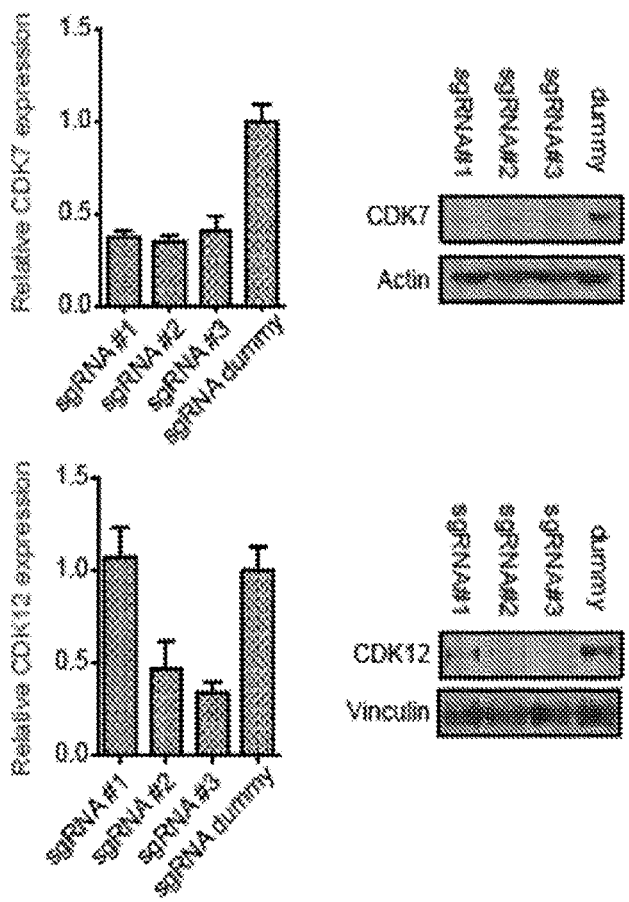

FIG. 54A shows the relative CDK7 and CDK12 expression (qRT-PCR) following knockdown with three different CDK7 or CDK12 single guide RNAs (sgRNA) and a dummy guide in PC9 cells. Mean (3 biological replicates)+/−SD shown. Corresponding immunoblot showing decreased expression with CDK7 or CDK12 knockdown for the three different sgRNAs compared to the dummy guide.

Figure 54B:
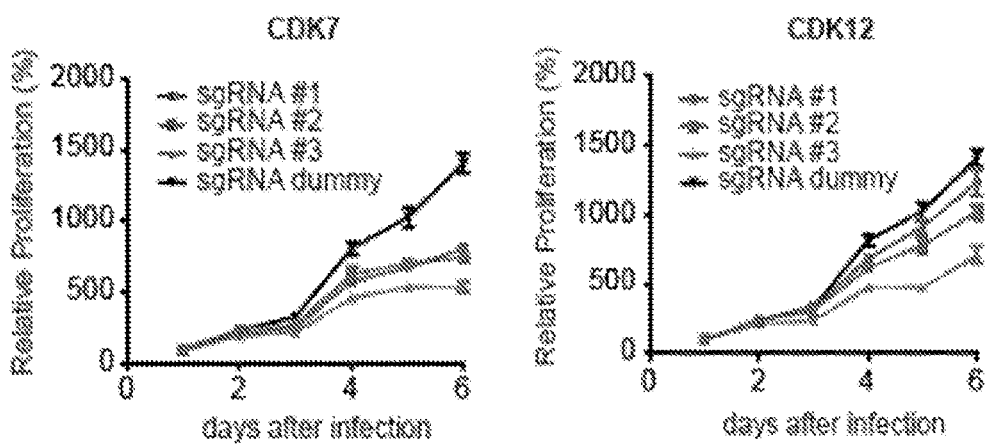

FIG. 54B shows the relative proliferation of PC9 cells following knockdown of CDK7 or CDK12 for the sgRNAs in FIG. 54A compared to the dummy guide. Mean (3 biological replicates)+/−SD shown.

Figure 54C:
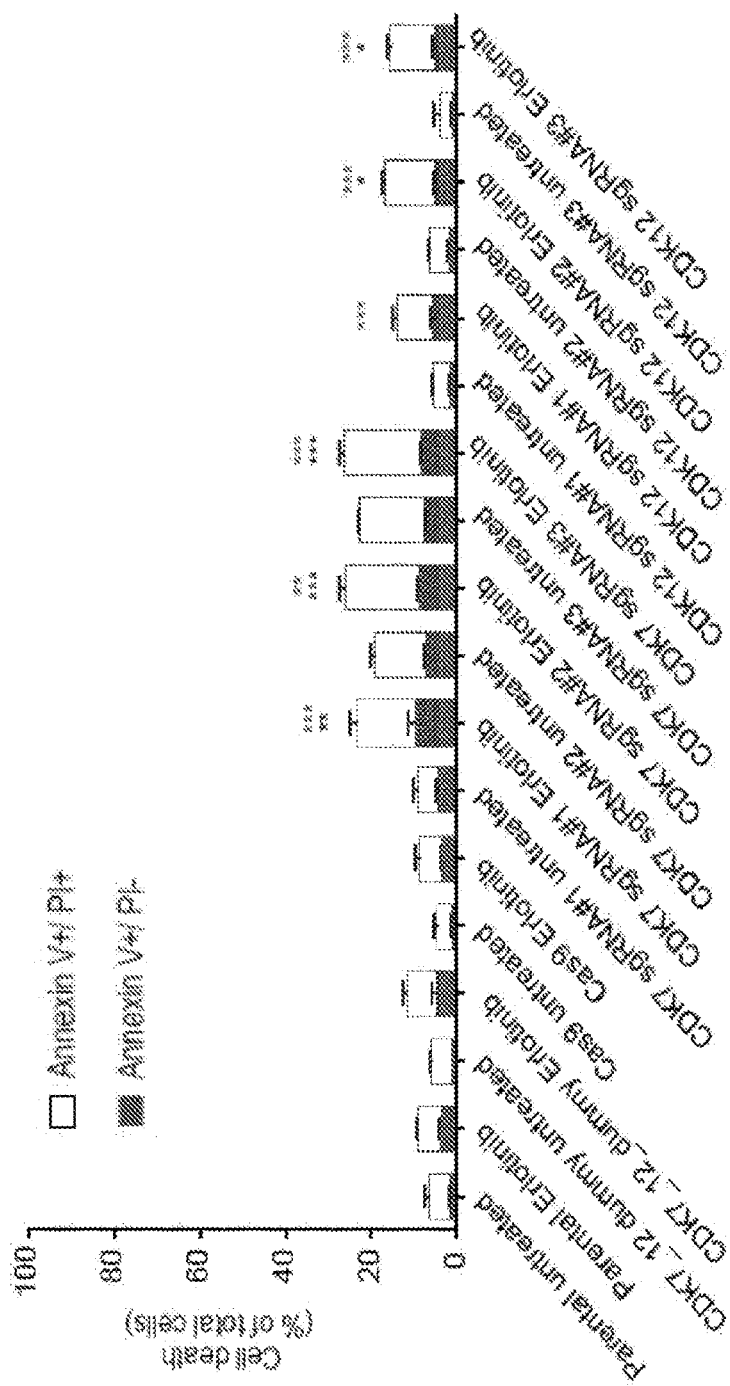

FIG. 54C shows the results of a cell death analysis by flow cytometry with Annexin V/PI staining in CDK7 and CDK12-deficient PC9 cells, following 48 hours of treatment with vehicle or erlotinib (1 µM). Mean (3 biological replicates)+/−SD shown (*p-value<0.05, <0.005, *<0.0005, two-tailed t-test, red asterix=compared to CDK7 or CDK12 sgRNA untreated, black asterix=compared to CDK7_12 dummy_Erlotinib).

Figure 55A:
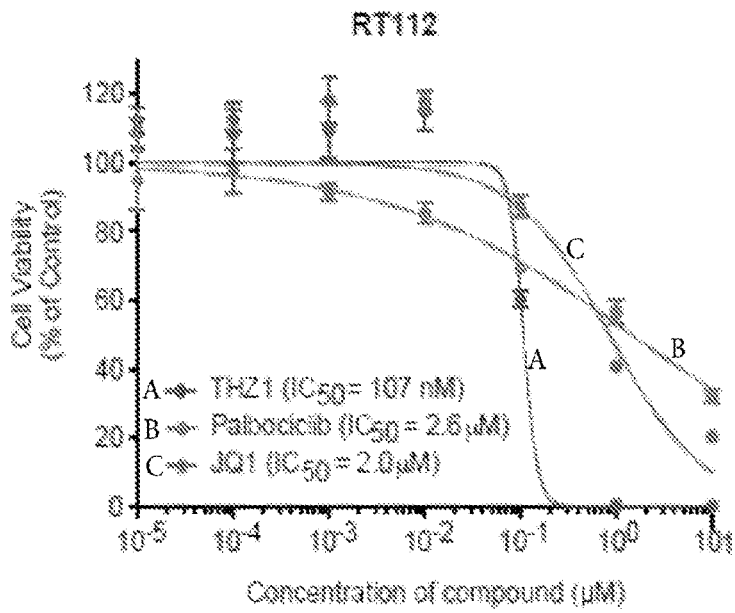

FIG. 55A shows dose response curves for PC9 cells, assayed by Cell TiterGlo (96 hours), for THZ1, palbociclib (CDK4/6 inhibitor) and JQ1 (BRD4 inhibitor). Mean (3 biological replicates)+/−SD shown. IC50 values are shown in parentheses.

Figure 55B:
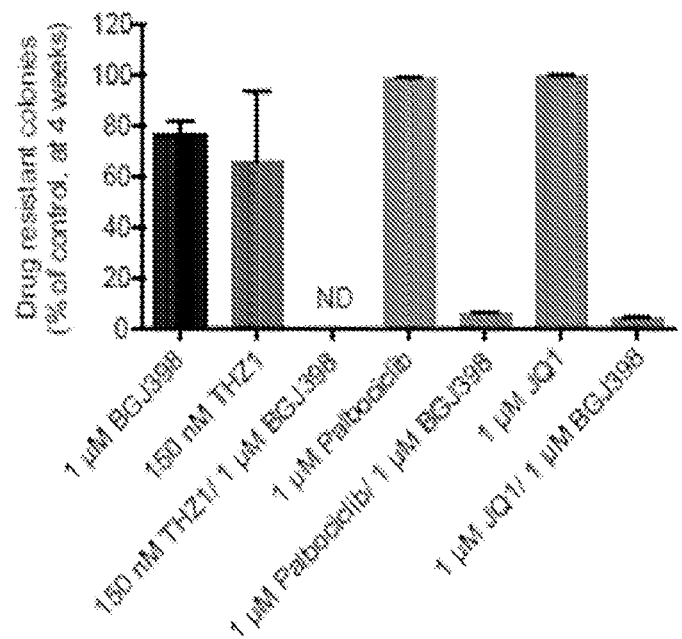

FIG. 55B shows the results of a colony formation assay in PC9 cells, assayed at 4 weeks by crystal violet with compounds in FIG. 55A. Mean (2 biological replicates)+/−standard deviation (SD) shown. ND=not detectable.

Figure 55C:
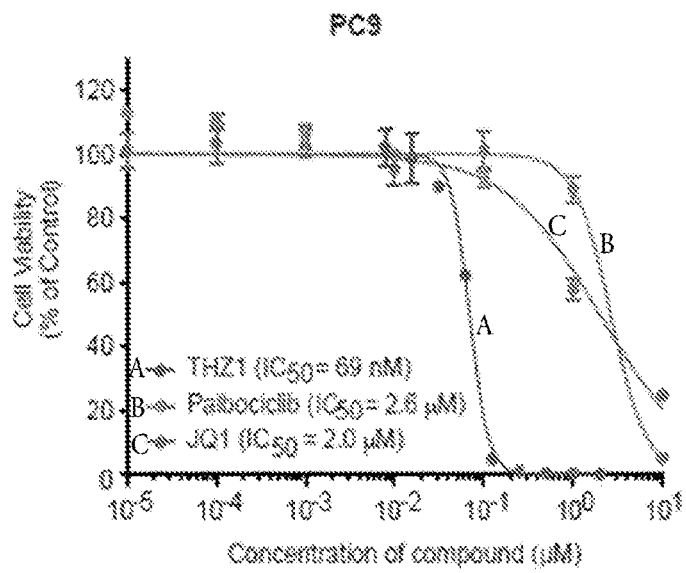

FIG. 55C shows dose response curves for RT112 cells, assayed by Cell TiterGlo (96 hours), with compounds as in FIG. 55A. Mean (3 biological replicates)+/−SD shown. IC50 values are shown in brackets.

Figure 55D:
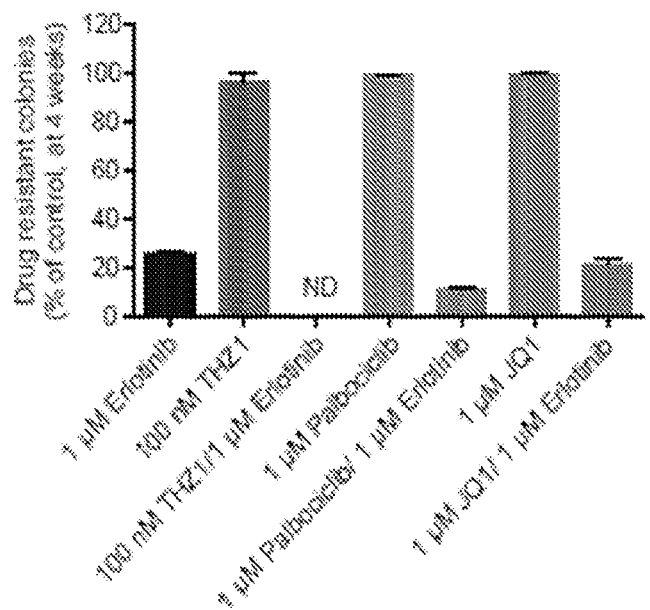

FIG. 55D shows the results of a colony formation assay in RT112 cells, assayed at 4 weeks by crystal violet with compounds in FIG. 55C. Mean (2 biological replicates)+/−standard deviation (SD) shown. ND=not detectable.

Figure 56A:
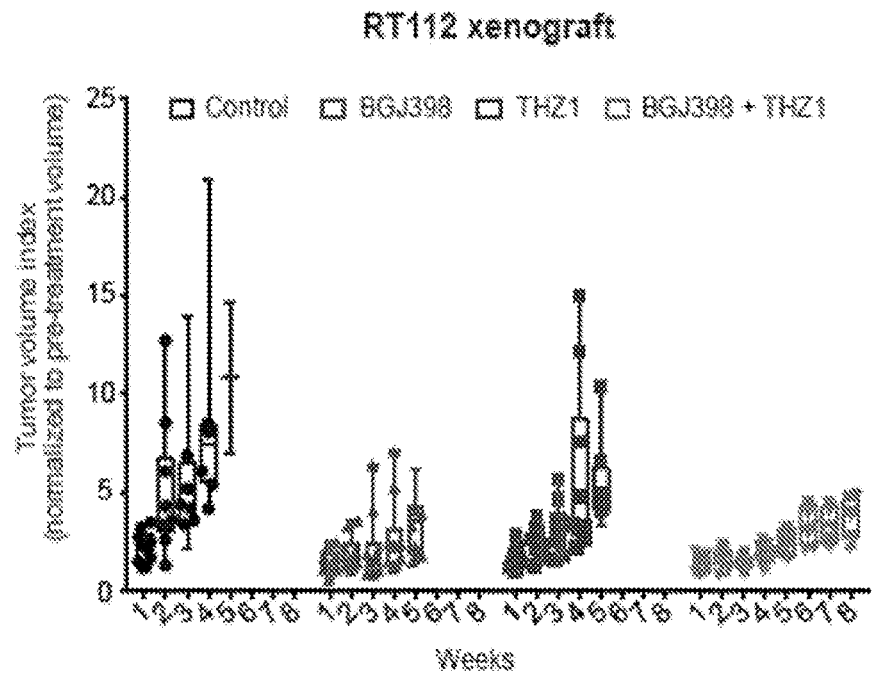

FIG. 56A shows a tumor volume index normalized to pre-treatment volume for mice bearing RT112 tumors treated with the indicated drugs for 8 weeks (n=5 mice in each treatment group, equivalent to 10 tumours in each group).

Figure 56B:
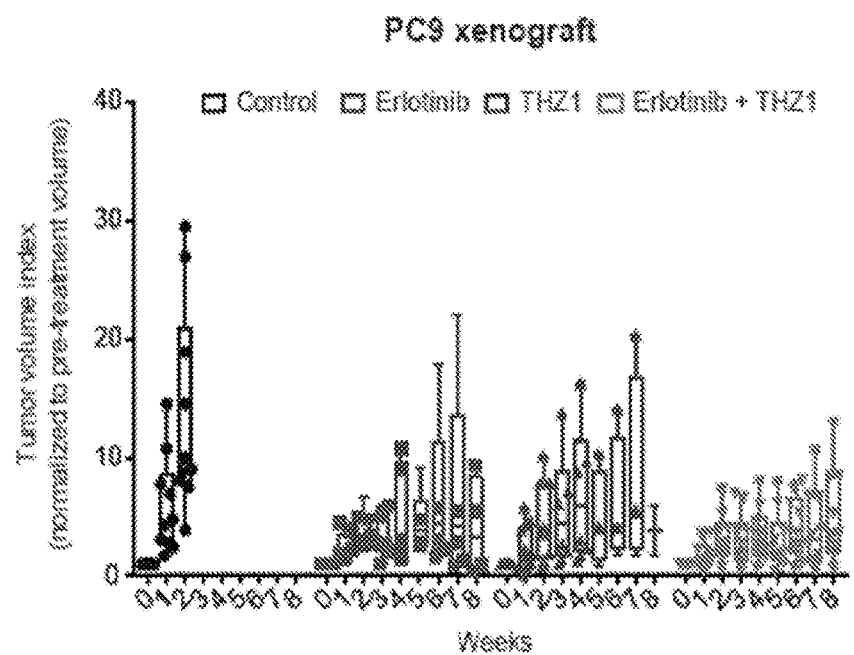

FIG. 56B shows a tumor volume index normalized to pre-treatment volume for mice bearing PC9 tumors, treated with the indicated drugs for 8 weeks (n=5 mice in each treatment group, equivalent to 10 tumours in each group).

Figure 56C:
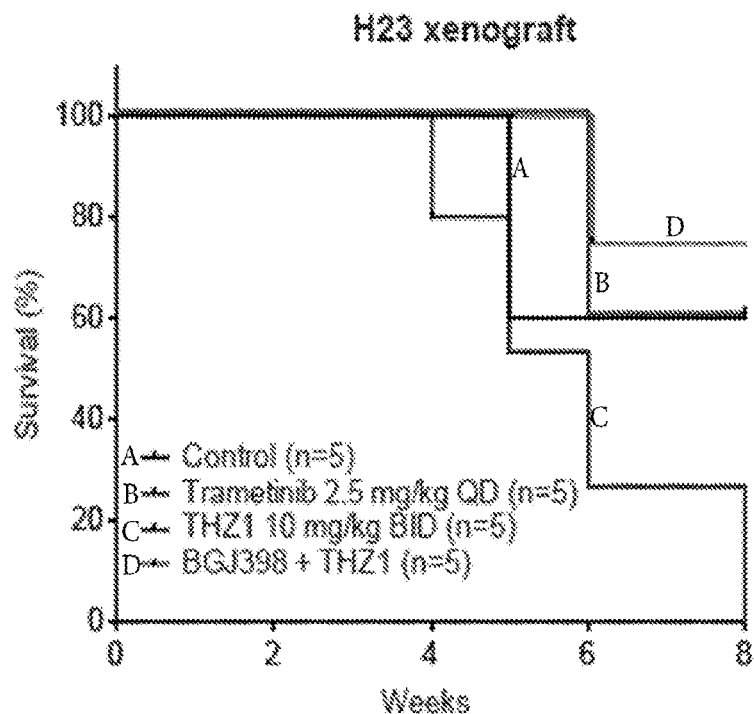

FIG. 56C shows survival curves for mice bearing H23 tumors that were treated with the indicated drugs for 8 weeks (n=5 mice in each treatment group, equivalent to 10 tumours in each group). Survival over time is shown as a percentage for each treatment group. P-value is based on log-rank (Mantel-Cox) test analysis.

Figure 56D:
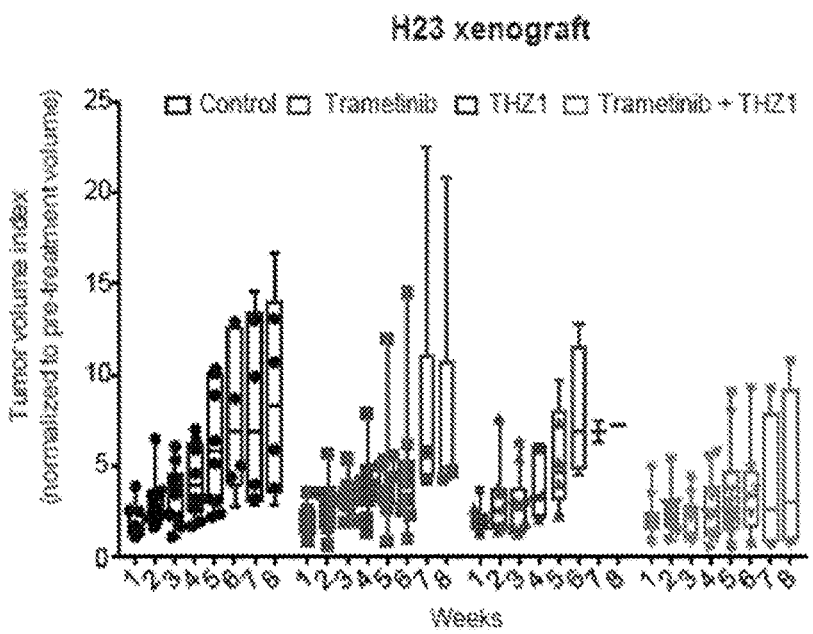

FIG. 56D shows a tumor volume index for mice with H23 tumors treated with the indicated drugs for weeks (n=5 mice in each treatment group, equivalent to 10 tumours in each group).

FIG. 57A shows the results of gene ontology term (Go-term) analysis of biological processes enriched based on gene expression data following 7 days of treatment with BGJ398 (RT112 cells) or erlotinib (PC9).

FIG. 57B shows the results of Ingenuity upstream regulator analysis of gene expression profiles from RT112 and PC9 cells treated with BGJ398 (RT112) or erlotinib (PC9) for 7 days.

Figure 58A:
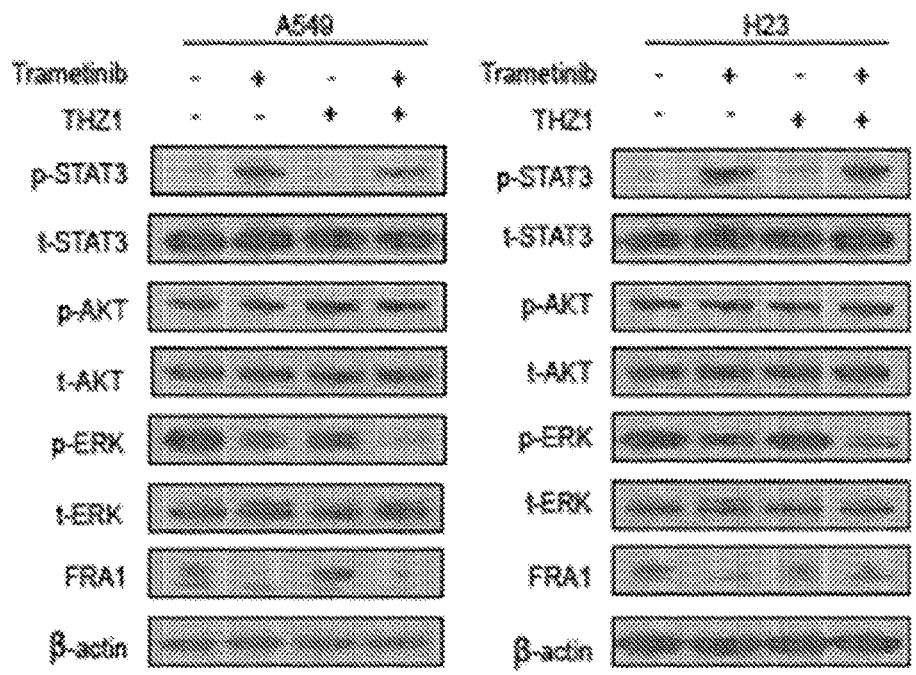

FIG. 58A shows immunoblot analyses in A549 and H23 at 24 hours treated with trametinib (250 nM and 500 nM, respectively), THZ1 (150 nM, and 100 nM, respectively), or these in combination as indicated.

Figure 58B:
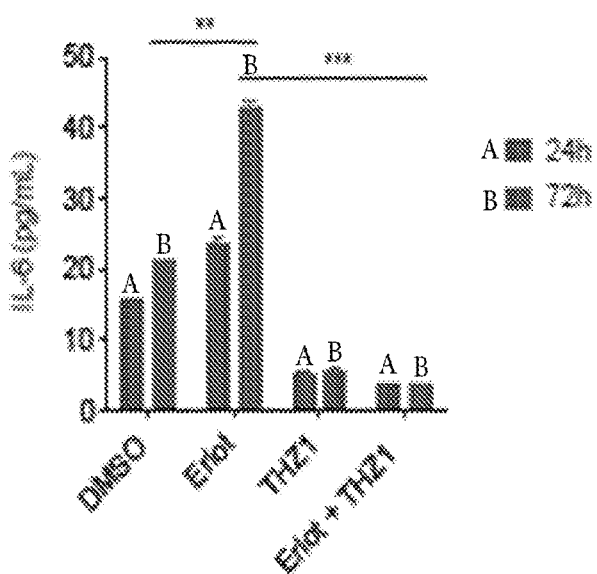

FIG. 58B shows a graph of IL-6 levels in PC9-derived cell culture supernatants with control, erlotinib (1 µM), THZ1 (100 nM), or erlotinib and THZ1 combined, at 24 and 72 hours as determined by Luminex-based cytokine analysis. Mean (2 technical replicates)+/−SD shown. (*p value<0.05, <0.005, *<0.0005, two-tailed t-test).

Figure 58C:
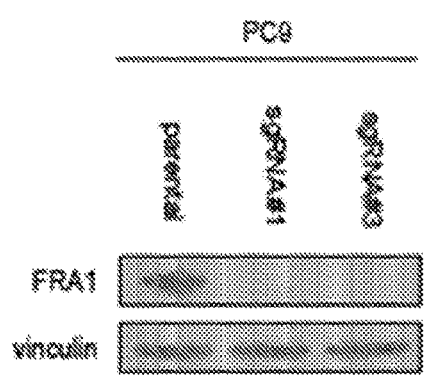

FIG. 58C shows an immunoblot analysis of total FRA1 protein levels in parental PC9 cells and PC9 cells transduced with sgRNAs targeting FRA1.

Figure 58D:
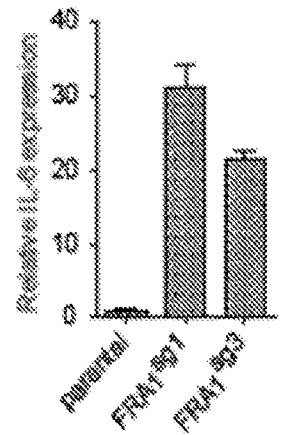

FIG. 58D shows a graph of the relative IL-6 expression (qRT-PCR) in PC9 parental cells and FRA1-deficient PC9 cells with sgRNA #1 and sgRNA #3. Mean (3 biological replicates)+/−SD shown.

Figure 58E:
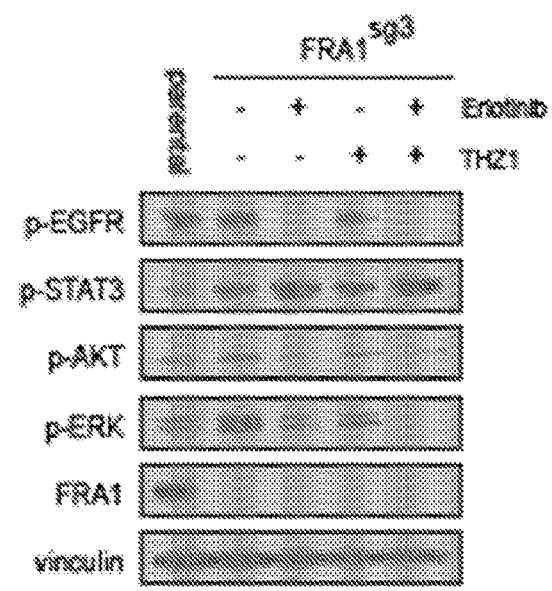

FIG. 58E are immunoblot analyses showing signaling changes in PC9 cells transduced with sgRNA #3 targeting FRA1, compared to PC9 parental cells. Cells were treated with erlotinib (1 µM), THZ1 (100 nM), or erlotinib and THZ1 combined for 24 hours as indicated.

Figure 58F:
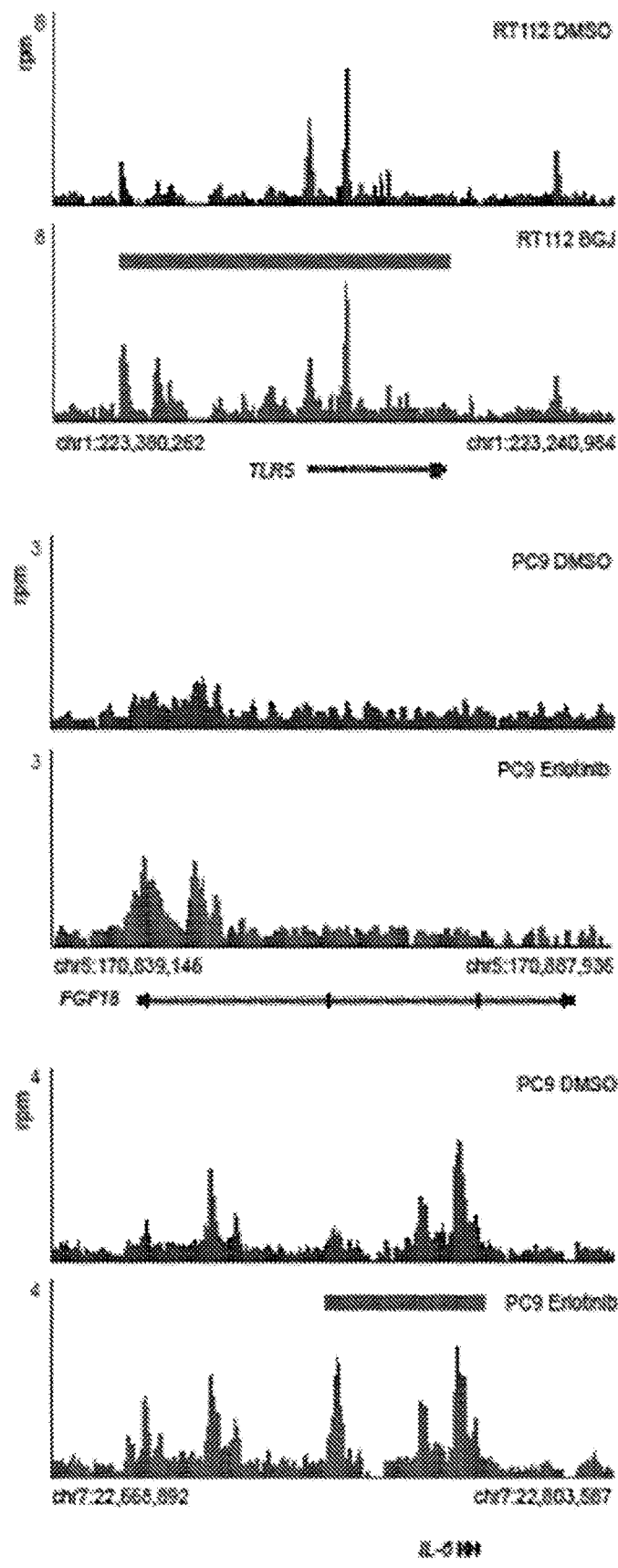

FIG. 58F shows gene tracks of H3K27Ac ChIP-seq occupancy a t the TLR5 gene locus in RT112 cells and FGF18 and IL-6 loci in PC9 following 7-day treatment with DMSO, BGJ398 (RT112) or erlotinib (PC9). Signal of ChIP-seq occupancy is in units of reads per million (rpm). Solid bars indicate super-enhancers.

Figure 59A:
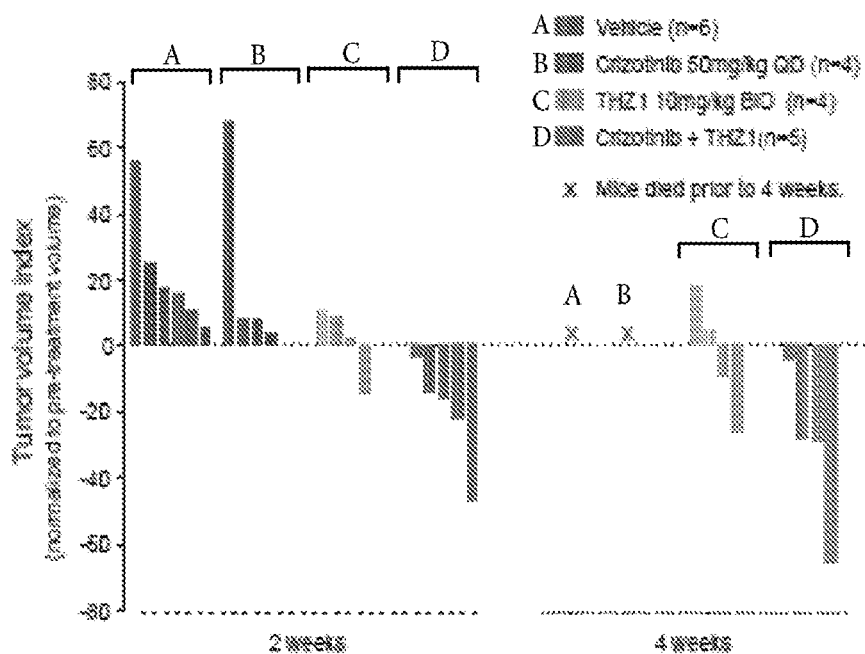

FIG. 59A shows a tumor volume index after 2 and 4 weeks normalized to pre-treatment volume for an EML4-ALK-mutant genetically engineered mouse model in which the floxed EML4-ALK fusion oncogene is induced in the lung by installation of Cre recombinase by adenovirus. Cells were treated with either vehicle, crizotinib, THZ1, or THZ1 and crizotinib.

Figure 59B:
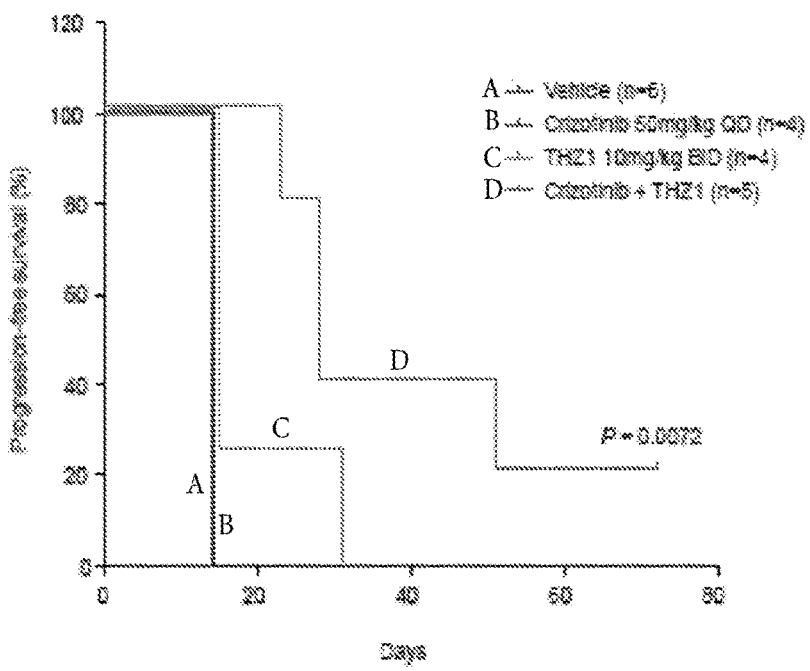

FIG. 59B shows the progression free survival for the ALK-mutant genetically engineered mouse model in FIG. 59A during treatment with vehicle, crizotinib, THZ1, or THZ1 and crizotinib.

Figure 60:
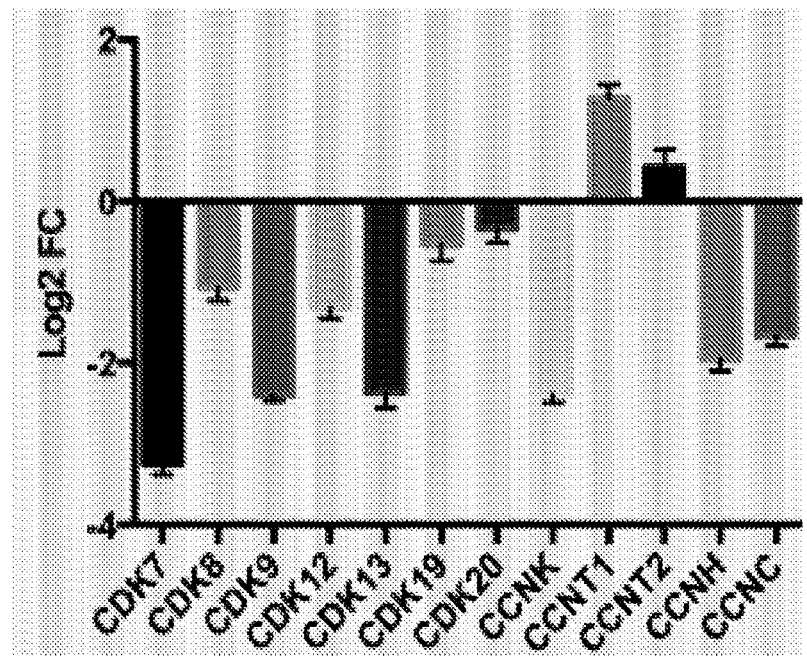

FIG. 60 shows synergy among genetic depletion of CDK and cyclin genes using CRISPR in combination with erlotinib. Genes which show negative enrichment (e.g. CDK7, CDK9 and CDK12 demonstrate synergy with erlotinib).

FIG. 61 shows the results of colony formation assays PC9 cells treated with DMSO, THZ5-31-1, erlotinib, or a combination of THZ5-31-1 and erlotinib, at the nM concentrations of THZ5-31-1 indicated.

Figure 62:
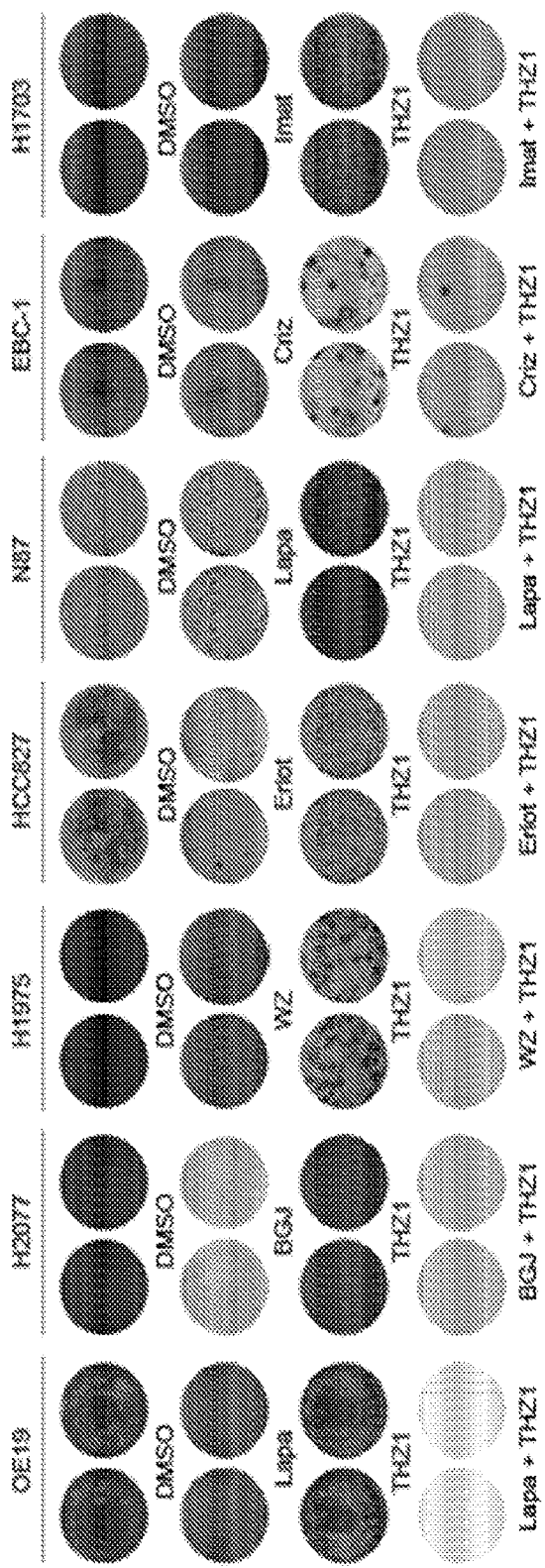

FIG. 62 shows the results of colony formation assays at 4 weeks for receptor tyrosine kinase-dependent cell lines, OE19 (HER2), H2077 (FGFR1), H1975 (EGFR), HCC827 (EGFR), N87 (HER2), EBC-1 (MET), and H1703 (PDGFR) that were treated with DMSO, the corresponding tyrosine kinase inhibitor (lapatinib (Lapa), BGJ398 (BGJ), WZ4002 (WZ), erlotinib (Erlot), crizotinib (Criz), imatinib (Imat)), THZ1, or THZ1 in combination with the corresponding TKI. Two representative wells from a minimum of three biological replicates are shown per condition.

Figure 63A:
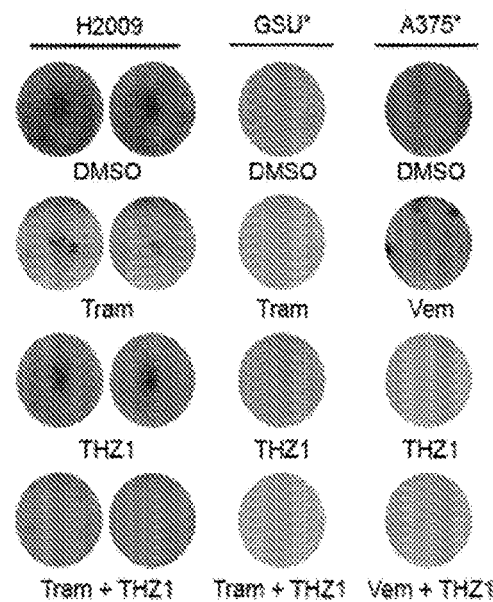

FIG. 63A the results of colony formation assays at 4 weeks for KRAS and BRAF-driven models, H2009 (KRAS), GSU (KRAS), A375 (BRAF), that were treated with DMSO, the corresponding kinase inhibitor (trametinib (Tram) or vemurafenib (Vem)), THZ1, or THZ1 in combination with the corresponding kinase inhibitor. Two representative wells from a minimum of three biological replicates are shown per condition. GSU and A375 are semi-adherent cell lines for which the effect is better depicted in FIG. 63B.

Figure 63B:
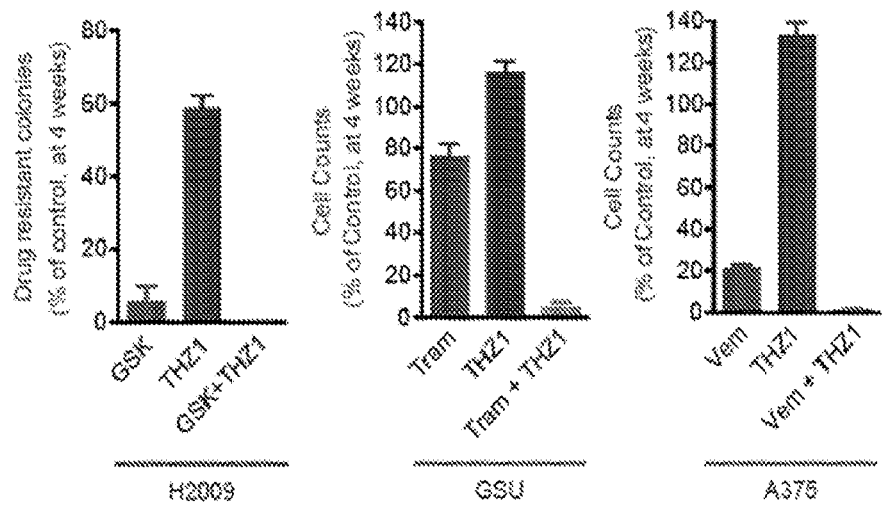

FIG. 63B shows graphs quantifying the colony formation described in FIG. 63A as a percentage of the control at 4 weeks. GSK=trametinib.

Figure 64A:
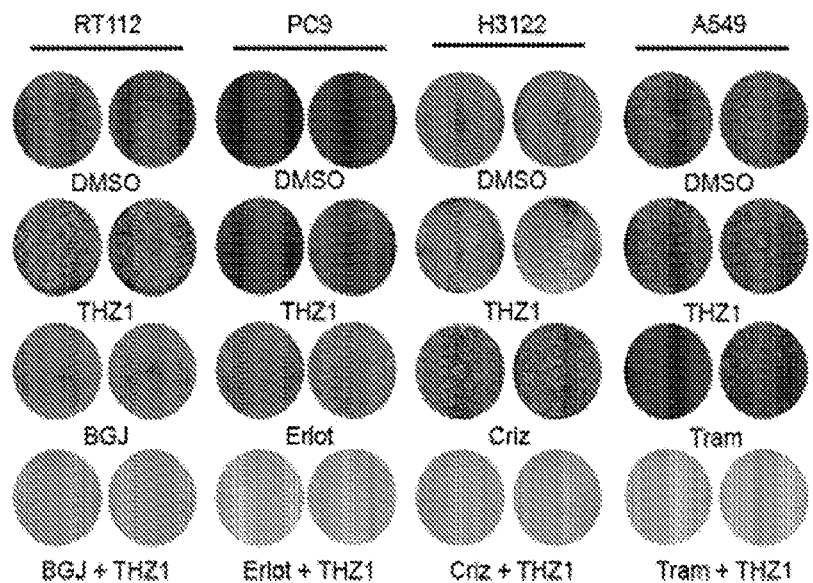

FIG. 64A the results of colony formation assays at 3 months for oncogene-dependent models RT112 (FGFR), PC9 (EGFR), H3122 (ALK), and A549 (KRAS), treated with DMSO, the corresponding kinase inhibitor (BGJ398 (BGJ), erlotinib (Erlot), crizotinib (Criz), or trametinib (Tram)), THZ1, or THZ1 in combination with the corresponding kinase inhibitor. Two representative wells from a minimum of three biological replicates are shown per condition.

Figure 64B:
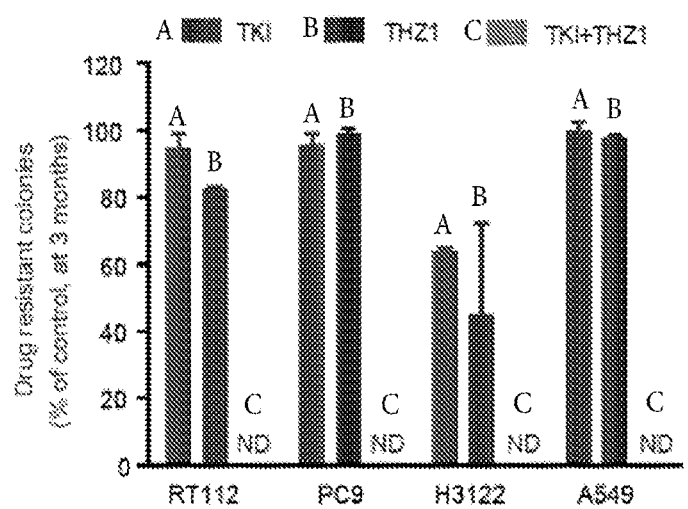

FIG. 64B shows a graph quantifying the colony formation described in FIG. 64A as a percentage of the control at 3 months. ND=not detectable.

Figure 65A:
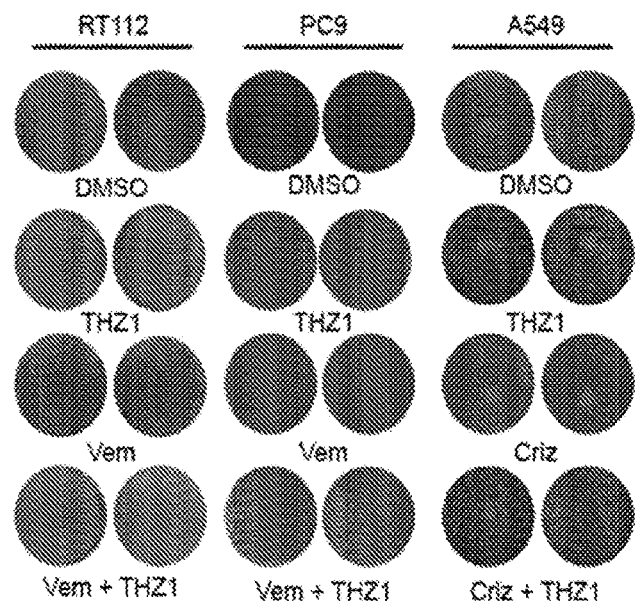

FIG. 65A shows the results of colony formation assays at 4 weeks for oncogene-dependent models RT112 (FGFR), PC9 (EGFR), and A549 (KRAS), treated with DMSO, a non-corresponding kinase inhibitor (vemurafenib (Vem) or crizotinib (Criz)), THZ1, or THZ1 in combination with the non-corresponding kinase inhibitor. Two representative wells from a minimum of three biological replicates are shown per condition. The non-corresponding kinase inhibitors for these assays were selected to not correspond with the cell line mutation, as shown: a BRAF inhibitor (vemurafenib) does not show effectiveness on an FGFR mutant cell line (RT112) or EGFR mutant cell line (PC9), and an ALK inhibitor (crizotinib) is ineffective against a KRAS mutant cell line (A549).

Figure 65B:
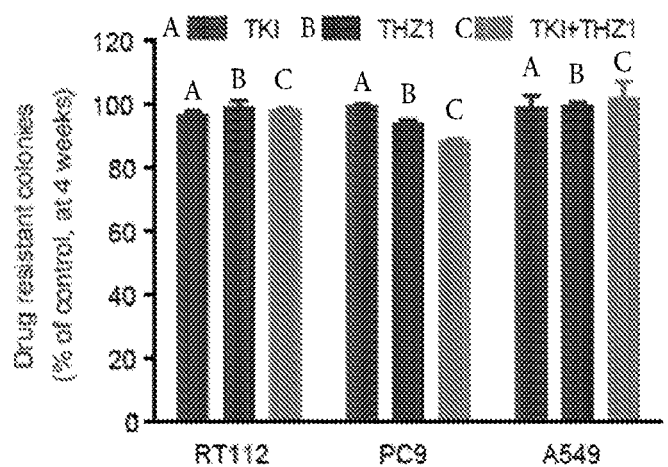

FIG. 65B shows a graph quantifying the colony formation described in FIG. 65A as a percentage of the control at 4 weeks.

Figure 66:
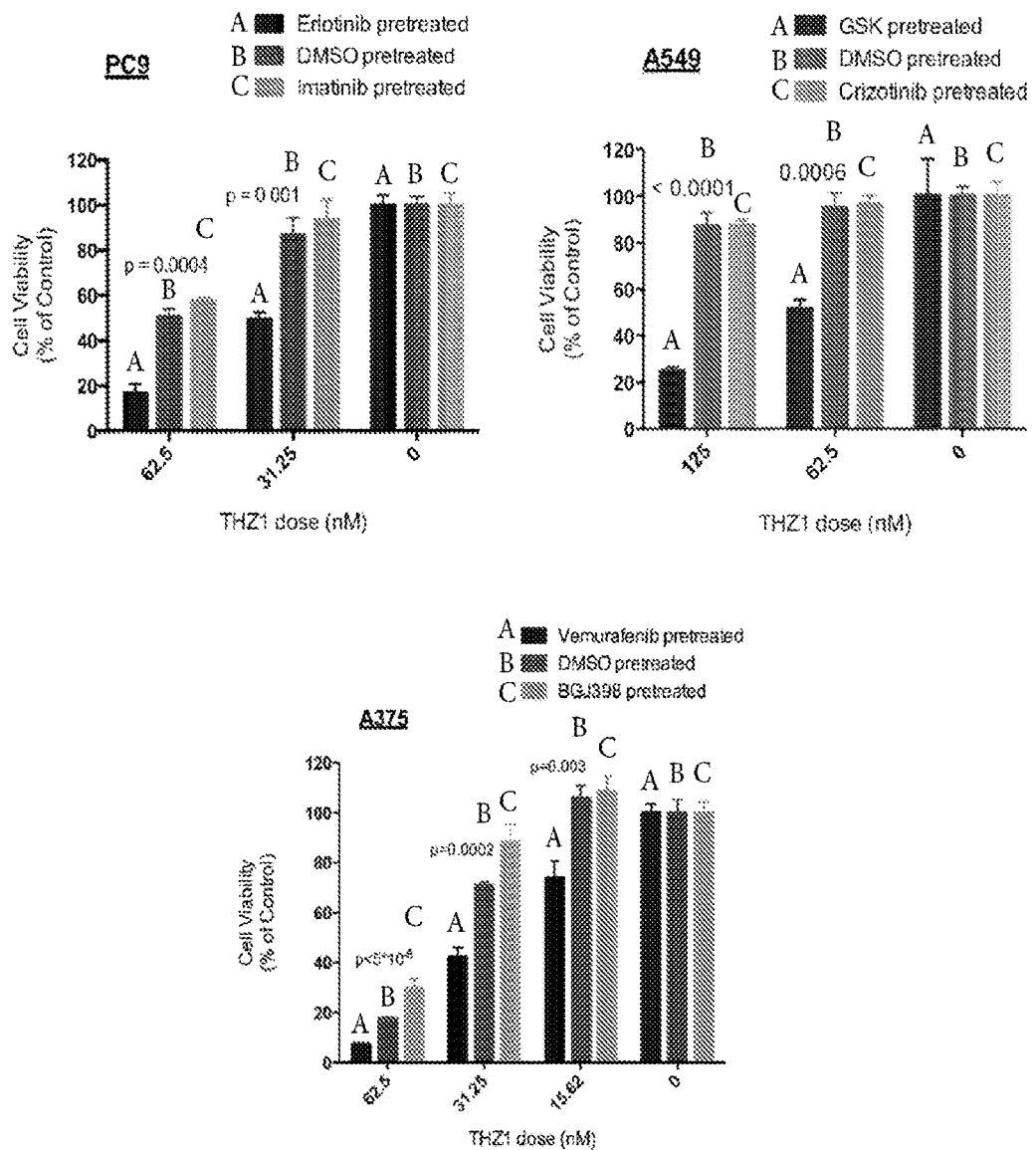

FIG. 66 shows the cell viability for PC9 (EGFR), A549 (KRAS), and A375 (BRAF) cells after pretreatment with either DMSO, a corresponding kinase inhibitor (erlotinib, trametinib (GSK), or vemurafenib), or a non-corresponding kinase inhibitor (imatinib, crizotinib, or BGJ398), followed by treatment with THZ1.

Figure 67:
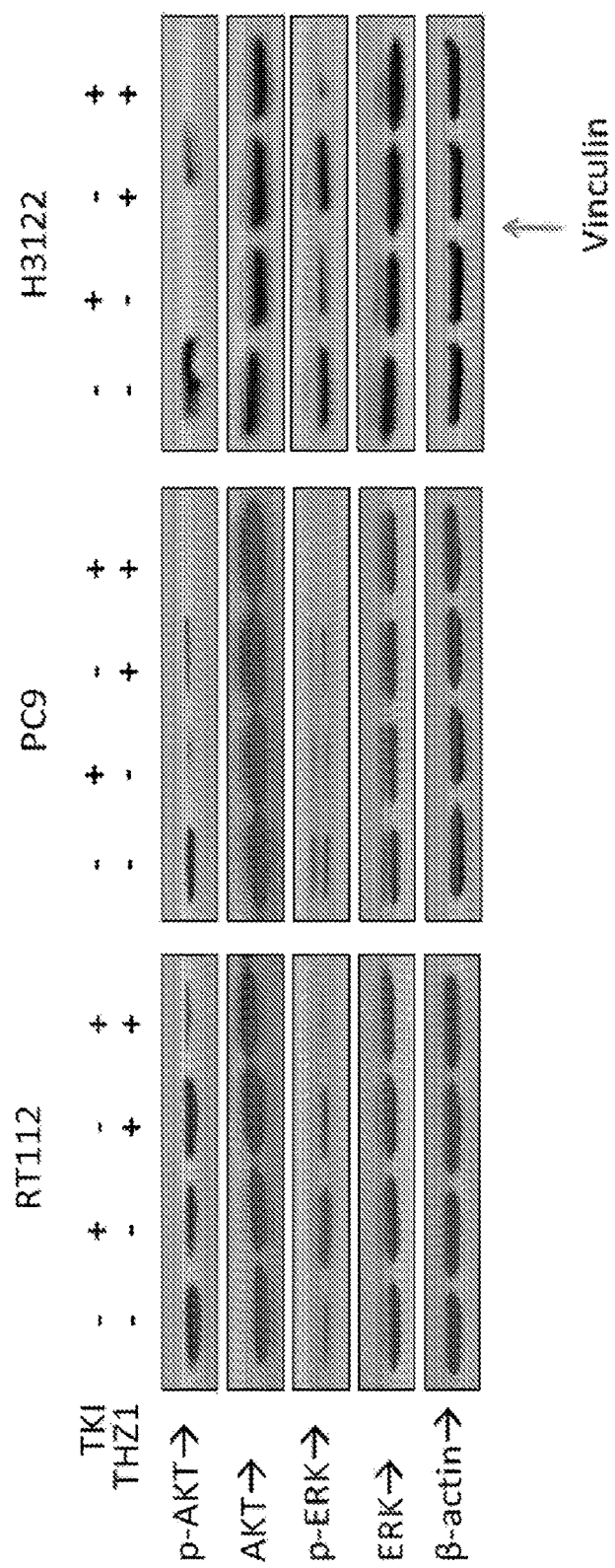
Figure 67:
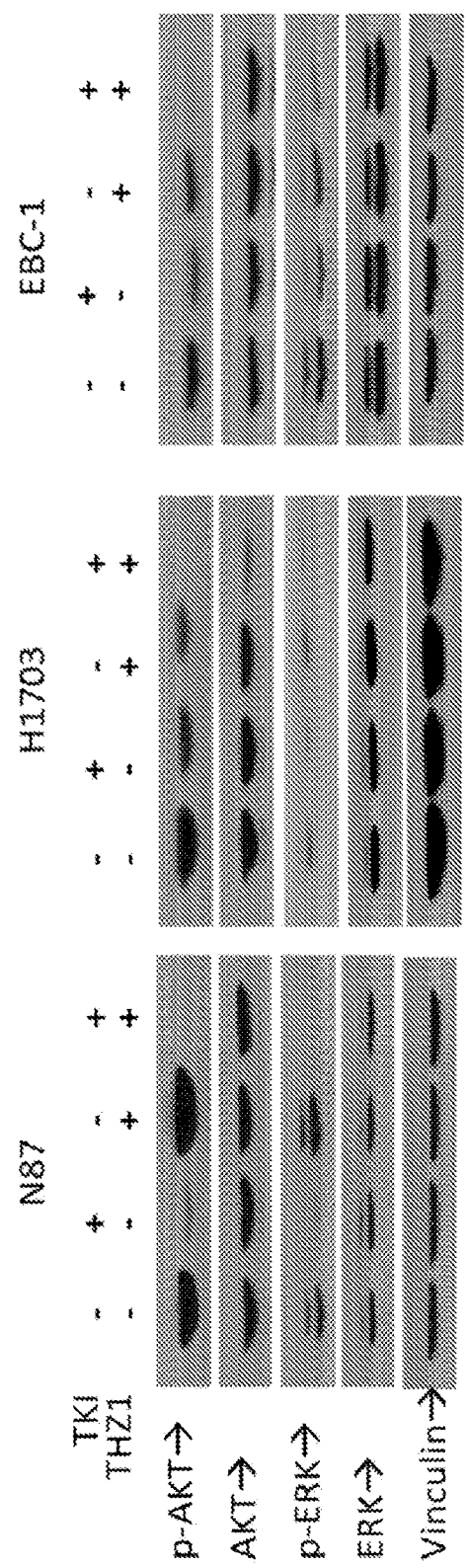
Figure 67:
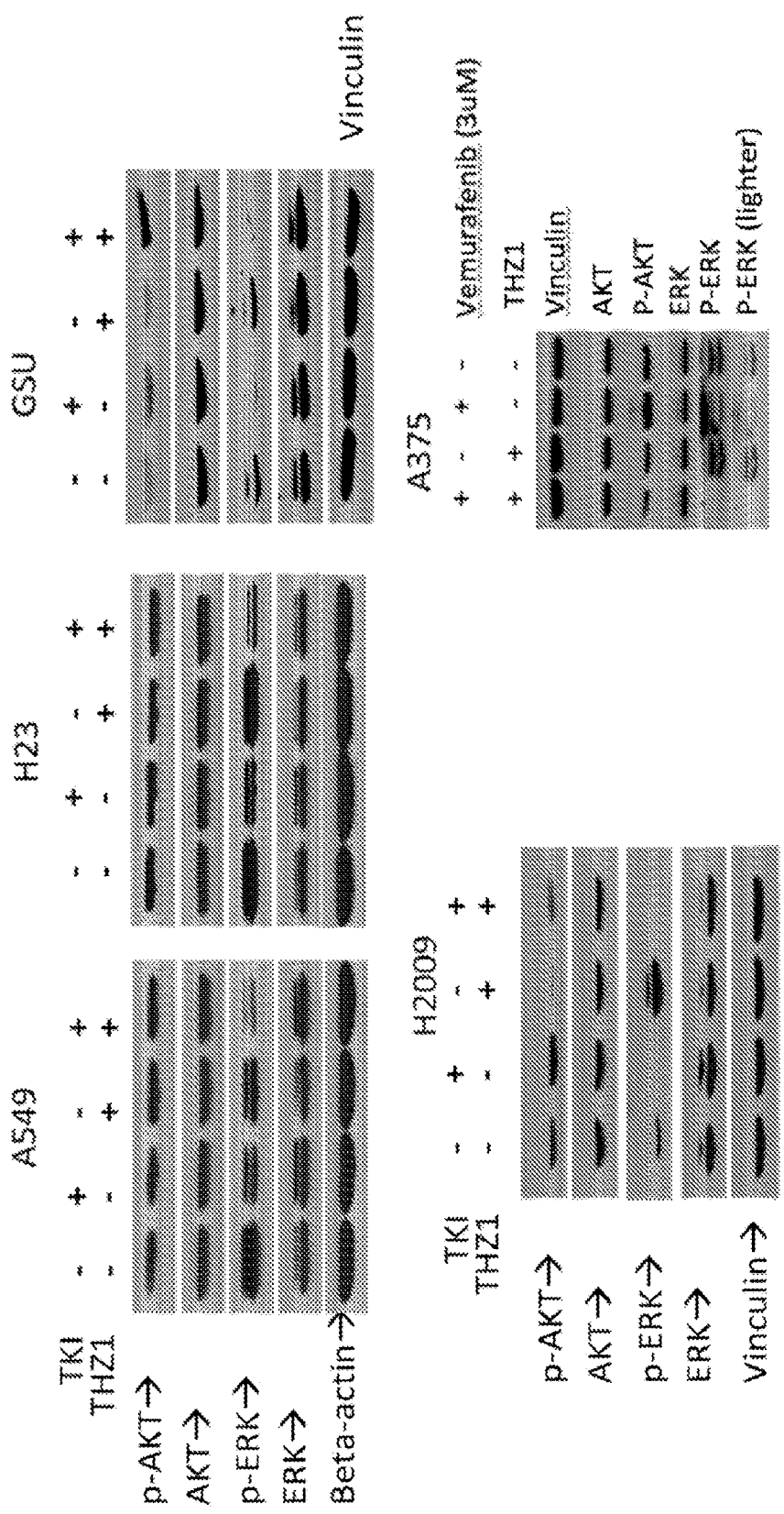

FIG. 67 shows Western blot results for the RT112, PC9, H3122, N87, H1703, EBC-1, A549, H23, GSU, H2009, and A375 cell lines, after either no treatment, treatment with a kinase inhibitor (labeled TKI or vemurafenib), treatment with THZ1, or treatment with the kinase inhibitor and THZ1. Notably, p-ERK is suppressed with the combination treatment of kinase inhibitor and THZ1.

Figure 68:
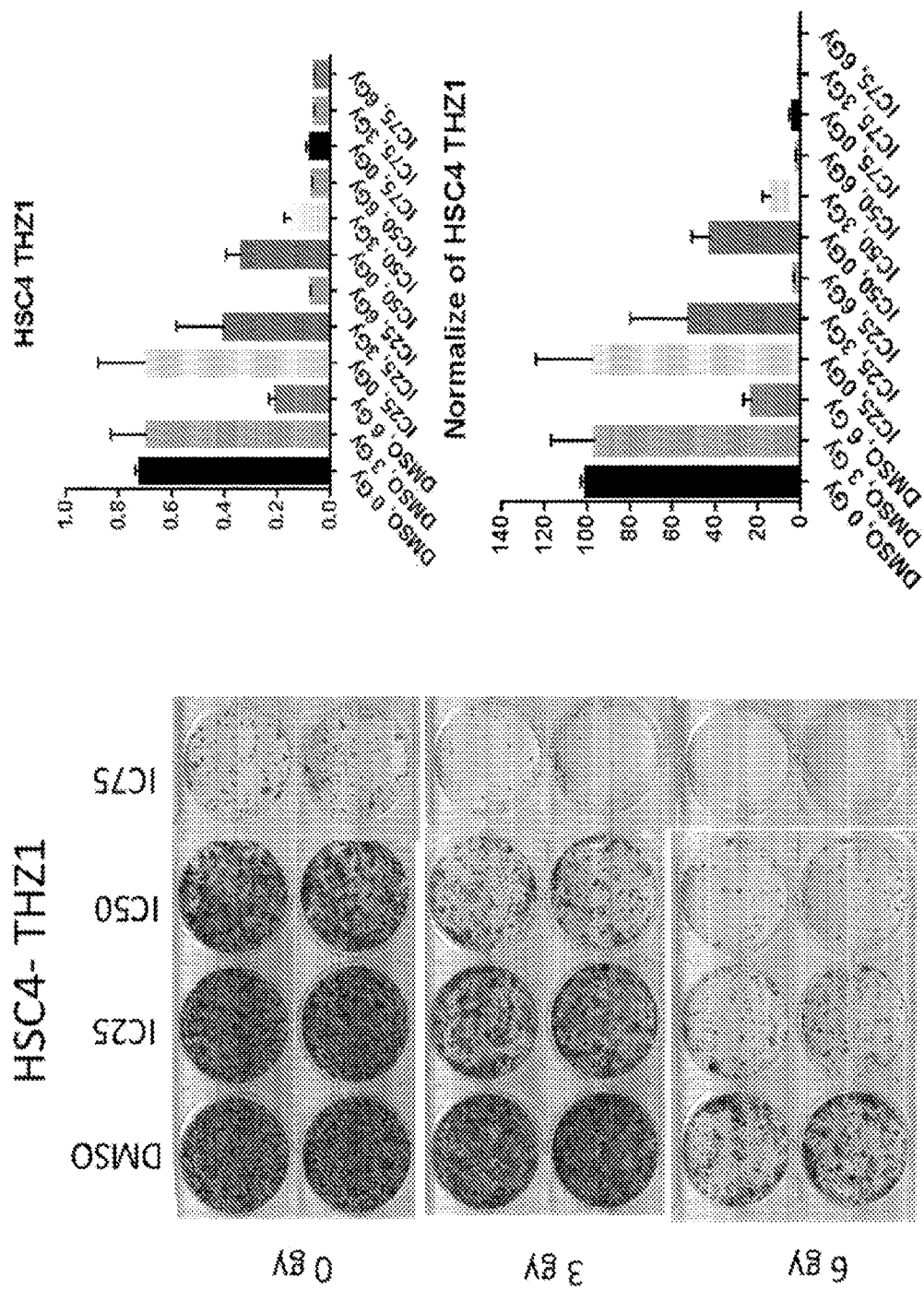

FIG. 68 shows the results of colony formation assays for HSC4 cells treated with radiation (0 Gy, 3 Gy, 6 Gy) and either DMSO or transcription inhibitor THZ1 (IC25, IC50, or IC75).

Figure 69:
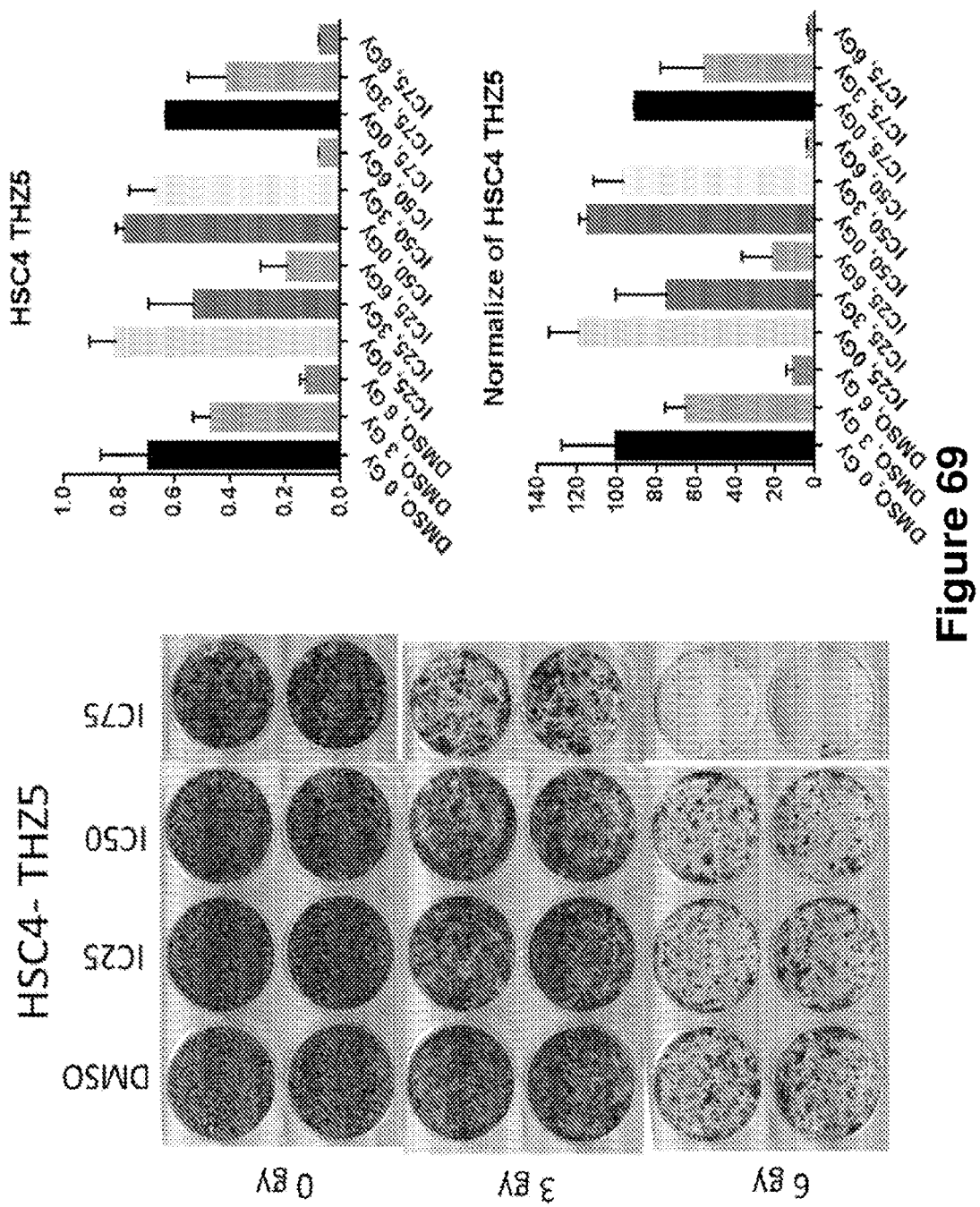

FIG. 69 shows the results of colony formation assays for HSC4 cells treated with radiation (0 Gy, 3 Gy, 6 Gy) and either DMSO or transcription inhibitor THZ5-31-1 (IC25, IC50, or IC75).

Figure 70:
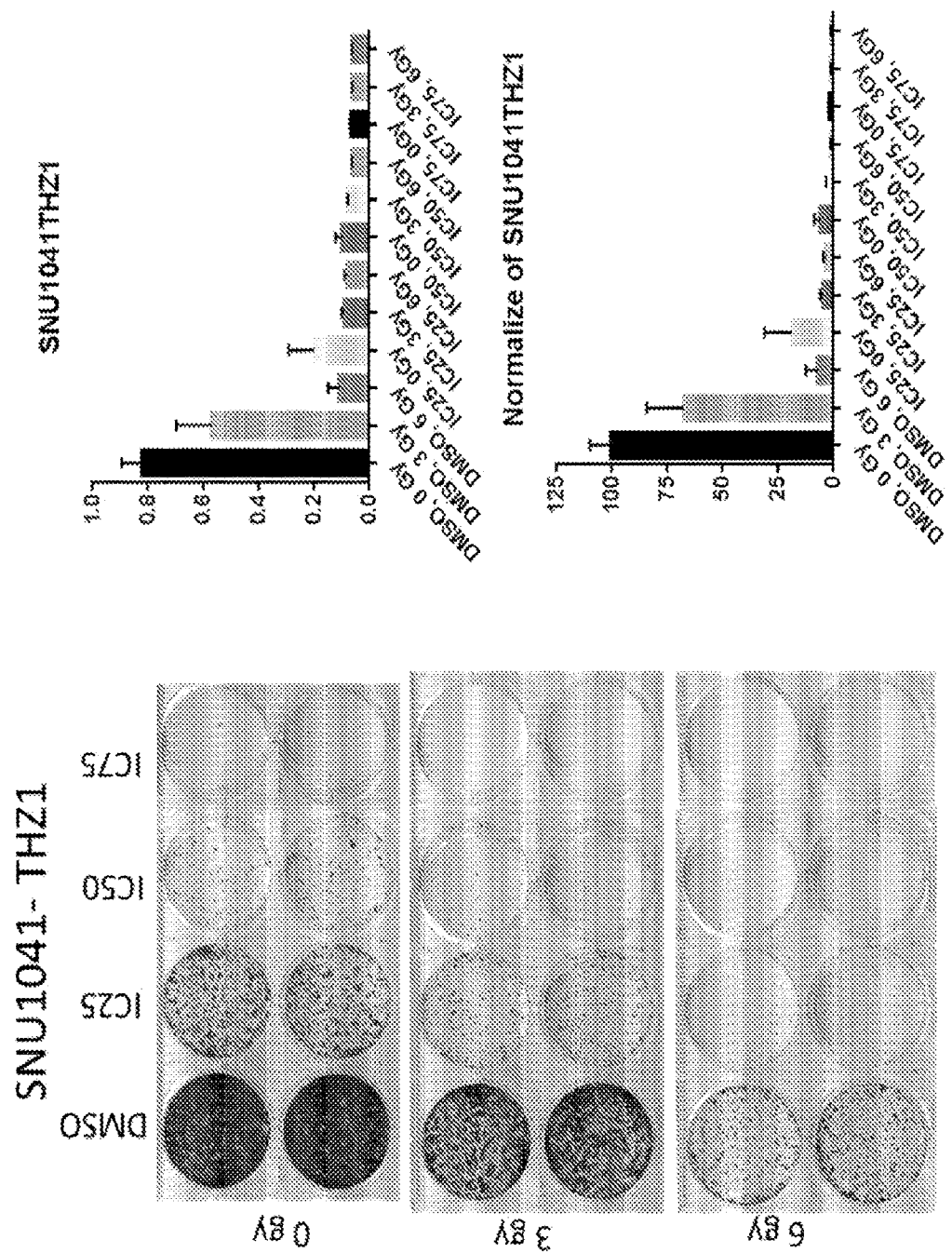

FIG. 70 shows the results of colony formation assays for SNU1041 cells treated with radiation (0 Gy, 3 Gy, 6 Gy) and either DMSO or transcription inhibitor THZ1 (IC25, IC50, or IC75).

Figure 71:
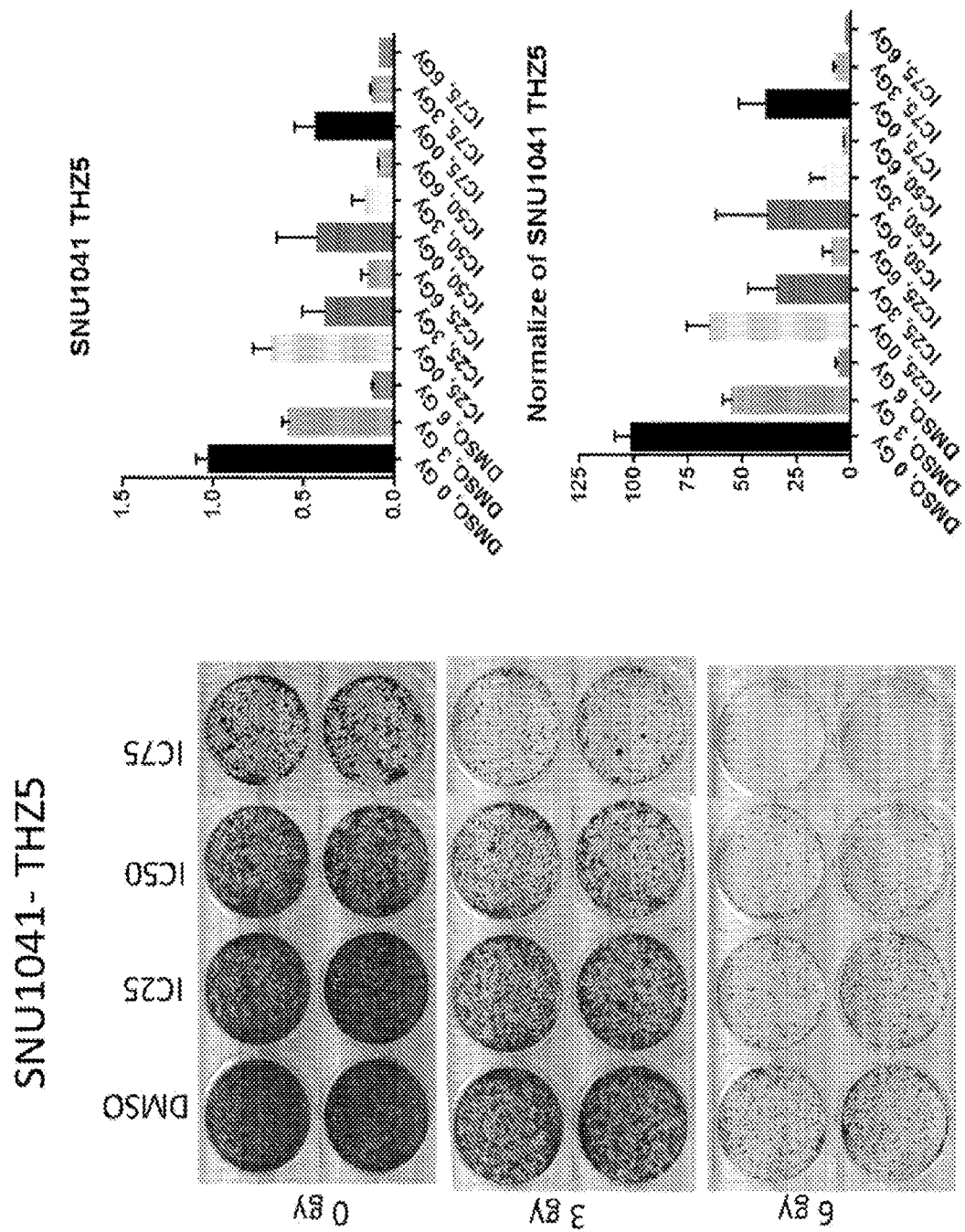

FIG. 71 shows the results of colony formation assays for SNU1041 cells treated with radiation (0 Gy, 3 Gy, 6 Gy) and either DMSO or transcription inhibitor THZ5-31-1 (IC25, IC50, or IC75).

Figure 72:
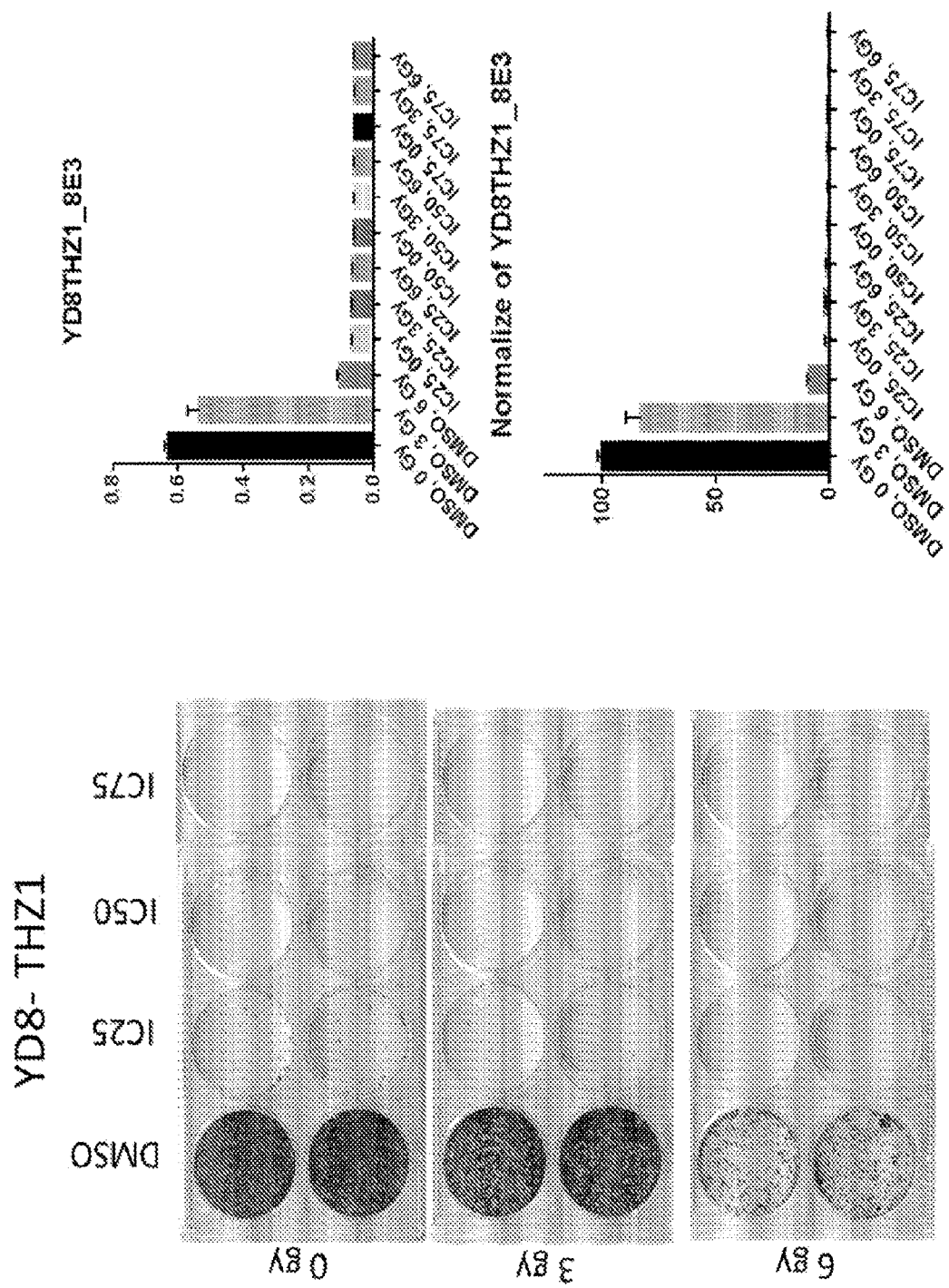

FIG. 72 shows the results of colony formation assays for YD8 cells treated with radiation (0 Gy, 3 Gy, 6 Gy) and either DMSO or transcription inhibitor THZ1 (IC25, IC50, or IC75).

Figure 73:
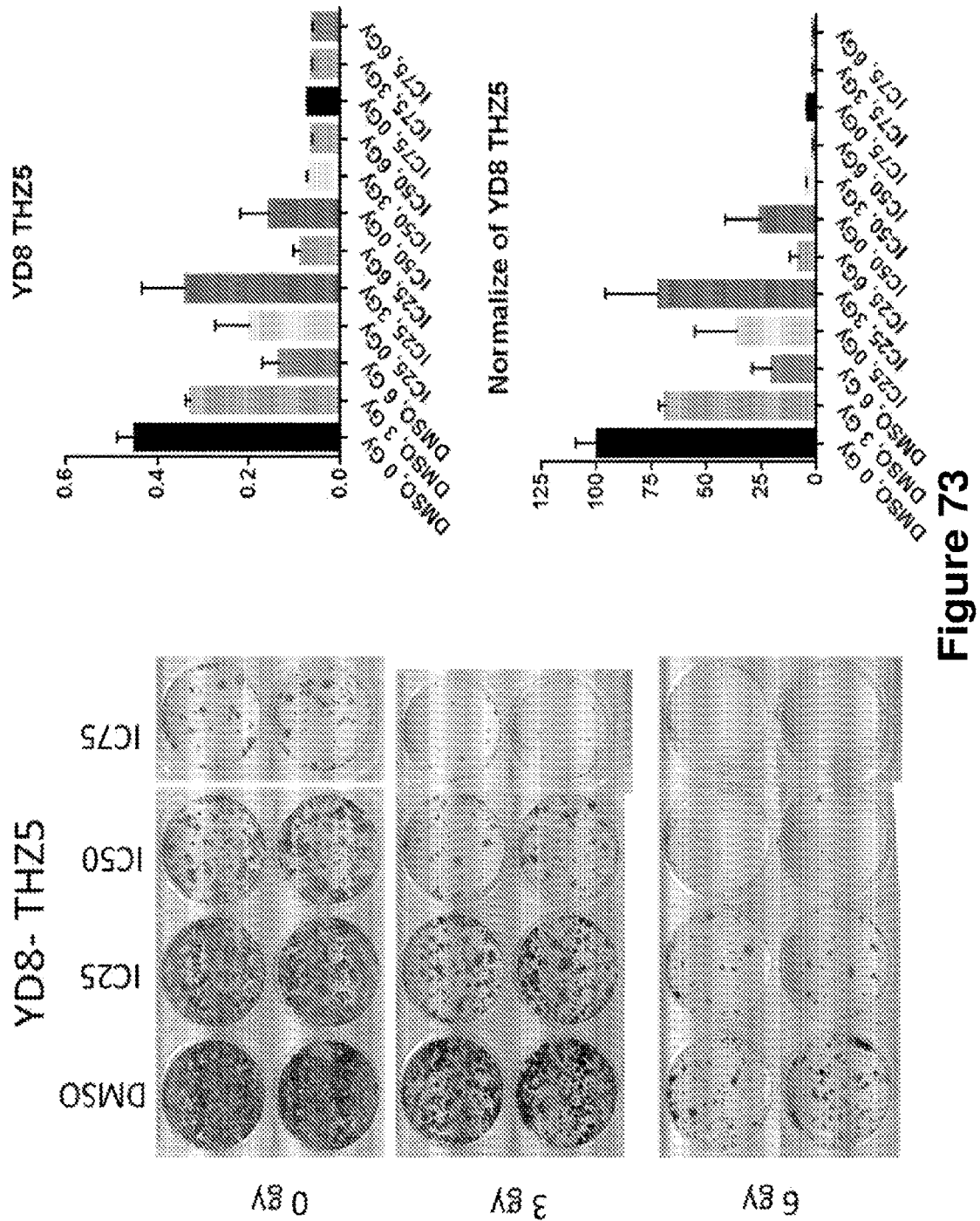

FIG. 73 shows the results of colony formation assays for YD8 cells treated with radiation (0 Gy, 3 Gy, 6 Gy) and either DMSO or transcription inhibitor THZ5-31-1 (IC25, IC50, or IC75).

DETAILED DESCRIPTION OF CERTAIN EMBODIMENTS

The present disclosure provides combination therapy of transcription inhibitors and kinase inhibitors. It has been found that a combination of a transcription inhibitor and a kinase inhibitor may be useful in treating and/or preventing in a subject in need thereof proliferative diseases, such as proliferative diseases that are resistant to the transcription inhibitor alone or kinase inhibitor alone. The combination of a transcription inhibitor and a kinase inhibitor is expected to be synergistic.

Pharmaceutical Compositions, Kits, and Administration

One aspect of the present disclosure relates to pharmaceutical compositions that comprise a transcription inhibitor and a kinase inhibitor, and optionally a pharmaceutically acceptable excipient, wherein the transcription inhibitor and the kinase inhibitor are not the same. The pharmaceutical compositions described herein may be useful in treating and/or preventing in a subject in need thereof proliferative diseases, such as proliferative diseases that are resistant to or are at risk of becoming resistant to a transcription inhibitor or a kinase inhibitor. The pharmaceutical compositions described herein may also be useful in reducing, delaying, and/or preventing in a subject in need thereof the resistance of a proliferative disease to treatment with a transcription inhibitor or kinase inhibitor. The pharmaceutical compositions described herein may further be useful in inhibiting the proliferation of a cell, and/or reducing, delaying, and/or preventing the resistance of a cell to a transcription inhibitor or kinase inhibitor. The pharmaceutical compositions described herein are expected to be synergistic in treating and/or preventing in the subject the proliferative diseases, in reducing, delaying, and/or preventing in the subject the resistance of proliferative diseases to a transcription inhibitor or kinase inhibitor, in inhibiting the proliferation of the cell, and/or reducing, delaying, and/or preventing the resistance of the cell to a transcription inhibitor or kinase inhibitor, compared to the transcription inhibitor or the kinase inhibitor alone. In certain embodiments, the kinase inhibitor included in a pharmaceutical composition is the same as the kinase inhibitor to which a proliferative disease or cell shows resistance.

A pharmaceutical composition described herein comprises a transcription inhibitor. In certain embodiments, the transcription inhibitor is a cyclin-dependent kinase (CDK) inhibitor (e.g., CDK1, CDK2, CDK3, CDK4, CDK5, CDK6, CDK7, CDK8, CDK9, CDK10, CDK11, or CDK12 inhibitor). In certain embodiments, the transcription inhibitor is a bromodomain-containing protein inhibitor (e.g., bromodomain-containing protein 2 (BRD2) inhibitor, bromodomain-containing protein 3 (BRD3) inhibitor, bromodomain-containing protein 4 (BRD4) inhibitor, TBP (TATA box binding protein)-associated factor protein (TAF) inhibitor, CREB-binding protein (CBP) inhibitor, or E1A binding protein p300 (EP300) inhibitor).

In certain embodiments, the transcription inhibitor is of Formula (I):

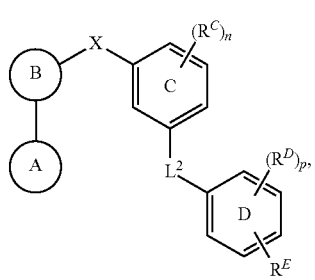

(I)

or a pharmaceutically acceptable salt, solvate, hydrate, polymorph, co-crystal, tautomer, stereoisomer, isotopically labeled derivative, or prodrug thereof, wherein:

Ring A is an optionally substituted heteroaryl ring of any one of the Formulae (i-1)-(i-5):

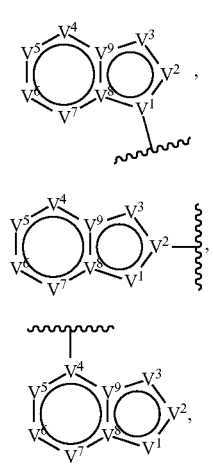

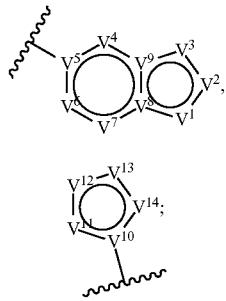

each instance of $V^1, V^2, V^3, V^4, V^5, V^6, V^7, V^8, V^9, V^{10}, V^{11}, V^{12}, V^{13}$, and $V^{14}$ is independently O, S, N, $NR^{A1}$, C, or $CR^{A2}$;

each instance of $R^{A1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group;

each instance of $R^{A2}$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $—OR^{A2a}$, $—N(R^{A2a})_2$, and $—SR^{A2a}$, wherein each occurrence of $R^{A2a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or about two $R^{A2a}$ groups are joined to form an optionally substituted heterocyclic ring;

optionally any about two of $R^{A1}, R^{A2}$, and $R^{A2a}$ groups are joined to form an optionally substituted carbocyclic, optionally substituted heterocyclic, optionally substituted aryl, or optionally substituted heteroaryl ring;

Ring B is of the formula:

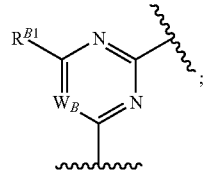

$R^{B1}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $—OR^{B1a}$, $—N(R^{B1a})_2$, and $—SR^{B1a}$, wherein each occurrence of $R^{B1a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or about two $R^{B1a}$ groups are joined to form an optionally substituted heterocyclic ring;

$W_B$ is N or $CR^{B2}$, wherein $R^{B2}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{B2a}$, $-N(R^{B2a})_2$, and $-SR^{B2a}$, wherein each occurrence of $R^{B2a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or about two $R^{B2a}$ groups are joined to form an optionally substituted heterocyclic ring;

optionally $R^{B1}$ and $R^{B2}$ are joined to form an optionally substituted carbocyclyl, optionally substituted heterocyclyl, optionally substituted heteroaryl, or optionally substituted aryl ring;

X is an optionally substituted $C_{1-4}$ hydrocarbon chain, optionally wherein one or more carbon units of the hydrocarbon chain is replaced with $-O-$, $-S-$, or $-NR^X-$, wherein $R^X$ is hydrogen, $C_{1-6}$ alkyl, or a nitrogen protecting group;

$L^2$ is a bond, $-O-$, $-S-$, $-NR^{L2a}-$, $-NR^{L2a}C(=O)-$, $-C(=O)NR^{L2a}-$, $-SC(=O)-$, $-C(=O)S-$, $-OC(=O)-$, $-C(=O)O-$, $-NR^{L2a}C(=S)-$, $-C(=S)NR^{L2a}-$, trans-$CR^{L2b}=CR^{L2b}-$, cis-$CR^{L2b}=CR^{L2b}-$, $-C\equiv C-$, $-OC(R^{L2b})_2-$, $-C(R^{L2b})_2O-$, $-NR^{L2a}C(R^{L2b})_2-$, $-C(R^{L2b})_2NR^{L2a}-$, $-SC(R^{L2b})_2-$, $-C(R^{L2b})_2S-$, $-S(=O)_2O-$, $-OS(=O)_2-$, $-S(=O)_2NR^{L2a}-$, $-NR^{L2a}S(=O)_2-$, or an optionally substituted $C_{1-4}$ hydrocarbon chain, optionally wherein one or more carbon units of the hydrocarbon chain is replaced with $-O-$, $-S-$, $-NR^{L2a}-$, $-NR^{L2a}C(=O)-$, $-C(=O)NR^{L2a}-$, $-SC(=O)-$, $-C(=O)S-$, $-OC(=O)-$, $-C(=O)O-$, $-NR^{La}C(=S)-$, $-C(=S)NR^{L2a}-$, trans-$CR^{L2b}=CR^{L2b}-$, cis-$CR^{L2b}=CR^{L2b}-$, $-C\equiv C-$, $-S(=O)_2O-$, $-OS(=O)_2-$, $-S(=O)_2NR^{L2a}-$, or $-NR^{L2a}S(=O)_2-$, wherein $R^{L2a}$ is hydrogen, $C_{1-6}$ alkyl, or a nitrogen protecting group, and wherein each occurrence of $R^{L2b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or about two $R^{L2b}$ groups are joined to form an optionally substituted carbocyclic or optionally substituted heterocyclic ring;

each instance of $R^C$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{C1}$, $-N(R^{C1})_2$, and $-SR^{C1}$, wherein each occurrence of $R^{C1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or about two $R^{C1}$ groups are joined to form an optionally substituted heterocyclic ring;

n is 0, 1, 2, 3, or 4;

each instance of $R^D$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{D1}$, $-N(R^{D1})_2$, and $-SR^{D1}$, wherein each occurrence of $R^{D1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or about two $R^{D1}$ groups are joined to form an optionally substituted heterocyclic ring;

p is 0, 1, 2, 3, or 4;

$R^E$ is any one of the Formulae (ii-1)-(ii-17):

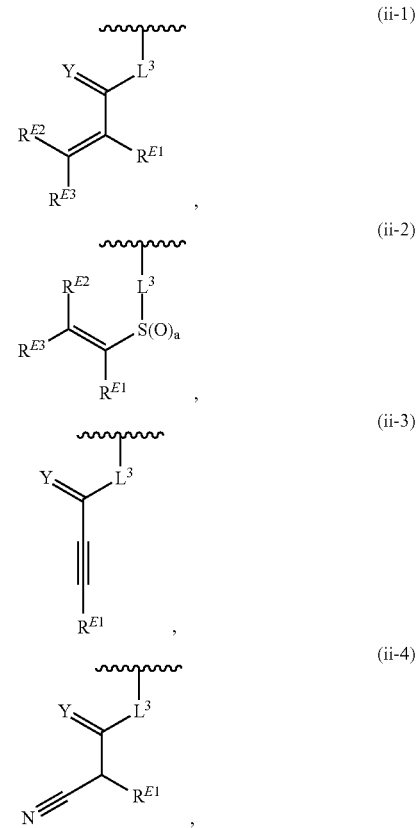

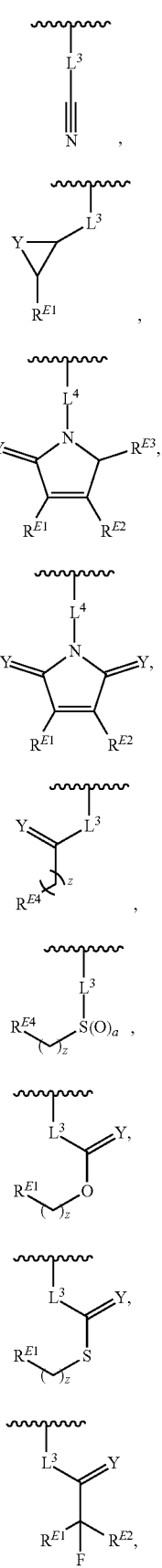

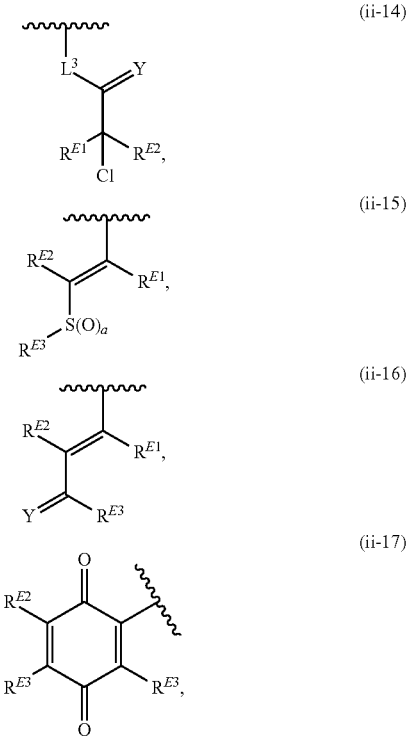

$R^E$ and $L^2$ are para or meta to each other;

$L^3$ is a bond, —O—, —S—, —NR$^{L3a}$—, or an optionally substituted $C_{1-4}$ hydrocarbon chain, optionally wherein one or more carbon units of the hydrocarbon chain is replaced with —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, $C_{1-6}$ alkyl, or a nitrogen protecting group, and wherein each occurrence of R$^{L3b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or about two R$^{L3b}$ groups are joined to form an optionally substituted carbocyclic or optionally substituted heterocyclic ring;

$L^4$ is a bond or an optionally substituted $C_{1-4}$ hydrocarbon chain;

$R^{E1}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CH$_2$OR$^{E1a}$, —CH$_2$N(R$^{E1a}$)$_2$, —CH$_2$SR$^{E1a}$, —OR$^{E1a}$, —N(R$^{E1a}$)$_2$, and —SR$^{E1a}$, wherein each occurrence of R$^{E1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or about two R$^{E1a}$ groups are joined to form an optionally substituted heterocyclic ring;

$R^{E2}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CH$_2$OR$^{E2a}$, —CH$_2$N(R$^{E2a}$)$_2$, —CH$_2$SR$^{E2a}$, —OR$^{E2a}$, —N(R$^{E2a}$)$_2$, and —SR$^{E2a}$, wherein each occurrence of R$^{E2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or about two R$^{E2a}$ groups are joined to form an optionally substituted heterocyclic ring;

$R^{E3}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CH$_2$OR$^{E3a}$, —CH$_2$N(R$^{E3a}$)$_2$, —CH$_2$SR$^{E3a}$, —OR$^{E3a}$, —N(R$^{E3a}$)$_2$, and —SR$^{E3a}$, wherein each occurrence of R$^{E3a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or about two R$^{E3a}$ groups are joined to form an optionally substituted heterocyclic ring;

optionally R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;

Y is O, S, or NR$^{E5}$, wherein R$^{E5}$ is hydrogen, C$_{1-6}$ alkyl, or a nitrogen protecting group;

a is 1 or 2; and z is 0, 1, 2, 3, 4, 5, or 6.

In certain embodiments, the transcription inhibitor is of the formula:

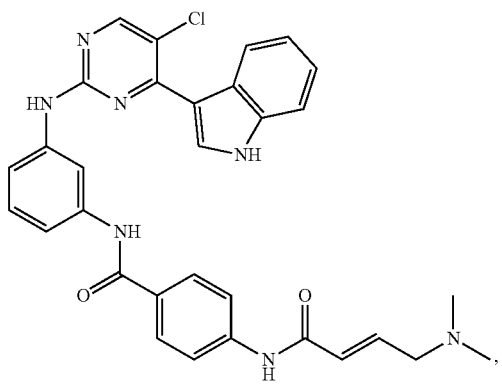

(THZ1)

or a pharmaceutically acceptable salt, solvate, hydrate, polymorph, co-crystal, tautomer, stereoisomer, isotopically labeled derivative, or prodrug thereof.

In certain embodiments, the transcription inhibitor is of the formula:

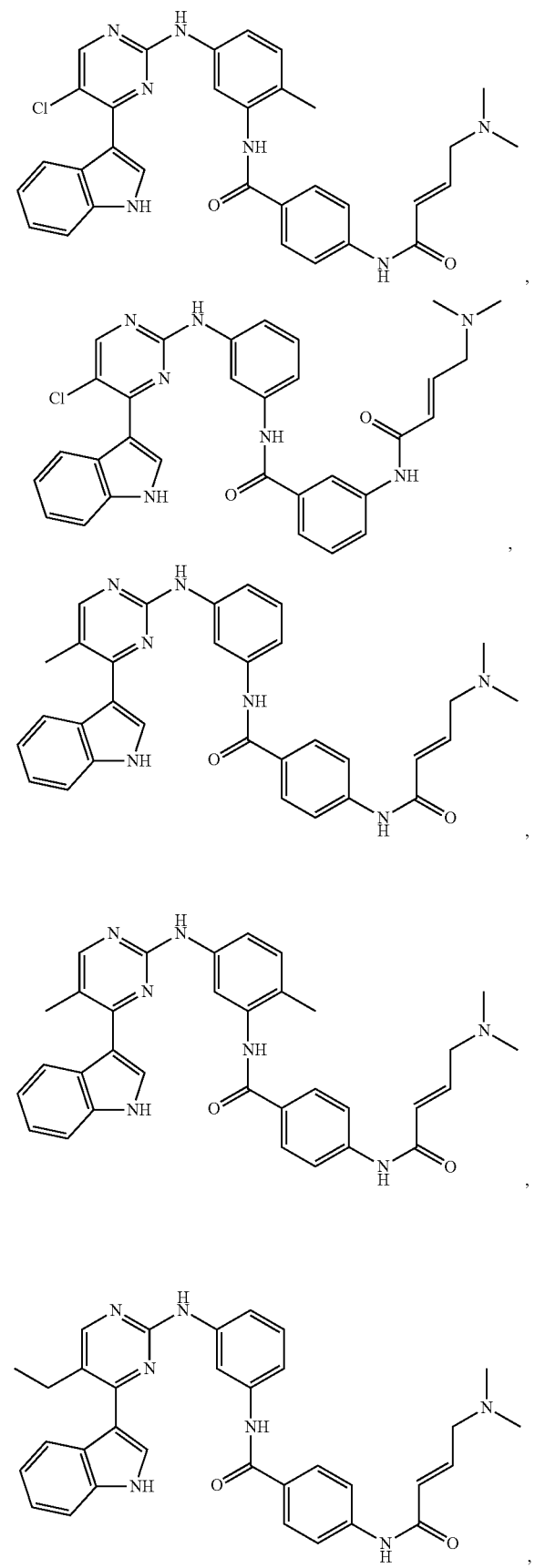

57
-continued
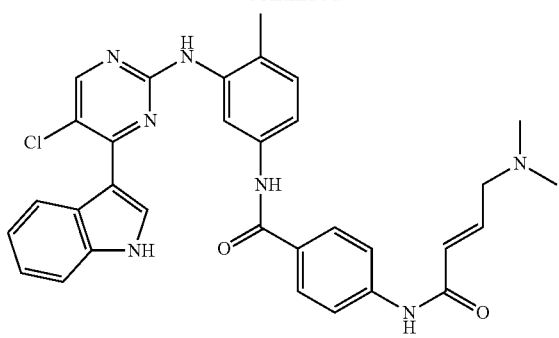
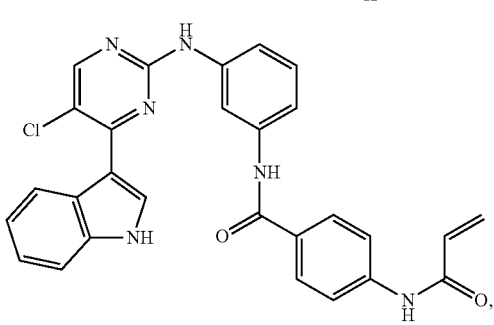
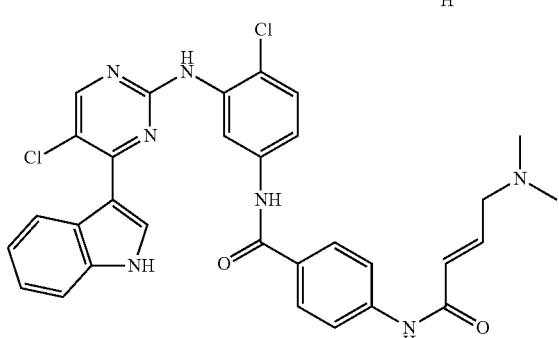
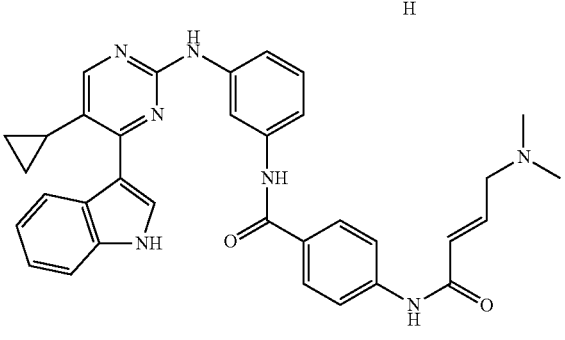
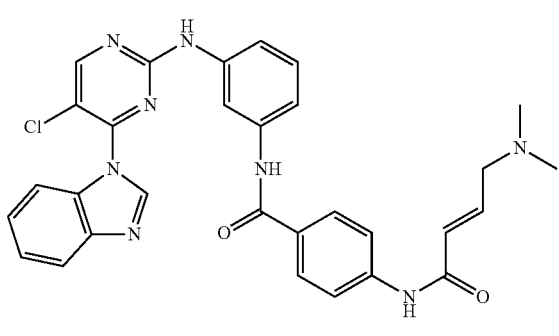
58
-continued
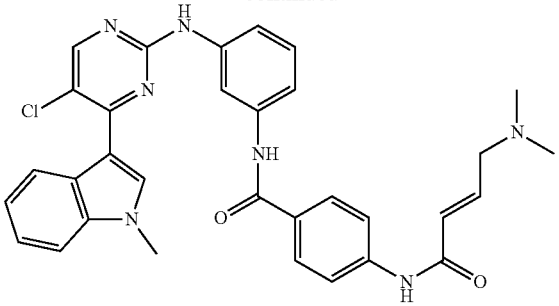
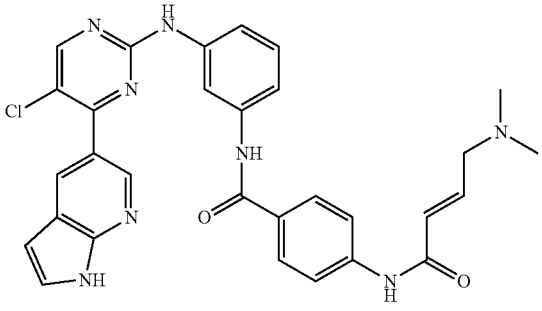
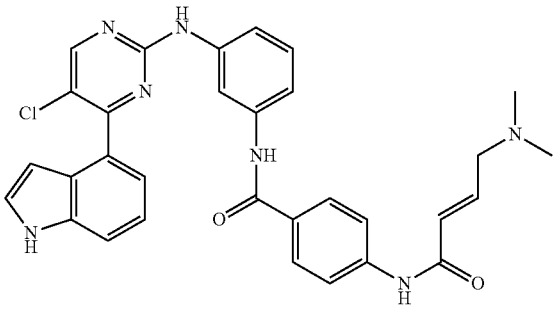
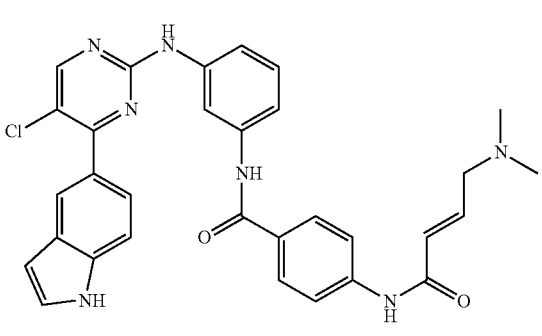
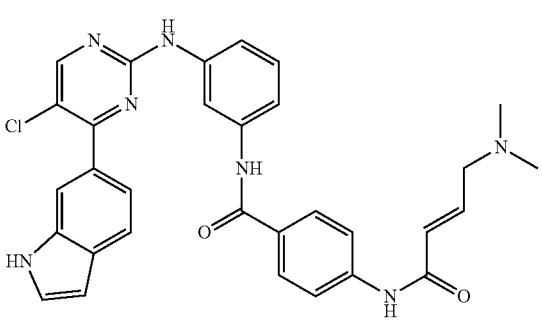

59
-continued
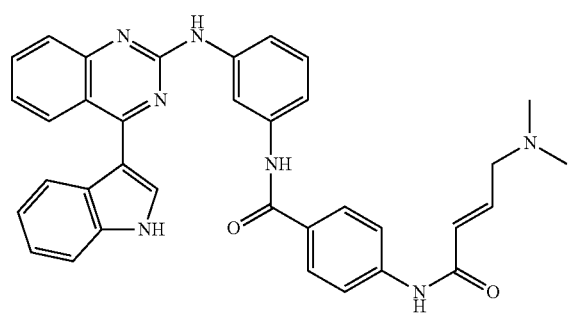
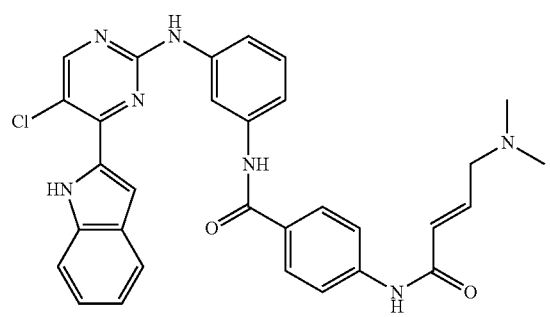
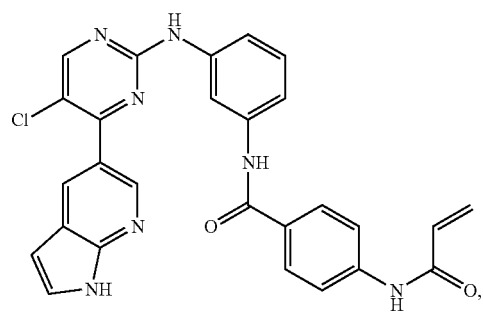
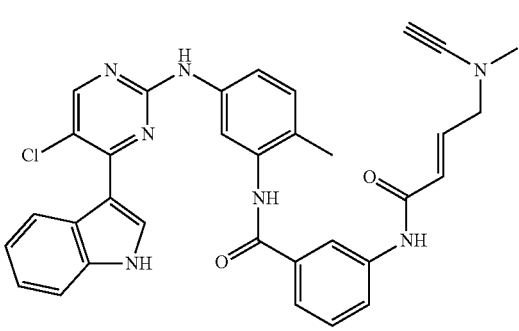
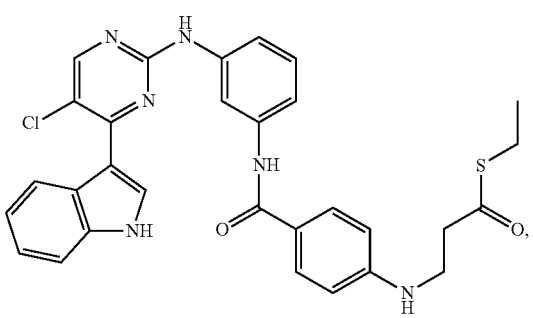
60
-continued
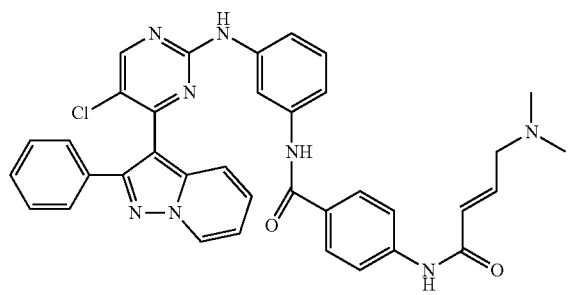
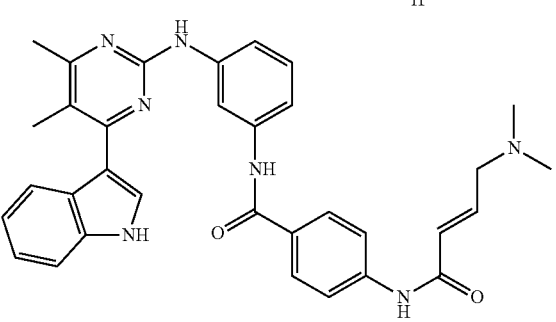
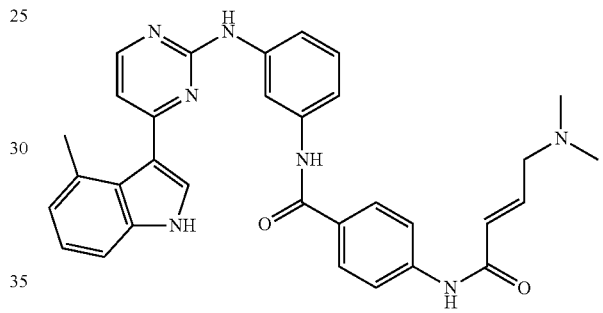
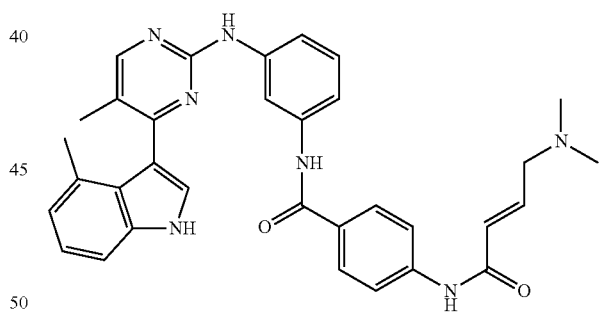
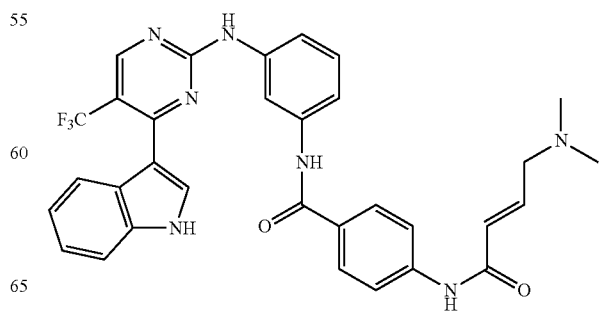

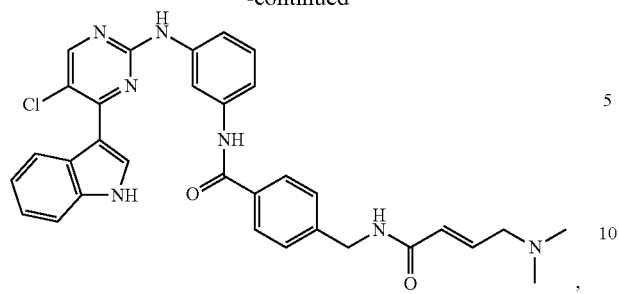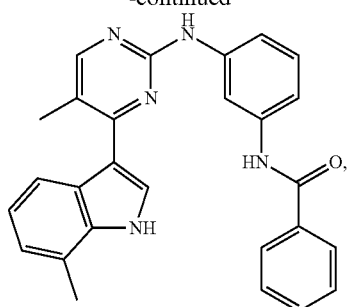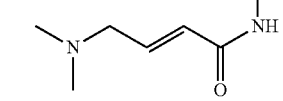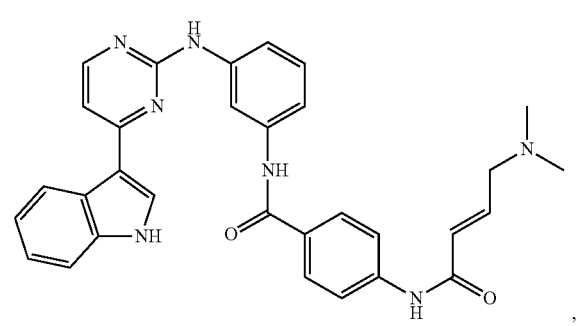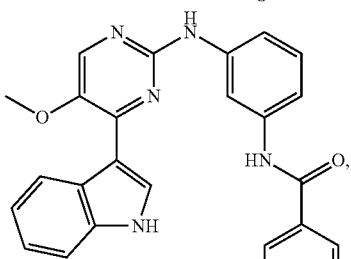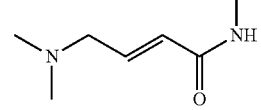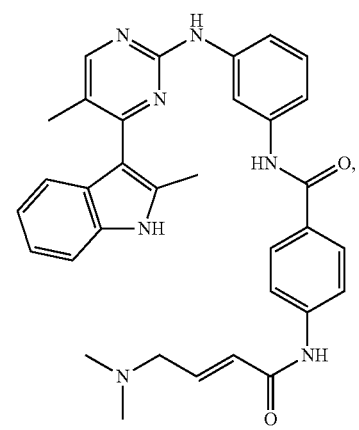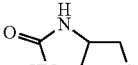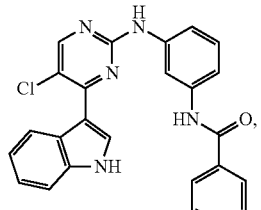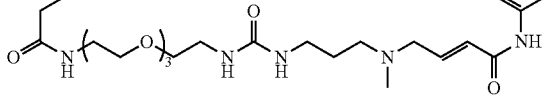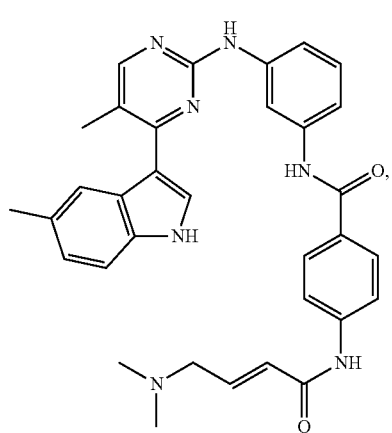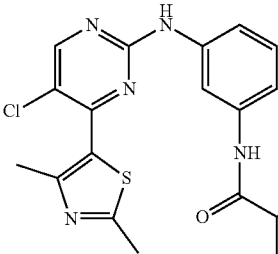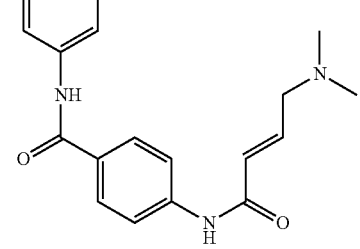

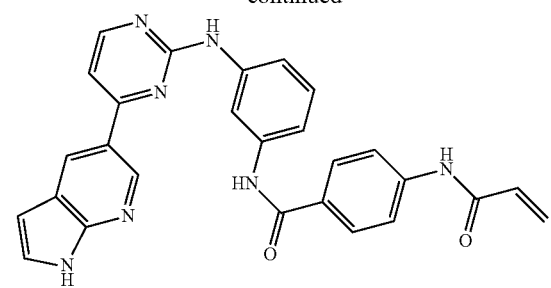
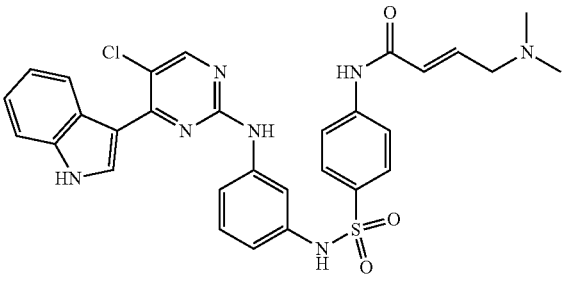
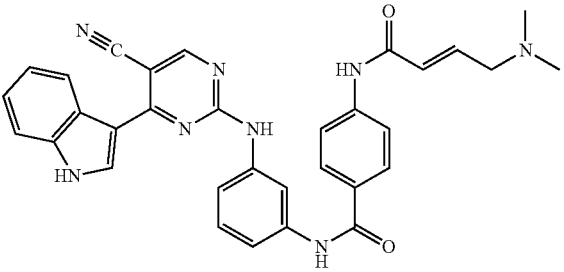
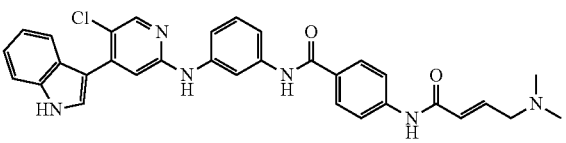
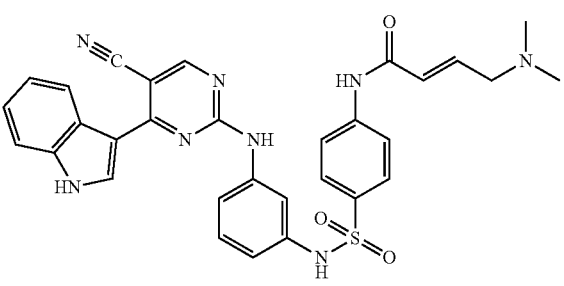
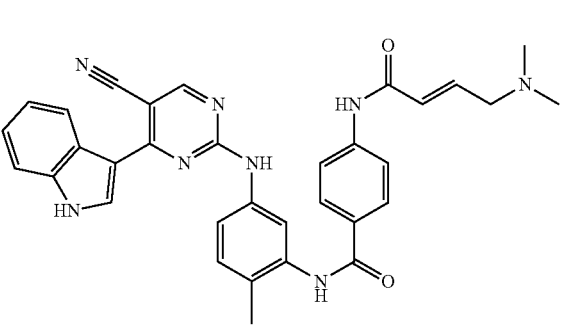
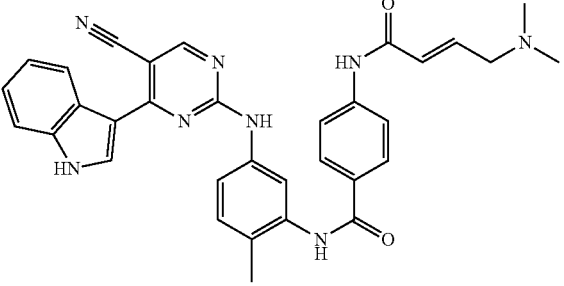
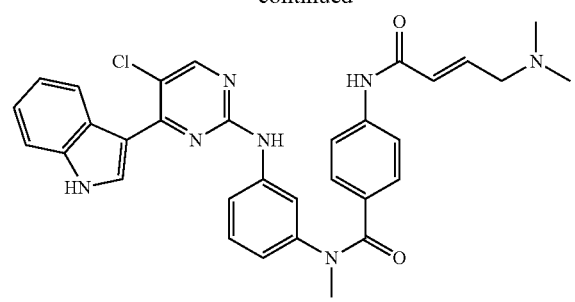

-continued

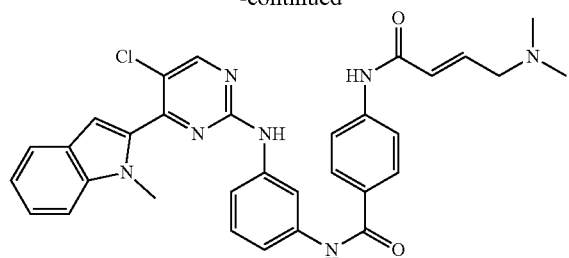

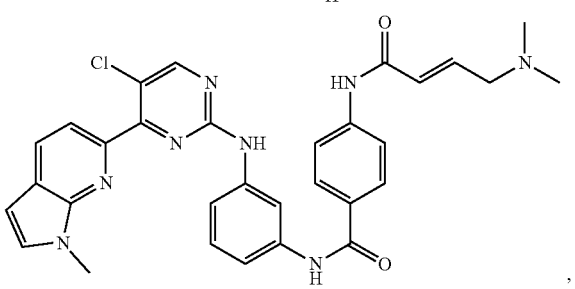

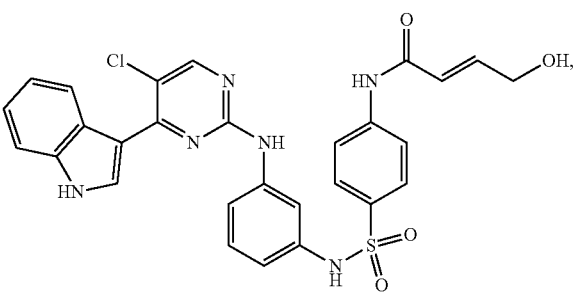

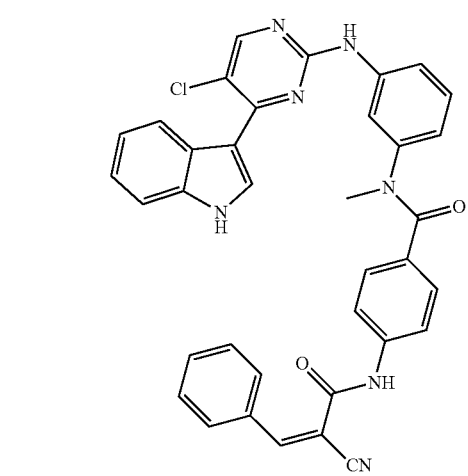

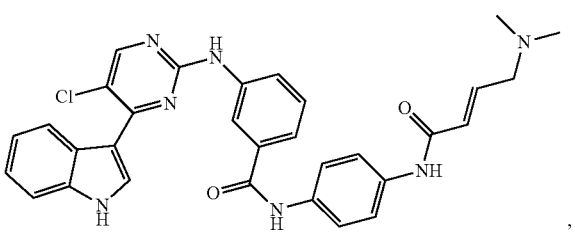

-continued

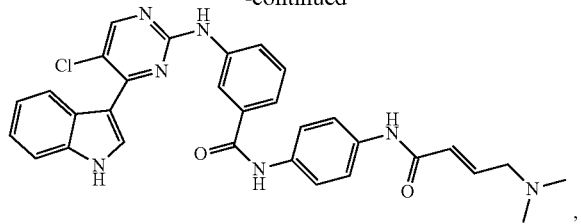

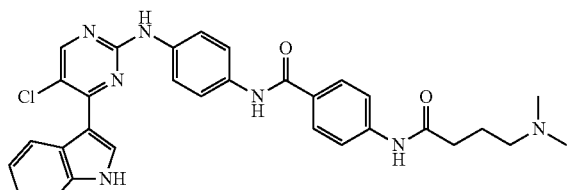

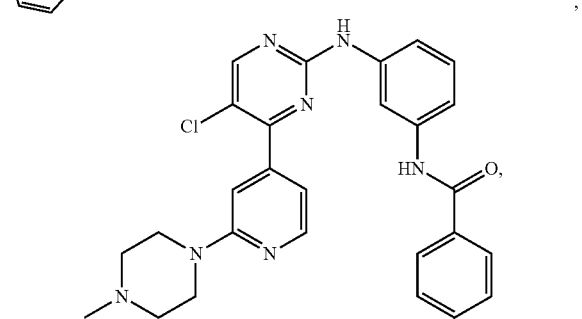

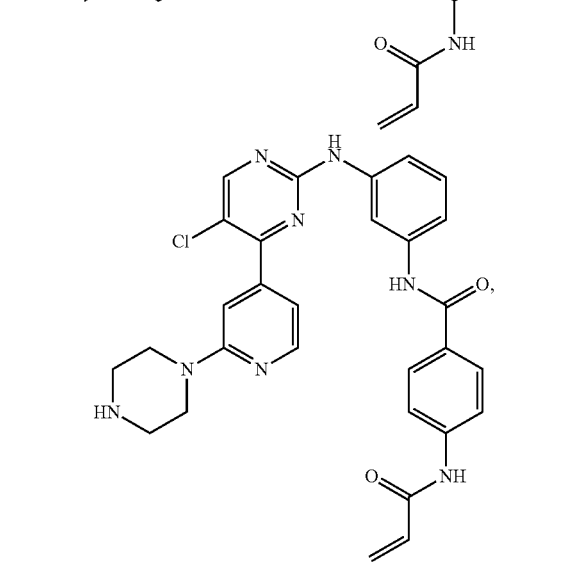

or a pharmaceutically acceptable salt, solvate, hydrate, polymorph, co-crystal, tautomer, stereoisomer, isotopically labeled derivative, or prodrug thereof.

In certain embodiments, the transcription inhibitor is of Formula (II):

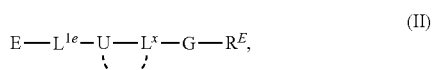

or a pharmaceutically acceptable salt, solvate, hydrate, polymorph, co-crystal, tautomer, stereoisomer, isotopically labeled derivative, or prodrug thereof, wherein:

G is group of atoms ranging a total length between 20 to 30 Å;

$R^E$ is an electrophile with any one of the Formulae (ii-1)-(ii-17):
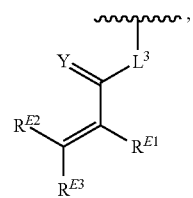
(ii-1)
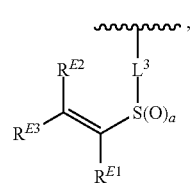
(ii-2)
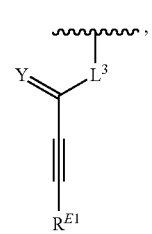
(ii-3)
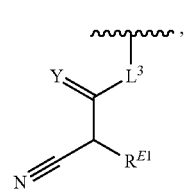
(ii-4)
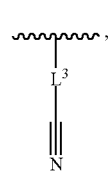
(ii-5)
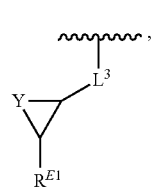
(ii-6)
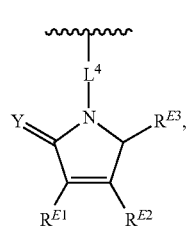
(ii-7)
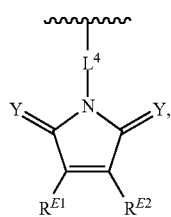
(ii-8)
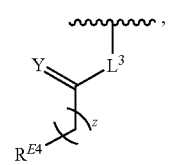
(ii-9)
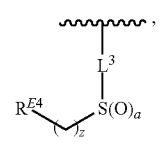
(ii-10)
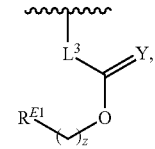
(ii-11)
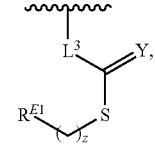
(ii-12)
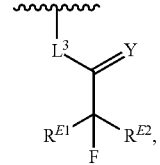
(ii-13)
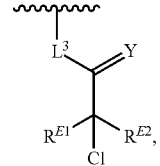
(ii-14)
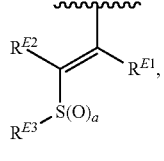
(ii-15)
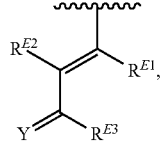
(ii-16)

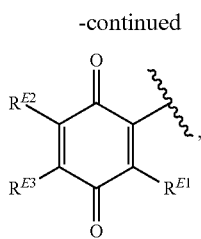
(ii-17)

$L^3$ is a bond, —O—, —S—, —NR$^{L3a}$—, or an optionally substituted C$_{1-4}$ hydrocarbon chain, optionally wherein one or more carbon units of the hydrocarbon chain is replaced with —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, C$_{1-6}$ alkyl, or a nitrogen protecting group, and wherein each occurrence of R$^{L3b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or about two R$^{L3b}$ groups are joined to form an optionally substituted carbocyclic or optionally substituted heterocyclic ring;

$L^4$ is a bond or an optionally substituted C$_{1-4}$ hydrocarbon chain;

$R^{E1}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E1a}$, —CH$_2$N(R$^{E1a}$)$_2$, —CH$_2$SR$^{E1a}$, —OR$^{E1a}$, —N(R$^{E1a}$)$_2$, and —SR$^{E1a}$, wherein each occurrence of R$^{E1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or about two R$^{E1a}$ groups are joined to form an optionally substituted heterocyclic ring;

$R^{E2}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E2a}$, —CH$_2$N(R$^{E2a}$)$_2$, —CH$_2$SR$^{E2a}$, —OR$^{E2a}$, —N(R$^{E2a}$)$_2$, and —SR$^{E2a}$, wherein each occurrence of R$^{E2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or about two R$^{E2a}$ groups are joined to form an optionally substituted heterocyclic ring;

$R^{E3}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E3a}$, —CH$_2$N(R$^{E3a}$)$_2$, —CH$_2$SR$^{E3a}$, —OR$^{E3a}$, —N(R$^{E3a}$)$_2$, and —SR$^{E3a}$, wherein each occurrence of R$^{E3a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or about two R$^{E3a}$ groups are joined to form an optionally substituted heterocyclic ring;

optionally R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

$R^{E4}$ is a leaving group;

Y is O, S, or NR$^{E5}$, wherein R$^{E5}$ is hydrogen, C$_{1-6}$ alkyl, or a nitrogen protecting group;

a is 1 or 2; and z is 0, 1 or 2;

$L^{1e}$ is a linker ranging between 0 to 3 atoms in length;

$L^x$ is a linker ranging between 0 to 5 atoms in length;

optionally, the IC$_{50}$ for CDK7 is less than approximately 100 nM; and optionally, the CDK inhibitor is selective for CDK7.

In certain embodiments, the transcription inhibitor is of Formula (III):

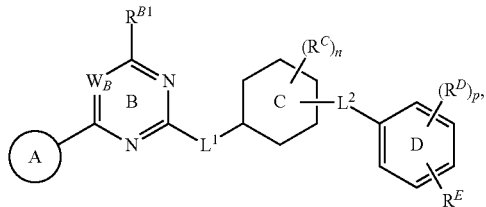
(III)

or a pharmaceutically acceptable salt, solvate, hydrate, polymorph, co-crystal, tautomer, stereoisomer, isotopically labeled derivative, or prodrug thereof, wherein:

Ring A is an optionally substituted heteroaryl ring of any one of the Formulae (i-1)-(i-6):

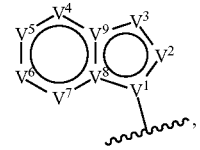
(i-1)

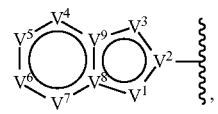
(i-2)

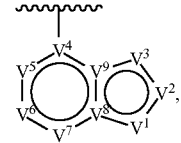
(i-3)

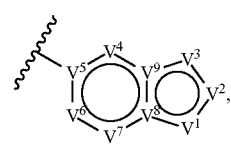
(i-4)

-continued

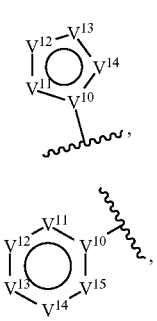

(i-5)

(i-6)

wherein:
each instance of $V^1$, $V^2$, $V^3$, $V^4$, $V^5$, $V^6$, $V^7$, $V^8$, $V^9$, $V^{10}$, $V^{11}$, $V^{12}$, $V^{13}$, $V^{14}$, and $V^{15}$ is independently O, S, N, $NR^{A1}$, C, or $CR^{A2}$;

each instance of $R^{A1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group;

each instance of $R^{A2}$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$OR^{A2a}$, —$N(R^{A2a})_2$, and —$SR^{A2a}$, wherein each occurrence of $R^{A2a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or about two $R^{A2a}$ groups are joined to form an optionally substituted heterocyclic ring; and optionally any about two of $R^{A1}$, $R^{A2}$, and $R^{A2a}$ groups are joined to form an optionally substituted carbocyclic, optionally substituted heterocyclic, optionally substituted aryl, or optionally substituted heteroaryl ring;

$R^{B1}$ is selected from the group consisting of hydrogen, halogen, optionally substituted acyl, optionally substituted alkyl, optionally substituted alkenyl, optionally substituted alkynyl, optionally substituted carbocyclyl, optionally substituted aryl, optionally substituted heteroaryl, —CN, —$OR^{B1a}$, —$N(R^{B1a})_2$, and —$SR^{B1a}$, wherein each occurrence of $R^{B1a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or $R^{B1}$ and $R^{B2}$ are joined to form an optionally substituted carbocyclic, optionally substituted heterocyclic, optionally substituted aryl, or optionally substituted heteroaryl ring;

$W_B$ is N or $CR^{B2}$, wherein $R^{B2}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$OR^{B2a}$, —$N(R^{B2a})_2$, and —$SR^{B2a}$, or $R^{B2}$ and $R^{B1}$ are joined to form an optionally substituted carbocyclic, optionally substituted heterocyclic, optionally substituted aryl, or optionally substituted heteroaryl ring, wherein each occurrence of $R^{B2a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or about two $R^{B2a}$ groups are joined to form an optionally substituted heterocyclic ring;

$L^1$ is a bond or an optionally substituted $C_{1-4}$ hydrocarbon chain, optionally wherein one or more carbon units of the optionally substituted $C_{1-4}$ hydrocarbon chain are independently replaced with —O—, —S—, —$NR^{L1}$—, —S(=O)—, or —S(=O)$_2$—, wherein $R^{L1}$ is hydrogen, substituted or unsubstituted $C_{1-6}$ alkyl, or a nitrogen protecting group, and optionally wherein about two substituents on the optionally substituted $C_{1-4}$ hydrocarbon chain are taken together to form an optionally substituted carbocyclic or optionally substituted heterocyclic ring;

$L^2$ is a bond or an optionally substituted $C_{1-4}$ hydrocarbon chain, optionally wherein one or more carbon units of the optionally substituted $C_{1-4}$ hydrocarbon chain are independently replaced with —O—, —S—, —$NR^{L2}$—, —S(=O)—, or —S(=O)$_2$—, wherein $R^{L2}$ is hydrogen, substituted or unsubstituted $C_{1-6}$ alkyl, or a nitrogen protecting group, and optionally wherein about two substituents on the optionally substituted $C_{1-4}$ hydrocarbon chain are taken together to form an optionally substituted carbocyclic or optionally substituted heterocyclic ring;

each instance of $R^C$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, =O, —CN, —$OR^{C1}$, —$N(R^{C1})_2$, and —$SR^{C1}$; or about two $R^C$ groups are taken together to form an optionally substituted, carbocyclic, heterocyclic, aryl, or heteroaryl ring, wherein about two substituents on the substituted heterocyclic ring or substituted carbocyclic ring, or one substituent on the substituted heterocyclic ring or substituted carbocyclic ring and a third $R^C$ group, are taken together to form another optionally substituted heterocyclic ring or optionally substituted carbocyclic ring; wherein each occurrence of $R^{C1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or about two $R^{C1}$ groups are joined to form an optionally substituted heterocyclic ring;

n is 0, 1, 2, 3, 4, 5, 6, 7, 8, 9, or 10;

each instance of $R^D$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$OR^{D1}$, —$N(R^{D1})_2$, and —$SR^{D1}$, wherein each occurrence of $R^{D1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or about two $R^{D1}$ groups are joined to form an optionally substituted heterocyclic ring;

p is 0, 1, 2, 3, or 4;

$R^E$ is of any one of the Formulae (ii-1)-(ii-20):

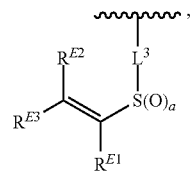
(ii-1)

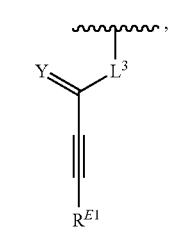
(ii-2)

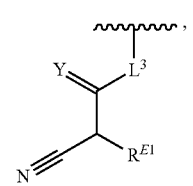
(ii-3)

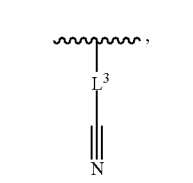
(ii-4)

(ii-5)

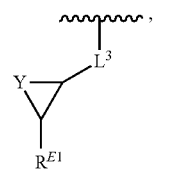
(ii-6)

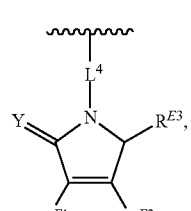
(ii-7)

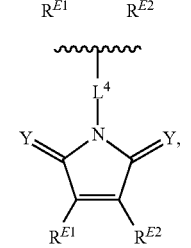
(ii-8)

(ii-9)

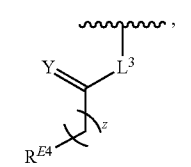
(ii-10)

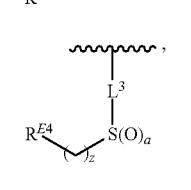
(ii-11)

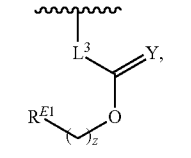
(ii-12)

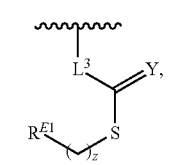
(ii-13)

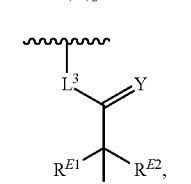
(ii-14)

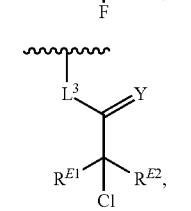

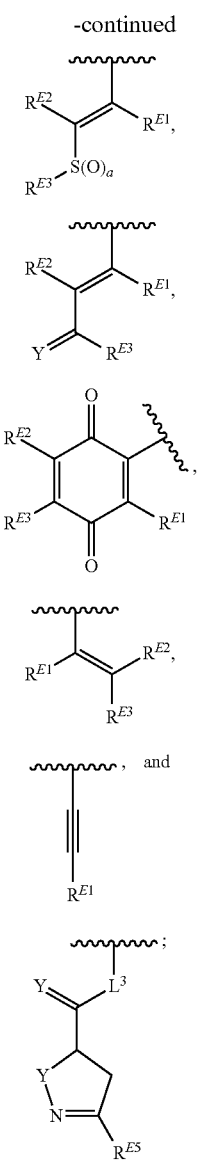

(ii-15)

(ii-16)

(ii-17)

(ii-18)

(ii-19)

(ii-20)

L³ is a bond, —O—, —S—, —NR^{L3a}—, or an optionally substituted C_{1-4} hydrocarbon chain, optionally wherein one or more carbon units of the hydrocarbon chain are independently replaced with —O—, —S—, —NR^{L3a}—, —NR^{L3a}C(=O)—, —C(=O)NR^{L3a}—, —SC(=O)—, —C(=O)S—, —OC(=O)—, —C(=O)O—, —NR^{L3a}C(=S)—, —C(=S)NR^{L3a}—, trans-CR^{L3b}=CR^{L3b}—, cis-CR^{L3b}=CR^{L3b}—, —C≡C—, —S(=O)—, —S(=O)O—, —OS(=O)—, —S(=O)NR^{L3a}—, —NR^{L3a}S(=O)—, —S(=O)_2—, —S(=O)_2O—, —OS(=O)_2—, —S(=O)_2NR^{L3a}—, or —NR^{L3a}S(=O)_2—, wherein R^{L3a} is hydrogen, substituted or unsubstituted C_{1-6} alkyl, or a nitrogen protecting group, and wherein each occurrence of R^{L3b} is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or about two R^{L3b} groups are joined to form an optionally substituted carbocyclic or optionally substituted heterocyclic ring;

L⁴ is a bond or an optionally substituted C_{1-4} hydrocarbon chain;

$R^{E1}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH_2OR^{E1a}, —CH_2N(R^{E1a})_2, —CH_2SR^{E1a}, —OR^{E1a}, —N(R^{E1a})_2, —Si(R^{E1a})_3, and —SR^{E1a}, wherein each occurrence of R^{E1a} is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or about two R^{E1a} groups are joined to form an optionally substituted heterocyclic ring;

$R^{E2}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH_2OR^{E2a}, —CH_2N(R^{E2a})_2, —CH_2SR^{E2a}, —OR^{E2a}, —N(R^{E2a})_2, and —SR^{E2a}, wherein each occurrence of R^{E2a} is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or about two R^{E2a} groups are joined to form an optionally substituted heterocyclic ring;

$R^{E3}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH_2OR^{E3a}, —CH_2N(R^{E3a})_2, —CH_2SR^{E3a}, —OR^{E3a}, —N(R^{E3a})_2, and —SR^{E3a}, wherein each occurrence of R^{E3a} is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or about two R^{E3a} groups are joined to form an optionally substituted heterocyclic ring;

optionally $R^{E1}$ and $R^{E3}$, or $R^{E2}$ and $R^{E3}$, or $R^{E1}$ and $R^{E2}$ are joined to form an optionally substituted carbocyclic or optionally substituted heterocyclic ring;

$R^{E4}$ is a leaving group;

$R^{E5}$ is halogen;

Y is O, S, or NR^{E6}, wherein R^{E6} is hydrogen, substituted or unsubstituted C_{1-6} alkyl, or a nitrogen protecting group;

a is 1 or 2; and z is 0, 1, 2, 3, 4, 5, or 6.

In certain embodiments, the transcription inhibitor is of the formula:

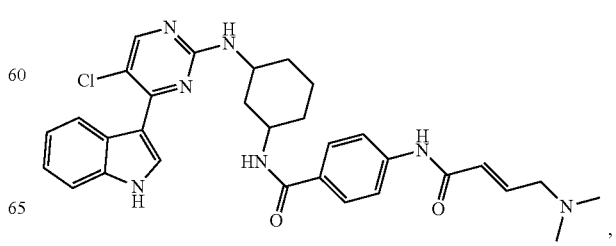

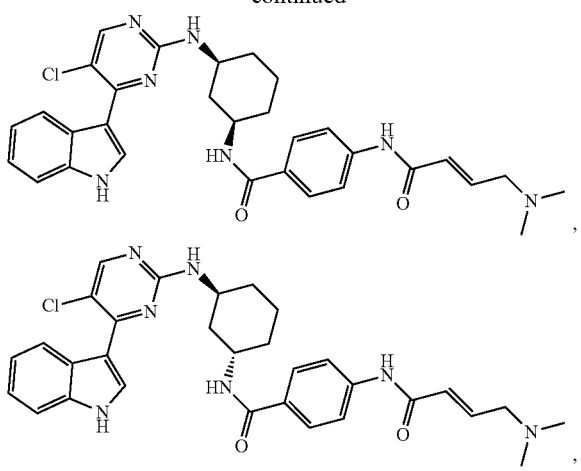

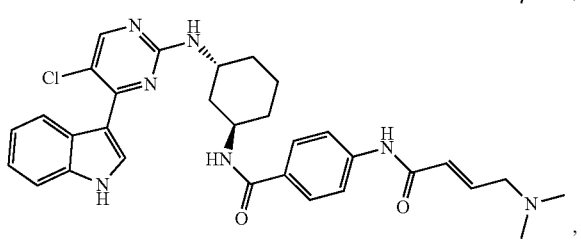

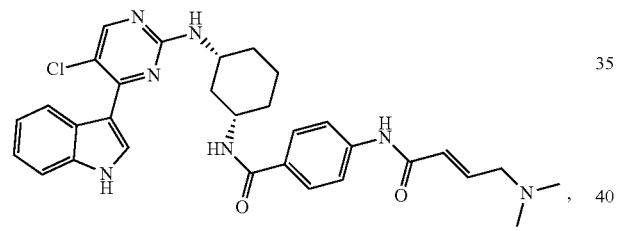

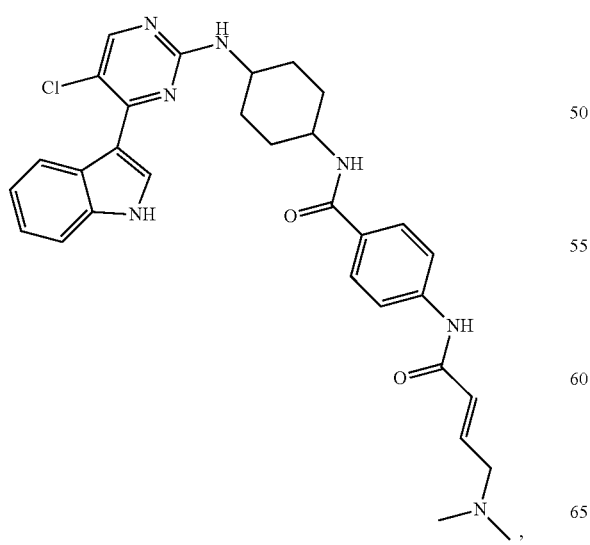

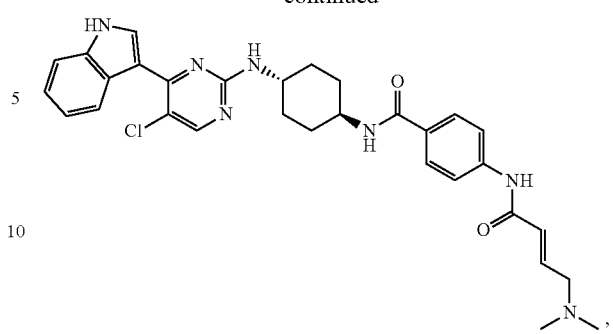

or a pharmaceutically acceptable salt, solvate, hydrate, polymorph, co-crystal, tautomer, stereoisomer, isotopically labeled derivative, or prodrug thereof.

In certain embodiments, the transcription inhibitor is of Formula (IV):

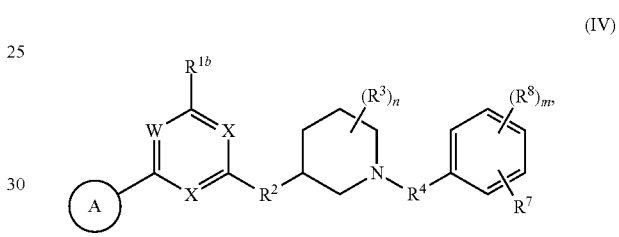

(IV)

or a pharmaceutically acceptable salt, solvate, hydrate, tautomer, or stereoisomer thereof, wherein:

Ring A is an optionally substituted heteroaryl ring of any one of the Formulae (i-1)-(i-6):

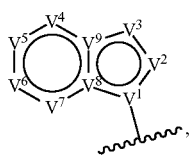

(i-1)

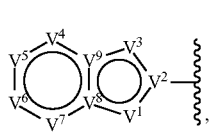

(i-2)

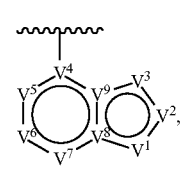

(i-3)

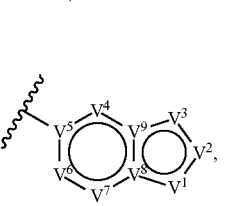

(i-4)

-continued

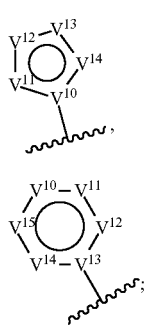

(i-5)

(i-6)

wherein:

each instance of $V^1$, $V^2$, $V^3$, $V^4$, $V^5$, $V^6$, $V^7$, $V^8$, $V^9$, $V^{10}$, $V^{11}$, $V^{12}$, $V^{13}$, $V^{14}$ and $V^{15}$ is independently O, S, N, N($R^{41}$), C, or C($R^{42}$);

each instance of $R^{41}$ is independently selected from hydrogen, deuterium, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl;

each instance of $R^{42}$ is independently selected from hydrogen, deuterium, halogen, —CN, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{42a}$, —N($R^{42a}$)$_2$, and —$SR^{42a}$, wherein each occurrence of $R^{42a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, or any about two $R^{41}$, any about two $R^{42}$, or one $R^{41}$ and one $R^{42}$ are joined to form an optionally substituted carbocyclic, optionally substituted heterocyclic, optionally substituted aryl, or optionally substituted heteroaryl ring;

each X is independently selected from N and CH, wherein at least one X is N;

W is selected from N and C($R^{1a}$);

each of $R^{1a}$, if present, and $R^{1b}$ is independently selected from hydrogen, deuterium, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$OR^{B1a}$, —N($R^{B1a}$)$_2$, and —$SR^{B1a}$, wherein each occurrence of $R^{B1a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, or $R^{1a}$ and $R^{1b}$ are joined to form an optionally substituted carbocyclic, optionally substituted heterocyclic, optionally substituted aryl, or optionally substituted heteroaryl ring;

$R^2$ is an optionally substituted $C_1$-$C_4$ alkylene or an optionally substituted $C_2$-$C_4$ alkenylene or alkynylene, wherein one or more methylene units of the alkylene, alkenylene or alkynylene are optionally and independently replaced with —O—, —S—, or —N($R^6$)—;

each instance of $R^3$, if present, is independently selected from deuterium, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{C1}$, —N($R^{C1}$)$_2$, and —$SR^{C1}$, wherein each occurrence of $R^{C1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, or about two $R^3$ groups bound to the same ring carbon atom are taken together to form =O, or about two $R^3$ groups bound to the same or different ring carbon atoms are joined to form an optionally substituted carbocyclyl, optionally substituted heterocyclyl, optionally substituted aryl, or optionally substituted heteroaryl ring;

$R^4$ is selected from a bond, an optionally substituted $C_1$-$C_4$ alkylene, and an optionally substituted $C_2$-$C_4$ alkenylene or alkynylene, wherein:

one or more methylene units of the alkylene, alkenylene or alkynylene other than a methylene unit bound to a nitrogen atom is optionally and independently replaced with —O—, —S—, —N($R^6$)—, or —S(=O)$_2$—, and about two substituents on either the same or adjacent carbon atoms in the alkylene, alkenylene or alkynylene are taken together to form an optionally substituted carbocyclic or optionally substituted heterocyclic ring;

each $R^6$ is independently selected from hydrogen, and —$C_1$-$C_6$ alkyl;

$R^7$ is any one of the Formulae (ii-1)-(ii-20):

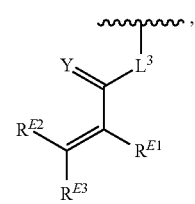

(ii-1)

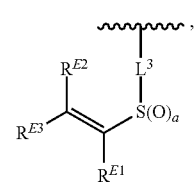

(ii-2)

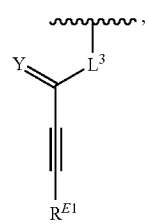

(ii-3)

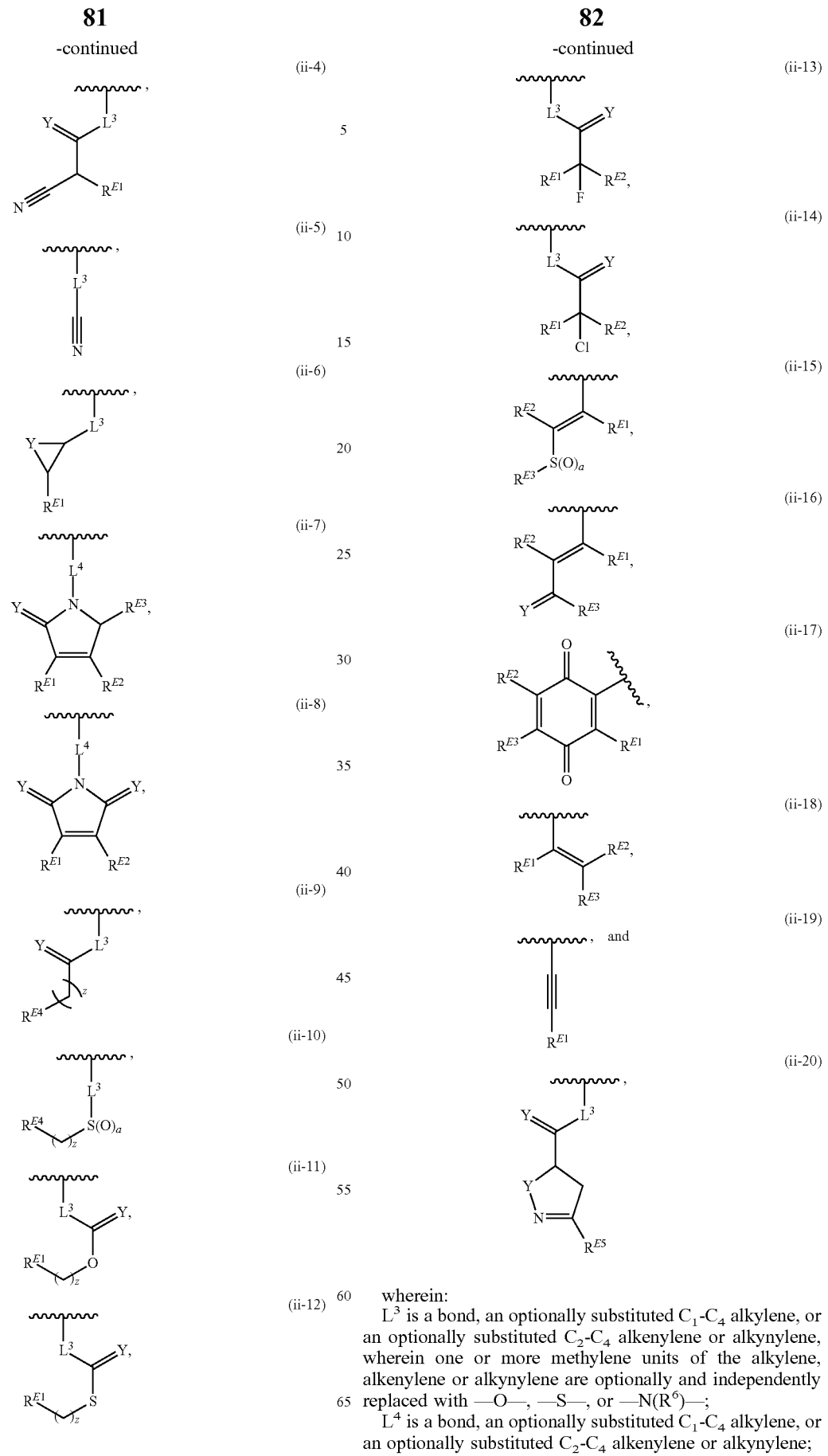

wherein:
L³ is a bond, an optionally substituted C₁-C₄ alkylene, or an optionally substituted C₂-C₄ alkenylene or alkynylene, wherein one or more methylene units of the alkylene, alkenylene or alkynylene are optionally and independently replaced with —O—, —S—, or —N(R⁶)—;
L⁴ is a bond, an optionally substituted C₁-C₄ alkylene, or an optionally substituted C₂-C₄ alkenylene or alkynylene;

$R^{E1}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E1a}$, —CH$_2$N(R$^{E1a}$)$_2$, —CH$_2$SR$^{E1a}$, —OR$^{E1a}$, —N(R$^{E1a}$)$_2$, —Si(R$^{E1a}$)$_3$, and —SR$^{E1a}$, wherein each occurrence of R$^{E1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or about two R$^{E1a}$ groups are joined to form an optionally substituted heterocyclic ring;

$R^{E2}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E2a}$, —CH$_2$N(R$^{E2a}$)$_2$, —CH$_2$SR$^{E2a}$, —OR$^{E2a}$, —N(R$^{E2a}$)$_2$, and —SR$^{E2a}$, wherein each occurrence of R$^{E2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or about two R$^{E2a}$ groups are joined to form an optionally substituted heterocyclic ring;

$R^{E3}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E3a}$, —CH$_2$N(R$^{E3a}$)$_2$, —CH$_2$SR$^{E3a}$, —OR$^{E3a}$, —N(R$^{E3a}$)$_2$, and —SR$^{E3a}$, wherein each occurrence of R$^{E3a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or about two R$^{E3a}$ groups are joined to form an optionally substituted heterocyclic ring;

optionally $R^{E1}$ and $R^{E3}$, or $R^{E2}$ and $R^{E3}$, or $R^{E1}$ and $R^{E2}$ are joined to form an optionally substituted carbocyclic or optionally substituted heterocyclic ring;

$R^{E4}$ is a leaving group;

$R^{E5}$ is halogen;

Y is O, S, or NR$^{E6}$, wherein R$^{E6}$ is hydrogen, substituted or unsubstituted C$_{1-6}$ alkyl, or a nitrogen protecting group;

a is 1 or 2;

z is 0, 1, 2, 3, 4, 5, or 6;

each instance of R$^8$, if present, is independently selected from deuterium, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{D1}$, —N(R$^{D1}$)$_2$, and —SR$^{D1}$, wherein each occurrence of R$^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, and optionally substituted aryl, optionally substituted heteroaryl, or about two R$^8$ groups are joined to form an optionally substituted carbocyclyl, optionally substituted heterocyclyl, optionally substituted aryl, or optionally substituted heteroaryl ring;

m is 0, 1, 2, 3 or 4; and n is 0, 1, 2, 3, 4, 5 or 6.

In certain embodiments, the transcription inhibitor is of formula:

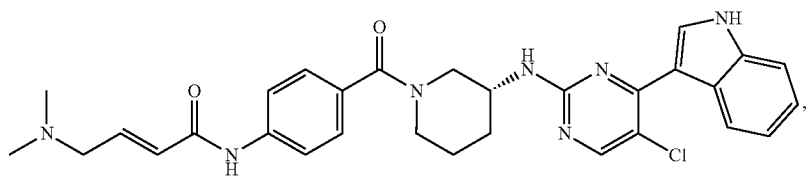

(THZ5-31-1)

or a pharmaceutically acceptable salt, solvate, hydrate, polymorph, co-crystal, tautomer, stereoisomer, isotopically labeled derivative, or prodrug thereof.

In certain embodiments, the transcription inhibitor is of formula:

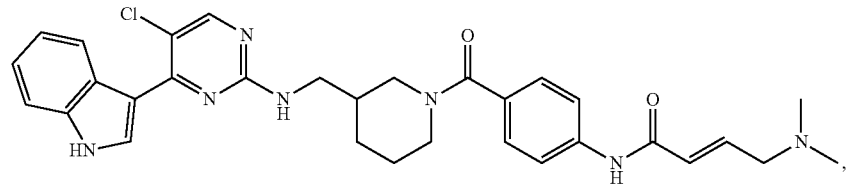

-continued

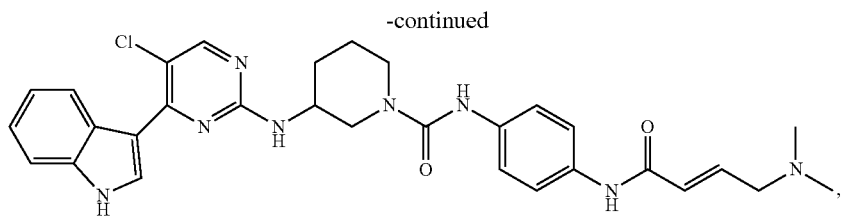

10 or a pharmaceutically acceptable salt, solvate, hydrate, polymorph, co-crystal, tautomer, stereoisomer, isotopically labeled derivative, or prodrug thereof.

In certain embodiments, the transcription inhibitor is of Formula (V):

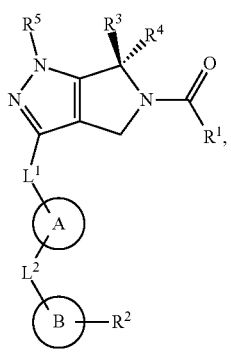

(V)

or a pharmaceutically acceptable salt, solvate, hydrate, polymorph, co-crystal, tautomer, stereoisomer, isotopically labeled derivative, or prodrug thereof, wherein:

$R^1$ is —$NR^aR^b$, —$CHR^aR^b$ or —$OR^a$, wherein each of $R^a$ and $R^b$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, or an oxygen protecting group when attached to an oxygen atom, or $R^a$ and $R^b$ are joined to form an optionally substituted carbocyclic, optionally substituted heterocyclic, optionally substituted aryl, or optionally substituted heteroaryl ring;

each of $R^3$ and $R^4$ is independently hydrogen, halogen, or optionally substituted $C_1$-$C_6$ alkyl, or $R^3$ and $R^4$ are joined to form an optionally substituted $C_3$-$C_6$ carbocyclyl ring;

$R^5$ is hydrogen, optionally substituted $C_1$-$C_6$ alkyl, or a nitrogen protecting group;

$L^1$ is —$NR^{L1}$, —$NR^{L1}C(=O)$—, —$C(=O)NR^{L1}$—, —O—, or —S—, wherein $R^{L1}$ is hydrogen, optionally substituted $C_1$-$C_6$ alkyl, or a nitrogen protecting group;

Ring A is optionally substituted carbocyclyl, optionally substituted heterocyclyl, optionally substituted aryl, or optionally substituted heteroaryl;

$L^2$ is a bond, —C(=O)—, —$NR^{L2}$—, —C(=O)$NR^{L2}$—, —$NR^{L2}$C(=O)—, —O—, or —S—, wherein $R^{L2}$ is hydrogen, optionally substituted $C_1$-$C_6$ alkyl, or a nitrogen protection group;

Ring B is absent, optionally substituted carbocyclyl, optionally substituted heterocyclyl, optionally substituted aryl, or optionally substituted heteroaryl; and $R^2$ is any of Formulae (i-1)-(i-46):

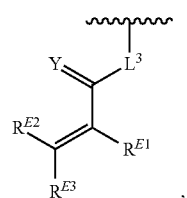

(i-1)

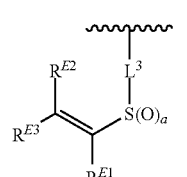

(i-2)

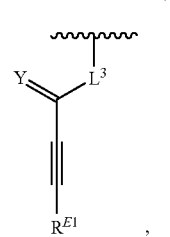

(i-3)

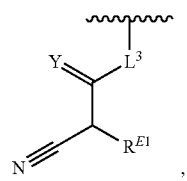

(i-4)

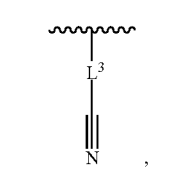

(i-5)

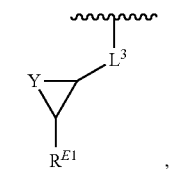

(i-6)

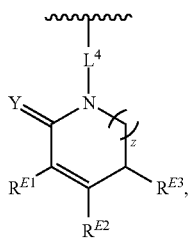

(i-7)

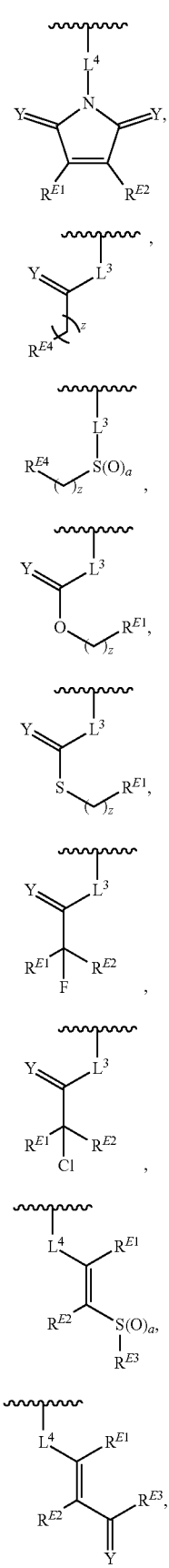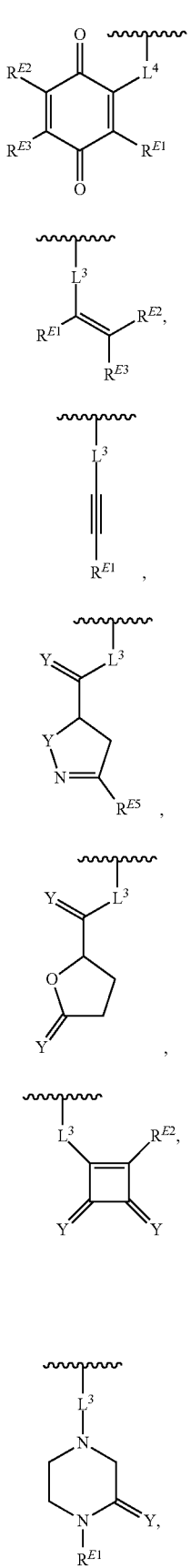

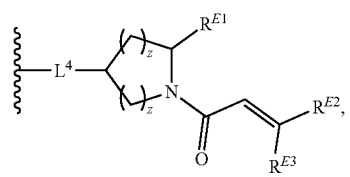 (i-24)
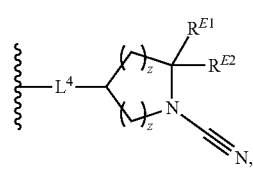 (i-25)
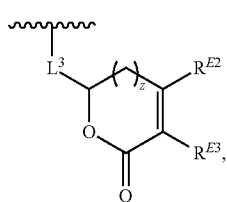 (i-26)
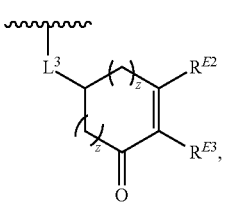 (i-27)
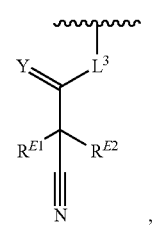 (i-28)
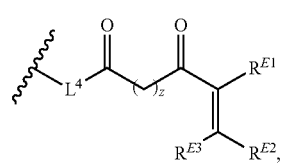 (i-29)
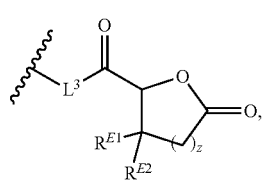 (i-30)
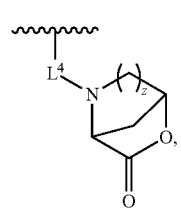 (i-31)
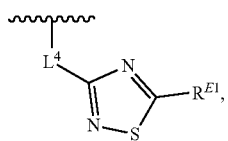 (i-32)
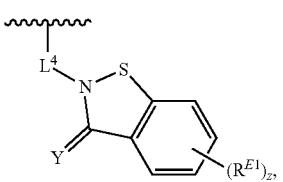 (i-33)
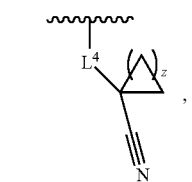 (i-34)
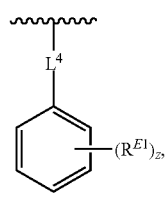 (i-35)
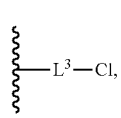 (i-36)
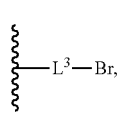 (i-37)
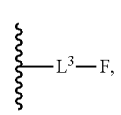 (i-38)
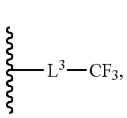 (i-39)
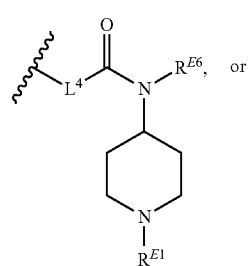 (i-40)

91

-continued

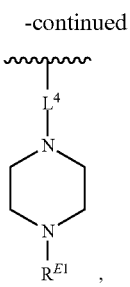
(i-41)

wherein:

L³ is a bond or an optionally substituted C₁₋₄ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)₂—, —S(=O)₂O—, —OS(=O)₂—, —S(=O)₂NR$^{L3a}$—, or —NR$^{L3a}$S(=O)₂—, wherein R$^{L3a}$ is hydrogen, substituted or unsubstituted C₁₋₆ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or about two R$^{L3b}$ groups are joined to form an optionally substituted carbocyclic or optionally substituted heterocyclic ring;

L⁴ is a bond or an optionally substituted, branched or unbranched C₁₋₆ hydrocarbon chain;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH₂OR$^{EE}$, —CH₂N(R$^{EE}$)₂, —CH₂SR$^{EE}$, —OR$^{EE}$, —N(R$^{EE}$)₂, —Si(R$^{EE}$)₃, and —SR$^{EE}$, wherein each occurrence of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or about two R$^{EE}$ groups are joined to form an optionally substituted heterocyclic ring;

or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;

R$^{E5}$ is halogen;

R$^{E6}$ is hydrogen, substituted or unsubstituted C₁₋₆ alkyl, or a nitrogen protecting group;

92 each instance of Y is independently O, S, or NR$^{E7}$, wherein R$^{E7}$ is hydrogen, substituted or unsubstituted C₁₋₆ alkyl, or a nitrogen protecting group;

a is 1 or 2; and each instance of z is independently 0, 1, 2, 3, 4, 5, or 6, as valency permits.

In certain embodiments, the transcription inhibitor is of the formula:

(YKL-01-116)

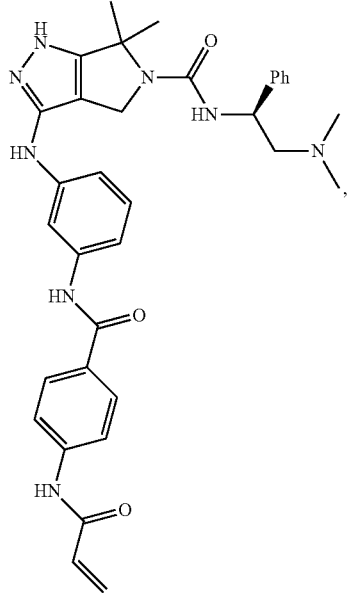

or a pharmaceutically acceptable salt, solvate, hydrate, polymorph, co-crystal, tautomer, stereoisomer, isotopically labeled derivative, or prodrug thereof.

In certain embodiments, the transcription inhibitor is of the formula:

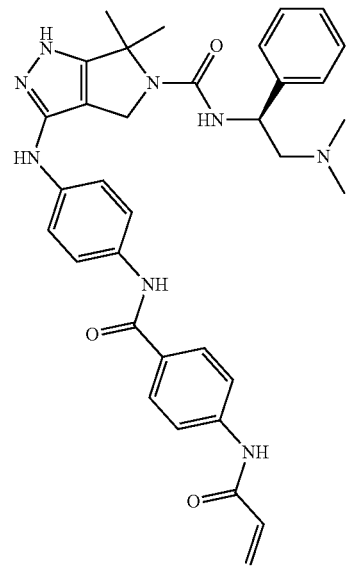

93
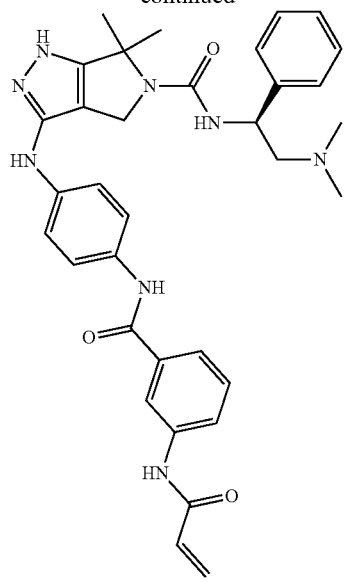
,
94
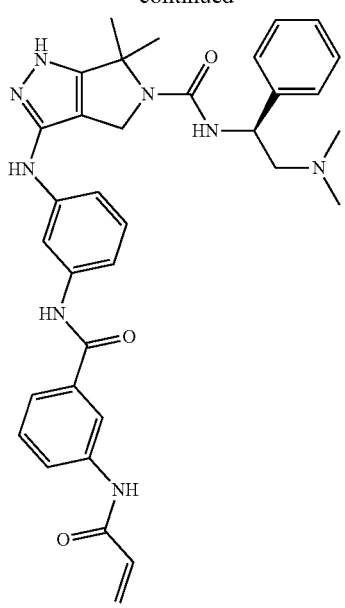
,
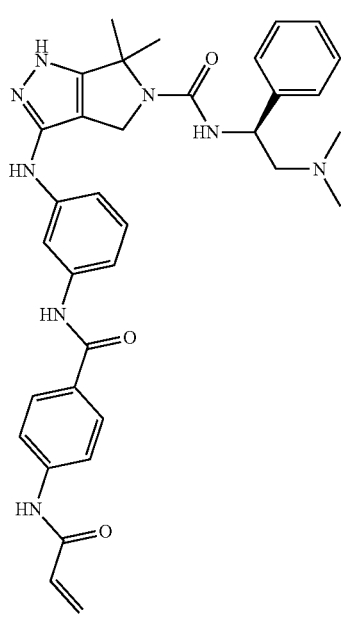
,
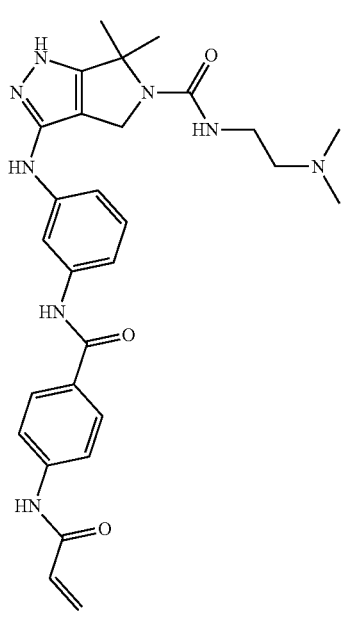
,

95
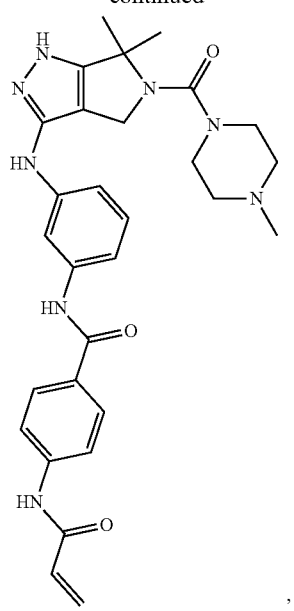
96
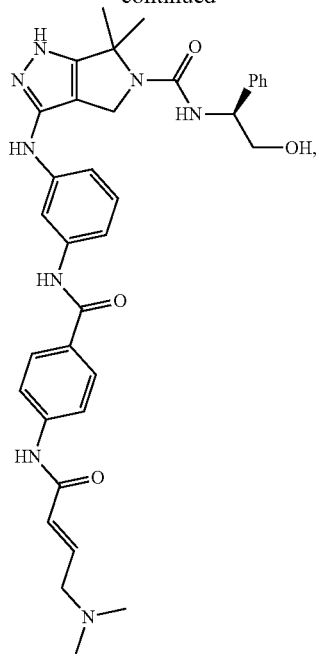
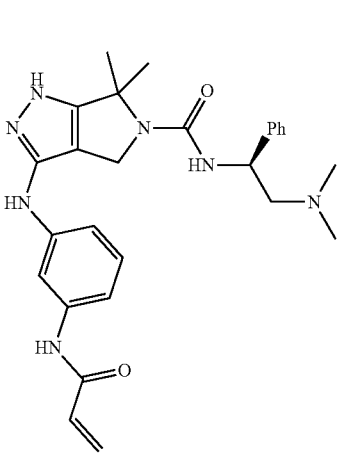
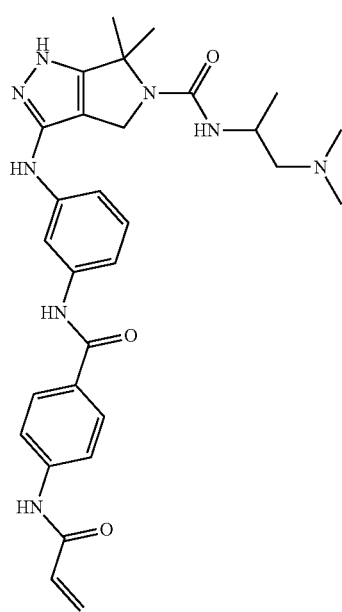
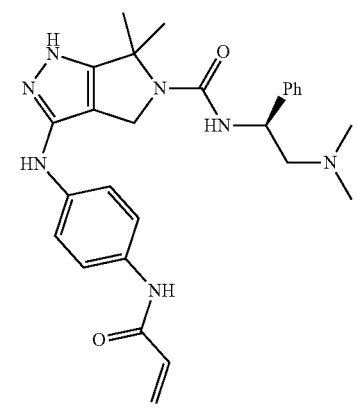

97
-continued
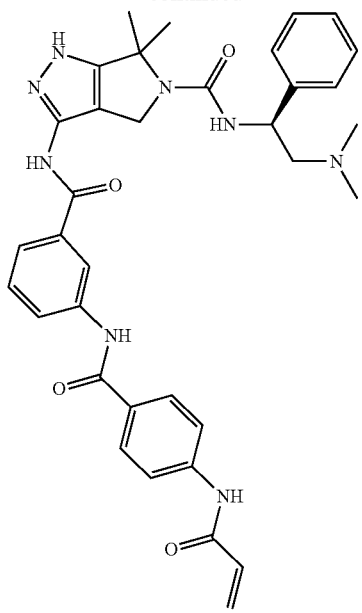
98
-continued
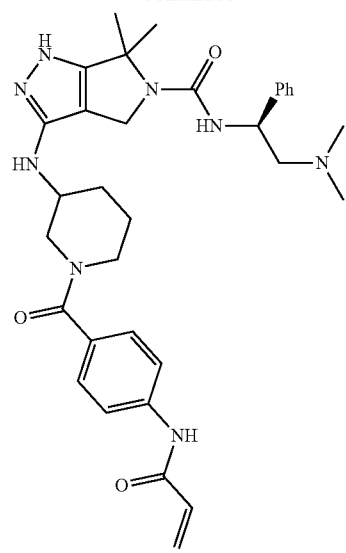
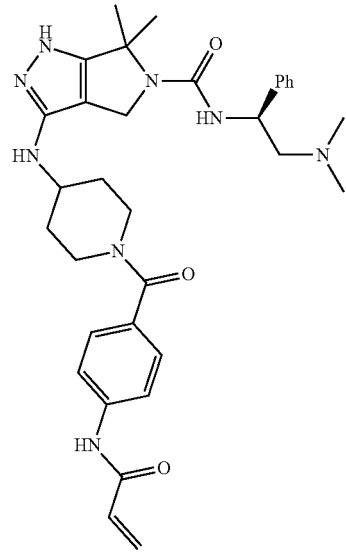
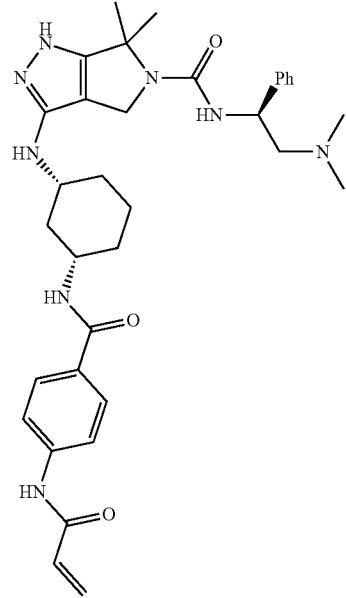

99
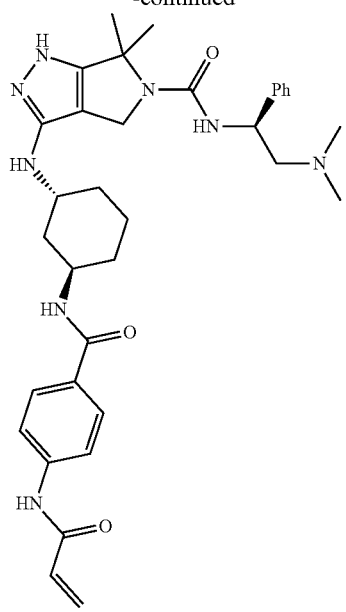
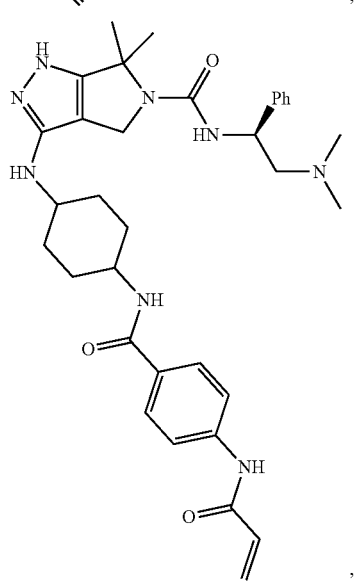
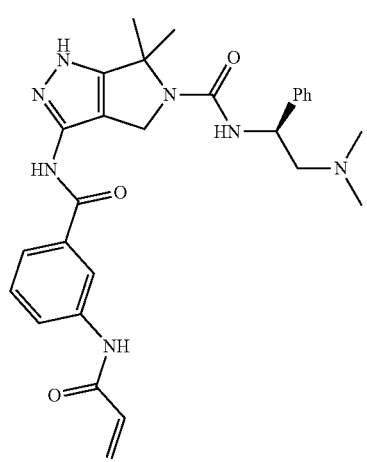
100
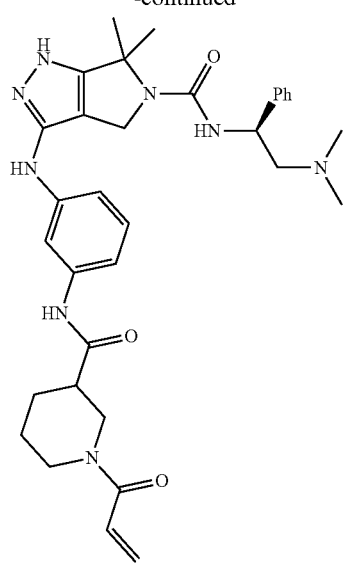
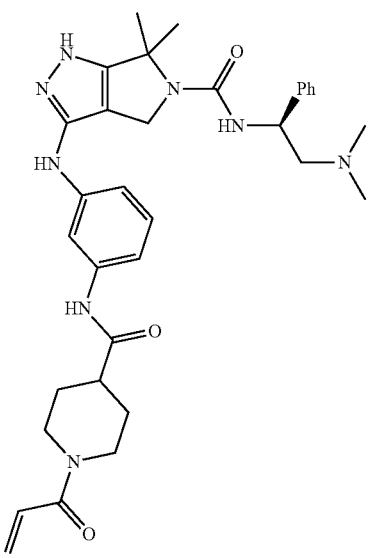
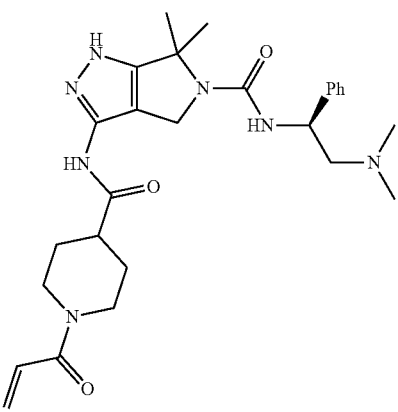

101
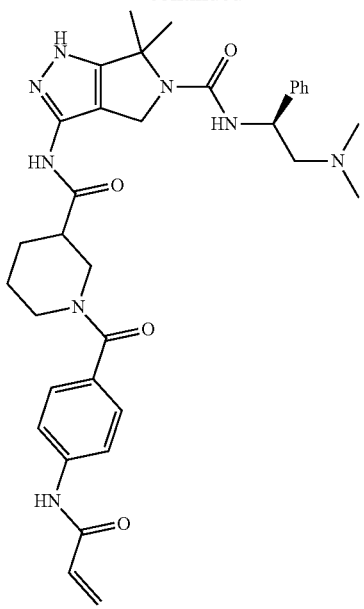
102
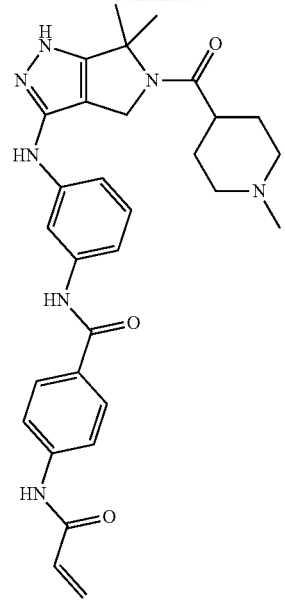
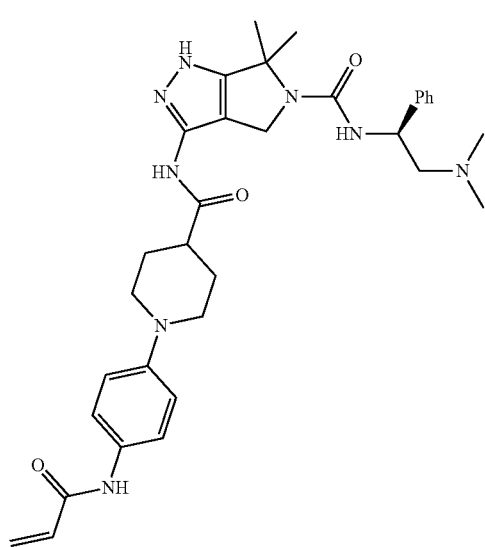
or a pharmaceutically acceptable salt, solvate, hydrate, polymorph, co-crystal, tautomer, stereoisomer, isotopically labeled derivative, or prodrug thereof.
In certain embodiments, the transcription inhibitor is of Formula (VI):

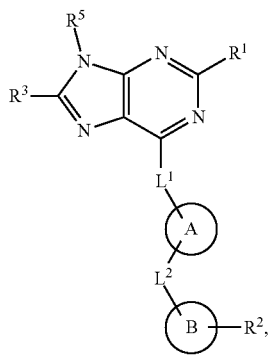

(VI)

or a pharmaceutically acceptable salt, solvate, hydrate, polymorph, co-crystal, tautomer, stereoisomer, isotopically labeled derivative, or prodrug thereof, wherein:

$R^1$ is optionally substituted alkyl, optionally substituted alkenyl, optionally substituted alkynyl, optionally substituted carbocyclyl, optionally substituted aryl, optionally substituted heterocyclyl, optionally substituted heteroaryl, —$NR^aR^b$, —$OR^b$, —$SR^b$, —$C(=O)R^b$, —$C(=O)OR^b$, or —$C(=O)NR^aR^b$, wherein each instance of $R^a$ and $R^b$ is independently hydrogen, optionally substituted alkyl, optionally substituted alkenyl, optionally substituted alkynyl, optionally substituted carbocyclyl, optionally substituted aryl, optionally substituted heterocyclyl, optionally substituted aryl, optionally substituted heteroaryl, or a nitrogen protecting group when attached to nitrogen, or an oxygen protecting group when attached to oxygen, or a sulfur protecting group when attached to sulfur; or $R^a$ and $R^b$ are joined to form an optionally substituted heterocyclic or optionally substituted heteroaryl ring;

$R^3$ is hydrogen, halogen, or optionally substituted $C_1$-$C_6$ alkyl;

$R^5$ is hydrogen, optionally substituted $C_1$-$C_6$ alkyl, or a nitrogen protecting group;

$L^1$ is a bond, —$NR^{L1}$—$(CH_2)_t$—, —O—, or —S—;

$R^{L1}$ is hydrogen, optionally substituted $C_1$-$C_6$ alkyl, or a nitrogen protecting group;

t is 0 or an integer between 1 and 5, inclusive;

Ring A is optionally substituted carbocyclyl, optionally substituted heterocyclyl, optionally substituted aryl, or optionally substituted heteroaryl;

$L^2$ is a bond, optionally substituted $C_{1-4}$ alkylene, —$C(=O)$—, —$NR^{L2}$—, —$C(=O)NR^{L2}$—, —$NR^LC(=O)$—, —O—, or —S—, wherein $R^{L2}$ is hydrogen, optionally substituted $C_1$-$C_6$ alkyl, or a nitrogen protection group;

Ring B is absent, optionally substituted carbocyclyl, optionally substituted heterocyclyl, optionally substituted aryl, or optionally substituted heteroaryl; and $R^2$ is any of Formulae (i-1)-(i-46):

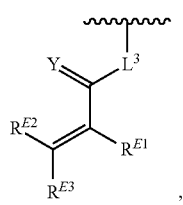 (i-1)

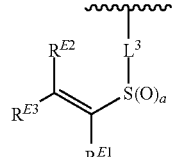 (i-2)

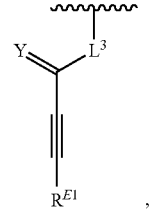 (i-3)

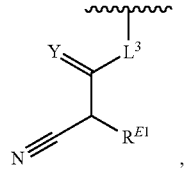 (i-4)

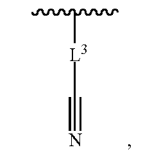 (i-5)

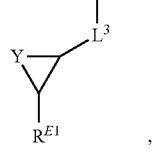 (i-6)

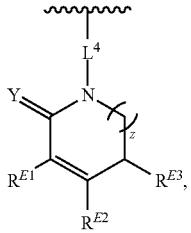 (i-7)

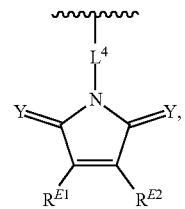 (i-8)

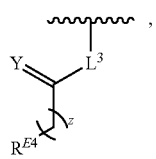 (i-9)

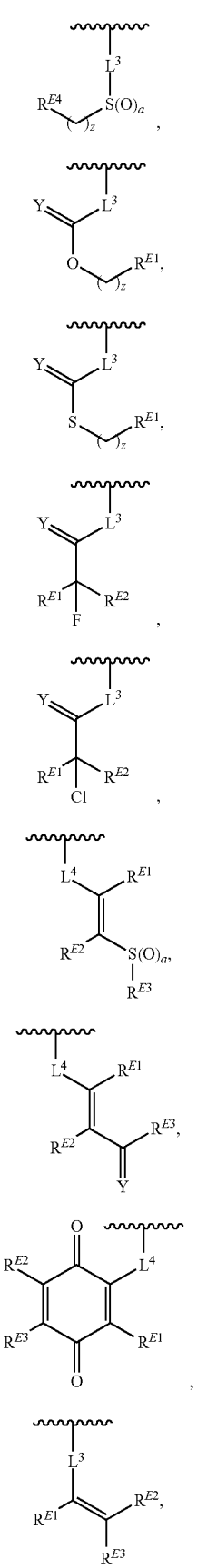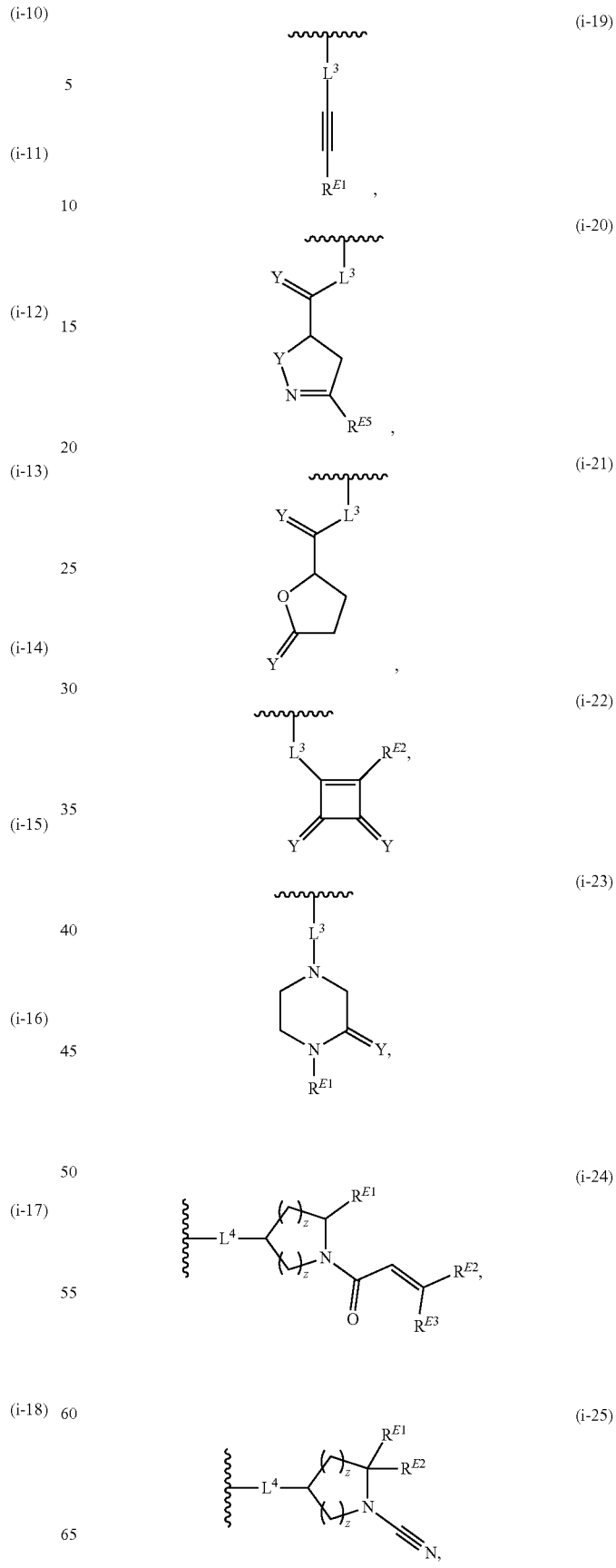

(i-26) 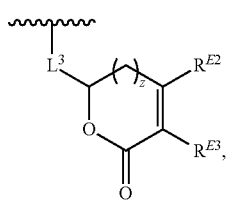

(i-27) 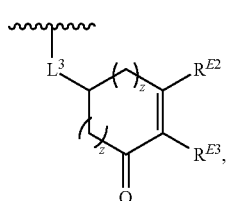

(i-28) 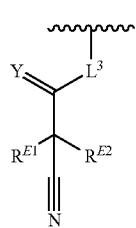

(i-29) 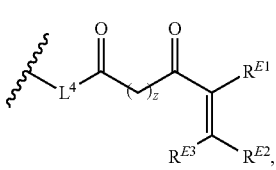

(i-30) 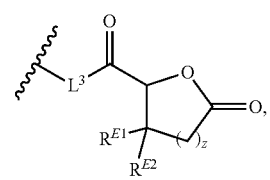

(i-31) 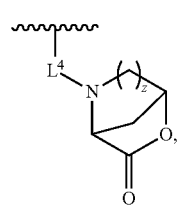

(i-32) 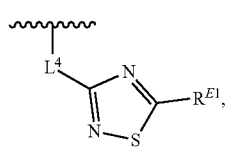

(i-33) 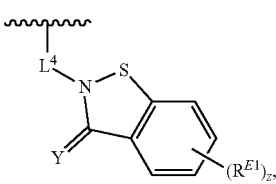

(i-34) 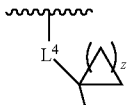

(i-35) 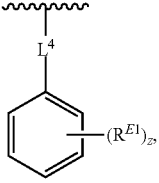

(i-36) 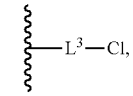

(i-37) 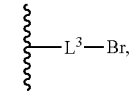

(i-38) 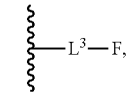

(i-39) 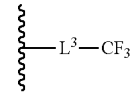

(i-40) 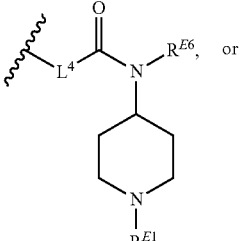

(i-41) 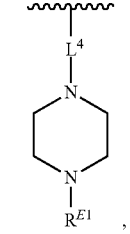

wherein:
$L^3$ is a bond or an optionally substituted $C_{1-4}$ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted C$_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

L$^4$ is a bond or an optionally substituted, branched or unbranched C$_{1-6}$ hydrocarbon chain;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, and —SR$^{EE}$, wherein each occurrence of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring;

or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;

R$^{E5}$ is halogen;

R$^{E6}$ is hydrogen, substituted or unsubstituted C$_{1-6}$ alkyl, or a nitrogen protecting group;

each instance of Y is independently O, S, or NR$^{E7}$, wherein R$^{E7}$ is hydrogen, substituted or unsubstituted C$_{1-6}$ alkyl, or a nitrogen protecting group;

a is 1 or 2; and each instance of z is independently 0, 1, 2, 3, 4, 5, or 6, as valency permits.

In certain embodiments, the transcription inhibitor of Formula (VI) is not of the formula:

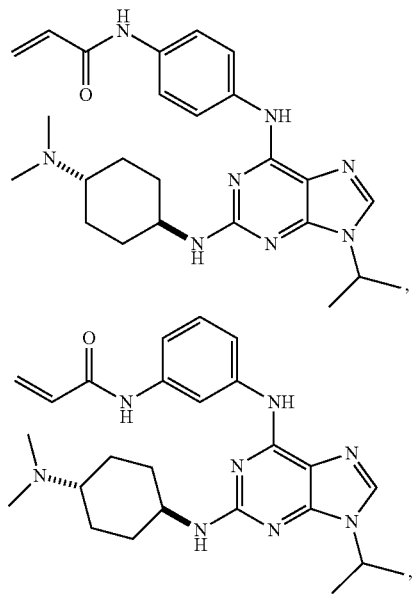

or a pharmaceutically acceptable salt, solvate, hydrate, polymorph, co-crystal, tautomer, stereoisomer, isotopically labeled derivative, or prodrug thereof.

In certain embodiments, the transcription inhibitor of Formula (VI) is of the formula:

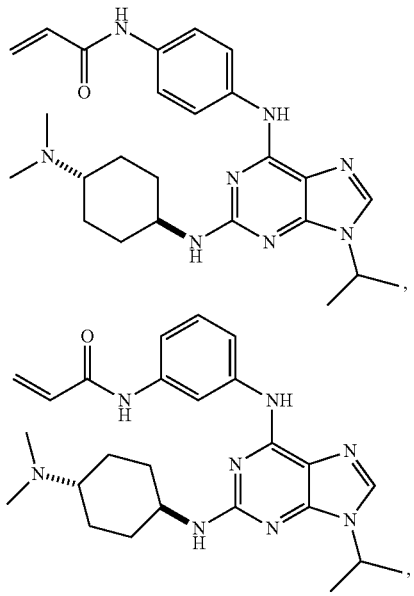

or a pharmaceutically acceptable salt, solvate, hydrate, polymorph, co-crystal, tautomer, stereoisomer, isotopically labeled derivative, or prodrug thereof.

In certain embodiments, the transcription inhibitor is of Formula (VII):

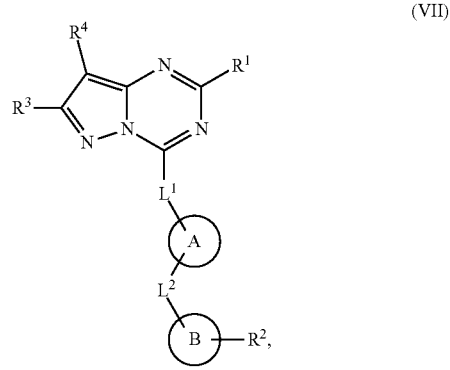

(VII)

or a pharmaceutically acceptable salt, solvate, hydrate, polymorph, co-crystal, tautomer, stereoisomer, isotopically labeled derivative, or prodrug thereof, wherein:

R$^1$ is optionally substituted alkyl, optionally substituted alkenyl, optionally substituted alkynyl, optionally substituted carbocyclyl, optionally substituted aryl, optionally substituted heterocyclyl, optionally substituted heteroaryl, —NR$^a$R$^b$, —OR$^b$, —SR$^b$, —C(=O)R$^b$, —C(=O)OR$^b$, or —C(=O)NR$^a$R$^b$, wherein each instance of R$^a$ and R$^b$ is independently hydrogen, optionally substituted alkyl, optionally substituted alkenyl, optionally substituted alkynyl, optionally substituted carbocyclyl, optionally substituted aryl, optionally substituted heterocyclyl, optionally substituted aryl, optionally substituted heteroaryl, or a nitrogen protecting group when attached to nitrogen, or an oxygen protecting group when attached to oxygen, or a sulfur protecting group when attached to sulfur; or $R^a$ and $R^b$ are joined to form an optionally substituted heterocyclic or optionally substituted heteroaryl ring;

each of $R^3$ and $R^4$ is independently hydrogen, halogen, or optionally substituted $C_1$-$C_6$ alkyl;

$L^1$ is a bond, —$NR^{L1}$—$(CH_2)_t$—, —O—, or —S—;

$R^{L1}$ is hydrogen, optionally substituted $C_1$-$C_6$ alkyl, or a nitrogen protecting group;

t is 0 or an integer between 1 and 5, inclusive;

Ring A is optionally substituted carbocyclyl, optionally substituted heterocyclyl, optionally substituted aryl, or optionally substituted heteroaryl;

$L^2$ is a bond, optionally substituted $C_{1-4}$ alkylene, —C(=O)—, —$NR^{L2}$—, —C(=O)$NR^{L2}$—, —$NR^{L2}$C(=O)—, —O—, or —S—, wherein $R^{L2}$ is hydrogen, optionally substituted $C_1$-$C_6$ alkyl, or a nitrogen protection group;

Ring B is absent, optionally substituted carbocyclyl, optionally substituted heterocyclyl, optionally substituted aryl, or optionally substituted heteroaryl; and $R^2$ is any of Formulae (i-1)-(i-46):

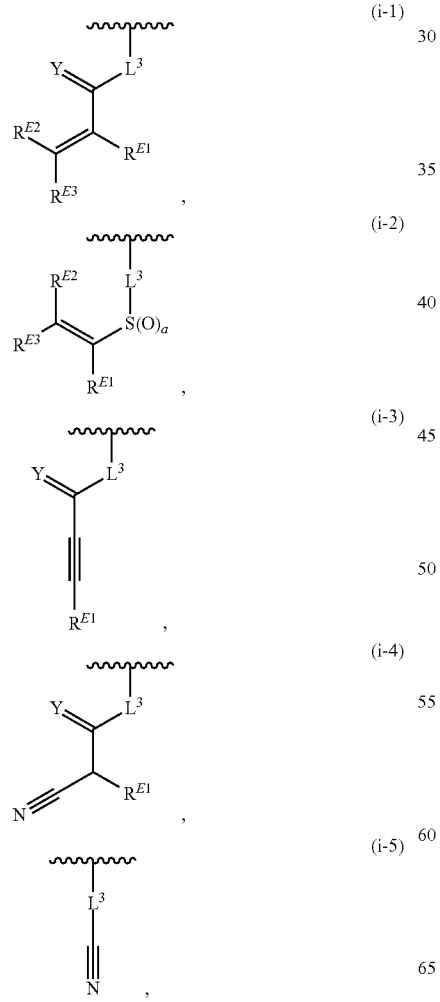

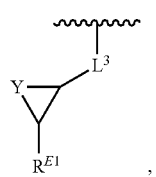

(i-6)

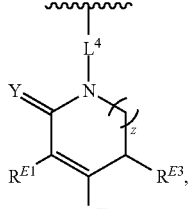

(i-7)

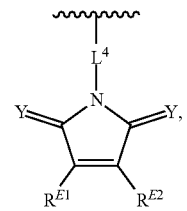

(i-8)

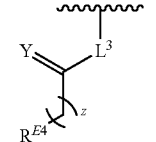

(i-9)

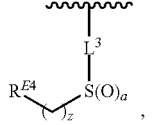

(i-10)

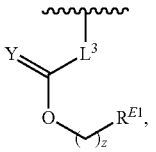

(i-11)

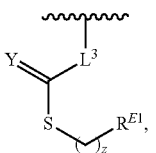

(i-12)

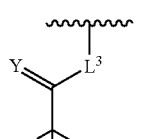

(i-13)

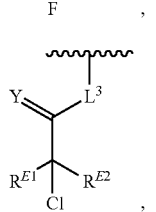

(i-14)

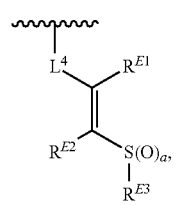 (i-15)
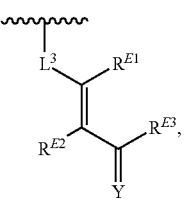 (i-16)
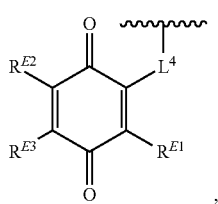 (i-17)
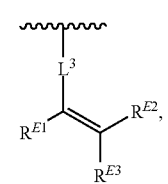 (i-18)
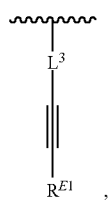 (i-19)
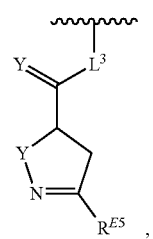 (i-20)
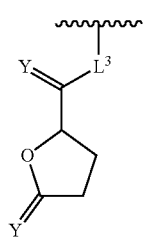 (i-21)
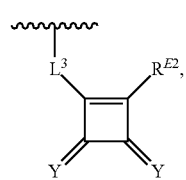 (i-22)
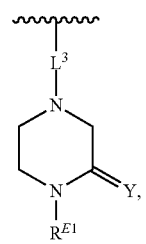 (i-23)
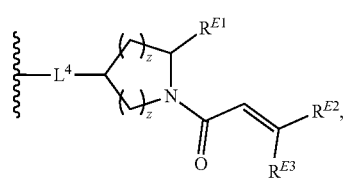 (i-24)
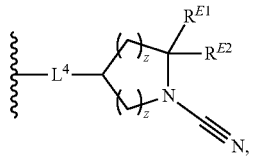 (i-25)
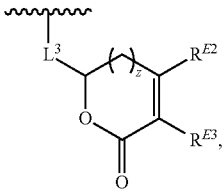 (i-26)
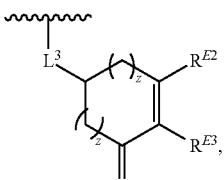 (i-27)
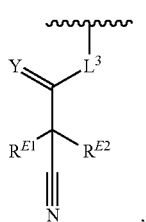 (i-28)
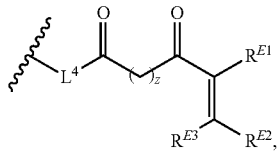 (i-29)

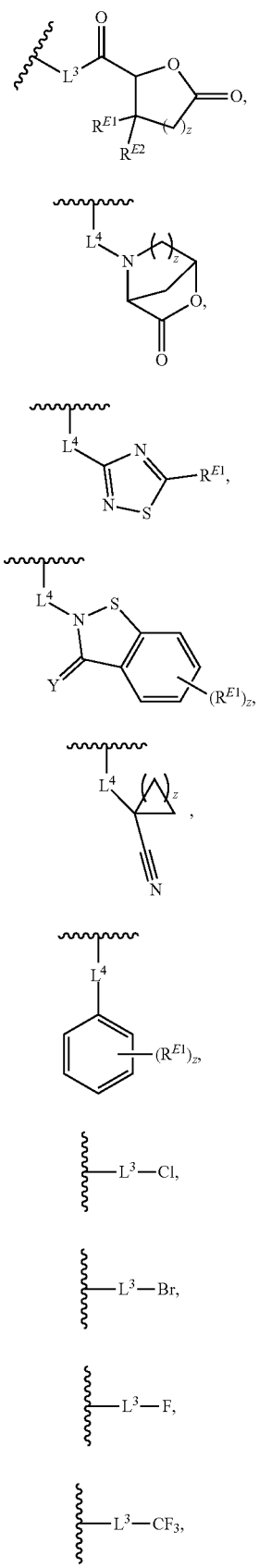

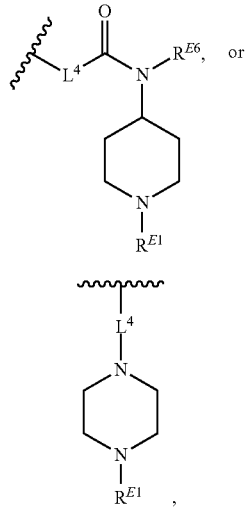

wherein:

$L^3$ is a bond or an optionally substituted $C_{1-4}$ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein $R^{L3a}$ is hydrogen, substituted or unsubstituted $C_{1-6}$ alkyl, or a nitrogen protecting group, and wherein each occurrence of $R^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{L3b}$ groups are joined to form an optionally substituted carbocyclic or optionally substituted heterocyclic ring;

$L^4$ is a bond or an optionally substituted, branched or unbranched $C_{1-6}$ hydrocarbon chain;

each of $R^{E1}$, $R^{E2}$, and $R^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, and —SR$^{EE}$, wherein each occurrence of $R^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two $R^{EE}$ groups are joined to form an optionally substituted heterocyclic ring;

or $R^{E1}$ and $R^{E3}$, or $R^{E2}$ and $R^{E3}$, or $R^{E1}$ and $R^{E2}$ are joined to form an optionally substituted carbocyclic or optionally substituted heterocyclic ring;

$R^{E4}$ is a leaving group;

$R^{E5}$ is halogen;

$R^{E6}$ is hydrogen, substituted or unsubstituted $C_{1-6}$ alkyl, or a nitrogen protecting group;

each instance of Y is independently O, S, or $NR^{E7}$, wherein $R^{E7}$ is hydrogen, substituted or unsubstituted $C_{1-6}$ alkyl, or a nitrogen protecting group;

a is 1 or 2; and each instance of z is independently 0, 1, 2, 3, 4, 5, or 6, as valency permits.

In certain embodiments, the transcription inhibitor is of Formula (VIII):

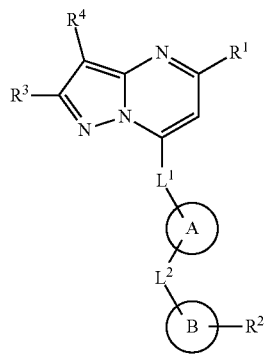

(VIII)

or a pharmaceutically acceptable salt, solvate, hydrate, polymorph, co-crystal, tautomer, stereoisomer, isotopically labeled derivative, or prodrug thereof, wherein:

$R^1$ is optionally substituted alkyl, optionally substituted alkenyl, optionally substituted alkynyl, optionally substituted carbocyclyl, optionally substituted aryl, optionally substituted heterocyclyl, optionally substituted heteroaryl, $-NR^aR^b$, $-OR^b$, $-SR^b$, $-C(=O)R^b$, $-C(=O)OR^b$, or $-C(=O)NR^aR^b$, wherein each instance of $R^a$ and $R^b$ is independently hydrogen, optionally substituted alkyl, optionally substituted alkenyl, optionally substituted alkynyl, optionally substituted carbocyclyl, optionally substituted aryl, optionally substituted heterocyclyl, optionally substituted aryl, optionally substituted heteroaryl, or a nitrogen protecting group when attached to nitrogen, or an oxygen protecting group when attached to oxygen, or a sulfur protecting group when attached to sulfur; or $R^a$ and $R^b$ are joined to form an optionally substituted heterocyclic or optionally substituted heteroaryl ring;

each of $R^3$ and $R^4$ is independently hydrogen, halogen, or optionally substituted $C_1$-$C_6$ alkyl;

$R^5$ is hydrogen, optionally substituted $C_1$-$C_6$ alkyl, or a nitrogen protecting group;

$L^1$ is a bond, $-NR^{L1}-(CH_2)_t-$, $-O-$, or $-S-$;

$R^{L1}$ is hydrogen, optionally substituted $C_1$-$C_6$ alkyl, or a nitrogen protecting group;

t is 0 or an integer between 1 and 5, inclusive;

Ring A is optionally substituted carbocyclyl, optionally substituted heterocyclyl, optionally substituted aryl, or optionally substituted heteroaryl;

$L^2$ is a bond, optionally substituted $C_{1-4}$ alkylene, $-C(=O)-$, $-NR^{L2}-$, $-C(=O)NR^{L2}-$, $-NR^{L2}C(=O)-$, $-O-$, or $-S-$, wherein $R^{L2}$ is hydrogen, optionally substituted $C_1$-$C_6$ alkyl, or a nitrogen protection group;

Ring B is absent, optionally substituted carbocyclyl, optionally substituted heterocyclyl, optionally substituted aryl, or optionally substituted heteroaryl; and $R^2$ is any of Formulae (i-1)-(i-46):

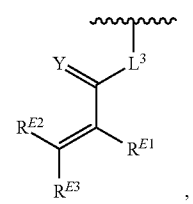
(i-1)

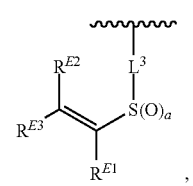
(i-2)

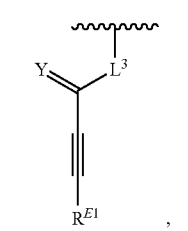
(i-3)

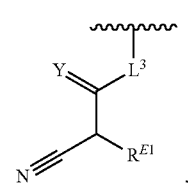
(i-4)

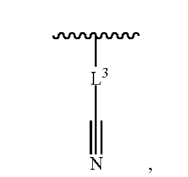
(i-5)

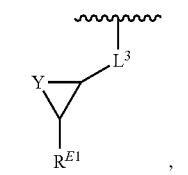
(i-6)

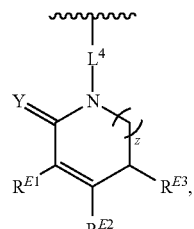
(i-7)

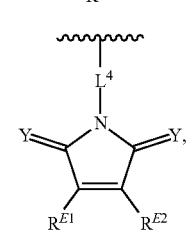
(i-8)

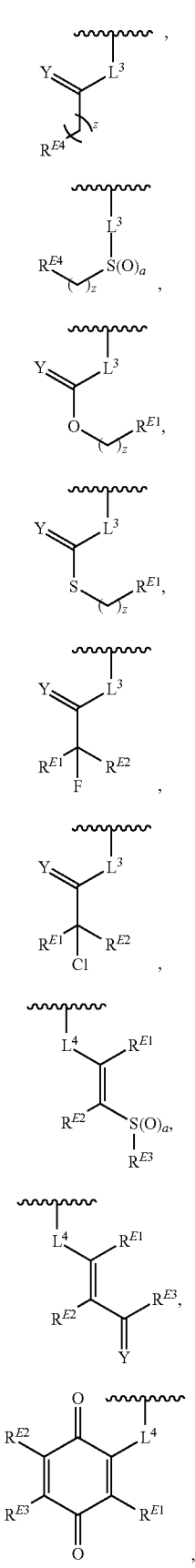
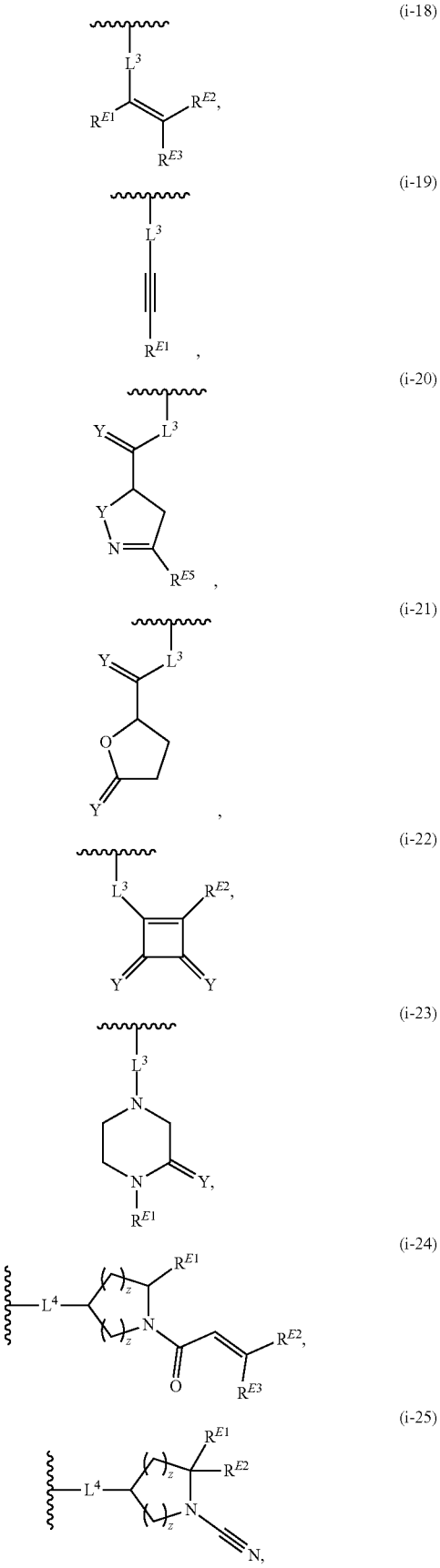

-continued (i-26) 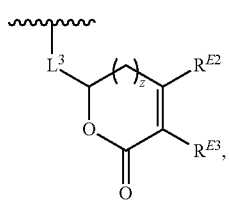

(i-27) 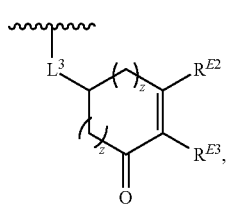

(i-28) 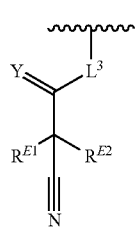

(i-29) 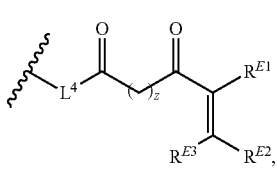

(i-30) 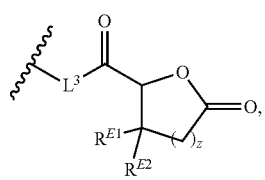

(i-31) 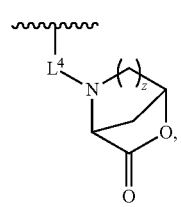

(i-32) 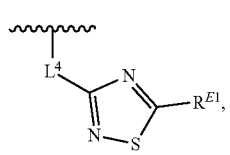

(i-33) 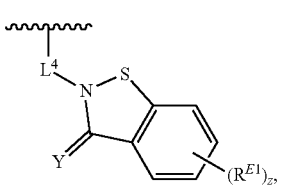

(i-34) 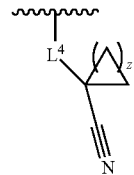

(i-35) 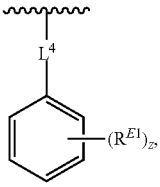

(i-36) 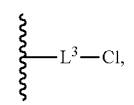

(i-37) 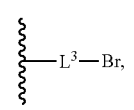

(i-38) 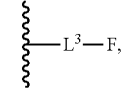

(i-39) 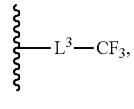

(i-40) 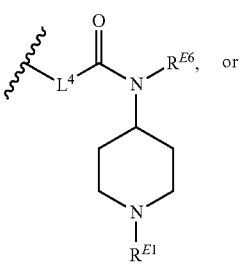

or (i-41) 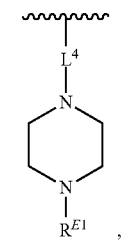

wherein:

$L^3$ is a bond or an optionally substituted $C_{1-4}$ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted C$_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

L$^4$ is a bond or an optionally substituted, branched or unbranched C$_{1-6}$ hydrocarbon chain;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, and —SR$^{EE}$, wherein each occurrence of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring;

or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;

R$^{E5}$ is halogen;

R$^{E6}$ is hydrogen, substituted or unsubstituted C$_{1-6}$ alkyl, or a nitrogen protecting group;

each instance of Y is independently O, S, or NR$^{E7}$, wherein R$^{E7}$ is hydrogen, substituted or unsubstituted C$_{1-6}$ alkyl, or a nitrogen protecting group;

a is 1 or 2; and each instance of z is independently 0, 1, 2, 3, 4, 5, or 6, as valency permits.

In certain embodiments, the transcription inhibitor is of the formula:

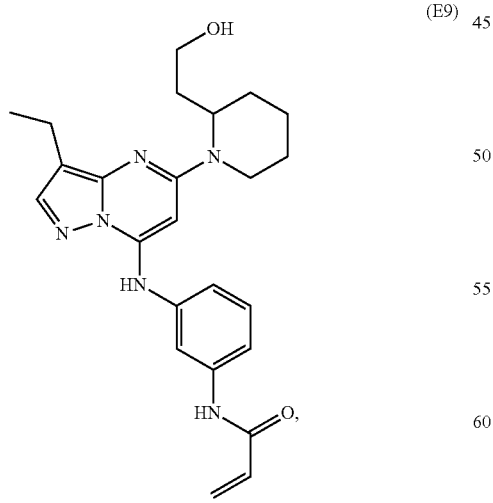

(E9)

or a pharmaceutically acceptable salt, solvate, hydrate, polymorph, co-crystal, tautomer, stereoisomer, isotopically labeled derivative, or prodrug thereof.

In certain embodiments, the transcription inhibitor is of the formula:

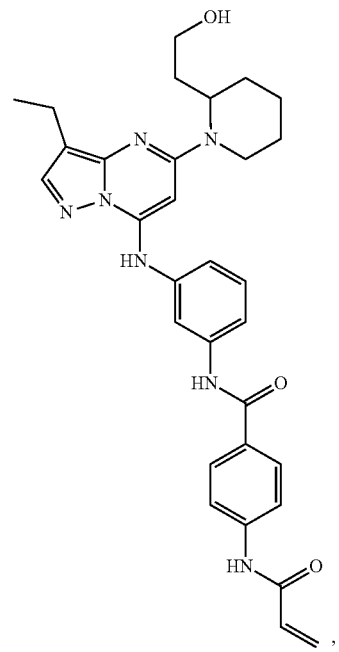

,

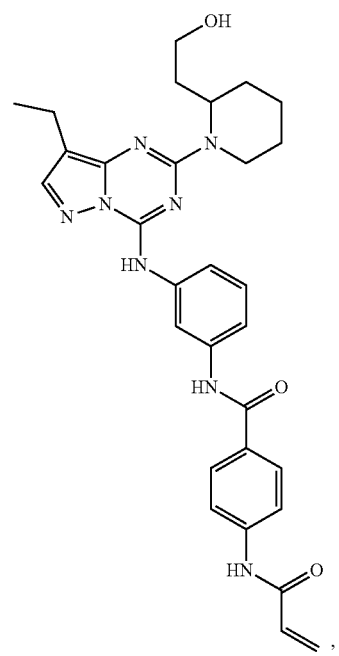

,

125
-continued
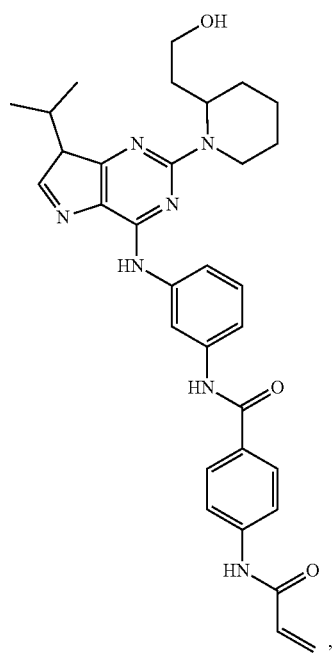
126
-continued
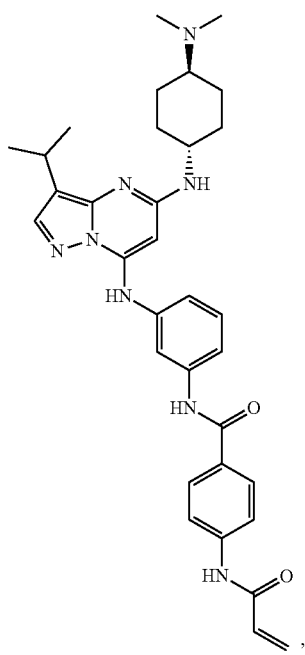
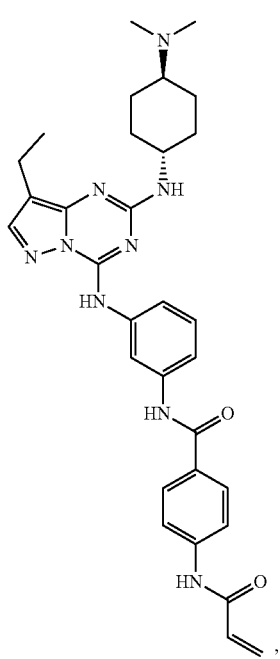
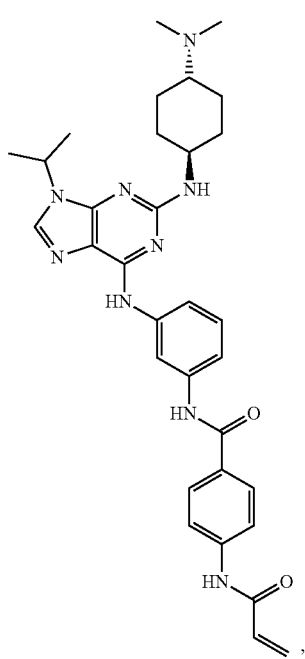

127
-continued
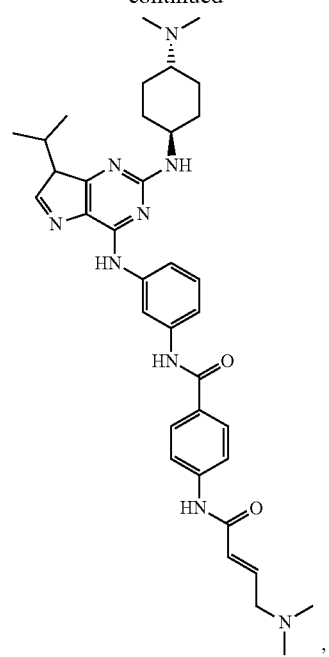
128
-continued
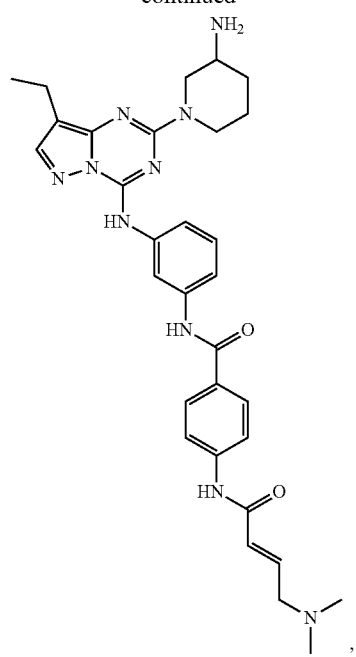

129
-continued
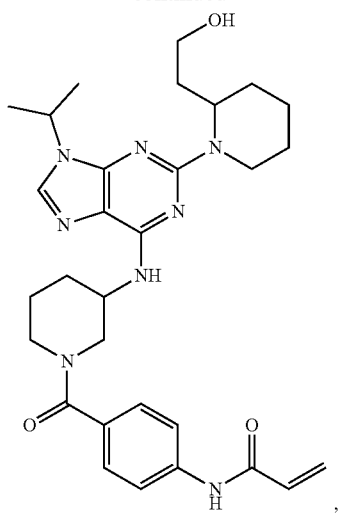
130
-continued
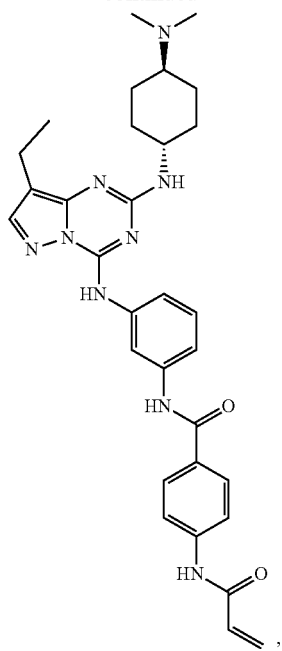
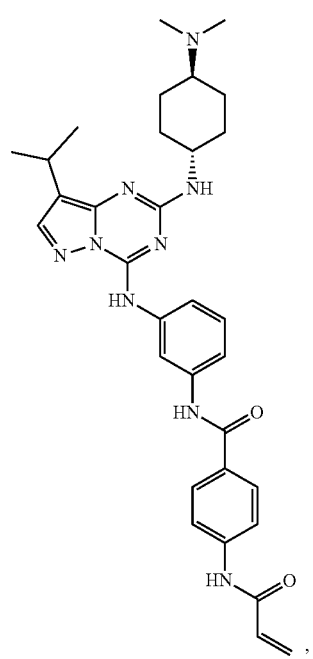
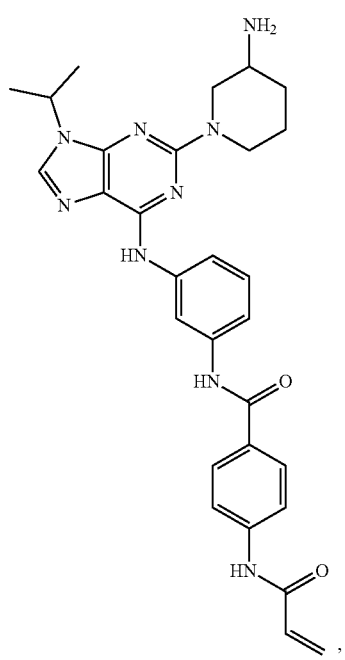

131
-continued
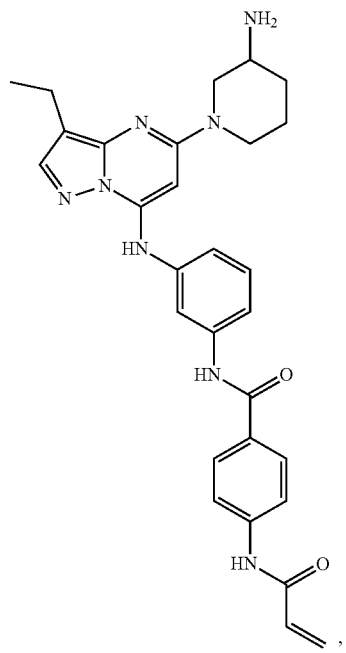
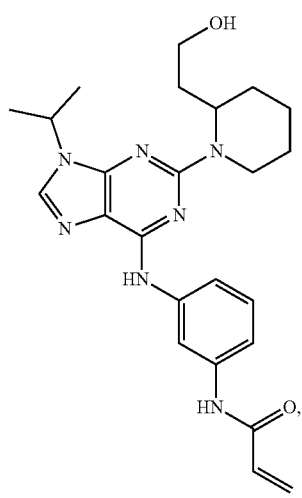
132
-continued
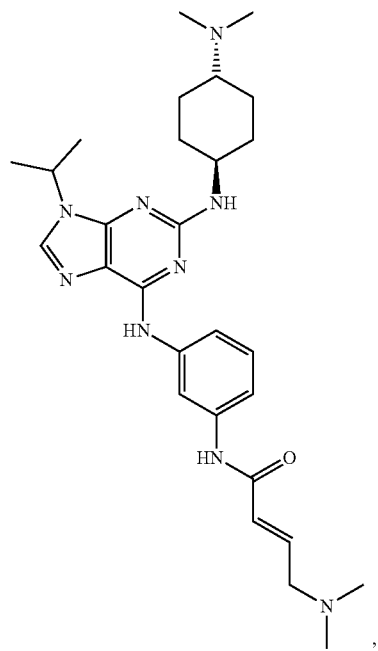
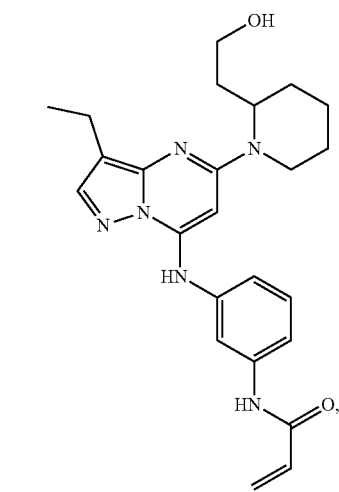

133
-continued
134
-continued
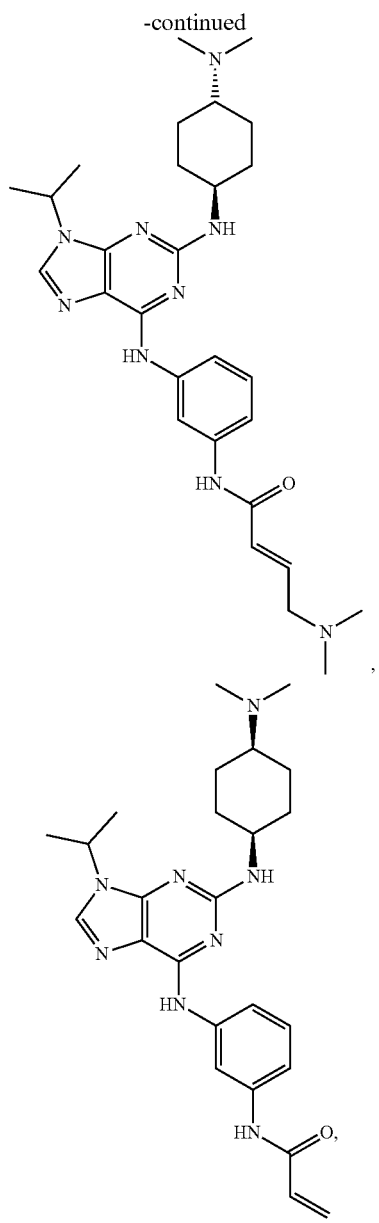
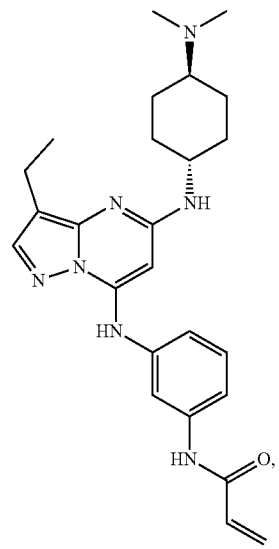
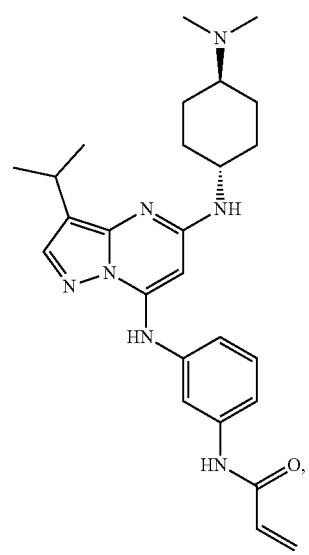
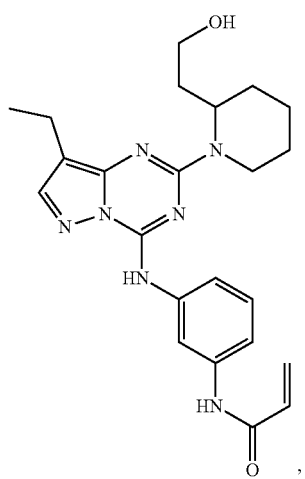
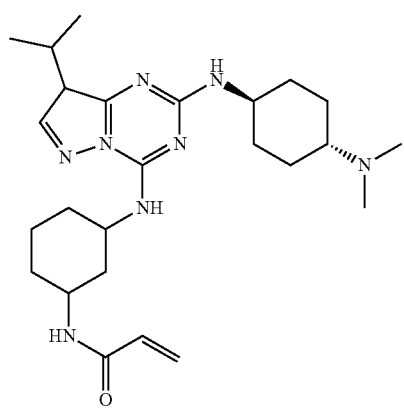

135
-continued
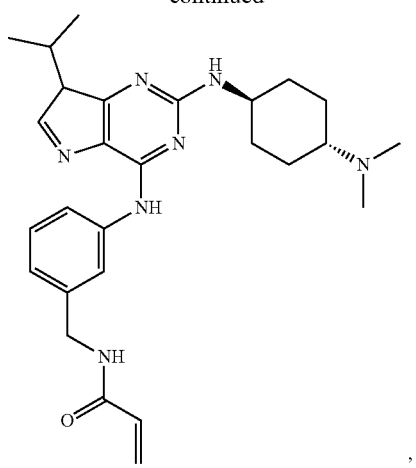
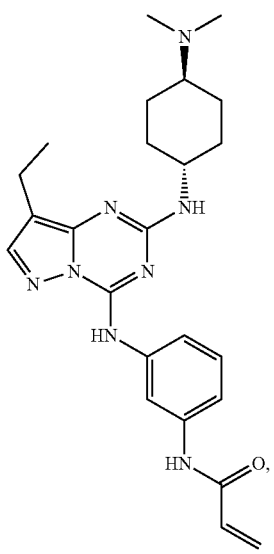
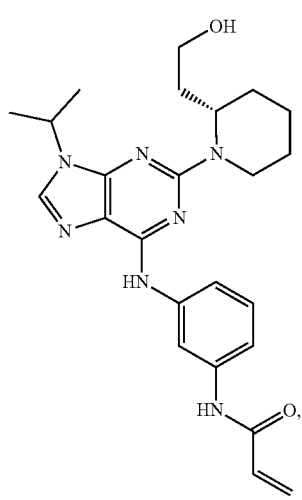
136
-continued
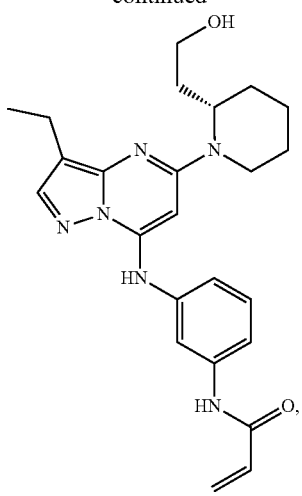
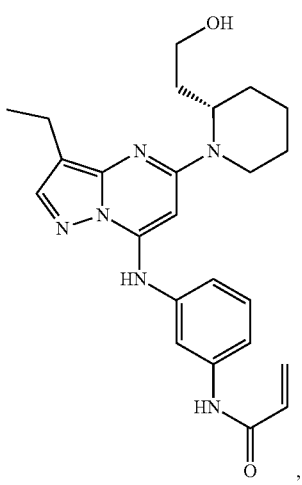
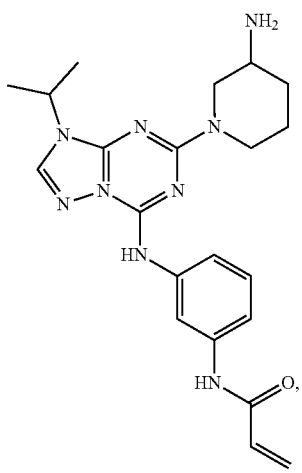

137
-continued
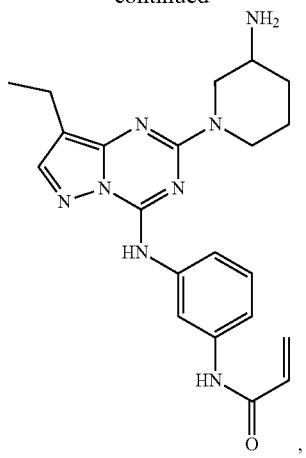
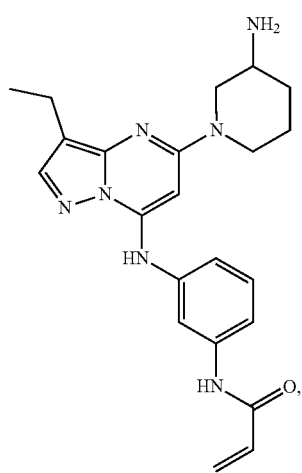
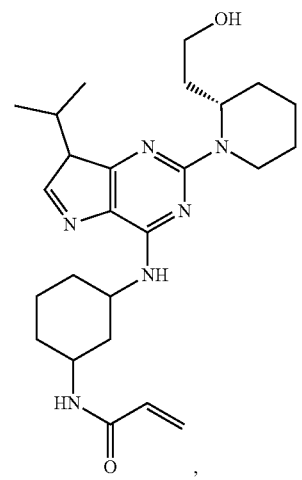
138
-continued
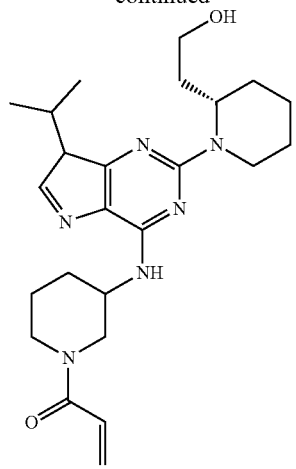
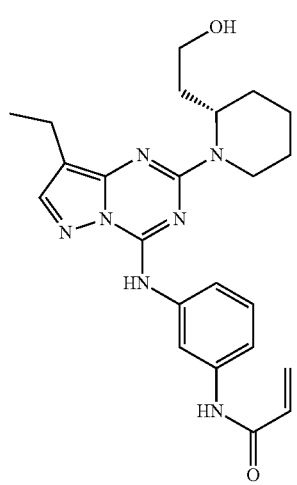
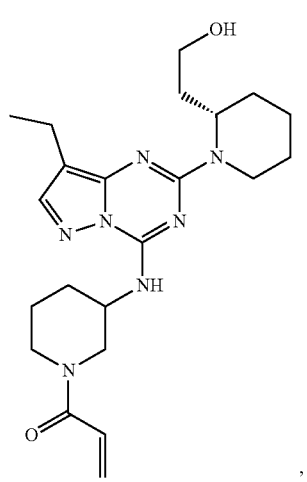 [SMILES: C=CC(=O)N1CCCC(Nc2nc(N3CCCC[C@H]3CCO)nc3c2N=CC3C(C)C)C1]

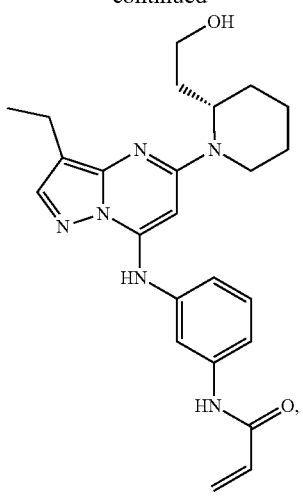

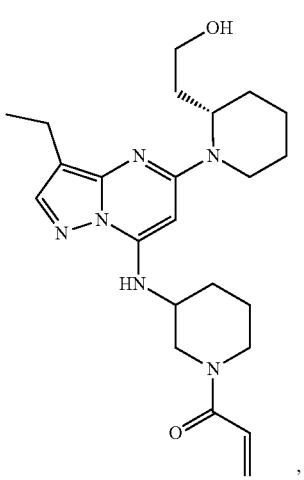

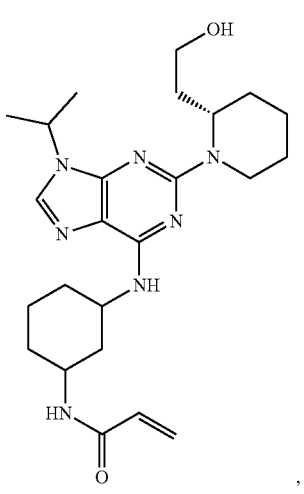

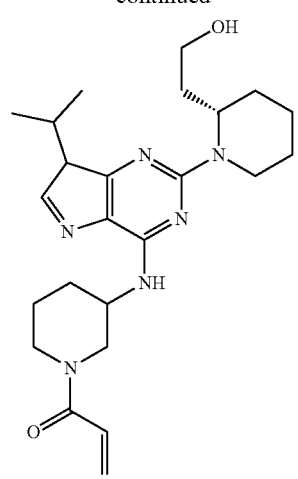

or a pharmaceutically acceptable salt, solvate, hydrate, polymorph, co-crystal, tautomer, stereoisomer, isotopically labeled derivative, or prodrug thereof.

In certain embodiments, the transcription inhibitor is of Formula (IX):

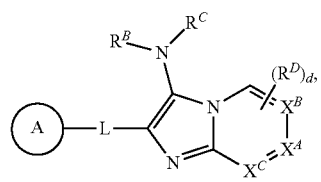

or a pharmaceutically acceptable salt, solvate, hydrate, polymorph, co-crystal, tautomer, stereoisomer, isotopically labeled derivative, or prodrug thereof, wherein:

$X^A$ is $C(R^D)$ or N;

$X^B$ is $C(R^D)$ or N;

$X^C$ is $C(R^D)$ or N;

wherein no more than about two of $X^A$, $X^B$, and $X^C$ can be N;

Ring A is of the formula:

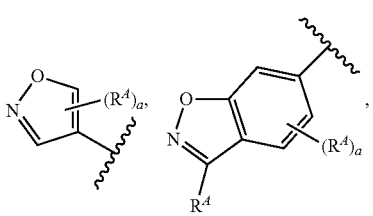

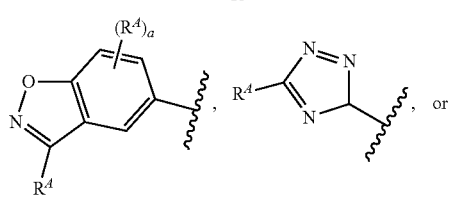

-continued

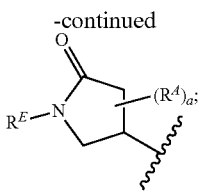

L is a bond or of the formula:

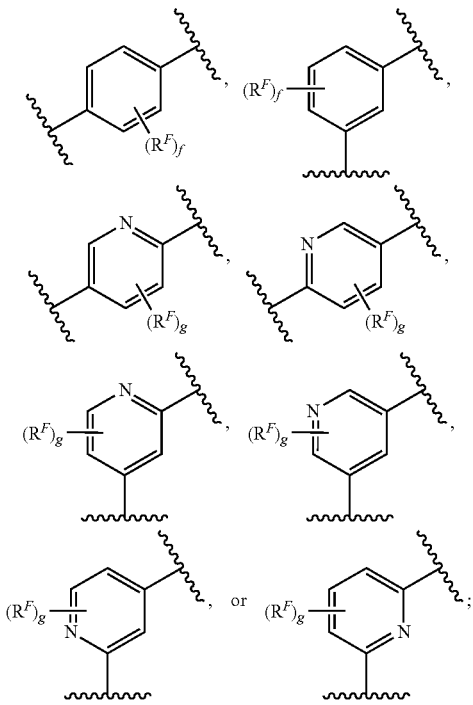

each instance of $R^A$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{A1}$, $-N(R^{A1})_2$, $-SR^{A1}$, $-CN$, $-SCN$, $-C(=NR^{A1})R^{A1}$, $-C(=NR^{A1})OR^{A1}$, $-C(=NR^{A1})N(R^{A1})_2$, $-C(=O)R^{A1}$, $-C(=O)OR^{A1}$, $-C(=O)N(R^{A1})_2$, $-NO_2$, $-NR^{A1}C(=O)R^{A1}$, $-NR^{A1}C(=O)OR^{A1}$, $-NR^{A1}C(=O)N(R^{A1})_2$, $-OC(=O)R^{A1}$, $-OC(=O)OR^{A1}$, or $-OC(=O)N(R^{A1})_2$, or about two instances of $R^A$ are joined to form a substituted or unsubstituted carbocyclic, substituted or unsubstituted heterocyclic, substituted or unsubstituted aryl, or substituted or unsubstituted heteroaryl ring;

each instance of $R^{A1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two instances of $R^{A1}$ are joined to form a substituted or unsubstituted heterocyclic ring;

$R^B$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-C(=O)R^{B1}$, $-C(=O)OR^{B1}$, $-C(=O)N(R^{B1})_2$, or a nitrogen protecting group, or $R^B$ and $R^C$ are joined to form a substituted or unsubstituted heterocyclic ring;

each instance of $R^{B1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or an oxygen protecting group when attached to an oxygen atom, or about two instances of $R^{B1}$ are joined to form a substituted or unsubstituted heterocyclic ring;

$R^C$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-C(=O)R^{C1}$, $-C(=O)OR^{C1}$, $-C(=O)N(R^{C1})_2$, or a nitrogen protecting group, or $R^C$ and $R^B$ are joined to form a substituted or unsubstituted heterocyclic ring;

each instance of $R^{C1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or an oxygen protecting group when attached to an oxygen atom, or about two instances of $R^{C1}$ are joined to form a substituted or unsubstituted heterocyclic ring;

each instance of $R^D$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{D1}$, $-N(R^{D1})_2$, $-SR^{D1}$, $-CN$, $-SCN$, $-C(=NR^{D1})R^{D1}$, $-C(=NR^{D1})OR^{D1}$, $-C(=NR^{D1})N(R^{D1})_2$, $-C(=O)R^{D1}$, $-C(=O)OR^{D1}$, $-C(=O)N(R^{D1})_2$, $-NO_2$, $-NR^{D1}C(=O)R^{D1}$, $-NR^{D1}C(=O)OR^{D1}$, $-NR^{D1}C(=O)N(R^{D1})_2$, $-OC(=O)R^{D1}$, $-OC(=O)OR^{D1}$, or $-OC(=O)N(R^{D1})_2$, or about two instances of $R^D$ are joined to form a substituted or unsubstituted carbocyclic, substituted or unsubstituted heterocyclic, substituted or unsubstituted aryl, or substituted or unsubstituted heteroaryl ring;

each instance of $R^{D1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two instances of $R^{D1}$ are joined to form a substituted or unsubstituted heterocyclic ring;

$R^E$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)R$^{E1}$, —C(=O)OR$^{E1}$, —C(=O)N(R$^{E1}$)$_2$, or a nitrogen protecting group;

each instance of R$^{E1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or an oxygen protecting group when attached to an oxygen atom, or about two instances of R$^{E1}$ are joined to form a substituted or unsubstituted heterocyclic ring;

each instance of R$^F$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{F1}$, —N(R$^{F1}$)$_2$, —SR$^{F1}$, —CN, —SCN, —C(=NR$^{F1}$)R$^{F1}$, —C(=NR$^{F1}$)OR$^{F1}$, —C(=NR$^{F1}$)N(R$^{F1}$)$_2$, —C(=O)R$^{F1}$, —C(=O)OR$^{F1}$, —C(=O)N(R$^{F1}$)$_2$, —NO$_2$, —NR$^{F1}$C(=O)R$^{F1}$, —NR$^{F1}$C(=O)OR$^{F1}$, —NR$^{F1}$C(=O)N(R$^{F1}$)$_2$, —OC(=O)R$^{F1}$, —OC(=O)OR$^{F1}$, or —OC(=O)N(R$^{F1}$)$_2$, or about two instances of RF are joined to form a substituted or unsubstituted carbocyclic, substituted or unsubstituted heterocyclic, substituted or unsubstituted aryl, or substituted or unsubstituted heteroaryl ring;

each instance of R$^{F1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two instances of R$^{F1}$ are joined to form a substituted or unsubstituted heterocyclic ring;

a is 0, 1, 2, 3, 4, or 5;

d is 0, 1, or 2;

f is 0, 1, 2, 3 or 4; and g is 0, 1, 2, or 3.

In certain embodiments, the transcription inhibitor is of the formula:

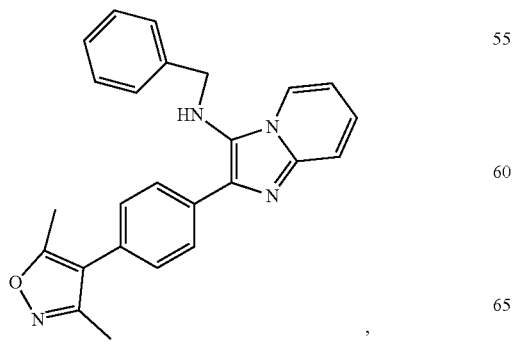

-continued

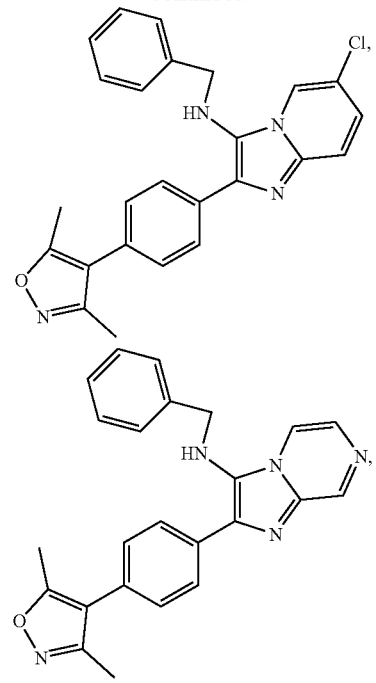

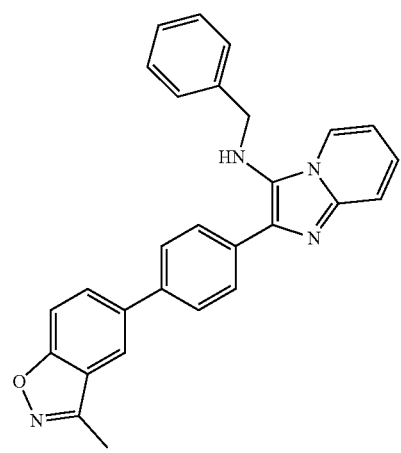

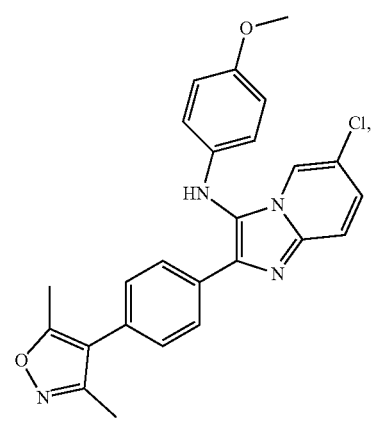

-continued
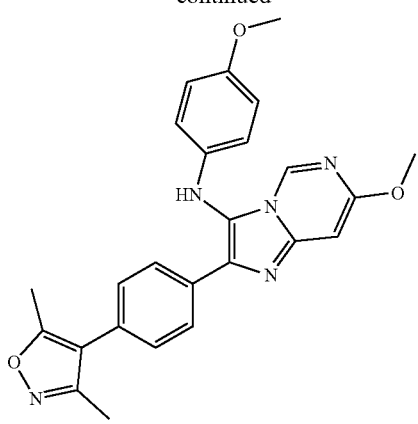,
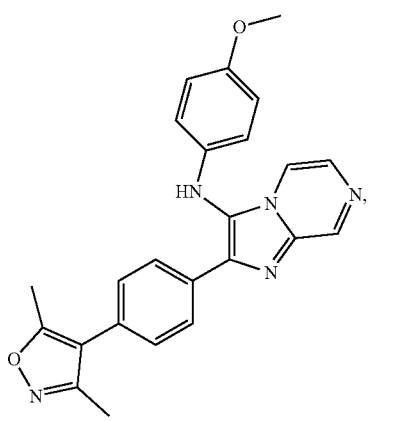,
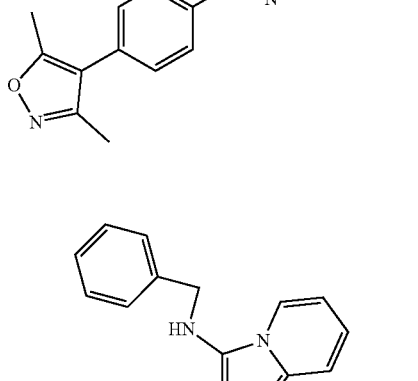,
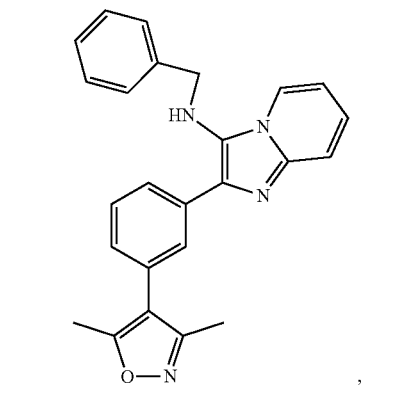,
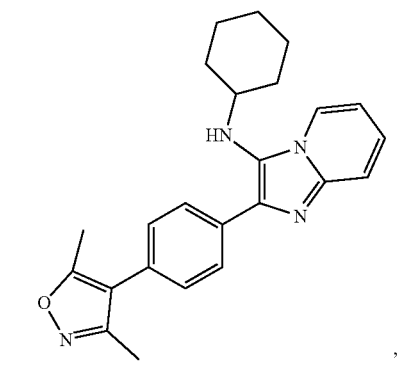,
-continued
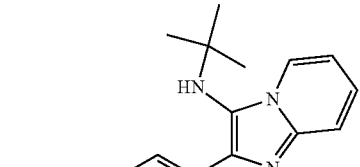,
,
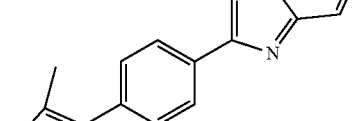,
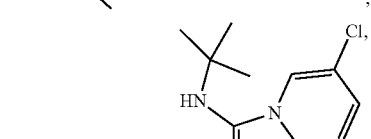,
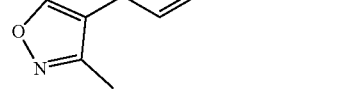,
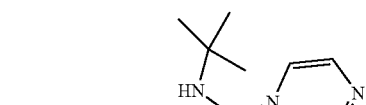,

147
-continued
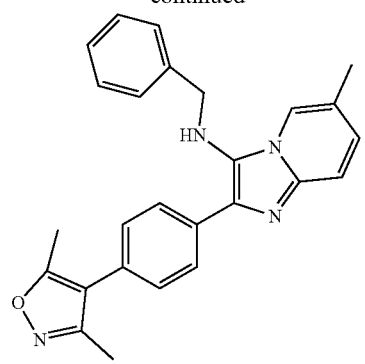
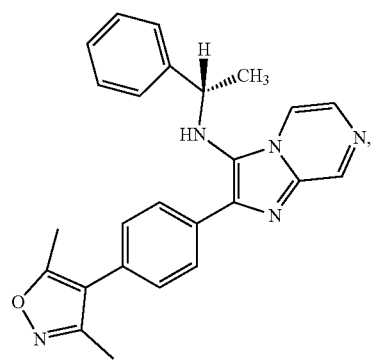
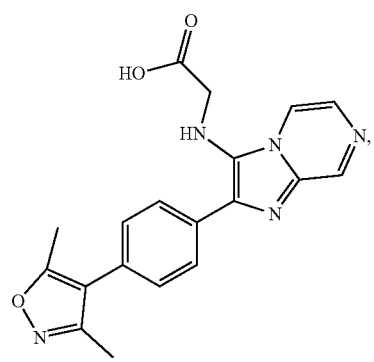
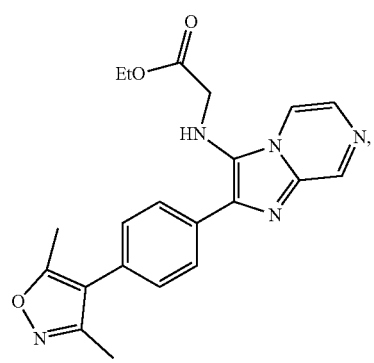
148
-continued
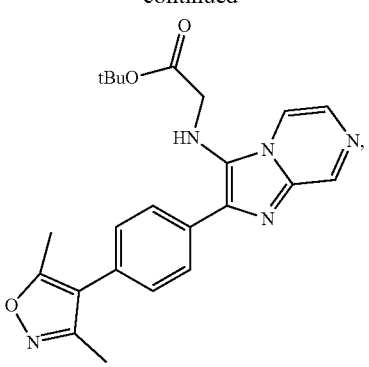
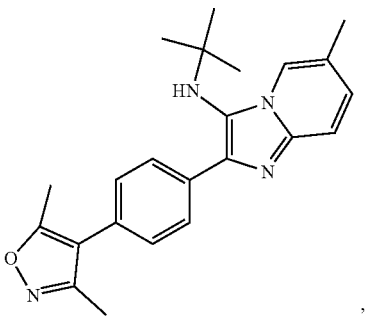
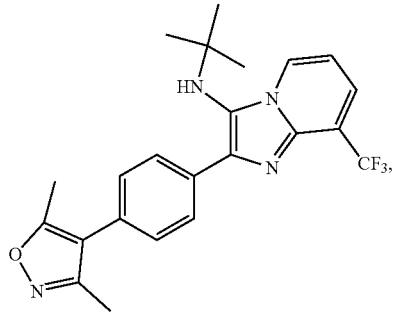
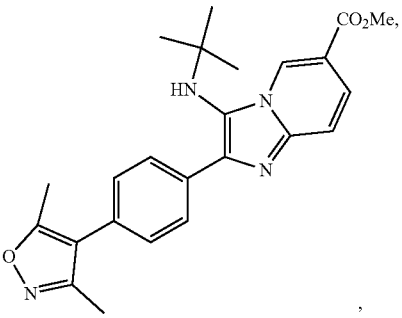
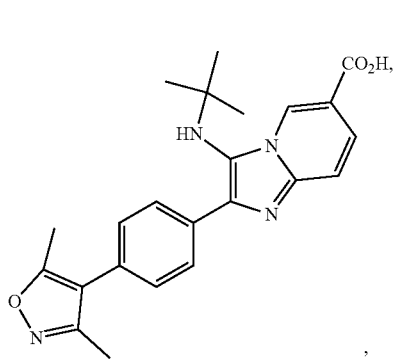

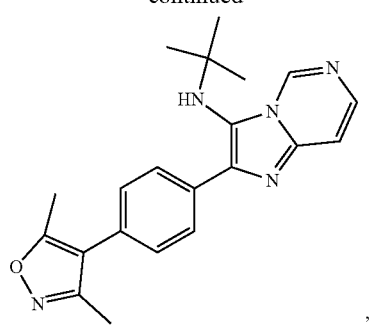
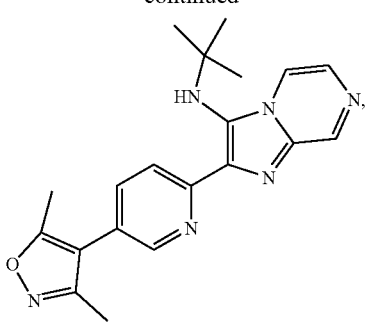
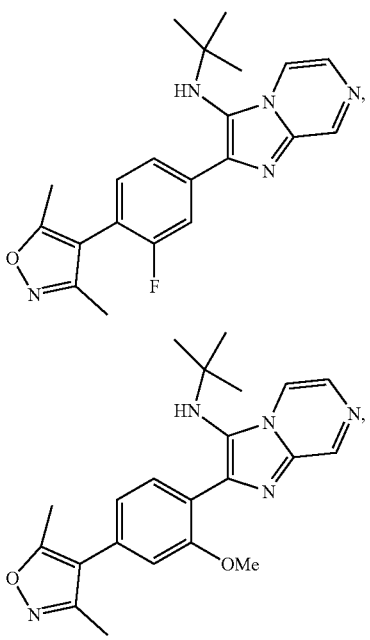
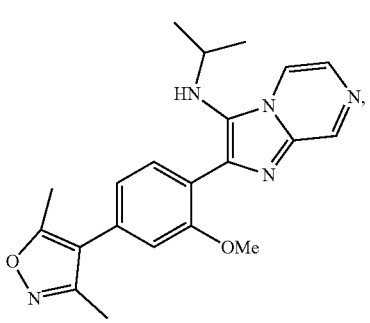
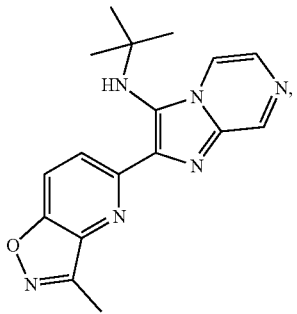

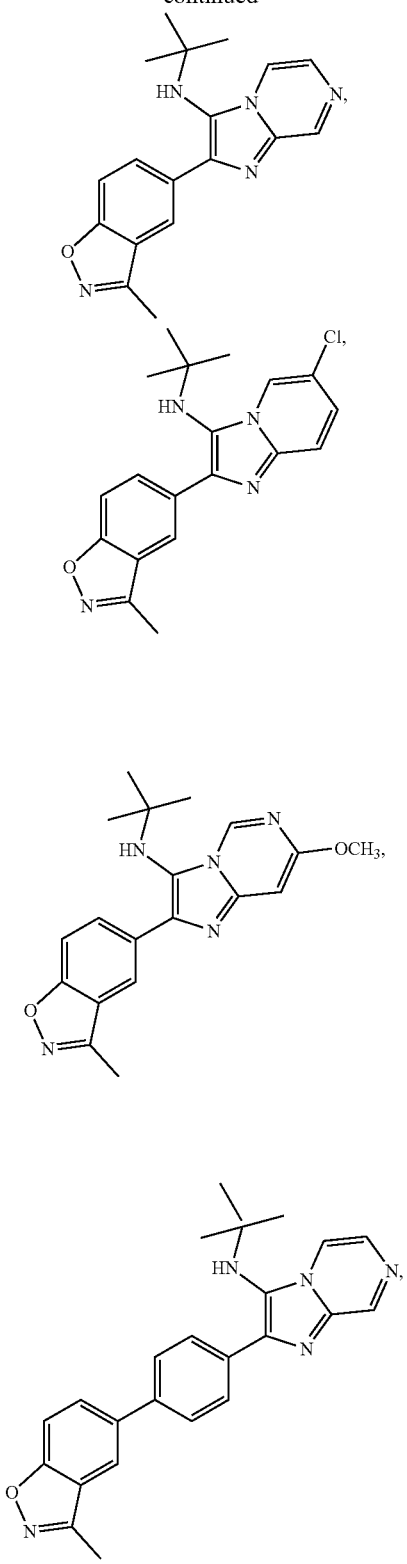

or a pharmaceutically acceptable salt, solvate, hydrate, polymorph, co-crystal, tautomer, stereoisomer, isotopically labeled derivative, or prodrug thereof.

In certain embodiments, the transcription inhibitor is of the formula:

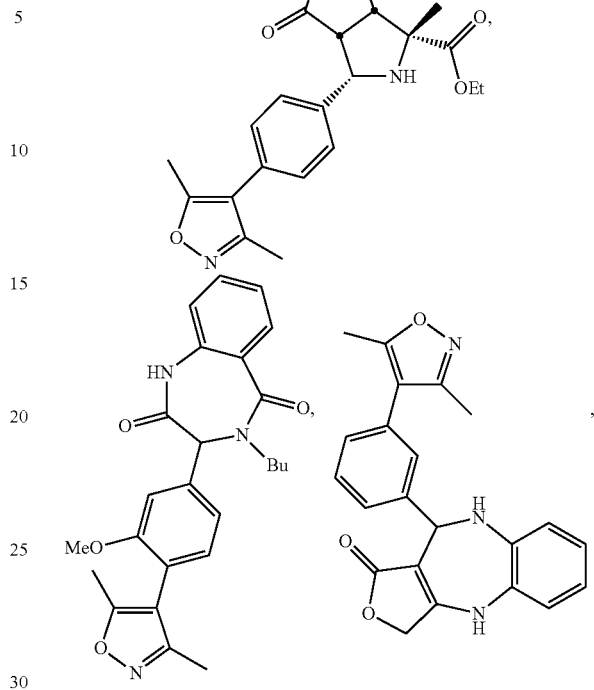

or a pharmaceutically acceptable salt, solvate, hydrate, polymorph, co-crystal, tautomer, stereoisomer, isotopically labeled derivative, or prodrug thereof.

In certain embodiments, the transcription inhibitor is of Formula (X):

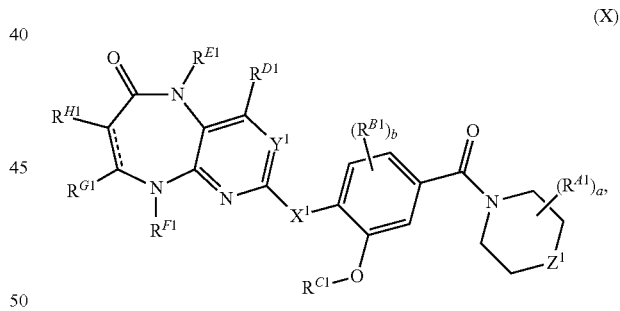

or a pharmaceutically acceptable salt, solvate, hydrate, polymorph, co-crystal, tautomer, stereoisomer, isotopically labeled derivative, or prodrug thereof, wherein:

═══ is a single or double bond;

$X^1$ is —O—, —S—, or —C($R^{X1}$)$_2$—, wherein each instance of $R^{X1}$ is independently hydrogen, halogen, or substituted or unsubstituted $C_{1-6}$ alkyl;

$Y^1$ is N or $CR^{Y1}$, wherein $R^{Y1}$ is hydrogen, halogen, or substituted or unsubstituted $C_{1-6}$ alkyl;

$Z^1$ is —O—, —N($R^{Z1}$)— or —C($R^{Z1}$)$_2$—, wherein each instance of $R^{Z1}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group when attached to a nitrogen atom, or about two instances of $R^{Z1}$ are joined to form a substituted or unsubstituted carbocyclic or substituted or unsubstituted heterocyclic ring;

each instance of $R^{A1}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A1a}$, —N($R^{A1a})_2$, —$SR^{A1a}$, —CN, —SCN, —C(=$NR^{A1a}$)$R^{A1a}$, —C(=$NR^{A1a}$)$OR^{A1a}$, —C(=$NR^{A1a}$)N($R^{A1a})_2$, —C(=O)$R^{A1a}$, —C(=O)$OR^{A1a}$, —C(=O)N($R^{A1a})_2$, —$NO_2$, —$NR^{A1a}$C(=O)$R^{A1a}$, —$NR^{A1a}$C(=O)$OR^{A1a}$, —$NR^{A1a}$C(=O)N($R^{A1a})_2$, —OC(=O)$R^{A1a}$, —OC(=O)$OR^{A1a}$, or —OC(=O)N($R^{A1a})_2$, wherein each instance of $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two $R^{A1a}$ groups are joined to form a substituted or unsubstituted heterocyclic or substituted or unsubstituted heteroaryl ring;

a is 0, 1, 2, 3, 4, 5, 6, 7, or 8;

each instance of $R^{B1}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{B1a}$, —N($R^{B1a})_2$, —$SR^{B1a}$, —CN, —SCN, —C(=$NR^{B1a}$)$R^{B1a}$, —C(=$NR^{B1a}$)$OR^{B1a}$, —C(=$NR^{B1a}$)N($R^{B1a})_2$, —C(=O)$R^{B1a}$, —C(=O)$OR^{B1a}$, —C(=O)N($R^{B1a})_2$, —$NO_2$, —$NR^{B1a}$C(=O)$R^{B1a}$, —$NR^{B1a}$C(=O)$OR^{B1a}$, —$NR^{B1a}$C(=O)N($R^{B1a})_2$, —OC(=O)$R^{B1a}$, —OC(=O)$OR^{B1a}$, or —OC(=O)N($R^{B1a})_2$, wherein each instance of $R^{B1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two $R^{B1a}$ groups are joined to form a substituted or unsubstituted heterocyclic or substituted or unsubstituted heteroaryl ring;

b is 0, 1, 2, or 3;

$R^{C1}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group;

$R^{D1}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{D1a}$, —N($R^{D1a})_2$, —$SR^{D1a}$, —CN, —SCN, —C(=$NR^{D1a}$)$R^{D1a}$, —C(=$NR^{D1a}$)$OR^{D1a}$, —C(=$NR^{D1a}$)N($R^{D1a})_2$, —C(=O)$R^{D1a}$, —C(=O)$OR^{D1a}$, —C(=O)N($R^{D1a})_2$, —$NO_2$, —$NR^{D1a}$C(=O)$R^{D1a}$, —$NR^{D1a}$C(=O)$OR^{D1a}$, —$NR^{D1a}$C(=O)N($R^{D1a})_2$, —OC(=O)$R^{D1a}$, —OC(=O)$OR^{D1a}$, or —OC(=O)N($R^{D1a})_2$, wherein each instance of $R^{D1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two $R^{D1a}$ groups are joined to form a substituted or unsubstituted heterocyclic or substituted or unsubstituted heteroaryl ring;

$R^{E1}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^{F1}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^{G1}$ is hydrogen, halogen, or substituted or unsubstituted $C_{1-6}$ alkyl; and $R^{H1}$ is hydrogen, halogen, or substituted or unsubstituted $C_{1-6}$ alkyl;

or $R^{G1}$ and $R^{H1}$ are joined to form a substituted or unsubstituted phenyl ring.

In certain embodiments, the transcription inhibitor is of the formula:

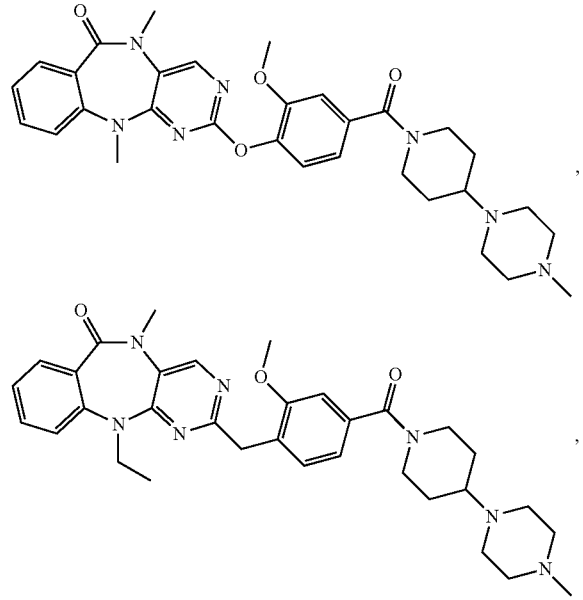

or a pharmaceutically acceptable salt, solvate, hydrate, polymorph, co-crystal, tautomer, stereoisomer, isotopically labeled derivative, or prodrug thereof.

In certain embodiments, the transcription inhibitor is of Formula (XI):

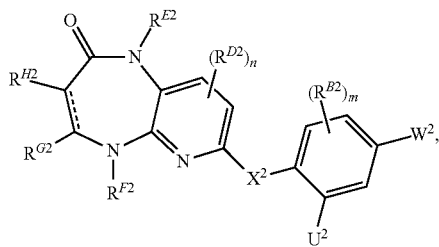

(XI)

or a pharmaceutically acceptable salt, solvate, hydrate, polymorph, co-crystal, tautomer, stereoisomer, isotopically labeled derivative, or prodrug thereof, wherein:
≡≡≡ is a single or double bond;
$W^2$ is $-S(=O)OR^{W2}$, $-S(=O)N(R^{W2})_2$, $-S(=O)_2OR^{W2}$, $-S(=O)_2N(R^{W2})_2$,

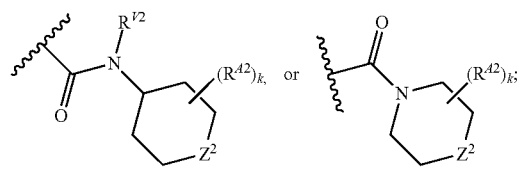

each instance of $R^{W2}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a nitrogen protecting group when attached to a nitrogen atom, or about two instances of $R^{W2}$ are joined to form a substituted or unsubstituted heterocyclic or substituted or unsubstituted heteroaryl ring; and
$R^{V2}$ is hydrogen, substituted or unsubstituted $C_{1-6}$ alkyl, or a nitrogen protecting group;
$U^2$ is $R^{B2}$ or $-OR^{C2}$;
$X^2$ is $-O-$, $-S-$, $-N(R^{X2})-$, or $-C(R^{X2})_2-$, wherein each instance of $R^{X2}$ is independently hydrogen, halogen, substituted or unsubstituted $C_{1-6}$ alkyl, or a nitrogen protecting group when attached to a nitrogen atom;
$Z^2$ is $-O-$, $-N(R^{Z2})-$ or $-C(R^{Z2})_2-$, wherein each instance of $R^{Z2}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group when attached to a nitrogen atom, or about two instances of $R^{Z2}$ are joined to form a substituted or unsubstituted carbocyclic or substituted or unsubstituted heterocyclic ring;
each instance of $R^{A2}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{A2a}$, $-N(R^{A2a})_2$, $-SR^{A2a}$, $-CN$, $-SCN$, $-C(=NR^{A2a})R^{A2a}$, $-C(=NR^{A2a})OR^{A2a}$, $-C(=NR^{A2a})N(R^{A2a})_2$, $-C(=O)R^{A2a}$, $-C(=O)OR^{A2a}$, $-C(=O)N(R^{A2a})_2$, $-NO_2$, $-NR^{A2a}C(=O)R^{A2a}$, $-NR^{A2a}C(=O)OR^{A2a}$, $-NR^{A2a}C(=O)N(R^{A2a})_2$, $-OC(=O)R^{A2a}$, $-OC(=O)OR^{A2a}$, or $-OC(=O)N(R^{A2a})_2$, wherein each instance of $R^{A2a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two $R^{A2a}$ groups are joined to form a substituted or unsubstituted heterocyclic or substituted or unsubstituted heteroaryl ring;
k is 0, 1, 2, 3, 4, 5, 6, 7, 8, or 9;
each instance of $R^{B2}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{B2a}$, $-N(R^{B2a})_2$, $-SR^{B2a}$, $-CN$, $-SCN$, $-C(=NR^{B2a})R^{B2a}$, $-C(=NR^{B2a})OR^{B2a}$, $-C(=NR^{B2a})N(R^{B2a})_2$, $-C(=O)R^{B2a}$, $-C(=O)OR^{B2a}$, $-C(=O)N(R^{B2a})_2$, $-NO_2$, $-NR^{B2a}C(=O)R^{B2a}$, $-NR^{B2a}C(=O)OR^{B2a}$, $-NR^{B2a}C(=O)N(R^{B2a})_2$, $-OC(=O)R^{B2a}$, $-OC(=O)OR^{B2a}$, or $-OC(=O)N(R^{B2a})_2$, wherein each instance of $R^{B2a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two $R^{B2a}$ groups are joined to form a substituted or unsubstituted heterocyclic or substituted or unsubstituted heteroaryl ring;
m is 0, 1, 2, or 3;
$R^{C2}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group;
each instance of $R^{D2}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{D2a}$, $-N(R^{D2a})_2$, $-SR^{D2a}$, $-CN$, $-SCN$, $-C(=NR^{D2a})R^{D2a}$, $-C(=NR^{D2a})OR^{D2a}$, $-C(=NR^{D2a})N(R^{D2a})_2$, $-C(=O)R^{D2a}$, $-C(=O)OR^{D2a}$, $-C(=O)N(R^{D2a})_2$, $-NO_2$, $-NR^{D2a}C(=O)R^{D2a}$, $-NR^{D2a}C(=O)OR^{D2a}$, $-NR^{D2a}C(=O)N(R^{D2a})_2$, $-OC(=O)R^{D2a}$, $-OC(=O)OR^{D2a}$, or $-OC(=O)N(R^{D2a})_2$, wherein each instance of $R^{D2a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two $R^{D2a}$ groups are joined to form a substituted or unsubstituted heterocyclic or substituted or unsubstituted heteroaryl ring;

n is 0, 1, or 2;

$R^{E2}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^{F2}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^{G2}$ is hydrogen, halogen, or substituted or unsubstituted $C_{1-6}$ alkyl; and $R^{H2}$ is hydrogen, halogen, or substituted or unsubstituted $C_{1-6}$ alkyl;

or $R^{G2}$ and $R^{H2}$ are joined to form a substituted or unsubstituted phenyl ring.

In certain embodiments, the transcription inhibitor is of the formula:

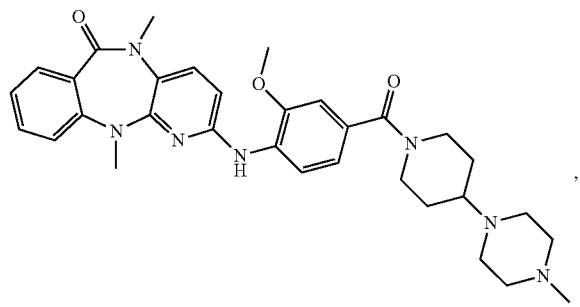

,

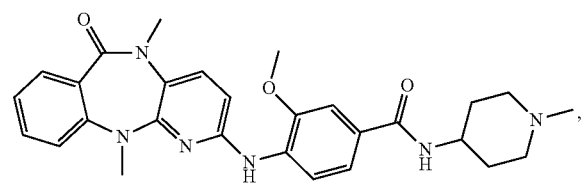

,

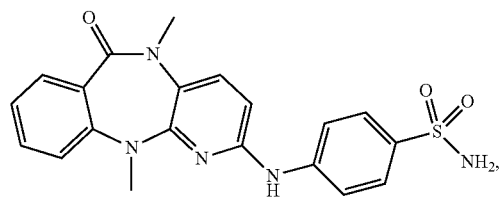

or a pharmaceutically acceptable salt, solvate, hydrate, polymorph, co-crystal, tautomer, stereoisomer, isotopically labeled derivative, or prodrug thereof.

In certain embodiments, the transcription inhibitor is of Formula (XII):

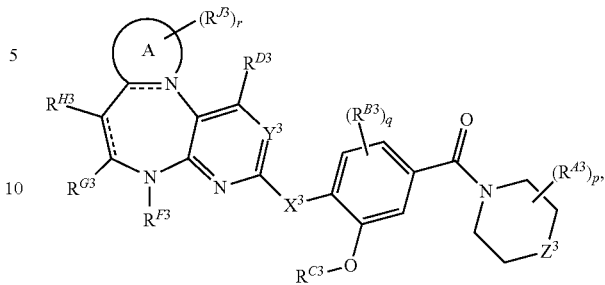

(XII)

or a pharmaceutically acceptable salt, solvate, hydrate, polymorph, co-crystal, tautomer, stereoisomer, isotopically labeled derivative, or prodrug thereof, wherein:

each instance of $\equiv\equiv\equiv$ is independently a single or double bond;

$X^3$ is —O—, —S—, —N($R^{X3}$)—, or —C($R^{X3}$)$_2$—, wherein each instance of $R^{X3}$ is independently hydrogen, halogen, substituted or unsubstituted $C_{1-6}$ alkyl, or a nitrogen protecting group when attached to a nitrogen atom;

$Y^3$ is N or $CR^{Y3}$, wherein $R^{Y3}$ is hydrogen, halogen, or substituted or unsubstituted $C_{1-6}$ alkyl;

$Z^3$ is —O—, —N($R^{Z3}$)— or —C($R^{Z3}$)$_2$—, wherein each instance of $R^{Z3}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group when attached to a nitrogen atom, or about two instances of $R^{Z3}$ are joined to form a substituted or unsubstituted carbocyclic or substituted or unsubstituted heterocyclic ring;

each instance of $R^{A3}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{A3a}$, —N(R$^{A3a}$)$_2$, —SR$^{A3a}$, —CN, —SCN, —C(=NR$^{A3a}$)R$^{A3a}$, —C(=NR$^{A3a}$)OR$^{A3a}$, —C(=NR$^{A3a}$)N(R$^{A3a}$)$_2$, —C(=O)R$^{A3a}$, —C(=O)OR$^{A3a}$, —C(=O)N(R$^{A3a}$)$_2$, —NO$_2$, —NR$^{A3a}$C(=O)R$^{A3a}$, —NR$^{A3a}$C(=O)OR$^{A3a}$, —NR$^{A3a}$C(=O)N(R$^{A3a}$)$_2$, —OC(=O)R$^{A3a}$, —OC(=O)OR$^{A3a}$, or —OC(=O)N(R$^{A3a}$)$_2$, wherein each instance of R$^{A3a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two R$^{A3a}$ groups are joined to form a substituted or unsubstituted heterocyclic or substituted or unsubstituted heteroaryl ring;

p is 0, 1, 2, 3, 4, 5, 6, 7, or 8;

each instance of R$^{B3}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{B3a}$, —N ($R^{B3a}$)$_2$, —S$R^{B3a}$, —CN, —SCN, —C(=N$R^{B3a}$)$R^{B3a}$, —C(=N$R^{B3a}$)O$R^{B3a}$, —C(=N$R^{B3a}$)N($R^{B3a}$)$_2$, —C(=O)$R^{B3a}$, —C(=O)O$R^{B3a}$, —C(=O)N($R^{B3a}$)$_2$, —NO$_2$, —N$R^{B3a}$C(=O)$R^{B3a}$, —N$R^{B3a}$C(=O)O$R^{B3a}$, —N$R^{B3a}$C(=O)N($R^{B3a}$)$_2$, —OC(=O)$R^{B3a}$, —OC(=O)O$R^{B3a}$, or —OC(=O)N($R^{B3a}$)$_2$, wherein each instance of $R^{B3a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two $R^{B3a}$ groups are joined to form a substituted or unsubstituted heterocyclic or substituted or unsubstituted heteroaryl ring;

q is 0, 1, 2, or 3;

$R^{C3}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group;

$R^{D3}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^{D3a}$, —N($R^{D3a}$)$_2$, —S$R^{D3a}$, —CN, —SCN, —C(=N$R^{D3a}$)$R^{D3a}$, —C(=N$R^{D3a}$)O$R^{D3a}$, —C(=N$R^{D3a}$)N($R^{D3a}$)$_2$, —C(=O)$R^{D3a}$, —C(=O)O$R^{D3a}$, —C(=O)N($R^{D3a}$)$_2$, —NO$_2$, —N$R^{D3a}$C(=O)$R^{D3a}$, —N$R^{D3a}$C(=O)O$R^{D3a}$, —N$R^{D3a}$C(=O)N($R^{D3a}$)$_2$, —OC(=O)$R^{D3a}$, —OC(=O)O$R^{D3a}$, or —OC(=O)N($R^{D3a}$)$_2$, wherein each instance of $R^{D3a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two $R^{D3a}$ groups are joined to form a substituted or unsubstituted heterocyclic or substituted or unsubstituted heteroaryl ring;

Ring A is substituted or unsubstituted, 5- to 6-membered, monocyclic, heterocyclic or heteroaryl ring;

each instance of $R^{J3}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^{J3a}$, —N($R^{J3a}$)$_2$, —S$R^{J3a}$, —CN, —SCN, —C(=N$R^{J3a}$)$R^{J3a}$, —C(=N$R^{J3a}$)O$R^{J3a}$, —C(=N$R^{J3a}$)N($R^{J3a}$)$_2$, —C(=O)$R^{J3a}$, —C(=O)O$R^{J3a}$, —C(=O)N($R^{J3a}$)$_2$, —NO$_2$, —N$R^{J3a}$C(=O)$R^{J3a}$, —N$R^{J3a}$C(=O)O$R^{J3a}$, —N$R^{J3a}$C(=O)N($R^{J3a}$)$_2$, —OC(=O)$R^{J3a}$, —OC(=O)O$R^{J3a}$, —OC(=O)N($R^{J3a}$)$_2$, or a nitrogen protecting group when attached to a nitrogen atom, wherein each instance of $R^{J3a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two $R^{J3a}$ groups are joined to form a substituted or unsubstituted heterocyclic or substituted or unsubstituted heteroaryl ring;

r is 0, 1, 2, 3, 4, 5, 6, 7, or 8;

$R^{F3}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^{G3}$ is hydrogen, halogen, or substituted or unsubstituted $C_{1-6}$ alkyl; and $R^{H3}$ is hydrogen, halogen, or substituted or unsubstituted $C_{1-6}$ alkyl;

or $R^{G3}$ and $R^{H3}$ are joined to form a substituted or unsubstituted phenyl ring.

In certain embodiments, the transcription inhibitor is of the formula:

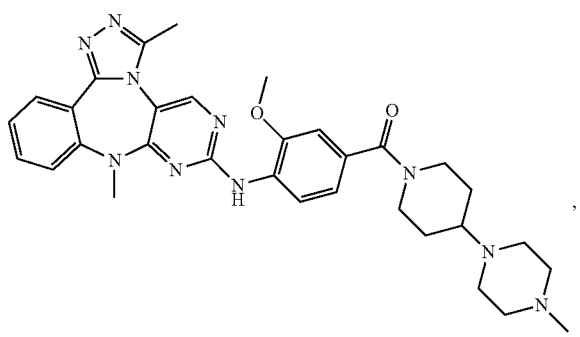 [SMILES: COc1cc(C(=O)N2CCC(N3CCN(C)CC3)CC2)ccc1Nc1ncc2c(n1)N(C)c1ccccc1-c1nnc(C)n1-2]

or a pharmaceutically acceptable salt, solvate, hydrate, polymorph, co-crystal, tautomer, stereoisomer, isotopically labeled derivative, or prodrug thereof.

In certain embodiments, the transcription inhibitor is of Formula (XIII):

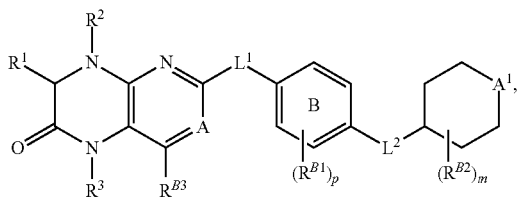

(XIII)

or pharmaceutically acceptable salt, solvate, hydrate, polymorph, co-crystal, tautomer, stereoisomer, isotopically labeled derivative, or prodrug thereof, wherein:

A is =N— or =C($R^{B4}$)—;

$A^1$ is —N($R^4$)— or —C($R^4$)$_2$—;

$R^1$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^2$ and $R^3$ are each independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)$R^{D1}$, —C(=O)O$R^{D1}$, —C(=O)N($R^{D1}$)$_2$, or a nitrogen protecting group, wherein each instance of $R^{D1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two $R^{D1}$ groups are joined to form a substituted or unsubstituted heterocyclic or substituted or unsubstituted heteroaryl ring, or a nitrogen protecting group when attached to a nitrogen atom;

$R^4$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)$R^{D1}$, —C(=O)O$R^{D1}$, or —C(=O)N($R^{D1}$)$_2$, wherein each instance of RD is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two $R^{D1}$ groups are joined to form a substituted or unsubstituted heterocyclic or substituted or unsubstituted heteroaryl ring, or a nitrogen protecting group when attached to a nitrogen atom;

each instance of $R^{B1}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^{B1a}$, —N($R^{B1a}$)$_2$, —S$R^{B1a}$, —CN, —SCN, —C(=N$R^{B1a}$)$R^{B1a}$, —C(=N$R^{B1a}$)O$R^{B1a}$, —C(=N$R^{B1a}$)N($R^{B1a}$)$_2$, —C(=O)$R^{B1a}$, —C(=O)O$R^{B1a}$, —C(=O)N($R^{B1a}$)$_2$, —NO$_2$, —N$R^{B1a}$C(=O)$R^{B1a}$, —N$R^{B1a}$C(=O)O$R^{B1a}$, —N$R^{B1a}$C(=O)N($R^{B1a}$)$_2$, —OC(=O)$R^{B1a}$, —OC(=O)O$R^{B1a}$, or —OC(=O)N($R^{B1a}$)$_2$, wherein each instance of $R^{B1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two $R^{B1a}$ groups are joined to form a substituted or unsubstituted heterocyclic or substituted or unsubstituted heteroaryl ring;

each instance of $R^{B2}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^{B2a}$, —N($R^{B2a}$)$_2$, —S$R^{B2a}$, —CN, —SCN, —C(=N$R^{B2a}$)$R^{B2a}$, —C(=N$R^{B2a}$)O$R^{B2a}$, —C(=N$R^{B2a}$)N($R^{B2a}$)$_2$, —C(=O)$R^{B2a}$, —C(=O)O$R^{B2a}$, —C(=O)N($R^{B2a}$)$_2$, —NO$_2$, —N$R^{B2a}$C(=O)$R^{B2a}$, —N$R^{B2a}$C(=O)O$R^{B2a}$, —N$R^{B2a}$C(=O)N($R^{B2a}$)$_2$, —OC(=O)$R^{B2a}$, —OC(=O)O$R^{B2a}$, or —OC(=O)N($R^{B2a}$)$_2$, wherein each instance of $R^{B2a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two $R^{B2a}$ groups are joined to form a substituted or unsubstituted heterocyclic or substituted or unsubstituted heteroaryl ring;

each instance of $R^{B3}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^{B3a}$, —N($R^{B3a}$)$_2$, —S$R^{B3a}$, —CN, —SCN, —C(=N$R^{B3a}$)$R^{B3a}$, —C(=N$R^{B3a}$)O$R^{B3a}$, —C(=N$R^{B3a}$)N($R^{B3a}$)$_2$, —C(=O)$R^{B3a}$, —C(=O)O$R^{B3a}$, —C(=O)N($R^{B3a}$)$_2$, —NO$_2$, —N$R^{B3a}$C(=O)$R^{B3a}$, —N$R^{B3a}$C(=O)O$R^{B3a}$, —N$R^{B3a}$C(=O)N($R^{B3a}$)$_2$, —OC(=O)$R^{B3a}$, —OC(=O)O$R^{B3a}$, or —OC(=O)N($R^{B3a}$)$_2$, wherein each instance of $R^{B3a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two $R^{B3a}$ groups are joined to form a substituted or unsubstituted heterocyclic or substituted or unsubstituted heteroaryl ring;

each instance of $R^{B4}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^{B4a}$, —N($R^{B4a}$)$_2$, —S$R^{B4a}$, —CN, —SCN, —C(=N$R^{B4a}$)$R^{B4a}$, —C(=N$R^{B4a}$)O$R^{B4a}$, —C(=N$R^{B4a}$)N($R^{B4a}$)$_2$, —C(=O)$R^{B4a}$, —C(=O)O$R^{B4a}$, —C(=O)N($R^{B4a}$)$_2$, —N$_2$, —N$R^{B4a}$C(=O)$R^{B4a}$, —N$R^{B4a}$C(=O)O$R^{B4a}$, —N$R^{B4a}$C(=O)N($R^{B4a}$)$_2$, —OC(=O)$R^{B4a}$, —OC(=O)O$R^{B4a}$, or —OC(=O)N($R^{B4a}$)$_2$, wherein each instance of $R^{B4a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two $R^{B4a}$ groups are joined to form a substituted or unsubstituted heterocyclic or substituted or unsubstituted heteroaryl ring;

m is 0 or an integer between 1 and 8, inclusive;
p is 0 or an integer between 1 and 4, inclusive;
each of $L^1$ and $L^2$ is independently a bond,

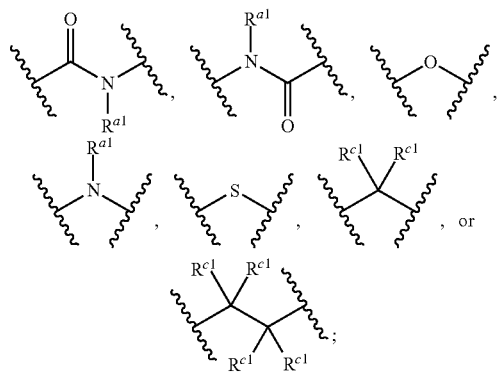

each instance of $R^{a1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group; or, if $L^1$ is

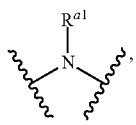

then $R^{a1}$ of $L^1$ and one instance of $R^{B1}$ that is ortho to $L^1$ are joined to form a substituted or unsubstituted heterocyclic ring or substituted or unsubstituted heteroaryl ring; and each instance of $R^{c1}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{c1a}$, —$N(R^{c1a})_2$, —$SR^{c1a}$, —CN, —C(=O)$R^{c1a}$, —C(=O)$OR^{c1a}$, —C(=O)N($R^{c1a}$)$_2$, —$NR^{c1a}$C(=O)$R^{c1a}$, —$NR^{c1a}$C(=O)$OR^{c1a}$, —$NR^{c1a}$C(=O)N($R^{c1a}$)$_2$, —OC(=O)$R^{c1a}$, or —OC(=O)N($R^{c1a}$)$_2$, wherein each instance of $R^{c1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two $R^{c1a}$ groups are joined to form a substituted or unsubstituted heterocyclic or substituted or unsubstituted heteroaryl ring.

In certain embodiments, the transcription inhibitor is of the formula

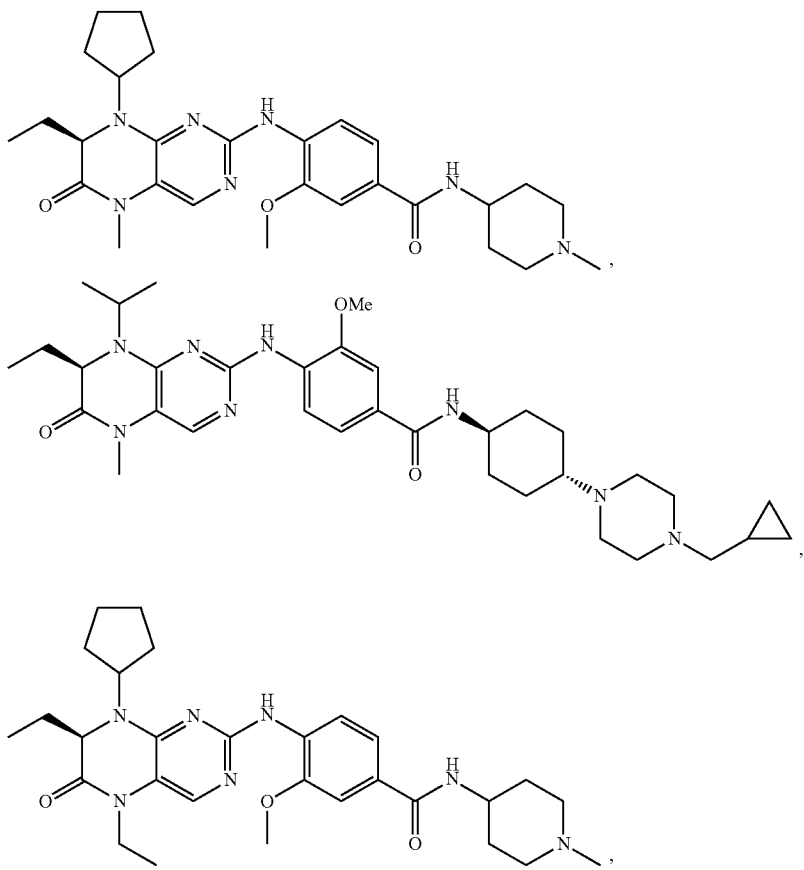

-continued
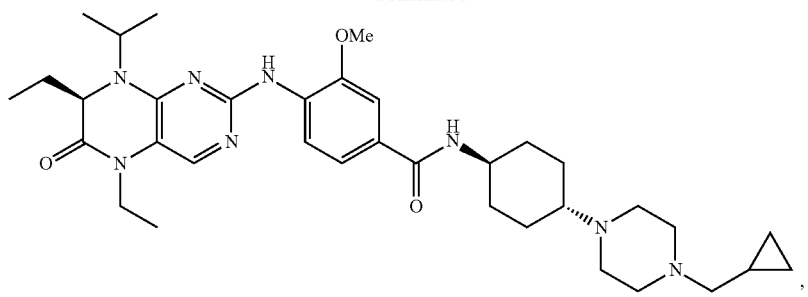
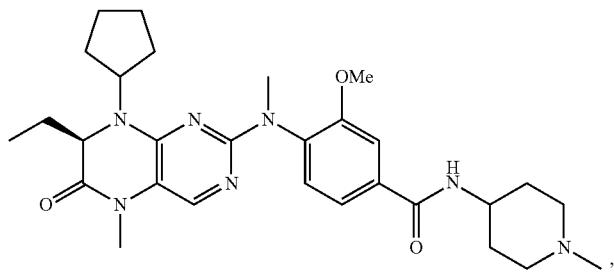
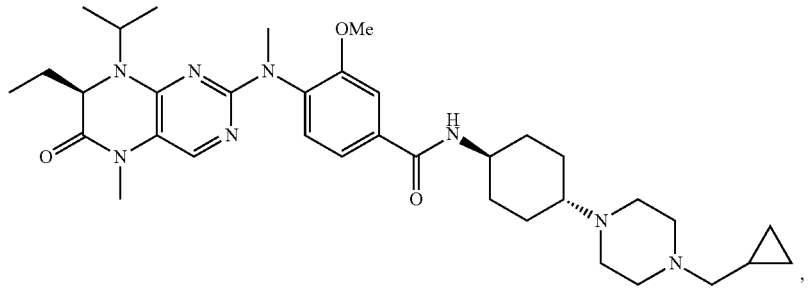
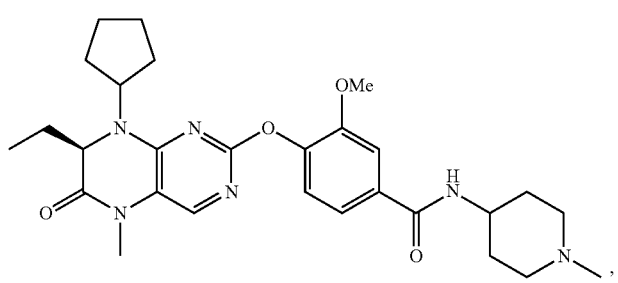
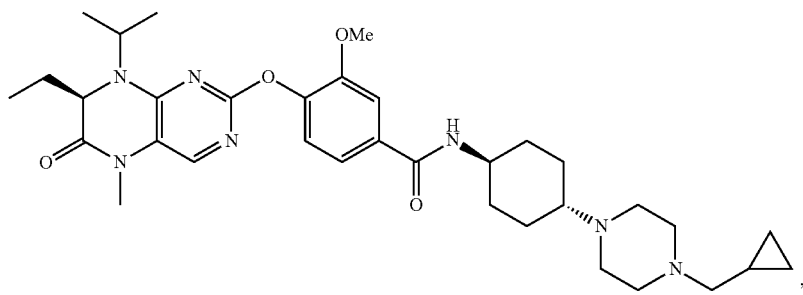
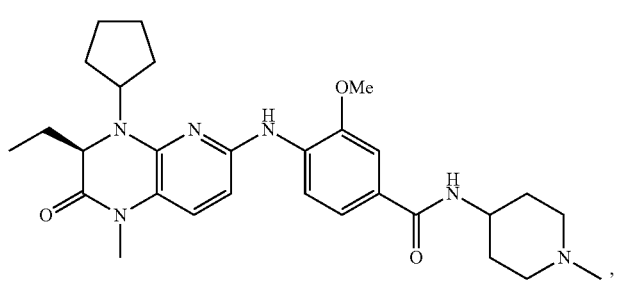

-continued
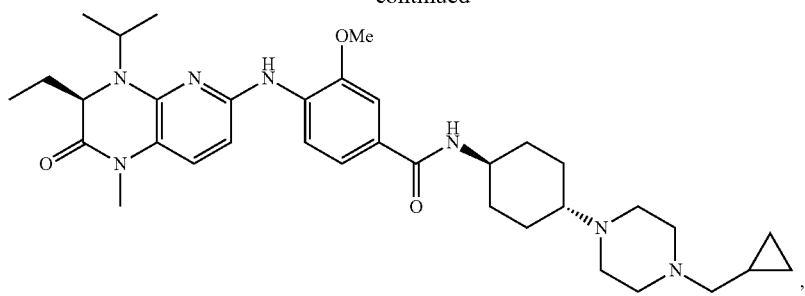
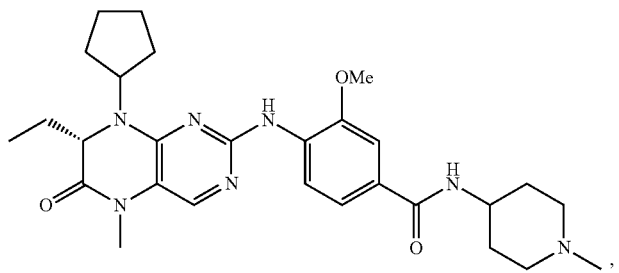
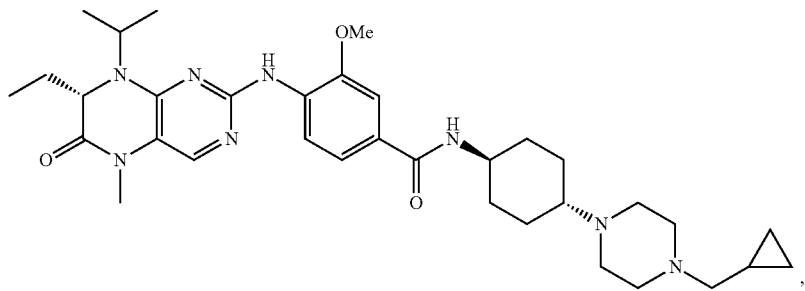
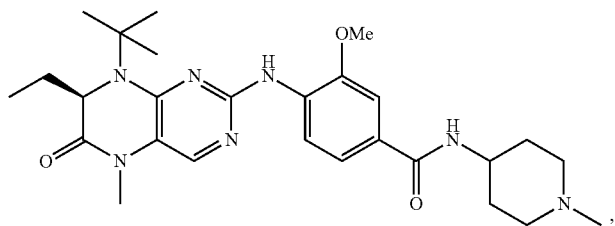
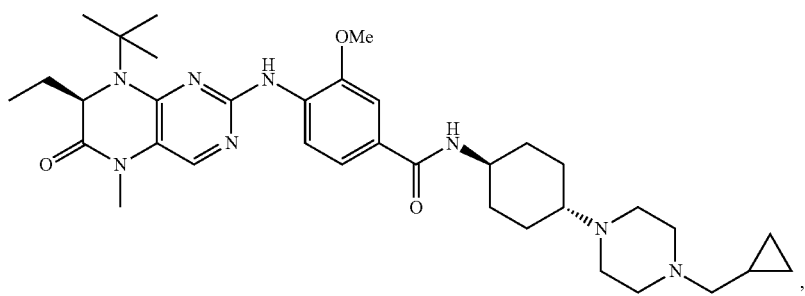
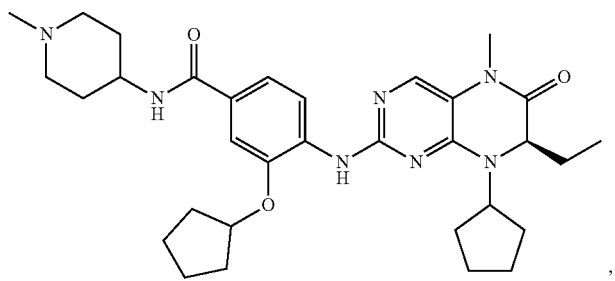

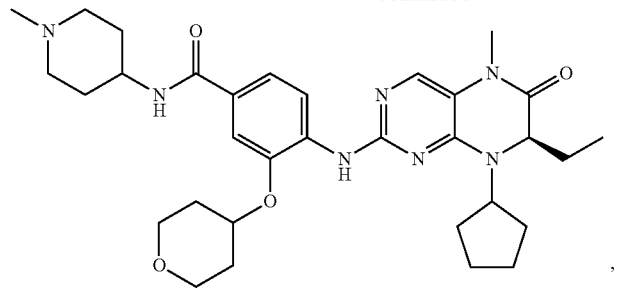,
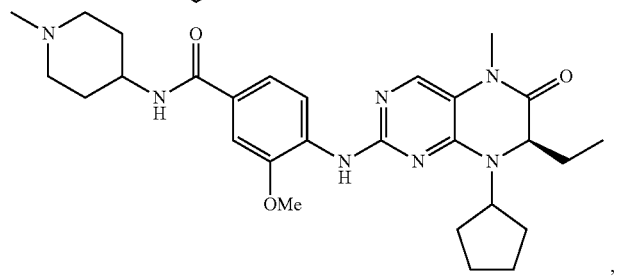,
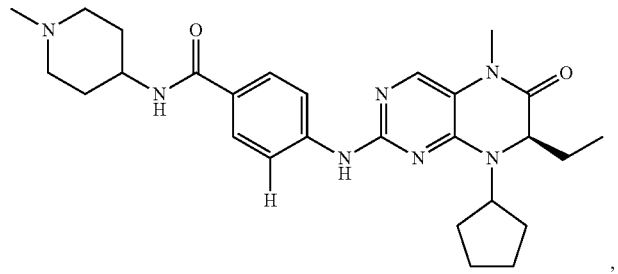,
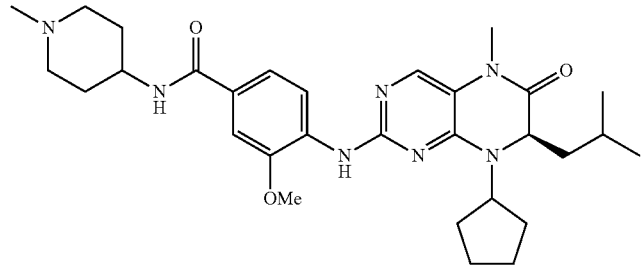,
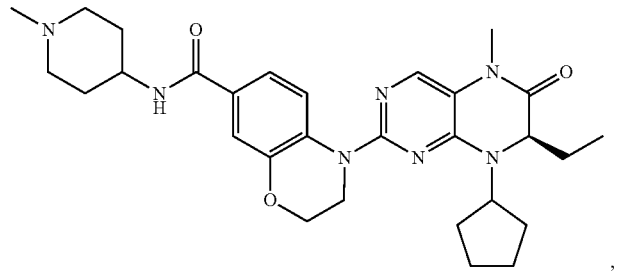,
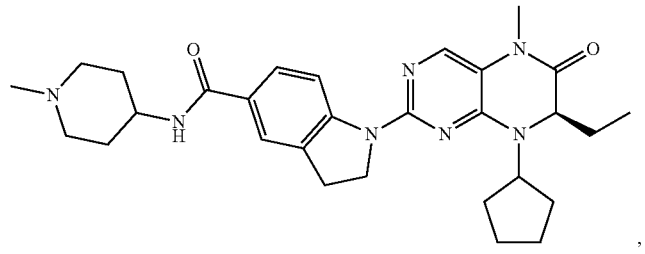,

-continued

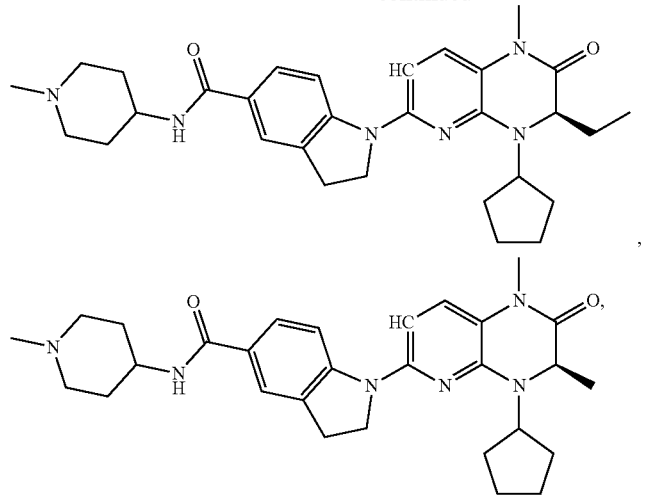

,

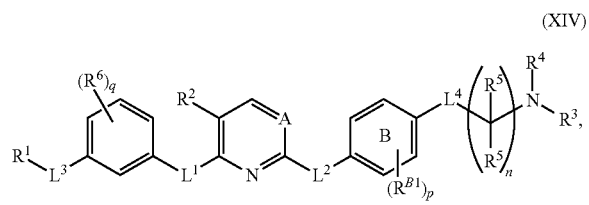

or a pharmaceutically acceptable salt, solvate, hydrate, polymorph, co-crystal, tautomer, stereoisomer, isotopically labeled derivative, or prodrug thereof.

In certain embodiments, the transcription inhibitor is of Formula (XIV):

$$(XIV)$$

or pharmaceutically acceptable salt, solvate, hydrate, polymorph, co-crystal, tautomer, stereoisomer, isotopically labeled derivative, or prodrug thereof, wherein:

$R^1$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group when attached to a nitrogen atom;

$R^2$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{D1}$, —$N(R^{D1})_2$, —$SR^{D1}$, —CN, —SCN, —$C(=NR^{D1})R^{D1}$, —$C(=NR^{D1})OR^{D1}$, —$C(=NR^{D1})N(R^{D1})_2$, —$C(=O)R^{D1}$, —$C(=O)OR^{D1}$, —$C(=O)N(R^{D1})_2$, —$NO_2$, —$NR^{D1}C(=O)R^{D1}$, —$NR^{D1}C(=O)OR^{D1}$, —$NR^{D1}C(=O)N(R^{D1})_2$, —$OC(=O)R^{D1}$, —$OC(=O)OR^{D1}$, or —$OC(=O)N(R^{D1})_2$, wherein each instance of $R^{D1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two $R^{D1}$ groups are joined to form a substituted or unsubstituted heterocyclic or substituted or unsubstituted heteroaryl ring;

$R^3$ and $R^4$ are each independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group; or $R^3$ and $R^4$ groups are joined to form an substituted or unsubstituted heterocyclic or substituted or unsubstituted heteroaryl ring;

each instance of $R^5$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

each instance of $R^6$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{B1a}$, —$N(R^{B1a})_2$, —$SR^{B1a}$, —CN, —SCN, —$C(=NR^{B1a})R^{B1a}$, —$C(=NR^{B1a})OR^{B1a}$, —$C(=NR^{B1a})N(R^{B1a})_2$, —$C(=O)R^{B1a}$, —$C(=O)OR^{B1a}$, —$C(=O)N(R^{B1a})_2$, —$NO_2$, —$NR^{B1a}C(=O)R^{B1a}$, —$NR^{B1a}C(=O)OR^{B1a}$, —$NR^{B1a}C(=O)N(R^{B1a})_2$, —$OC(=O)R^{B1a}$, —$OC(=O)OR^{B1a}$, or —$OC(=O)N(R^{B1a})_2$;

q is 0, 1, 2, 3, or 4;

A is =N— or =$C(R^2)$—;

each instance of $R^{B1}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{B1a}$, —$N(R^{B1a})_2$, —$SR^{B1a}$, —CN, —SCN, —$C(=NR^{B1a})R^{B1a}$, —$C(=NR^{B1a})OR^{B1a}$, —$C(=NR^{B1a})N(R^{B1a})_2$, —$C(=O)R^{B1a}$, —$C(=O)OR^{B1a}$, —$C(=O)N(R^{B1a})_2$, —$NO_2$, —$NR^{B1a}C(=O)R^{B1a}$, —$NR^{B1a}C(=O)OR^{B1a}$, —$NR^{B1a}C(=O)N(R^{B1a})_2$, —$OC(=O)R^{B1a}$, —$OC(=O)OR^{B1a}$, or —$OC(=O)N(R^{B1a})_2$;

each instance of $R^{B1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two $R^{B1a}$ groups are joined to form a substituted or unsubstituted heterocyclic or substituted or unsubstituted heteroaryl ring;

p is 0 or an integer between 1 and 4, inclusive;

n is 0, 1, 2, 3, 4, 5, or 6;

$L^1$, $L^2$, and $L^4$ are each independently a bond,

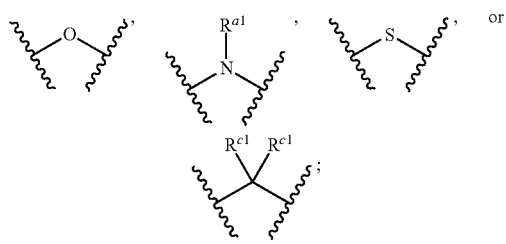

$L^3$ is

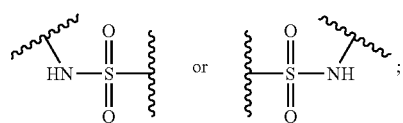

$R^{a1}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group; and each instance of $R^{c1}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{c1a}$, $-N(R^{c1a})_2$, $-SR^{c1a}$, $-CN$, $-C(=O)R^{c1a}$, $-C(=O)OR^{c1a}$, $-C(=O)N(R^{c1a})_2$, $-NR^{c1a}C(=O)R^{c1a}$, $-NR^{c1a}C(=O)OR^{c1a}$, $-NR^{c1a}C(=O)N(R^{c1a})_2$, $-OC(=O)R^{c1a}$, or $-OC(=O)N(R^{c1a})_2$, wherein each instance of $R^{c1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two $R^{c1a}$ groups are joined to form a substituted or unsubstituted heterocyclic or substituted or unsubstituted heteroaryl ring.

In certain embodiments, the transcription inhibitor is of the formula:

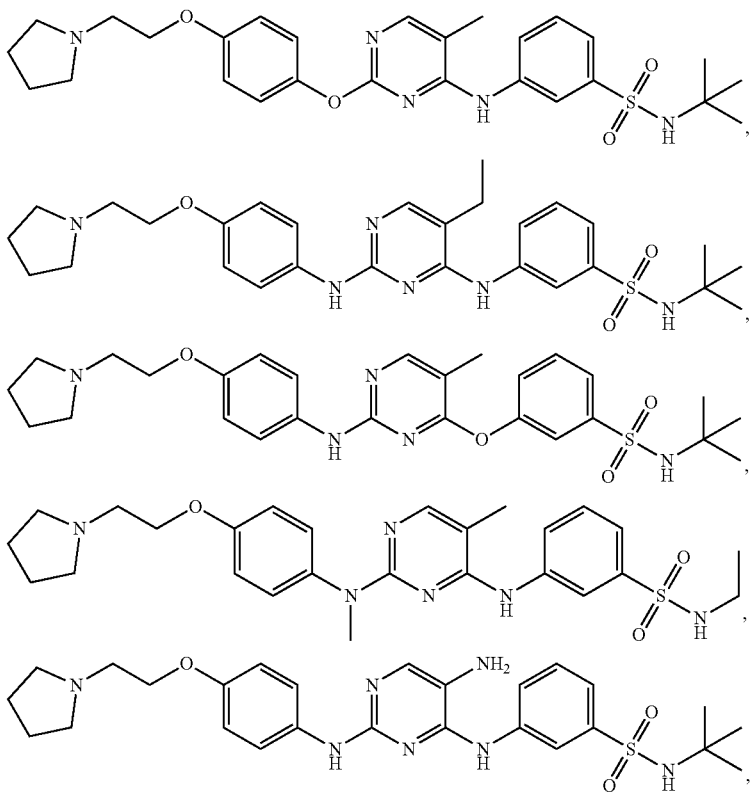

-continued

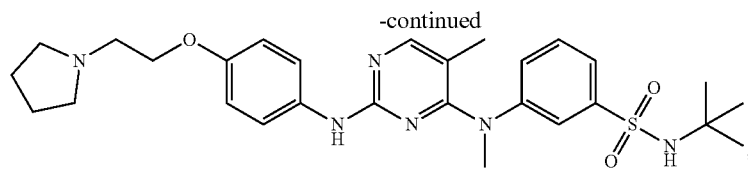

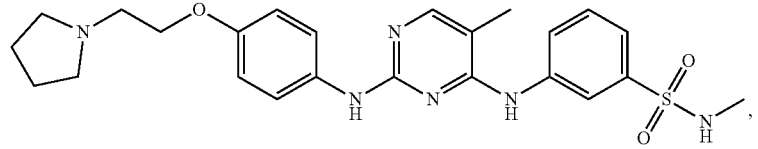

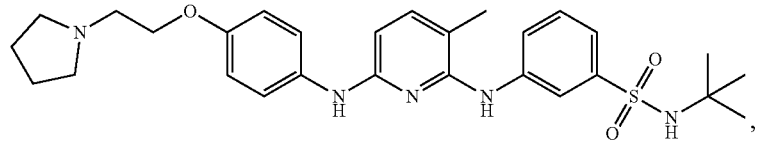

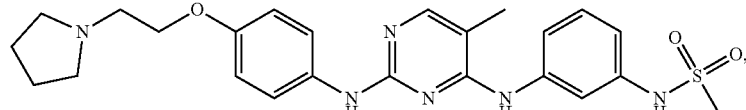

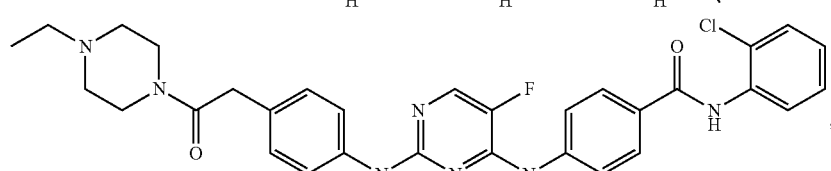

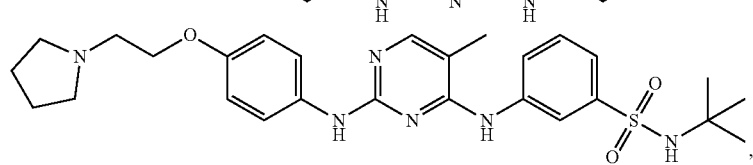

or a pharmaceutically acceptable salt, solvate, hydrate, polymorph, co-crystal, tautomer, stereoisomer, isotopically labeled derivative, or prodrug thereof.

In certain embodiments, the transcription inhibitor is of Formula (XV):

(XV)

![structure]

or a pharmaceutically acceptable salt, solvate, hydrate, polymorph, co-crystal, tautomer, stereoisomer, isotopically labeled derivative, or prodrug thereof, wherein:

=== is a single or double bond;

W is —C(=O)OR$^{Z1}$, —C(=O)N(R$^{Z1}$)$_2$, —S(=O)OR$^{Z1}$, —S(=O)N(R$^{Z1}$)$_2$, —S(=O)$_2$OR$^{Z1}$, —S(=O)$_2$N(R$^{Z1}$)$_2$, or

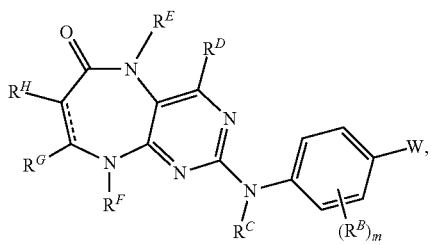

Z is —O—, —N(R$^Z$)— or —C(R$^Z$)$_2$—, wherein each instance of R$^Z$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{Z1}$, —SR$^{Z1}$, —N(R$^{Z1}$)$_2$, or a nitrogen protecting group when attached to a nitrogen atom, or about two instances of R$^Z$ are joined to form a substituted or unsubstituted carbocyclic or substituted or unsubstituted heterocyclic ring;

each instance of R$^{Z1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, or a nitrogen protecting group when attached to a nitrogen atom, or about two instances of R$^{Z1}$ are joined to form a substituted or unsubstituted heterocyclic or substituted or unsubstituted heteroaryl ring;

each instance of R$^A$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{A1}$, —N(R$^{A1}$)$_2$, —SR$^{A1}$, —CN, —SCN, —C(=NR$^{A1}$)R$^{A1}$, —C(=NR$^{A1}$)OR$^{A1}$, —C(=NR$^{A1}$)N(R$^{A1}$)$_2$, —C(=O)R$^{A1}$, —C(=O)OR$^{A1}$, —C(=O)N(R$^{A1}$)$_2$, —NO$_2$, —NR$^{A1}$C(=O)R$^{A1}$, —NR$^{A1}$C(=O)OR$^{A1}$, —NR$^{A1}$C(=O)N(R$^{A1}$)$_2$, —OC(=O)R$^{A1}$, —OC(=O)OR$^{A1}$, or —OC(=O)N(R$^{A1}$)$_2$, wherein each instance of R$^{A1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two R$^{A1}$ groups are joined to form a substituted or unsubstituted heterocyclic or substituted or unsubstituted heteroaryl ring;

n is 0, 1, 2, 3, 4, 5, 6, 7, or 8;

X is absent, —C(=O)—, or —C(R$^X$)$_2$—, wherein each instance of R$^X$ is independently hydrogen, halogen, or substituted or unsubstituted C$_{1-6}$ alkyl;

each instance of R$^B$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{B1}$, —N(R$^{B1}$)$_2$, —SR$^{B1}$, —CN, —SCN, —C(=NR$^{B1}$)R$^{B1}$, —C(=NR$^{B1}$)OR$^{B1}$, —C(=NR$^{B1}$)N(R$^{B1}$)$_2$, —C(=O)R$^{B1}$, —C(=O)OR$^{B1}$, —C(=O)N(R$^{B1}$)$_2$, —NO$_2$, —NR$^{B1}$C(=O)R$^{B1}$, —NR$^{B1}$C(=O)OR$^{B1}$, —NR$^{B1}$C(=O)N(R$^{B1}$)$_2$, —OC(=O)R$^{B1}$, —OC(=O)OR$^{B1}$, or —OC(=O)N(R$^{B1}$)$_2$, wherein each instance of R$^{B1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two R$^{B1}$ groups are joined to form a substituted or unsubstituted heterocyclic or substituted or unsubstituted heteroaryl ring;

m is 0, 1, 2, 3, or 4;

R$^C$ is hydrogen or substituted or unsubstituted C$_{1-6}$ alkyl;

R$^D$ is hydrogen or substituted or unsubstituted alkyl;

R$^E$ is hydrogen or substituted or unsubstituted alkyl;

R$^F$ is hydrogen, substituted or unsubstituted alkyl, substituted or unsubstituted alkenyl, substituted or unsubstituted carbocyclyl, substituted or unsubstituted heterocyclyl, substituted or unsubstituted aryl, or substituted or unsubstituted heteroaryl;

R$^G$ is hydrogen, substituted or unsubstituted alkyl, substituted or unsubstituted alkenyl, substituted or unsubstituted carbocyclyl, substituted or unsubstituted heterocyclyl, substituted or unsubstituted aryl, or substituted or unsubstituted heteroaryl; and R$^H$ is hydrogen, substituted or unsubstituted alkyl, substituted or unsubstituted alkenyl, substituted or unsubstituted carbocyclyl, substituted or unsubstituted heterocyclyl, substituted or unsubstituted aryl, or substituted or unsubstituted heteroaryl;

or R$^G$ and R$^H$ are joined to form a substituted or unsubstituted phenyl ring.

In certain embodiments, the transcription inhibitor is of the formula:

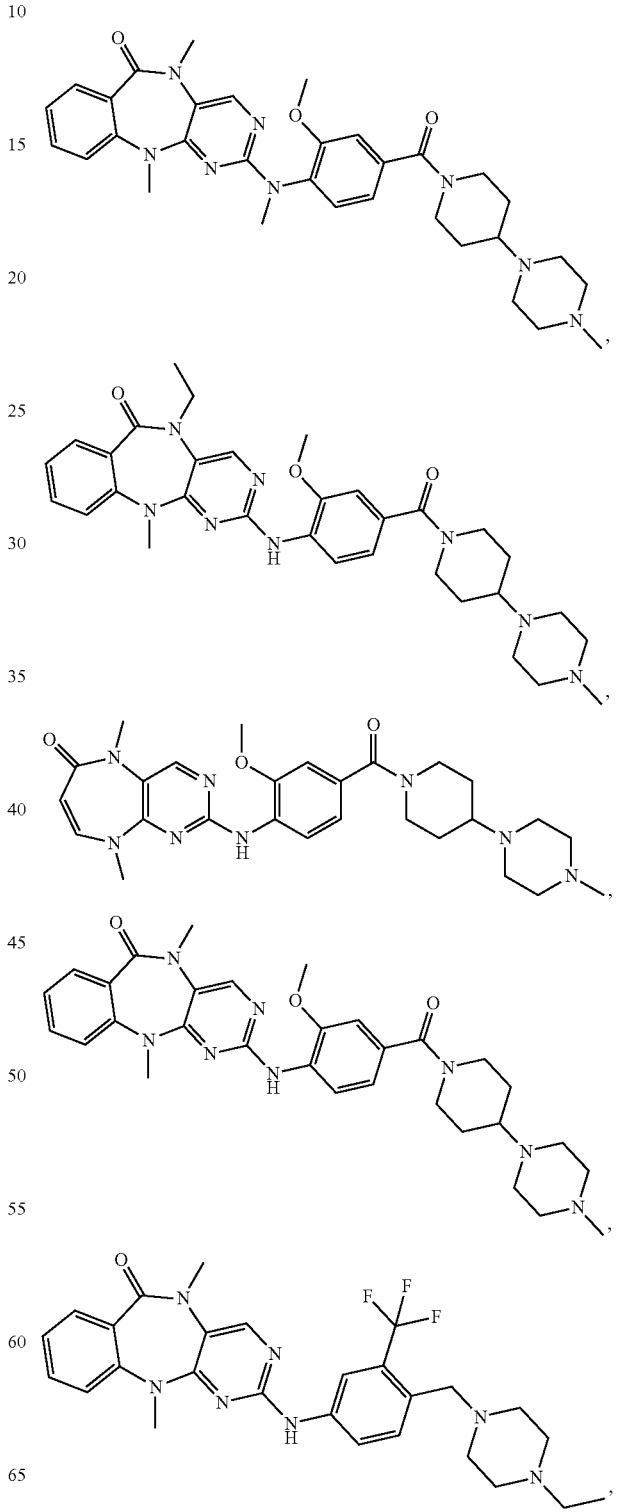

-continued

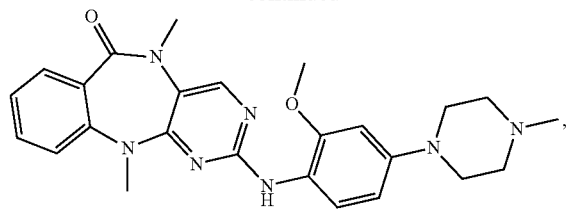

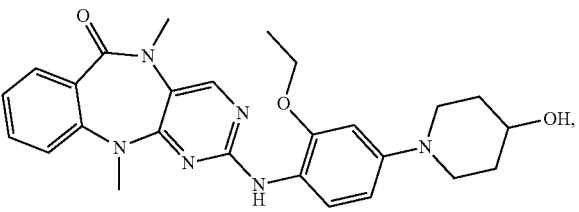

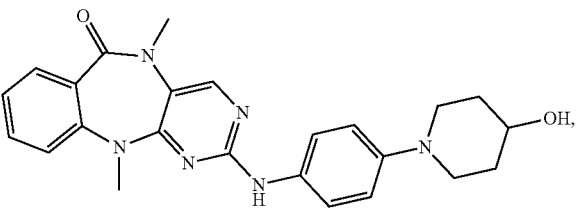

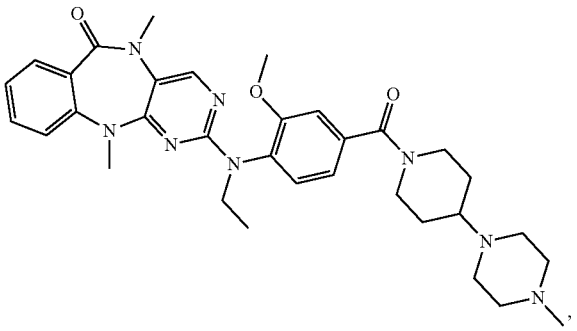

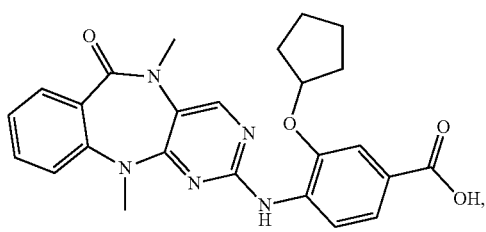

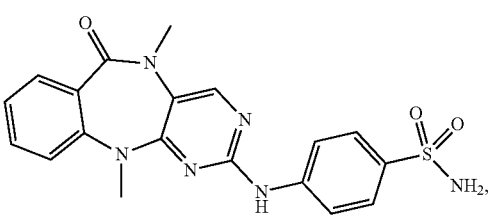

or a pharmaceutically acceptable salt, solvate, hydrate, polymorph, co-crystal, tautomer, stereoisomer, isotopically labeled derivative, or prodrug thereof.

In certain embodiments, the transcription inhibitor is of Formula (XVI):

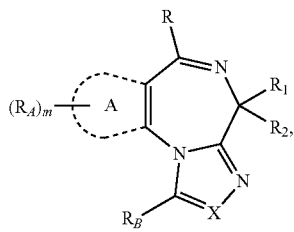

(XVI)

or a salt, solvate or hydrate thereof, wherein:

X is N or $CR_5$;

$R_5$ is H, alkyl, cycloalkyl, heterocycloalkyl, aryl, or heteroaryl, each of which is optionally substituted;

$R_B$ is H, alkyl, hydroxylalkyl, aminoalkyl, alkoxyalkyl, haloalkyl, hydroxy, alkoxy, or —C(=O)O—$R_3$, each of which is optionally substituted;

Ring A is aryl or heteroaryl;

each $R_A$ is independently alkyl, cycloalkyl, heterocycloalkyl, aryl, or heteroaryl, each of which is optionally substituted; or any about two $R_A$ together with the atoms to which each is attached, form a fused aryl or heteroaryl group;

R is alkyl, cycloalkyl, heterocycloalkyl, aryl, or heteroaryl; each of which is optionally substituted;

$R_1$ is —$(CH_2)_n$-L, wherein n is 0, 1, 2, or 3, and L is H, —C(=O)O—$R_3$, —C(=O)—$R_3$, —C(=O)—N($R_3R_4$), —S(=O)$_2$—$R_3$, —S(=O)$_2$—N($R_3R_4$), —N($R_3R_4$), —N($R_4$)C(=O)$R_3$, optionally substituted aryl, or optionally substituted heteroaryl;

$R_2$ is H, D, halogen, or optionally substituted alkyl;

each $R_3$ is independently selected from the group consisting of:

(i) H, aryl, substituted aryl, heteroaryl, or substituted heteroaryl;

(ii) heterocycloalkyl or substituted heterocycloalkyl;

(iii) $C_{1-8}$ alkyl, $C_{2-8}$ alkenyl, or $C_{2-8}$ alkynyl, each containing 0, 1, 2, or 3 heteroatoms selected from O, S, and N; $C_{3-12}$ cycloalkyl, substituted $C_{3-12}$ cycloalkyl, $C_{3-12}$ cycloalkenyl, or substituted $C_{3-12}$ cycloalkenyl, each of which is optionally substituted; and (iv) —$NH_2$, —N=$CR_4R_6$;

each $R_4$ is independently H, alkyl, alkyl, cycloalkyl, heterocycloalkyl, aryl, or heteroaryl, each of which is optionally substituted;

or $R_3$ and $R_4$ are taken together with the nitrogen atom to which they are attached to form a 4- to 10-membered ring; and $R_6$ is alkyl, alkenyl, cycloalkyl, cycloalkenyl, heterocycloalkyl, aryl, or heteroaryl, each of which is optionally substituted;

or $R_4$ and $R_6$ are taken together with the carbon atom to which they are attached to form a 4- to 10-membered ring;

m is 0, 1, 2, or 3;

provided that:

(a) if Ring A is thienyl, X is N, R is phenyl or substituted phenyl, $R_2$ is H, $R_B$ is methyl, $R_1$ is —$(CH_2)_n$-L, n is 1, and L is —C(=O)—N($R_3R_4$), then $R_3$ and $R_4$ are not taken together with the nitrogen atom to which they are attached to form a morpholino ring;

(b) if Ring A is thienyl, X is N, R is substituted phenyl, $R_2$ is H, $R_B$ is methyl, $R_1$ is —$(CH_2)_n$-L, n is 1, L is —C(=O)—N($R_3R_4$), and one of $R_3$ and $R_4$ is H, then the other of $R_3$ and $R_4$ is not methyl, hydroxyethyl, alkoxy, phenyl, substituted phenyl, pyridyl or substituted pyridyl; and (c) if Ring A is thienyl, X is N, R is substituted phenyl, $R_2$ is H, $R_B$ is methyl, $R_1$ is —$(CH_2)_n$-L, n is 1, and L is —C(=O)O—$R_3$, then $R_3$ is not methyl or ethyl.

In certain embodiments, the transcription inhibitor is of the formula:

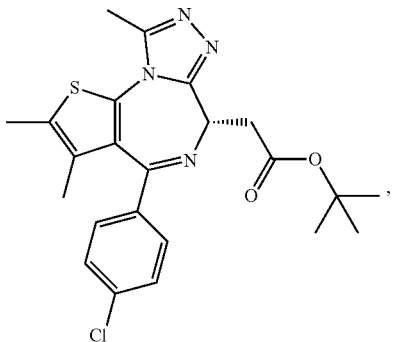
(JQ1)

or a pharmaceutically acceptable salt, solvate, hydrate, polymorph, co-crystal, tautomer, stereoisomer, isotopically labeled derivative, or prodrug thereof.

In certain embodiments, the transcription inhibitor is of the formula:

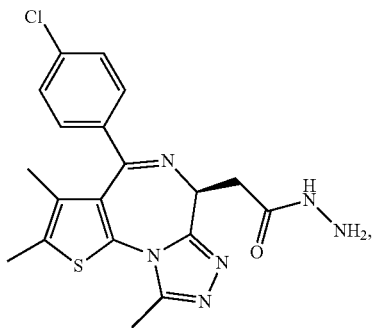

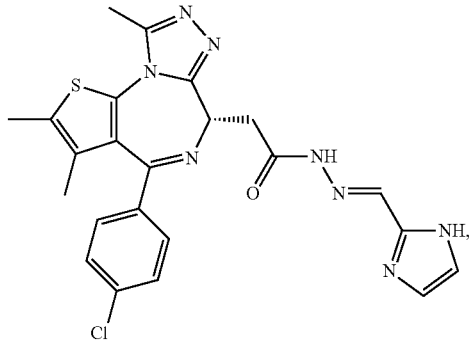

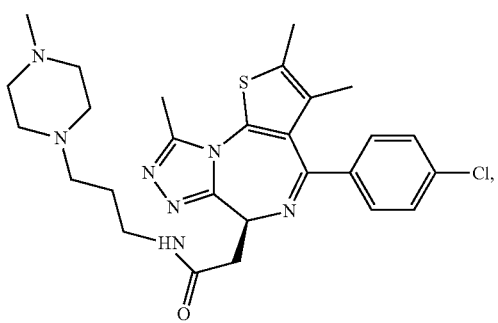

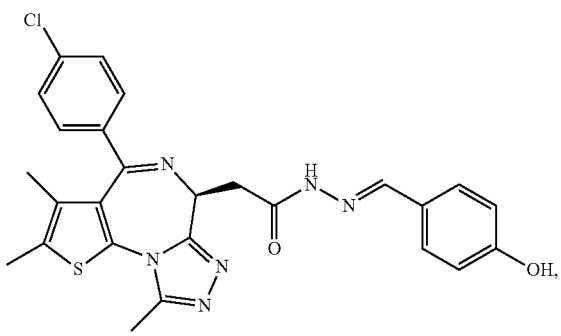

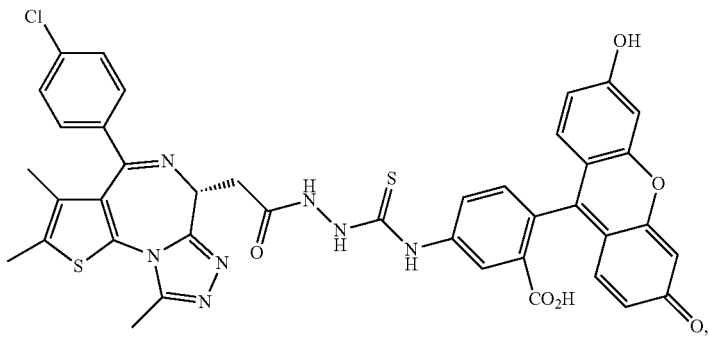

-continued
183
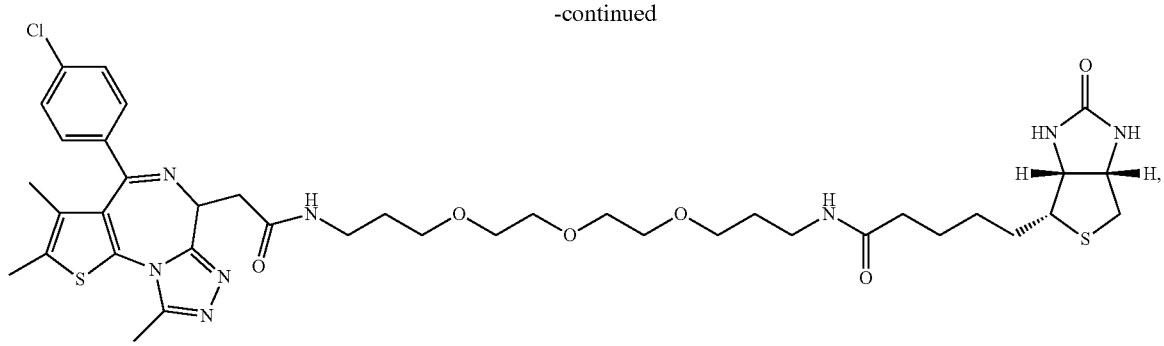
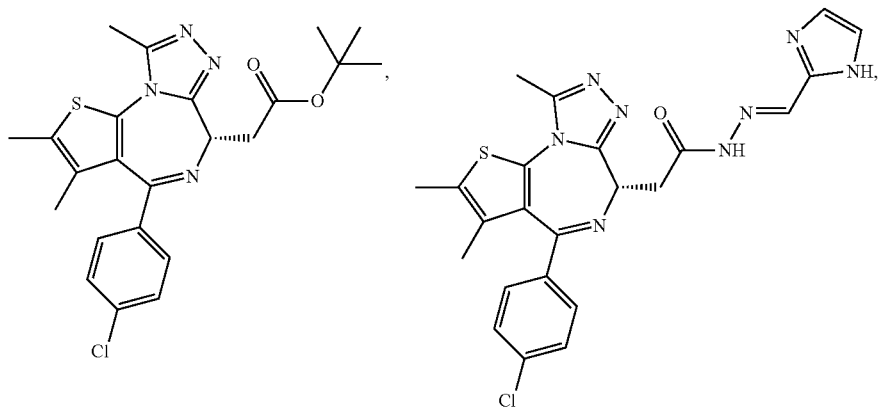
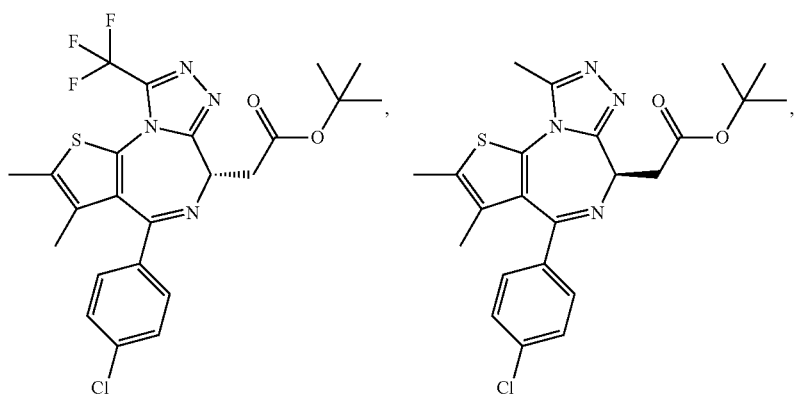
184
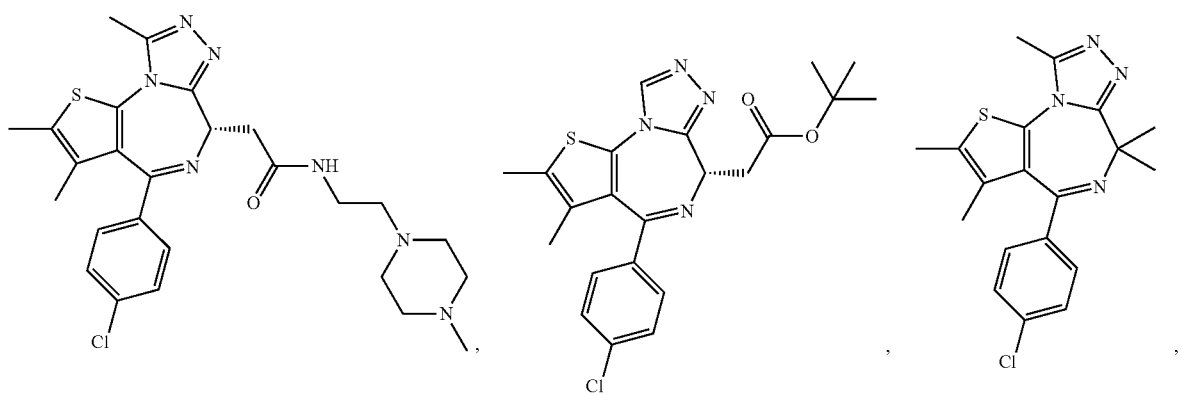

185 186
-continued
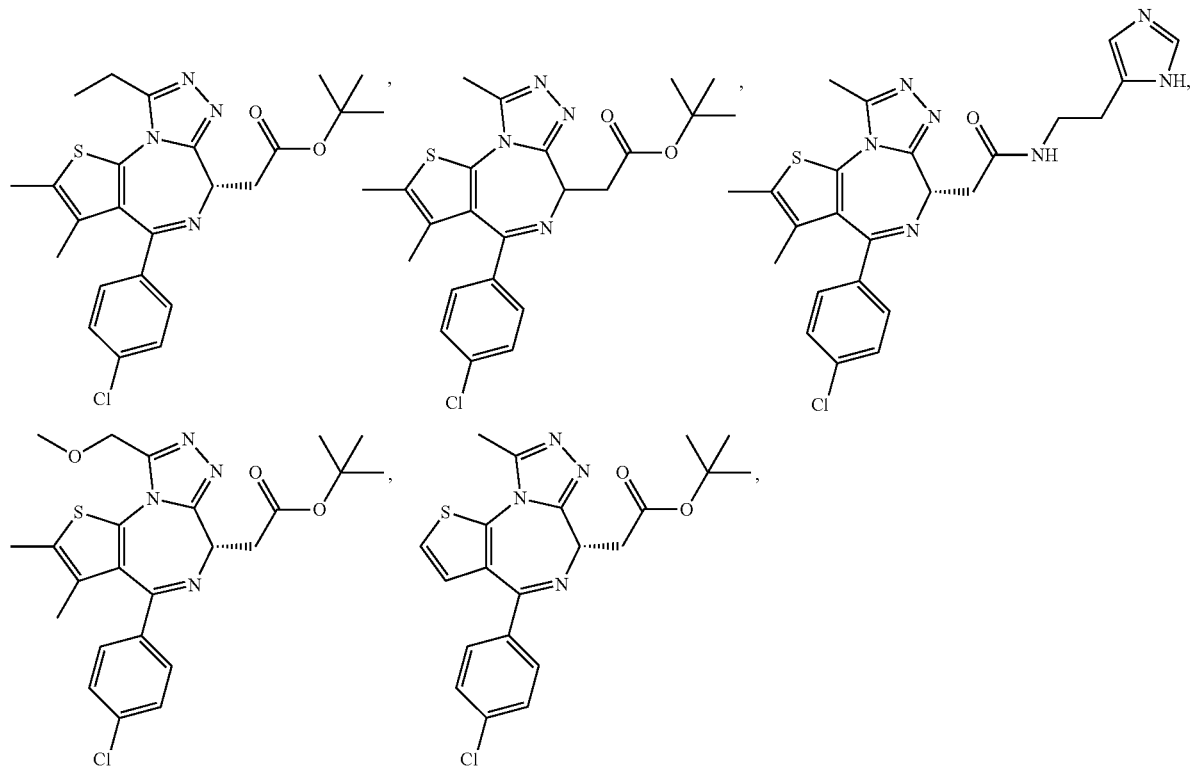
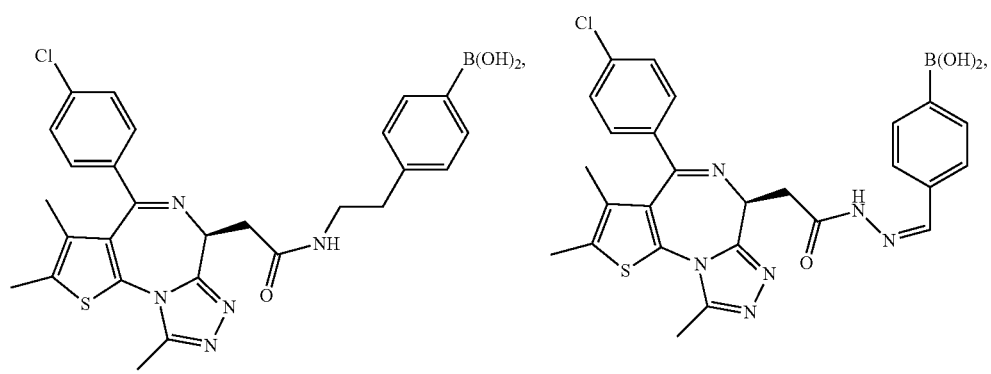
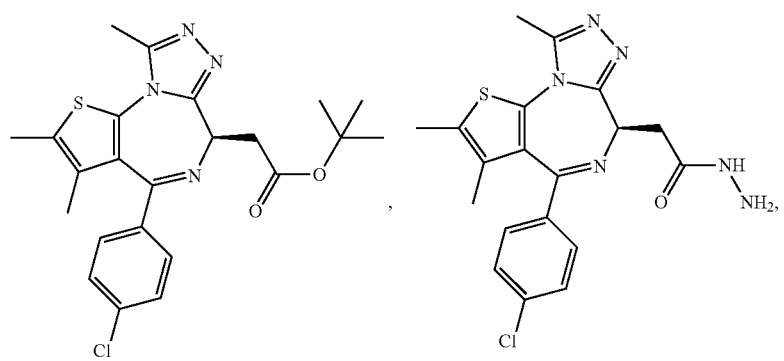

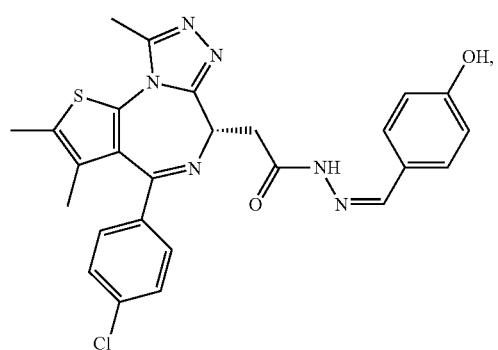
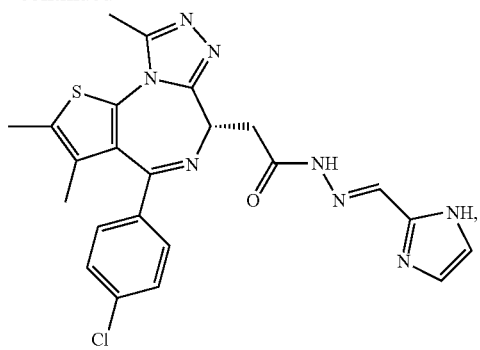
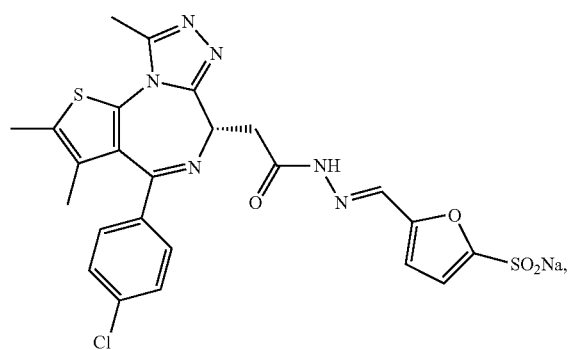
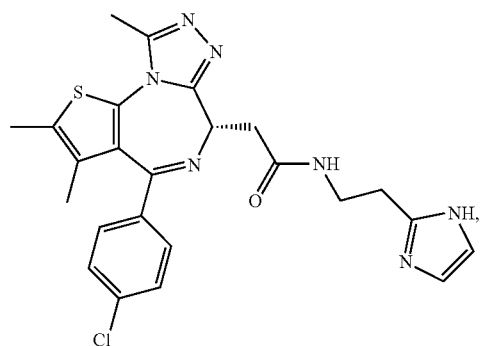
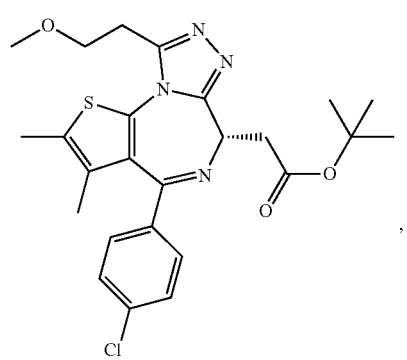
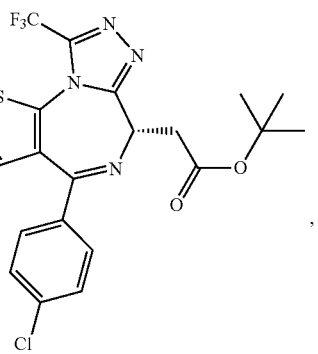
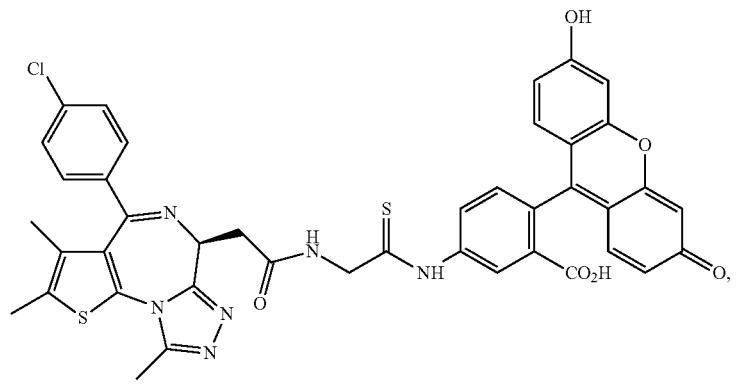

-continued
189 190
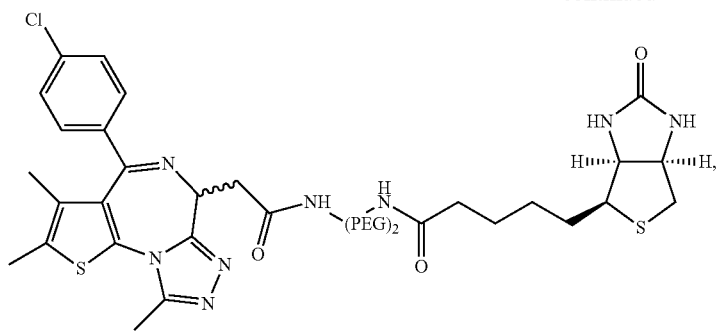
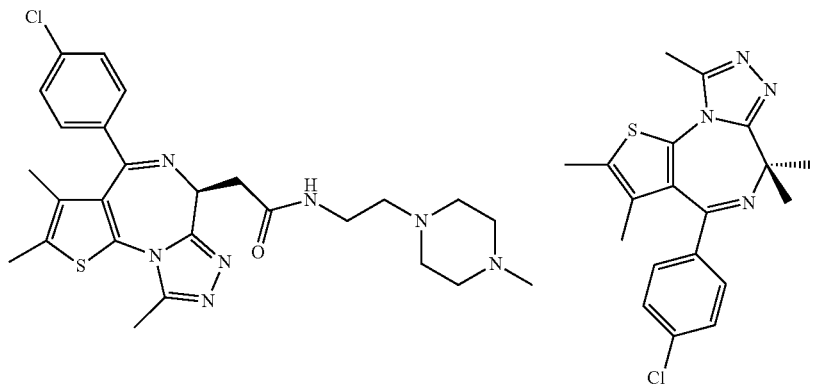
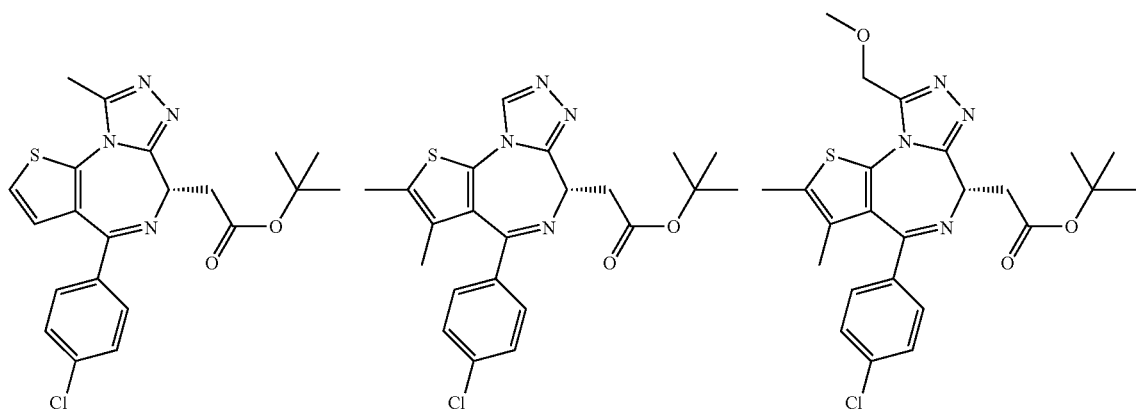
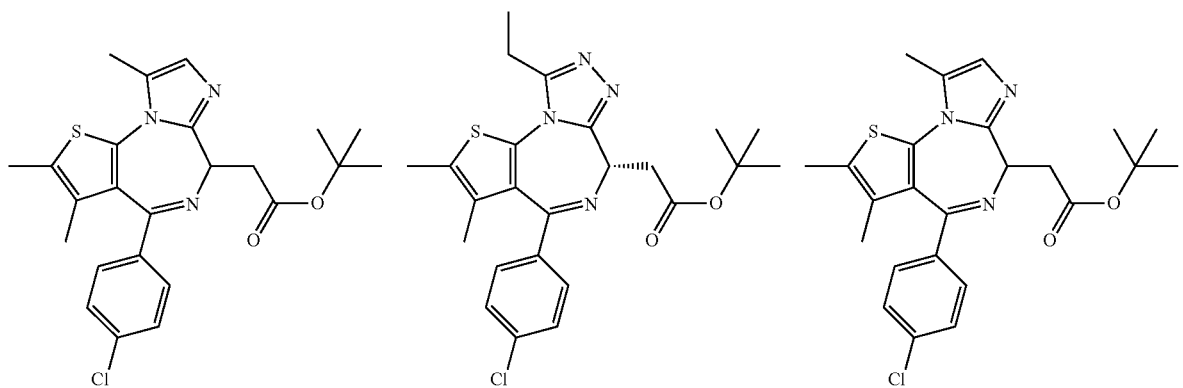

191    192
-continued
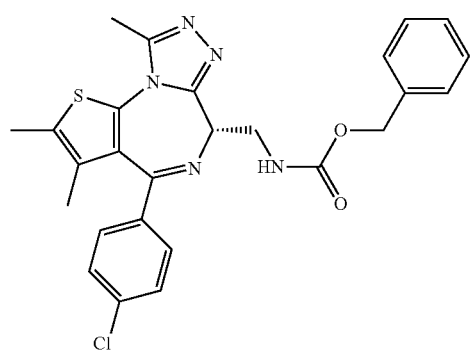 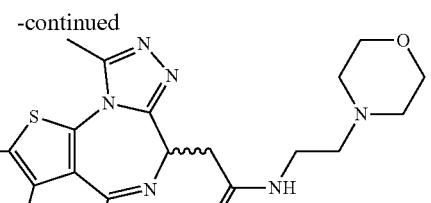
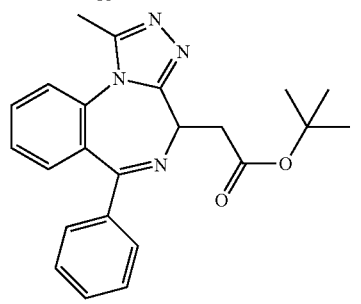 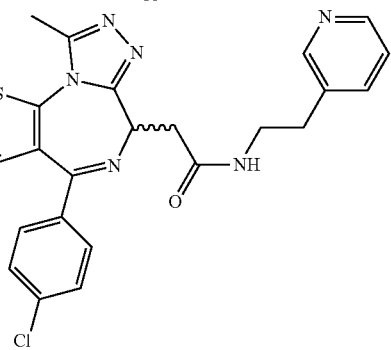
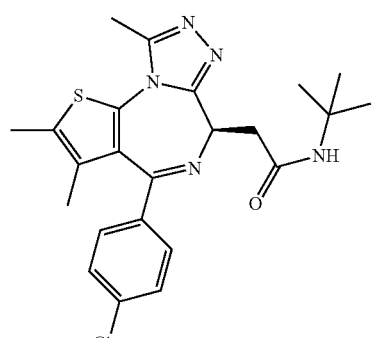 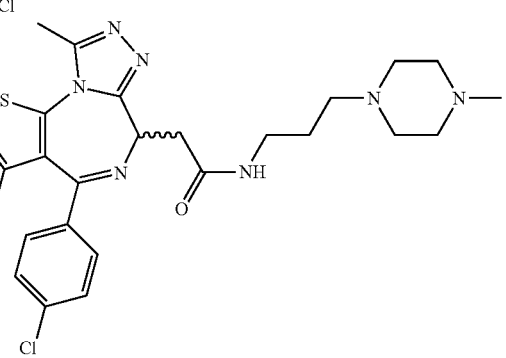
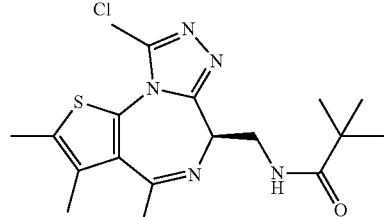 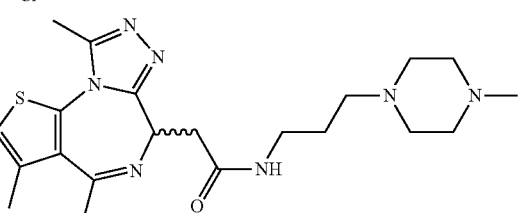
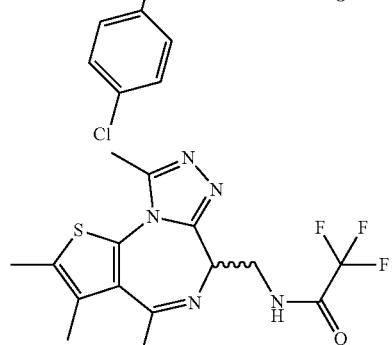 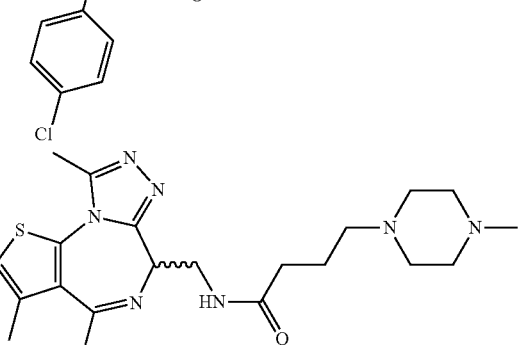
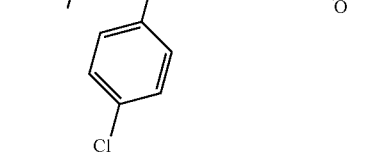

193
194
-continued
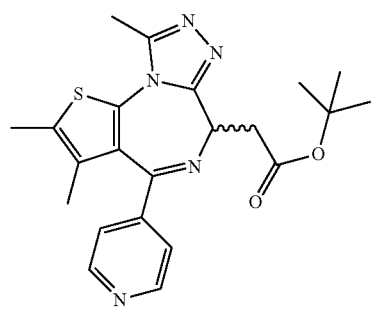
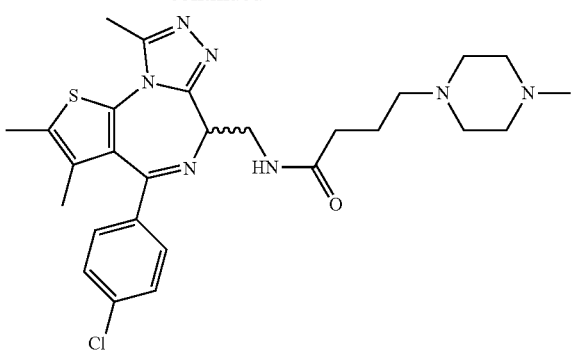
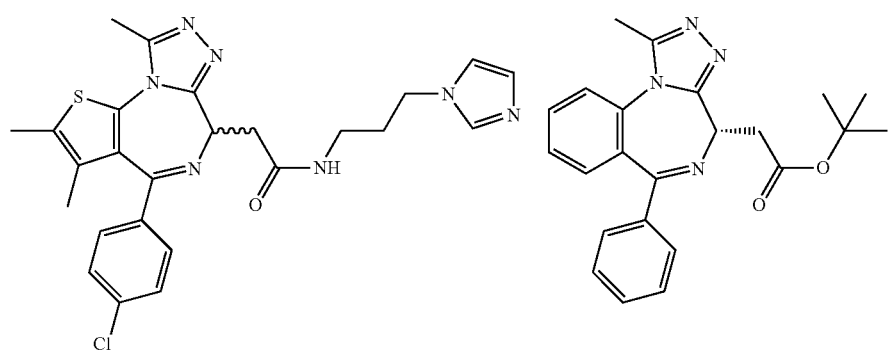
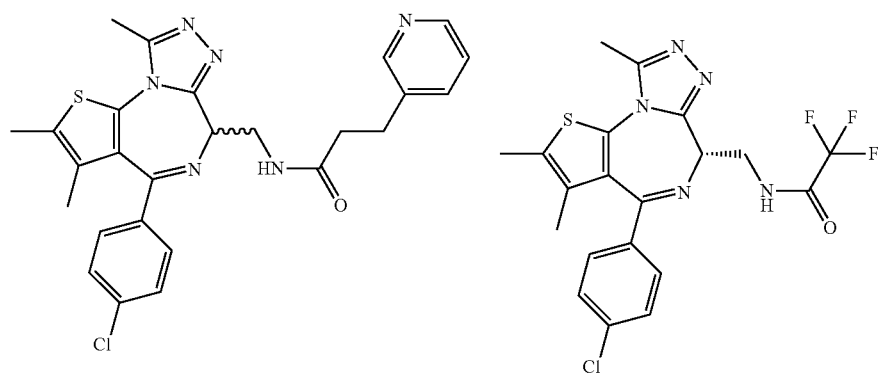
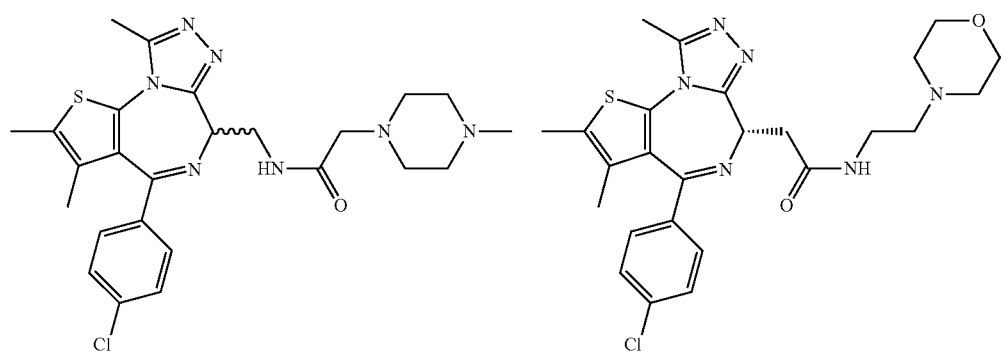

-continued
195
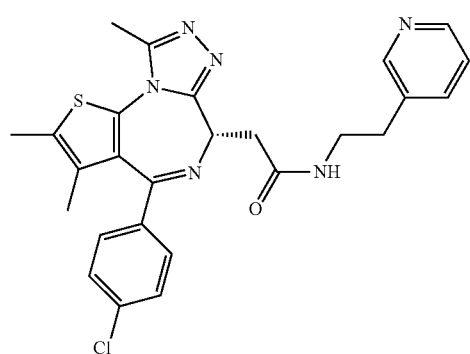
196
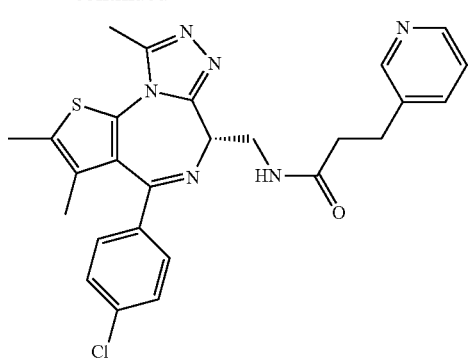
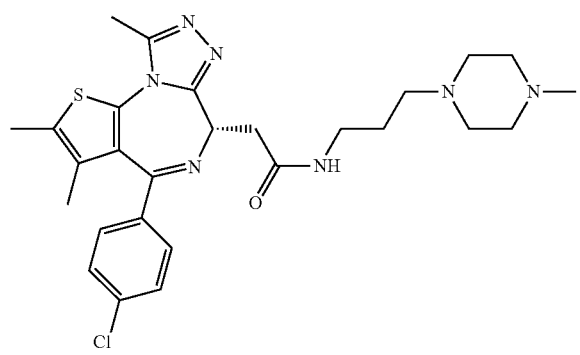
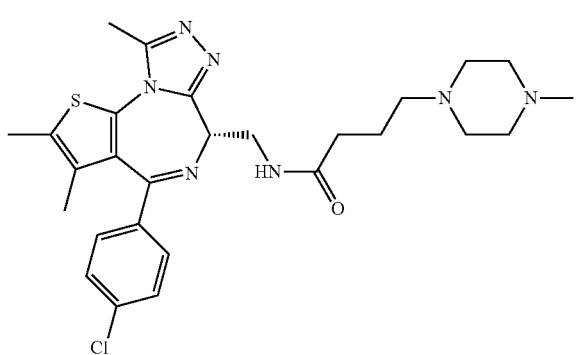
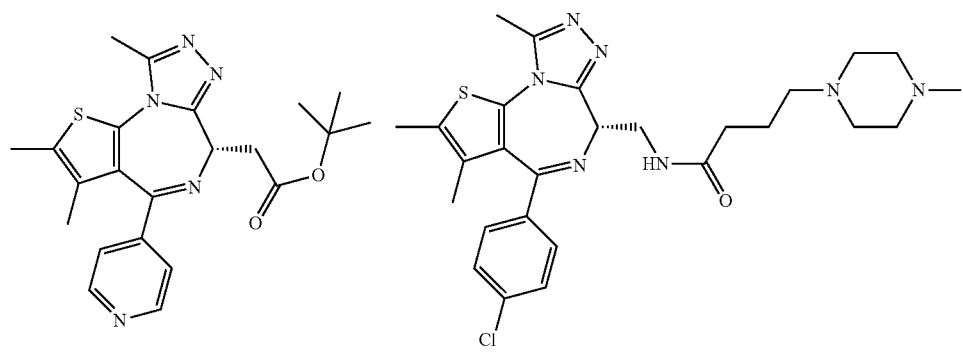
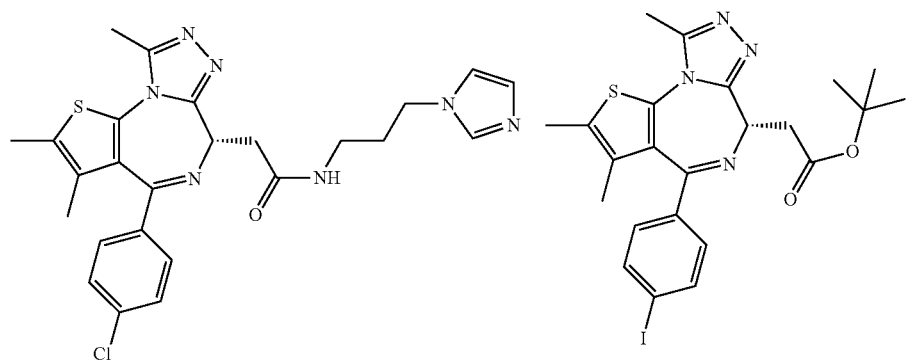

197
198
-continued
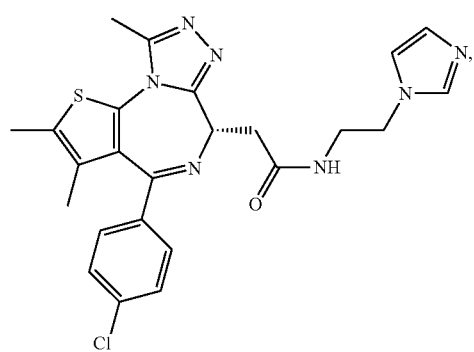
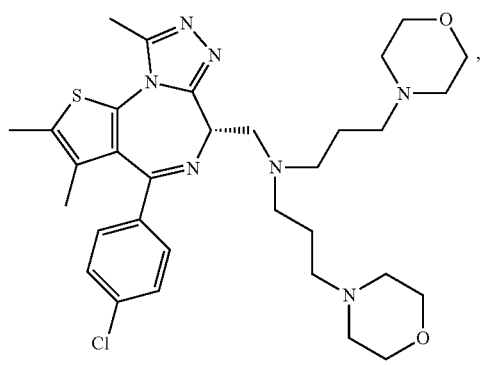
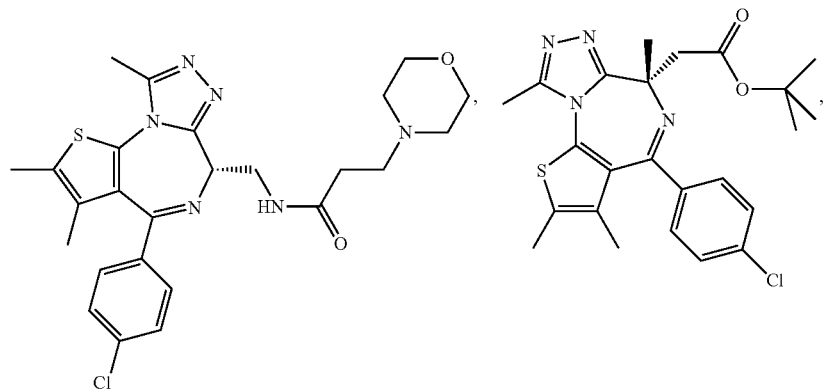
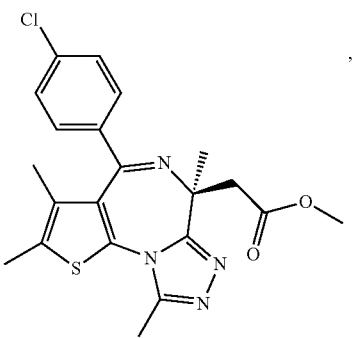
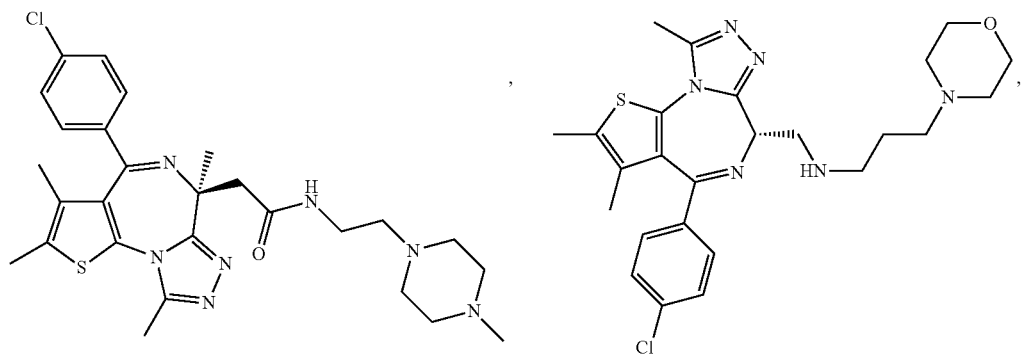

-continued
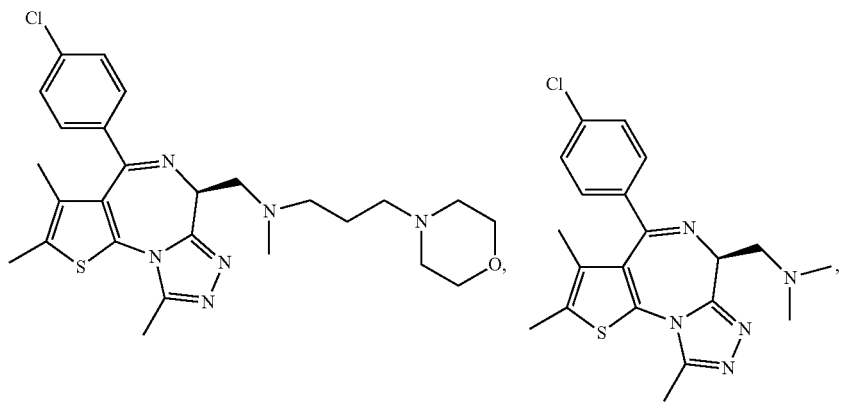
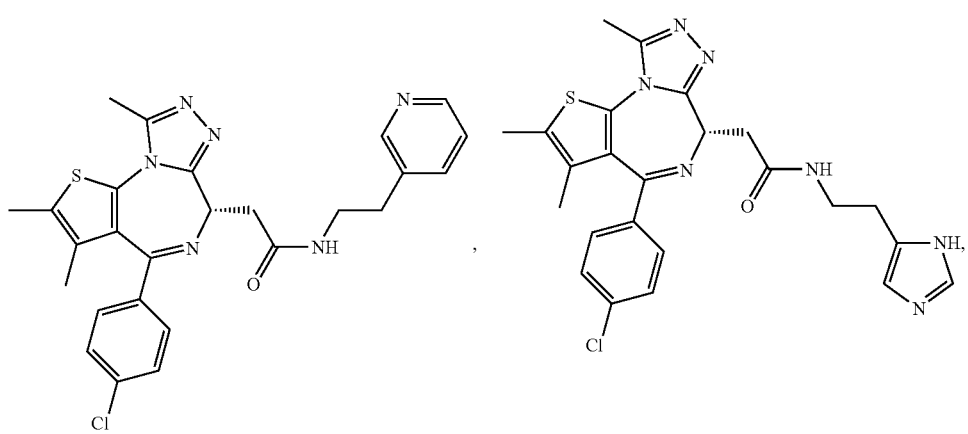
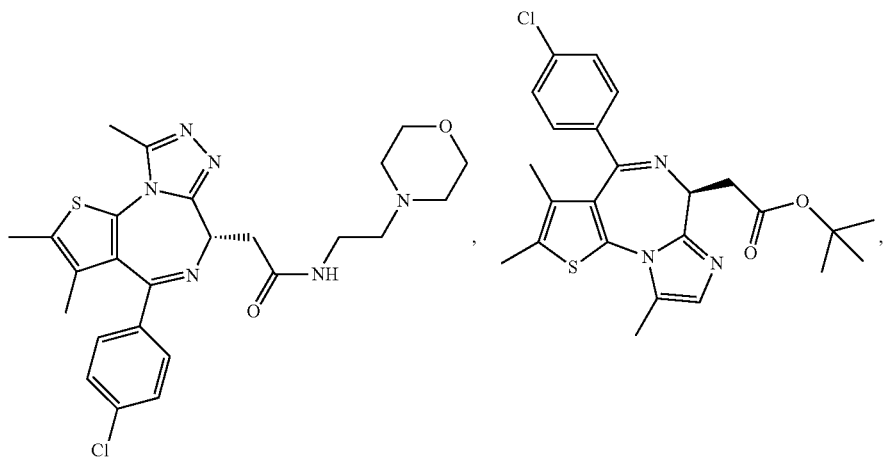

or a pharmaceutically acceptable salt, solvate, hydrate, polymorph, co-crystal, tautomer, stereoisomer, isotopically labeled derivative, or prodrug thereof.

In certain embodiments, the transcription inhibitor is of Formula (XVII):

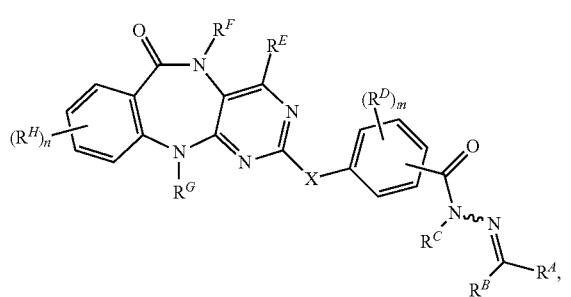

(XVII)

or a pharmaceutically acceptable salt, solvate, hydrate, polymorph, co-crystal, tautomer, stereoisomer, isotopically labeled derivative, or prodrug thereof, wherein:

$R^A$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^B$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

or $R^A$ and $R^B$ are joined to form a substituted or unsubstituted, carbocyclic ring, or a substituted or unsubstituted, heterocyclic ring;

$R^C$ is hydrogen, substituted or unsubstituted $C_{1-6}$ alkyl, or a nitrogen protecting group;

each instance of $R^D$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two R$^a$ groups are joined to form a substituted or unsubstituted, heterocyclic ring, or a substituted or unsubstituted, heteroaryl ring;

m is 0, 1, 2, 3, or 4;

X is —O—, —S—, —N(R$^{X1}$)—, or —C(R$^{X2}$)$_2$—, wherein R$^{X1}$ is hydrogen or substituted or unsubstituted $C_{1-6}$ alkyl, or a nitrogen protecting group, and wherein each instance of R$^{X2}$ is independently hydrogen, halogen, or substituted or unsubstituted $C_{1-6}$ alkyl;

$R^E$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

$R^F$ is hydrogen, substituted or unsubstituted $C_{1-6}$ alkyl, or a nitrogen protecting group;

$R^G$ is hydrogen, substituted or unsubstituted alkyl, substituted or unsubstituted carbocyclyl, substituted or unsubstituted phenyl, or a nitrogen protecting group;

each instance of $R^H$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$; and n is 0, 1, 2, 3, or 4.

In certain embodiments, the transcription inhibitor is of the formula:

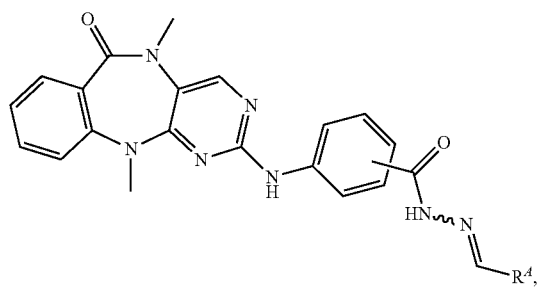

wherein $R^A$ is

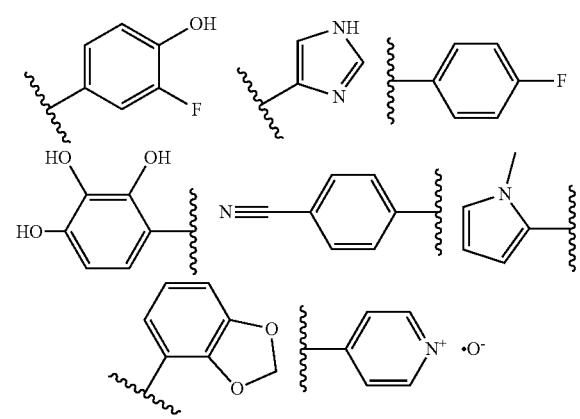

-continued
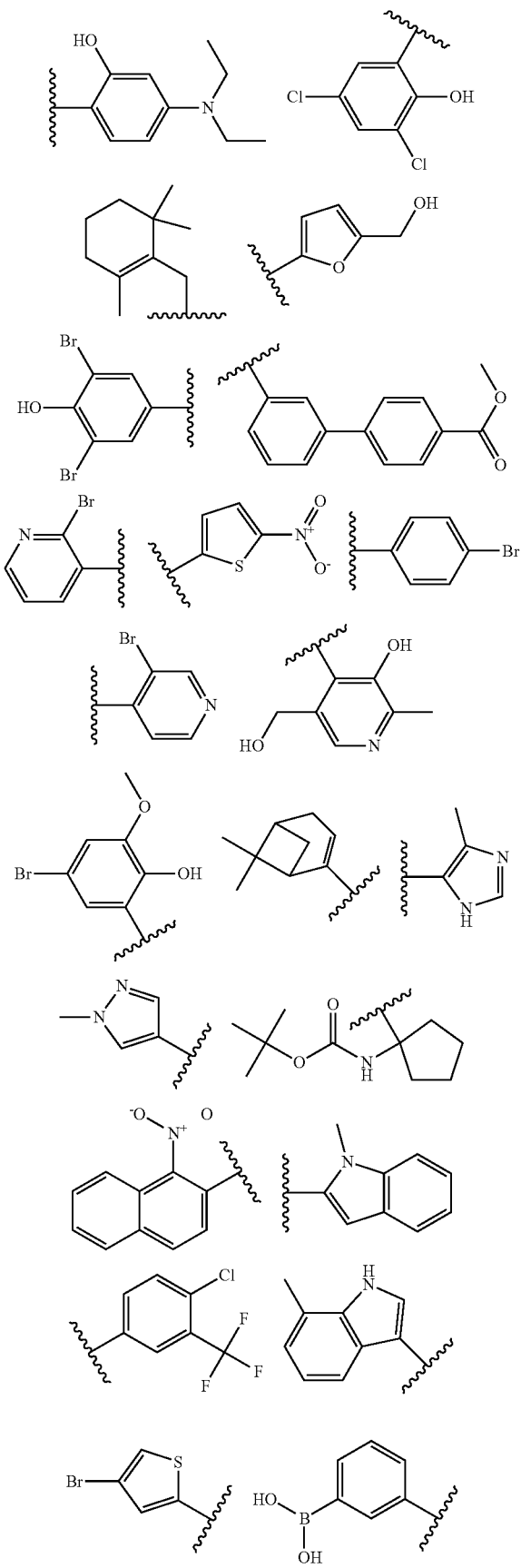
-continued
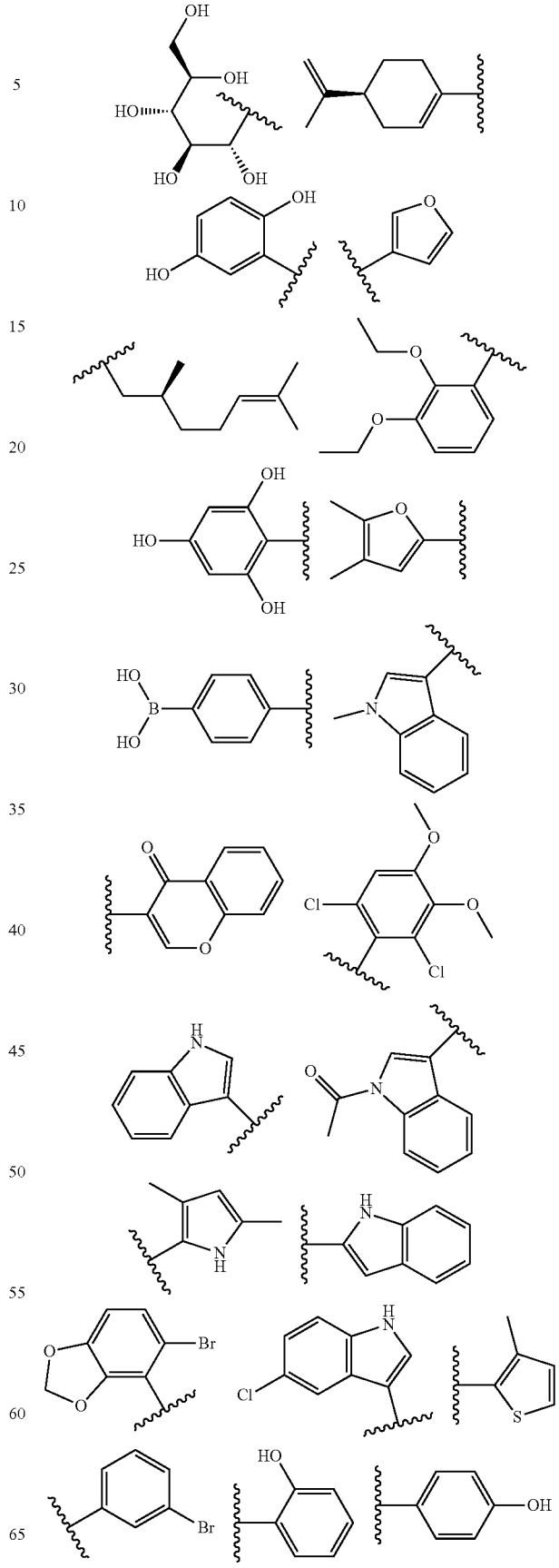

-continued
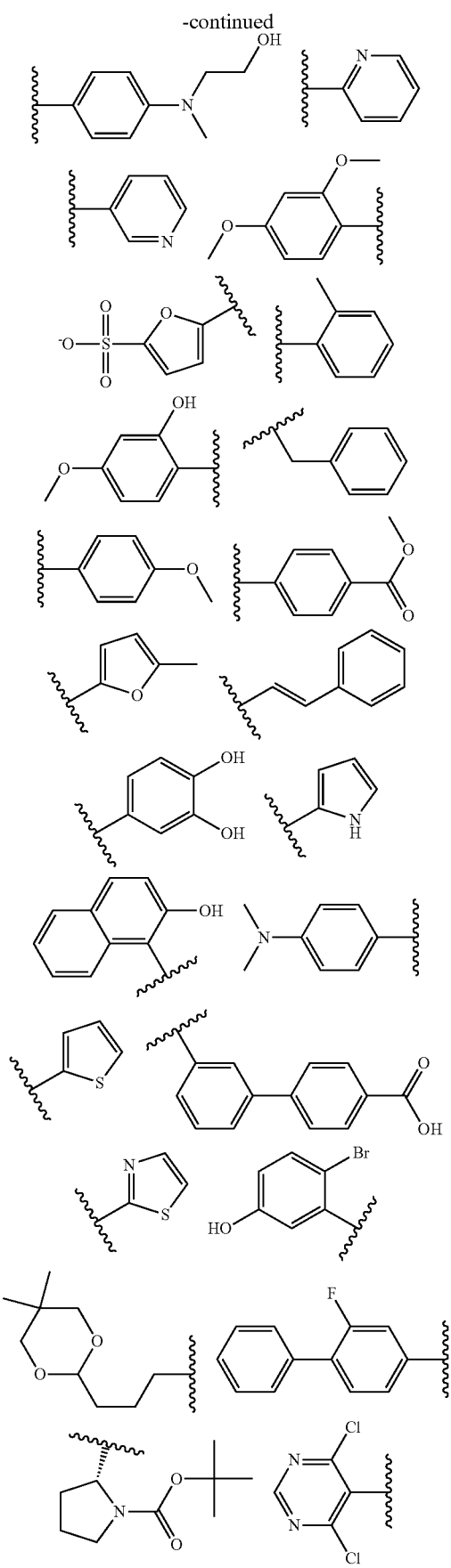
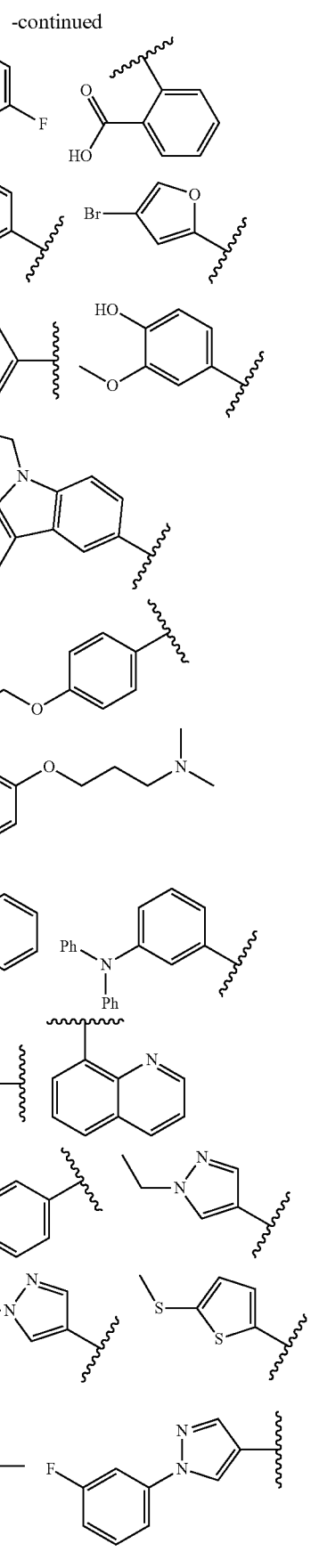

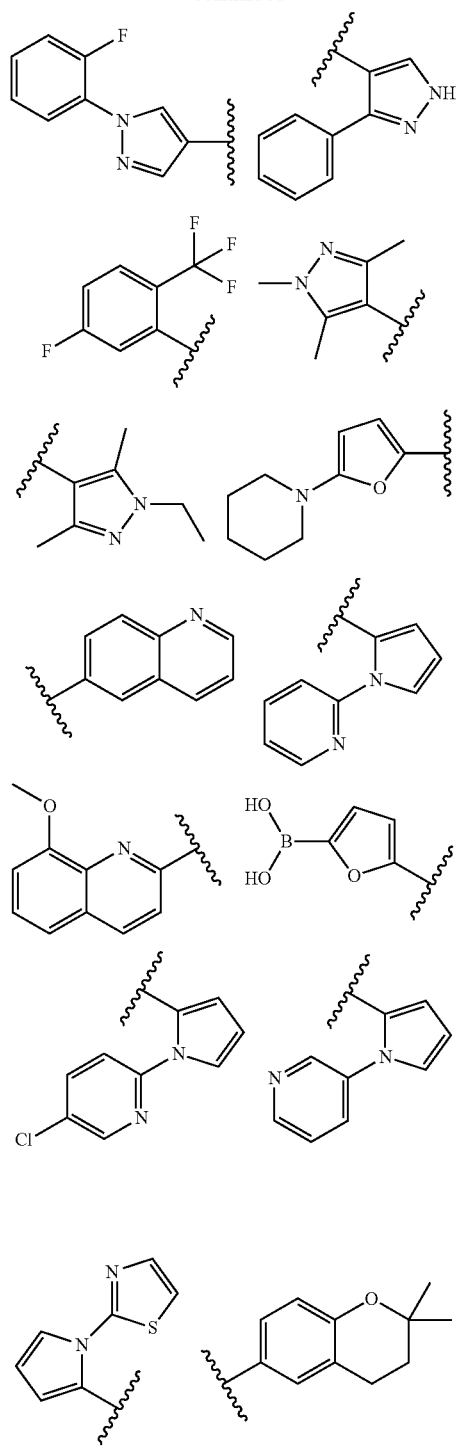
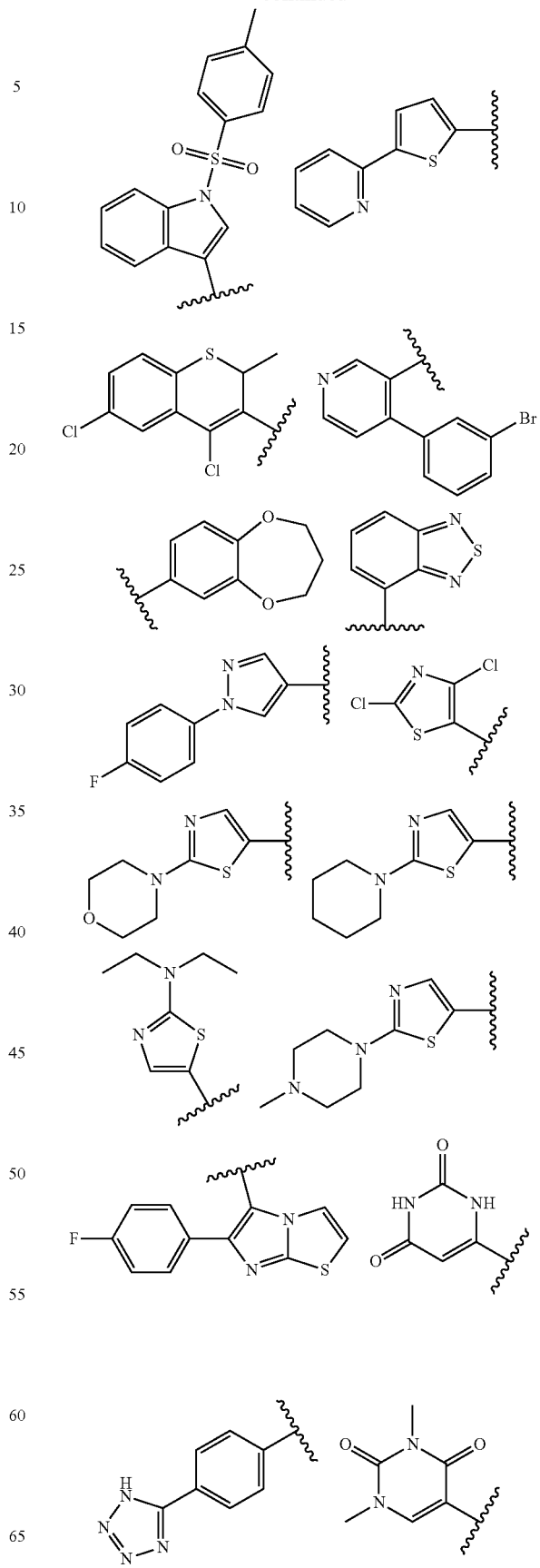

-continued
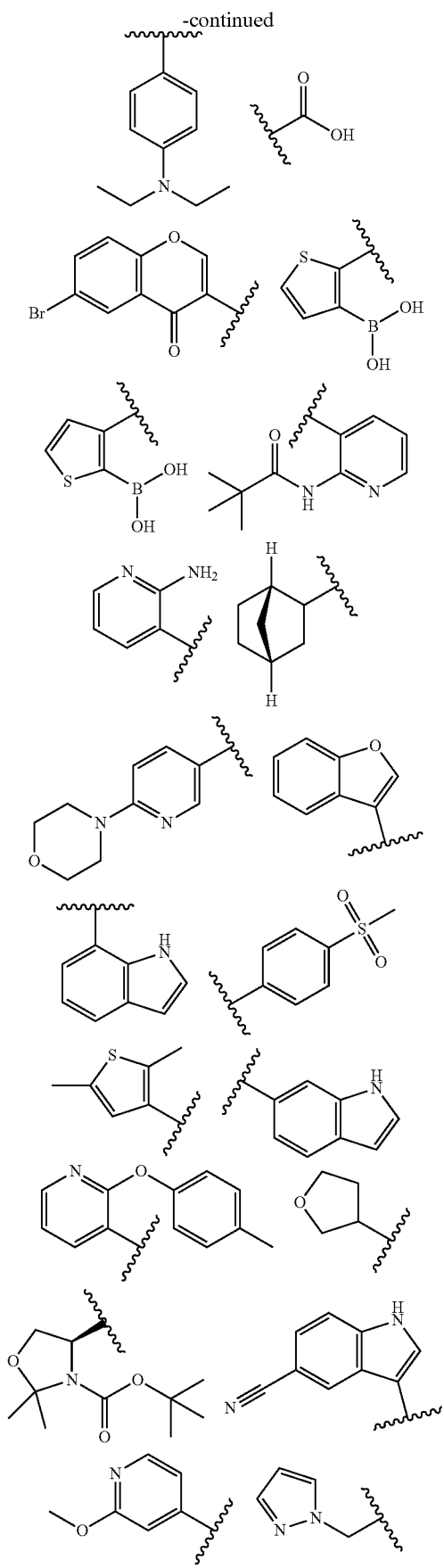
-continued
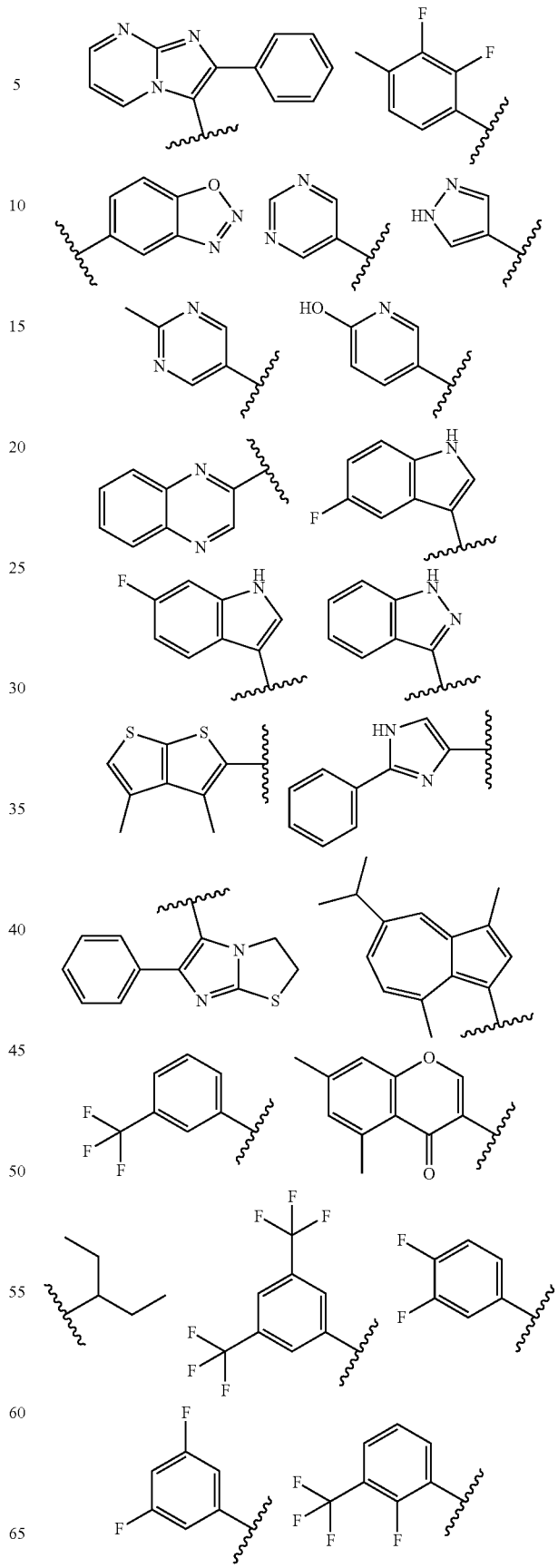

211
-continued
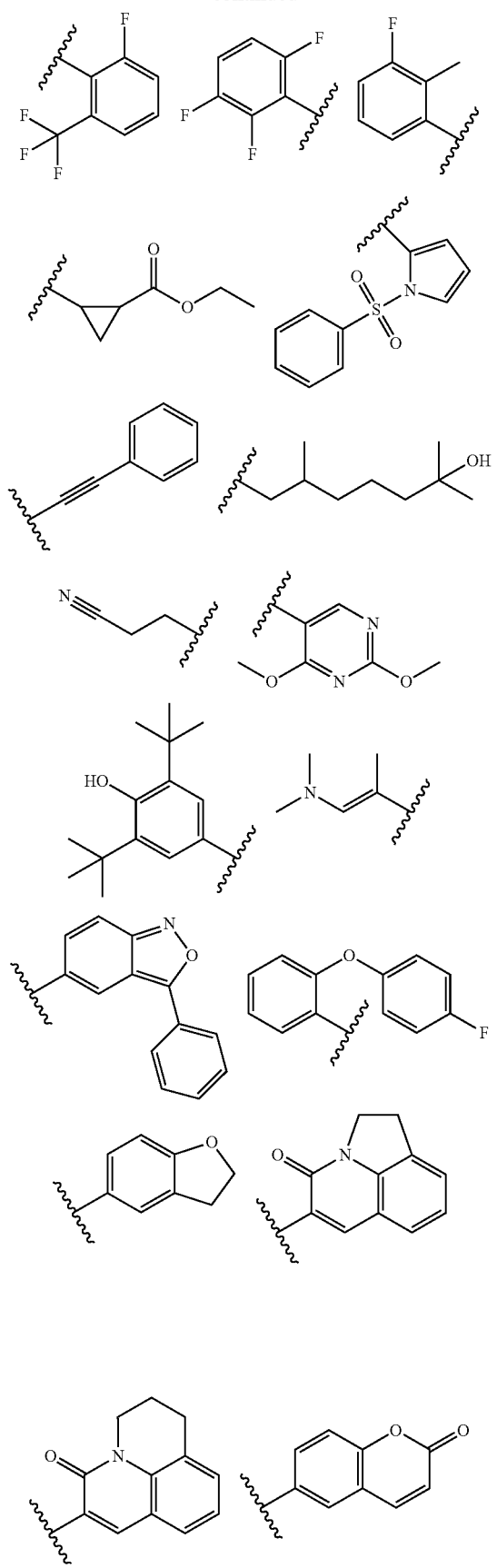
212
-continued
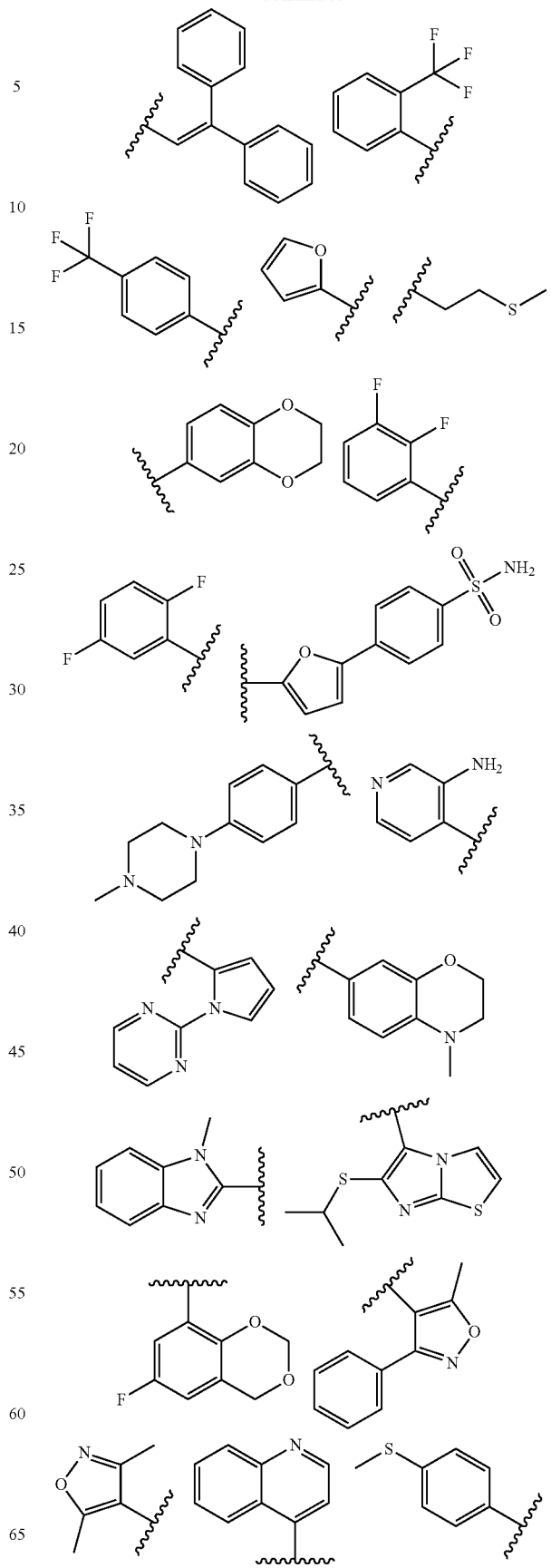

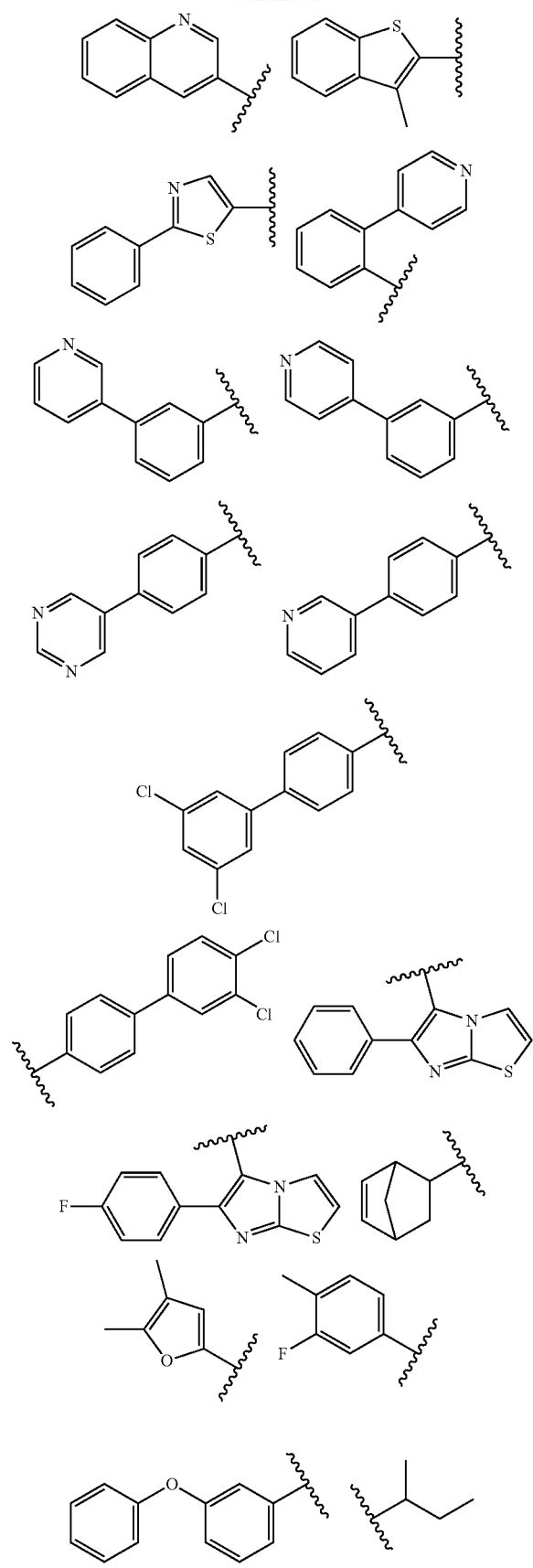
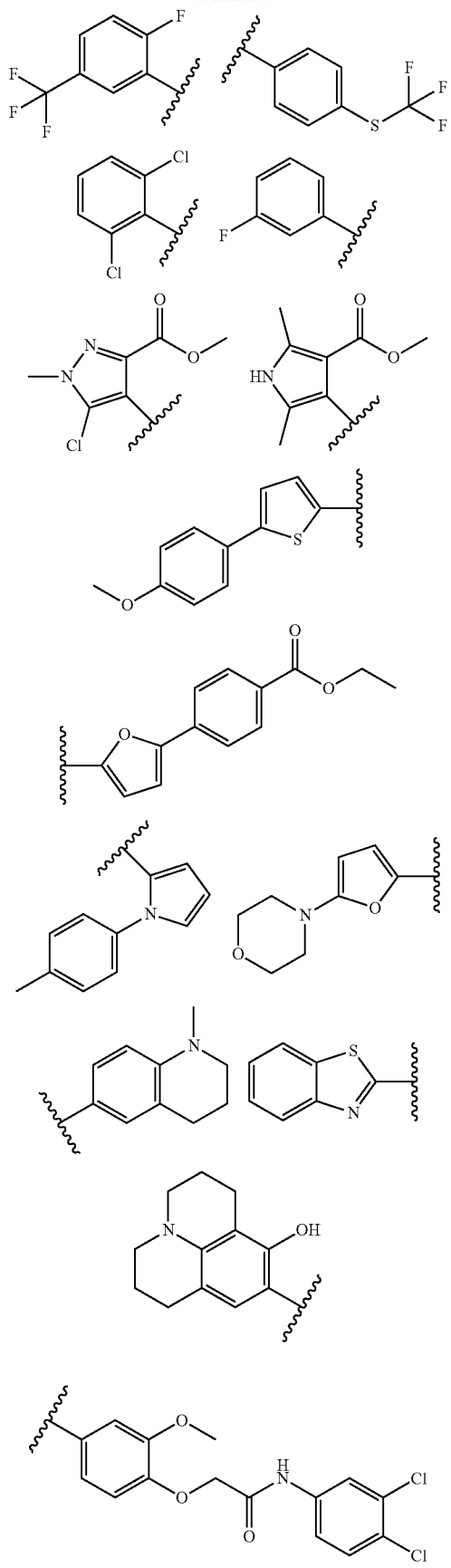

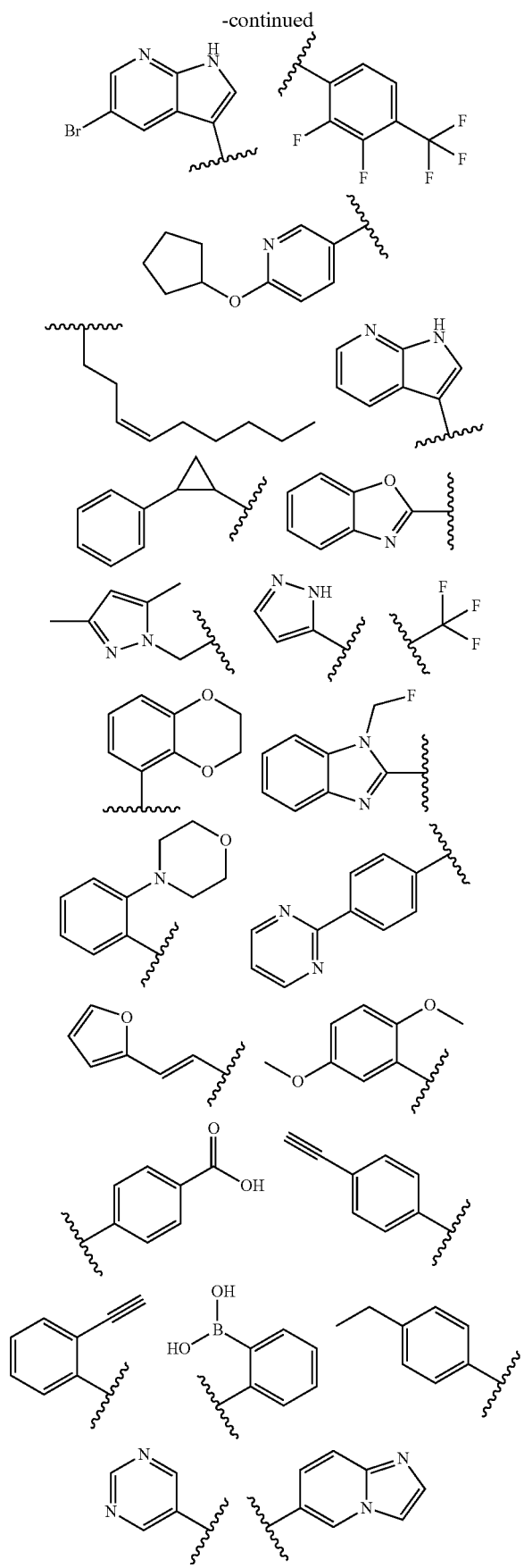
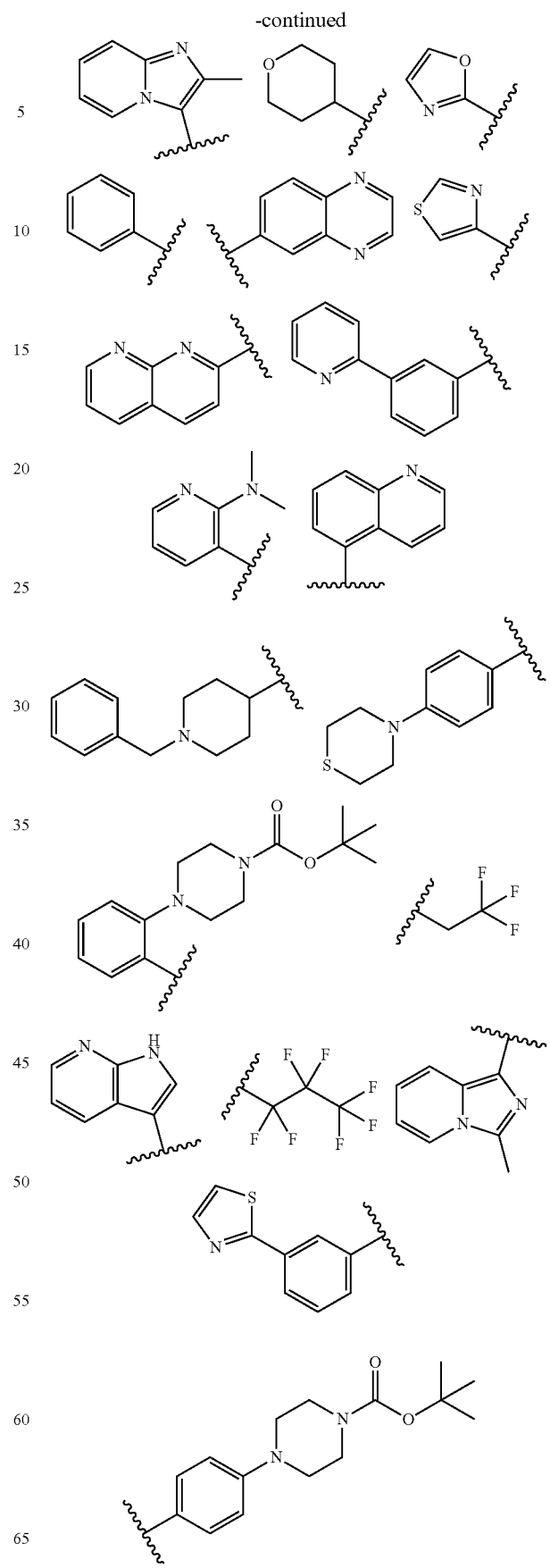

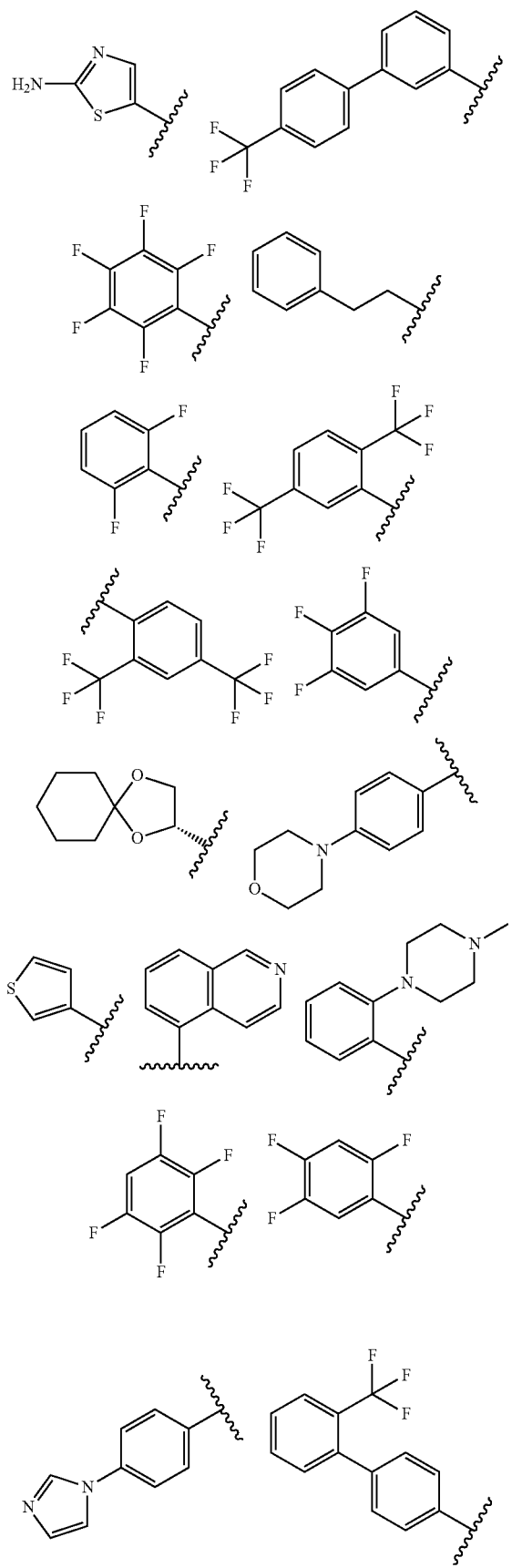
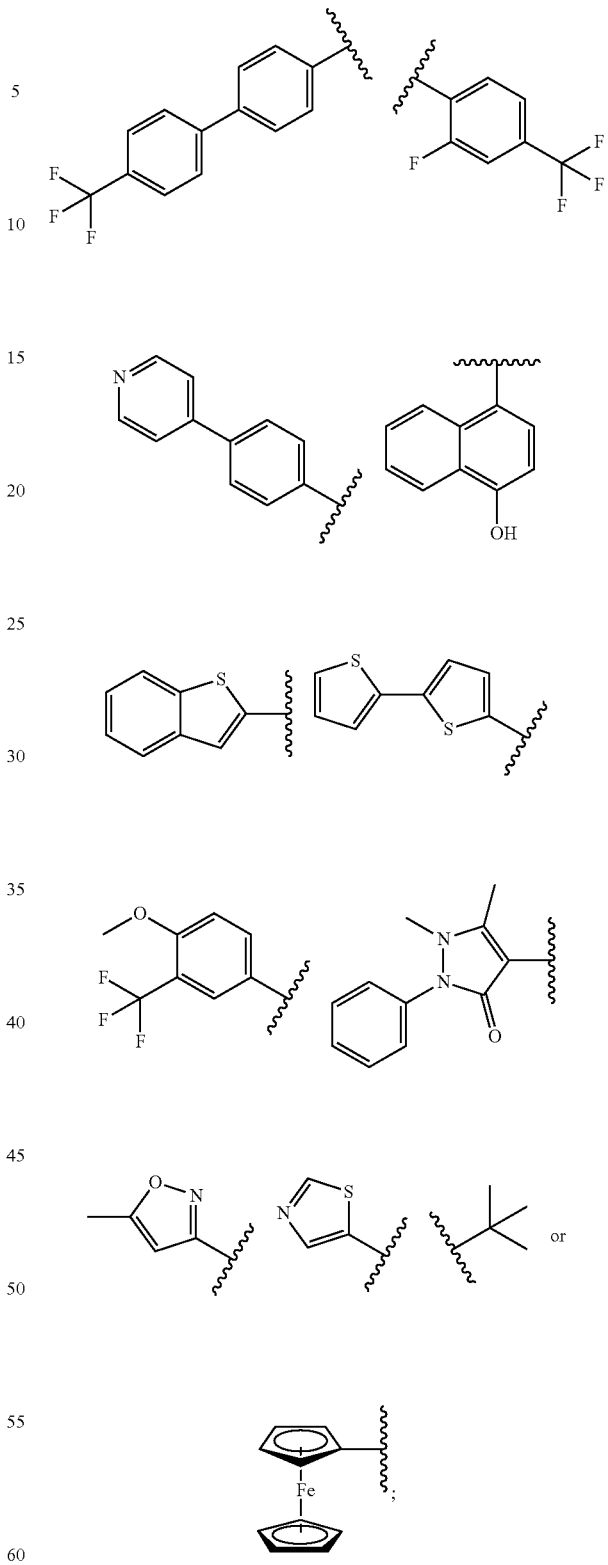
or a pharmaceutically acceptable salt, solvate, hydrate, polymorph, co-crystal, tautomer, stereoisomer, isotopically labeled derivative, or prodrug thereof.
In certain embodiments, the transcription inhibitor is of the formula:

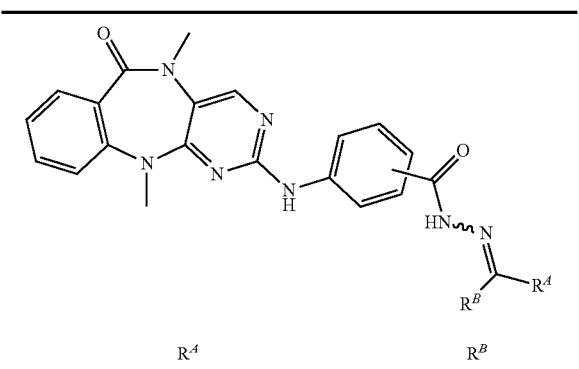
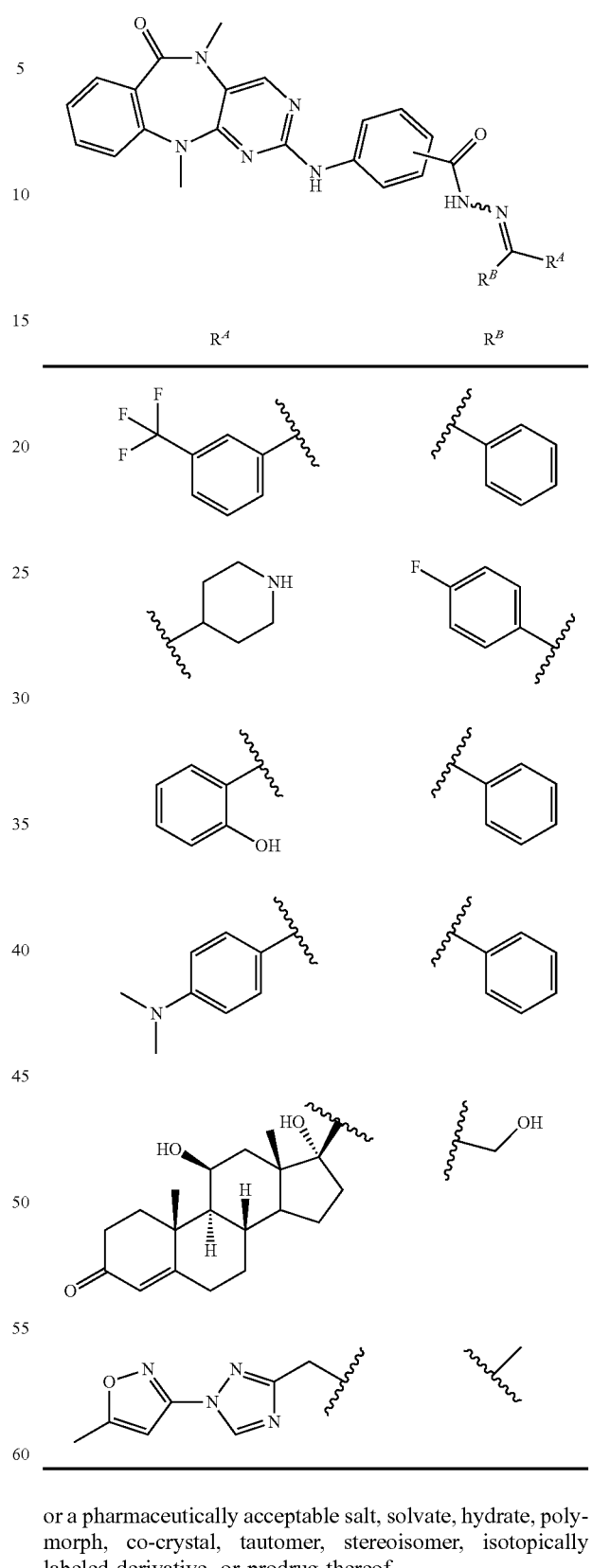
or a pharmaceutically acceptable salt, solvate, hydrate, polymorph, co-crystal, tautomer, stereoisomer, isotopically labeled derivative, or prodrug thereof.
In certain embodiments, the transcription inhibitor is of the formula:

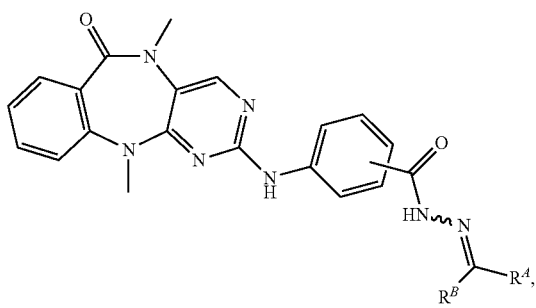

wherein

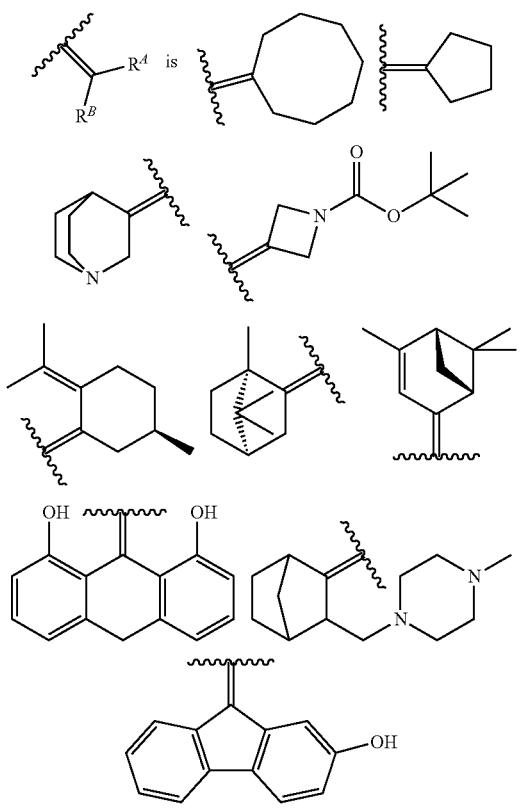

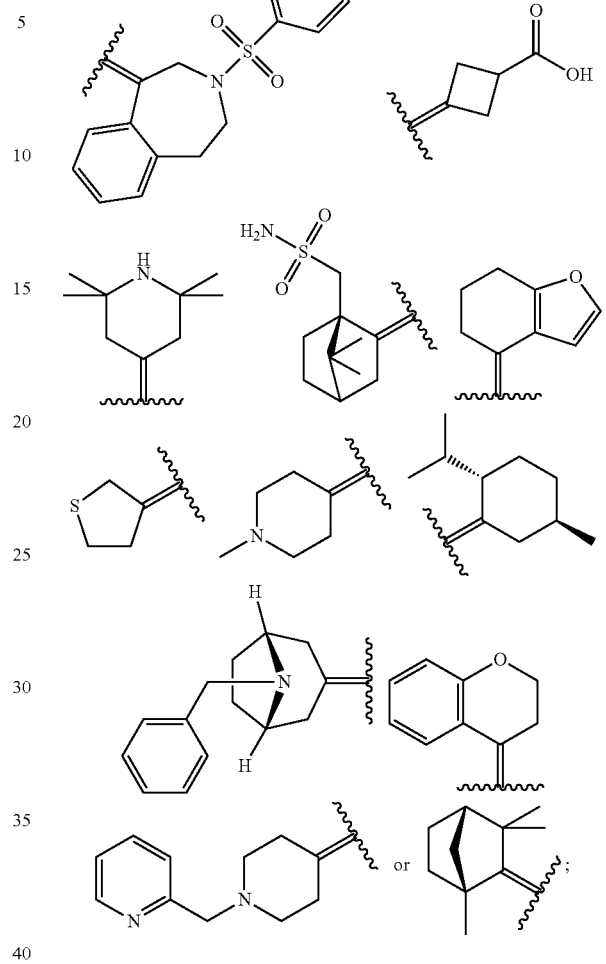

or a pharmaceutically acceptable salt, solvate, hydrate, polymorph, co-crystal, tautomer, stereoisomer, isotopically labeled derivative, or prodrug thereof.

In certain embodiments, the transcription inhibitor is of Formula (XVIII):

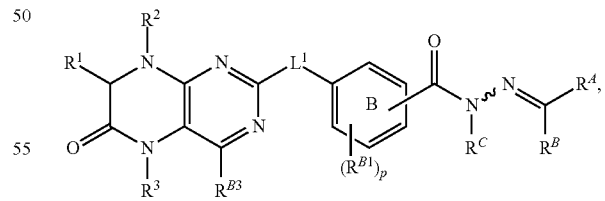

(XVIII)

or pharmaceutically acceptable salt, solvate, hydrate, polymorph, co-crystal, tautomer, stereoisomer, isotopically labeled derivative, or prodrug thereof, wherein:

$R^A$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

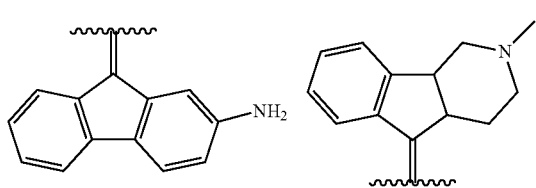

$R^B$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

or $R^A$ and $R^B$ are joined to form a substituted or unsubstituted, carbocyclic ring, or a substituted or unsubstituted, heterocyclic ring;

$R^C$ is hydrogen, substituted or unsubstituted $C_{1-6}$ alkyl, or a nitrogen protecting group;

$R^1$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^2$ and $R^3$ are each independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)$R^{D1}$, —C(=O)O$R^{D1}$, —C(=O)N($R^{D1}$)$_2$, or a nitrogen protecting group, wherein each instance of $R^{D1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two $R^{D1}$ groups are joined to form a substituted or unsubstituted heterocyclic or substituted or unsubstituted heteroaryl ring, or a nitrogen protecting group when attached to a nitrogen atom;

each instance of $R^{B1}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^{B1a}$, —N($R^{B1a}$)$_2$, —S$R^{B1a}$, —CN, —SCN, —C(=N$R^{B1a}$)$R^{B1a}$, —C(=N$R^{B1a}$)O$R^{B1a}$, —C(=N$R^{B1a}$)N($R^{B1a}$)$_2$, —C(=O)$R^{B1a}$, —C(=O)O$R^{B1a}$, —C(=O)N($R^{B1a}$)$_2$, —NO$_2$, —N$R^{B1a}$C(=O)$R^{B1a}$, —N$R^{B1a}$C(=O)O$R^{B1a}$, —N$R^{B1a}$C(=O)N($R^{B1a}$)$_2$, —OC(=O)$R^{B1a}$, —OC(=O)O$R^{B1a}$, or —OC(=O)N($R^{B1a}$)$_2$, wherein each instance of $R^{B1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two $R^{B1a}$ groups are joined to form a substituted or unsubstituted heterocyclic or substituted or unsubstituted heteroaryl ring;

each instance of $R^{B3}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^{B3a}$, —N($R^{B3a}$)$_2$, —S$R^{B3a}$, —CN, —SCN, —C(=N$R^{B3a}$)$R^{B3a}$, —C(=N$R^{B3a}$)O$R^{B3a}$, —C(=N$R^{B3a}$)N($R^{B3a}$)$_2$, —C(=O)$R^{B3a}$, —C(=O)O$R^{B3a}$, —C(=O)N($R^{B3a}$)$_2$, —NO$_2$, —N$R^{B3a}$C(=O)$R^{B3a}$, —N$R^{B3a}$C(=O)O$R^{B3a}$, —N$R^{B3a}$C(=O)N($R^{B3a}$)$_2$, —OC(=O)$R^{B3a}$, —OC(=O)O$R^{B3a}$, or —OC(=O)N($R^{B3a}$)$_2$, wherein each instance of $R^{B3a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two $R^{B3a}$ groups are joined to form a substituted or unsubstituted heterocyclic or substituted or unsubstituted heteroaryl ring;

p is 0 or an integer between 1 and 4, inclusive;

L is a bond,

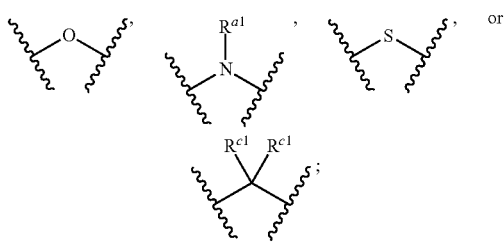

$R^{a1}$ is hydrogen, substituted or unsubstituted alkyl, substituted or unsubstituted alkenyl is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group; and each instance of $R^{c1}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^{c1a}$, —N($R^{c1a}$)$_2$, —S$R^{c1a}$, —CN, —C(=O)$R^{c1a}$, —C(=O)O$R^{c1a}$, —C(=O)N($R^{c1a}$)$_2$, —N$R^{c1a}$C(=O)$R^{c1a}$, —N$R^{c1a}$C(=O)O$R^{c1a}$, —N$R^{c1a}$C(=O)N($R^{c1a}$)$_2$, —OC(=O)$R^{c1a}$, or —OC(=O)N($R^{c1a}$)$_2$, wherein each instance of $R^{c1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or about two $R^{c1a}$ groups are joined to form a substituted or unsubstituted heterocyclic or substituted or unsubstituted heteroaryl ring.

In certain embodiments, the transcription inhibitor is of the formula:

225
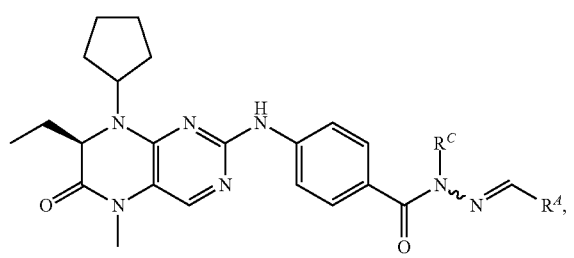
wherein $R^A$ is
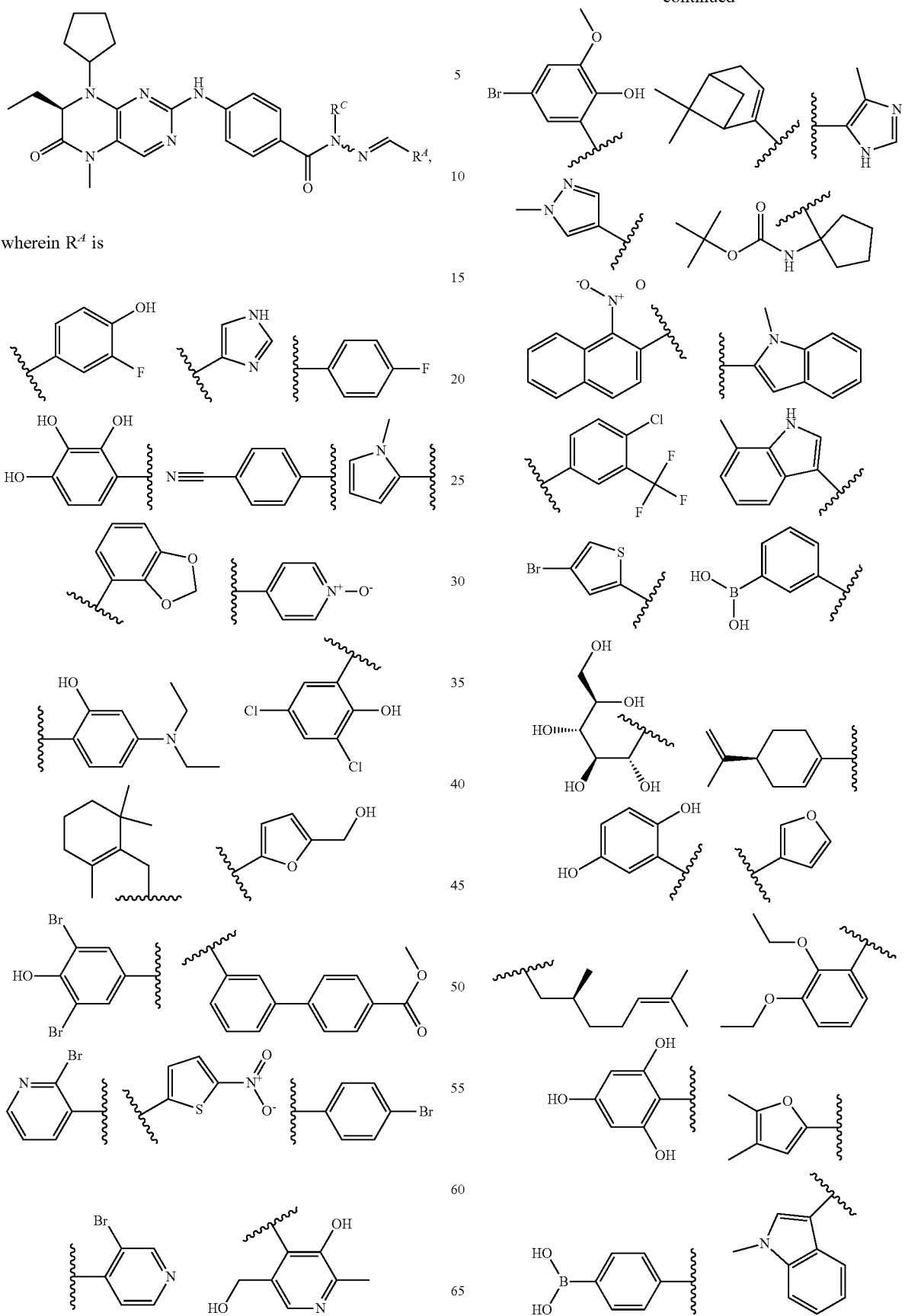

227
-continued
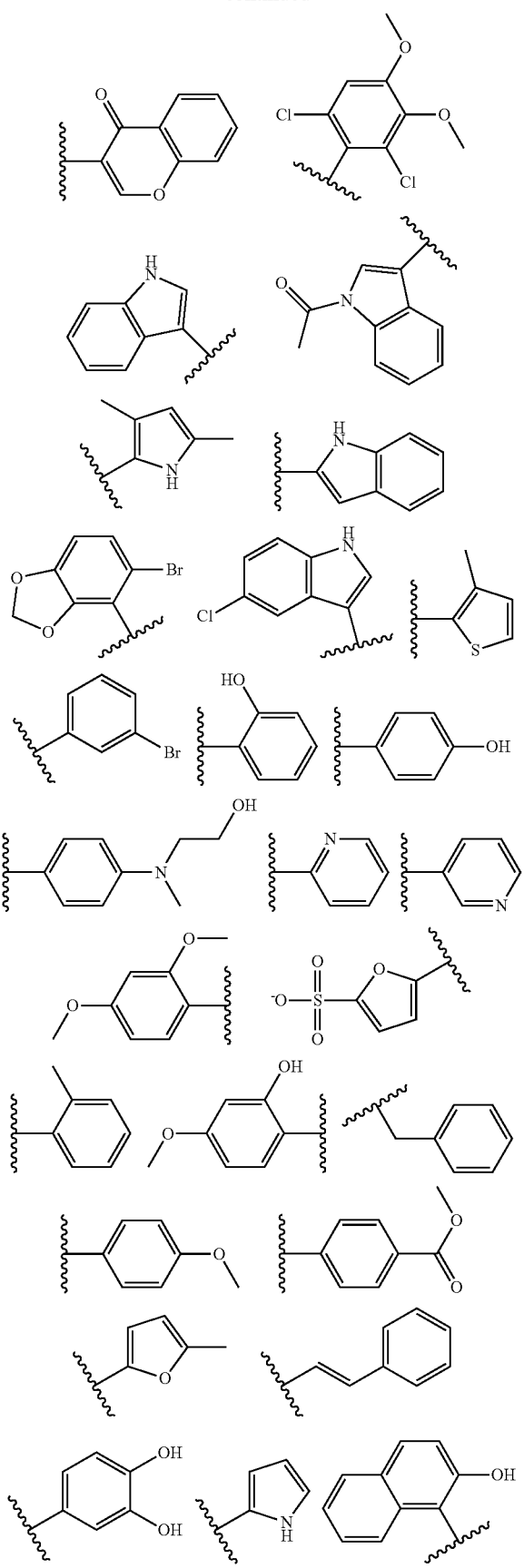
228
-continued
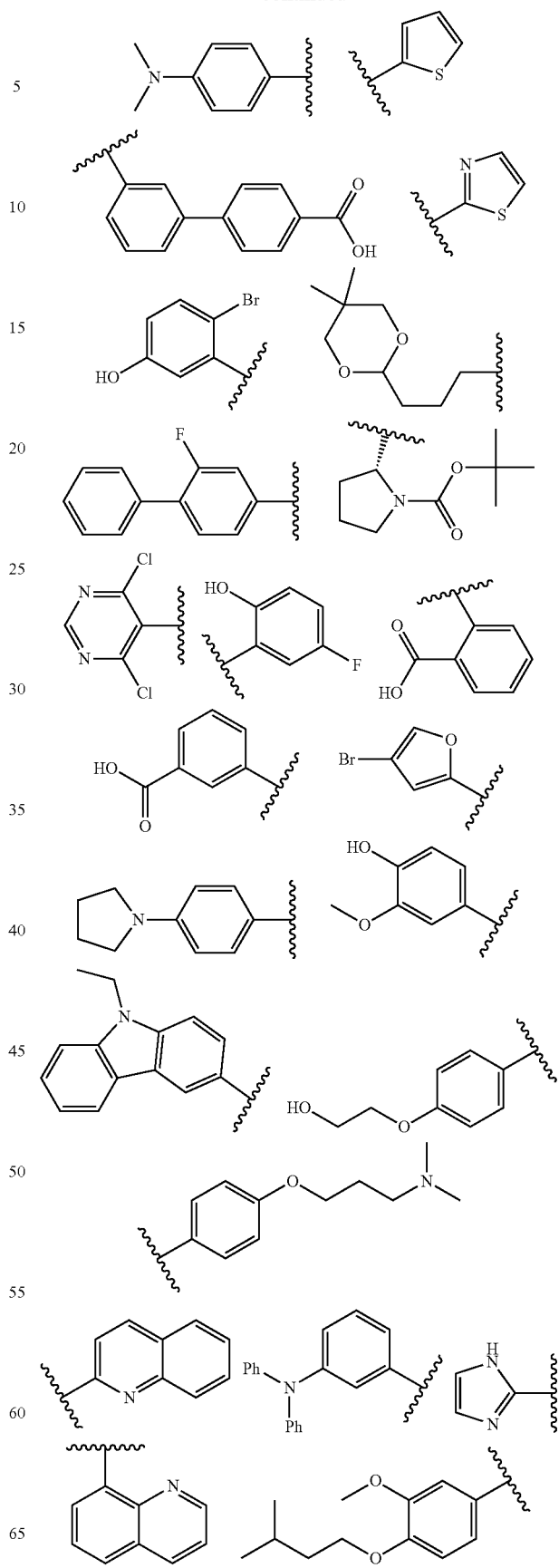

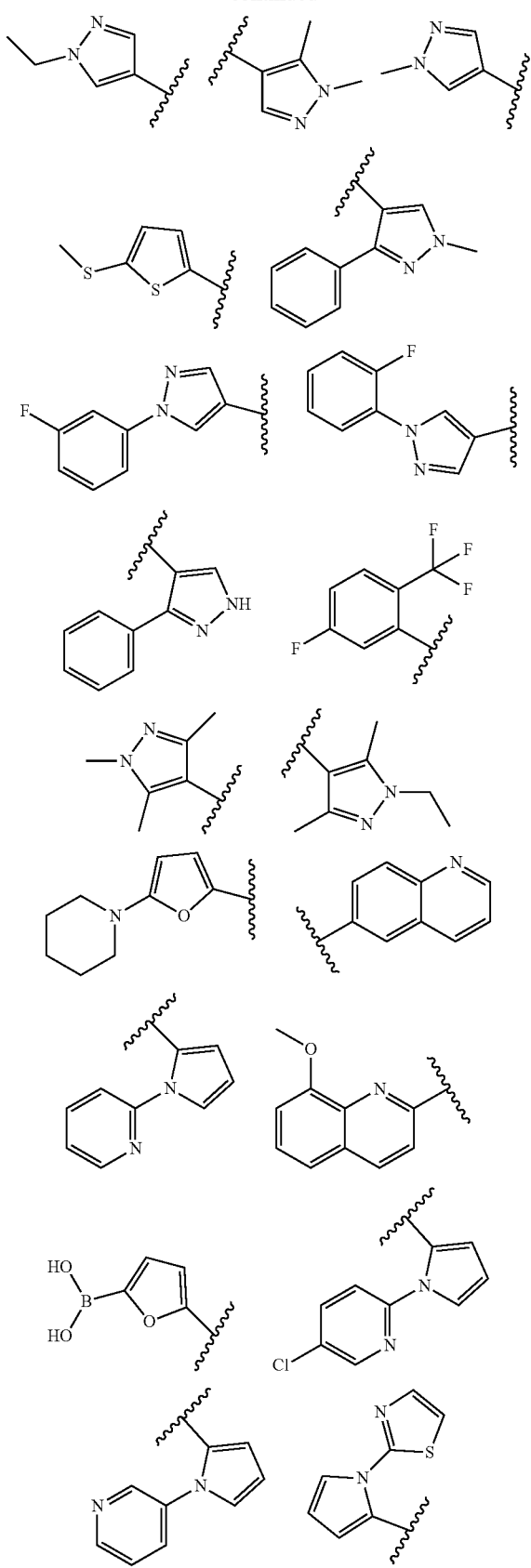
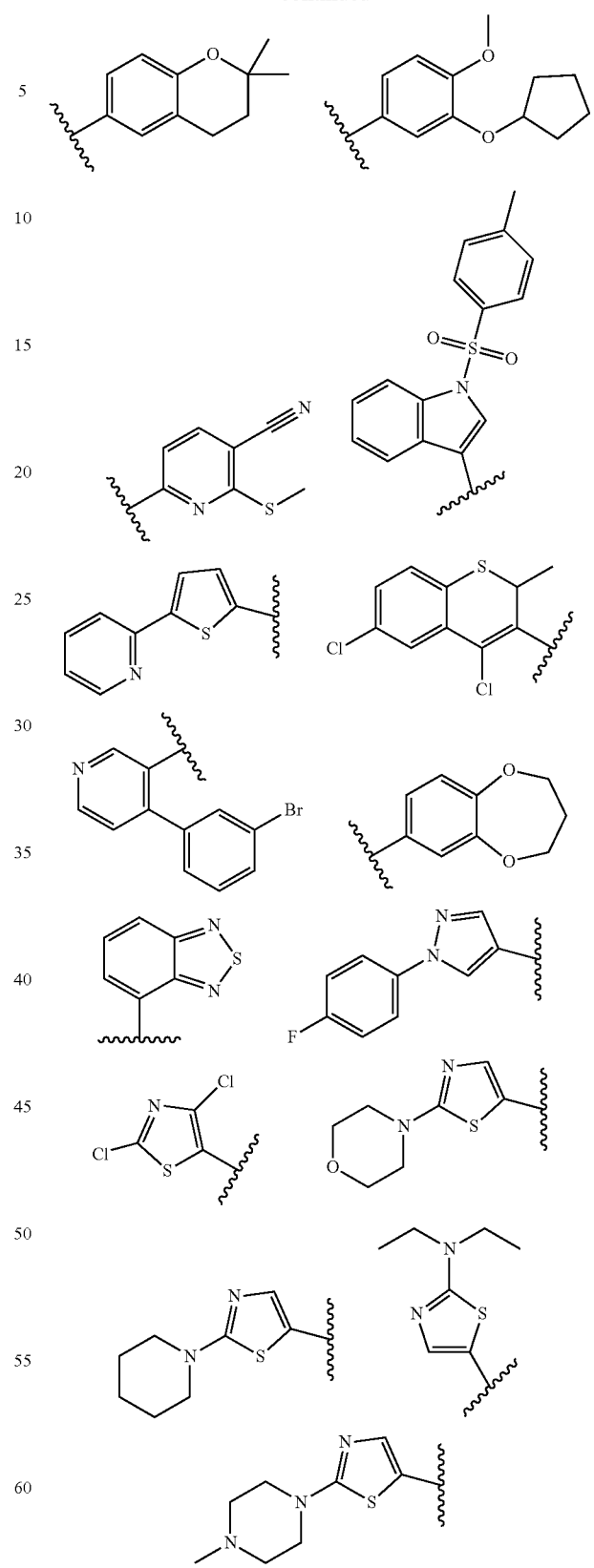

231
-continued
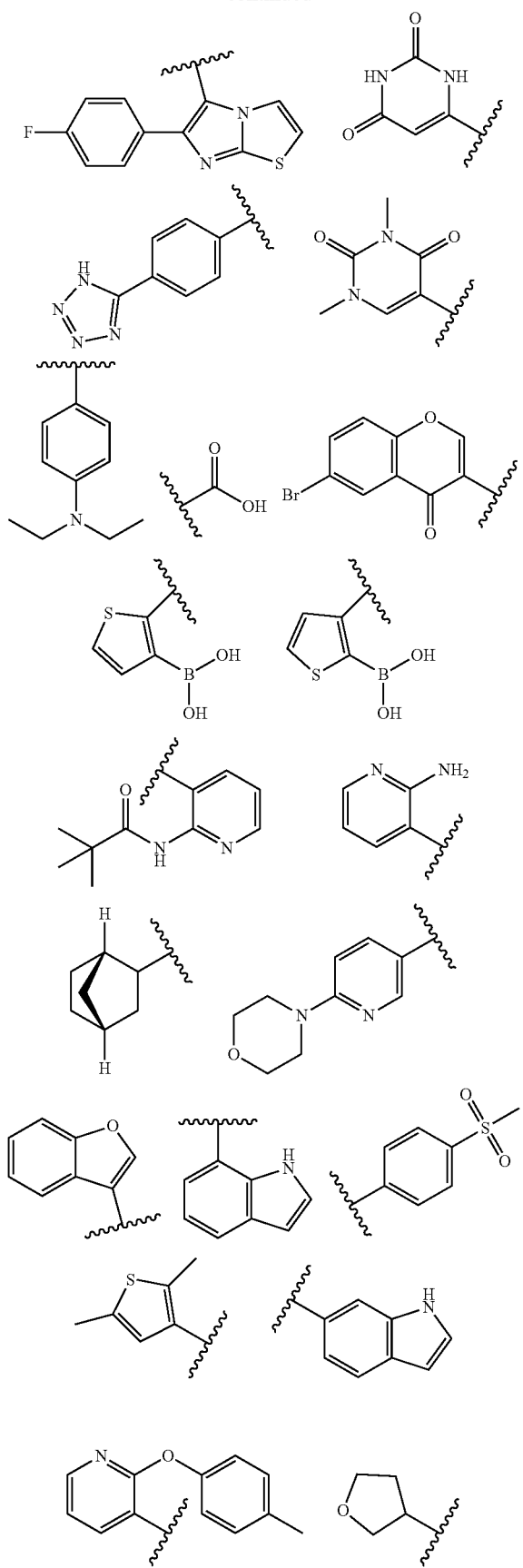
232
-continued
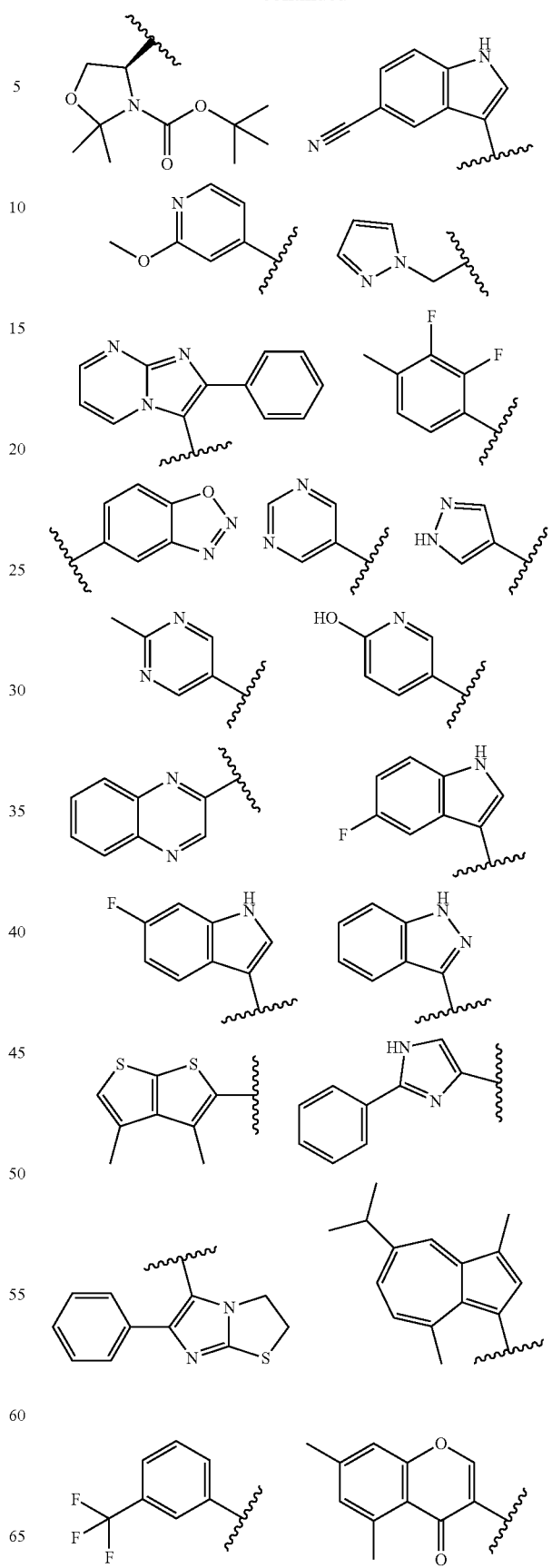

233
-continued
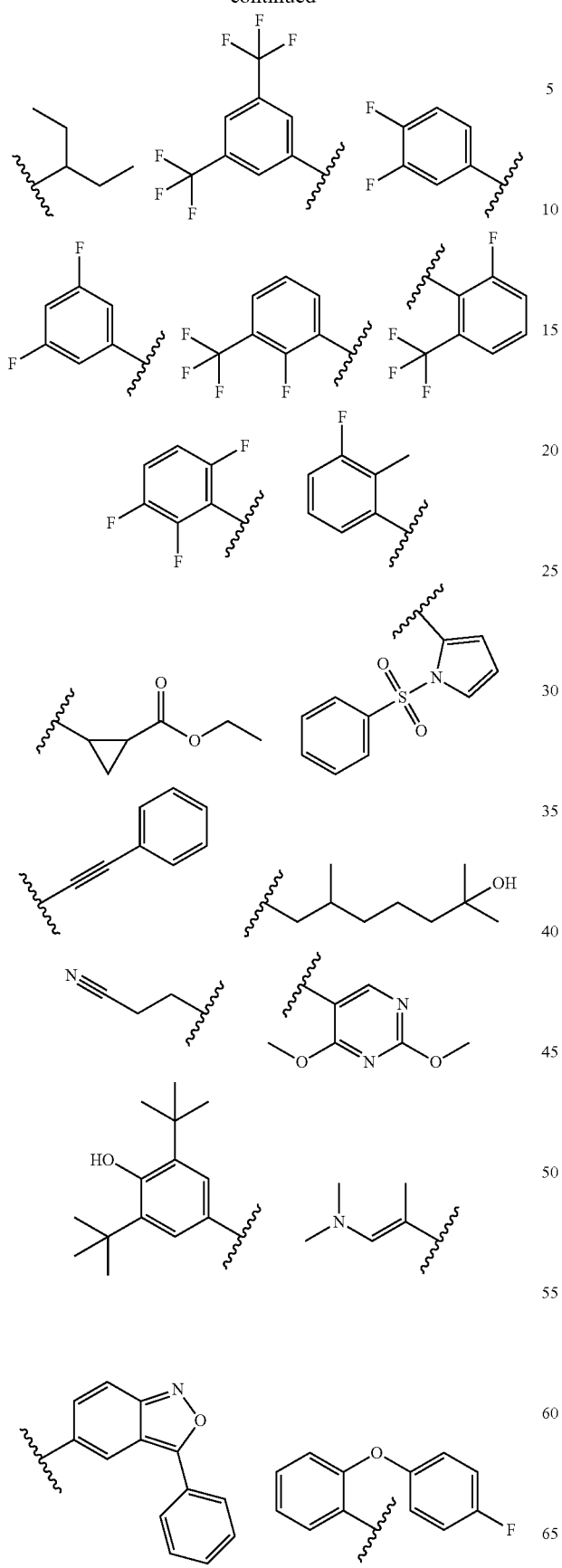
234
-continued
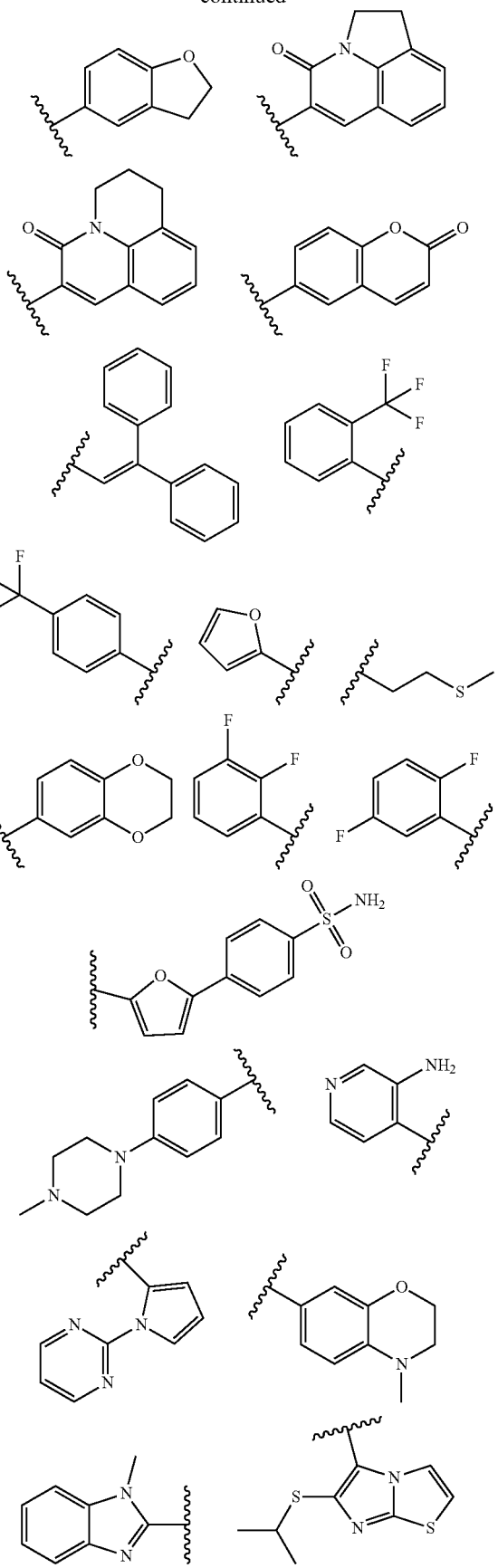

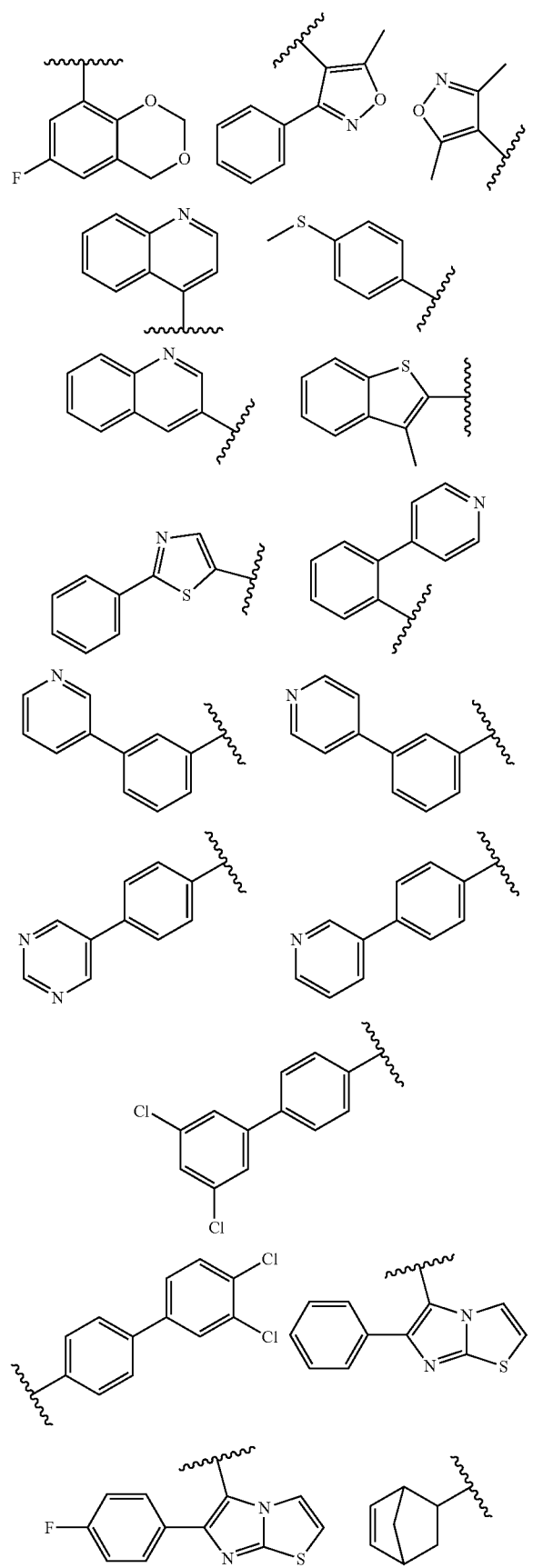
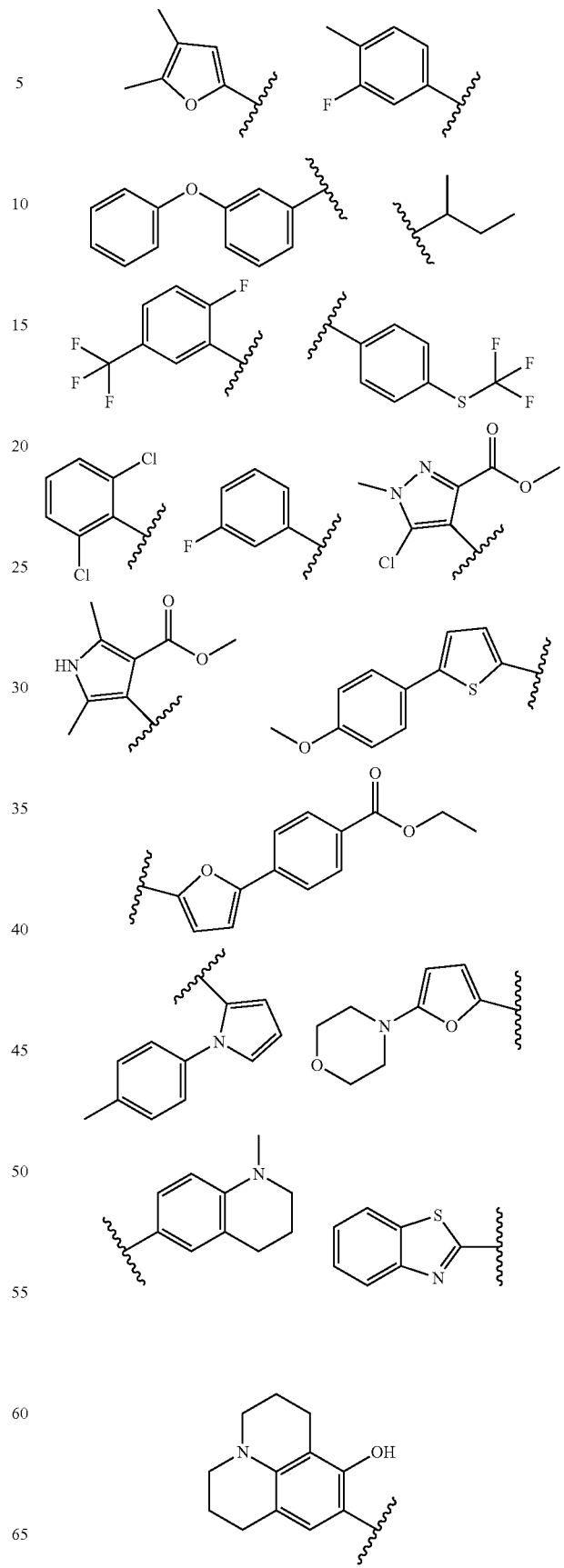

237
-continued
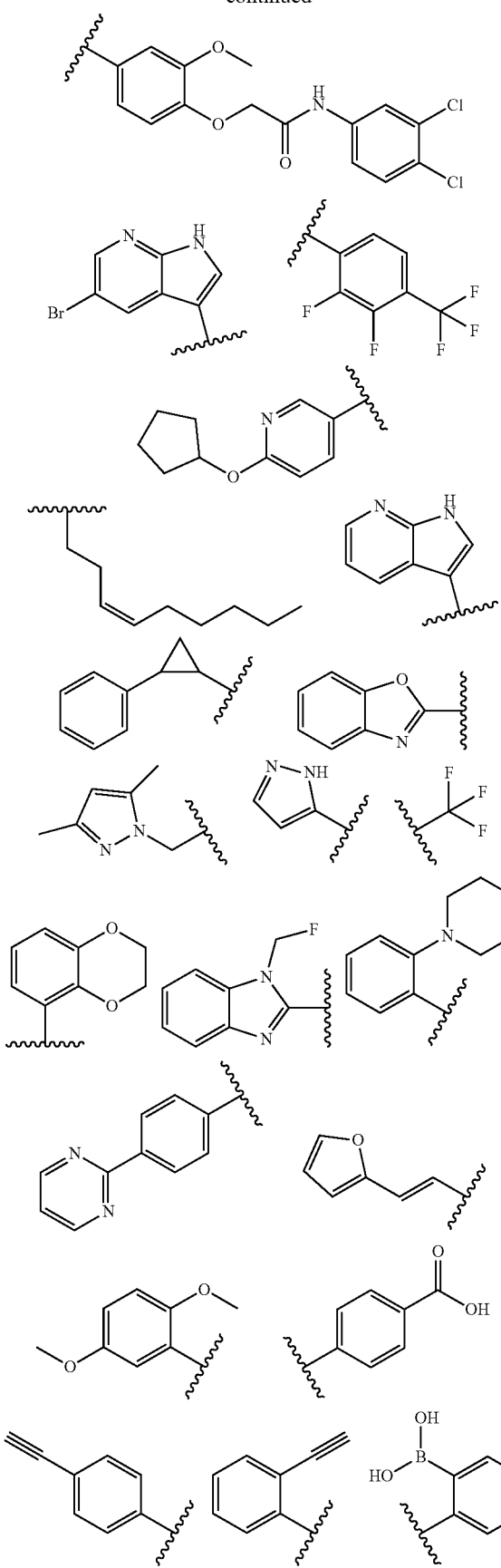
238
-continued
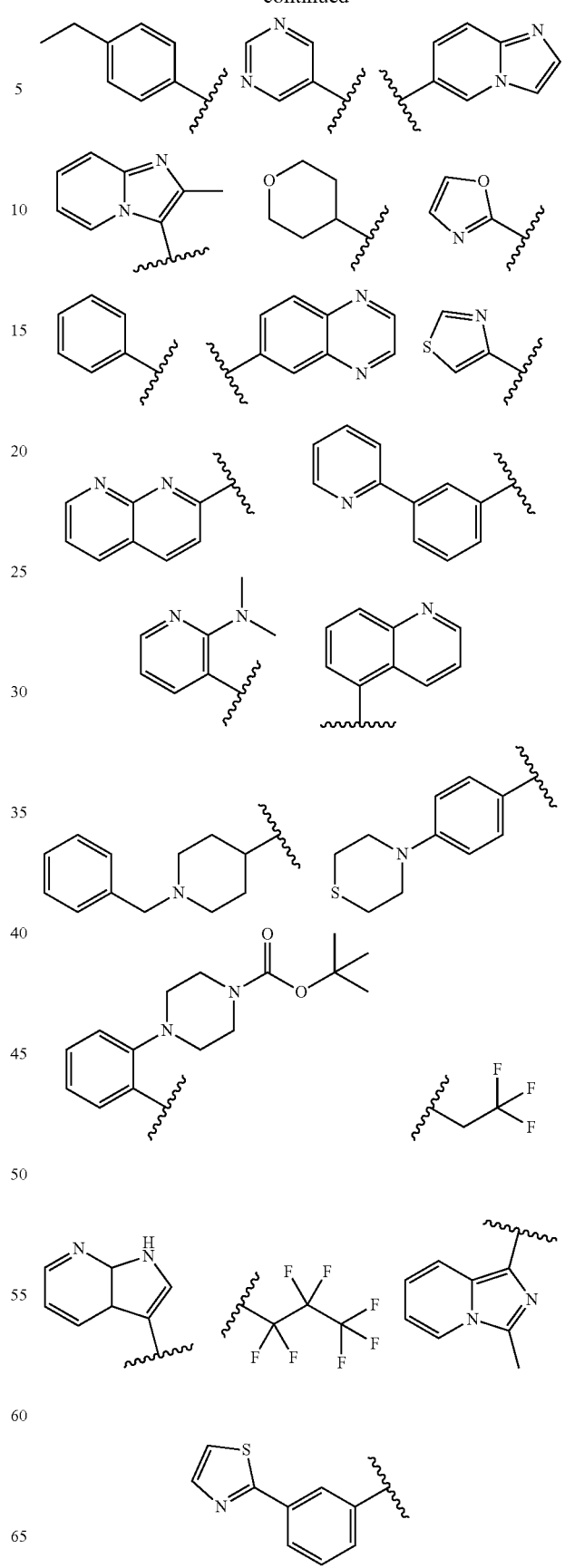

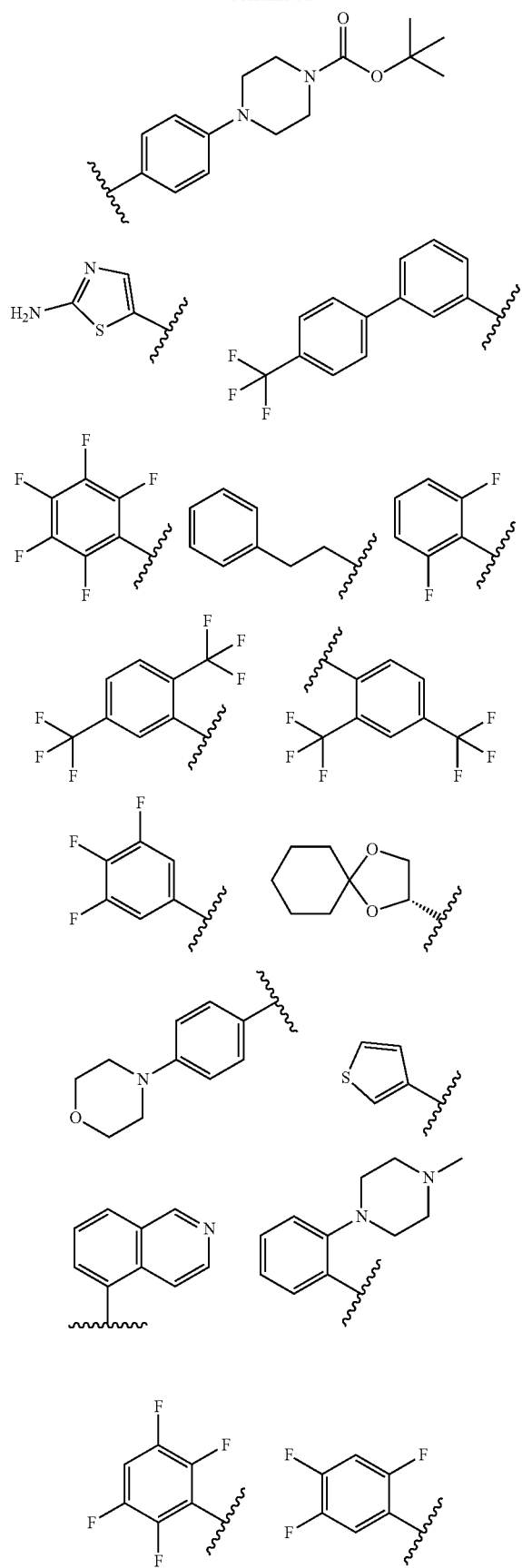
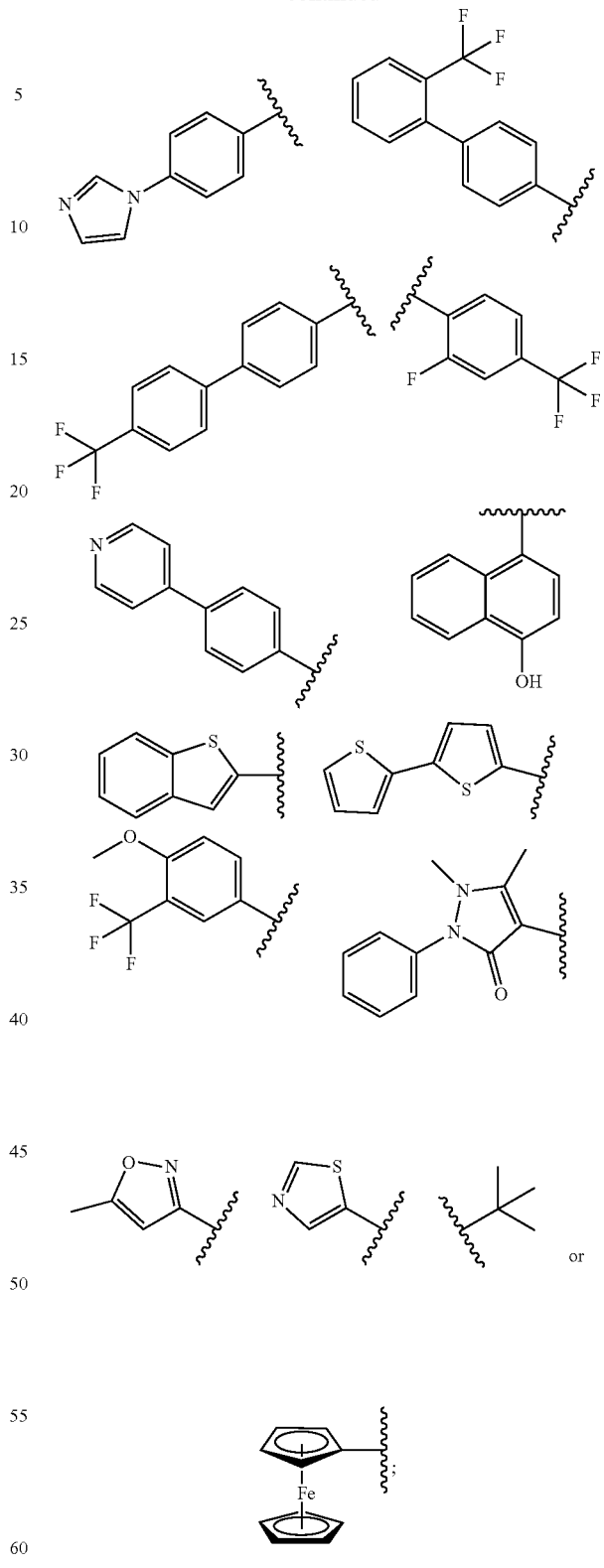
or a pharmaceutically acceptable salt, solvate, hydrate, polymorph, co-crystal, tautomer, stereoisomer, isotopically labeled derivative, or prodrug thereof.
In certain embodiments, the transcription inhibitor is of the formula:

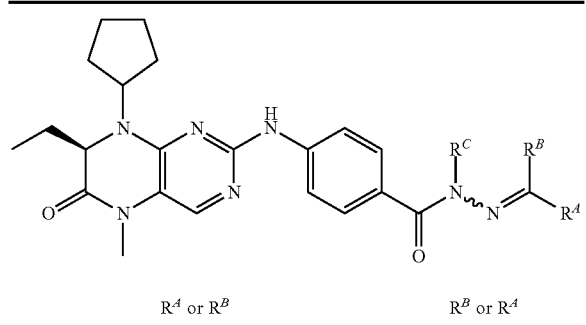
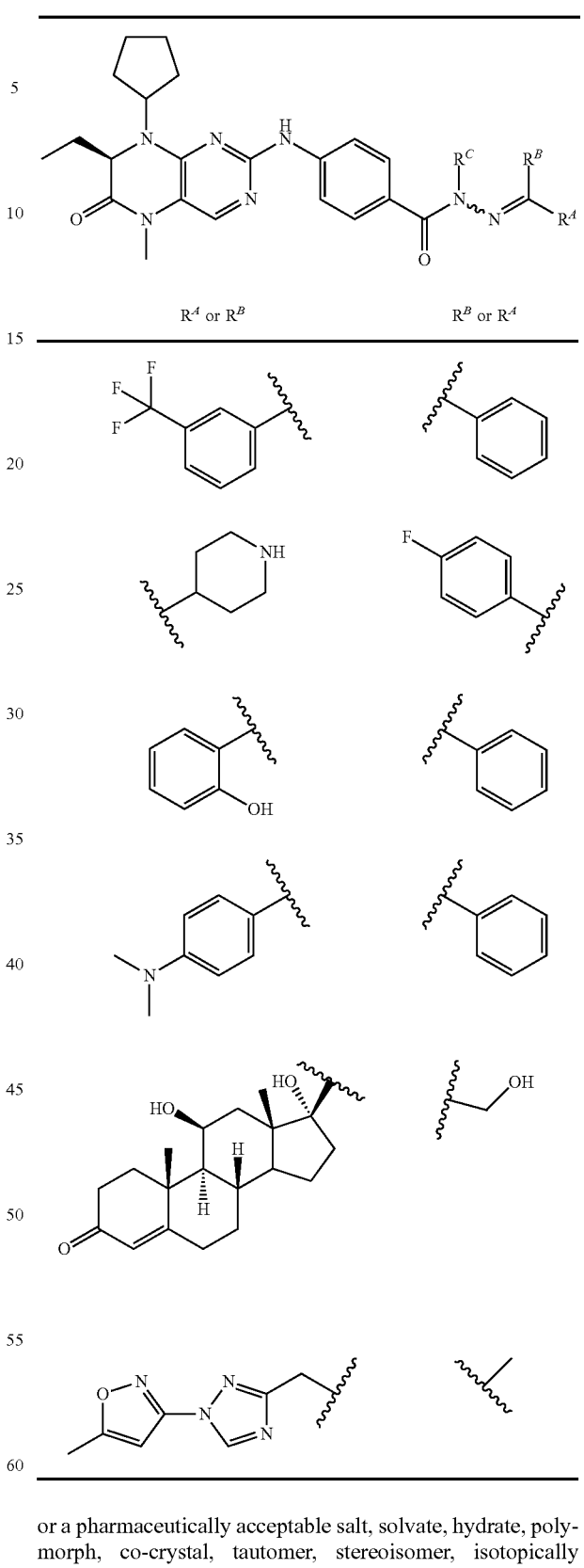
or a pharmaceutically acceptable salt, solvate, hydrate, polymorph, co-crystal, tautomer, stereoisomer, isotopically labeled derivative, or prodrug thereof.
In certain embodiments, the transcription inhibitor is of the formula:

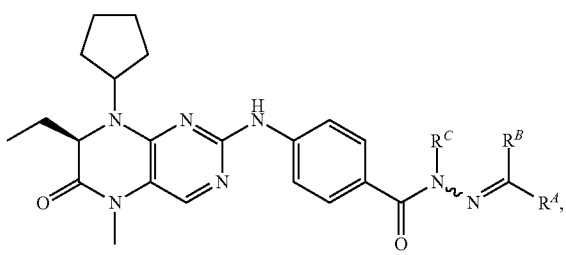

wherein

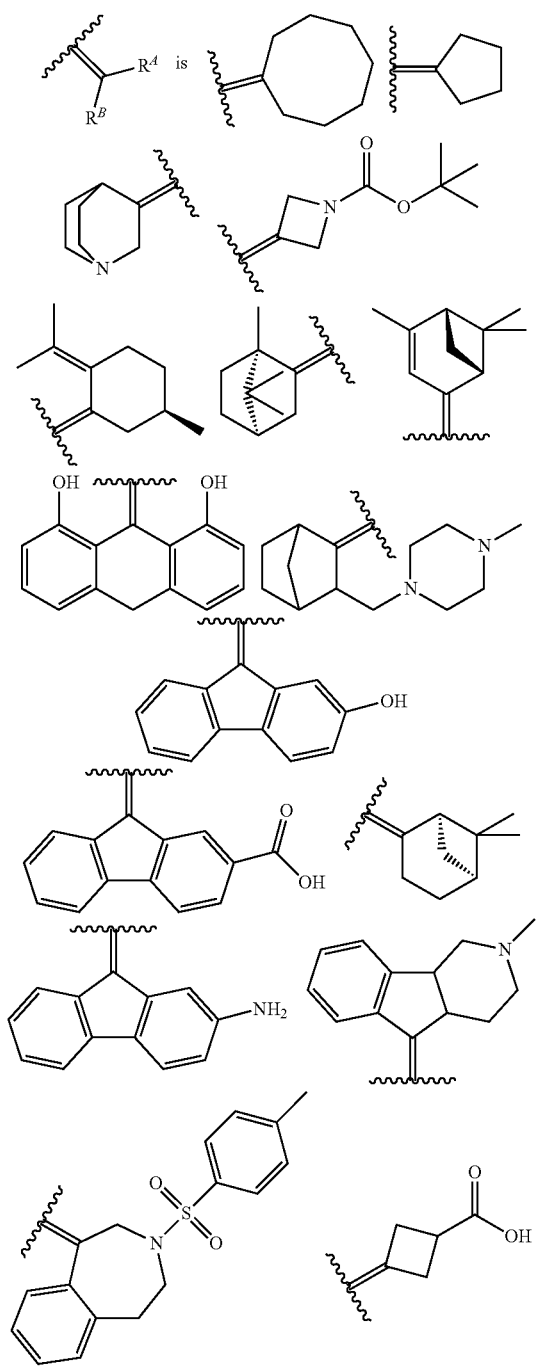

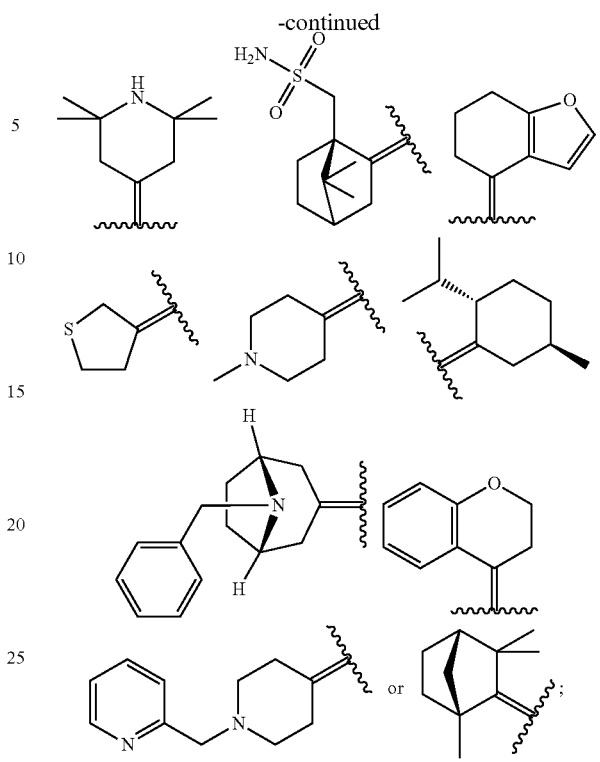

or a pharmaceutically acceptable salt, solvate, hydrate, polymorph, co-crystal, tautomer, stereoisomer, isotopically labeled derivative, or prodrug thereof.

In certain embodiments, the transcription inhibitor is a CDK inhibitor, such as dinaciclib, DCA, palbociclib, or a pharmaceutically acceptable salt, solvate, hydrate, polymorph, co-crystal, tautomer, stereoisomer, isotopically labeled derivative, or prodrug thereof. In certain embodiments, the transcription inhibitor is dinaciclib, or a pharmaceutically acceptable salt, solvate, hydrate, polymorph, co-crystal, tautomer, stereoisomer, isotopically labeled derivative, or prodrug thereof. In certain embodiments, the transcription inhibitor is DCA, or a pharmaceutically acceptable salt, solvate, hydrate, polymorph, co-crystal, tautomer, stereoisomer, isotopically labeled derivative, or prodrug thereof. In certain embodiments, the transcription inhibitor is palbociclib, or a pharmaceutically acceptable salt, solvate, hydrate, polymorph, co-crystal, tautomer, stereoisomer, isotopically labeled derivative, or prodrug thereof. In certain embodiments, the transcription inhibitor is a CDK inhibitor, such as AT7519M, P1446A-05, AG-024322, (R)-roscovitine, P276-00, SNS-032, LEE011, PD 0332991, GT28-01, NSC 638850, aminopurvalanol A, arcyriaflavin A, AZD 5438, (R)—CR8, (R)-DRF053, dihydrochloride, flavopiridol, 10Z-hymenialdisine, irdirubin-3'-oxime, kenpaullone, NSC 625987, NSC 663284, NSC 693868, NU 2058, NU 6140, olomoucine, PHA 767491, purvalanol A, purvalanol B, RO 3306, ryuvidine, senexin A, SNS 032, SU 9516, or a pharmaceutically acceptable salt, solvate, hydrate, polymorph, co-crystal, tautomer, stereoisomer, isotopically labeled derivative, or prodrug thereof. In certain embodiments, the transcription inhibitor is a CDK inhibitor, such as p16 protein, p15 protein, p18 protein, p19 protein, p21/WAF1 protein, p27 protein, or p57 protein. In certain embodiments, the transcription inhibitor is a bromodomain-containing protein inhibitor, such as I-BET 151, I-BET 762, OTX-015, TEN-010, CPI-203, CPI-0610, RVX-208, LY294002, BMS-986158, GSK525762, or a pharmaceutically acceptable salt, solvate, hydrate, polymorph, co-crystal, tautomer, stereoisomer, isotopically labeled derivative, or prodrug thereof.

A pharmaceutical composition described herein may include two or more different transcription inhibitors described herein.

A pharmaceutical composition described herein further includes a kinase inhibitor, wherein the transcription inhibitor and the kinase inhibitor are not the same. In certain embodiments, the kinase inhibitor is not a CDK inhibitor.

In certain embodiments, the kinase inhibitor is a receptor tyrosine kinase (RTK) inhibitor (e.g., afatinib, axitinib, cediranib, erlotinib, gefitinib, grandinin, lapatinib, lestaurtinib, neratinib, pazopanib, quizartinib, regorafenib, semaxanib, sorafenib, sunitinib, tivozanib, toceranib, vandetanib, or a pharmaceutically acceptable salt thereof).

In certain embodiments, the kinase inhibitor is a fibroblast growth factor receptor (FGFR) inhibitor. In certain embodiments, the FGFR inhibitor is BGJ398, or a pharmaceutically acceptable salt, solvate, hydrate, polymorph, co-crystal, tautomer, stereoisomer, isotopically labeled derivative, or prodrug thereof. In certain embodiments, the FGFR inhibitor is PD173074, pazopanib, masatinib, dovitinib, ponatinib, regorafenib, pirfenidone, nintedanib, brivanib, lenvatinib, cediranib, AZD4547, SU6668, BGJ398, ENMD2076, picropodophyllin, RG1507, dalotuzumab, figitumumab, cixutumumab, BIIB022, AMG479, FP1039, IMCA1, PRO001, R3Mab, MK-2461, SSR128129E, tyrphostin AG 1296, CH5183284, LY2874455, JNJ-42756493, lucitanib, orantinib, danusertib, or a pharmaceutically acceptable salt, solvate, hydrate, polymorph, co-crystal, tautomer, stereoisomer, isotopically labeled derivative, or prodrug thereof.

In certain embodiments, the kinase inhibitor is an epidermal growth factor receptor (EGFR) inhibitor. In certain embodiments, the EGFR inhibitor is erlotinib, lapatinib, AZD8931, WZ4002, or a pharmaceutically acceptable salt, solvate, hydrate, polymorph, co-crystal, tautomer, stereoisomer, isotopically labeled derivative, or prodrug thereof. In certain embodiments, the EGFR inhibitor is panitumumab, vandetanib, icotinib, afatinib, brigatinib, CO-1686, AZD-4769, poziotinib, CUDC-101, S-222611, AC-480, imgatuzumab, sapitinib, TAS-2913, theiiatinib, XGFR-2421, HM-61713B, epitinib, NRC-2694, MLBS-42, JRP-890, cetuximab, AL-6802, TAK-285, BGB-102, AEE788, gefitinib, DMS-3008, TX-2036, KI-6783, KI-6896, or a pharmaceutically acceptable salt, solvate, hydrate, polymorph, co-crystal, tautomer, stereoisomer, isotopically labeled derivative, or prodrug thereof.

In certain embodiments, the kinase inhibitor is a mitogen-activated protein kinase (MEK) inhibitor. In certain embodiments, the MEK inhibitor is trametinib, or a pharmaceutically acceptable salt, solvate, hydrate, polymorph, co-crystal, tautomer, stereoisomer, isotopically labeled derivative, or prodrug thereof. In certain embodiments, the MEK inhibitor is selumetinib, MEK162, PD325901, PD98059, XL518, CI-1040, antroquinonol, AS-1940477, AS-703988, BI-847325, E-6201, GDC-0623, GDC-0973, RG422, RO4987655, RO5126766, SL327, WX-554, U0126, BAY869766, vemurafenib, TAK-733, pimasertib, binimetinib, YopJ polypeptide, or a pharmaceutically acceptable salt, solvate, hydrate, polymorph, co-crystal, tautomer, stereoisomer, isotopically labeled derivative, or prodrug thereof.

In certain embodiments, the kinase inhibitor is vemurafenib, or a pharmaceutically acceptable salt, solvate, hydrate, polymorph, co-crystal, tautomer, stereoisomer, isotopically labeled derivative, or prodrug thereof. In certain embodiments, the MEK inhibitor is vemurafenib, or a pharmaceutically acceptable salt, solvate, hydrate, polymorph, co-crystal, tautomer, stereoisomer, isotopically labeled derivative, or prodrug thereof.

In certain embodiments, the kinase inhibitor is a phosphatidylinositol-4,5-bisphosphate 3-kinase (PI3K) inhibitor. In certain embodiments, the PI3K inhibitor is BKM120, BEZ235, or a pharmaceutically acceptable salt, solvate, hydrate, polymorph, co-crystal, tautomer, stereoisomer, isotopically labeled derivative, or prodrug thereof. In certain embodiments, the PI3K inhibitor is GDC0941, tozasertib, GSK1059615, PX866, LY294002, SF1126, XL147, XL765, BGT226, BYL719, BAY80946, BAY841236, GDC-0941, GDC-0032, GDC-0980, GDC-0941, PX-866, GSK2126458, CAL-101, INK1117, ZSTK474, PWT33597, AEZS-136, PKI-587, PF-4691502, PF-05212384, wortmannin, demethoxyviridin, pictilisib, idelalisib, IPI-145, or a pharmaceutically acceptable salt, solvate, hydrate, polymorph, co-crystal, tautomer, stereoisomer, isotopically labeled derivative, or prodrug thereof.

In certain embodiments, the kinase inhibitor is a receptor tyrosine-protein kinase erbB-2 (HER2) inhibitor. In certain embodiments, the HER2 inhibitor is lapatinib, or a pharmaceutically acceptable salt, solvate, hydrate, polymorph, co-crystal, tautomer, stereoisomer, isotopically labeled derivative, or prodrug thereof. In certain embodiments, the HER2 inhibitor is trastuzumab, ado-trastuzumab emtansine, pertuzumab, neratinib, BMS690514, BIBW-2992, BMS 599626, canertinib, XL647, ertumaxomab, gefitinib, erlotinib, pelitinib, CP-654577, CP-724714, HKI-272, neratinib, PKI166, AEE788, BMS-599626, HKI-727, HKI-357, BIBW 2992, AG1478, ARRY-380, ARRY-334543, BAY846, D69491, DXL-702, JNJ-26483327, or a pharmaceutically acceptable salt, solvate, hydrate, polymorph, co-crystal, tautomer, stereoisomer, isotopically labeled derivative, or prodrug thereof.

In certain embodiments, the kinase inhibitor is a mammalian target of rapamycin (mTOR) inhibitor. In certain embodiments, the mTOR inhibitor is Torin2, or a pharmaceutically acceptable salt, solvate, hydrate, polymorph, co-crystal, tautomer, stereoisomer, isotopically labeled derivative, or prodrug thereof. In certain embodiments, the mTOR inhibitor is GDC-0980, OSI-027, AZD8055, INK-128, sirolimus, temsirolimus, everolimus, ridaforolimus, AP23573, rapamycin, simapimod, AZD8055, PF04691502, deforolimus, intercellular protein FKBP38, wortmannin, SF1126, or a pharmaceutically acceptable salt, solvate, hydrate, polymorph, co-crystal, tautomer, stereoisomer, isotopically labeled derivative, or prodrug thereof.

In certain embodiments, the kinase inhibitor is an anaplastic lymphoma kinase (ALK) inhibitor (e.g., crizotinib, AP26113, LDK378, TAE-684, CEP-14083, CEP-14513, CEP-11988, WHI-P131, ceritinib, alectinib, staurosporine, CH5424802 (RO5424802), ASP3026, TSR-011, X-396, WHI-P154, or a pharmaceutically acceptable salt, solvate, hydrate, polymorph, co-crystal, tautomer, stereoisomer, isotopically labeled derivative, or prodrug thereof).

In certain embodiments, the kinase inhibitor is a platelet-derived growth factor receptor (PDGFR) inhibitor. In certain embodiments, the kinase inhibitor is a platelet-derived growth factor receptor alpha (PDGFRα) inhibitor. In certain embodiments, the kinase inhibitor is a platelet-derived growth factor receptor beta (PDGFRβ) inhibitor. In certain embodiments, the kinase inhibitor is imantinib, or a pharmaceutically acceptable salt, solvate, hydrate, polymorph, co-crystal, tautomer, stereoisomer, isotopically labeled derivative, or prodrug thereof. In certain embodiments, the kinase inhibitor is tyrphostin A23, tyrphostin AG 1295, AG-494, masitinib, AP-24534, motesanib, DMPQ, oxindole I, AG-370, tivozanib, PP121, sunitinib, pazopanib, PD-161570, dovitinib, sorafenib, ponatinib, axitinib, nintedanib, AZD2932, MK-2461, sennoside B, TSU-68, amuvantinib, KRN633, linifanib, telatinib, cernolanib, or tyrphostin 47, or a pharmaceutically acceptable salt, solvate, hydrate, polymorph, co-crystal, tautomer, stereoisomer, isotopically labeled derivative, or prodrug thereof.

In certain embodiments, the kinase inhibitor is an inhibitor of AAK1, ABL, ACK, ACTR2, ACTR2B, AKT1, AKT2, AKT3, AMPKa1, AMPKa2, ANKRD3, ANPa, ANPb, ARAF, ARAFps, ARG, AurA, AurAps1, AurAps2, AurB, AurBps1, AurC, AXL, BARK1, BARK2, BIKE, BLK, BMPR1A, BMPR1Aps1, BMPR1Aps2, BMPR1B, BMPR2, BMX, BRAF, BRAFps, BRK, BRSK1, BRSK2, BTK, BUB1, BUBR1, CaMK1a, CaMK1b, CaMK1d, CaMK1g, CaMK2a, CaMK2b, CaMK2d, CaMK2g, CaMK4, CaMKK1, CaMKK2, caMLCK, CASK, CCK4, CCRK, CDC2, CDC7, CDK10, CDK11, CDK2, CDK3, CDK4, CDK4ps, CDK5, CDK5ps, CDK6, CDK7, CDK7ps, CDK8, CDK8ps, CDK9, CDKL1, CDKL2, CDKL3, CDKL4, CDKL5, CGDps, CHED, CHK1, CHK2, CHK2ps1, CHK2ps2, CK1a, CK1a2, CK1aps1, CK1aps2, CK1aps3, CK1d, CK1e, CK1g1, CK1g2, CK1g2ps, CK1g3, CK2a1, CK2a1-rs, CK2a2, CLIK1, CLIKIL, CLK1, CLK2, CLK2ps, CLK3, CLK3ps, CLK4, COT, CRIK, CRK7, CSK, CTK, CYGD, CYGF, DAPK1, DAPK2, DAPK3, DCAMKL1, DCAMKL2, DCAMKL3, DDR1, DDR2, DLK, DMPK1, DMPK2, DRAK1, DRAK2, DYRK1A, DYRK1B, DYRK2, DYRK3, DYRK4, EphA1, EphA10, EphA2, EphA3, EphA4, EphA5, EphA6, EphA7, EphA8, EphB 1, EphB2, EphB3, EphB4, EphB6, Erk1, Erk2, Erk3, Erk3ps1, Erk3ps2, Erk3ps3, Erk3ps4, Erk4, Erk5, Erk7, FAK, FER, FERps, FES, FGR, FLT1, FLT1ps, FLT3, FLT4, FMS, FRK, Fused, FYN, GAK, GCK, GCN2, GCN22, GPRK4, GPRK5, GPRK6, GPRK6ps, GPRK7, GSK3A, GSK3B, Haspin, HCK, ErbB2, HER3/ErbB3, HER4/ErbB4, HH498, HIPK1, HIPK2, HIPK3, HIPK4, HPK1, HRI, HRIps, HSER, HUNK, ICK, IGF1R, IKKa, IKKb, IKKe, ILK, INSR, IRAK1, IRAK2, IRAK3, IRAK4, IRE1, IRE2, IRR, ITK, JAK1, JAK2, JAK3, JNK1, JNK2, JNK3, KDR, KHS1, KHS2, KIS, KIT, KSGCps, KSR1, KSR2, LATS1, LATS2, LCK, LIMK1, LIMK2, LIMK2ps, LKB1, LMR1, LMR2, LMR3, LOK, LRRK1, LRRK2, LTK, LYN, LZK, MAK, MAP3K1, MAP3K2, MAP3K3, MAP3K4, MAP3K5, MAP3K6, MAP3K7, MAP3K8, MAPKAPK2, MAPKAPK3, MAPKAPK5, MAPKAPKpsl, MARK1, MARK2, MARK3, MARK4, MARKps01, MARKps02, MARKps03, MARKps04, MARKps05, MARKps07, MARKps08, MARKps09, MARKps10, MARKps11, MARKps12, MARKps13, MARKps15, MARKps16, MARKps17, MARKps18, MARKps19, MARKps20, MARKps21, MARKps22, MARKps23, MARKps24, MARKps25, MARKps26, MARKps27, MARKps28, MARKps29, MARKps30, MAST1, MAST2, MAST3, MAST4, MASTL, MELK, MER, MET, MISR2, MLK1, MLK2, MLK3, MLK4, MLKL, MNK1, MNK1ps, MNK2, MOK, MOS, MPSK1, MPSK1ps, MRCKa, MRCKb, MRCKps, MSK1, MSK12, MSK2, MSK22, MSSK1, MST1, MST2, MST3, MST3ps, MST4, MUSK, MYO3A, MYO3B, MYT1, NDR1, NDR2, NEK1, NEK10, NEK11, NEK2, NEK2ps1, NEK2ps2, NEK2ps3, NEK3, NEK4, NEK4ps, NEK5, NEK6, NEK7, NEK8, NEK9, NIK, NIM1, NLK, NRBP1, NRBP2, NuaK1, NuaK2, Obscn, Obscn2, OSR1, p38a, p38b, p38d, p38g, p70S6K, p70S6Kb, p70S6Kps1, p70S6Kps2, PAK1, PAK2, PAK2ps, PAK3, PAK4, PAK5, PAK6, PASK, PBK, PCTAIRE1, PCTAIRE2, PCTAIRE3, PDGFRa, PDGFRb, PDK1, PEK, PFTAIRE1, PFTAIRE2, PHKg1, PHKg1ps1, PHKg1ps2, PHKg1ps3, PHKg2, PIK3R4, PIM1, PIM2, PIM3, PINK1, PITSLRE, PKACa, PKACb, PKACg, PKCa, PKCb, PKCd, PKCe, PKCg, PKCh, PKCi, PKCips, PKCt, PKCz, PKD1, PKD2, PKD3, PKG1, PKG2, PKN1, PKN2, PKN3, PKR, PLK1, PLK1ps1, PLK1ps2, PLK2, PLK3, PLK4, PRKX, PRKXps, PRKY, PRP4, PRP4ps, PRPK, PSKH1, PSKH1ps, PSKH2, PYK2, QIK, QSK, RAF1, RAFlps, RET, RHOK, RIPK1, RIPK2, RIPK3, RNAseL, ROCK1, ROCK2, RON, ROR1, ROR2, ROS, RSK1, RSK12, RSK2, RSK22, RSK3, RSK32, RSK4, RSK42, RSKL1, RSKL2, RYK, RYKps, SAKps, SBK, SCYL1, SCYL2, SCYL2ps, SCYL3, SGK, SgK050ps, SgK069, SgK071, SgK085, SgK110, SgK196, SGK2, SgK223, SgK269, SgK288, SGK3, SgK307, SgK384ps, SgK396, SgK424, SgK493, SgK494, SgK495, SgK496, SIK (e.g., SIK1, SIK2), skMLCK, SLK, Slob, smMLCK, SNRK, SPEG, SPEG2, SRC, SRM, SRPK1, SRPK2, SRPK2ps, SSTK, STK33, STK33ps, STLK3, STLK5, STLK6, STLK6ps1, STLK6-rs, SuRTK106, SYK, TAK1, TAO1, TAO2, TAO3, TBCK, TBK1, TEC, TESK1, TESK2, TGFbR1, TGFbR2, TIE1, TIE2, TLK1, TLK1ps, TLK2, TLK2ps1, TLK2ps2, TNK1, Trad, Trb1, Trb2, Trb3, Trio, TRKA, TRKB, TRKC, TSSK1, TSSK2, TSSK3, TSSK4, TSSKps1, TSSKps2, TTBK1, TTBK2, TTK, TTN, TXK, TYK2, TYK22, TYRO3, TYRO3ps, ULK1, ULK2, ULK3, ULK4, VACAMKL, VRK1, VRK2, VRK3, VRK3ps, Wee1, Wee1B, Wee1Bps, Wee1ps1, Wee1ps2, Wnk1, Wnk2, Wnk3, Wnk4, YANK1, YANK2, YANK3, YES, YESps, YSK1, ZAK, ZAP70, ZC 1/HGK, ZC2/TNIK, ZC3/MINK, ZC4/NRK, or a combination thereof.

A pharmaceutical composition described herein may include two or more different kinase inhibitors described herein.

In certain embodiments, the transcription inhibitor is a CDK inhibitor; and the kinase inhibitor is an RTK inhibitor. In certain embodiments, the transcription inhibitor is a CDK inhibitor; and the kinase inhibitor is an FGFR inhibitor (e.g., BGJ398), MEK inhibitor (e.g., trametinib), PI3K inhibitor (e.g., BKM120 or BEZ235), EGFR inhibitor (e.g., erlotinib, AZD8931, or WZ4002), HER2 inhibitor (e.g., lapatinib), mTOR inhibitor (e.g., Torin2), or ALK inhibitor (e.g., crizotinib). In certain embodiments, the transcription inhibitor is a bromodomain-containing protein inhibitor; and the kinase inhibitor is an RTK inhibitor. In certain embodiments, the transcription inhibitor is a bromodomain-containing protein inhibitor; and the kinase inhibitor is an FGFR inhibitor (e.g., BGJ398), MEK inhibitor (e.g., trametinib), PI3K inhibitor (e.g., BKM120 or BEZ235), EGFR inhibitor (e.g., erlotinib, AZD8931, or WZ4002), HER2 inhibitor (e.g., lapatinib), mTOR inhibitor (e.g., Torin2), or ALK inhibitor (e.g., crizotinib). In certain embodiments, the transcription inhibitor is THZ1, E9, YKL-01-116, THZ5-31-1, or a pharmaceutically acceptable salt, solvate, hydrate, polymorph, co-crystal, tautomer, stereoisomer, isotopically labeled derivative, or prodrug thereof; and the kinase inhibitor is an FGFR inhibitor (e.g., BGJ398), MEK inhibitor (e.g., trametinib), PI3K inhibitor (e.g., BKM120 or BEZ235), EGFR inhibitor (e.g., erlotinib, AZD8931, or WZ4002), HER2 inhibitor (e.g., lapatinib), mTOR inhibitor (e.g., Torin2), or ALK inhibitor (e.g., crizotinib). In certain embodiments, the transcription inhibitor is JQ1, or a pharmaceutically acceptable salt, solvate, hydrate, polymorph, co-crystal, tautomer, stereoisomer, isotopically labeled derivative, or prodrug thereof; and the kinase inhibitor is an FGFR inhibitor (e.g., BGJ398), MEK inhibitor (e.g., trametinib), PI3K inhibitor (e.g., BKM120 or BEZ235), EGFR inhibitor (e.g., erlotinib, AZD8931, or WZ4002), HER2 inhibitor (e.g., lapatinib), mTOR inhibitor (e.g., Torin2), or ALK inhibitor (e.g., crizotinib). In certain embodiments, the transcription inhibitor is dinaciclib, DCA, palbociclib, or a pharmaceutically acceptable salt, solvate, hydrate, polymorph, co-crystal, tautomer, stereoisomer, isotopically labeled derivative, or prodrug thereof; and the kinase inhibitor is an FGFR inhibitor (e.g., BGJ398), MEK inhibitor (e.g., trametinib), PI3K inhibitor (e.g., BKM120 or BEZ235), EGFR inhibitor (e.g., erlotinib, AZD8931, or WZ4002), HER2 inhibitor (e.g., lapatinib), mTOR inhibitor (e.g., Torin2), or ALK inhibitor (e.g., crizotinib).

In certain embodiments, the transcription inhibitor is a CDK inhibitor; and the kinase inhibitor is a PGDFR inhibitor (e.g., imatinib). In certain embodiments, the transcription inhibitor is a CDK inhibitor; and the kinase inhibitor is a MEK inhibitor (e.g., trametinib, vemurafenib).

In certain embodiments, the transcription inhibitor is a bromodomain-containing protein inhibitor; and the kinase inhibitor is an PDGFR inhibitor (e.g., imatinib). In certain embodiments, the transcription inhibitor is a bromodomain-containing protein inhibitor; and the kinase inhibitor is a MEK inhibitor (e.g., trametinib, vemurafenib). In certain embodiments, the transcription inhibitor is THZ1, E9, YKL-01-116, THZ5-31-1, or a pharmaceutically acceptable salt, solvate, hydrate, polymorph, co-crystal, tautomer, stereoisomer, isotopically labeled derivative, or prodrug thereof; and the kinase inhibitor is a PDGFR inhibitor (e.g., imatinib) or MEK inhibitor (e.g., trametinib, vemurafenib). In certain embodiments, the transcription inhibitor is JQ1, or a pharmaceutically acceptable salt, solvate, hydrate, polymorph, co-crystal, tautomer, stereoisomer, isotopically labeled derivative, or prodrug thereof; and the kinase inhibitor is a PDGFR inhibitor (e.g., imatinib) or MEK inhibitor (e.g., trametinib, vemurafenib). In certain embodiments, the transcription inhibitor is dinaciclib, DCA, palbociclib, or a pharmaceutically acceptable salt, solvate, hydrate, polymorph, co-crystal, tautomer, stereoisomer, isotopically labeled derivative, or prodrug thereof; and the kinase inhibitor is a PDGFR inhibitor (e.g., imatinib) or MEK inhibitor (e.g., trametinib, vemurafenib).

In certain embodiments, the transcription inhibitor is THZ1, or a pharmaceutically acceptable salt, solvate, hydrate, polymorph, co-crystal, tautomer, stereoisomer, isotopically labeled derivative, or prodrug thereof, and the kinase inhibitor is BGJ398, or a pharmaceutically acceptable salt, solvate, hydrate, polymorph, co-crystal, tautomer, stereoisomer, isotopically labeled derivative, or prodrug thereof.

In certain embodiments, the transcription inhibitor is THZ1, or a pharmaceutically acceptable salt, solvate, hydrate, polymorph, co-crystal, tautomer, stereoisomer, isotopically labeled derivative, or prodrug thereof, and the kinase inhibitor is erlotinib, or a pharmaceutically acceptable salt, solvate, hydrate, polymorph, co-crystal, tautomer, stereoisomer, isotopically labeled derivative, or prodrug thereof.

In certain embodiments, the transcription inhibitor is THZ1, or a pharmaceutically acceptable salt, solvate, hydrate, polymorph, co-crystal, tautomer, stereoisomer, isotopically labeled derivative, or prodrug thereof, and the kinase inhibitor is GSK1120212, or a pharmaceutically acceptable salt, solvate, hydrate, polymorph, co-crystal, tautomer, stereoisomer, isotopically labeled derivative, or prodrug thereof.

In certain embodiments, the transcription inhibitor is THZ1, or a pharmaceutically acceptable salt, solvate, hydrate, polymorph, co-crystal, tautomer, stereoisomer, isotopically labeled derivative, or prodrug thereof, and the kinase inhibitor is BEZ235, or a pharmaceutically acceptable salt, solvate, hydrate, polymorph, co-crystal, tautomer, stereoisomer, isotopically labeled derivative, or prodrug thereof.

In certain embodiments, the transcription inhibitor is THZ1, or a pharmaceutically acceptable salt, solvate, hydrate, polymorph, co-crystal, tautomer, stereoisomer, isotopically labeled derivative, or prodrug thereof, and the kinase inhibitor is WZ4002, or a pharmaceutically acceptable salt, solvate, hydrate, polymorph, co-crystal, tautomer, stereoisomer, isotopically labeled derivative, or prodrug thereof.

In certain embodiments, the transcription inhibitor is THZ1, or a pharmaceutically acceptable salt, solvate, hydrate, polymorph, co-crystal, tautomer, stereoisomer, isotopically labeled derivative, or prodrug thereof, and the kinase inhibitor is lapatinib, or a pharmaceutically acceptable salt, solvate, hydrate, polymorph, co-crystal, tautomer, stereoisomer, isotopically labeled derivative, or prodrug thereof.

In certain embodiments, the transcription inhibitor is THZ1, or a pharmaceutically acceptable salt, solvate, hydrate, polymorph, co-crystal, tautomer, stereoisomer, isotopically labeled derivative, or prodrug thereof, and the kinase inhibitor is imatinib, or a pharmaceutically acceptable salt, solvate, hydrate, polymorph, co-crystal, tautomer, stereoisomer, isotopically labeled derivative, or prodrug thereof.

In certain embodiments, the transcription inhibitor is THZ1, or a pharmaceutically acceptable salt, solvate, hydrate, polymorph, co-crystal, tautomer, stereoisomer, isotopically labeled derivative, or prodrug thereof, and the kinase inhibitor is trametinib, or a pharmaceutically acceptable salt, solvate, hydrate, polymorph, co-crystal, tautomer, stereoisomer, isotopically labeled derivative, or prodrug thereof.

In certain embodiments, the transcription inhibitor is THZ1, or a pharmaceutically acceptable salt, solvate, hydrate, polymorph, co-crystal, tautomer, stereoisomer, isotopically labeled derivative, or prodrug thereof, and the kinase inhibitor is vemurafenib, or a pharmaceutically acceptable salt, solvate, hydrate, polymorph, co-crystal, tautomer, stereoisomer, isotopically labeled derivative, or prodrug thereof.

In certain embodiments, the transcription inhibitor is THZ1, or a pharmaceutically acceptable salt, solvate, hydrate, polymorph, co-crystal, tautomer, stereoisomer, isotopically labeled derivative, or prodrug thereof, and the kinase inhibitor is crizotinib, or a pharmaceutically acceptable salt, solvate, hydrate, polymorph, co-crystal, tautomer, stereoisomer, isotopically labeled derivative, or prodrug thereof.

In certain embodiments, the transcription inhibitor is dinaciclib, or a pharmaceutically acceptable salt, solvate, hydrate, polymorph, co-crystal, tautomer, stereoisomer, isotopically labeled derivative, or prodrug thereof, and the kinase inhibitor is BGJ398, or a pharmaceutically acceptable salt, solvate, hydrate, polymorph, co-crystal, tautomer, stereoisomer, isotopically labeled derivative, or prodrug thereof.

In certain embodiments, the transcription inhibitor is E9, or a pharmaceutically acceptable salt, solvate, hydrate, polymorph, co-crystal, tautomer, stereoisomer, isotopically labeled derivative, or prodrug thereof, and the kinase inhibitor is BGJ398, or a pharmaceutically acceptable salt, solvate, hydrate, polymorph, co-crystal, tautomer, stereoisomer, isotopically labeled derivative, or prodrug thereof.

In certain embodiments, the transcription inhibitor is JQ1, or a pharmaceutically acceptable salt, solvate, hydrate, polymorph, co-crystal, tautomer, stereoisomer, isotopically labeled derivative, or prodrug thereof, and the kinase inhibitor is BGJ398, or a pharmaceutically acceptable salt, solvate, hydrate, polymorph, co-crystal, tautomer, stereoisomer, isotopically labeled derivative, or prodrug thereof.

In certain embodiments, the transcription inhibitor is DCA, or a pharmaceutically acceptable salt, solvate, hydrate, polymorph, co-crystal, tautomer, stereoisomer, isotopically labeled derivative, or prodrug thereof, and the kinase inhibitor is BGJ398, or a pharmaceutically acceptable salt, solvate, hydrate, polymorph, co-crystal, tautomer, stereoisomer, isotopically labeled derivative, or prodrug thereof.

In certain embodiments, the molar ratio of the transcription inhibitor to the kinase inhibitor is between 0.00001:1 and 100:1 (e.g., between 0.0001:1 and 100:1, between 0.001:1 and 100:1, between 0.01:1 and 100:1, between 0.1:1 and 100:1, between 1:1 and 100:1, between 0.0001:1 and 10:1, between 0.001:1 and 10:1, between 0.01:1 and 10:1, between 0.1:1 and 10:1, between 1:1 and 10:1, between 0.00001:1 and 1:1, between 0.0001:1 and 1:1, between 0.001:1 and 1:1, between 0.01:1 and 1:1, between 0.1:1 and 1:1, between 0.00001:1 and 0.1:1, between 0.0001:1 and 0.1:1, between 0.001:1 and 0.1:1, or between 0.01:1 and 0.1:1), inclusive. In certain embodiments, the molar ratio of the transcription inhibitor to the kinase inhibitor is between 0.001:1 and 1:1, inclusive.

In certain embodiments, a transcription inhibitor and a kinase inhibitor described herein are not the same. In certain embodiments, a kinase inhibitor that is or is to be combined with a transcription inhibitor is the same as the kinase inhibitor to which a proliferative disease or cell shows resistance.

In certain embodiments, the transcription inhibitor and the kinase inhibitor are provided in an effective amount in the pharmaceutical composition. In certain embodiments, the effective amount is a therapeutically effective amount. In certain embodiments, a therapeutically effective amount is an amount effective for treating a proliferative disease in a subject in need thereof. In certain embodiments, therapeutically effective amount is an amount effective for reducing, delaying, and/or preventing in a subject in need thereof the resistance of a proliferative disease to a transcription inhibitor or kinase inhibitor. In certain embodiments, the effective amount is a prophylactically effective amount (e.g., amount effective for preventing a proliferative disease in a subject in need thereof).

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile. In certain embodiments, the subject is with a proliferative disease. In certain embodiments, the subject is with a proliferative disease and has failed therapy of the proliferative disease with a kinase inhibitor alone. In certain embodiments, the subject is with a proliferative disease and has failed therapy of the proliferative disease with a transcription inhibitor alone.

In certain embodiments, the cell is in vitro. In certain embodiments, the cell is in vivo. In certain embodiments, the cell is a cell of a tissue or biological sample. In certain embodiments, the cell is a cancer cell.

In certain embodiments, the proliferative disease is resistant to the transcription inhibitor or kinase inhibitor. In certain embodiments, the proliferative disease is a cancer. In certain embodiments, the cancer is bladder cancer, optionally wherein: the transcription inhibitor is a CDK inhibitor (e.g., THZ1, or a pharmaceutically acceptable salt, solvate, hydrate, polymorph, co-crystal, tautomer, stereoisomer, isotopically labeled derivative, or prodrug thereof), and the kinase inhibitor is a FGFR inhibitor (e.g., BGJ398, or a pharmaceutically acceptable salt, solvate, hydrate, polymorph, co-crystal, tautomer, stereoisomer, isotopically labeled derivative, or prodrug thereof); the transcription inhibitor is a CDK inhibitor (e.g., THZ1, or a pharmaceutically acceptable salt, solvate, hydrate, polymorph, co-crystal, tautomer, stereoisomer, isotopically labeled derivative, or prodrug thereof), and the kinase inhibitor is an EGFR inhibitor (e.g., erlotinib, or a pharmaceutically acceptable salt, solvate, hydrate, polymorph, co-crystal, tautomer, stereoisomer, isotopically labeled derivative, or prodrug thereof); the transcription inhibitor is a CDK inhibitor (e.g., dinaciclib, or a pharmaceutically acceptable salt, solvate, hydrate, polymorph, co-crystal, tautomer, stereoisomer, isotopically labeled derivative, or prodrug thereof), and the kinase inhibitor is a FGFR inhibitor (e.g., BGJ398, or a pharmaceutically acceptable salt, solvate, hydrate, polymorph, co-crystal, tautomer, stereoisomer, isotopically labeled derivative, or prodrug thereof); the transcription inhibitor is a CDK inhibitor (e.g., E9, or a pharmaceutically acceptable salt, solvate, hydrate, polymorph, co-crystal, tautomer, stereoisomer, isotopically labeled derivative, or prodrug thereof), and the kinase inhibitor is a FGFR inhibitor (e.g., BGJ398, or a pharmaceutically acceptable salt, solvate, hydrate, polymorph, co-crystal, tautomer, stereoisomer, isotopically labeled derivative, or prodrug thereof); the transcription inhibitor is a bromodomain-containing protein inhibitor (e.g., JQ1, or a pharmaceutically acceptable salt, solvate, hydrate, polymorph, co-crystal, tautomer, stereoisomer, isotopically labeled derivative, or prodrug thereof), and the kinase inhibitor is a FGFR inhibitor (e.g., BGJ398, or a pharmaceutically acceptable salt, solvate, hydrate, polymorph, co-crystal, tautomer, stereoisomer, isotopically labeled derivative, or prodrug thereof); or the transcription inhibitor is a CDK inhibitor (e.g., DCA, or a pharmaceutically acceptable salt, solvate, hydrate, polymorph, co-crystal, tautomer, stereoisomer, isotopically labeled derivative, or prodrug thereof), and the kinase inhibitor is a FGFR inhibitor (e.g., BGJ398, or a pharmaceutically acceptable salt, solvate, hydrate, polymorph, co-crystal, tautomer, stereoisomer, isotopically labeled derivative, or prodrug thereof).

In certain embodiments, the cancer is lung cancer (e.g., bronchogenic carcinoma, small cell lung cancer (SCLC), non-small cell lung cancer (NSCLC), adenocarcinoma of the lung), optionally wherein: the transcription inhibitor is a CDK inhibitor (e.g., THZ1, or a pharmaceutically acceptable salt, solvate, hydrate, polymorph, co-crystal, tautomer, stereoisomer, isotopically labeled derivative, or prodrug thereof), and the kinase inhibitor is a FGFR inhibitor (e.g., BGJ398, or a pharmaceutically acceptable salt, solvate, hydrate, polymorph, co-crystal, tautomer, stereoisomer, isotopically labeled derivative, or prodrug thereof); the transcription inhibitor is a CDK inhibitor (e.g., THZ1, or a pharmaceutically acceptable salt, solvate, hydrate, polymorph, co-crystal, tautomer, stereoisomer, isotopically labeled derivative, or prodrug thereof), and the kinase inhibitor is an EGFR inhibitor (e.g., erlotinib, or a pharmaceutically acceptable salt, solvate, hydrate, polymorph, co-crystal, tautomer, stereoisomer, isotopically labeled derivative, or prodrug thereof); or the transcription inhibitor is a CDK inhibitor (e.g., THZ1, or a pharmaceutically acceptable salt, solvate, hydrate, polymorph, co-crystal, tautomer, stereoisomer, isotopically labeled derivative, or prodrug thereof), and the kinase inhibitor is a MEK inhibitor (e.g., GSK1120212, or a pharmaceutically acceptable salt, solvate, hydrate, polymorph, co-crystal, tautomer, stereoisomer, isotopically labeled derivative, or prodrug thereof).

In certain embodiments, the cancer is lung cancer (e.g., bronchogenic carcinoma, small cell lung cancer (SCLC), non-small cell lung cancer (NSCLC), adenocarcinoma of the lung), optionally wherein: the transcription inhibitor is a RTK inhibitor (e.g., THZ1, or a pharmaceutically acceptable salt, solvate, hydrate, polymorph, co-crystal, tautomer, stereoisomer, isotopically labeled derivative, or prodrug thereof), and the kinase inhibitor is a MET inhibitor (e.g., crizotinib, or a pharmaceutically acceptable salt, solvate, hydrate, polymorph, co-crystal, tautomer, stereoisomer, isotopically labeled derivative, or prodrug thereof). In certain embodiments, the cancer is lung cancer (e.g., bronchogenic carcinoma, small cell lung cancer (SCLC), non-small cell lung cancer (NSCLC), adenocarcinoma of the lung), optionally wherein: the transcription inhibitor is a RTK inhibitor (e.g., THZ1, or a pharmaceutically acceptable salt, solvate, hydrate, polymorph, co-crystal, tautomer, stereoisomer, isotopically labeled derivative, or prodrug thereof), and the kinase inhibitor is a PDGFR inhibitor (e.g., imatinib, or a pharmaceutically acceptable salt, solvate, hydrate, polymorph, co-crystal, tautomer, stereoisomer, isotopically labeled derivative, or prodrug thereof).

In certain embodiments, the cancer is esophageal cancer (e.g., adenocarcinoma of the esophagus, Barrett's adenocarcinoma).

In certain embodiments, the cancer is esophageal cancer (e.g., adenocarcinoma of the esophagus, Barrett's adenocarcinoma), optionally wherein: the transcription inhibitor is a CDK inhibitor (e.g., THZ1, or a pharmaceutically acceptable salt, solvate, hydrate, polymorph, co-crystal, tautomer, stereoisomer, isotopically labeled derivative, or prodrug thereof), and the kinase inhibitor is an RTK inhibitor (e.g., lapatinib).

In certain embodiments, the cancer is stomach cancer (e.g., gastric carcinoma), optionally wherein: the transcription inhibitor is a CDK inhibitor (e.g., THZ1, or a pharmaceutically acceptable salt, solvate, hydrate, polymorph, co-crystal, tautomer, stereoisomer, isotopically labeled derivative, or prodrug thereof), and the kinase inhibitor is an MEK inhibitor (e.g., trametinib, vemurafenib).

In certain embodiments, the cancer is skin cancer (e.g., squamous cell carcinoma (SCC) (e.g., oral SCC or tongue SCC), keratoacanthoma (KA), melanoma, basal cell carcinoma (BCC)), optionally wherein: the transcription inhibitor is a CDK inhibitor (e.g., THZ1, or a pharmaceutically acceptable salt, solvate, hydrate, polymorph, co-crystal, tautomer, stereoisomer, isotopically labeled derivative, or prodrug thereof), and the kinase inhibitor is a MEK inhibitor (e.g., GSK1120212, or a pharmaceutically acceptable salt, solvate, hydrate, polymorph, co-crystal, tautomer, stereoisomer, isotopically labeled derivative, or prodrug thereof); the transcription inhibitor is a CDK inhibitor (e.g., THZ1, or a pharmaceutically acceptable salt, solvate, hydrate, polymorph, co-crystal, tautomer, stereoisomer, isotopically labeled derivative, or prodrug thereof), and the kinase inhibitor is a PI3K inhibitor (e.g., BEZ235, or a pharmaceutically acceptable salt, solvate, hydrate, polymorph, co-crystal, tautomer, stereoisomer, isotopically labeled derivative, or prodrug thereof); the transcription inhibitor is a CDK inhibitor (e.g., THZ1, or a pharmaceutically acceptable salt, solvate, hydrate, polymorph, co-crystal, tautomer, stereoisomer, isotopically labeled derivative, or prodrug thereof), and the kinase inhibitor is an EGFR inhibitor (e.g., erlotinib, or a pharmaceutically acceptable salt, solvate, hydrate, polymorph, co-crystal, tautomer, stereoisomer, isotopically labeled derivative, or prodrug thereof); or the transcription inhibitor is a CDK inhibitor (e.g., THZ1, or a pharmaceutically acceptable salt, solvate, hydrate, polymorph, co-crystal, tautomer, stereoisomer, isotopically labeled derivative, or prodrug thereof), and the kinase inhibitor is a FGFR inhibitor (e.g., BGJ398, or a pharmaceutically acceptable salt, solvate, hydrate, polymorph, co-crystal, tautomer, stereoisomer, isotopically labeled derivative, or prodrug thereof).

In certain embodiments, the cancer is skin cancer (e.g., squamous cell carcinoma (SCC) (e.g., oral SCC or tongue SCC), keratoacanthoma (KA), melanoma, basal cell carcinoma (BCC)), optionally wherein: the transcription inhibitor is a CDK inhibitor (e.g., THZ1, or a pharmaceutically acceptable salt, solvate, hydrate, polymorph, co-crystal, tautomer, stereoisomer, isotopically labeled derivative, or prodrug thereof), and the kinase inhibitor is a MEK inhibitor (e.g., vemurafenib, or a pharmaceutically acceptable salt, solvate, hydrate, polymorph, co-crystal, tautomer, stereoisomer, isotopically labeled derivative, or prodrug thereof).

In certain embodiments, the cancer is a throat cancer (e.g., laryngeal cancer, pharyngeal cancer, nasopharyngeal cancer, oropharyngeal cancer). In certain embodiments, the cancer is associated with a mutation in an epidermal growth factor receptor (EGFR) gene, optionally wherein the transcription inhibitor is a CDK inhibitor (e.g., THZ1, or a pharmaceutically acceptable salt, solvate, hydrate, polymorph, co-crystal, tautomer, stereoisomer, isotopically labeled derivative, or prodrug thereof), and the kinase inhibitor is an EGFR inhibitor (e.g., WZ4002, or a pharmaceutically acceptable salt, solvate, hydrate, polymorph, co-crystal, tautomer, stereoisomer, isotopically labeled derivative, or prodrug thereof). In certain embodiments, the cancer is associated with a T790M mutation in an EGFR gene. In certain embodiments, the cancer is associated with an L858R mutation in an EGFR gene. In certain embodiments, the cancer is associated with an exon 19 deletion mutation in an EGFR gene. In certain embodiments, the cancer is associated with fibroblast growth factor-2 (FGF2)-fibroblast growth factor receptor (FGFR, e.g., FGFR1) activation through amplification, FGFR3-TACC3 fusion, EML4-ALK fusion, HER2 amplification, or KRAS codons 12, 13 or 61 mutations. In certain embodiments, the cancer is associated with a mutation (e.g., Q61R mutation) in neuroblastoma RAS viral oncogene homolog (NRAS). In certain embodiments, the cancer is associated with mesenchymal-epithelial transition (MET) amplification. In certain embodiments, the cancer is associated with feedback activation of signal transducer and activator of transcription 3 (STAT3), optionally wherein: the transcription inhibitor is a CDK inhibitor (e.g., THZ1, or a pharmaceutically acceptable salt, solvate, hydrate, polymorph, co-crystal, tautomer, stereoisomer, isotopically labeled derivative, or prodrug thereof), and the kinase inhibitor is an EGFR inhibitor (e.g., erlotinib, or a pharmaceutically acceptable salt, solvate, hydrate, polymorph, co-crystal, tautomer, stereoisomer, isotopically labeled derivative, or prodrug thereof); or the transcription inhibitor is a CDK inhibitor (e.g., THZ1, or a pharmaceutically acceptable salt, solvate, hydrate, polymorph, co-crystal, tautomer, stereoisomer, isotopically labeled derivative, or prodrug thereof), and the kinase inhibitor is a FGFR inhibitor (e.g., BGJ398, or a pharmaceutically acceptable salt, solvate, hydrate, polymorph, co-crystal, tautomer, stereoisomer, isotopically labeled derivative, or prodrug thereof). In certain embodiments, the proliferative disease is a benign neoplasm. In certain embodiments, the proliferative disease is associated with pathological angiogenesis. In certain embodiments, the proliferative disease is an inflammatory disease. In certain embodiments, the proliferative disease is an autoimmune disease.

Pharmaceutical compositions described herein can be prepared by any method known in the art of pharmacology. In general, such preparatory methods include bringing the transcription inhibitors and/or kinase inhibitors described herein (i.e., the "active ingredients") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a transcription inhibitor and/or kinase inhibitor described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the transcription inhibitor and/or kinase inhibitor in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The transcription inhibitors and/or kinase inhibitors provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The transcription inhibitors, kinase inhibitors, and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the transcription inhibitors, kinase inhibitors, and pharmaceutical compositions described herein are suitable for topical administration to the eye of a subject.

The exact amount (e.g., combined amount) of a transcription inhibitor and a kinase inhibitor required to achieve an effective amount will vary from subject to subject, depending, for example, on species, age, and general condition of a subject, severity of the side effects or disorder, identity of the particular transcription inhibitor, identity of the particular kinase inhibitor, mode of administration, and the like. An effective amount may be included in a single dose (e.g., single oral dose) or multiple doses (e.g., multiple oral doses). Each dose is a combination of the transcription inhibitor and the kinase inhibitor. For each dose, the transcription inhibitor and the kinase inhibitor may be independently administered at the same time or administered separately at different times in any order. In certain embodiments, the duration between an administration of the transcription inhibitor and an administration of the kinase inhibitor is about one hour, about two hours, about six hours, about twelve hours, about one day, about two days, about four days, or about one week, wherein the administration of the transcription inhibitor and the administration of the kinase inhibitor are consecutive administrations. The transcription inhibitor in each dose may be independently administered at the same time or administered separately at different times. The kinase inhibitor in each dose may also be independently administered at the same time or administered separately at different times. For example, in the following administrations: the kinase inhibitor in amount A, followed by the transcription inhibitor in amount B1, and followed by the transcription inhibitor in amount B2, the dose is the kinase inhibitor in amount A plus the transcription inhibitor in amount (B1+B2). In certain embodiments, when multiple doses (e.g., multiple combinations of the transcription inhibitor and the kinase inhibitor) are administered to a subject or applied to a biological sample, tissue, or cell, any about two doses of the multiple doses include different or substantially the same amounts of a transcription inhibitor and/or kinase inhibitor described herein. In certain embodiments, when multiple doses are administered to a subject or applied to a biological sample, tissue, or cell, the frequency of administering the multiple doses to the subject or applying the multiple doses to the biological sample, tissue, or cell is about three doses a day, about two doses a day, about one dose a day, about one dose every other day, about one dose every third day, about one dose every week, about one dose every about two weeks, about one dose every about three weeks, or about one dose every about four weeks. In certain embodiments, the frequency of administering the multiple doses to the subject or applying the multiple doses to the biological sample, tissue, or cell is about one dose per day. In certain embodiments, the frequency of administering the multiple doses to the subject or applying the multiple doses to the biological sample, tissue, or cell is about two doses per day. In certain embodiments, the frequency of administering the multiple doses to the subject or applying the multiple doses to the biological sample, tissue, or cell is about three doses per day. In certain embodiments, when multiple doses are administered to a subject or applied to a biological sample, tissue, or cell, the duration between the first dose and last dose of the multiple doses is about one day, about two days, about four days, about one week, about two weeks, about three weeks, about one month, about two months, about three months, about four months, about six months, about nine months, about one year, about two years, about three years, about four years, about five years, about seven years, about ten years, fifteen years, twenty years, or the lifetime of the subject, tissue, or cell. In certain embodiments, the duration between the first dose and last dose of the multiple doses is about three months, about six months, or about one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, as the combined weight of a transcription inhibitor and a kinase inhibitor described herein. In certain embodiments, a dose described herein includes independently between 1 mg and 3 mg, inclusive, as the combined weight of a transcription inhibitor and a kinase inhibitor described herein. In certain embodiments, a dose described herein includes independently between 3 mg and 10 mg, inclusive, as the combined weight of a transcription inhibitor and a kinase inhibitor described herein. In certain embodiments, a dose described herein includes independently between 10 mg and 30 mg, inclusive, as the combined weight of a transcription inhibitor and a kinase inhibitor described herein. In certain embodiments, a dose described herein includes independently between 30 mg and 100 mg, inclusive, as the combined weight of a transcription inhibitor and a kinase inhibitor described herein.

Doses and dose ranges described herein provide guidance for the administration of provided pharmaceutical compositions to an adult (e.g., an adult whose body weight is 70 kg). The amount to be administered to, for example, a child or an adolescent can be determined by a medical practitioner or person skilled in the art and can be lower or the same as that administered to an adult.

The combinations of the transcription inhibitor and the kinase inhibitor are expected to be synergistic in treating and/or preventing in the subject the proliferative diseases, in reducing, delaying, and/or preventing in the subject the resistance of proliferative diseases to a transcription inhibitor or kinase inhibitor, in inhibiting the proliferation of the cell, and/or reducing, delaying, and/or preventing the resistance of the cell to a transcription inhibitor or kinase inhibitor, compared to the transcription inhibitor alone or the kinase inhibitor alone. To result in the same effect in treating and/or preventing in the subject the proliferative diseases, in reducing, delaying, and/or preventing in the subject the resistance of proliferative diseases to a transcription inhibitor or kinase inhibitor, in inhibiting the proliferation of the cell, and/or reducing, delaying, and/or preventing the resistance of the cell to a transcription inhibitor or kinase inhibitor, a dose of a combination of the transcription inhibitor and the kinase inhibitor may be lower than (e.g., lower than 0.1%, lower than 1%, lower than 10%, or lower than 30%) a dose of the transcription inhibitor alone and lower than a dose of the kinase inhibitor alone. To result in the same effect in treating and/or preventing in the subject the proliferative diseases, in reducing, delaying, and/or preventing in the subject the resistance of proliferative diseases to a transcription inhibitor or kinase inhibitor, in inhibiting the proliferation of the cell, and/or reducing, delaying, and/or preventing the resistance of the cell to a transcription inhibitor or kinase inhibitor, the frequency of multiple doses of a combination of the transcription inhibitor and the kinase inhibitor may be lower than (e.g., lower than 0.1%, lower than 1%, lower than 10%, or lower than 30%) the frequency of multiple doses of the transcription inhibitor alone and lower than a dose of the kinase inhibitor alone. To result in the same effect in treating and/or preventing in the subject the proliferative diseases, in reducing, delaying, and/or preventing in the subject the resistance of proliferative diseases to a transcription inhibitor or kinase inhibitor, in inhibiting the proliferation of the cell, and/or reducing, delaying, and/or preventing the resistance of the cell to a transcription inhibitor or kinase inhibitor, the total amount of multiple doses of a combination of the transcription inhibitor and the kinase inhibitor may be lower than (e.g., lower than 0.1%, lower than 1%, lower than 10%, or lower than 30%) the total amount of multiple doses of the transcription inhibitor alone and lower than a dose of the kinase inhibitor alone.

A transcription inhibitor, kinase inhibitor, or composition, as described herein, can be administered in combination with one or more additional pharmaceutical agents (e.g., therapeutically and/or prophylactically active agents). The transcription inhibitor, kinase inhibitor, or composition can be administered in combination with additional pharmaceutical agents that improve their activity (e.g., activity (e.g., potency and/or efficacy) in treating a proliferative disease in a subject in need thereof, in preventing a proliferative disease in a subject in need thereof, in reducing, delaying, and/or preventing in a subject in need thereof the resistance of proliferative diseases to a transcription inhibitor or kinase inhibitor, in inhibiting the proliferation of a cell, in reducing, delaying, and/or preventing the resistance of a cell to a transcription inhibitor or kinase inhibitor), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including (1) a transcription inhibitor and a kinase inhibitor described herein, and (2) an additional pharmaceutical agent shows a synergistic effect, compared with a pharmaceutical composition including one of (1) and (2), but not both (1) and (2).

The transcription inhibitor, kinase inhibitor, or composition can be independently administered concurrently with, prior to, or subsequent to one or more additional pharmaceutical agents. In certain embodiments, the additional pharmaceutical agents and the transcription inhibitor are not the same, and the additional pharmaceutical agents and the kinase inhibitor are not the same. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, inflammatory disease, autoimmune disease, genetic disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the transcription inhibitor, kinase inhibitor, or composition described herein at the same time or administered separately at different times. The particular combination to employ in a regimen will take into account compatibility of the transcription inhibitor and/or kinase inhibitor described herein with the additional pharmaceutical agent(s), and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In certain embodiments, the additional pharmaceutical agent is an anti-proliferative agent (e.g., anti-cancer agent, cytotoxic agent). In certain embodiments, the additional pharmaceutical agent is abiraterone acetate (e.g., ZYTIGA), ABVD, ABVE, ABVE-PC, AC, AC-T, ADE, ado-trastuzumab emtansine (e.g., KADCYLA), afatinib dimaleate (e.g., GILOTRIF), aldesleukin (e.g., PROLEUKIN), alemtuzumab (e.g., CAMPATH), anastrozole (e.g., ARIMIDEX), arsenic trioxide (e.g., TRISENOX), asparaginase Erwinia chrysanthemi (e.g., ERWINAZE), axitinib (e.g., INLYTA), azacitidine (e.g., MYLOSAR, VIDAZA), BEACOPP, belinostat (e.g., BELEODAQ), bendamustine hydrochloride (e.g., TREANDA), BEP, bevacizumab (e.g., AVASTIN), bicalutamide (e.g., CASODEX), bleomycin (e.g., BLENOXANE), blinatumomab (e.g., BLINCYTO), bortezomib (e.g., VELCADE), bosutinib (e.g., BOSULIF), brentuximab vedotin (e.g., ADCETRIS), busulfan (e.g., BUSULFEX, MYLERAN), cabazitaxel (e.g., JEVTANA), cabozantinib-s-malate (e.g., COMETRIQ), CAF, capecitabine (e.g., XELODA), CAPOX, carboplatin (e.g., PARAPLAT, PARAPLATIN), carboplatin-taxol, carfilzomib (e.g., KYPROLIS), carmustine (e.g., BECENUM, BICNU, CARMUBRIS), carmustine implant (e.g., GLIADEL WAFER, GLIADEL), ceritinib (e.g., ZYKADIA), cetuximab (e.g., ERBITUX), chlorambucil (e.g., AMBOCHLORIN, AMBOCLORIN, LEUKERAN, LINFOLIZIN), chlorambucil-prednisone, CHOP, cisplatin (e.g., PLATINOL, PLATINOL-AQ), clofarabine (e.g., CLOFAREX, CLOLAR), CMF, COPP, COPP-ABV, crizotinib (e.g., XALKORI), CVP, cyclophosphamide (e.g., CLAFEN, CYTOXAN, NEOSAR), cytarabine (e.g., CYTOSAR-U, TARABINE PFS), dabrafenib (e.g., TAFINLAR), dacarbazine (e.g., DTIC-DOME), dactinomycin (e.g., COSMEGEN), dasatinib (e.g., SPRYCEL), daunorubicin hydrochloride (e.g., CERUBIDINE), decitabine (e.g., DACOGEN), degarelix, denileukin diftitox (e.g., ONTAK), denosumab (e.g., PROLIA, XGEVA), Dinutuximab (e.g., UNITUXIN), docetaxel (e.g., TAXOTERE), doxorubicin hydrochloride (e.g., ADRIAMYCIN PFS, ADRIAMYCIN RDF), doxorubicin hydrochloride liposome (e.g., DOXIL, DOX-SL, EVACET, LIPODOX), enzalutamide (e.g., XTANDI), epirubicin hydrochloride (e.g., ELLENCE), EPOCH, erlotinib hydrochloride (e.g., TARCEVA), etoposide (e.g., TOPOSAR, VEPESID), etoposide phosphate (e.g., ETOPOPHOS), everolimus (e.g., AFINITOR DISPERZ, AFINITOR), exemestane (e.g., AROMASIN), FEC, fludarabine phosphate (e.g., FLUDARA), fluorouracil (e.g., ADRUCIL, EFUDEX, FLUOROPLEX), FOLFIRI, FOLFIRI-BEVACIZUMAB, FOLFIRI-CETUXIMAB, FOLFIRINOX, FOLFOX, FU-LV, fulvestrant (e.g., FASLODEX), gefitinib (e.g., IRESSA), gemcitabine hydrochloride (e.g., GEMZAR), gemcitabine-cisplatin, gemcitabine-oxaliplatin, goserelin acetate (e.g., ZOLADEX), Hyper-CVAD, ibritumomab tiuxetan (e.g., ZEVALIN), ibrutinib (e.g., IMBRUVICA), ICE, idelalisib (e.g., ZYDELIG), ifosfamide (e.g., CYFOS, IFEX, IFOSFAMIDUM), imatinib mesylate (e.g., GLEEVEC), imiquimod (e.g., ALDARA), ipilimumab (e.g., YERVOY), irinotecan hydrochloride (e.g., CAMPTOSAR), ixabepilone (e.g., IXEMPRA), lanreotide acetate (e.g., SOMATULINE DEPOT), lapatinib ditosylate (e.g., TYKERB), lenalidomide (e.g., REVLIMID), lenvatinib (e.g., LENVIMA), letrozole (e.g., FEMARA), leucovorin calcium (e.g., WELLCOVORIN), leuprolide acetate (e.g., LUPRON DEPOT, LUPRON DEPOT-3 MONTH, LUPRON DEPOT-4 MONTH, LUPRON DEPOT-PED, LUPRON, VIADUR), liposomal cytarabine (e.g., DEPOCYT), lomustine (e.g., CEENU), mechlorethamine hydrochloride (e.g., MUSTARGEN), megestrol acetate (e.g., MEGACE), mercaptopurine (e.g., PURINETHOL, PURIXAN), methotrexate (e.g., ABITREXATE, FOLEX PFS, FOLEX, METHOTREXATE LPF, MEXATE, MEXATE-AQ), mitomycin c (e.g., MITOZYTREX, MUTAMYCIN), mitoxantrone hydrochloride, MOPP, nelarabine (e.g., ARRANON), nilotinib (e.g., TASIGNA), nivolumab (e.g., OPDIVO), obinutuzumab (e.g., GAZYVA), OEPA, ofatumumab (e.g., ARZERRA), OFF, olaparib (e.g., LYNPARZA), omacetaxine mepesuccinate (e.g., SYNRIBO), OPPA, oxaliplatin (e.g., ELOXATIN), paclitaxel (e.g., TAXOL), paclitaxel albumin-stabilized nanoparticle formulation (e.g., ABRAXANE), PAD, palbociclib (e.g., IBRANCE), pamidronate disodium (e.g., AREDIA), panitumumab (e.g., VECTIBIX), panobinostat (e.g., FARYDAK), pazopanib hydrochloride (e.g., VOTRIENT), pegaspargase (e.g., ONCASPAR), peginterferon alfa-2b (e.g., PEG-INTRON), peginterferon alfa-2b (e.g., SYLATRON), pembrolizumab (e.g., KEYTRUDA), pemetrexed disodium (e.g., ALIMTA), pertuzumab (e.g., PERJETA), plerixafor (e.g., MOZOBIL), pomalidomide (e.g., POMALYST), ponatinib hydrochloride (e.g., ICLUSIG), pralatrexate (e.g., FOLOTYN), prednisone, procarbazine hydrochloride (e.g., MATULANE), radium 223 dichloride (e.g., XOFIGO), raloxifene hydrochloride (e.g., EVISTA, KEOXIFENE), ramucirumab (e.g., CYRAMZA), R-CHOP, recombinant HPV bivalent vaccine (e.g., CERVARIX), recombinant human papillomavirus (e.g., HPV) nonavalent vaccine (e.g., GARDASIL 9), recombinant human papillomavirus (e.g., HPV) quadrivalent vaccine (e.g., GARDASIL), recombinant interferon alfa-2b (e.g., INTRON A), regorafenib (e.g., STIVARGA), rituximab (e.g., RITUXAN), romidepsin (e.g., ISTODAX), ruxolitinib phosphate (e.g., JAKAFI), siltuximab (e.g., SYLVANT), sipuleucel-t (e.g., PROVENGE), sorafenib tosylate (e.g., NEXAVAR), STANFORD V, sunitinib malate (e.g., SUTENT), TAC, tamoxifen citrate (e.g., NOLVADEX, NOVALDEX), temozolomide (e.g., METHAZOLASTONE, TEMODAR), temsirolimus (e.g., TORISEL), thalidomide (e.g., SYNOVIR, THALOMID), thiotepa, topotecan hydrochloride (e.g., HYCAMTIN), toremifene (e.g., FARESTON), tositumomab and iodine I 131 tositumomab (e.g., BEXXAR), TPF, trametinib (e.g., MEKINIST), trastuzumab (e.g., HERCEPTIN), VAMP, vandetanib (e.g., CAPRELSA), VEIP, vemurafenib (e.g., ZELBORAF), vinblastine sulfate (e.g., VELBAN, VELSAR), vincristine sulfate (e.g., VINCASAR PFS), vincristine sulfate liposome (e.g., MARQIBO), vinorelbine tartrate (e.g., NAVELBINE), vismodegib (e.g., ERIVEDGE), vorinostat (e.g., ZOLINZA), XELIRI, XELOX, ziv-aflibercept (e.g., ZALTRAP), zoledronic acid (e.g., ZOMETA), or a combination thereof. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and *vinca* alkaloids), hormone receptor modulators (e.g., estrogen receptor modulators and androgen receptor modulators), cell signaling pathway inhibitors, modulators of protein stability (e.g., proteasome inhibitors), Hsp90 inhibitors, glucocorticoids, all-trans retinoic acids, and other agents that promote differentiation.

Also encompassed by the disclosure are kits (e.g., pharmaceutical packs). The kits provided may comprise a transcription inhibitor and a kinase inhibitor described herein, or a pharmaceutical composition described herein. The kits may comprise a transcription inhibitor and a kinase inhibitor in a first container. The kits may comprise a transcription inhibitor in a first container and a kinase inhibitor in a second container. The kits may comprise a pharmaceutical composition in a first container. In some embodiments, the kits further include a third container comprising a pharmaceutical excipient for dilution or suspension of the transcription inhibitor, kinase inhibitor, and/or pharmaceutical composition.

In some embodiments, the transcription inhibitor, kinase inhibitor, or pharmaceutical composition provided in the first container, optionally the second container, and optionally the third container are combined to form one unit dosage form. Each of the first container, second container, and third container may independently be a vial, ampule, bottle, syringe, and/or dispenser package, or other suitable container. In certain embodiments, the kits are useful for treating a proliferative disease (e.g., proliferative disease that is resistant to a transcription inhibitor or kinase inhibitor) in a subject in need thereof. In certain embodiments, the kits are useful for preventing a proliferative disease (e.g., proliferative disease that is resistant to a transcription inhibitor or kinase inhibitor) in a subject in need thereof. In certain embodiments, the kits are useful for reducing, delaying, and/or preventing in a subject in need thereof the resistance of a proliferative disease to a transcription inhibitor or kinase inhibitor. In certain embodiments, the kits are useful in inhibiting the proliferation of a cell. In certain embodiments, the kits are useful in reducing, delaying, and/or preventing the resistance of a cell to a transcription inhibitor or kinase inhibitor. In certain embodiments, a kit described herein further includes instructions for using the transcription inhibitor and kinase inhibitor included in the kit, or for using the pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a proliferative disease (e.g., proliferative disease that is resistant to a transcription inhibitor or kinase inhibitor) in a subject in need thereof. In certain embodiments, the kits and instructions provide for preventing a proliferative disease (e.g., proliferative disease that is resistant to a transcription inhibitor or kinase inhibitor) in a subject in need thereof. In certain embodiments, the kits and instructions provide for reducing, delaying, and/or preventing in a subject in need thereof the resistance of a proliferative disease to a transcription inhibitor or kinase inhibitor. In certain embodiments, the kits and instructions provide for inhibiting the proliferation of a cell. In certain embodiments, the kits and instructions provide for reducing, delaying, and/or preventing the resistance of a cell to a transcription inhibitor or kinase inhibitor. A kit described herein may include one or more additional pharmaceutical agents described herein as a separate composition.

Methods of Treatment and Uses

The transcription inhibitors and kinase inhibitors described herein may be useful as combination therapies. The present disclosure thus also provides methods of treating and/or preventing a proliferative disease in a subject in need thereof, methods of reducing, delaying, and/or preventing in a subject in need thereof the resistance of a proliferative disease to a transcription inhibitor or kinase inhibitor, methods of inhibiting the proliferation of a cell, and methods of delaying and/or preventing the resistance of a cell to a transcription inhibitor or kinase inhibitor, using the transcription inhibitor and/or kinase inhibitor, or pharmaceutical composition thereof.

In another aspect, the present disclosure provides methods of treating a proliferative disease in a subject in need thereof, the methods comprising administering to the subject an effective amount (e.g., therapeutically effective amount) of (1) a transcription inhibitor and a kinase inhibitor described herein, or (2) a pharmaceutical composition described herein. In certain embodiments, the transcription inhibitor and kinase inhibitor are synergistic in treating the proliferative disease, compared to the transcription inhibitor alone or kinase inhibitor alone.

In another aspect, the present disclosure provides methods of preventing a proliferative disease in a subject in need thereof, the methods comprising administering to the subject an effective amount (e.g., prophylactically effective amount) of (1) a transcription inhibitor and a kinase inhibitor described herein, or (2) a pharmaceutical composition described herein. In certain embodiments, the transcription inhibitor and kinase inhibitor are synergistic in preventing the proliferative disease, compared to the transcription inhibitor alone or kinase inhibitor alone.

In another aspect, the present disclosure provides methods of reducing, delaying, and/or preventing in a subject in need thereof the resistance of a proliferative disease to a transcription inhibitor or kinase inhibitor, the methods comprising administering to the subject an effective amount of (1) a transcription inhibitor and a kinase inhibitor described herein, or (2) a pharmaceutical composition described herein. In certain embodiments, the transcription inhibitor and kinase inhibitor are synergistic in reducing, delaying, and/or preventing the resistance of the proliferative disease to the transcription inhibitor or kinase inhibitor, compared to the transcription inhibitor alone or kinase inhibitor alone.

In certain embodiments, the transcription inhibitor and kinase inhibitor are administered to the subject at the same time. In certain embodiments, the transcription inhibitor and kinase inhibitor are administered to the subject at different times.

In another aspect, the present disclosure provides methods of inhibiting the proliferation of a cell, the methods comprising contacting the cell with an effective amount of (1) a transcription inhibitor and a kinase inhibitor described herein, or (2) a pharmaceutical composition described herein. In certain embodiments, the transcription inhibitor and kinase inhibitor are synergistic in inhibiting the proliferation of the cell, compared to the transcription inhibitor alone or kinase inhibitor alone.

In another aspect, the present disclosure provides methods of reducing, delaying, and/or preventing the resistance of a cell to a transcription inhibitor or kinase inhibitor, the methods comprising contacting the cell with an effective amount of (1) a transcription inhibitor and a kinase inhibitor described herein, or (2) a pharmaceutical composition described herein. In certain embodiments, the transcription inhibitor and kinase inhibitor are synergistic in reducing, delaying, and/or preventing the resistance of the cell to the transcription inhibitor or kinase inhibitor, compared to the transcription inhibitor alone or kinase inhibitor alone.

In certain embodiments, the transcription inhibitor and kinase inhibitor are contacted with the cell at the same time. In certain embodiments, the transcription inhibitor and kinase inhibitor are contacted with the cell at different times.

In another aspect, the present disclosure provides the transcription inhibitors and kinase inhibitors described herein for use in a method described herein (e.g., a method of treating a proliferative disease in a subject in need thereof, a method of preventing a proliferative disease in a subject in need thereof, a method of reducing, delaying, and/or preventing in a subject in need thereof the resistance of a proliferative disease to a transcription inhibitor or kinase inhibitor, a method of inhibiting the proliferation of a cell, or a method of reducing, delaying, and/or preventing the resistance of a cell to a transcription inhibitor or kinase inhibitor). In certain embodiments, the present disclosure provides the transcription inhibitors and kinase inhibitors for use in treating a proliferative disease in a subject in need thereof. In certain embodiments, the present disclosure provides a combination of the transcription inhibitors and kinase inhibitors for use in treating a proliferative disease in a subject in need thereof.

In still another aspect, the present disclosure provides the pharmaceutical compositions described herein for use in a method described herein (e.g., a method of treating a proliferative disease in a subject in need thereof, a method of preventing a proliferative disease in a subject in need thereof, a method of reducing, delaying, and/or preventing in a subject in need thereof the resistance of a proliferative disease to a transcription inhibitor or kinase inhibitor, a method of inhibiting the proliferation of a cell, or a method of reducing, delaying, and/or preventing the resistance of a cell to a transcription inhibitor or kinase inhibitor). In certain embodiments, the present disclosure provides the pharmaceutical compositions for use in treating a proliferative disease in a subject in need thereof.

In certain embodiments, the transcription inhibitors and kinase inhibitors, or pharmaceutical compositions thereof, can be administered in combination with an anti-cancer therapy including, but not limited to, surgery, radiation therapy, transplantation (e.g., stem cell transplantation, bone marrow transplantation), immunotherapy, and chemotherapy. In certain embodiments the transcription inhibitors and kinase inhibitors, or pharmaceutical compositions thereof, can be administered in combination with radiation therapy.

In certain embodiments, the combination of administering transcription inhibitors and kinase inhibitors, or pharmaceutical compositions thereof, and radiation therapy is synergistic in treating a proliferative disease, compared to treatment with transcription inhibitors and kinase inhibitors, or pharmaceutical compositions thereof, alone, or compared to treatment with radiation therapy alone. The combination of transcription inhibitor, kinase inhibitor, and radiation may be useful in treating proliferative diseases that are resistant to transcription inhibitor alone, kinase inhibitor alone, and/or radiation alone. The combination of transcription inhibitor, kinase inhibitor, and radiation may be useful in treating a subject with a proliferative disease that has failed therapy of the proliferative disease with transcription inhibitor alone, kinase inhibitor alone, and/or radiation alone. The transcription inhibitors, kinase inhibitors, and radiation therapy may be administered at the same time or administered separately at different times in any order. In some embodiments, the transcription inhibitor and kinase inhibitor are administered before radiation therapy. In some embodiments, the transcription inhibitor and kinase inhibitor and administered after radiation therapy. In some embodiments, the transcription inhibitor and kinase inhibitor are administered concurrently with radiation therapy, e.g., on the same day. In some embodiments, the transcription inhibitor and kinase inhibitor are administered on an alternating basis, e.g., inhibitors one day and radiation therapy the next and so on.

In another aspect, the transcription inhibitor, or a pharmaceutical composition thereof, can be administered in combination with an anti-cancer therapy including, but not limited to, surgery, radiation therapy, transplantation (e.g., stem cell transplantation, bone marrow transplantation), immunotherapy, and chemotherapy. In certain embodiments, provided herein are methods for treating a proliferative disease in a subject in need thereof, comprising administering to the subject an effective amount of a transcription inhibitor, and radiation therapy. In some embodiments, the transcription inhibitor and radiation therapy are synergistic in treating the proliferative disease, compared to the transcription inhibitor alone or radiation therapy alone. In certain embodiments, provided herein are methods for treating a proliferative disease in a subject in need thereof, comprising administering to the subject an effective amount of a transcription inhibitor, and radiation therapy. In some embodiments, the transcription inhibitor and radiation therapy are synergistic in treating the proliferative disease, compared to the transcription inhibitor alone or radiation therapy alone. In certain embodiments, the transcription inhibitor combined with radiation therapy is a compound of Formula (I). In certain embodiments, the transcription inhibitor combined with radiation therapy is THZ1, or a pharmaceutically acceptable salt, solvate, hydrate, polymorph, co-crystal, tautomer, stereoisomer, isotopically labeled derivative, or prodrug thereof. In certain embodiments, the transcription inhibitor combined with radiation therapy is a compound of Formula (IV), or a pharmaceutically acceptable salt, solvate, hydrate, polymorph, co-crystal, tautomer, stereoisomer, isotopically labeled derivative, or prodrug thereof. In certain embodiments, the transcription inhibitor combined with radiation therapy is THZ5-31-1, or a pharmaceutically acceptable salt, solvate, hydrate, polymorph, co-crystal, tautomer, stereoisomer, isotopically labeled derivative, or prodrug thereof. In certain embodiments, the transcription inhibitor combined with radiation therapy is a compound of Formulae (II), (III), (V), (VI), (VII), (VIII), (IX), (X), (XI), (XII), (XIII), (XIV), (XV), (XVI), (XVII), or (XVIII), or a pharmaceutically acceptable salt, solvate, hydrate, polymorph, co-crystal, tautomer, stereoisomer, isotopically labeled derivative, or prodrug thereof. In certain embodiments, the transcription inhibitor combined with radiation therapy is a cyclin-dependent kinase (CDK) inhibitor (e.g., CDK1, CDK2, CDK3, CDK4, CDK5, CDK6, CDK7, CDK8, CDK9, CDK10, CDK11, or CDK12 inhibitor), or a or a pharmaceutically acceptable salt, solvate, hydrate, polymorph, co-crystal, tautomer, stereoisomer, isotopically labeled derivative, or prodrug thereof. In certain embodiments, the transcription inhibitor combined with radiation therapy is E9, or a pharmaceutically acceptable salt, solvate, hydrate, polymorph, co-crystal, tautomer, stereoisomer, isotopically labeled derivative, or prodrug thereof. In certain embodiments, the transcription inhibitor combined with radiation therapy is YKL-01-116, or a pharmaceutically acceptable salt, solvate, hydrate, polymorph, co-crystal, tautomer, stereoisomer, isotopically labeled derivative, or prodrug thereof. In certain embodiments, the transcription inhibitor combined with radiation therapy is dinaciclib, or a pharmaceutically acceptable salt, solvate, hydrate, polymorph, co-crystal, tautomer, stereoisomer, isotopically labeled derivative, or prodrug thereof. In certain embodiments, the transcription inhibitor combined with radiation therapy is DCA, or a pharmaceutically acceptable salt, solvate, hydrate, polymorph, co-crystal, tautomer, stereoisomer, isotopically labeled derivative, or prodrug thereof. In certain embodiments, the transcription inhibitor combined with radiation therapy is palbociclib, or a pharmaceutically acceptable salt, solvate, hydrate, polymorph, co-crystal, tautomer, stereoisomer, isotopically labeled derivative, or prodrug thereof. In certain embodiments, the transcription inhibitor combined with radiation therapy is JQ1, or a pharmaceutically acceptable salt, solvate, hydrate, polymorph, co-crystal, tautomer, stereoisomer, isotopically labeled derivative, or prodrug thereof. In certain embodiments, the transcription inhibitor combined with radiation therapy is a CDK inhibitor, such as AT7519M, P1446A-05, AG-024322, (R)-roscovitine, P276-00, SNS-032, LEE011, PD 0332991, GT28-01, NSC 638850, aminopurvalanol A, arcyriaflavin A, AZD 5438, (R)—CR8, (R)-DRF053, dihydrochloride, flavopiridol, 10Z-hymenialdisine, irdirubin-3'-oxime, kenpaullone, NSC 625987, NSC 663284, NSC 693868, NU 2058, NU 6140, olomoucine, PHA 767491, purvalanol A, purvalanol B, RO 3306, ryuvidine, senexin A, SNS 032, SU 9516, or a pharmaceutically acceptable salt, solvate, hydrate, polymorph, co-crystal, tautomer, stereoisomer, isotopically labeled derivative, or prodrug thereof. In certain embodiments, the transcription inhibitor combined with radiation therapy is a CDK inhibitor, such as p16 protein, p15 protein, p18 protein, p19 protein, p21/WAF1 protein, p27 protein, or p57 protein. In certain embodiments, the transcription inhibitor is a bromodomain-containing protein inhibitor, such as I-BET 151, I-BET 762, OTX-015, TEN-010, CPI-203, CPI-0610, RVX-208, LY294002, BMS-986158, GSK525762, or a pharmaceutically acceptable salt, solvate, hydrate, polymorph, co-crystal, tautomer, stereoisomer, isotopically labeled derivative, or prodrug thereof.

Radiation therapy includes external beam radiation therapy, brachytherapy, and administration of a radioisotope-containing agent (e.g., by infusion or ingestion). The dose of radiation depends on numerous factors as is well known in the art. Such factors include the organ being treated, the healthy organs in the path of the radiation that might inadvertently be adversely affected, the tolerance of the patient for radiation therapy, and the area of the body in need of treatment. The dose will typically be between 1 Gy and 100 Gy, and more particularly between 2 Gy and 80 Gy. It should be emphasized, however, that the methods described herein are not limited to any particular dose. The dose will be determined by the treating physician in accordance with the particular factors in a given situation, including the factors mentioned above. In some embodiments, the dose is between 1 Gy and 100 Gy, 2 Gy and 80 Gy, 5 Gy and 60 Gy, or 10 and 50 Gy.

In certain embodiments, the combination of administering the transcription inhibitor, or pharmaceutical composition thereof, and radiation therapy is synergistic in treating a proliferative disease, compared to treatment with transcription inhibitor, or pharmaceutical composition thereof, alone, or compared to treatment with radiation therapy alone. The combination of transcription inhibitor and radiation may be useful in treating proliferative diseases that are resistant to transcription inhibitor alone or radiation alone. The combination of transcription inhibitor and radiation may be useful in treating a subject with a proliferative disease that has failed therapy of the proliferative disease with transcription inhibitor alone or radiation alone. The transcription inhibitors and radiation therapy may be administered at the same time or administered separately at different times in any order. In some embodiments, the transcription inhibitor is administered before radiation therapy. In some embodiments, the transcription inhibitor is administered after radiation therapy. In some embodiments, the transcription inhibitor is administered concurrently with radiation therapy, e.g., on the same day. In some embodiments, the transcription inhibitor and radiation therapy are administered on an alternating basis, e.g., inhibitors one day and radiation therapy the next and so on.

The combination therapy with transcription inhibitor and radiation therapy (or transcription inhibitor, kinase inhibitor and radiation therapy) may be used to treat any proliferative disease. In certain embodiments, the proliferative disease is cancer. In certain embodiments, the cancer is a cancer that is commonly treated with radiation therapy. In some embodiments, the cancer is a cancer of the head, neck, or throat. In some embodiments, the cancer is head and neck cancer (e.g., head and neck squamous cell carcinoma). In some embodiments, the cancer is tongue cancer (e.g., tongue squamous cell carcinoma). In some embodiments, the cancer is hypopharyngeal cancer (e.g., hypopharyngeal squamous cell carcinoma). In some embodiments, the cancer is laryngeal cancer. In some embodiments, the cancer is nasopharyngeal cancer. In some embodiments, the cancer is lip cancer or oral cavity cancer (e.g., oral squamous cell carcinoma). In some embodiments, the cancer is metastatic squamous neck cancer. In some embodiments, the cancer is oropharyngeal cancer. In some embodiments, the cancer is paranasal sinus cancer or nasal cavity cancer. In some embodiments, the cancer is salivary gland cancer. In some embodiments, the cancer is thyroid cancer. In some embodiments, the cancer is parathyroid cancer. In some embodiments, the cancer is thyroid cancer. In some embodiments, the cancer is brain cancer (e.g., meningioma, glioblastomas, glioma (e.g., astrocytoma, oligodendroglioma), medulloblastoma).

EXAMPLES

In order that the present disclosure may be more fully understood, the following examples are set forth. The synthetic and biological examples described in this application are offered to illustrate the transcription inhibitors, kinase inhibitors, pharmaceutical compositions, and methods provided herein and are not to be construed in any way as limiting their scope.

Preparation of the Transcription Inhibitors and Kinase Inhibitors Described Herein The transcription inhibitors and kinase inhibitors provided herein can be prepared from readily available starting materials using the methods and procedures known in the art, for example, methods and procedures described in international PCT Application Publications, WO 2014/063068 and WO 2015/013635; international PCT Applications, PCT/US2014/061232, PCT/US2015/014109, PCT/US2015/014044, PCT/US2015/014039, and PCT/US2015/014120; U.S. Patent Application Publication, US 2013/0184264; and U.S. Provisional Patent Application, U.S. Ser. No. 61/892,842; each of which is incorporated herein by reference in its entirety. Where typical or preferred process conditions (e.g., reaction temperatures, times, mole ratios of reactants, solvents, pressures) are given, other process conditions can also be used unless otherwise stated. Optimum reaction conditions may vary with the particular reactants or solvents used, but such conditions can be determined by those skilled in the art by routine optimization procedures.

Biological Assays

Acquired drug resistance is a major factor limiting the effectiveness of targeted therapies in cancer[1-3]. Resistance often emerges following an initial period of drug responsiveness lasting several months through clonal evolution of the cancer cell population. This may entail acquisition of treatment-refractory mutations in the original target,[11,12] bypass reactivation of key downstream effectors of the targeted pathway,[13,14] activation of alternative pathways,[15,16] or cell state changes,[17] which render the cell population indifferent to the original therapy. The emergence of acquired resistance is facilitated by the rapid induction of a complex network of pro-survival and pro-proliferative pathways upon exposure to targeted therapy,[5-7] collectively promoting the persistence of a fraction of the original population in a drug-tolerant state[4] and leading to the eventual outgrowth of resistant clones.

Repression of the transcriptional changes induced by targeted therapy may interfere with the adaptive pro-survival and pro-proliferative responses, and hence, with the establishment of the drug tolerant state, leading to improved therapeutic efficacy. This would be advantageous clinically as it would circumvent having to anticipate, elucidate, and target the myriad of potential drug resistance mechanisms that might arise in a particular patient. THZ1 is an exemplary transcriptional repressor that is a covalent CDK7 inhibitor, and additionally targets CDK12 at higher doses.[8] CDK7 is a key regulator of the cell cycle,[18-20] and together with CDK12, regulates RNA polymerase II (RNAPII)-mediated transcription.[21-25]

To determine whether THZ1 can suppress the emergence of resistant cell populations, colony formation assays were performed in vitro in human RT112 bladder carcinoma cells (FGFR3-dependent) treated with vehicle, a clinically-relevant FGFR inhibitor, BGJ398, THZ1, or BGJ398 in combination with THZ1 (FIGS. 49A, 49B, and 52). RT112 cells are known to rapidly develop resistance to FGFR inhibitors,[15] thereby providing a suitable model for assessing the effect of THZ1 on resistance emergence. At four weeks, colony formation with THZ1 or BGJ398 was comparable to control. Combination treatment however, yielded few, or no, colonies depending on the dose of THZ1 used (FIGS. 49A, 49B, 55A, and 55B). Findings were confirmed in an additional FGFR-dependent model (NCI-H2077, a non-small cell lung cancer (NSCLC) cell line dependent on amplified FGFR1) (FIGS. 52, 53A, and 53B) and extended to additional well-established oncogene-dependency models, including two EGFR-dependent NSCLC models (PC9, NCI-H1975), a HER2-dependent esophageal carcinoma model (OE19), and an ALK-dependent NSCLC model (NCI93 H3122) (FIGS. 49A, 49B, 52, 53A, and 53B). We observed an equally striking effect when treating with THZ1 in combination with a MEK-inhibitor (GSK1120212; trametinib) in three NSCLC KRAS-mutant cellular models (A549, NCI96 H23, NCI-H1792) (FIGS. 49D, 49E, and 52). Combination treatment significantly enhanced cell death compared to either single agent alone (FIGS. 49C, 49F, and 52C) in the majority of cell lines. Taken together these data suggest that THZ1 broadly has the ability to prevent resistance emergence in diverse genetic contexts and lineages.

These results were compared with one of the current prominent approaches to address resistance, namely rational combination therapy employing two or more kinase inhibitors to simultaneously target both the driver-oncogene and previously identified resistance mechanisms.[3,26-28] We tested rational combination therapies in RT112 and in PC9 cells, using BGJ398 and erlotinib respectively, in combination with agents targeting known resistance mechanisms for these cell lines (pan-ERBB inhibitor, AZD8931; MEK inhibitor, trametinib; pan-PI3K inhibitor, BKM120; and FGFR inhibitor, BGJ398). Rational combination therapy decreased the proportion of cells surviving acute treatment at 96 hours (FIG. 53D), and reduced the outgrowth of resistant clones with variable success at four weeks (FIG. 53E). Nevertheless, drug resistance eventually developed for these rational combinations (FIG. 53E), suggesting that the addition of THZ1 to targeted therapy is able to suppress resistance emergence to a greater degree compared to rational targeted combination approaches.

To determine whether CDK7 and/or CDK12 depletion mimics the effects of THZ1, CDK7 and CDK12-deficient PC9 cells were generated using CRISPR-Cas gene editing (FIGS. 54A and 54B). Both CDK7 and CDK12-deficient PC9 cells displayed enhanced sensitivity to erlotinib at 48 hours as compared to PC9 cells with a control RNA guide (CDK7_12_dummy). CDK12 depletion, however, had more modest effects (FIG. 54C). Colony formation assays were also performed with the CDK7 and 12-deficient PC9 cells. The cytotoxicity of CDK7 or CDK12 depletion, however, prevented long-term experiments. To consider whether inhibition of the cell cycle contributes to the activity of THZ1 additional colony formation assays were performed with palbociclib, a CDK4/6 inhibitor and potent antagonist of the cell cycle.[29] Palbociclib showed a more modest effect compared to THZ1, suggesting that the effect of THZ1 is not mediated by inhibition of the cell cycle alone (FIGS. 55B and 55D). JQ1[30] was also tested. JQ1 is a transcriptional inhibitor that exerts its effects by inhibition of BRD4, a factor that indirectly promotes RNAPII phosphorylation and transcription. JQ1 has been shown to enhance sensitivity to lapatinib in HER-2 dependent models.31 JQ1 did not enhance sensitivity to erlotinib in PC9 cells, however did enhance sensitivity to BGJ398 in RT112, although less so than THZ1 (FIGS. 55B and 55D).

To assess the efficacy and toxicity of targeted therapy in combination with THZ1 in vivo, xenograft studies were performed using cell-line models of FGFR (RT112), EGFR (PC9), and KRAS mutant (NCI-H23) carcinomas (FIGS. 50A and 56). Tumor bearing mice were treated with a) vehicle, b) BGJ398 (RT112), erlotinib (PC9) or trametinib (NCI-H23), c) THZ1, or d) combination treatment with the appropriate targeted therapy and THZ1. THZ1 in combination with targeted therapy retarded tumor growth compared to THZ1 or targeted therapy alone (FIGS. 56A, 56B, and 56D), and significantly improved survival (FIGS. 50A and 56C). Importantly, combination therapy was well tolerated, with no weight loss or behavioral changes observed.

In addition, THZ1 was tested in combination with the covalent T790M-mutant-EGFR selective inhibitor WZ4002,[32] in a novel EGFR-T790M-L858R$^{LSL/-}$; p53-R172H$^{LSL/-}$ (TLP) genetically-engineered mouse model (GEMM) of NSCLC (FIG. 50B). This autochthonous preclinical model more closely mimics the stochastic nature of cancer progression and the tumor microenvironment in human NSCLC, as compared to xenograft models; p53 mutations are found in 38% of EGFR-mutant NSCLC and are associated with more advanced, aggressive disease.[33] Upon detectable tumor-burden by Magnetic Resonance Imaging (MRI) mice were randomized into treatment groups (FIG. 50B). Thereafter tumor growth was evaluated by MRI biweekly. Treatment with WZ4002 resulted in initial response at two weeks (p=0.0117, two-tailed t-test), however tumors rapidly developed resistance and rebounded by four weeks, reaching end-stage disease by five weeks of treatment, emphasizing the aggressive nature of this EGFR-mutant, p53-mutant GEMM. In stark contrast, combined THZ1-WZ4002 treatment, resulted in a dramatic response with extensive long-term tumor regression (FIGS. 50C and 50D). Mice in the combination arms continued to have significant tumor regression at 14 weeks of treatment (FIG. 50C). Furthermore, combination-treated mice had 100% survival vs. 0% survival for single-agent treated mice at 14 weeks (p=0.0019, log-rank test) (FIG. 50E). Consistent with xenograft studies, no overt toxicity was evident in the combination-treated animals despite long-term treatment.

To investigate the mechanisms by which THZ1 may suppress resistance emergence, THZ1 was evaluated for whether it blocks the adaptive response to targeted therapy by examining gene expression by RNAseq, global enhancer status by H3K27Ac ChIP-seq and immunoblotting of core signaling molecules with described roles in adaptive responses to cancer therapies in RT112 and PC9 cells. For the RNAseq experiments RT112 and PC9 cells were treated with BGJ398 and erlotinib, respectively, for one or seven days, alone or in combination with THZ1. Consistent with prior work[5,6] targeted therapy up-regulated the expression of genes involved in pro-survival programs, including NF—KB and STAT171 driven transcription programs, which were maintained in the drug tolerant population at seven days (FIG. 51A). In addition, both cell lines exhibited downregulation of negative regulators of the MAPK pathway, such as DUSP and SPRY family members (FIG. 51A). Both cell lines furthermore had FRA1 (FOSL1) downregulation consistent with activation of the previously described tumor secretome,[7] and upregulation of stemness factors, such as WNT/Hedgehog family members in RT112, and ALDH1A and CD38 in PC9. Downregulation of cell cycle genes and upregulation of cell senescence programs in these cells further suggested transition to a quiescent cell state (FIG. 51A). Gene Ontology analysis and upstream regulator analysis of gene expression profiles further corroborated the involvement of these transcriptional programs (FIG. 57). Importantly, the specific genes altered were generally distinct between the two cell lines, but highlighted programs serving similar functions. These programs have previously been implicated in drug-resistance.[5-7,34-36]

Consistent with these transcriptional changes it was found that targeted therapy increased STAT1 phosphorylation in RT112 and PC9, as well as STAT3 phosphorylation in PC9 cells, and decreased FRA1 protein levels in both lines (FIG. 51B). Similar findings were obtained in two KRAS-dependent lines, A549 and H23 (FIG. 58A). Luminex-based cytokine analysis further supported the activation of STAT3, as IL-6, a key factor in the NF-κB/STAT3-mediated adaptive response to erlotinib,[5,6] significantly increased in cell culture supernatants with erlotinib treatment (FIG. 58B). These results were confirmed using IL-6 ELISA (FIG. 51C). Also tested was the hypothesis that FRA1-deficient PC9 cells would parallel the erlotinib-induced tumor secretome and thus have an increase in IL-6 levels. Indeed, CRISPR depletion of FRA1 in PC9 cells led to elevated IL-6 levels, compared to parental cells, as shown by RT-PCR (FIG. 58D) and ELISA (FIG. 51C).

The addition of THZ1 to targeted therapy suppressed the increase in IL-6 levels in PC9 cells (FIG. 51C). THZ1 furthermore blocked ERBB2 activation in RT112 cells and FGFR activation in PC9 cells (FIG. 51B). This additionally suggests repression of secreted growth factors, as PC9 has previously been shown to secrete fibroblast growth factors in response to erlotinib as an acute survival mechanism[5] and to switch dependencies from EGFR to FGFR as a resistance mechanism.[37] Similarly, in RT112, resistance has been associated with a converse switch from FGFR to ERBB2/3 via NRG secretion.[15] THZ1 however, did not affect the phosphorylation status of STAT3, nor did it restore FRA1 levels, suggesting that THZ1 may be acting downstream of these factors. Interestingly, however, the addition of THZ1 to targeted therapy blocked STAT1 phosphorylation.

The effect of THZ1 on AKT and ERK activation was also explored. Combination treatment with THZ1 and targeted therapy resulted in enhanced ERK suppression in all cell lines tested (FIGS. 51B and 58A). Combination treatment also inhibited ERK activation in FRA1-deficient PC9 cells (FIG. 58E). These data, along with the finding that MAPK pathway repressors (e.g., DUSPs, SPRYs) are downregulated with targeted therapy (FIG. 51A), suggests that the transcriptional reprogramming engaged by targeted therapy alone may converge on MAPK reactivation. It further suggests that repression of this transcriptional reprogramming by THZ1 results in more complete ERK inhibition.

The effect of THZ1 on the transcriptional programs engaged by targeted therapy alone was also examined, and it was found that THZ1 led to an attenuation of these programs (FIG. 51D). This attenuation was present early on (24 hours), and was more profound at seven days (FIG. 51D). RT112 transcripts that were differentially expressed with combination treatment compared to targeted therapy alone included genes implicated in the NF-κB/STAT pathway (e.g., IGFBP5, TNFSF10, MX1, MX2) (FIG. 51E), suggesting that THZ1 may be directly interfering with the transcription of NF-κB/STAT target genes. Similar results were obtained in PC9 (FIG. 51E). A number of stemness-associated genes were, similarly, downregulated in the presence of THZ1 (FIG. 51E), suggesting that THZ1 may be preventing a cell-state change to a more drug-resistant phenotype. In line with the greater ERK inhibition noted with THZ1 in combination with targeted therapy, it was observed that negative regulators of the MAPK were more highly expressed in the presence of THZ1 (FIG. 51E).

Given that tumor cells acquire enhancers and super-enhancers at genes that control tumor cell identity,[38-41] and that THZ1 has been shown to disproportionally affect super enhancer driven transcription,[8-10] it was examined whether the targeted therapy-induced transcriptional activation of signaling pathways, such as NF-κB/STAT, coincided with changes in the enhancer landscape. Indeed, ChIP-Seq targeting a mark of active enhancers, H3K27Ac,[42] following seven days of treatment with targeted therapy, showed changes in the enhancer landscape, which paralleled differences in gene expression (FIGS. 51F, 51G, 51H, and 58F). Specifically, genes whose expression was increased after targeted therapy showed a concurrent increase in H3K27Ac signal at their associated enhancers leading to the formation of larger enhancers and super-enhancers (FIGS. 51F, 51H, and 58F). Genes gaining both enhancer signal and expression showed a relative lack of upregulation with combination therapy as compared to targeted therapy alone, consistent with THZ1 interfering with the adaptive up-regulation of targeted therapy-induced transcriptional programs (FIG. 51G). Thus, the changes observed in gene expression can be, at least in part, explained by the changes in enhancer landscape, suggesting that THZ1 may impinge on the ability of tumor cells to evolve enhancers that allow them to escape tyrosine kinase inhibition.

Preparation of Cell Lines.

PC9, RT112, NCI-H3122, OE19, NCI-H2077, NCI-H1975, A549, NCI-H23, NCI-H1792 were cultured in RPMI media, supplemented with 10% FBS, and penicillin/streptomycin/L-glutamine. All cell lines were cultured at 37° C. in a humidified chamber in the presence of 5% $CO_2$. Cell lines were obtained from ATCC and not further authenticated. PC9 and RT112 were additionally *mycoplasma* tested and negative.

Cell Viability Assays.

1500 cells were seeded in 96-well plates, allowed to adhere overnight, and then incubated with media containing vehicle or drug as indicated for 96 hours. Following 96 hours, cell viability was assessed using the CellTiter-Glo Luminescent Cell Viability assay (Promega). Plates were read on a Tecan Infinite M200 Pro plate reader. All conditions were tested in triplicate, unless otherwise noted. Drug curves and IC50 values were generated using GraphPad Prism 6 (GraphPad Software).

Colony Formation Assays.

100,000 cells were seeded in 6-well plates, allowed to adhere overnight, and then incubated with media containing vehicle or drug as indicated for 4 weeks. Media (and drug) were replaced weekly. At 4 weeks plates were, fixed with 1% paraformaldehyde, and then stained with 0.1% crystal violet as previously described (medicine.yale.edu/lab/kim/resources/protocols/cell/crystal- violet_stain.aspx) to assess colony formation. Results were quantified using an ImageJ Colony Area PlugIn.[44]

Apoptosis/Cell Death Analysis.

100,000 cells were seeded in 6-well plates, allowed to adhere overnight, and then incubated with media containing vehicle or drug as indicated for 24 or 48 hours. Cell death was quantified using the Alexa Fluor 488 Annexin V/Dead Cell Apoptosis kit for flow cytometry (Invitrogen), according to the manufacturer's protocol. All conditions were assayed in triplicate. Data were acquired using a BD LSR-Fortessa X-20 (BD Biosciences), and analyzed in FlowJo.

Xenograft Tumor Studies.

RT112, PC9, H23 and A549 xenograft models were established by subcutanoues (s.c.) injection of $2 \times 10^6$ cells in Matrigel (Corning) into both flanks of nude mice (NU/NU, #088 Charles River) when animals were 8-10 weeks of age. When tumors reached between 100-200 $mm^3$, as measured by caliper, mice were randomized to four groups of five female mice each, for each cell line: 1) vehicle, 2) BGJ398 (RT112), erlotinib (PC9) or trametinib (H23, A549), 3) THZ1, or 4) combination treatment with THZ1 plus BGJ398 (RT112), erlotinib (PC9) or trametinib (H23, A549). Investigators were not blinded to group allocation. The following dosing regimens were employed: BGJ398 15 mg/kg once daily (QD) by oral gavage, erlotinib 25 mg/kg QD by oral gavage, trametinib 2.5 mg/kg QD by oral gavage, and THZ1 10 mg/kg twice daily (BID) by intraperitoneal (i.p.) injection. Caliper measurements were then performed weekly and continued for eight weeks. A549 xenografts had severe ulcerations therefore were excluded from the study. H23 xenografts had one mouse in the trametinib-treated group that was censored at week 4, and two in the combination-treated group censored at weeks 6 and 7, due to ulcerations.

Genetically-Engineered EGFR-p53-Mutant NSCLC 660 Mouse Model.

Mice (both male and female) bred to contain conditional EGFR-T790M-L858R lox-stop-lox (LSL) allele and the p53-dominant negative R172H LSL allele to a final genotype of EGFR-T790M-L858R$^{LSL/-}$; p53-R172H$^{LSL/-}$ maintained on a mixed background, were induced at 6 weeks of age with Adenovirus-Cre recombinase by intranasal administration[45] to allow for mediated recombination of lox-stop-lox modified mutant-EGFR and p53 alleles. Upon clinical signs of disease, magnetic resonance imaging (MRI) was performed to establish pre-treatment tumor burden in the lungs (generally 16-20 weeks of age). Mice were imaged using a 7 Tesla BioSpec (Bruker Biospin) optimized for image requisition of pulmonary parenchyma and vessels in mice. Animals were anesthetized with 2% isoflurane IsoFlo; Abbott) in 100% oxygen via a nose cone. Respiratory and cardiac gating was applied to minimize motion artifacts during imaging. 24 slices (1 mm) were collected. Tumor volume per animal was quantified manually, based on a minimum of eight consecutive axial image sequences, using the 3D Slicer. Upon determination of the pre-treatment volume, mice were randomized into treatment groups as follows: 1) vehicle, 2) WZ4002 (covalent T790M-mutant-EGFR selective inhibitor, 50 mg/kg QD by oral gavage) 3) THZ1 (10 mg/kg, BID, i.p.) or 4) THZ1+WZ4002. Investigators were not blinded to group allocation. Mice were imaged biweekly by MRI until end-stage disease to determine tumor volume. Mice weights and signs of toxicity were monitored daily during the course of treatment. End-stage disease was reached when animals acquired clinical symptoms secondary to their lung tumors, in accordance with Dana Farber Cancer Institute Animal Care and Use Committee regulations.

RNA-Seq Analysis.

RNA was isolated from untreated RT112 cells and RT112 cells treated with 1 µM BGJ398, 100 nM THZ1, or combination treatment with THZ1 plus BGJ398, and similarly, untreated PC9 cells and PC9 cells treated with 1 µM erlotinib, 100 nM THZ1, or THZ1 plus erlotinib. Both cell lines were harvested at two time-points: following one day or seven days of treatment. Cell number was determined and total RNA was isolated using the RNeasy micro kit (Qiagen). Ambion® ERCC RNA Spike-In Mix (Life technology) was added to total RNA. cDNA libraries were prepared using the NEBNext® Ultra™ RNA Library Prep Kit for Illumina (New England Biolabs) according to the manufacturer's instructions. Library integrity was assessed on an Agilent 2100 Bioanalyzer (Agilent). Sequencing was performed on the Hiseq 2000 platform (Illumina) to a minimum depth of 30 million reads per sample.

QC-passed reads were aligned to the human reference genome (hg19) using PRADA.[46] Transcript per million (TPM) values were determined using RSEM.[47] TPM values were normalized with the voom transformation.[48] Expression changes for each gene in treated cells compared to untreated controls was determined using the limma package[49] as log 2-transformed fold change and a multiple-testing adjusted p-value. Heatmap visualization was performed using R. Log 2-transformed fold changes were not scaled and were colored on a blue-red scale.

Differentially expressed genes (defined as log 2-fold change value greater than 1.5 or less than −1.5, and p-value less than 0.01) were input into Ingenuity Pathway Analysis (www.ingenuity.com), to identify a) enriched pathways, 2) upstream regulators, andd 3) downstream effectors. Pathways were considered significantly enriched if the multiple-testing adjusted p-value of enrichment was less than [0.1]. We considered an activation z-score of greater than [2] to be activated, and less than [−2] to be inhibited. Gene ontology term (GO-term) enrichment analysis was performed using the Database for Annotation, Visualization and Integrated Discovery (DAVID) v6.7 (david.abcc.ncifcrf.gov/).

Chromatin Immunoprecipitation.

RT112 and PC9 cells treated for seven days with vehicle, 1 µM BGJ398 and erlotinib (respectively), 100 nM THZ1, or BGJ398/erlotinib in combination with THZ1. H3K27Ac ChIP-Seq was performed using Abcam antibody (cat # AB4729, lot # GR183922-1) as previously described,[8] with minor modifications (cells were crosslinked for 20 min, Dynal magnetic beads (Sigma) were bound with 10 µg of the indicated antibody).

ChIP-Seq Analysis.

Illumina sequencing libraries were generated and data was processed as described elsewhere.[50] In brief, libraries were generated for ChIP samples following the Illumina TruSeq™ DNA Sample Preparation v2 kit protocol with minor changes. All ChIP-Seq data sets were aligned using bowtie 1.0.1 to build NCBI36/hg19 of the human genome with -p 4—best -k 2 -m 2—sam -1 40. Wiggle files for gene tracks were created using Macs 1.4.2 with options -w -S -space=50 to count reads in 50 bp bins. These were divided by the number of treatment reads to normalize to mapped-reads-per million, and were displayed in the UCSC genome browser.

Regions enriched in H3K27Ac were identified using SICER[51] with corresponding input DNA control, and parameters -t 1 (max 1 read per position), -w 200 (window size 200), -i 150 (fragment size), -g 200 (gap size 200; 1 window), -t 0.74 (interrogable genome fraction), -e 200 (e-value), -p 1e-9 (significance p value cutoff). H3K27Ac islands were associated with the single RefSeq transcript whose transcription start site was nearest the center of the island. RefSeq transcripts were converted to Ensembl gene IDs for ChIP-seq vs. expression analysis using Ensembl BioMart. Super-enhancers were identified using SICER islands as input enhancers for the ROSE super-enhancer-identifying algorithm (github.com/BradnerLab/pipeline) with input DNA control parameters -s 12500 -t 1000.0

Density of H3K27Ac ChIP-Seq signal (FIG. 51F) was calculated using bamToGFF (github.com/BradnerLab/pipeline). Islands of H3K27Ac identified in RT112 BGJ398-treated cells or PC9 erlotinib-treated cells were treated as one bin (-m 1), reads were extended to be 200 bp (default) and the reads-per-million (-r) normalized density (-d) of reads was calculated therein.

Cytokine and ELISA Assays.

A Luminex Multiplex Custom Cytokine assay was used to assay cytokines in RT112 and PC9 cell culture supernatants treated with vehicle, 1 µM BGJ398 or erlotinib respectively, 100 nM THZ1, or THZ1 in combination with BGJ398 or erlotinib, at 24 and 72 hours. Cytokines assayed for were: CCL2/MCP-1, CCL5/RANTES, CXLC5, IL-1 alpha and beta, IL-2, IL-4, IL-5, IL-6, IL-8, IL-10, IL-17a, GM-CSF, TNF-alpha, VEGF, INF-gamma. IL-6 was also assayed in cell culture supernatants using the Quantikine IL-6 ELISA kit (D6050, R&D Systems) as per the manufacturer's protocol.

Immunoblotting.

Cells were lysed in RIPA buffer (Roche) containing protease inhibitors (Roche) and Phosphatase Inhibitor Cocktails I and II (CalBioChem). Protein concentrations were determined using a Bradford assay (Bio-Rad). Proteins were separated by SDS gel electrophoresis using NuPAGE 4-12% Bis-Tris gels (Life Technologies) in MOPS buffer. Resolved protein was transferred to nitrocellulose membranes, blocked in 10% milk and probed with primary antibodies recognizing EGFR (2232S), p-EGFR (2234S), FGFR3 (4574S), p-FGFR (3471S), HER2/ERBB2 (2165), p-ERBB2 (2243S), STAT1 (9172), p-STAT1 (9167), STAT3 (4904S), p-STAT3 (9145S), AKT (9272S), p-AKT (4060P), ERK (4695S), p-ERK (4370S), FRA1 (5281S), CDK12 (11973) (all from Cell Signaling Technology), CDK7 (sc-723, Santa Cruz), actin (A5441, Sigma-Aldrich) and vinculin (V9131, Sigma-Aldrich) in 5% milk or 3% bovine serum albumin as recommended by the manufacturer. After incubation with the appropriate secondary antibody (Pierce anti-mouse IgG/IgM (31444, Thermo Scientific) and anti-rabbit IgG (31460, Thermo Scientific)), blots were imaged on film.

CRISPR-CAS.

Target sequences for CRISPR interference were designed using the sgRNA designer (www.broadinstitute.org/rnai/public/analysis-tools/sgrna-design) and CRISPR Design tool (crispr.mit.edu), provided by the Broad Institute, MIT and Feng Zhang lab, MIT, respectively. Off-target effects were considered using www.genome-engineering.org. A non-targeting sgRNA from the Gecko library v2 was used as a dummy sgRNA for control.[52]

Sequences were as follows:

```
dummy guide:
                                    (SEQ ID NO: 1)
ATCGTTTCGCTTAACGGCG CDK7 sgRNA#1:
                                    (SEQ ID NO: 2)
TGTGATGCAAAGGTATTCCA CDK7 sgRNA#2:
                                    (SEQ ID NO: 3)
ATACACATCAGGTTGTAACC CDK7 sgRNA#3:
                                    (SEQ ID NO: 4)
TGAGAAGCTGGACTTCCTTG CDK12 sgRNA#1:
                                    (SEQ ID NO: 5)
GCTTGTGCTTCGATACCAAG CDK12 sgRNA #2:
                                    (SEQ ID NO: 6)
GCTCCCAGACTGGAATTAAG CDK12 sgRNA #3:
                                    (SEQ ID NO: 7)
GTAGGAGTCATAATTGCTCG FRA1 sgRNA #1:
                                    (SEQ ID NO: 8)
TATTCCTTAGAAGTTCCACC FRA1 sgRNA #3:
                                    (SEQ ID NO: 9)
TCACCCCCAGATCAGCCCGG
```

Lenti CRISPRv2 vectors were cloned as previously described.[52,53] Briefly, HEK-293T cells were transduced with lentiCRISPRv2 using X-treme Gene 9 (Roche) according to the manufacturer's instructions. On day 2, PC9 cells were seeded, and allowed to adhere overnight. On day 3 the supernatant of transduced HEK293T cells was collected and added to the PC9 cells through a 0.45 μm filter. Supernatant from transduced HEK293T cells was again collected and added to PC9 cells on day 4. On day 5, puromycin (1 mg/ml) was added to select infected cells (for four days).

RT-PCR.

Total cellular RNA was isolated from cells using an RNeasy Mini Ki (Qiagen) and 1.0 μg was then reverse transcribed to cDNA using the High Capacity RNA to c-DNA kit (Life Technologies). Quantitative PCR reactions were performed on an ABI Prism 7300 platform (Life Technologies). CDK7 expression was checked using the following forward primer: 5'-GGGACAGTTTGCCAC-CGTTT-3' (SEQ ID NO: 10) and reverse primer: 5'-ATGTC-CAAAAGCATCAAGGAGAC-3' (SEQ ID NO: 11). CDK12 expression was checked using the following forward primer: 5'-GAGGAGGCAGCAGAGAAGAG-3' (SEQ ID NO: 12) and reverse primer: 5'-TAAAAGTTGCA-GCAAGGCGG-3' (SEQ ID NO: 13). CDK7 and CDK12 primers were designed using Primer 3 software. IL-6 expression was checked using the following forward primer: 5'-AATAACCACCCCTGACCCAAC-3' (SEQ ID NO: 14), and reverse primer: 5'-ACATTTGCCGAAGAGCCCT-3' (SEQ ID NO: 15).[54] Relative gene expression was normalized to human glyceraldehyde-3-phosphate dehydrogenase (GAPDH) using the following forward primer: 5'-TTAG-GAAAGCCTGCCGGTGACTAA-3' (SEQ ID NO: 16) and reverse primer: 5'-AAAGCATCACCC GGAGGA-GAAATC-3' (SEQ ID NO: 17).[55]

Statistical Analysis.

Data are expressed as mean+/−standard deviation. Statistical significance was determined using Student's t-test. For survival analyses log-rank test (Mantel-Cox) was used. Statistical analyses were performed in Prism 6 (GraphPad Software). Significance was set at $p=0.05$.

The cells used in the following in vitro experiments fell broadly into three categories: the TKI sensitive, rapidly adaptive (less than two weeks) cells, which included RT 112 cells (bladder, FGFR3 amplified and with FGFR3-TACC3 fusion); the TKI sensitive, intermediately adaptive (approximately four weeks or longer) category, which contained the following cell lines: PC9 (NSCLC, EGFR exon 19 deletion), H2077 (NSCLC, FGFR1 amplified), OE-19 (esophageal, HER-2 amplified), and H3122 (NSCLC, EML4-ALK fusion); and the MEK/M inhibition sensitive (less TKI sensitive/insensitive than the other categories), which included the following: HSC-4 (HNSCC; co-dominant drivers), YD-8 (HNSCC; co-dominant drivers), and A549, H23, and H1792 (the latter three which are NSCLC KRAS mutant lines).

The OE-19 (HER2-dependent) and H3122 (ALK-dependent) cell lines showed similar results to those of the RT112, PC9, and H2077 cell lines.

The RNAseq libraries for PC9 and RT112 are complete. PC9 has been treated for 24 hours with the following: erlotinib, THZ1, erlotinib and THZ1, and DMSO. After 24 hours the effects of BGJ398 versus THZ1 versus the combination of the two versus DMSO in RT 112 cells were examined.

E9, a CDK12 inhibitor, works as well as THZ1. Dinaciclib was also found to be very potent, both alone and in combination with BGJ398 in RT112 cells. In comparison, DCA and JQ1 showed modest results, even in combination, in RT112 cells. A colony formation assay with THZ5-31-1 and YKL-01-116 still need to be undertaken and the compounds (at least JQ1) should be screened in an additional test.

Quantification of the Replicates at 24 and 48 Hours

Figure 1:
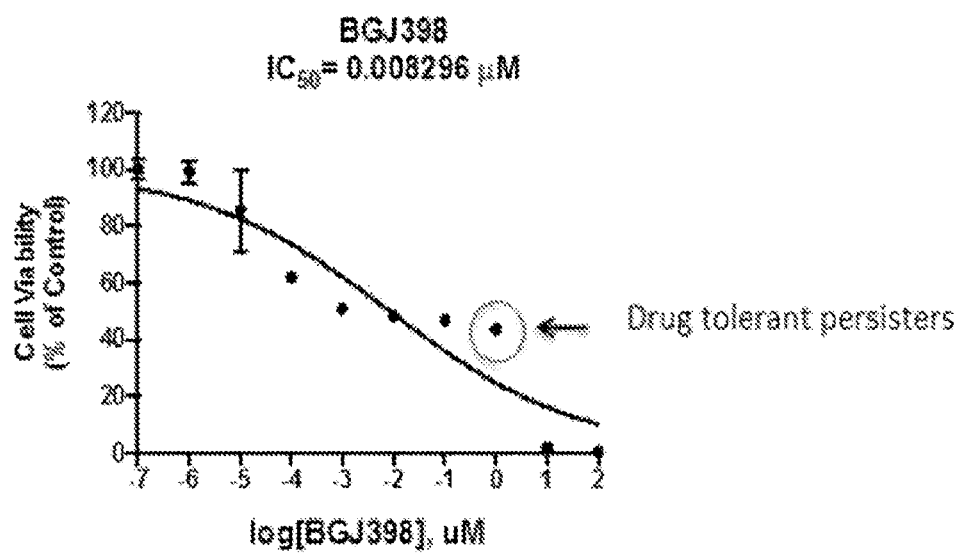
FIG. 1 shows that a treatment with BGJ398 led to resistance emergence in RT112 cells. One mechanism of resistance may be through the upregulation of NRG1 due to signaling via ERBB2/ERBB3 and is rapid (a matter of days) and reversible (Wang et al., *Oncogene*, 2015, 34(17):2167-77). The resistance may also be associated with EMT.
Figure 2:
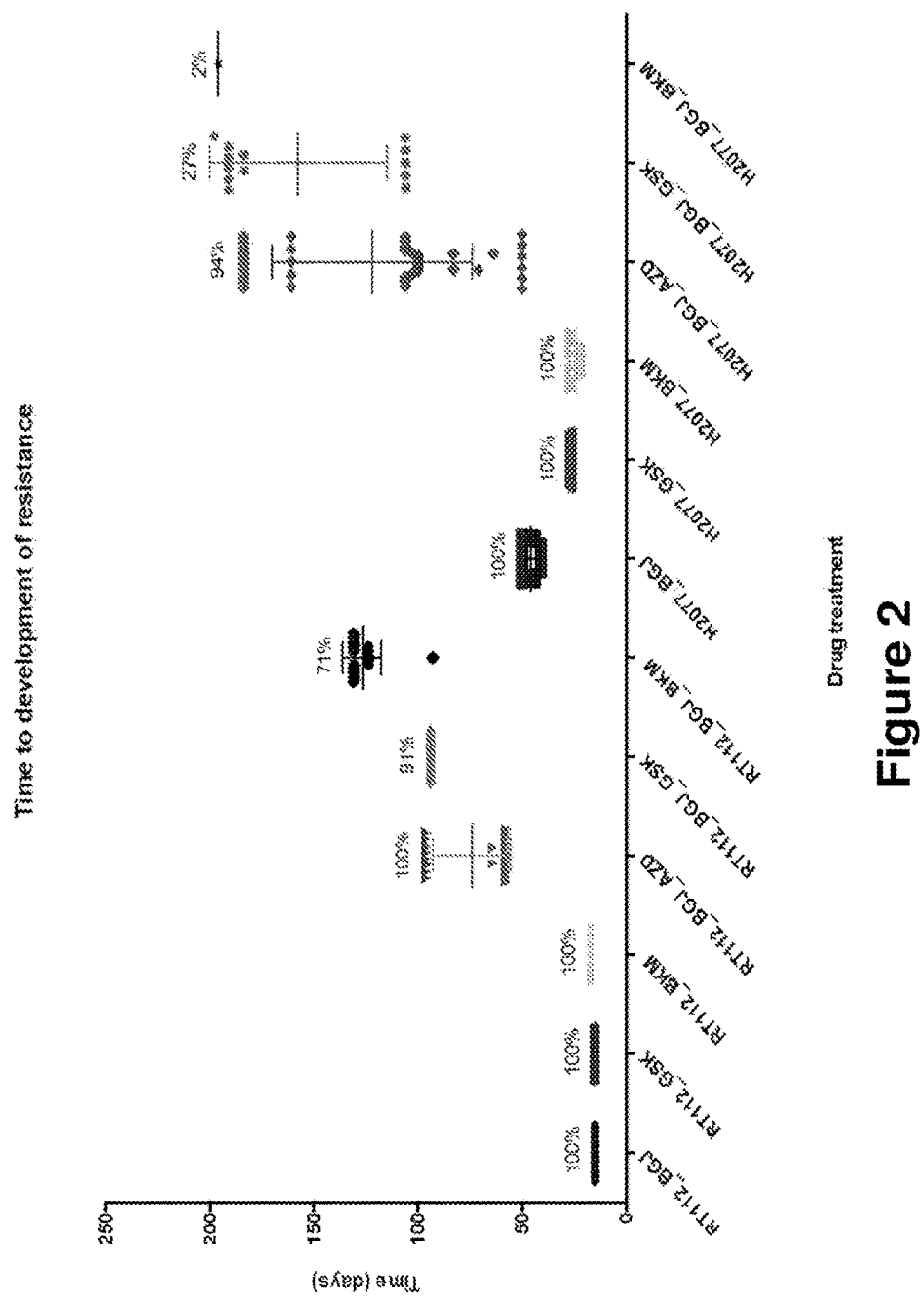
FIG. 2 shows the time to develop resistance under the treatment of various drugs or different combinations of various drugs. Each drug was administered at a concentration of 1 µM. RT112: RT112 cells. H2077: H2077 cells. BGJ: BGJ398. GSK: GSK1120212. BKM: BKM120. AZD: AZD8931.
Figure 3:
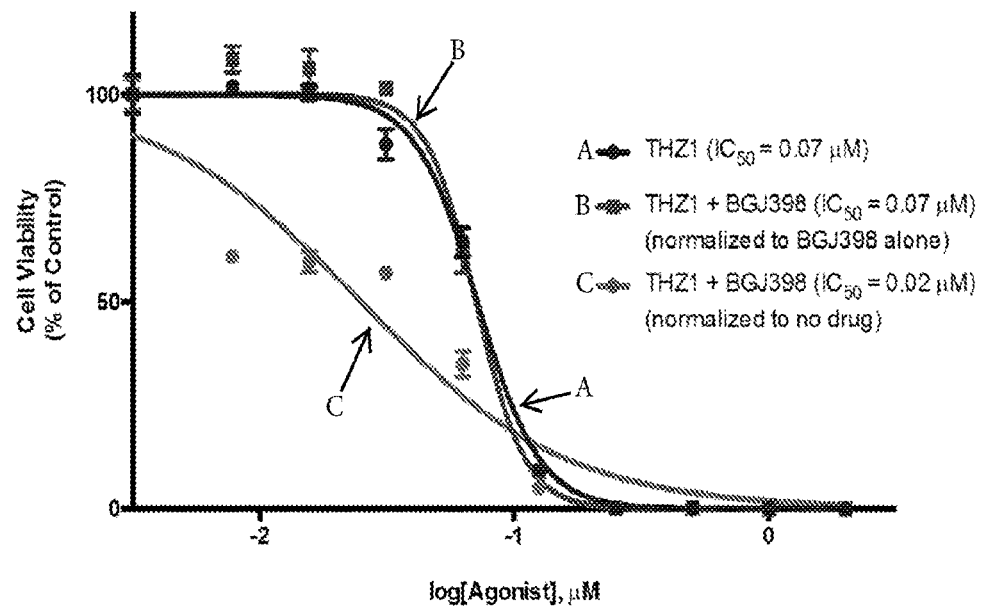
FIG. 3 shows the RT112 cell viability after the RT112 cells were treated with THZ1 or a combination of THZ1 and BGJ398. The concentration of BGJ398 was kept constant at 1 nM. [Agonist]: concentration of THZ1 in µM.
Figure 4:
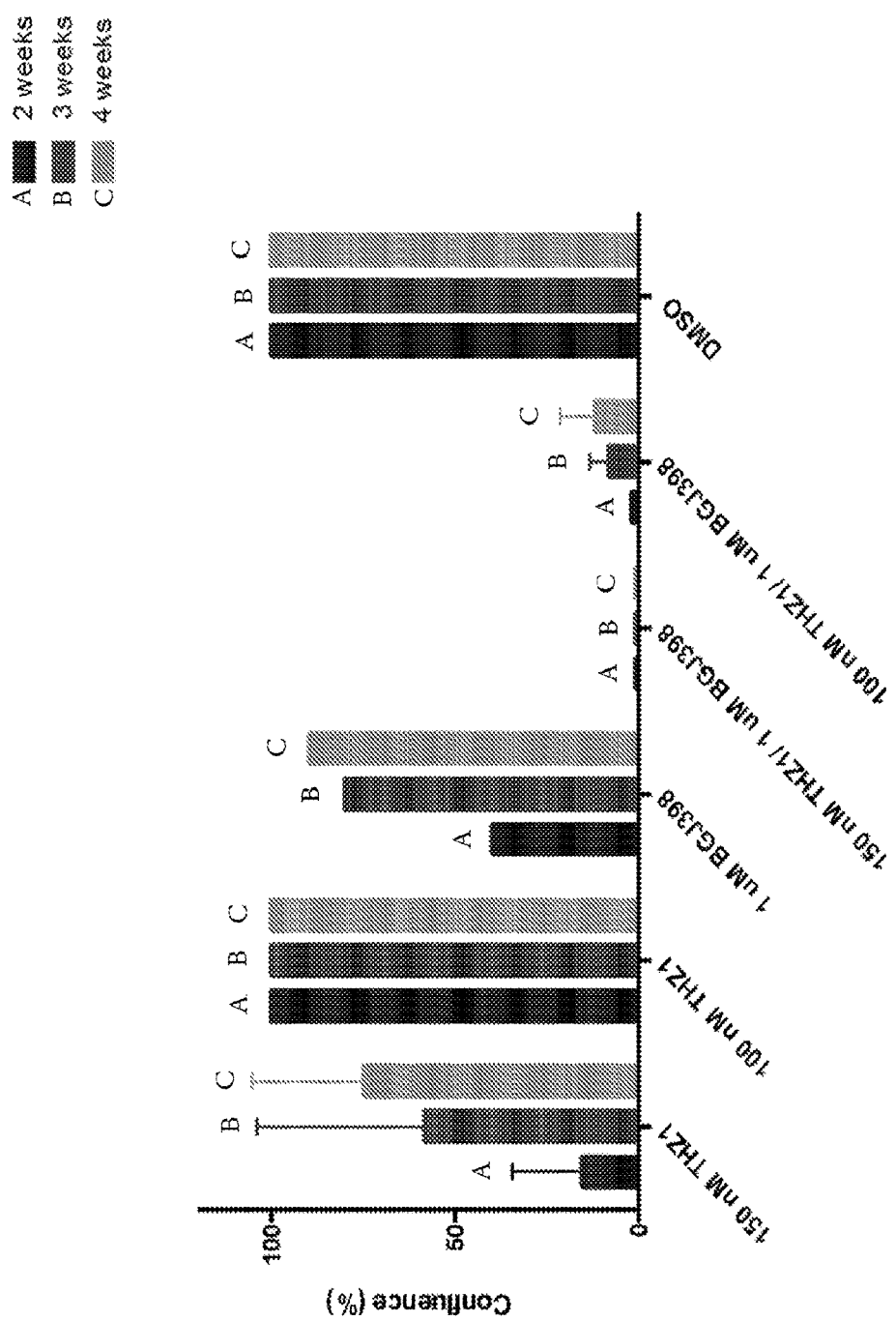
FIG. 4 shows the RT112 colony formation assay. RT112 cells were treated for two, three, or four weeks with each of DMSO (control), THZ1, BGJ398, and a combination of THZ1 and BGJ398. uM: µM.
Figure 6:
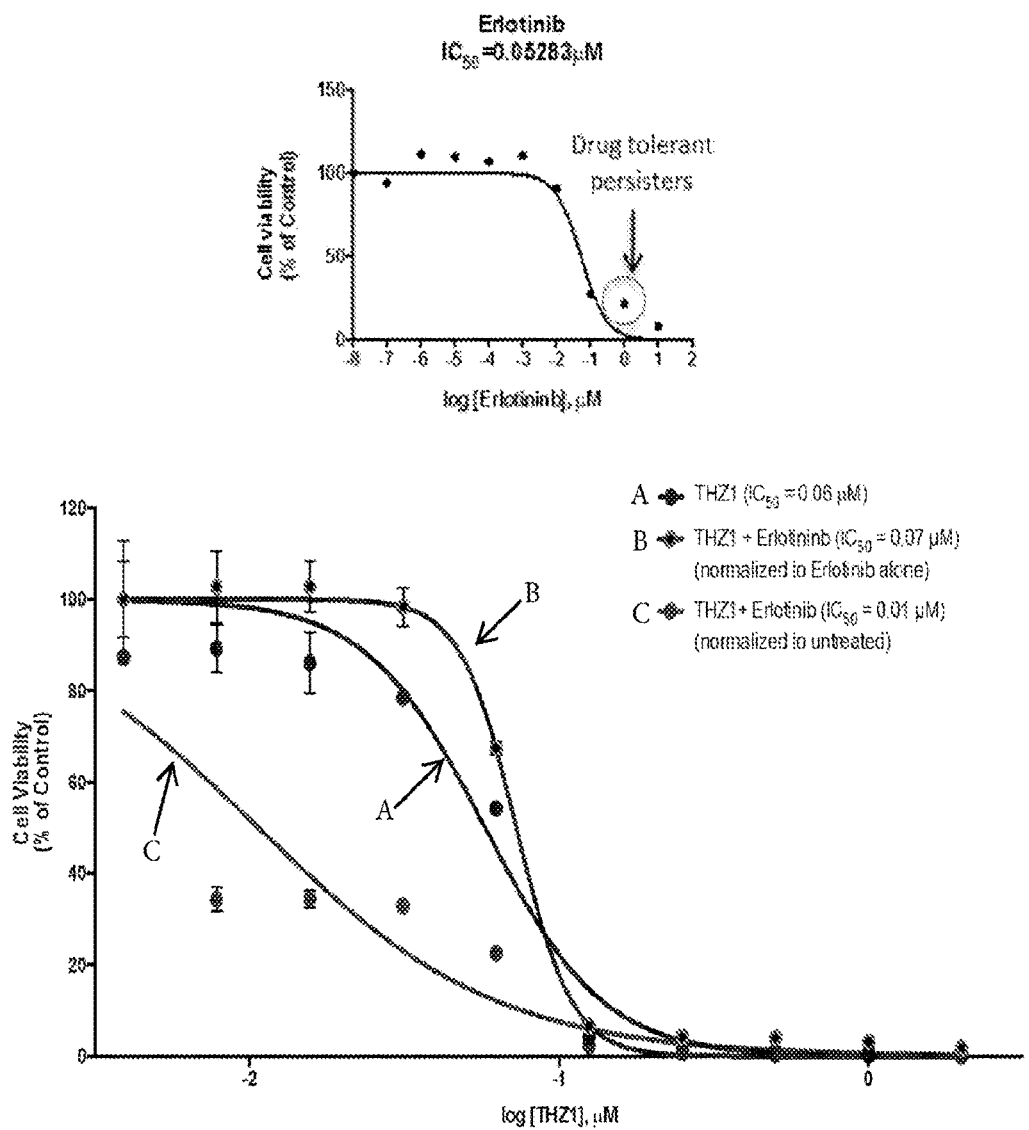
FIG. 6 shows PC9 cell viability after the PC9 cells were treated with erlotinib (top graph); and PC9 cell viability after the PC9 cells were treated with THZ1 or a combination of THZ1 and erlotinib (bottom graph). The concentration of erlotinib was kept constant at 100 nM in the bottom graph. The treatment of a combination of THZ1 and erlotinib prevented resistance emergence in PC9 cells. The mechanism of the acquired resistance to EGFR inhibition may be through a T790M EGFR mutation, through the FGF2-FGFR1 autocrine pathway, or through other RTK pathways.
Figure 7:
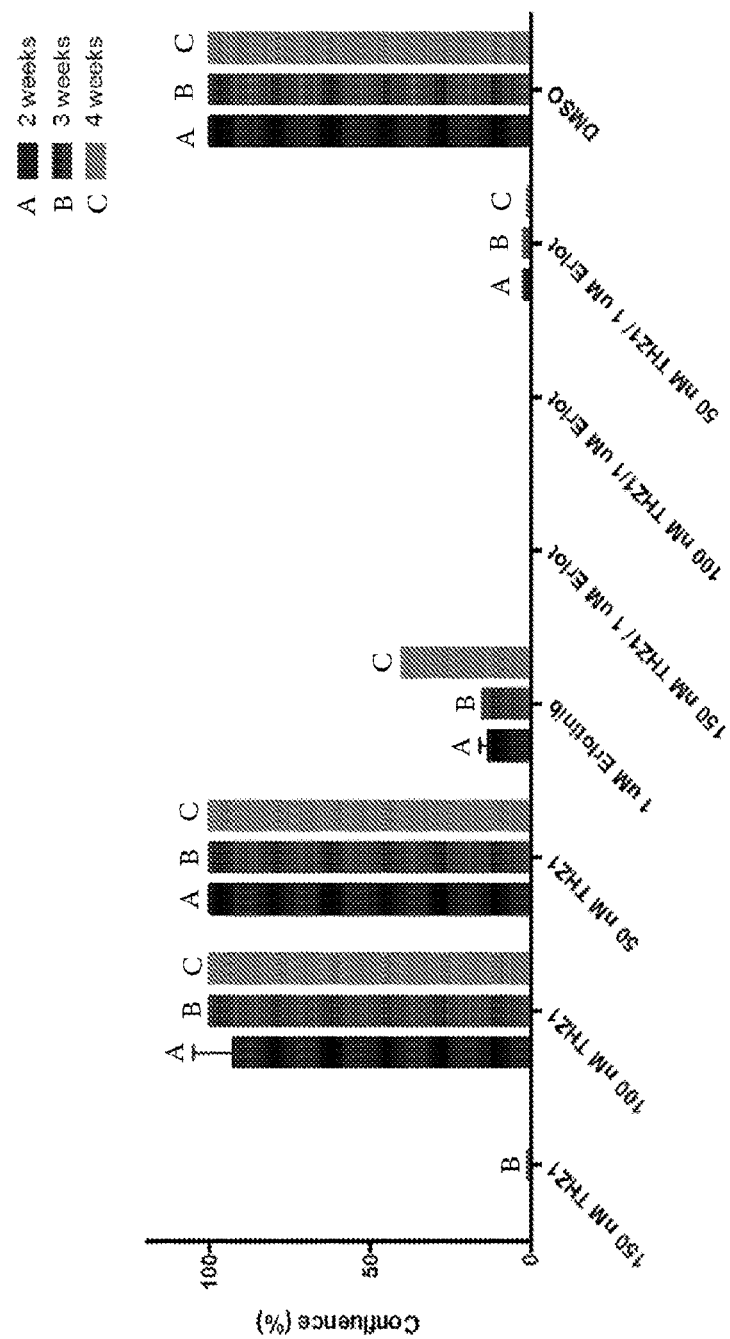
FIG. 7 shows the results of a PC9 colony formation assay. PC9 cells were treated for two, three, or four weeks with each of DMSO (control), THZ1, erlotinib, and a combination of THZ1 and erlotinib. Erlot: erlotinib. uM: µM.
Figure 8A:
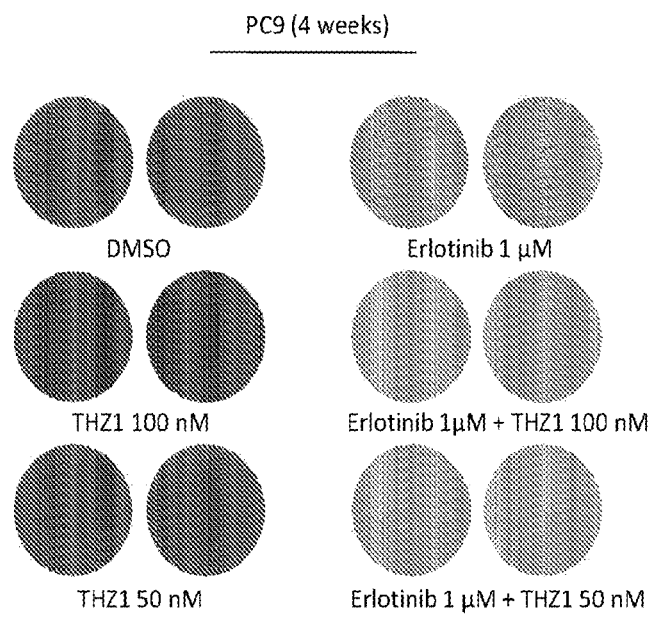
FIG. 8A shows images of stained PC9 cell colonies after treating PC9 cells for four weeks with DMSO (control), THZ1, erlotinib, and a combination of THZ1 and erlotinib.
Figure 8B:
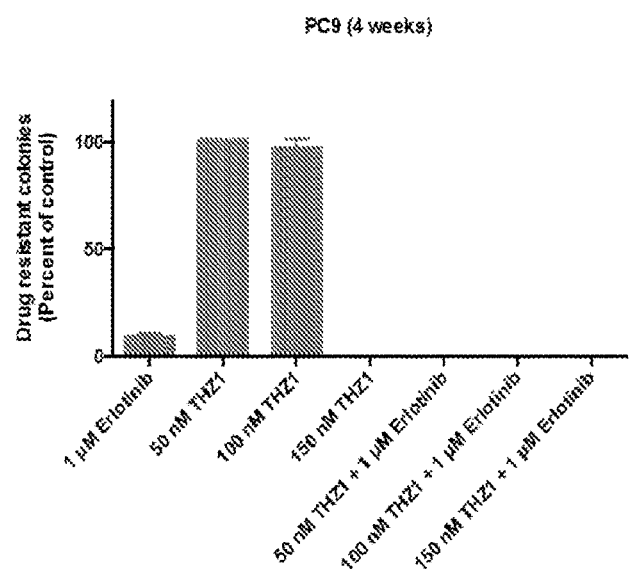
FIG. 8B shows the drug resistant colonies expressed as a percentage of the control, according to the results in FIG. 8A.
Figure 9:
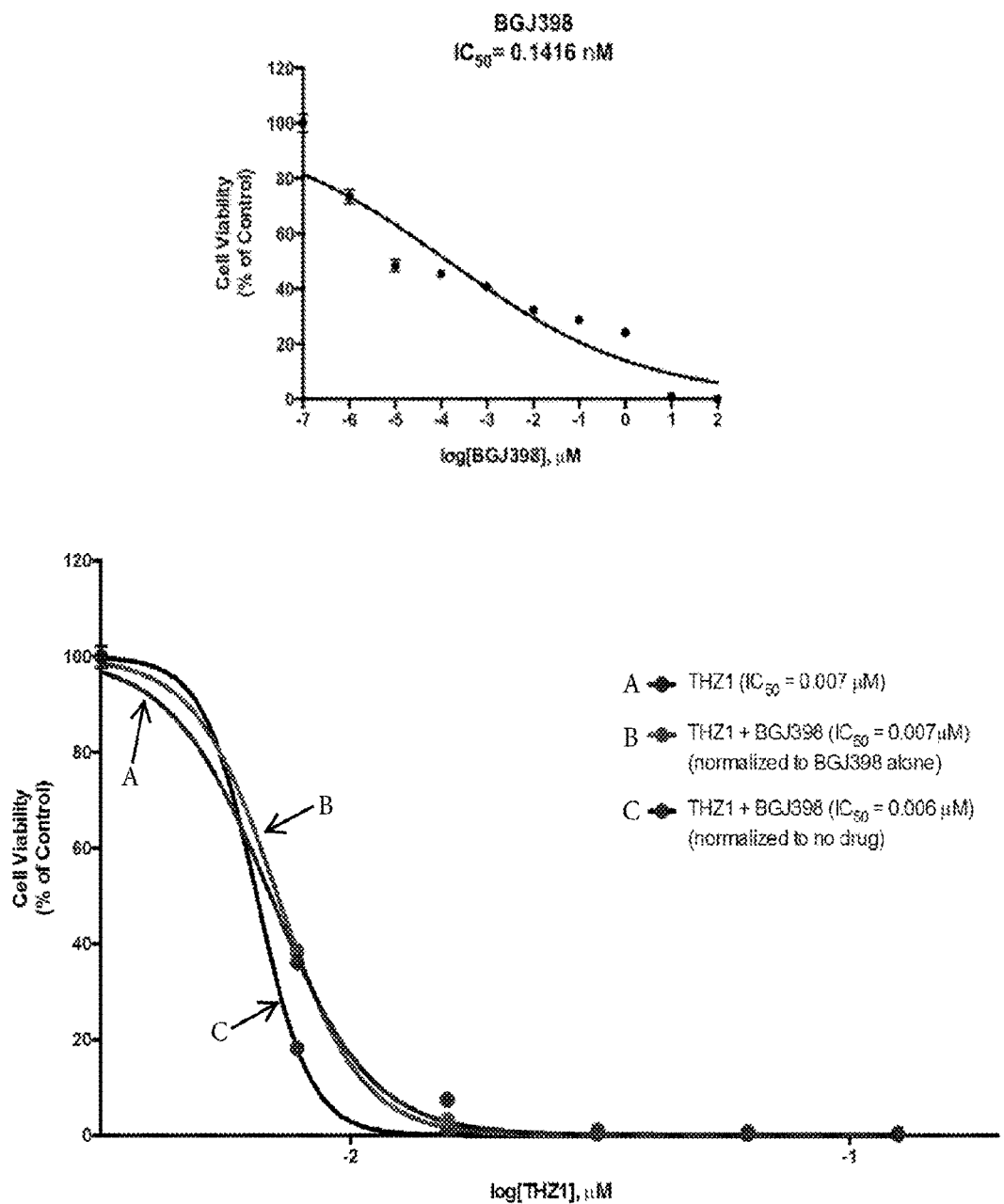
FIG. 9 shows the cell viability of H2077 (FGFR1 amplified) cells after the H2077 cells were treated with BGJ398 (top graph); and the cell viability of H2077 (FGFR1 amplified) cells after the H2077 cells were treated with THZ1 or a combination of THZ1 and BGJ398 (bottom graph). The concentration of BGJ398 was kept constant at 1 nM in the bottom graph. The mechanism of resistance to BGJ398 may be through an NRAS mutation (Q61R), or MET amplification and/or increased expression.
Figure 10:
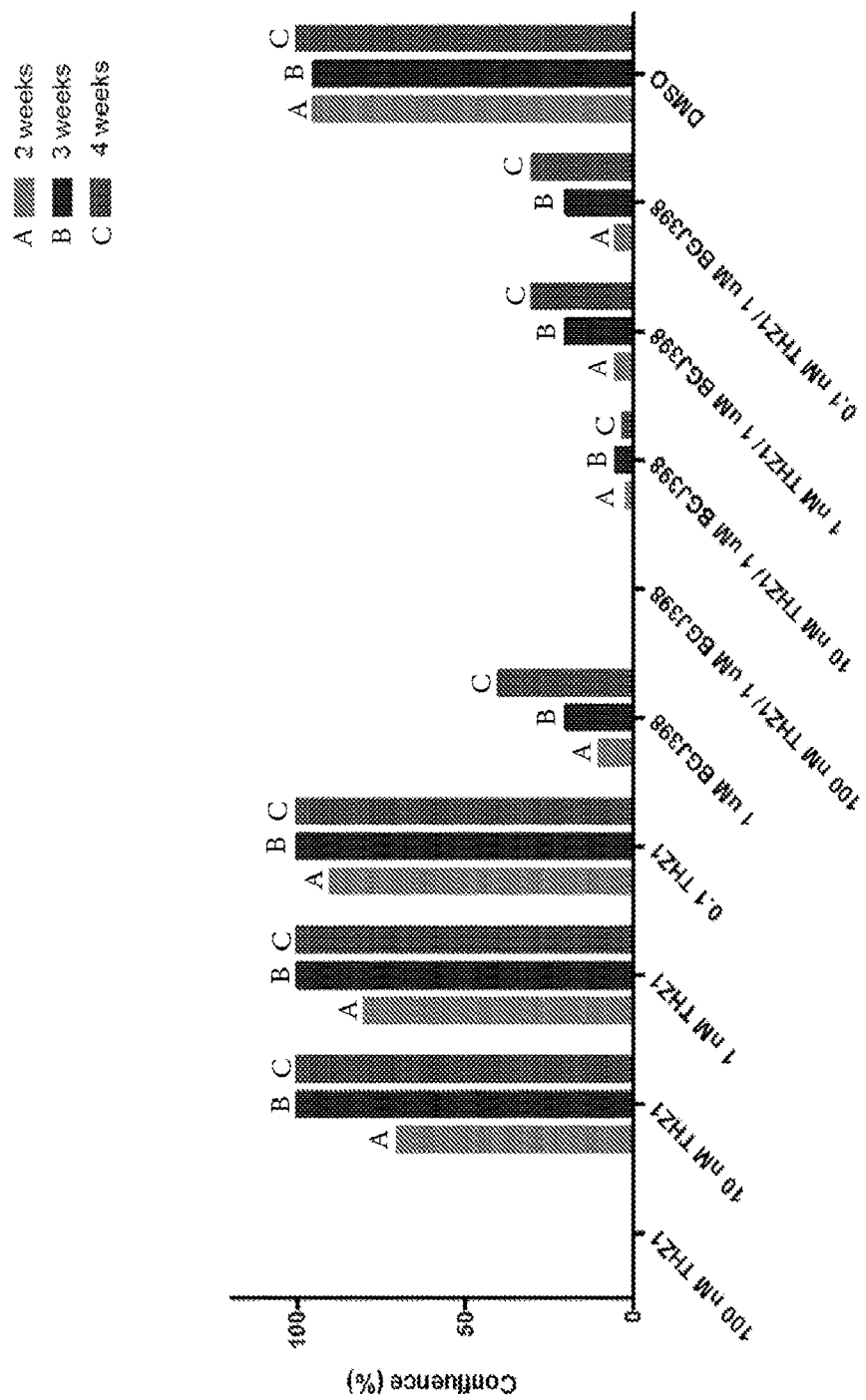
FIG. 10 shows the results of a H2077 colony formation assay. H2077 cells were treated for two, three, or four weeks with each of DMSO (control), THZ1, BGJ398, and a combination of THZ1 and BGJ398. uM: µM.
Figure 11A:
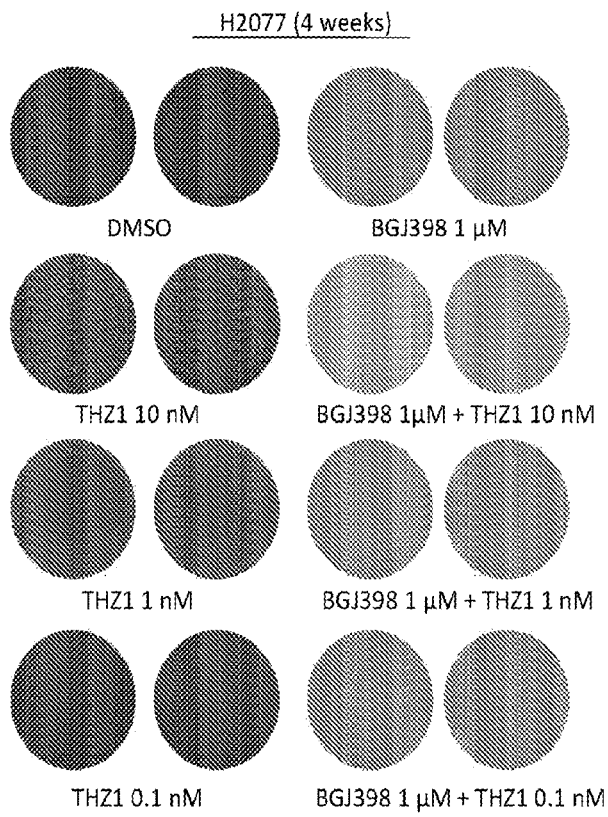
FIG. 11A shows the images of stained H2077 cell colonies after the H2077 cells were treated four weeks with DMSO (control), THZ1, BGJ398, or a combination of THZ1 and BGJ398.
Figure 11C:
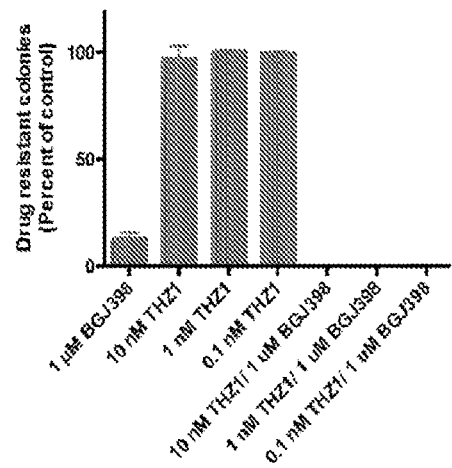
FIG. 11C shows the drug resistant colonies as a percentage of the control, according to the results in FIG. 11A.
Figure 11B:
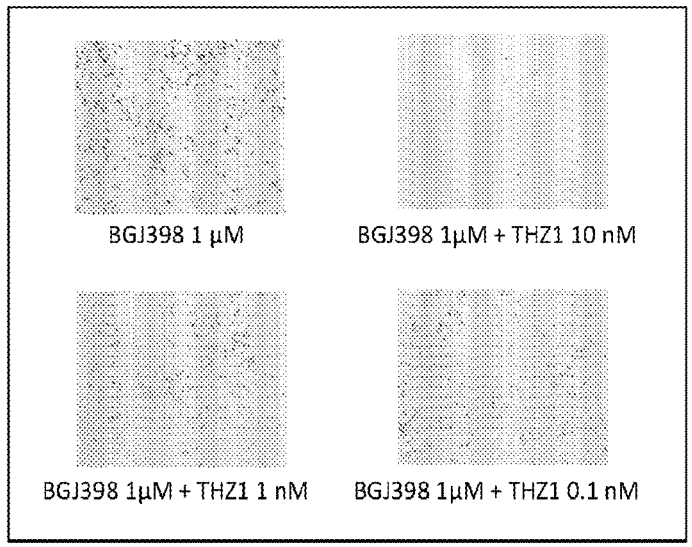
FIG. 11B shows the staining of the H2077 cells after the treatments of FIG. 11A.
Figure 12:
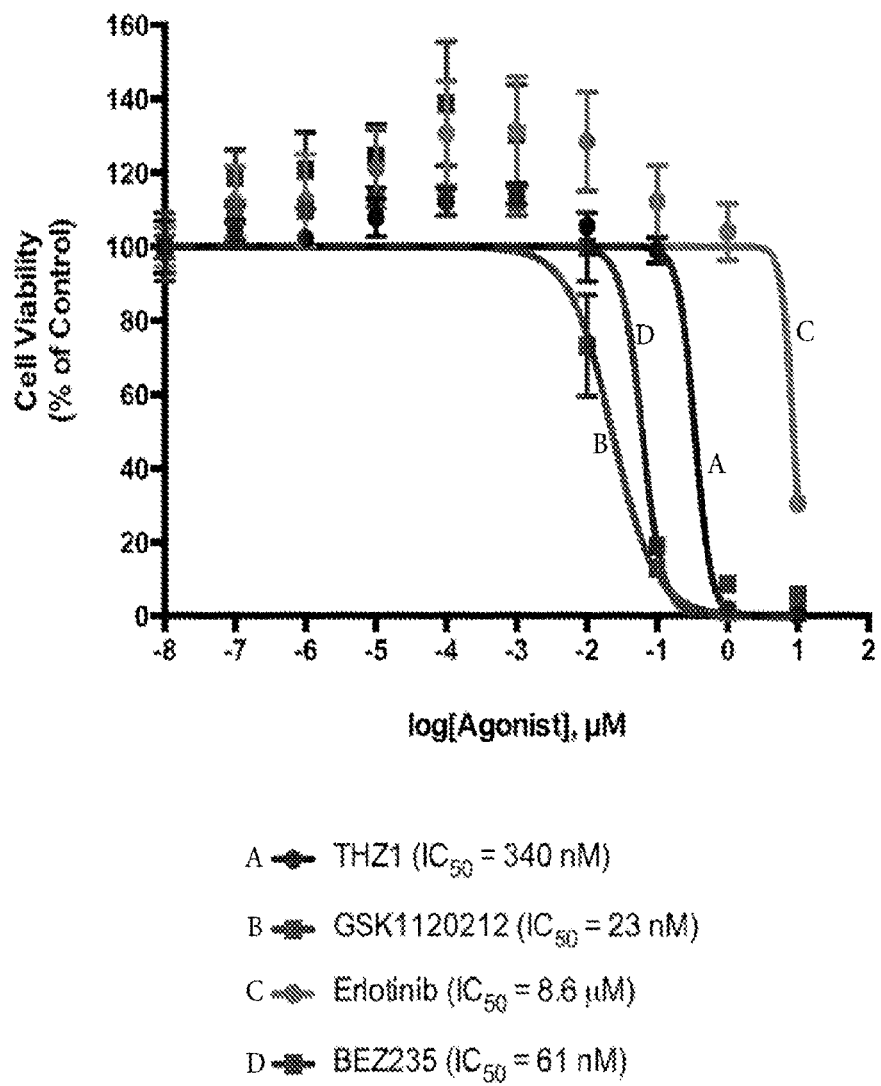
FIG. 12 shows the cell viability of H1792 cells (KRAS-mutant NSCLC cell line) after treatment with THZ1, GSK1120212, erlotinib, or BEZ235. [Agonist]: concentration of THZ1, GSK1120212, erlotinib, or BEZ235, in µM.
Figure 13:
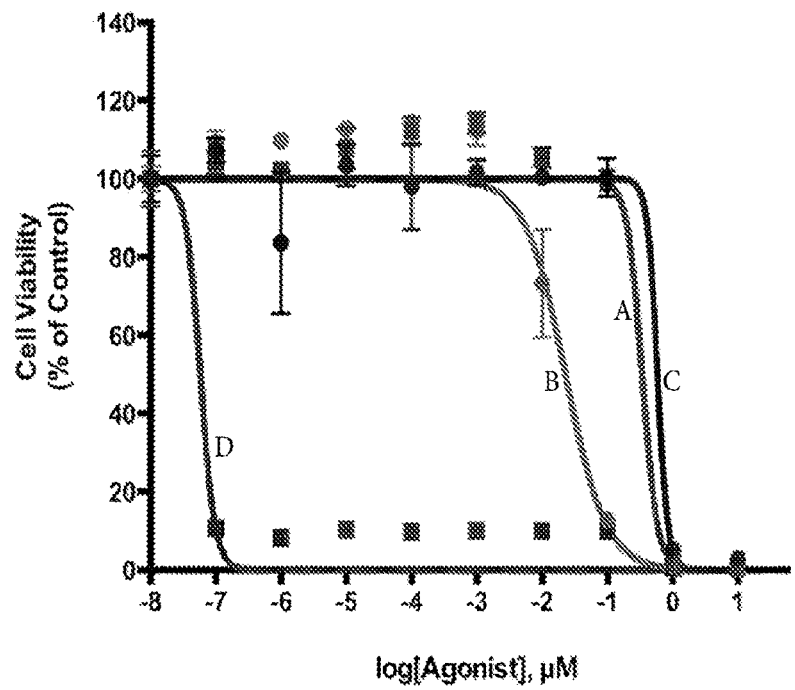
FIG. 13 shows the cell viability of H1792 cells after treatment with THZ1, GSK1120212, or a combination of THZ1 and GSK1120212. The concentration of GSK1120212 was kept constant at 50 nM. [Agonist]: concentration of THZ1 in µM. GSK: GSK1120212.
Figure 14A:
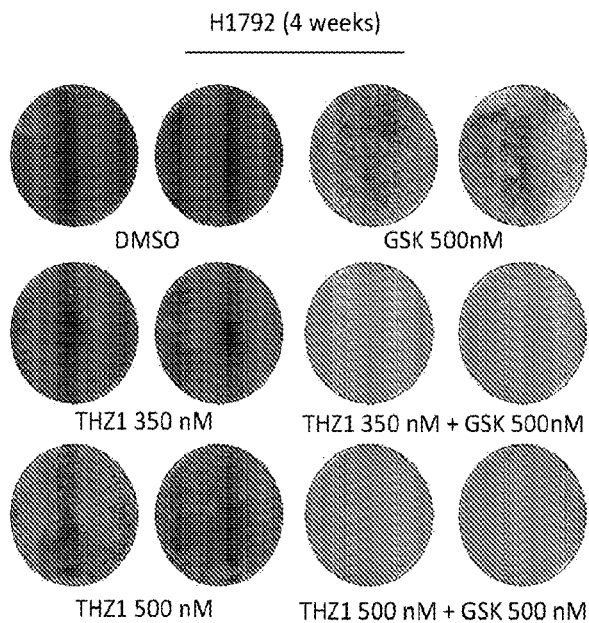
FIG. 14A shows images of stained H1792 cell colonies after treating H1792 cells for four weeks with DMSO (control), GSK1120212, THZ1, or a combination of GSK1120212 and THZ1. GSK: GSK1120212.
Figure 14B:
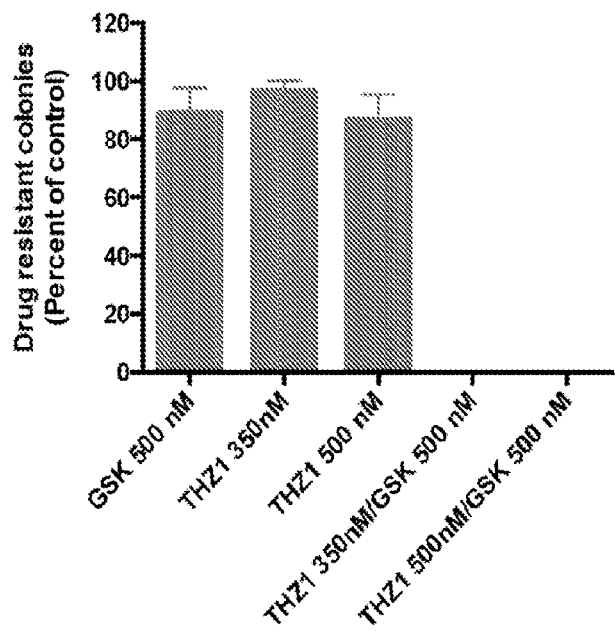
FIG. 14B shows the drug resistant colonies as a percentage of the control, according to the results in FIG. 14A. GSK: GSK1120212.
Figure 15:
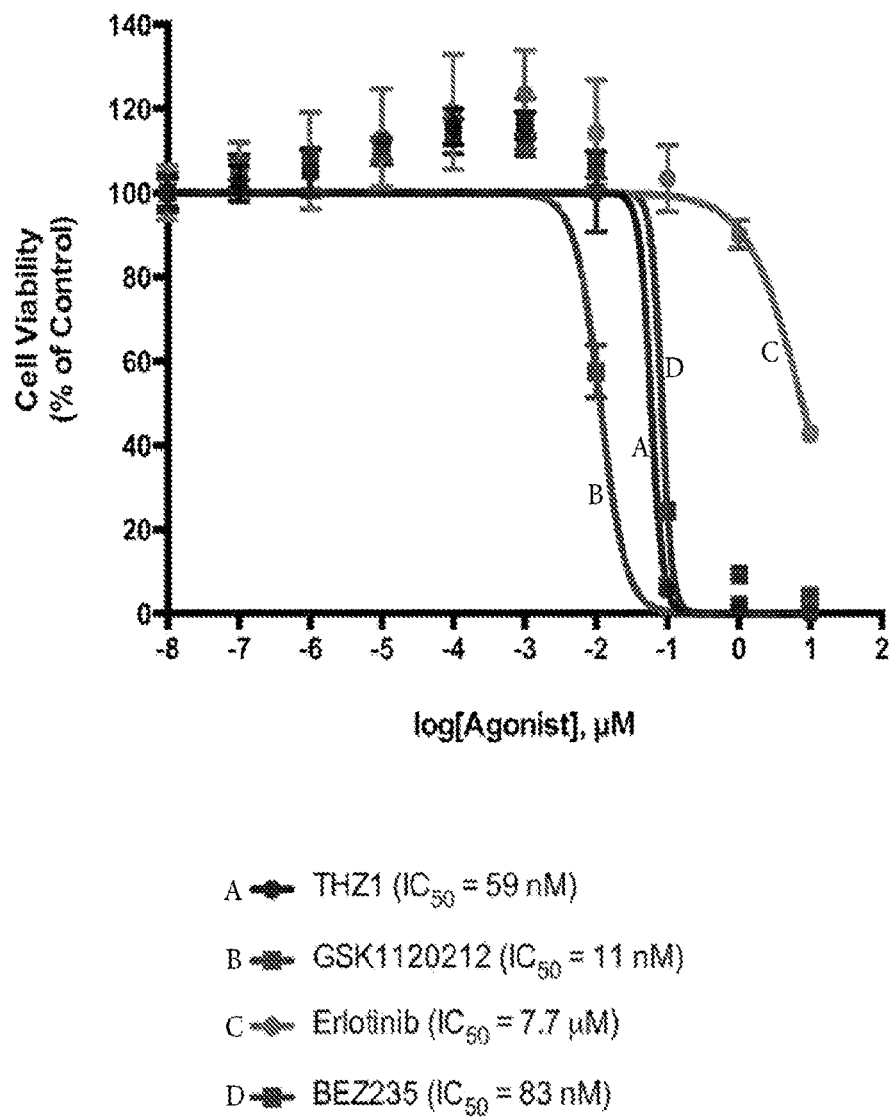
FIG. 15 shows the cell viability of H23 cells (KRAS-mutant NSCLC cell line) after treatment with THZ1, GSK1120212, erlotinib, or BEZ235. [Agonist]: concentration of THZ1, GSK1120212, erlotinib, or BEZ235, in µM.
Figure 16:
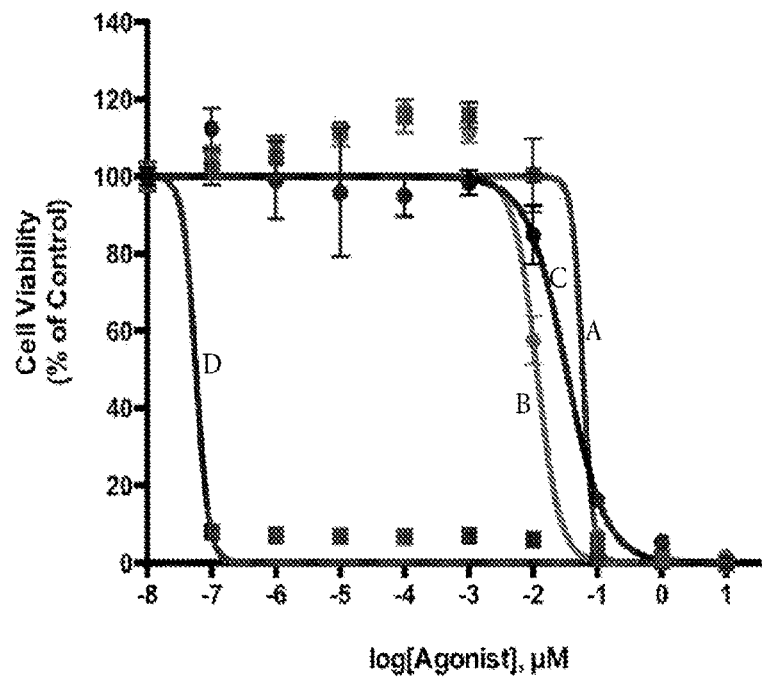
FIG. 16 shows the cell viability of H23 cells treated with THZ1, GSK1120212, or a combination of THZ1 and GSK1120212. The concentration of GSK112012 was kept constant at 25 nM. [Agonist]: concentration of THZ1 in µM.
Figure 17A:
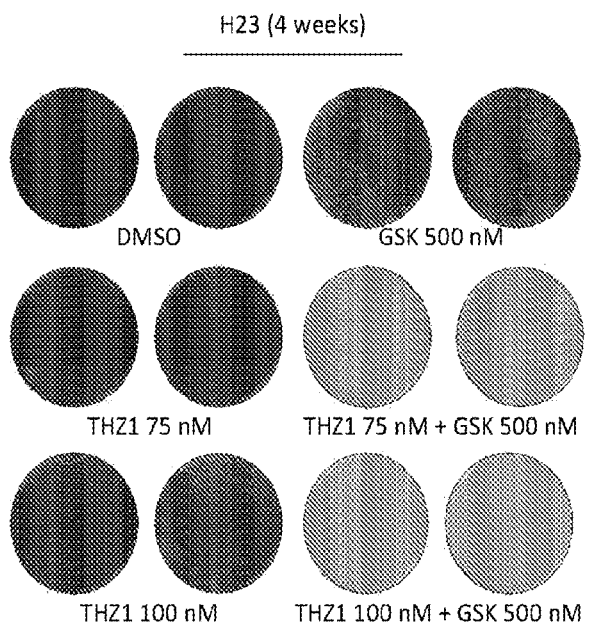
FIG. 17A shows images of stained H23 cell colonies after treating H23 cells for four weeks with DMSO (control), GSK1120212, THZ1, or a combination of THZ1 and GSK1120212. GSK: GSK1120212.
Figure 17B:
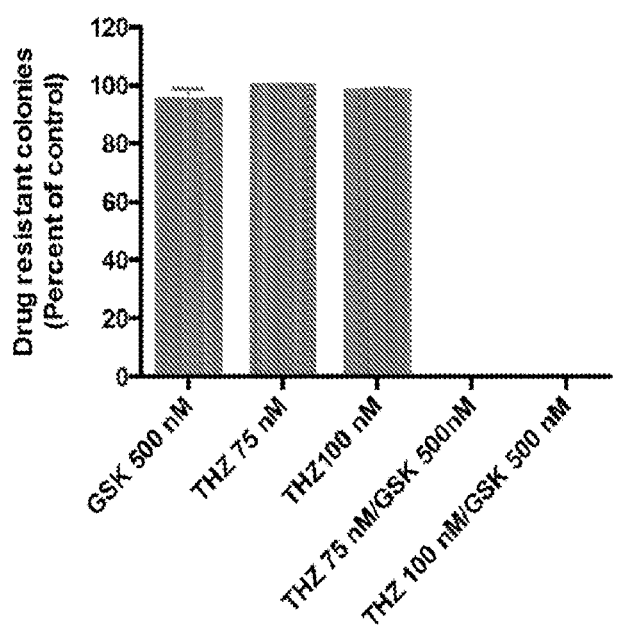
FIG. 17B shows the drug resistant colonies as a percentage of the control, according to the results in FIG. 17A.
Figure 18:
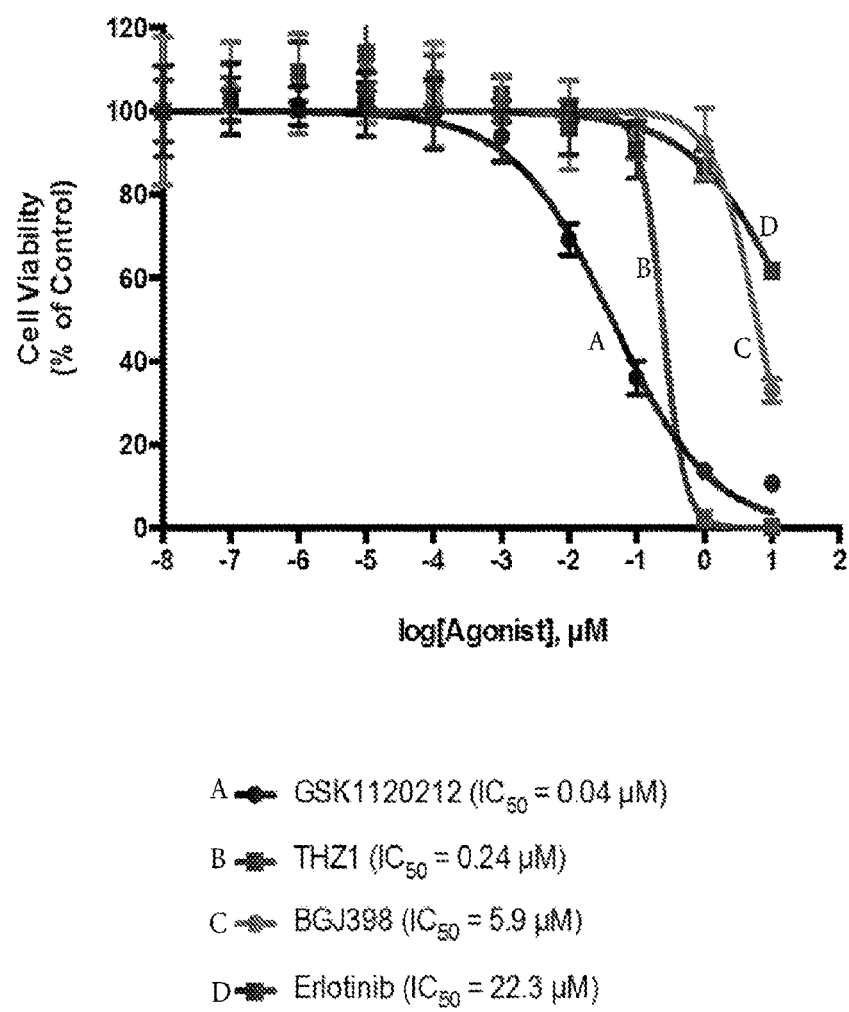
FIG. 18 shows the cell viability of A549 cells (KRAS-mutant NSCLC cell line) after treatment with GSK1120212, THZ1, BGJ398, or erlotinib. [Agonist]: concentration of GSK1120212, THZ1, BGJ398, or erlotinib, in µM.
Figure 19:
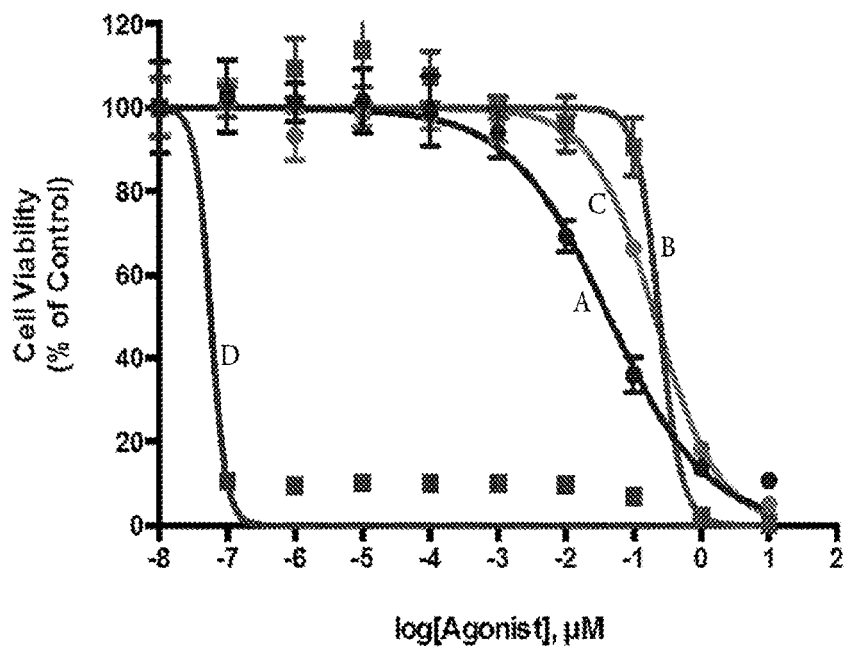
FIG. 19 shows the cell viability of A549 cells treated with GSK1120212, THZ1, or a combination of GSK1120212 and THZ1. The concentration of GSK112012 was kept constant at 1 µM. [Agonist]: concentration of THZ1 in µM.
Figure 20A:
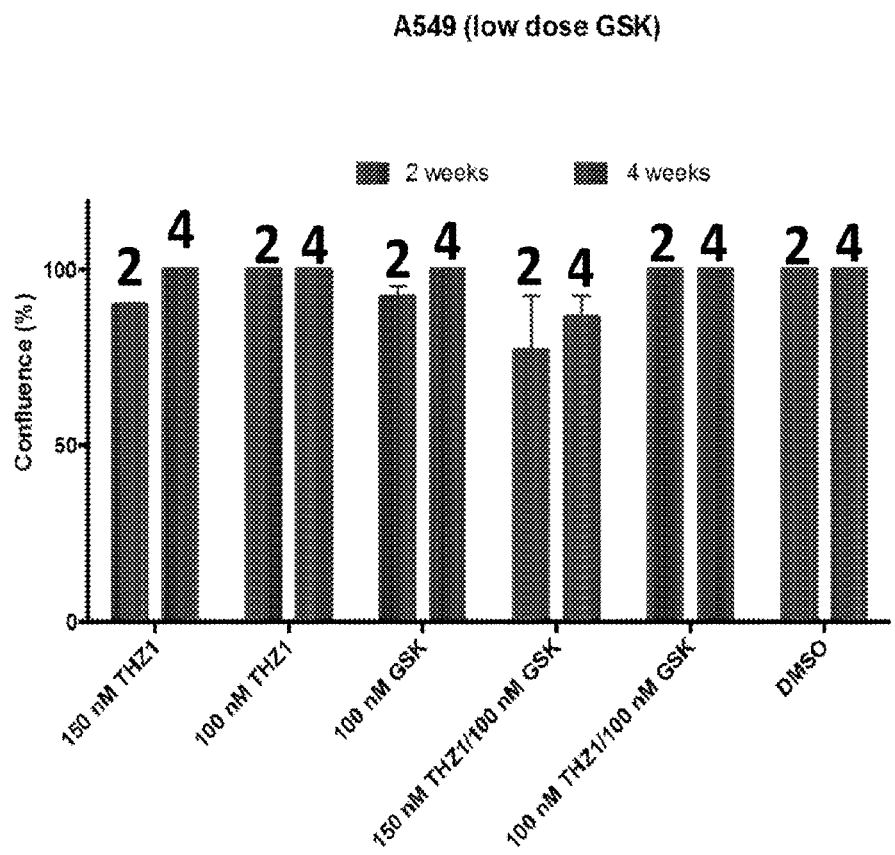
FIG. 20A shows the confluence of A549 cells treated for two or four weeks with THZ1, a low dose of GSK1120212, a combination of THZ1 and a low dose of GSK1120212, or DMSO (control).
Figure 20B:
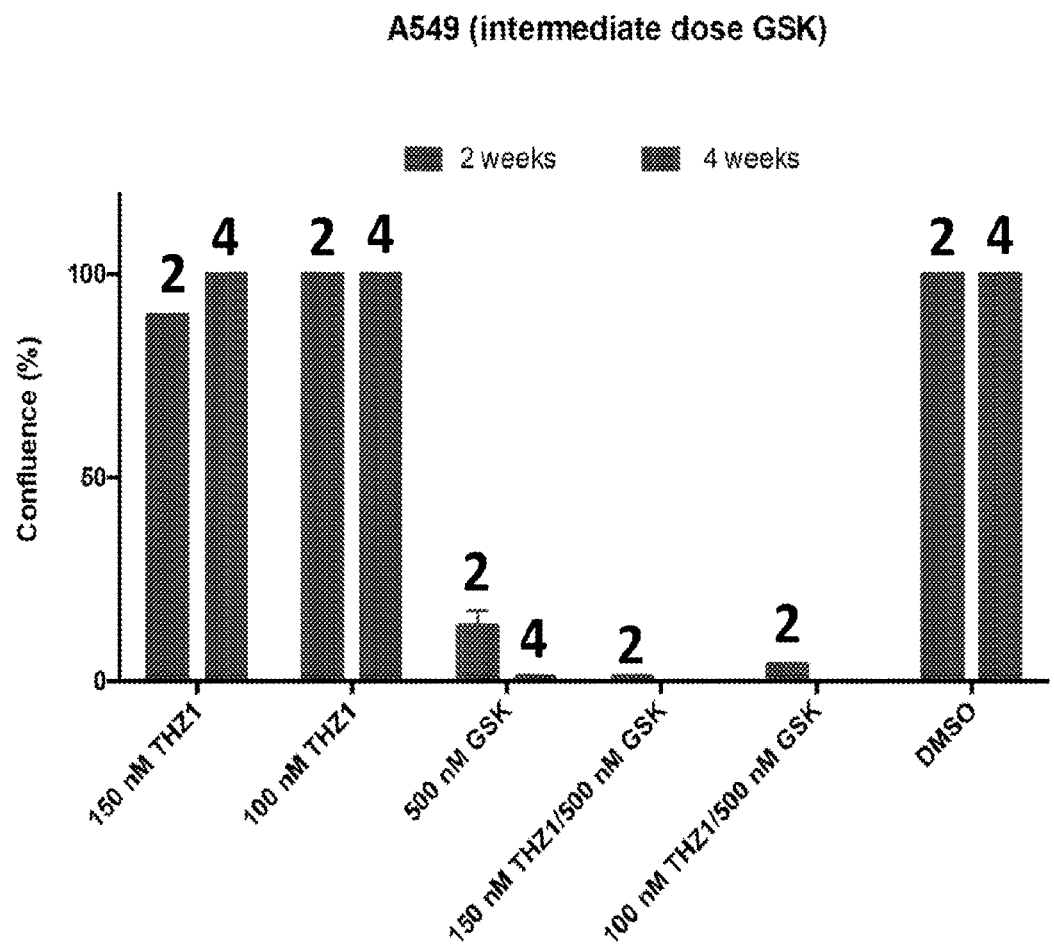
FIG. 20B shows the confluence of A549 cells treated for two or four weeks with THZ1, an intermediate dose of GSK1120212, a combination of THZ1 and an intermediate dose of GSK1120212, or DMSO (control).
Figure 20C:
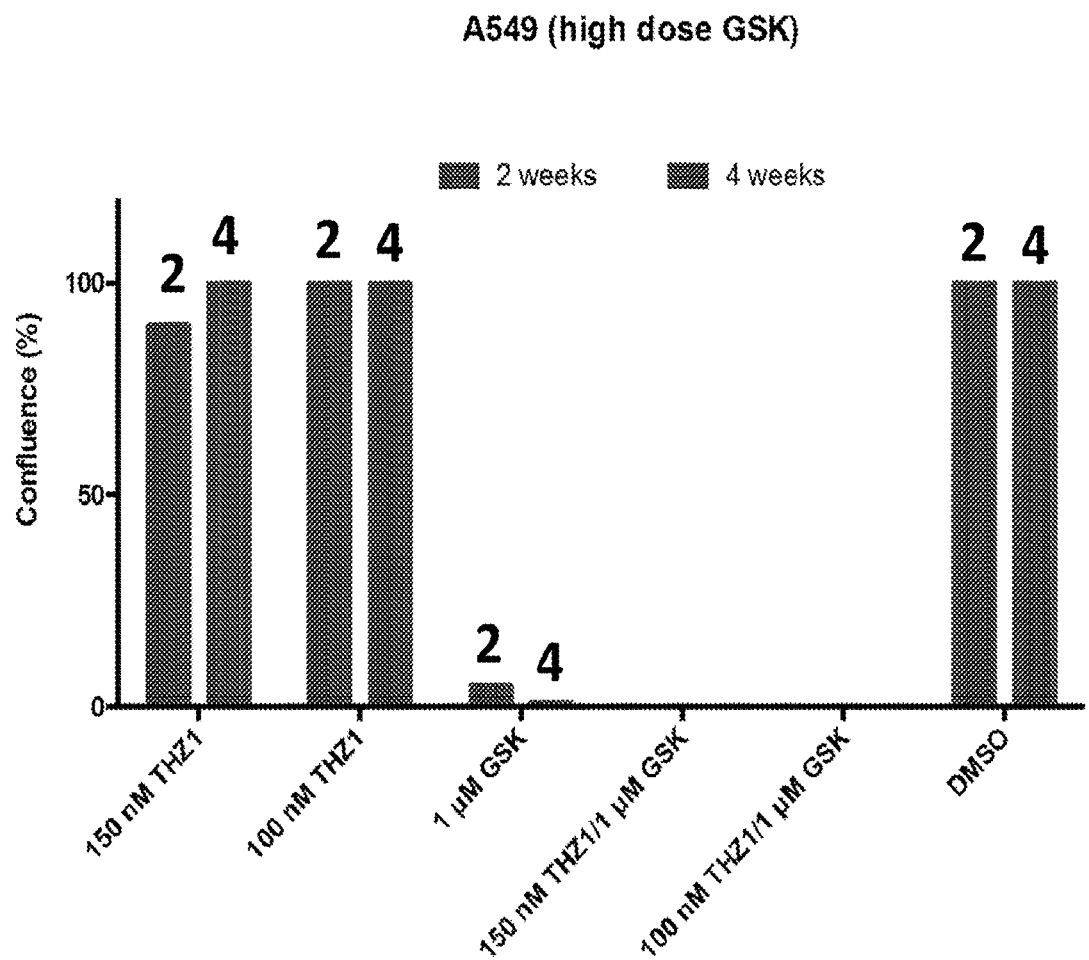
FIG. 20C shows the confluence of A549 cells treated for two or four weeks with THZ1, a high dose of GSK1120212, a combination of THZ1 and a high dose of GSK1120212, or DMSO (control).
Figure 21A:
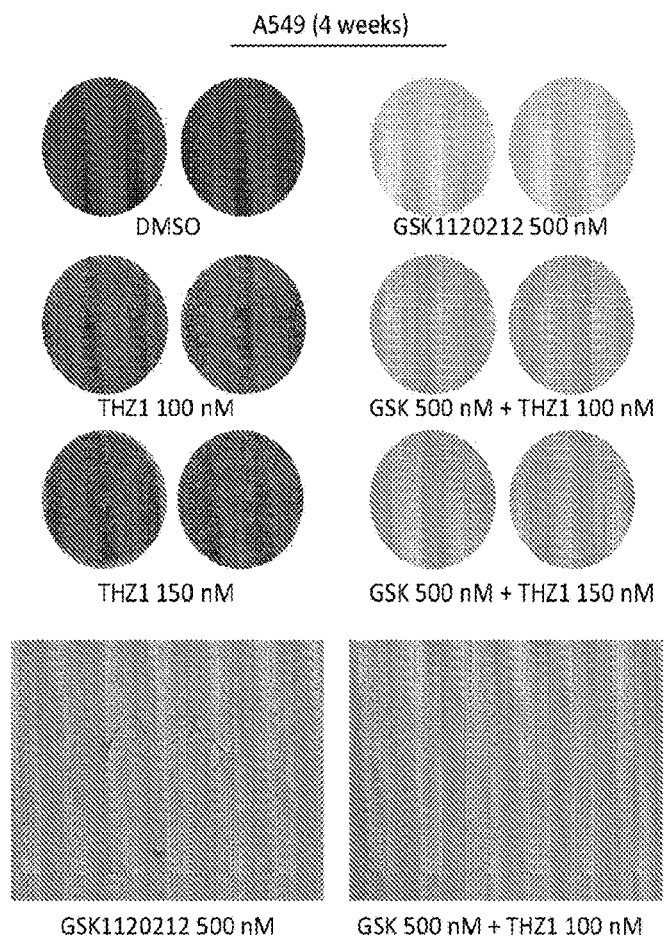
FIG. 21A shows images of stained A549 cell colonies after treating A549 cells for four weeks with DMSO (control), GSK1120212, or a combination of GSK1120212 and THZ1. GSK: GSK1120212.
Figure 21B:
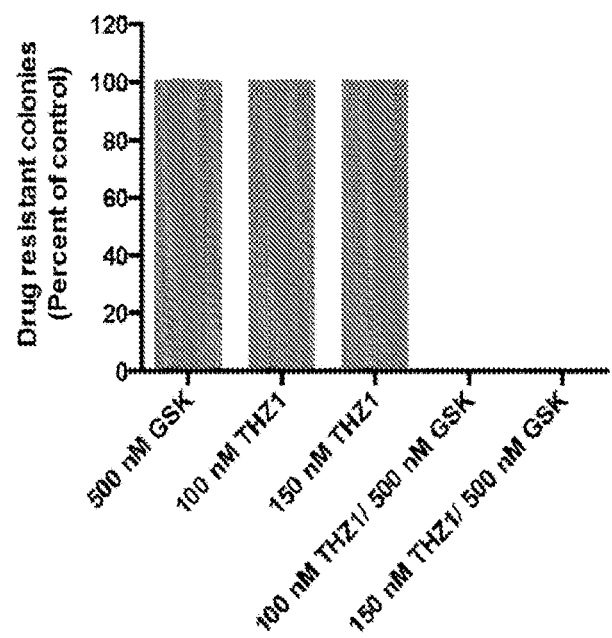
FIG. 21B shows the drug resistant colonies as a percentage of the control, according to the results in FIG. 21A. GSK: GSK1120212.
Figure 22A:
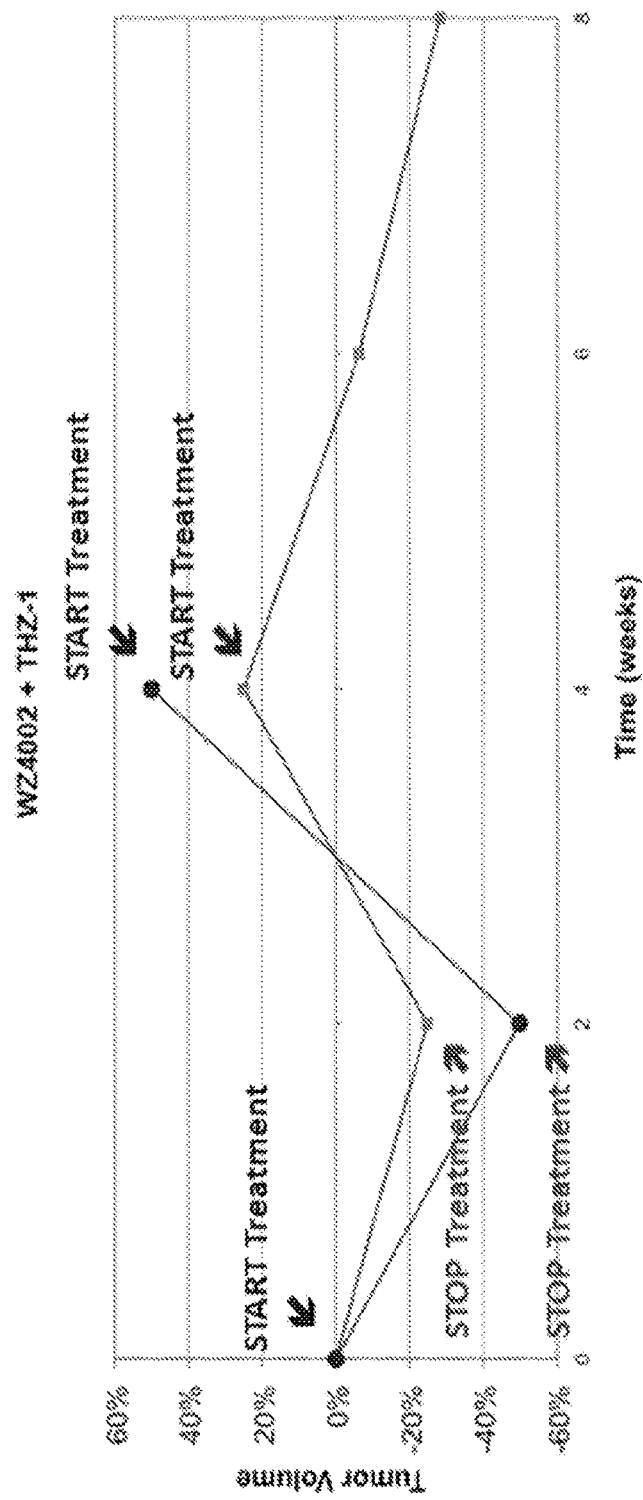
FIGS. 22A to 22C show the tumor volume in LSL-EGFR-T790M mice (n=2 per group) treated with a combination of WZ4002 and THZ-1 (THZ1, FIG. 22A), THZ-1 (FIG. 22B), and WZ4002 (FIG. 22C).
Figure 22B:
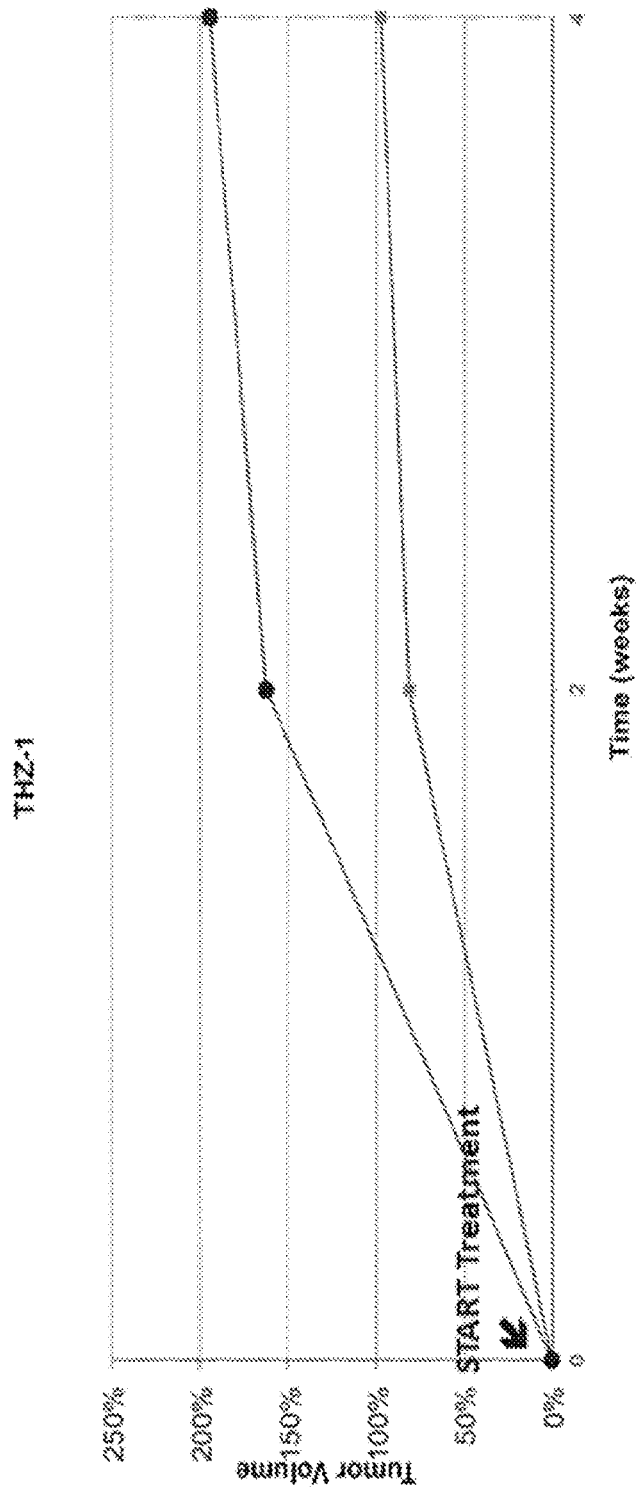
Figure 22C:
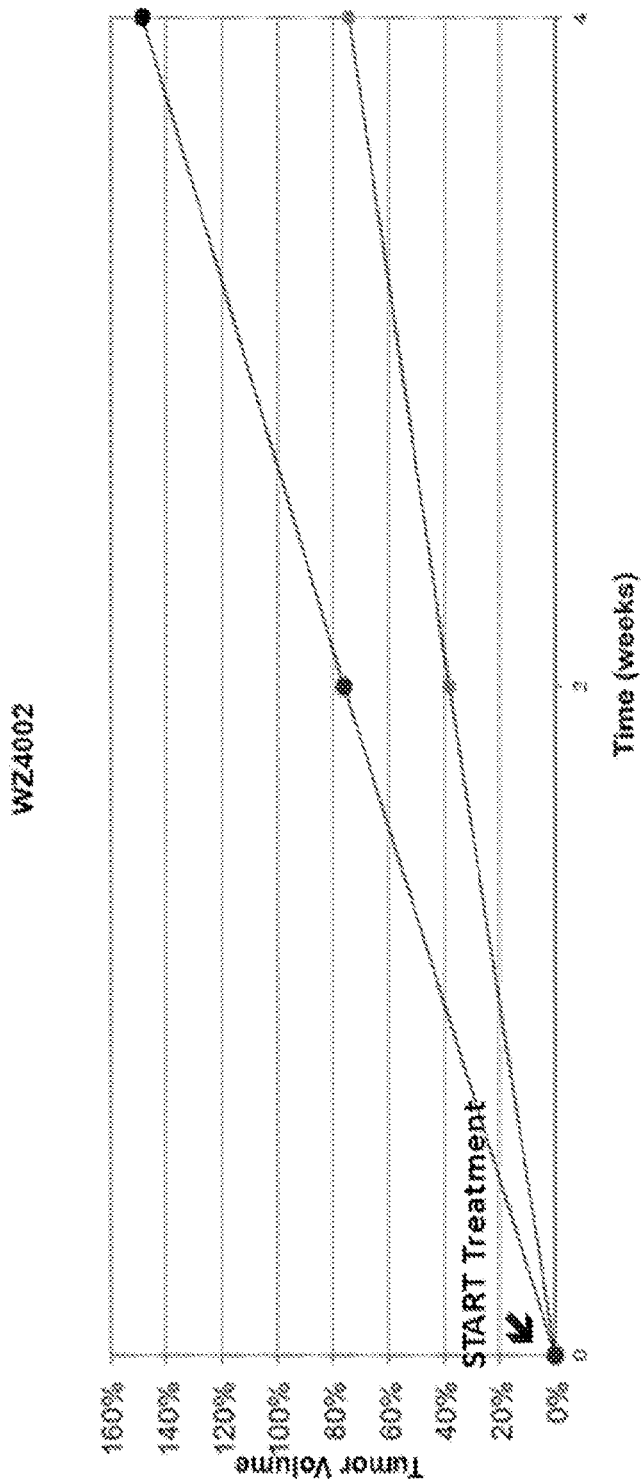
Figure 23:
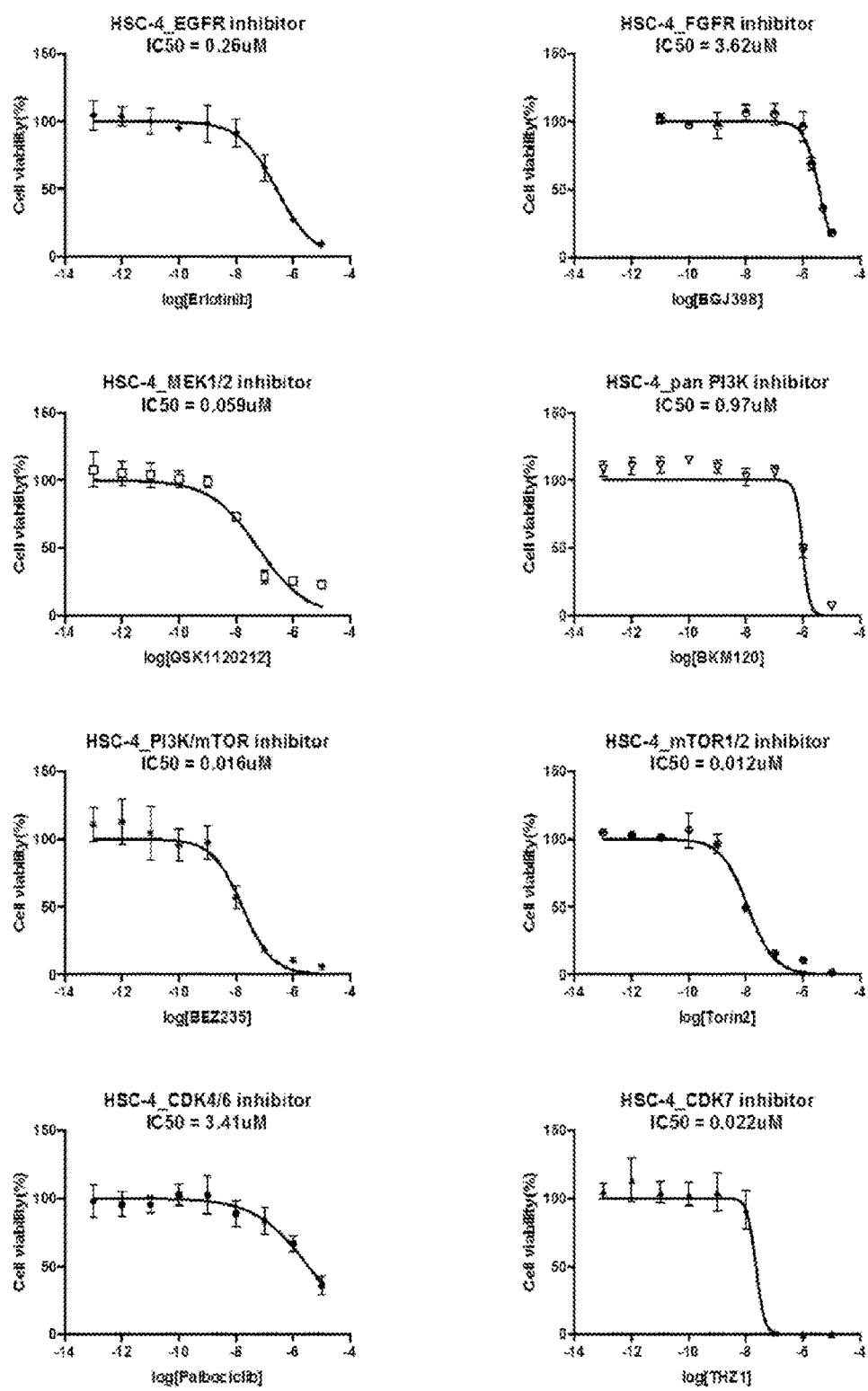
FIG. 23 shows the cell viability of HSC4 (HSC-4) cell lines treated with different drugs. The concentrations of the drugs are in molar.
Figure 24:
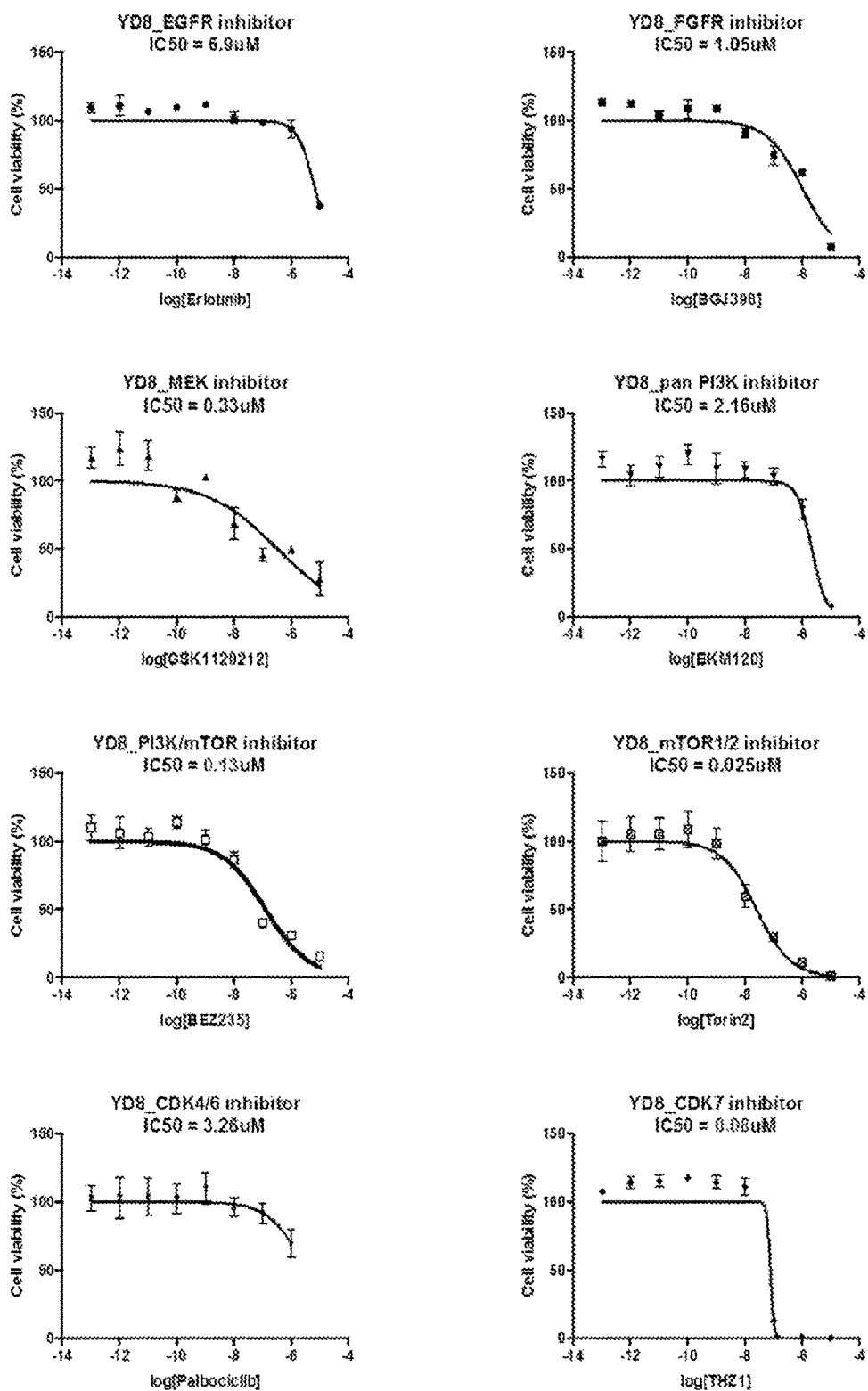
FIG. 24 shows the cell viability of YD8 cell lines treated with different drugs. The concentrations of the drugs are in molar.
Figure 25:
FIG. 25 shows the half maximal inhibitory concentrations of four different cell lines under different treatments.
Figure 25:
Figure 25:
Figure 25:
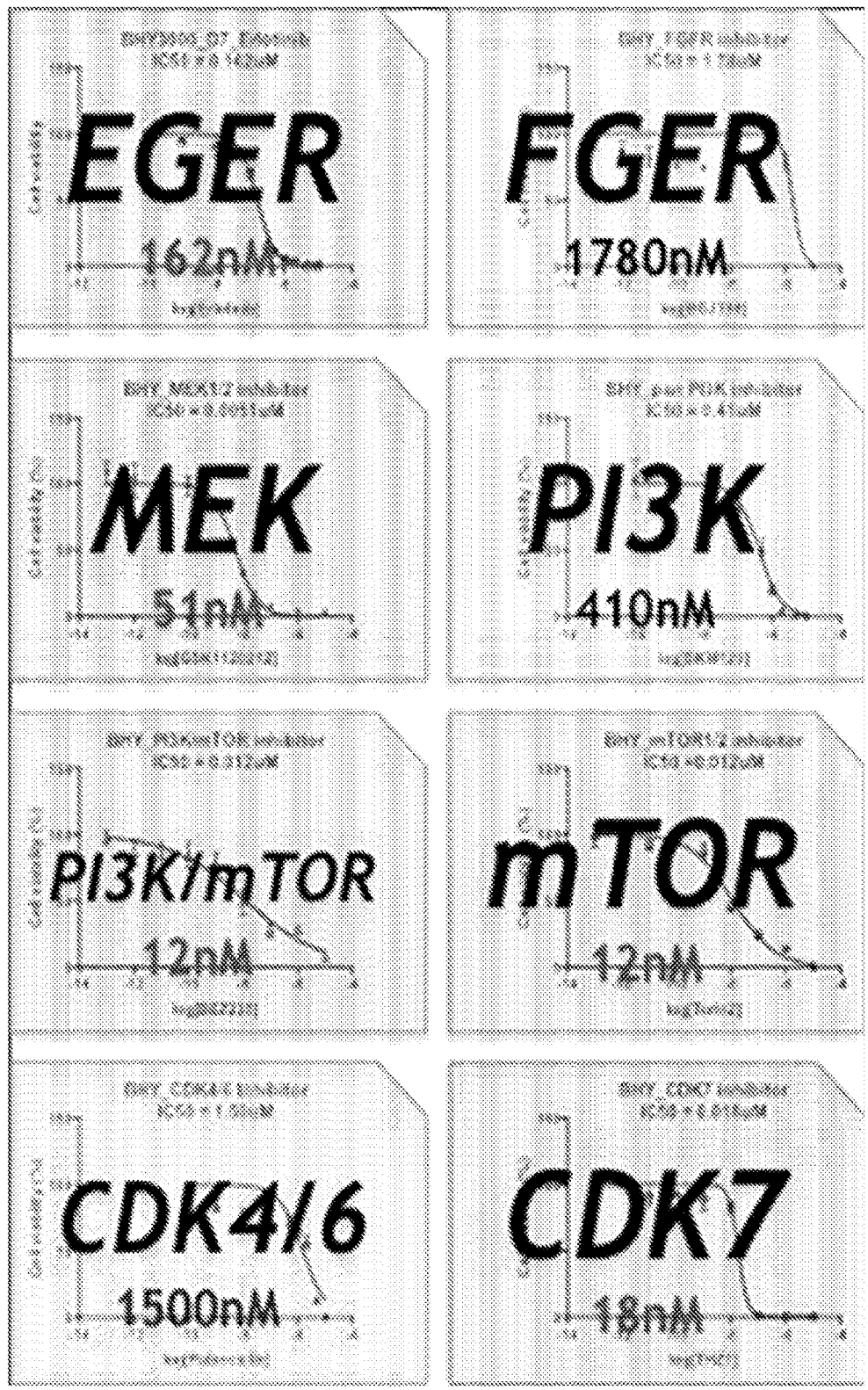
Figure 26:
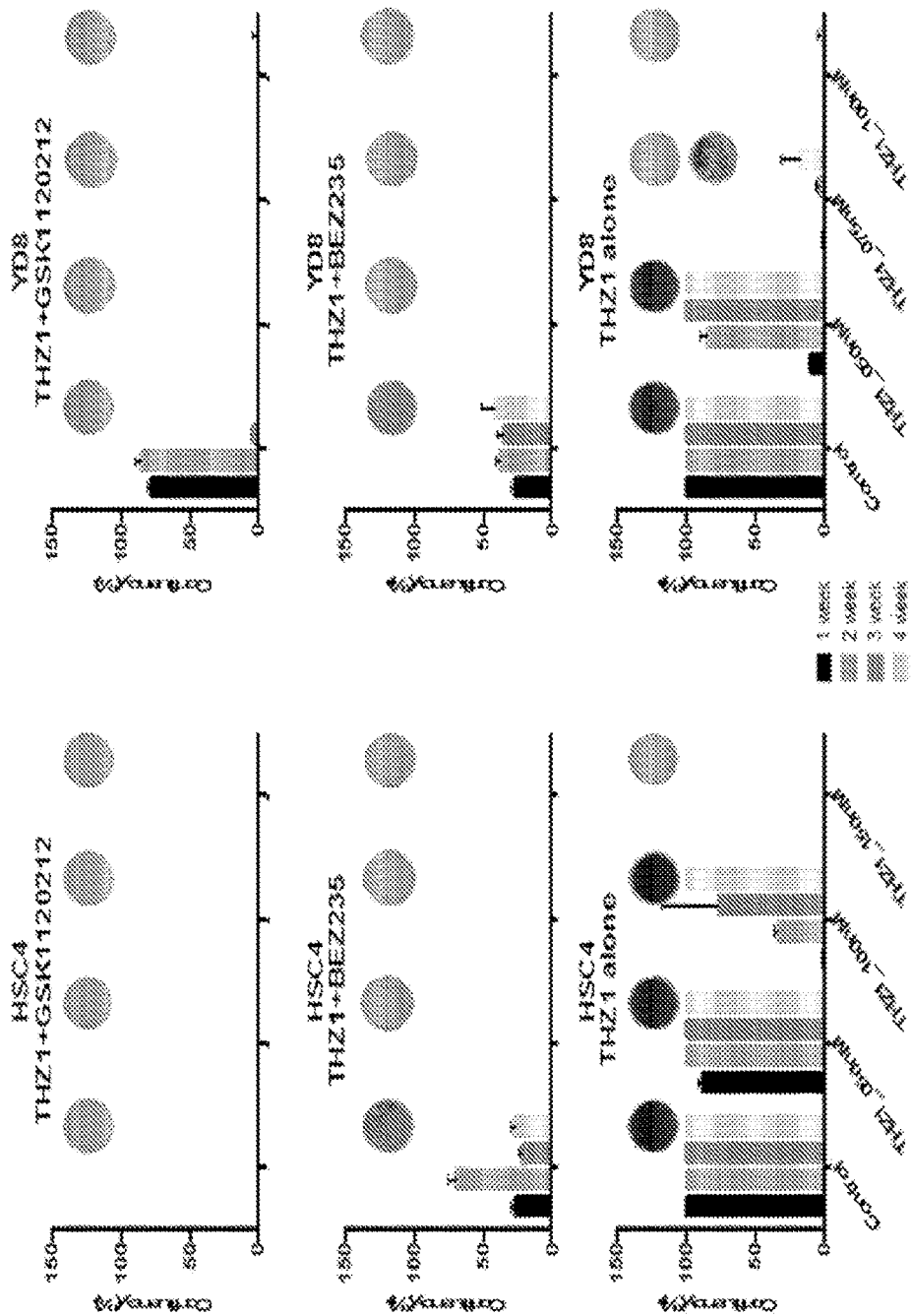
FIG. 26 shows the confluence of HSC4 and YD8 cell lines treated for one to four weeks with a combination of THZ1 and GSK1120212, a combination of THZ1 and BEZ235, or THZ1 alone.
Figure 28:
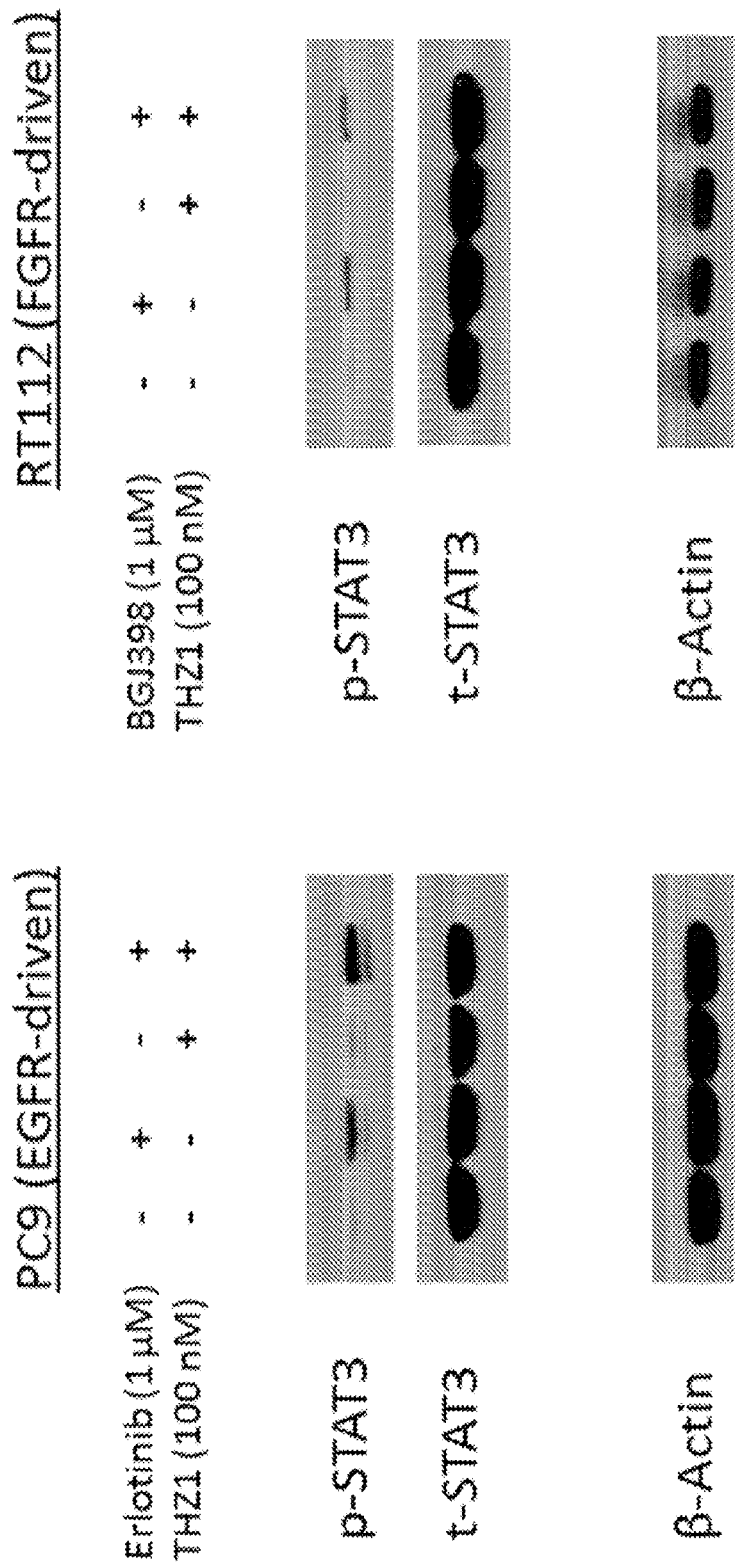
FIG. 28 shows that the feedback activation of STAT3 mediates the resistance and that THZ1 does not inhibit the feedback activation of STAT3 in the PC9 (EGFR-driven) and RT112 (FGFR-driven) cell lines. Treatment with a combination of erlotinib and THZ1 or a combination of BGJ398 and THZ1, for 24 hours, strongly activated STAT3.
Figure 29:
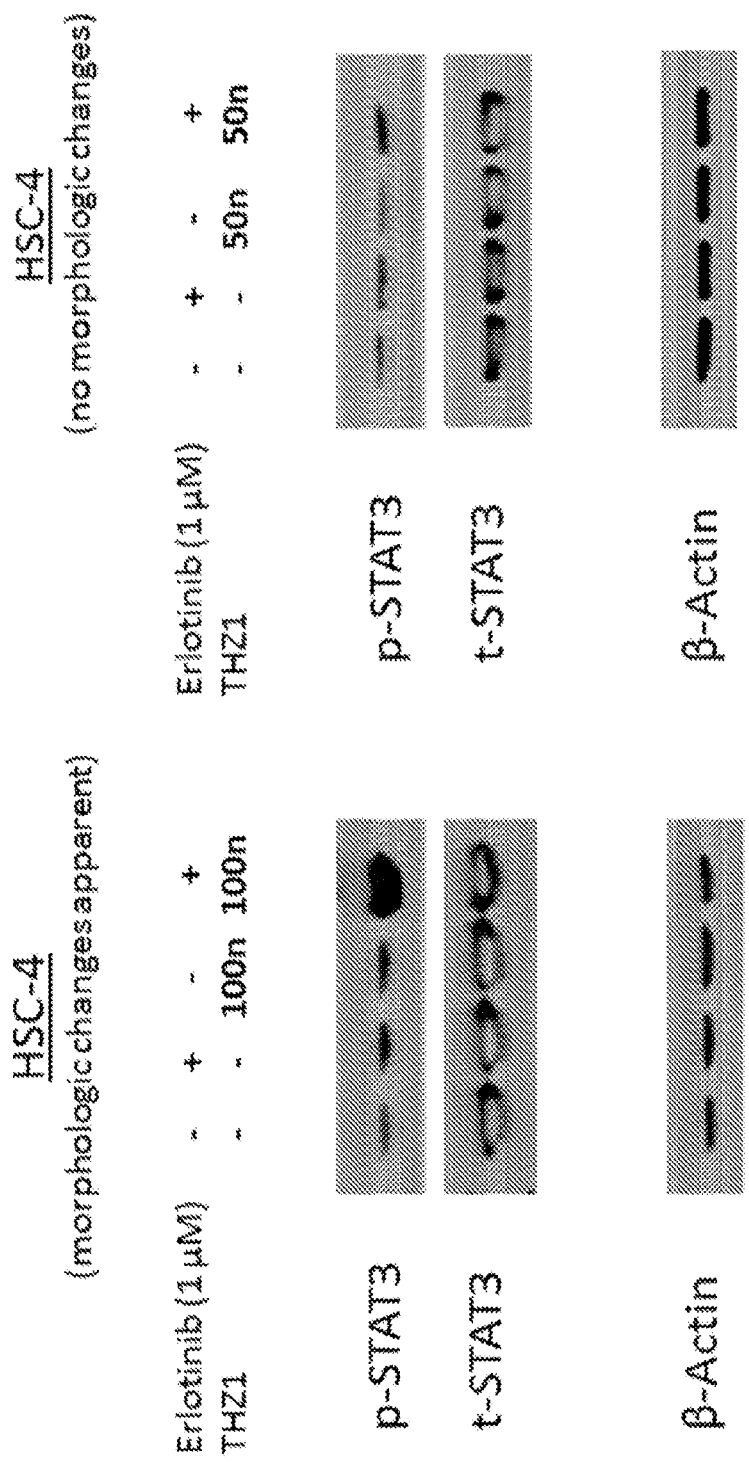
FIG. 29 shows that the feedback activation of STAT3 mediates the resistance and that THZ1 (100 nM, left panel; 50 nM, right panel) does not inhibit feedback activation of STAT3 with regard to cells undergoing morphologic changes. Combined RTK and CDK7 inhibition strongly activates STAT3 at 24 hours after treatment.
Figure 30:
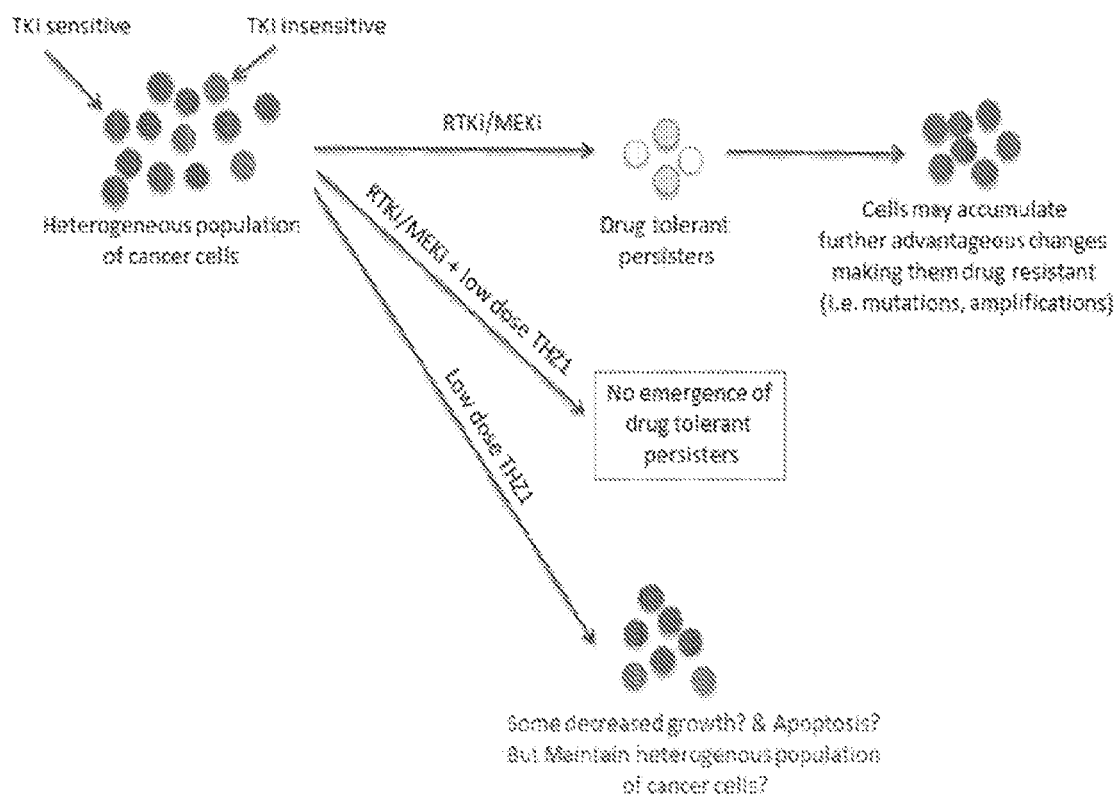
FIG. 30 shows a proposed mechanism that a combination of THZ1 and an RTK inhibitor (RTKi) or a combination of THZ1 and a MEK inhibitor (MEKi) prevents the emergence of drug resistance.
Figure 31:
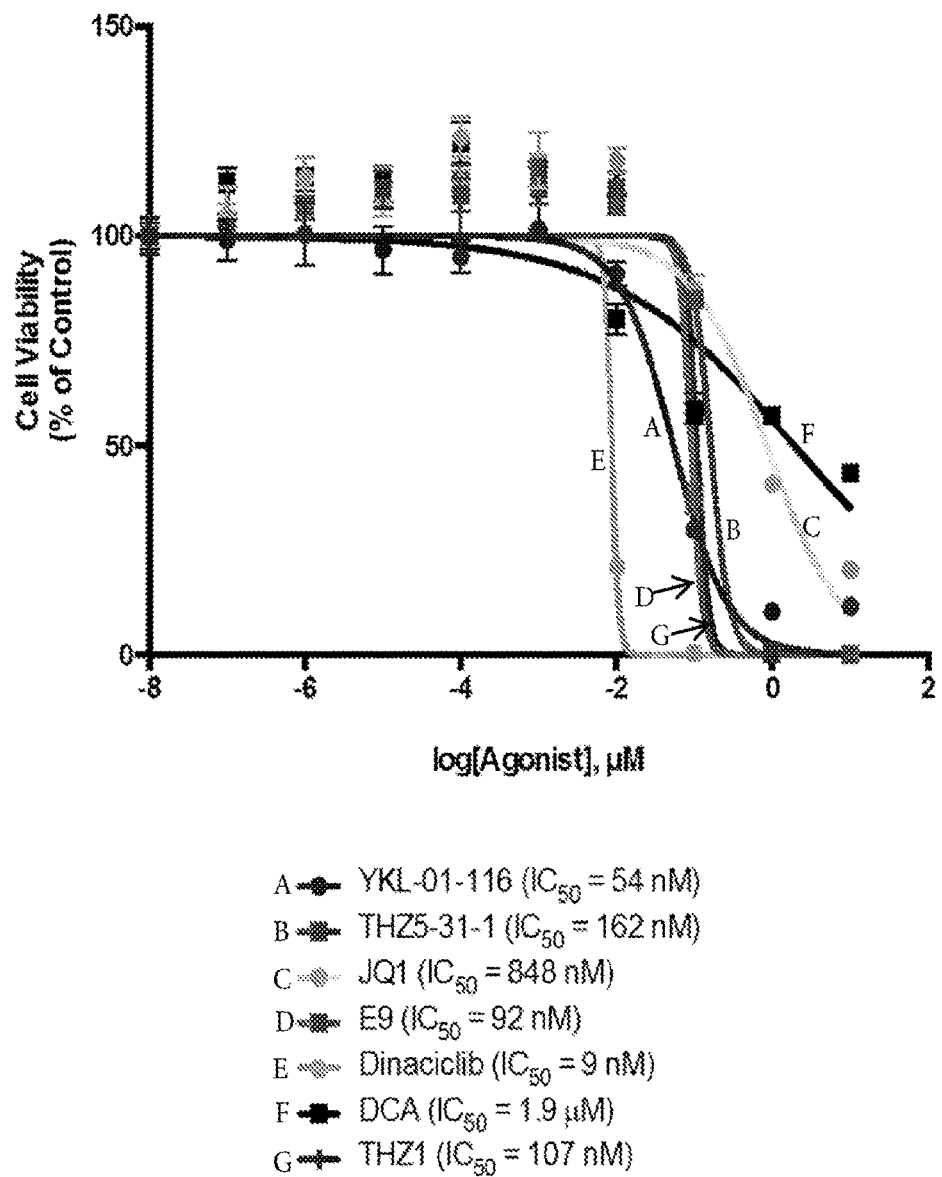
FIG. 31 shows the cell viability of RT 112 cells using a CELLTITER-GLO assay. RT112 cells were treated for 96 hours with YKL-01-116, THZ5-31-1, JQ1, E9, dinaciclib, DCA, or THZ1. [Agonist]: concentration of YKL-01-116, THZ5-31-1, JQ1, E9, dinaciclib, DCA, or THZ1, in µM.
Figure 32:
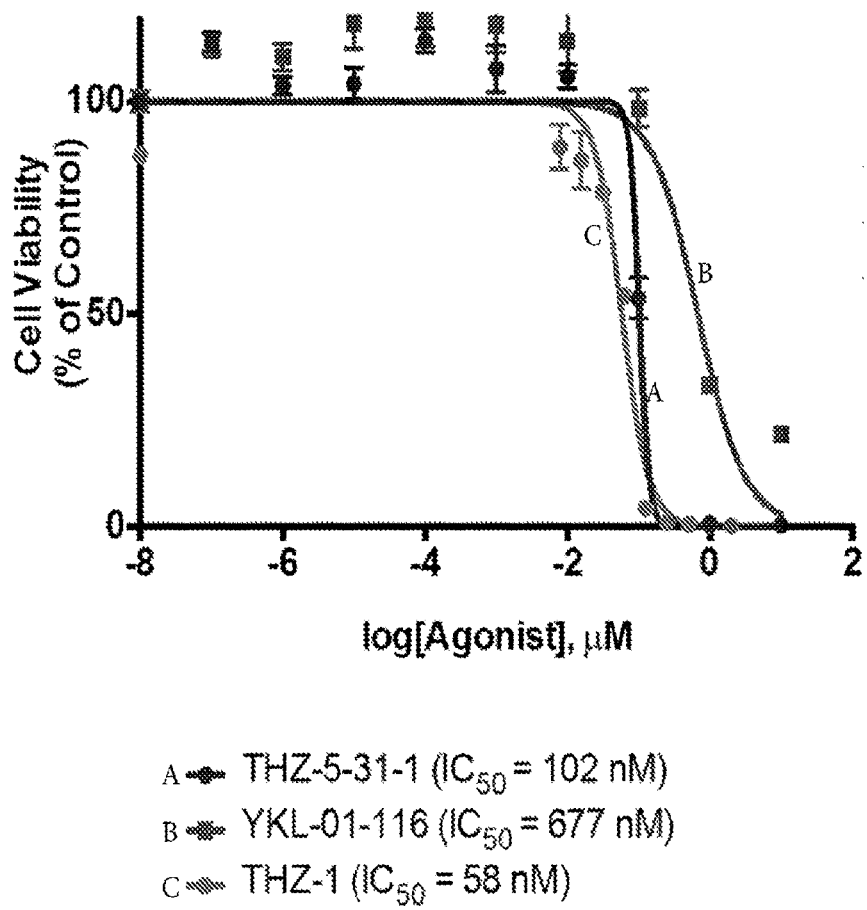
FIG. 32 shows the cell viability of PC9 cells using a CELLTITER-GLO assay. PC9 cells were treated for 96 hours with YKL-01-116, THZ5-31-1, or THZ1. [Agonist]: concentration of YKL-01-116, THZ5-31-1, or THZ1, in µM.
Figure 33:
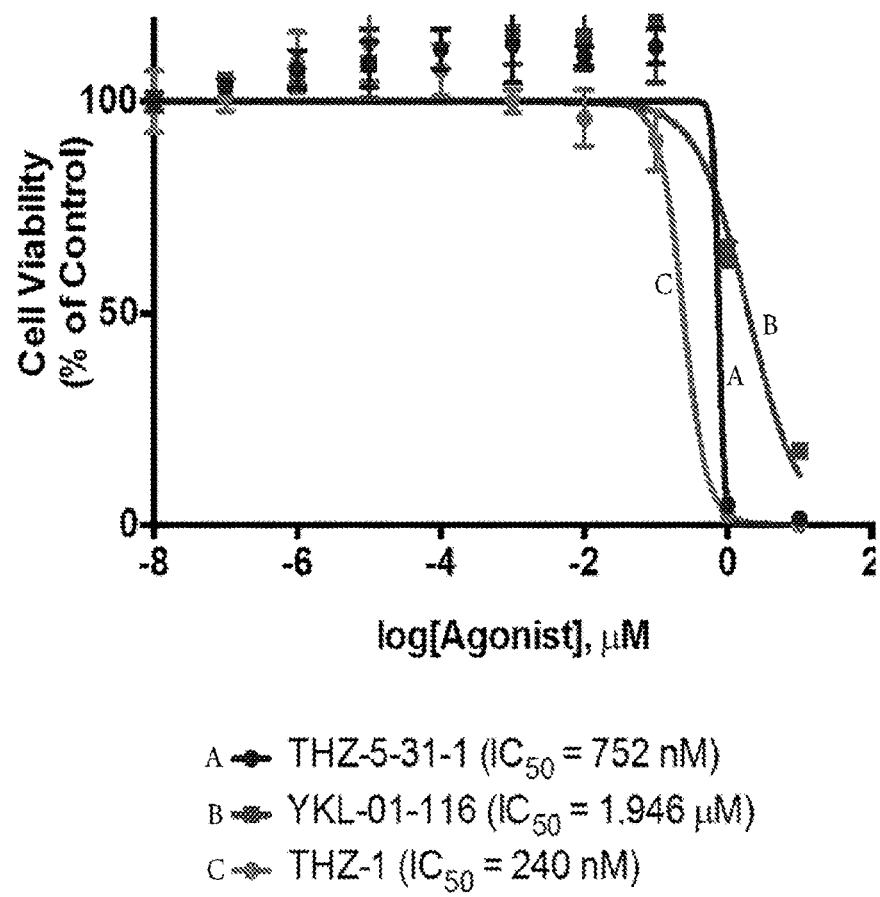
FIG. 33 shows the cell viability of A549 cells using a CELLTITER-GLO assay. A549 cells were treated for 96 hours with YKL-01-116, THZ5-31-1, or THZ1. [Agonist]: concentration of YKL-01-116, THZ5-31-1, or THZ1, in µM.
Figure 34:
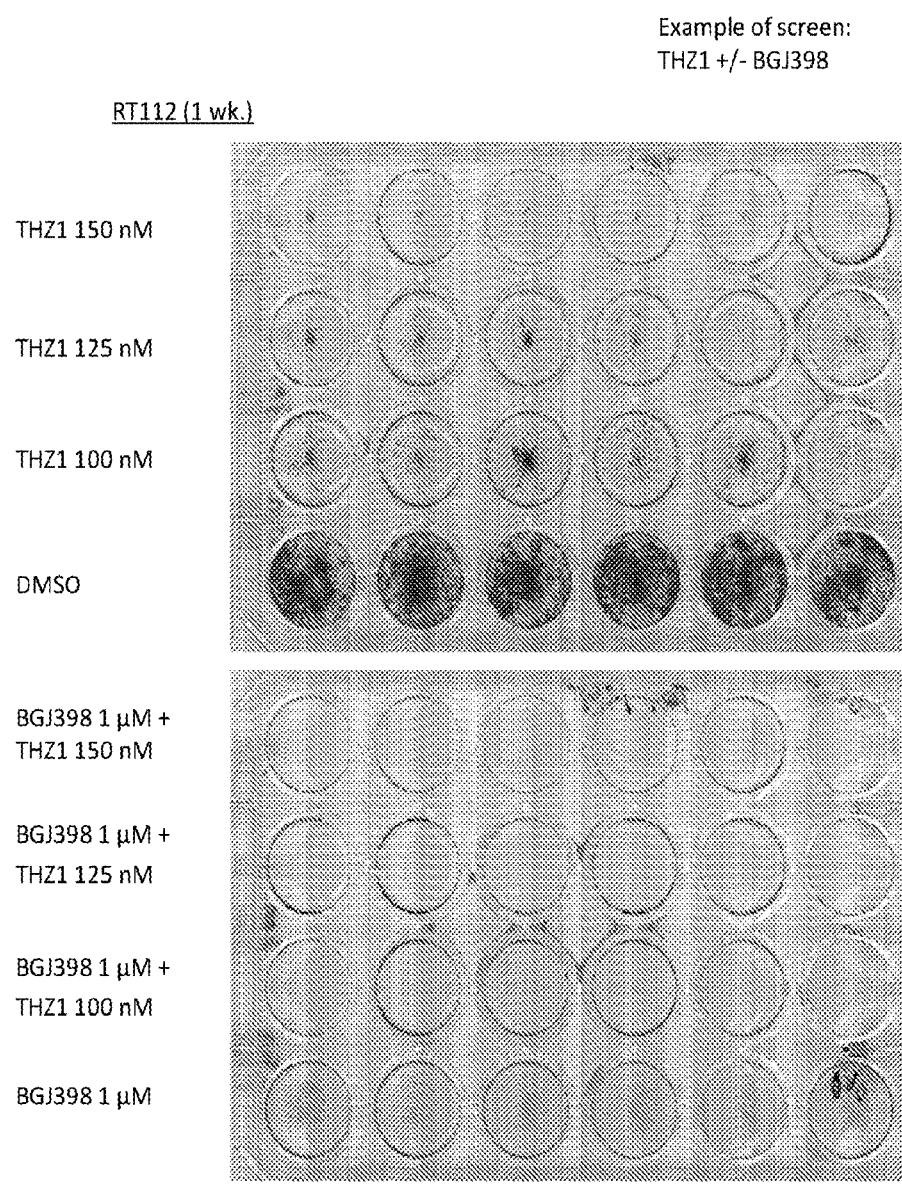
FIG. 34 shows images of stained RT112 cell colonies after treating RT112 cells for one week with THZ1, BGJ398, or a combination of THZ1 and BGJ398.
Figure 35:
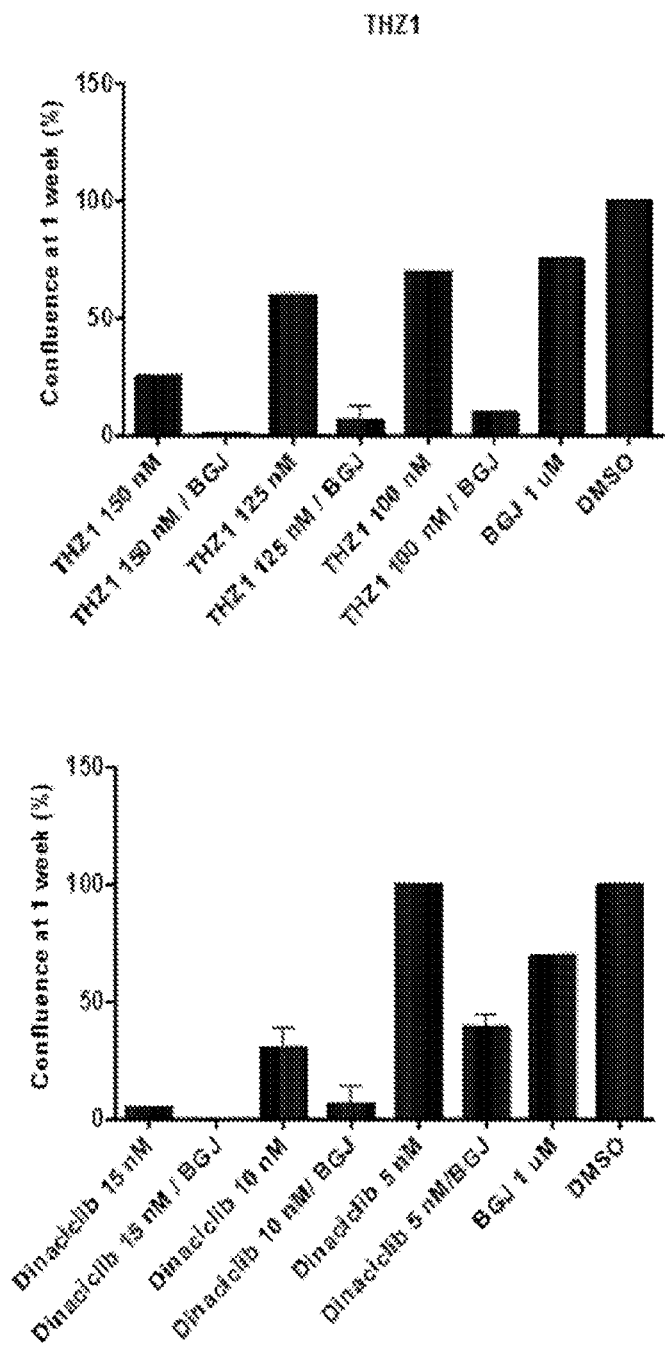
FIG. 35 shows the results of a colony formation assay. RT112 cells in a 24-well plate were treated for one week with THZ1, a combination of THZ1 and BGJ398, dinaciclib, a combination of dinaciclib and BGJ398, E9, a combination of E9 and BGJ398, JQ1, a combination of JQ1 and BGJ398, DCA, or a combination of DCA and BGJ398. BGJ: BGJ398.
Figure 35:
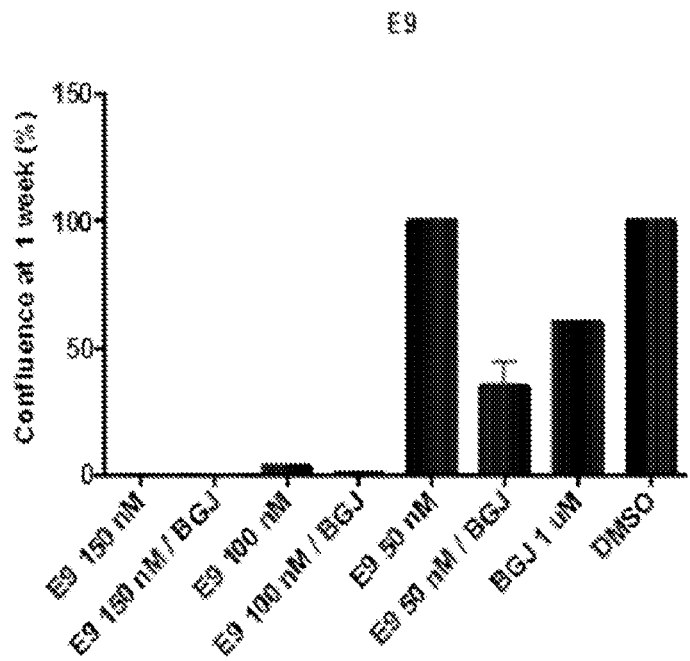
Figure 35:
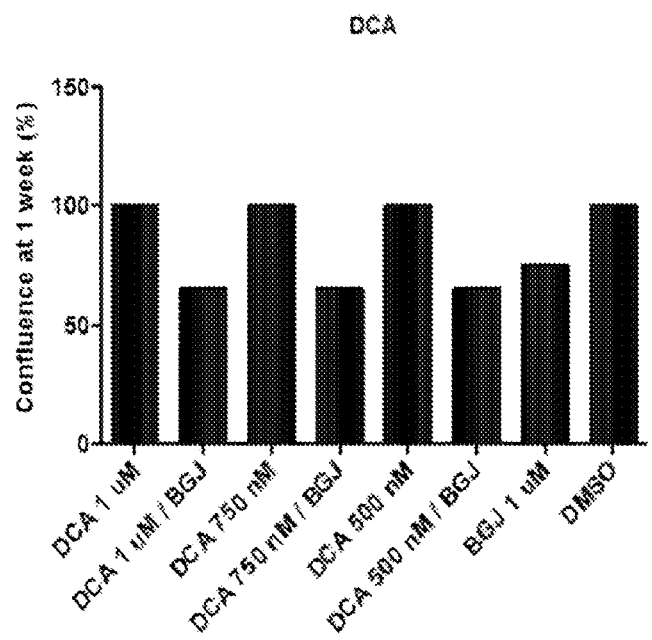
Figure 36:
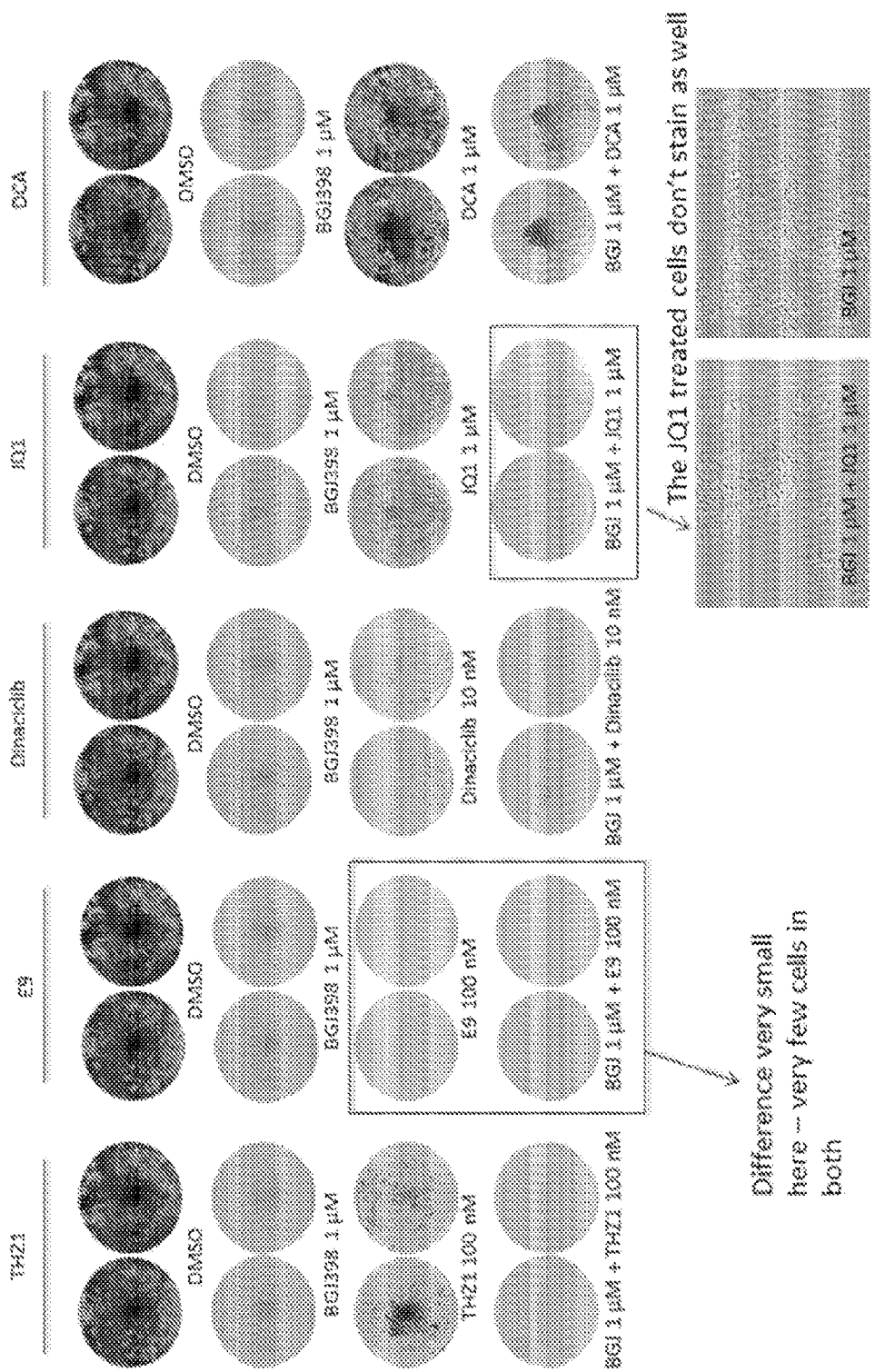
FIG. 36 shows images of the stained RT112 cell colonies in FIG. 35. BGJ: BGJ398.
Figure 37:
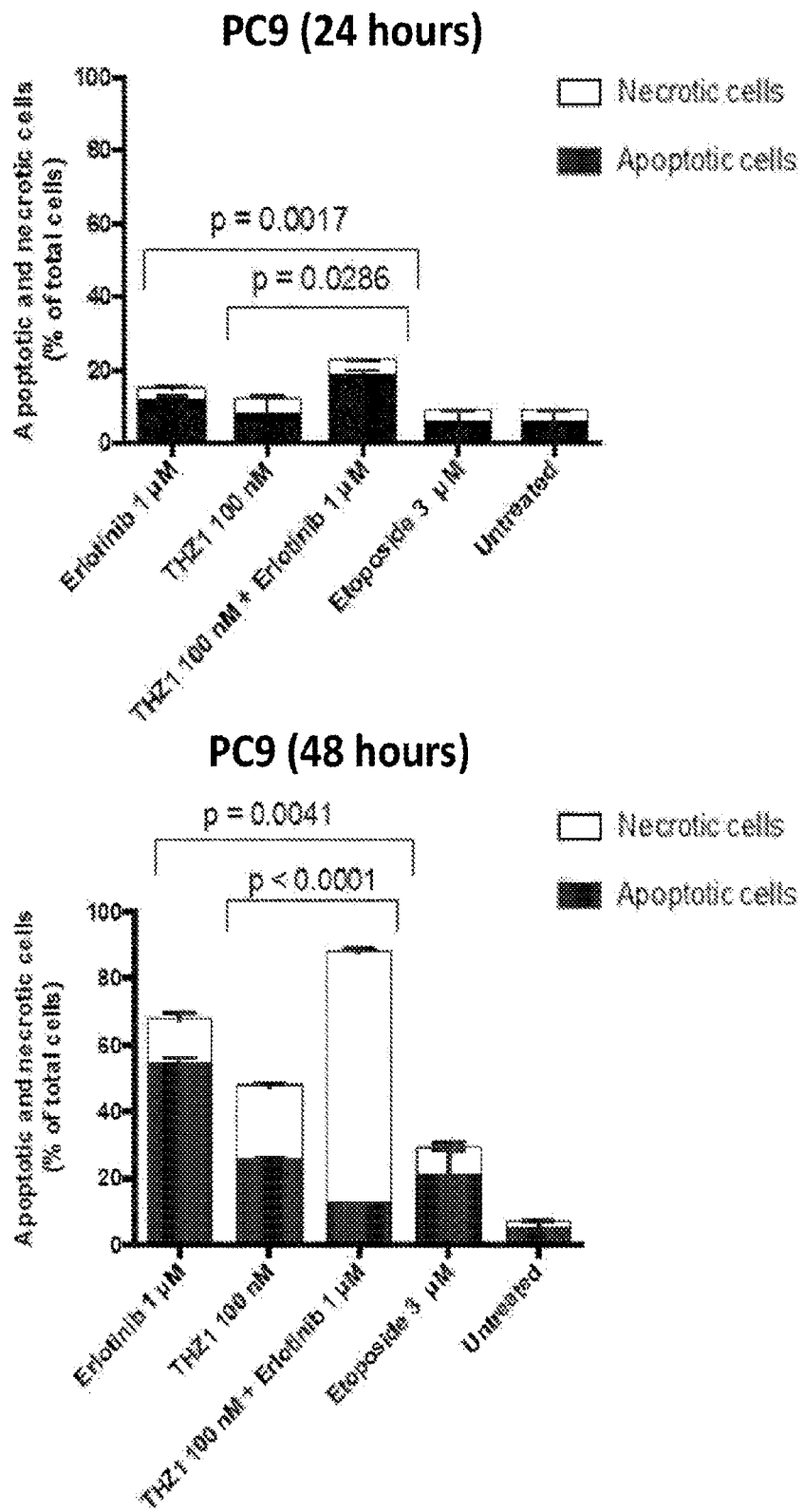
FIG. 37 shows the percentage of apoptotic (annexin-positive) and necrotic (double-positive) PC9 cells after 24 and 48 hours of the indicated treatments. A statistically significant increase was observed at 24 hours for the cells treated with a combination of erlotinib and THZ1, compared with the cells treated with erlotinib alone or THZ1 alone, and such increase was more apparent at 48 hours.
Figure 38:
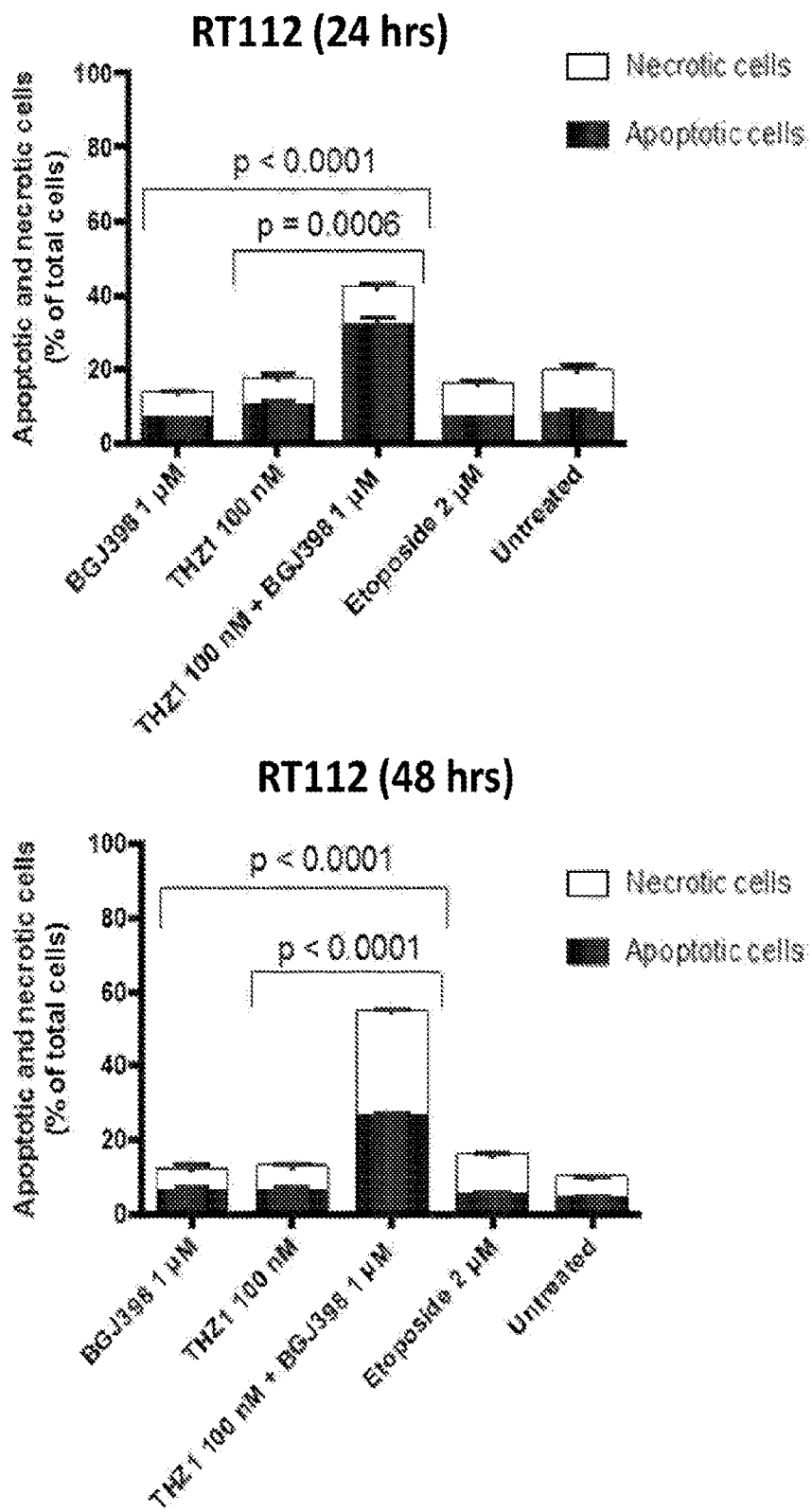
FIG. 38 shows the percentage of apoptotic (annexin-positive) and necrotic (double-positive) RT112 cells after 24 and 48 hours of the indicated treatments.
Figure 39:
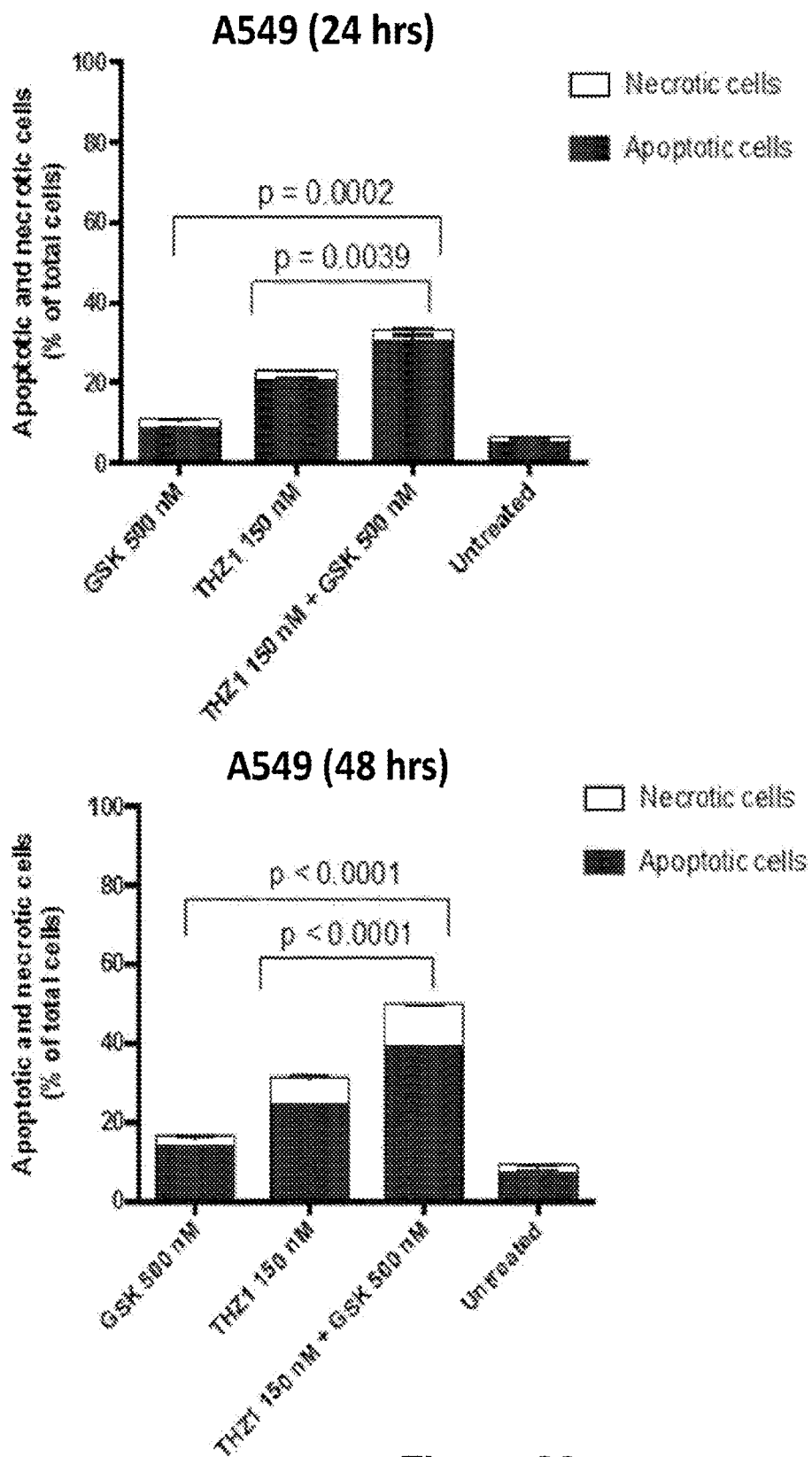
FIG. 39 shows the percentage of apoptotic (annexin-positive) and necrotic (double-positive) A549 cells after 24 and 48 hours of the indicated treatments. A statistically significant increase in cell death was overserved for the combination treatment, compared with the treatments that did not involve a combination.

In PC9 cells treated with erlotinib, THZ1, erlotinib and THZ1 ("combination treatment"), or untreated, there are statistically significant increases in the combination treatment group as compared to erlotinib alone or THZ alone (FIG. 37). This difference is even more pronounced after 48 hours of treatment (FIG. 37). The same trend is found in RT112 cells treated with BGJ398 and THZ1 (FIG. 38) and A549 cells treated with GSK and THZ1 (FIG. 39).

Proliferation of Guides

Figure 41:
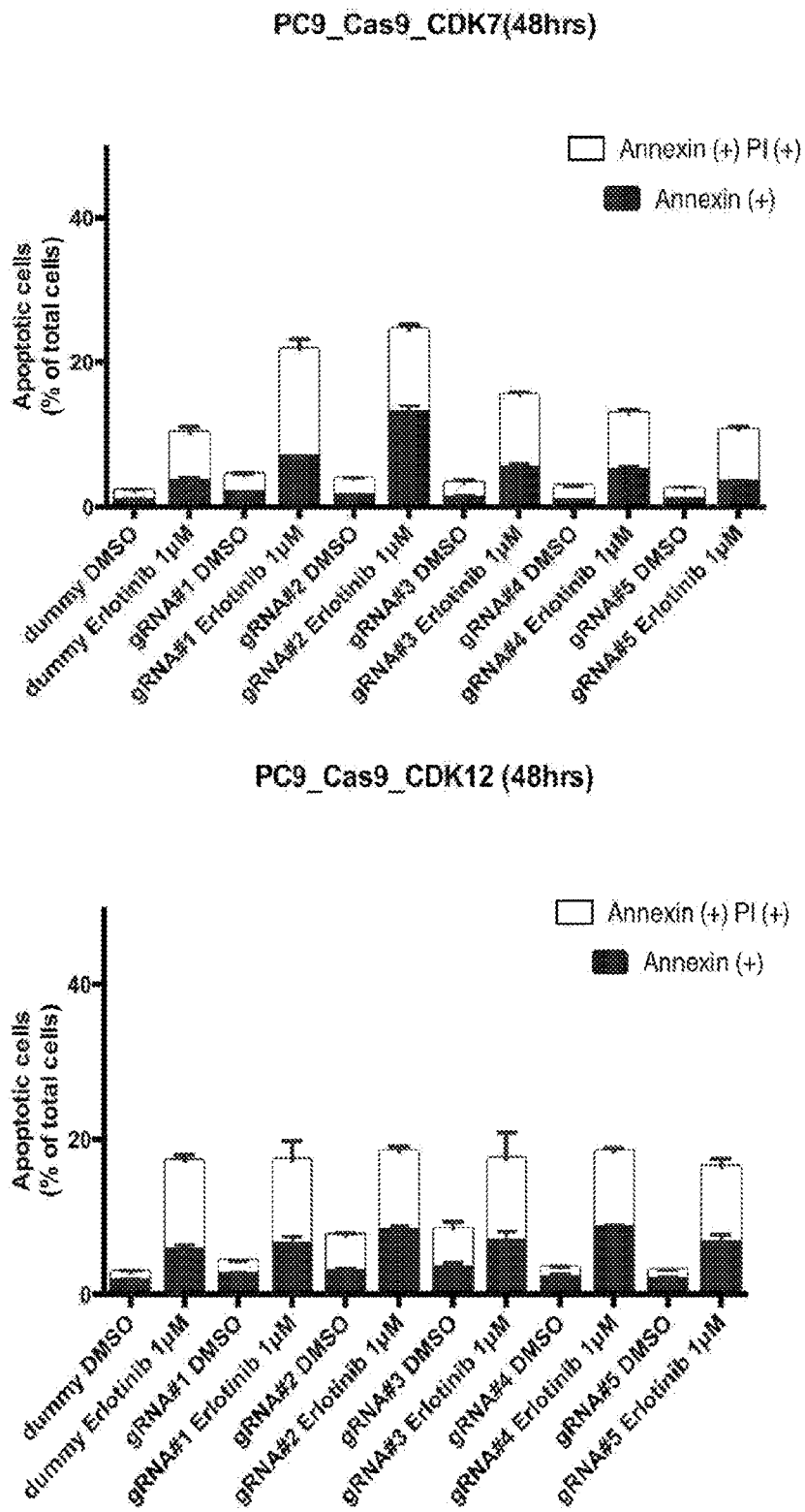
FIG. 41 shows the increased cell death after treatment with erlotinib alone or erlotinib with the various guides for CDK7 (left graph) and CDK12 (right graph). n was 2 for each group in the CDK7 experiment, and n was 3 for each group in the CDK12 experiment.

For CDK7, guides 2, 3 and 5 showed the greatest effect on proliferation, and for CDK12, guides 1, 3, and 5 had the strongest effect on proliferation (FIG. 40). Under the same conditions used in the initial apoptosis analysis, apoptosis with erlotinib and erlotinib with the various guides for CDK7 and CDK12 was examined (FIG. 41). The data is similar to the effect seen with THZ1, both with the CDK7 CRISPR, and with the CDK12 CRISPR.

Xenograft Studies

The effects of the combination therapy were further studying in vivo in a number of xenograft models. First, PC9, an EGFR-dependent cell line, was used. There was a significant increase in survival in the combination treatment group and in the time to reach the maximum tumor volume (FIG. 42). The increase in survival between the MEK inhibitor and the combination treatment was not readily apparent until after week 7 (FIG. 42).

Figure 43A:
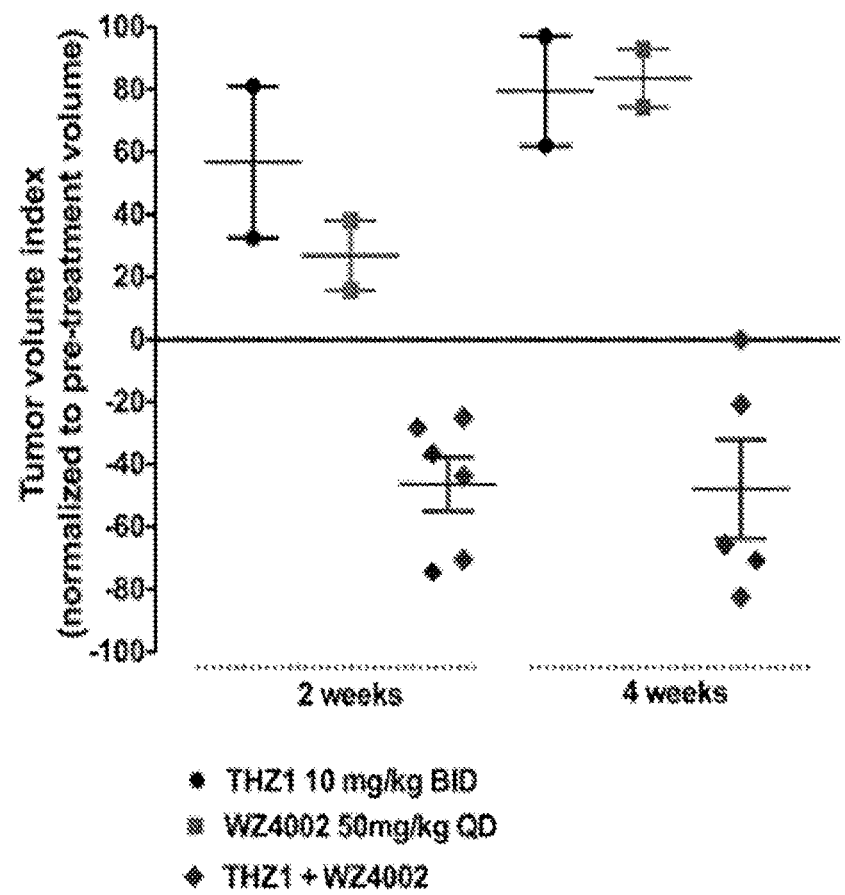
FIG. 43A shows the results of an experiment in a GEM model dependent on EGFR, where the EGFR allele has two mutations: an L858R and a T790M. The mice receiving the combination treatment (diamond symbols) show substantially smaller tumor volumes at both two and four weeks, as compared to mice treated with the individual components of the treatment.

The therapy was next tested in a GEM model, which is also dependent on EGFR, where the EGFR allele has two mutations: the L858R mutation and T790M mutation. The mice receiving the combination treatment showed lower tumor volume indices (tumor volume normalized to pretreatment volume) than the mice that received THZ1 only or WZ4002 only at 2 weeks and 4 weeks (FIG. 43A). One mouse is doing particularly well 16 weeks into the combination treatment (FIG. 43B).

Involved Signaling Pathways

Figure 44A:
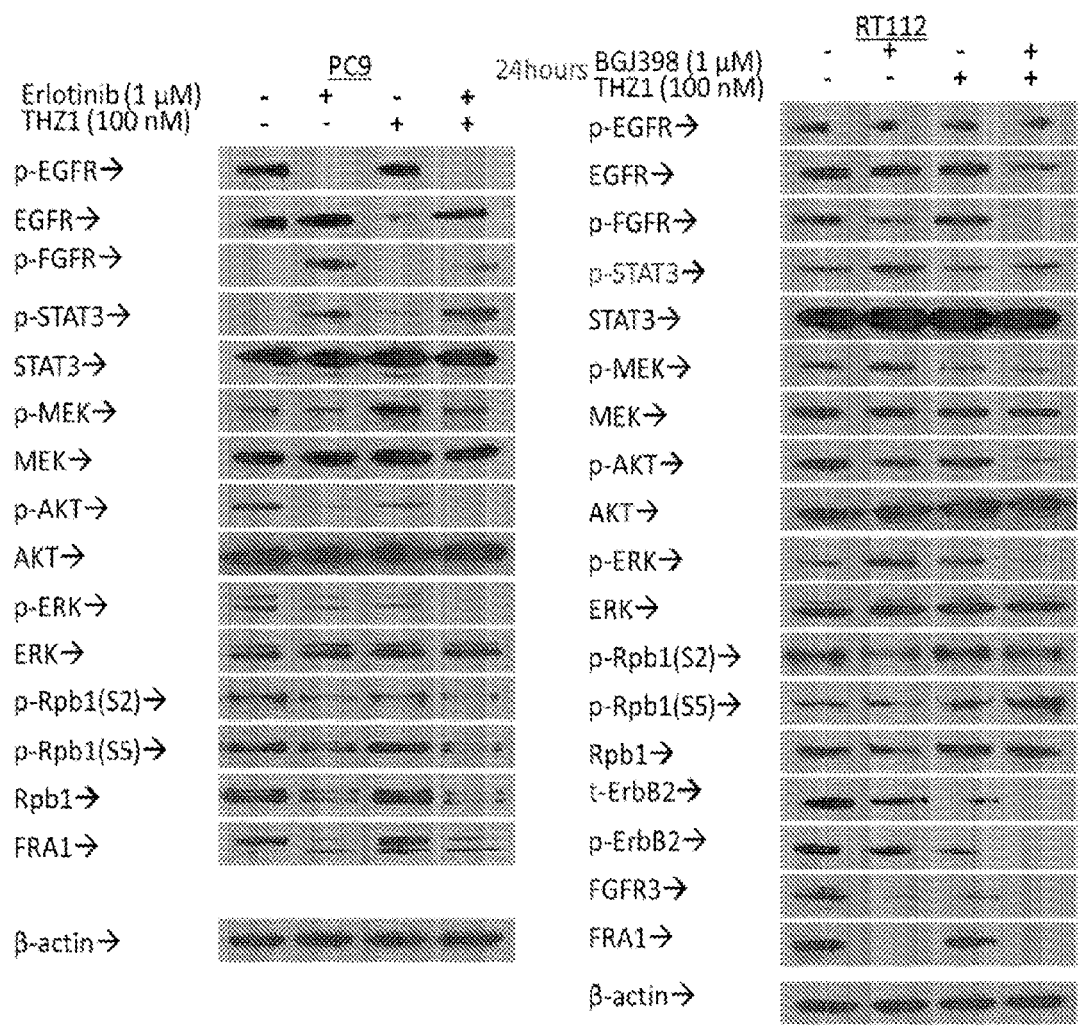
FIG. 44A shows Western blot results for the PC9 and RT112 cell lines. After 24 hours of no treatment, treatment with 1 µM erlotinib, treatment with 100 nM THZ1, or treatment with a combination of 1 µM erlotinib and 100 nM THZ1, signaling pathways were characterized. The doses used were identical to those used in the colony formation assays and RNAseq and ChIPseq experiments. Notably, p-STAT3 increases with erlotinib treatment, as expected based on what is disclosed in Sharma et al. (*Cell*, 2010, 141(1):69-80) and increases further with the combination treatment in PC9 cells. The same trend was also observed in the RT112 line. The data show that THZ1 is not blocking the activation of p-STAT3, but still may be blocking the activation of STAT3 targets. With erlotinib treatment, FGFR, a known bypass mechanism in PC9, is activated. The activation is not seen with THZ1 or with the combination treatment. Similar results are shown in the RT112 cell line with ERBB2. Therefore, the combination treatment blocks the potential bypass mechanism. In addition, a decrease in p-ERK in both the PC9 and RT112 cell lines was noted from the combination treatment. There was also an increase in RNAPII phosphorylation at 24 hours, which was decreased somewhat by the combination treatment. This is unexpected, given that THZ1 should block CDK7-mediated RNAPII phosphorylation. The finding may be related to the dose or time point assayed.

Western blots were used to characterize the signaling pathways in selected cell lines. The assays were performed at 24 hours under the following conditions: untreated, treated with 1 µM erlotinib, treated with 100 nM THZ1, or treated with a combination of erlotinib and THZ1, in PC9 and RT112 cells. These doses were also used in the colony formation assays and the RNAseq and ChIPseq experiments. It was observed that p-STAT3 increases with erlotinib treatment, as expected based on what is disclosed in Sharma et al., *Cell,* 2010, 141(1):69-80, and also that p-STAT3 levels were further increased with the combination (FIG. 44A). This is somewhat true in RT112 cells as well, so THZ1 is not blocking the activation of p-STAT3. However, it could be blocking the activation of downstream STAT3 targets. With erlotinib treatment, the activation of FGFR was also observed. FGFR is known to be a bypass mechanism in PC9, but this was not seen with THZ1 treatment or with the combination treatment. Similar findings were revealed in RT 112 with ERBB2: with the combination treatment, the potential bypass mechanism is blocked.—In addition, in both the PC9 and RT112 cell lines, there was a decrease in p-ERK in the combination treatment. Also, there is an increase in RNAPII phosphorylation with THZ1 at this time point, while the combination treatment yields a slight decrease. This is unexpected, given that THZ1 should block CDK7-mediated RNAPII phosphorylation. This may be due to the dose or the time point assayed.

Figure 44B:
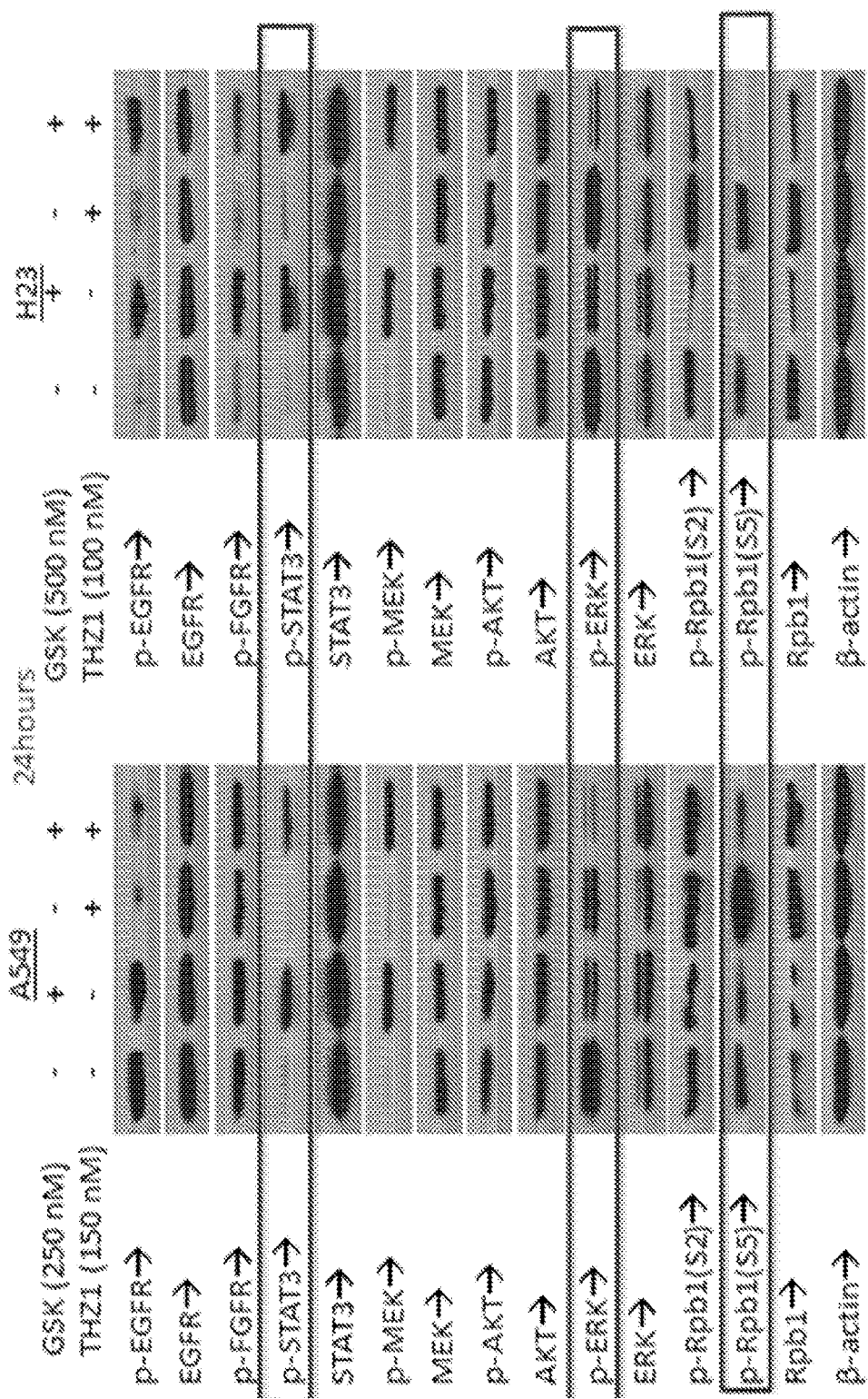
FIG. 44B shows Western blot results for the A549 and H23 cell lines under the same conditions as in FIG. 44A. p-STAT3 was increased with MEK inhibition and with the combination treatment. Both the A549 and H23 cell lines were shown to employ the STAT3 feedback loop in Sharma et al., Cell, 2010, 141(1):69-80. p-ERK was decreased with the combination treatment in both cell lines. RNAPII phosphorylation was increased with THZ1 treatment.
Figure 45A:
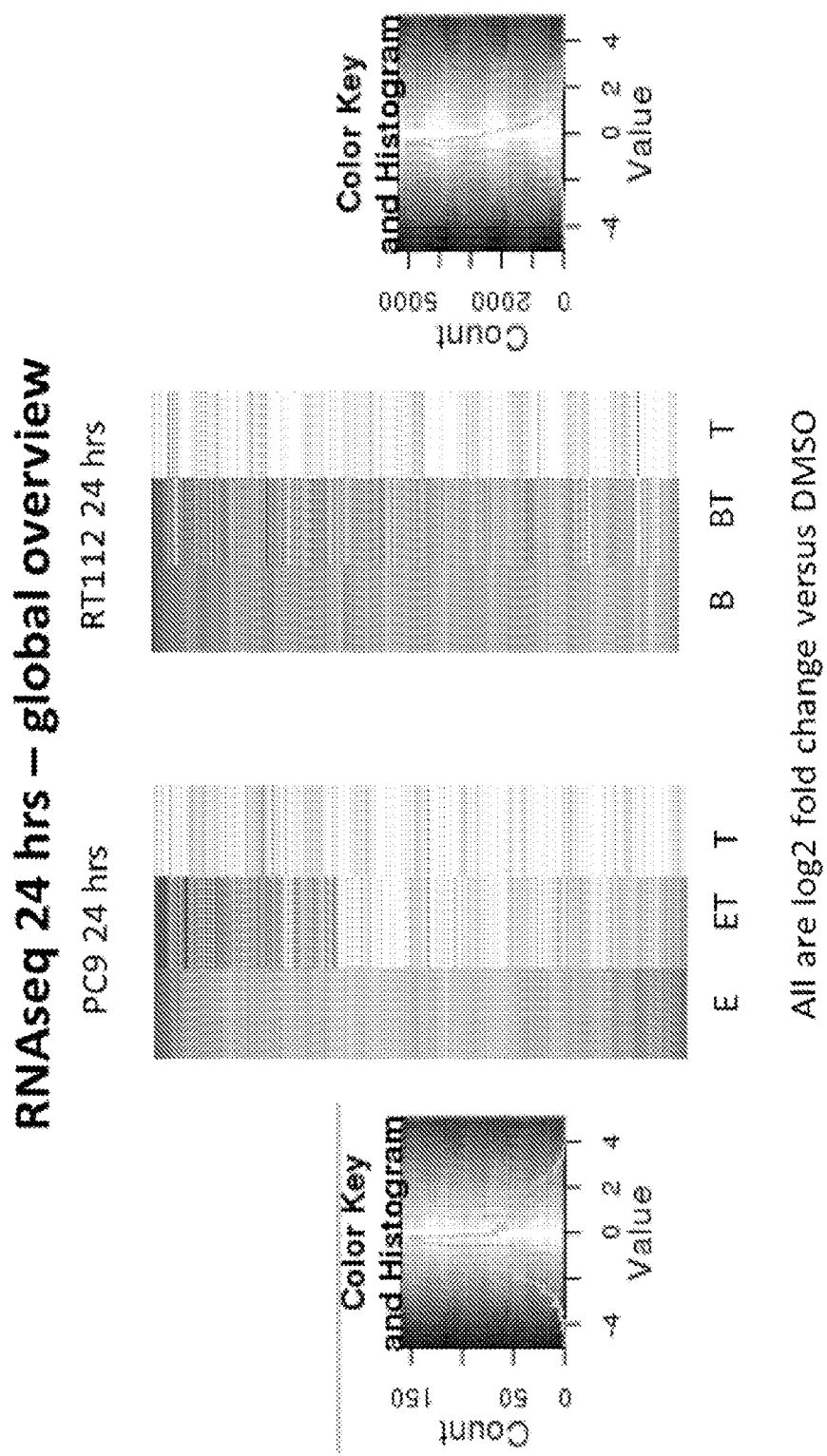
FIG. 45A shows RNAseq results at 24 hours to look for differences between cells treated with a TKI (tyrosine kinase inhibitor, e.g., erlotinib (E) or BGJ398 (B)), cells treated with THZ1 (T), and cells treated with a combination of a TKI or THZ1 (e.g., a combination of erlotinib and THZ1 (ET) or a combination of BGJ398 and THZ1 (BT)). This is a global overview of the data showing only the upregulated genes and the downregulated genes with the TKI, and the corresponding changes with the combination treatment and the THZ1 treatment. Overall, what was seen includes attenuation of the genes upregulated with erlotinib or BGJ398, with the combination treatment. There are also important differences in the genes that are downregulated for example MAPK repressors, such as SPRY and SPRED, are downregulated with the TKI treatment but much less so with the combination treatment. Similarly, cell cycle genes that are downregulated with the TKI are much less affected by the combination treatment.
Figure 45B:
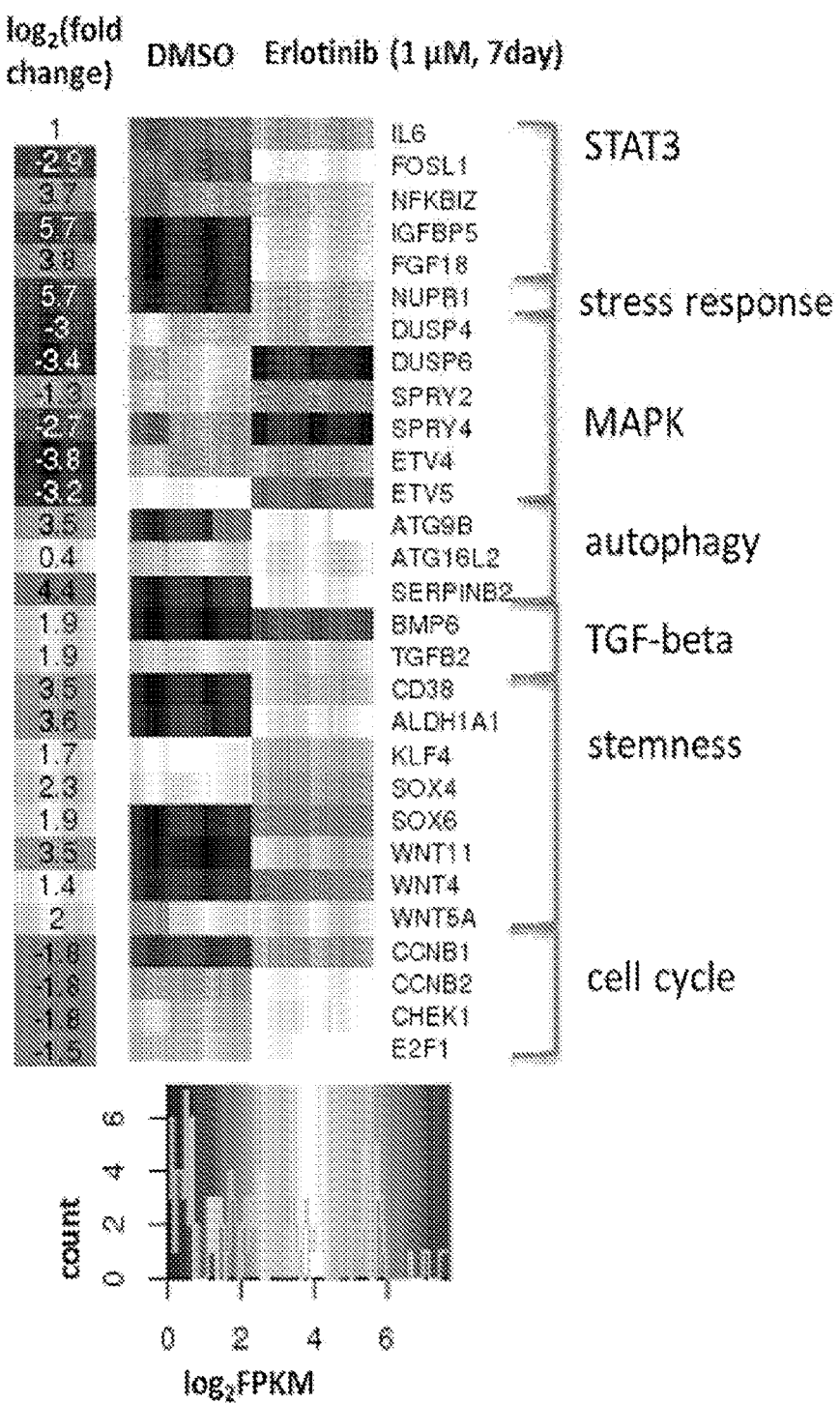
Figure 45D:
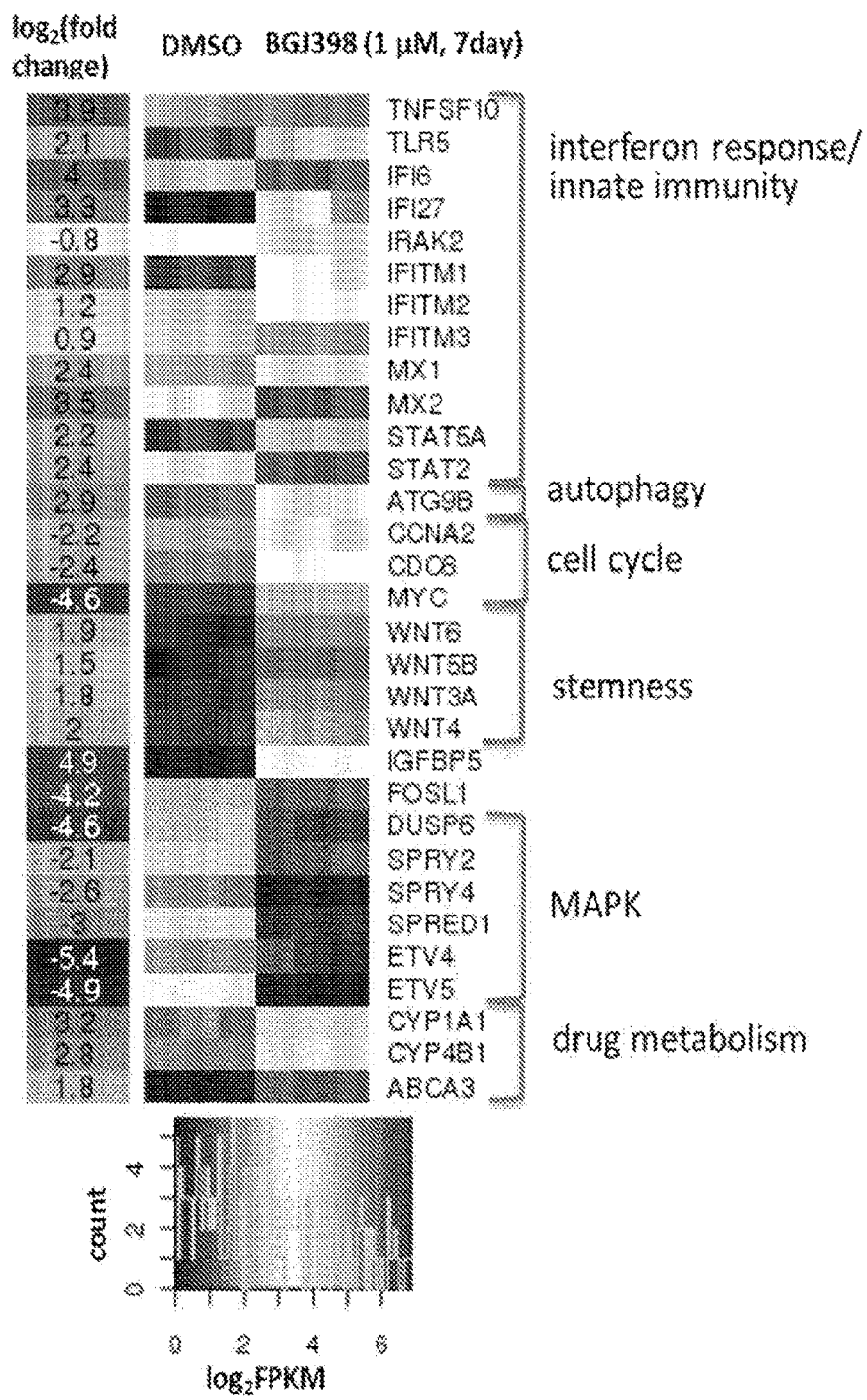
Figure 46:
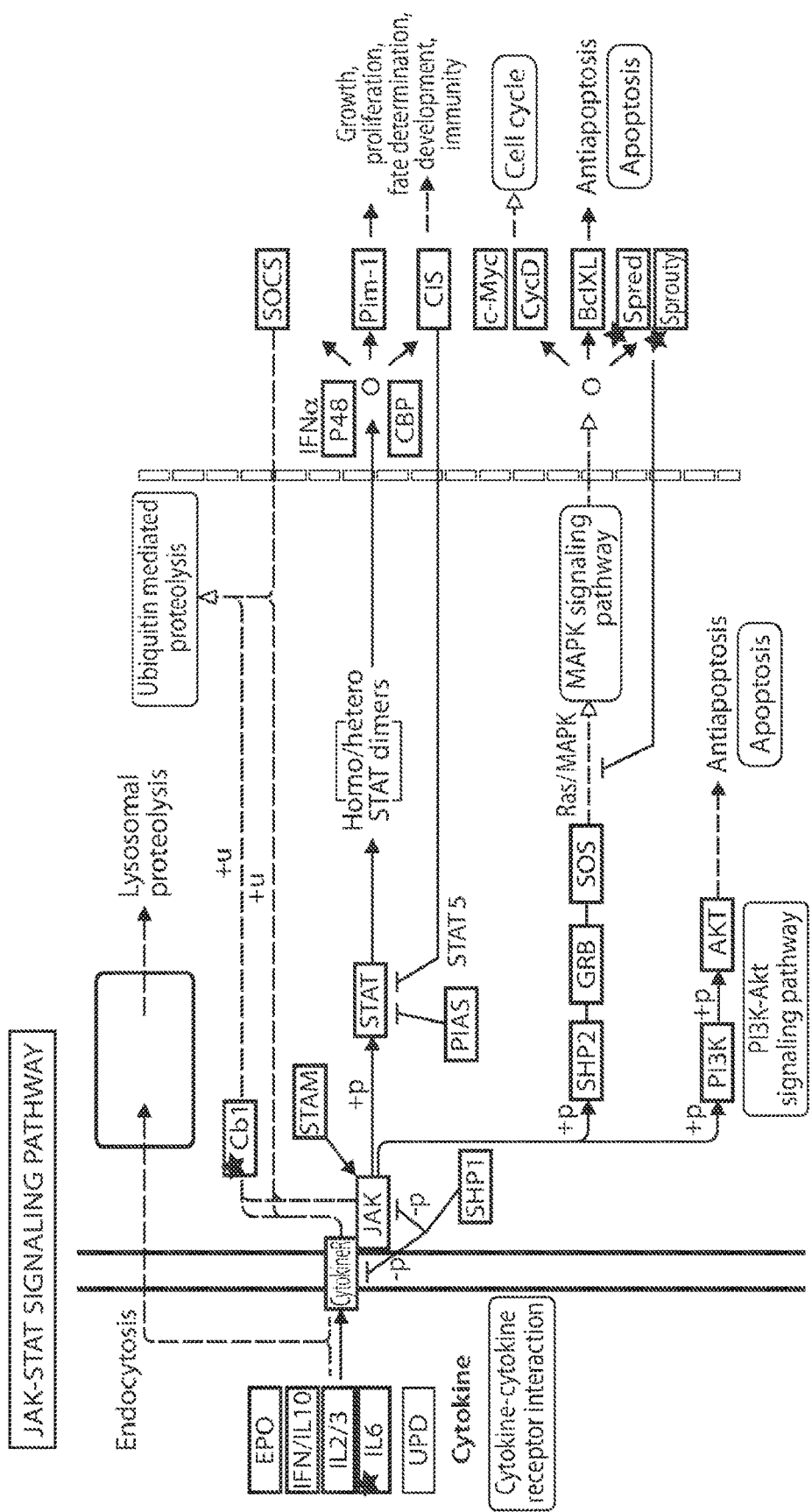
FIG. 46 shows an exemplary JAK-STAT signaling pathway.
Figure 47:
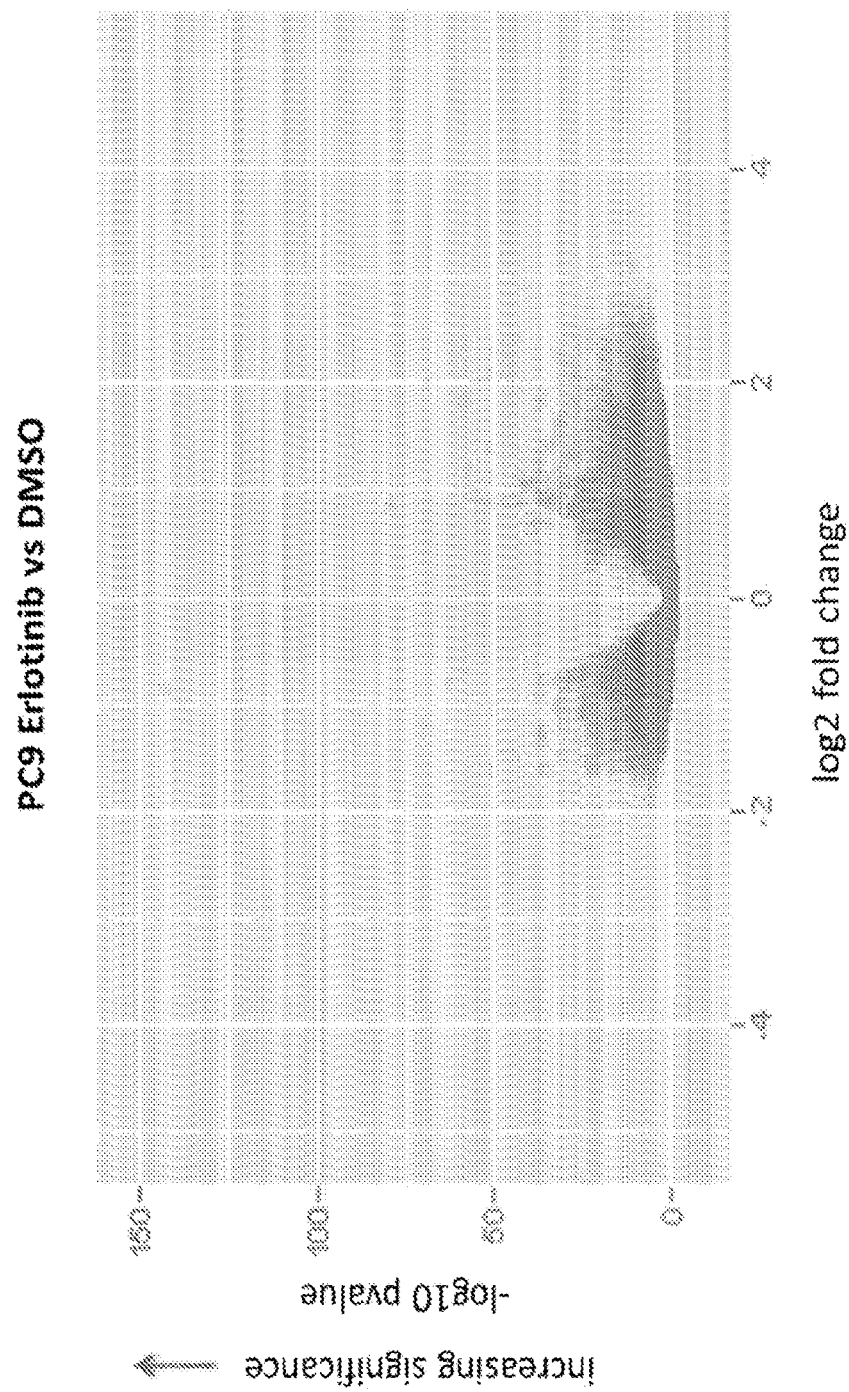
FIG. 47 shows the results of a ChipSeq assay (K27Ac). PC9 cells were treated for 7 days with erlotinib or THZ1. RT112 cells were treated for 7 days with BGJ398 (BGJ) or THZ1. The data show that SERPINB1, B2, B3, and B 10 were increased, while SPRY4/EVT4 was decreased, relative to the control (DMSO).
Figure 47:
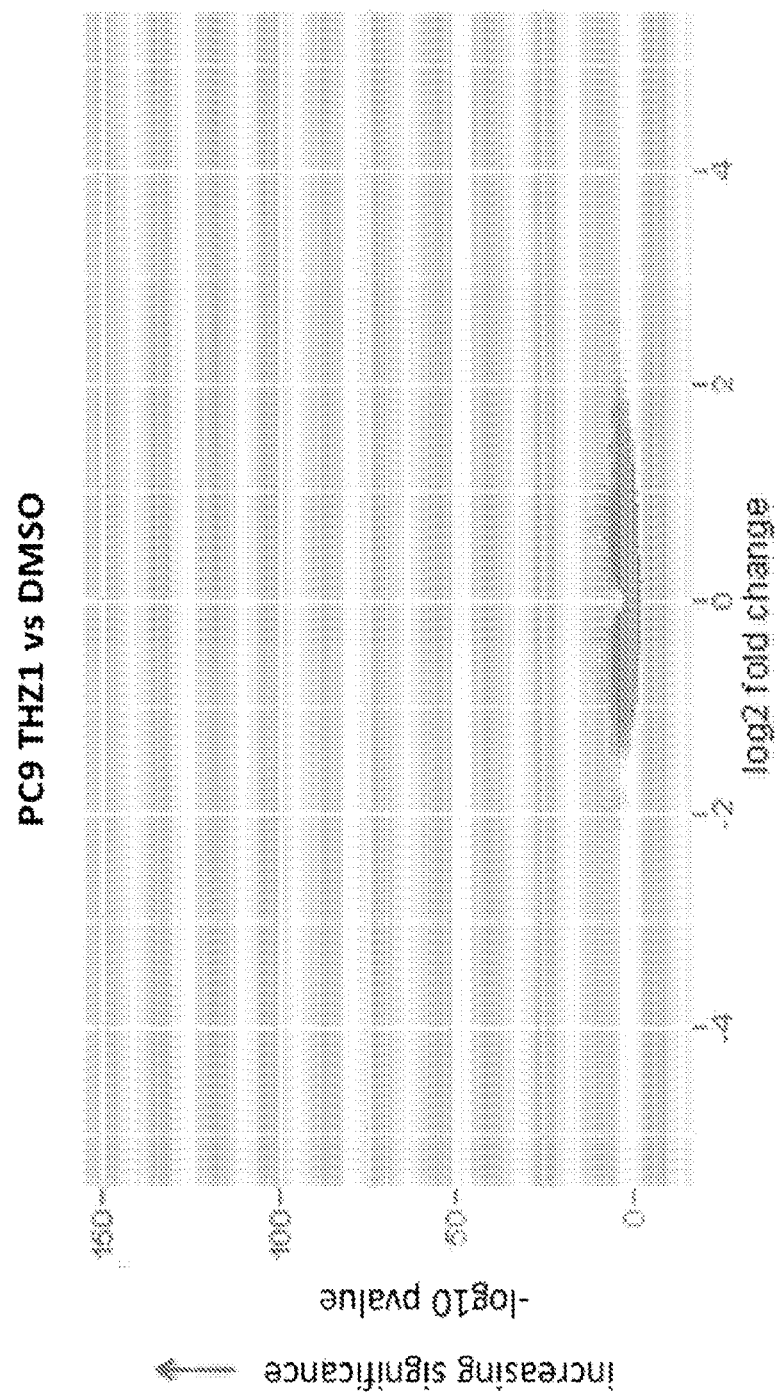
Figure 47:
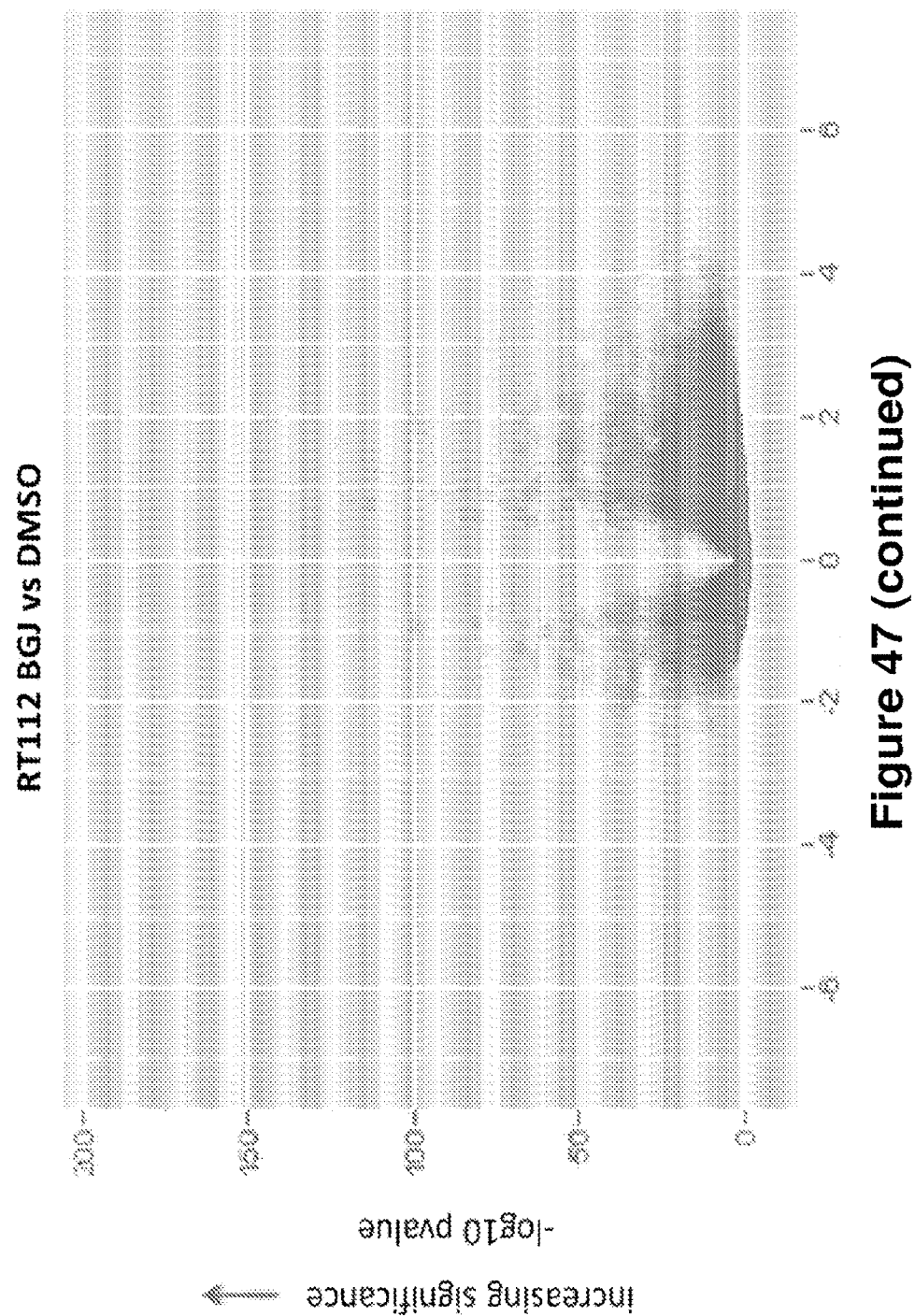
Figure 47:
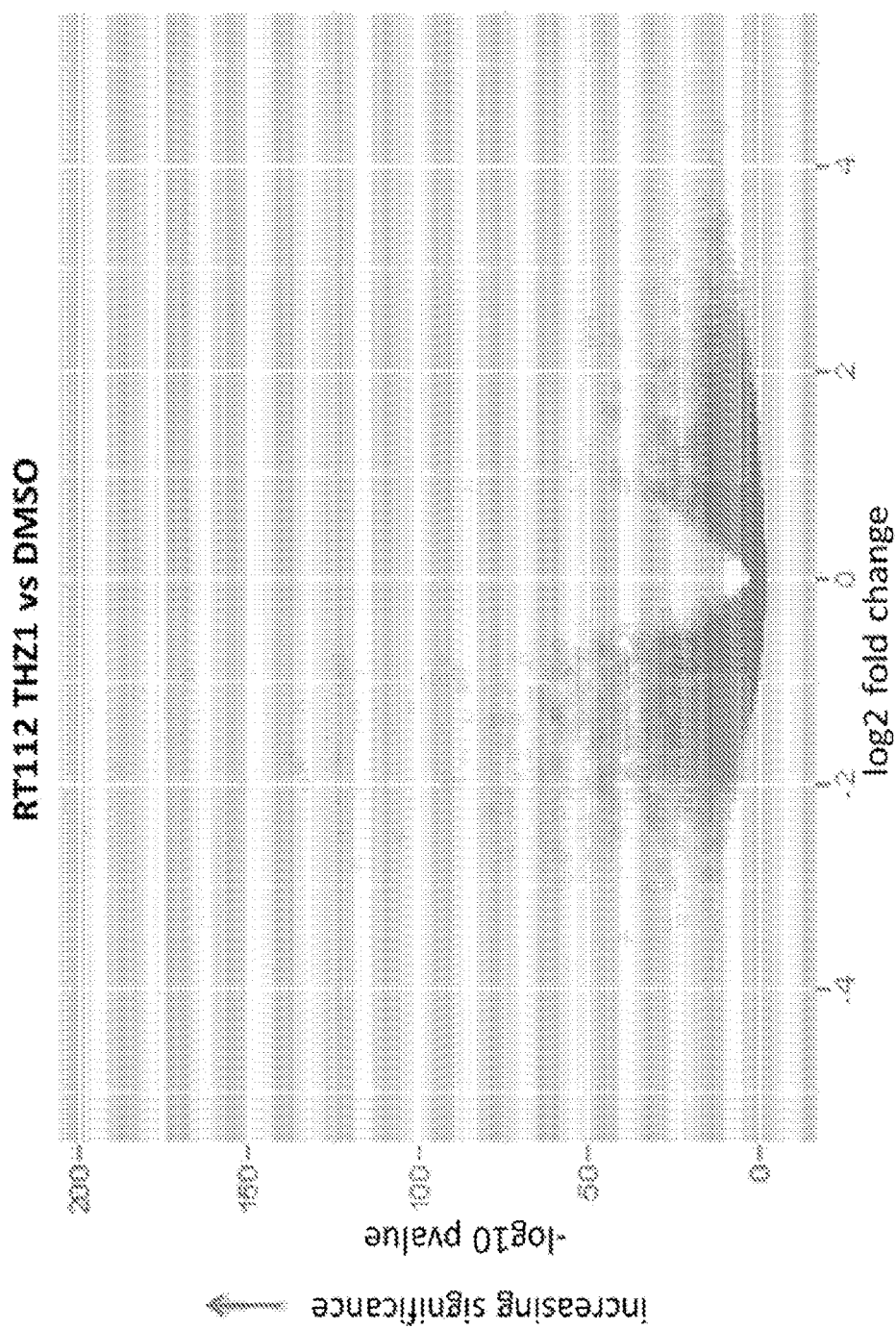
Figure 48:
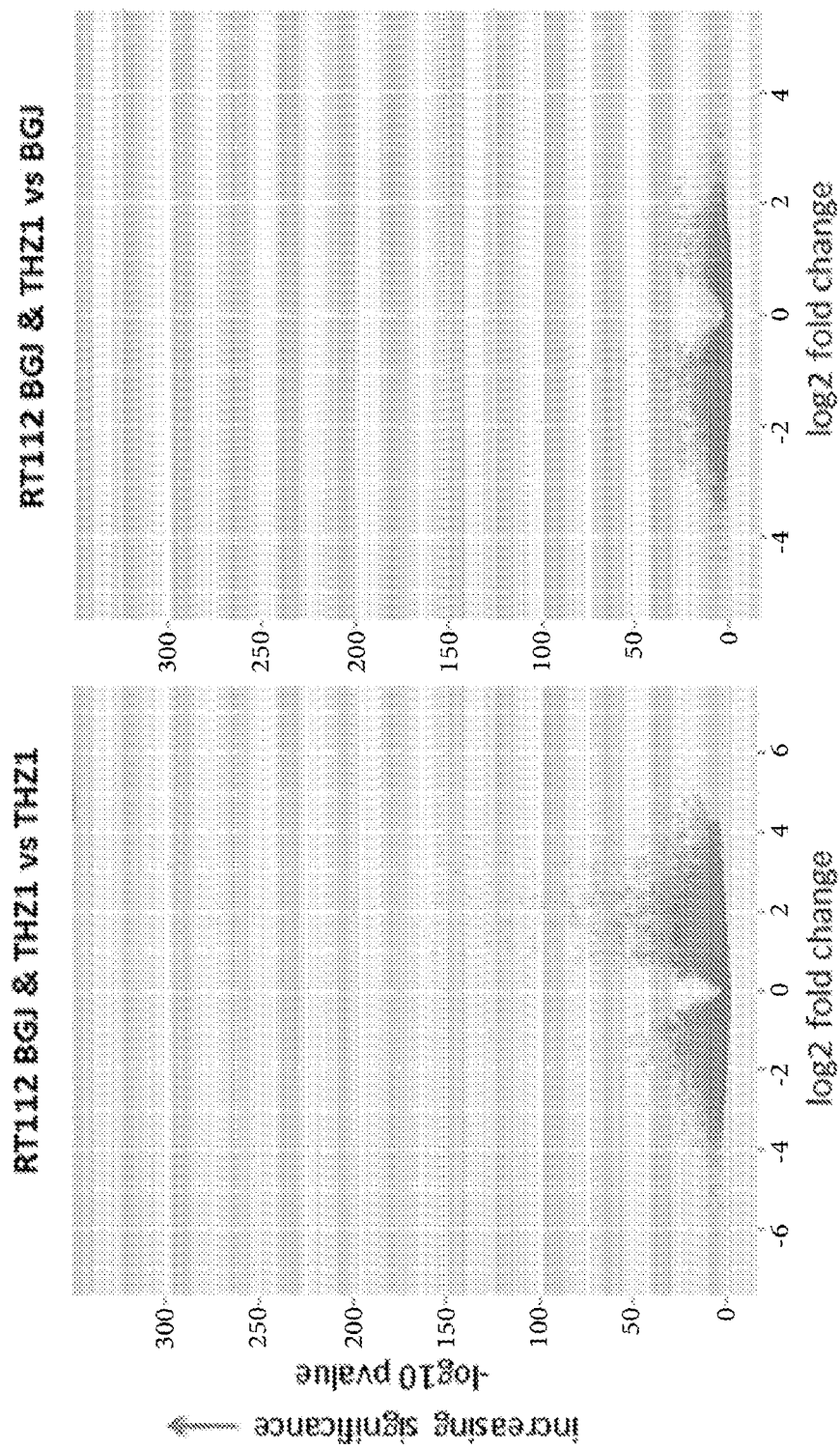
FIG. 48 shows the results of a ChipSeq assay. RT112 cells were treated for 7 days with BGJ398 (BGJ), THZ1, or a combination of BGJ398 and THZ1.

Two KRAS lines, A549 and H23 were also screened (FIG. 44B), with similar results. p-STAT3 was increased with MEK inhibition and further increased with dual treatment. These two lines were both shown in Sharma et al. (*Cell,* 2010, 141(1):69-80) to employ the STAT3 feedback loop. p-ERK was decreased in the combination treatment arm. RNAPII phosphorylation was again increased with THZ1. Therefore, there are some generalizable findings across the four lines.

REFERENCES

1. Ramos, P. & Bentires-Alj, M. Mechanism-based cancer therapy: resistance to therapy, therapy for resistance. Oncogene, doi:10.1038/onc.2014.314 (2014).
2. Housman, G. et al. Drug resistance in cancer: an overview. Cancers 6, 1769-1792, doi:10.3390/cancers6031769 (2014).
3. Holohan, C., Van Schaeybroeck, S., Longley, D. B. & Johnston, P. G. Cancer drug resistance: an evolving paradigm. Nature reviews. Cancer 13, 714-726, doi:10.1038/nrc3599 (2013).
4. Sharma, S. V. et al. A chromatin-mediated reversible drug-tolerant state in cancer cell subpopulations. Cell 141, 69-80, doi:10.1016/j.cell.2010.02.027 (2010).
5. Lee, H. J. et al. Drug resistance via feedback activation of Stat3 in oncogene addicted cancer cells. Cancer cell 26, 207-221, doi:10.1016/j.ccr.2014.05.019 (2014).
6. Blakely, C. M. et al. NF-kappaB-activating complex engaged in response to EGFR oncogene inhibition drives tumor cell survival and residual disease in lung cancer. Cell reports 11, 98-110, doi:10.1016/j.celrep.2015.03.012 (2015).
7. Obenauf, A. C. et al. Therapy-induced tumour secretomes promote resistance and tumour progression. Nature 520, 368-372, doi:10.1038/nature14336 (2015).
8. Kwiatkowski, N. et al. Targeting transcription regulation in cancer with a covalent CDK7 inhibitor. Nature 511, 616-620, doi:10.1038/nature13393 (2014).
9. Christensen, C. L. et al. Targeting Transcriptional Addictions in Small Cell Lung Cancer with a Covalent CDK7 Inhibitor. Cancer cell 26, 909-922, doi:10.1016/j.ccell.2014.10.019 (2014).
10. Chipumuro, E. et al. CDK7 inhibition suppresses super-enhancer-linked oncogenic transcription in MYCN-driven cancer. Cell 159, 1126-1139, doi:10.1016/j.cell.2014.10.024 (2014).
11. Chell, V. et al. Tumour cell responses to new fibroblast growth factor receptor tyrosine kinase inhibitors and identification of a gatekeeper mutation in FGFR3 as a mechanism of acquired resistance. Oncogene 32, 3059-3070, doi:10.1038/onc.2012.319 (2013).
12. Yun, C. H. et al. The T790M mutation in EGFR kinase causes drug resistance by increasing the affinity for ATP. Proceedings of the National Academy of Sciences of the United States of America 105, 2070-2075, doi:10.1073/pnas.0709662105 (2008).
13. Wilson, T. R. et al. Widespread potential for growth-factor-driven resistance to anticancer kinase inhibitors. Nature 487, 505-509, doi:10.1038/nature 11249 (2012).
14. Johannessen, C. M. et al. A melanocyte lineage program confers resistance to MAP kinase pathway inhibition. Nature 504, 138-142, doi:10.1038/nature12688 (2013).
15. Wang, J. et al. Ligand-associated ERBB2/3 activation confers acquired resistance to FGFR inhibition in FGFR3-dependent cancer cells. Oncogene, doi:10.1038/onc.2014.161 (2014).
16. Pettazzoni, P. et al. Genetic events that limit the efficacy of MEK and RTK inhibitor therapies in a mouse model of KRAS-driven pancreatic cancer. Cancer research 75, 1091-1101, doi:10.1158/0008-5472.CAN-14-1854 (2015).
17. Singh, A. & Settleman, J. EMT, cancer stem cells and drug resistance: an emerging axis of evil in the war on cancer. Oncogene 29, 4741-4751, doi:10.1038/onc.2010.215 (2010).
18. Fisher, R. P. & Morgan, D. O. A novel cyclin associates with MO15/CDK7 to form the CDK-activating kinase. Cell 78, 713-724 (1994).
19. Larochelle, S. et al. Requirements for Cdk7 in the assembly of Cdk1/cyclin B and activation of Cdk2 revealed by chemical genetics in human cells. Molecular cell 25, 839-850, doi:10.1016/j.molcel.2007.02.003 (2007).
20. Schachter, M. M. et al. A Cdk7-Cdk4 T-loop phosphorylation cascade promotes G1 progression. Molecular cell 50, 250-260, doi:10.1016/j.molcel.2013.04.003 (2013).
21. Akhtar, M. S. et al. TFIIH kinase places bivalent marks on the carboxy-terminal domain of RNA polymerase II. Molecular cell 34, 387-393, doi:10.1016/j.molcel.2009.04.016 (2009).
22. Drapkin, R., Le Roy, G., Cho, H., Akoulitchev, S. & Reinberg, D. Human cyclin dependent kinase-activating kinase exists in three distinct complexes. Proceedings of the National Academy of Sciences of the United States of America 93, 6488-6493 (1996).
23. Glover-Cutter, K. et al. TFIIH-associated Cdk7 kinase functions in phosphorylation of C-terminal domain Ser7 residues, promoter-proximal pausing, and termination by 23. RNA polymerase II. Molecular and cellular biology 29, 5455-5464, doi:10.1128/MCB.00637-09 (2009).
24. Larochelle, S. et al. Cyclin-dependent kinase control of the initiation-to-elongation switch of RNA polymerase II. Nature structural & molecular biology 19, 1108-1115, doi:10.1038/nsmb.2399 (2012).
25. Kelso, T. W. et al. Cyclin-dependent kinase 7 controls mRNA synthesis by affecting stability of preinitiation complexes, leading to altered gene expression, cell cycle progression, and survival of tumor cells. Molecular and cellular biology 34, 3675-3688, doi:10.1128/MCB.00595-14 (2014).
26. Kwong, L. N. & Davies, M. A. Targeted therapy for melanoma: rational combinatorial approaches. Oncogene 33, 1-9, doi:10.1038/onc.2013.34 (2014).
27. Al-Lazikani, B., Banerji, U. & Workman, P. Combinatorial drug therapy for cancer in the post-genomic era. Nature biotechnology 30, 679-692, doi:10.1038/nbt.2284 (2012).
28. Crystal, A. S. et al. Patient-derived models of acquired resistance can identify effective drug combinations for cancer. Science 346, 1480-1486, doi:10.1126/science.1254721 (2014).
29. Fry, D. W. et al. Specific inhibition of cyclin-dependent kinase 4/6 by PD 0332991 and associated antitumor activity in human tumor xenografts. Molecular cancer therapeutics 3, 1427-1438 (2004).
30. Filippakopoulos, P. et al. Selective inhibition of BET bromodomains. Nature 68, 1067-1073, doi:10.1038/nature09504 (2010).
31. Stuhlmiller, T. J. et al. Inhibition of Lapatinib-Induced Kinome Reprogramming in ERBB2-Positive Breast Cancer by Targeting BET Family Bromodomains. Cell reports 11, 390-404, doi:10.1016/j.celrep.2015.03.037 (2015).
32. Zhou, W. et al. Novel mutant-selective EGFR kinase inhibitors against EGFR T790M. Nature 462, 1070-1074, doi:10.1038/nature08622 (2009).
33. Yamaguchi, F., Kugawa, S., Tateno, H., Kokubu, F. & Fukuchi, K. Analysis of EGFR, KRAS and P53 mutations in lung cancer using cells in the curette lavage fluid obtained by bronchoscopy. Lung cancer 78, 201-206, doi:10.1016/j.lungcan.2012.08.014 (2012).
34. Ramsdale, R. et al. The transcription cofactor c-JUN mediates phenotype switching and BRAF inhibitor resistance in melanoma. Science signaling 8, ra82, doi: 10.1126/scisignal.aab1111 (2015).
35. Della Corte, C. M. et al. SMO gene amplification and activation of the hedgehog pathway as novel mechanisms of resistance to anti-epidermal growth factor receptor drugs in human lung cancer. Clinical cancer research: an official journal of the American Association for Cancer Research, doi:10.1158/1078-0432.CCR-14-3319 (2015).
36. Ercan, D. et al. Reactivation of ERK signaling causes resistance to EGFR kinase inhibitors. Cancer discovery 2, 934-947, doi:10.1158/2159-8290.CD-12-0103 (2012).
37. Terai, H. et al. Activation of the FGF2-FGFR1 autocrine pathway: a novel mechanism of acquired resistance to gefitinib in NSCLC. Molecular cancer research: MCR 11, 759-767, doi:10.1158/1541-7786.MCR-12-0652 (2013).
38. Mansour, M. R. et al. Oncogene regulation. An oncogenic super-enhancer formed through somatic mutation of a noncoding intergenic element. Science 346, 1373-1377, doi:10.1126/science.1259037 (2014).
39. Whyte, W. A. et al. Master transcription factors and mediator establish super enhancers at key cell identity genes. Cell 153, 307-319, doi:10.1016/j.cell.2013.03.035 (2013).
40. Hnisz, D. et al. Super-enhancers in the control of cell identity and disease. Cell 155, 934-947, doi:10.1016/j.cell.2013.09.053 (2013).
41. Hnisz, D. et al. Convergence of developmental and oncogenic signaling athways at transcriptional super-enhancers. Molecular cell 58, 362-370, doi:10.1016/j.molcel.2015.02.014 (2015).
42. Creyghton, M. P. et al. Histone $H_3K27Ac$ separates active from poised enhancers and predicts developmental state. Proceedings of the National Academy of Sciences of the United States of America 107, 21931-21936, doi: 10.1073/pnas.1016071107 (2010).
43. Wilson, F. H. et al. A functional landscape of resistance to ALK inhibition in lung cancer. Cancer cell 27, 397-408, doi:10.1016/j.ccell.2015.02.005 (2015).
44. Guzman, C., Bagga, M., Kaur, A., Westermarck, J. & Abankwa, D. ColonyArea: an ImageJ plugin to automatically quantify colony formation in clonogenic assays. PloS one 9, e92444, doi:10.1371/journal.pone.0092444 (2014).
45. DuPage, M., Dooley, A. L. & Jacks, T. Conditional mouse lung cancer models using adenoviral or lentiviral delivery of Cre recombinase. Nature protocols 4, 1064-1072, doi:10.1038/nprot.2009.95 (2009).
46. Torres-Garcia, W. et al. PRADA: pipeline for RNA sequencing data analysis. Bioinformatics 30, 2224-2226, doi:10.1093/bioinformatics/btu169 (2014).
47. Li B, D. C. RSEM:accurate transcript quantification from RNA-Seq data with or without a reference genome. BMC Bioinformatics, 323, doi:10.1186/1471-2105-12-323. (2011).
48. Law, C. W., Chen, Y., Shi, W. & Smyth, G. K. voom: Precision weights unlock linear model analysis tools for RNA-seq read counts. Genome biology 15, R29, doi: 10.1186/gb-2014-15-2-r29 (2014).
49. Ritchie, M. E. et al. limma powers differential expression analyses for RNA sequencing and microarray studies. Nucleic acids research, doi:10.1093/nar/gkv007 (2015).
50. Lin, C. Y. et al. Transcriptional amplification in tumor cells with elevated c-Myc. Cell 151, 56-67, doi:10.1016/j.cell.2012.08.026 (2012).
51. Zang, C. et al. A clustering approach for identification of enriched domains from histone modification ChIP-Seq data. Bioinformatics 25, 1952-1958, doi:10.1093/bioinformatics/btp340 (2009).
52. Sanjana, N. E., Shalem, O. & Zhang, F. Improved vectors and genome-wide libraries for CRISPR screening. Nature methods 11, 783-784, doi:10.1038/nmeth.3047 (2014).
53. Shalem, O. et al. Genome-scale CRISPR-Cas9 knockout screening in human cells. Science 343, 84-87, doi: 10.1126/science.1247005 (2014).
54. Chen, J. et al. CCL18 from tumor-associated macrophages promotes breast cancer metastasis via PITPNM3. Cancer cell 19, 541-555, doi:10.1016/j.ccr.2011.02.006 (2011).
55. Baranwal, S. et al. Molecular characterization of the tumor-suppressive function of nischarin in breast cancer. Journal of the National Cancer Institute 103, 1513-1528, doi:10.1093/jnci/djr350 (2011).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of treating a solid tumor in a subject in need thereof, the method comprising administering to the subject an effective amount of:
  a transcription inhibitor; and
  a kinase inhibitor, wherein the kinase inhibitor is an epidermal growth factor receptor (EGFR) inhibitor;
  wherein:
  the solid tumor is bladder cancer, lung cancer, esophageal cancer, skin cancer, or stomach cancer;
  the transcription inhibitor is of Formula (I):

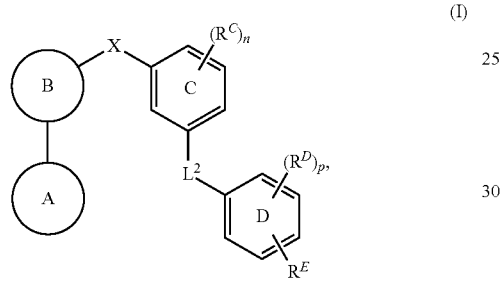

(I)

or a pharmaceutically acceptable salt, solvate, hydrate, polymorph, co-crystal, tautomer, or isotopically labeled compound thereof, wherein:
  Ring A is an optionally substituted heteroaryl ring of the formula:

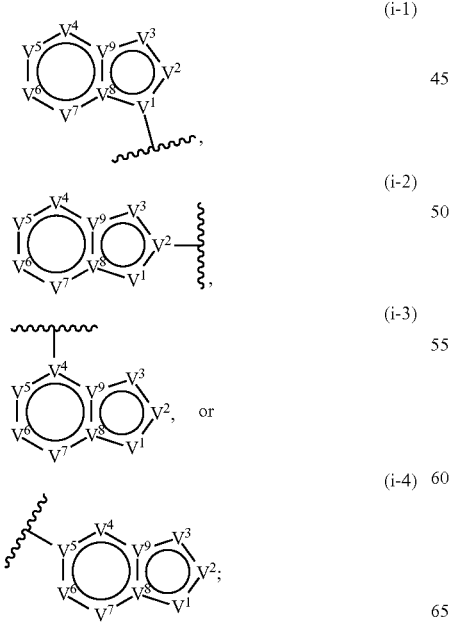

one or two instances of $V^1$, $V^2$, $V^3$, $V^4$, $V^5$, $V^6$, $V^7$, $V^8$, and $V^9$ are independently N or $NR^{A1}$, the remaining instances of $V^1$, $V^2$, $V^3$, $V^4$, $V^5$, $V^6$, $V^7$, $V^8$, and $V^9$ are independently C or $CR^{A2}$;

each instance of $R^{A1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group;

each instance of $R^{A2}$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{A2a}$, $-N(R^{A2a})_2$, and $-SR^{A2a}$, wherein each occurrence of $R^{A2a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{A2a}$ groups are joined to form an optionally substituted heterocyclic ring;

or any two of $R^{A1}$, $R^{A2}$, and $R^{A2a}$ groups are joined to form an optionally substituted carbocyclic, optionally substituted heterocyclic, optionally substituted aryl, or optionally substituted heteroaryl ring;

Ring B is of the formula:

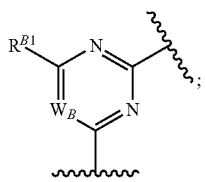

$R^{B1}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{B1a}$, $-N(R^{B1a})_2$, and $-SR^{B1a}$, wherein each occurrence of $R^{B1a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{B1a}$ groups are joined to form an optionally substituted heterocyclic ring;

$W_B$ is N or $CR^{B2}$, wherein $R^{B2}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{B2a}$, $-N(R^{B2a})_2$, and $-SR^{B2a}$, wherein each occurrence of $R^{B2a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{B2a}$ groups are joined to form an optionally substituted heterocyclic ring;

or $R^{B1}$ and $R^{B2}$ are joined to form an optionally substituted carbocyclyl, optionally substituted heterocyclyl, optionally substituted heteroaryl, or optionally substituted aryl ring;

X is $-NR^x-$;

$L^2$ is $-NR^{L2a}C(=O)-$, $-C(=O)NR^{L2a}-$, $-S(=O)_2NR^{L2a}-$, or $-NR^{L2a}S(=O)_2-$, wherein each instance of $R^{L2a}$ is independently hydrogen, optionally substituted $C_{1-6}$ alkyl, or a nitrogen protecting group;

each instance of $R^C$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{C1}$, $-N(R^{C1})_2$, and $-SR^{C1}$, wherein each occurrence of $R^{C1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{C1}$ groups are joined to form an optionally substituted heterocyclic ring;

n is 0, 1, 2, 3, or 4;

each instance of $R^D$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{D1}$, $-N(R^{D1})_2$, and $-SR^{D1}$, wherein each occurrence of $R^{D1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{D1}$ groups are joined to form an optionally substituted heterocyclic ring;

p is 0, 1, 2, 3, or 4;

$R^E$ is of the formula:

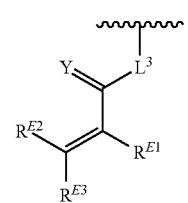

(ii-1)

$R^E$ and $L^2$ are para or meta to each other;

$L^3$ is a bond, $-O-$, $-S-$, $-NR^{L3a}-$, or an optionally substituted $C_{1-4}$ hydrocarbon chain, optionally wherein one or more carbon units of the hydrocarbon chain is replaced with $-O-$, $-S-$, $-NR^{L3a}-$, $-NR^{L3a}C(=O)-$, $-C(=O)NR^{L3a}-$, $-SC(=O)-$, $-C(=O)S-$, $-OC(=O)-$, $-C(=O)O-$, $-NR^{L3a}C(=S)-$, $-C(=S)NR^{L3a}-$, trans-$CR^{L3b}=CR^{L3b}-$, cis-$CR^{L3b}=CR^{L3b}-$, $-C\equiv-$, $-S(=O)_2O-$, $-OS(=O)_2-$, $-S(=O)_2NR^{L3a}-$, or $-NR^{L3a}S(=O)_2-$, wherein each instance of $R^{L3a}$ is independently hydrogen, optionally substituted $C_{1-6}$ alkyl, or a nitrogen protecting group, and wherein each occurrence of $R^{L3b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{L3b}$ groups are joined to form an optionally substituted carbocyclic or optionally substituted heterocyclic ring;

$R^{E1}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-CH_2OR^{E1a}$, $-CH_2N(R^{E1a})_2$, $-CH_2SR^{E1a}$, $-OR^{E1a}$, $-N(R^{E1a})_2$, and $-SR^{E1a}$, wherein each occurrence of $R^{E1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{E1a}$ groups are joined to form an optionally substituted heterocyclic ring;

$R^{E2}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CH$_2$OR$^{E2a}$, —CH$_2$N(R$^{E2a}$)$_2$, —CH$_2$SR$^{E2a}$, —OR$^{E2a}$, —N(R$^{E2a}$)$_2$, and —SR$^{E2a}$, wherein each occurrence of R$^{E2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{E2a}$ groups are joined to form an optionally substituted heterocyclic ring;

R$^{E3}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CH$_2$OR$^{E3a}$, —CH$_2$N(R$^{E3a}$)$_2$, —CH$_2$SR$^{E3a}$, —OR$^{E3a}$, —N(R$^{E3a}$)$_2$, and —SR$^{E3a}$, wherein each occurrence of R$^{E3a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{E3a}$ groups are joined to form an optionally substituted heterocyclic ring;

or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring; and Y is O, S, or NR$^{E5}$, wherein R$^{E5}$ is hydrogen, optionally substituted C$_{1-6}$ alkyl, or a nitrogen protecting group;

provided that the transcription inhibitor and the kinase inhibitor are not the same.

2. The method of claim 1, wherein the transcription inhibitor is of the formula:

(THZ1)

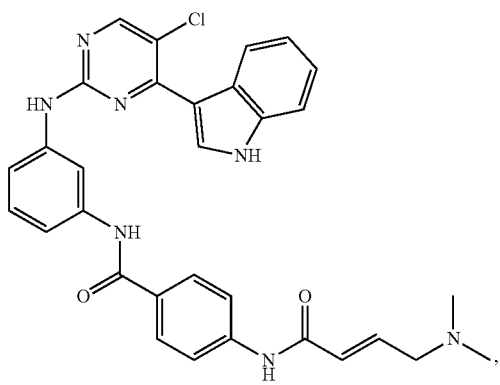

or a pharmaceutically acceptable salt, solvate, hydrate, polymorph, co-crystal, tautomer, or isotopically labeled compound thereof.

3. The method of claim 1, wherein:

Ring A is an optionally substituted heteroaryl ring of the formula:

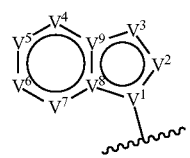

(i-1)

4. The method of claim 1, wherein each instance of R$^{A1}$ is independently selected from the group consisting of hydrogen and optionally substituted alkyl.

5. The method of claim 1, wherein each instance of R$^{A2}$ is independently selected from the group consisting of hydrogen, halogen, optionally substituted alkyl, optionally substituted heterocyclyl, and optionally substituted aryl.

6. The method of claim 1, wherein R$^{B1}$ is selected from the group consisting of hydrogen, halogen, and optionally substituted alkyl.

7. The method of claim 1, wherein W$_B$ is CR$^{B2}$.

8. The method of claim 7, wherein R$^{B2}$ is hydrogen, halogen, optionally substituted alkyl, optionally substituted carbocyclyl, or —OR$^{B2a}$.

9. The method of claim 1, wherein R$^X$ is hydrogen.

10. The method of claim 1, wherein each instance of R$^C$ is independently selected from the group consisting of hydrogen, halogen, and optionally substituted alkyl.

11. The method of claim 1, wherein L$^2$ is —NR$^{L2a}$C(=O)—.

12. The method of claim 11, wherein R$^{L2a}$ is hydrogen.

13. The method of claim 1, wherein each instance of R$^D$ is hydrogen.

14. The method of claim 1, wherein R$^{E3}$ is selected from the group consisting of hydrogen and optionally substituted alkyl.

15. The method of claim 1, wherein R$^{E3}$ is selected from the group consisting of —CH$_2$OR$^{E3a}$ and —CH$_2$N(R$^{E3a}$)$_2$.

16. The method of claim 1, wherein the transcription inhibitor is of the formula:

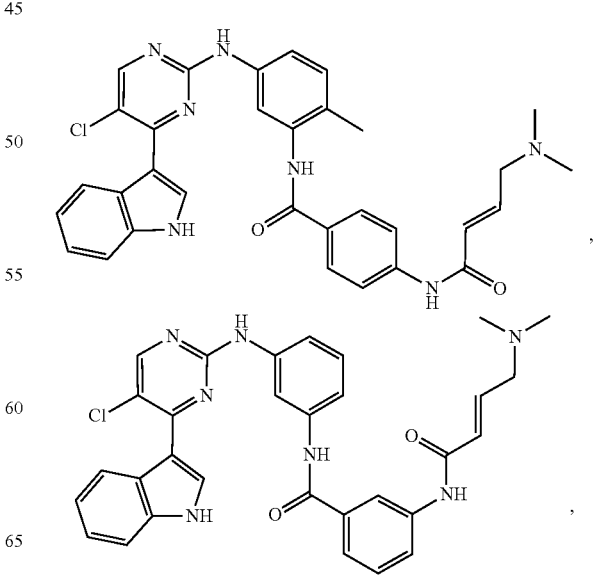

299
-continued
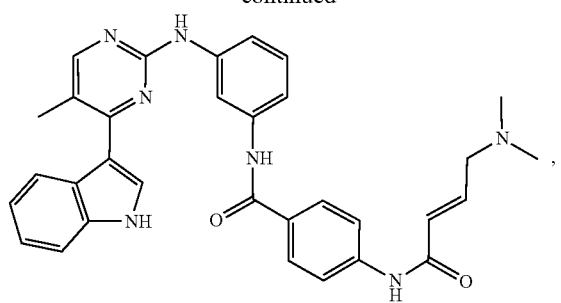
300
-continued
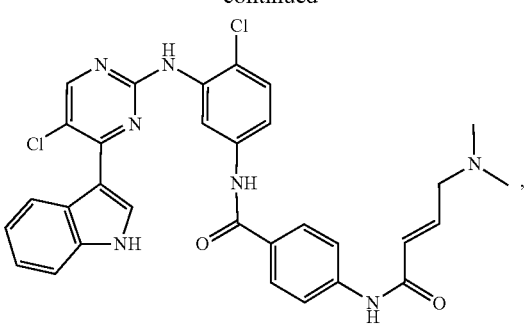
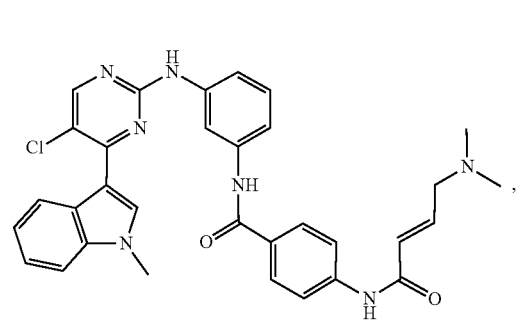
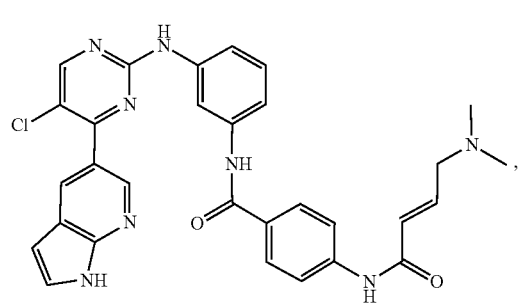

301
-continued
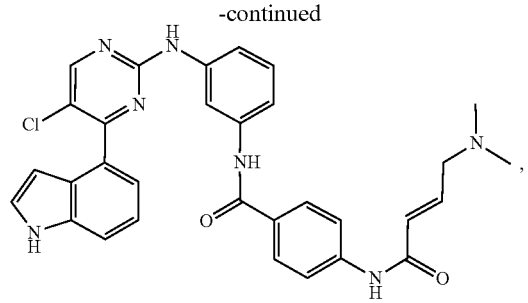
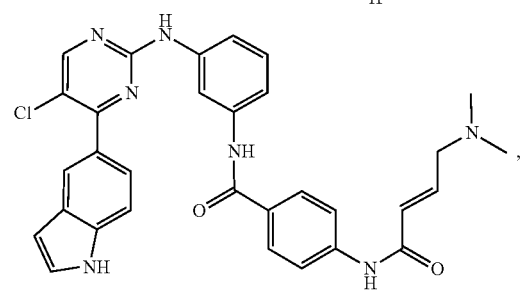
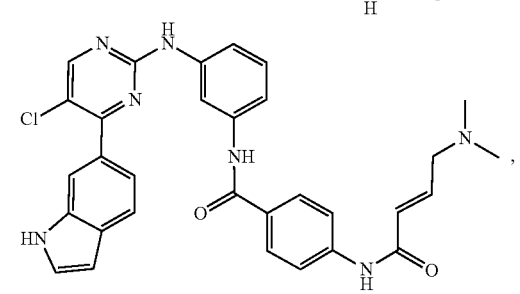
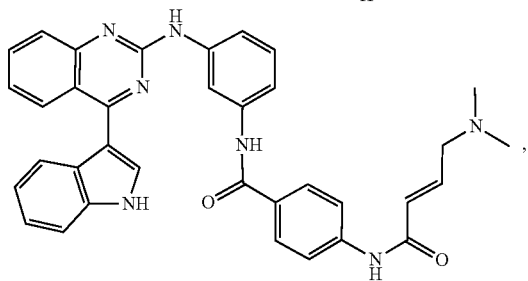
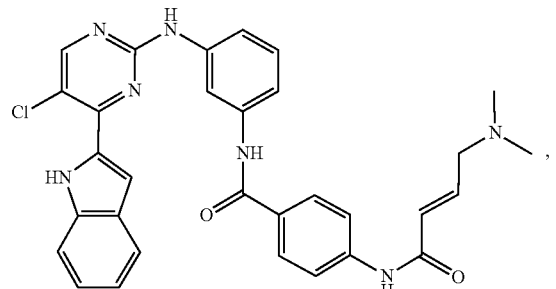
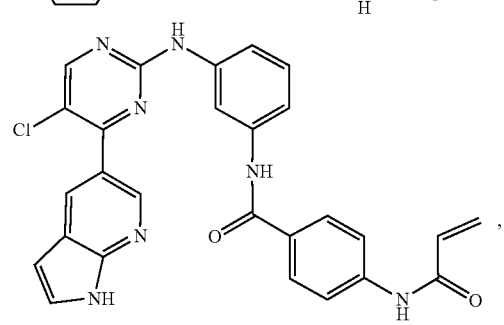
302
-continued
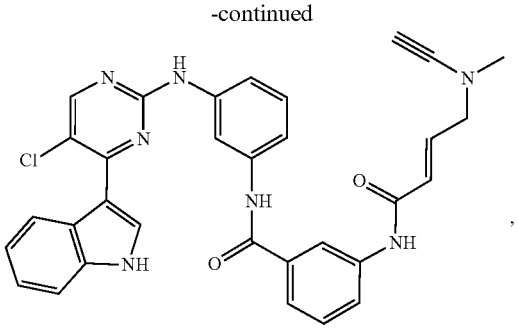
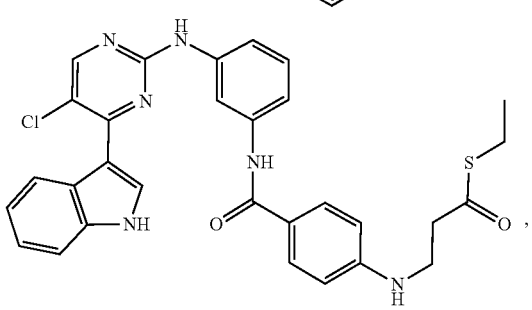
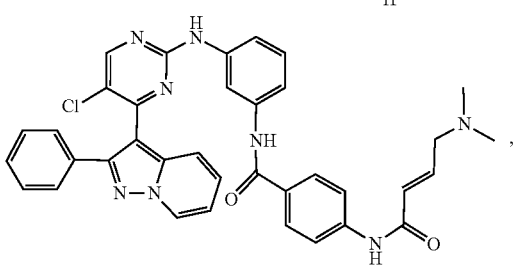
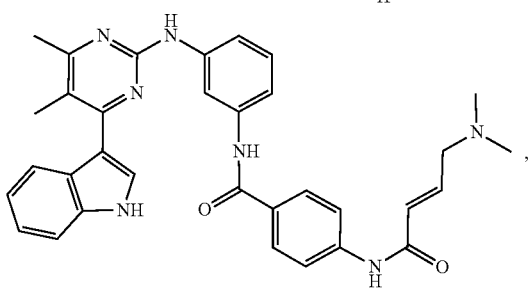
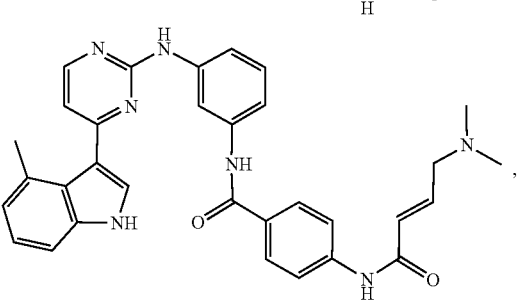
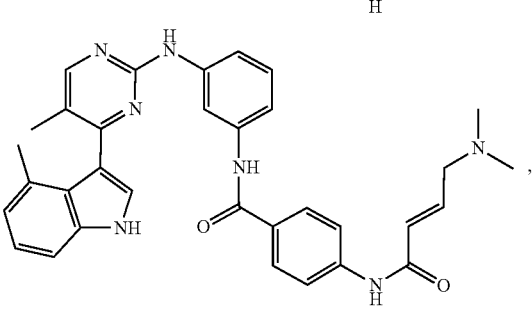

303
-continued
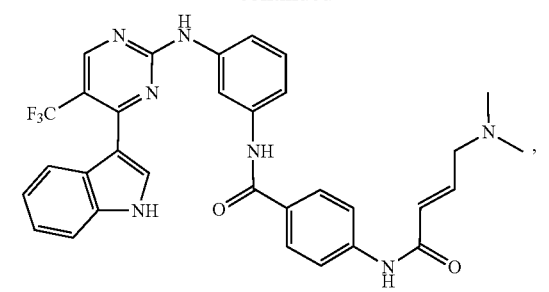
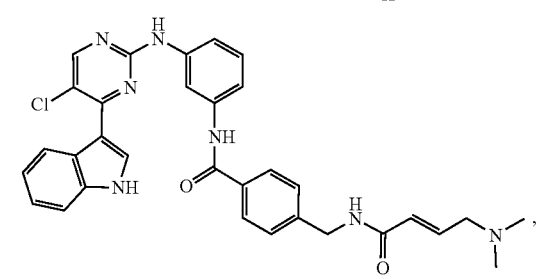
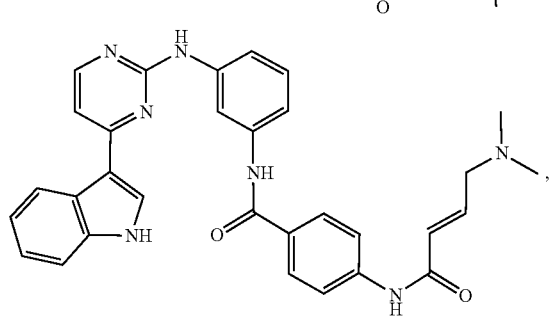
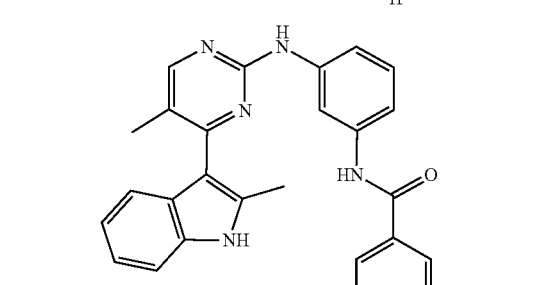
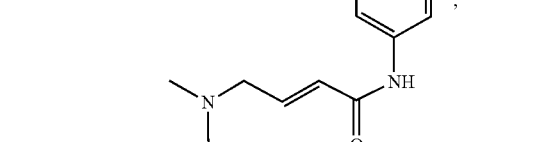
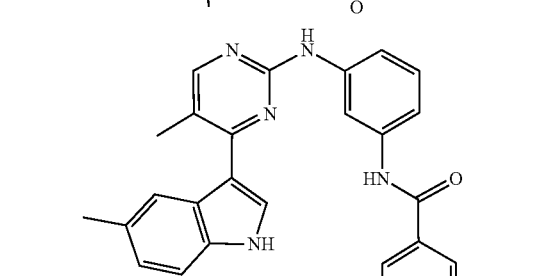
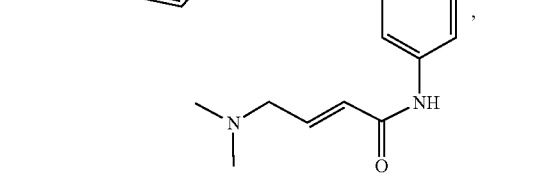
304
-continued
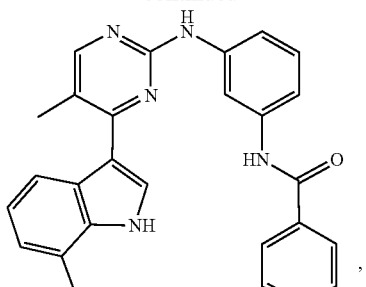
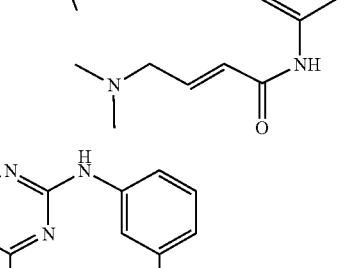
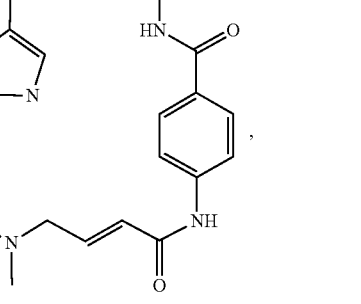
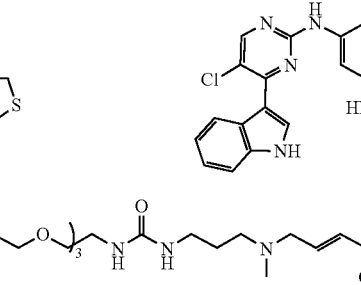
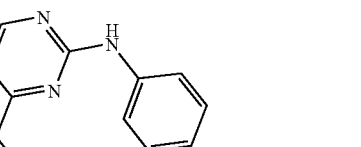
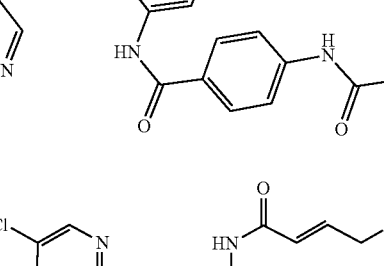
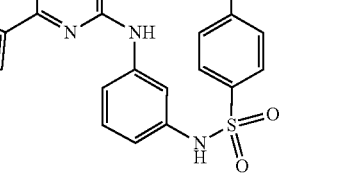

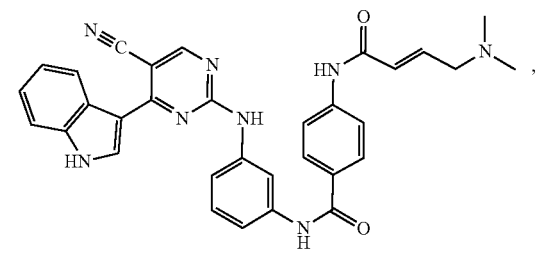
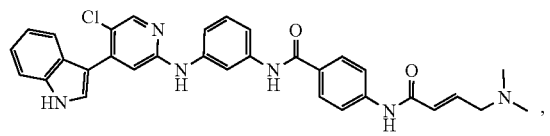
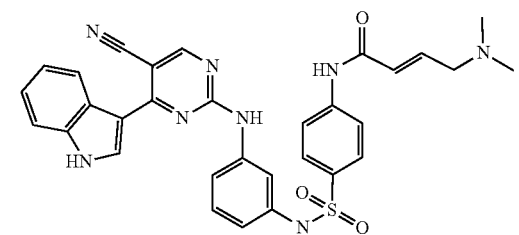
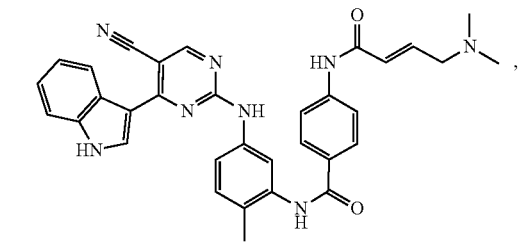
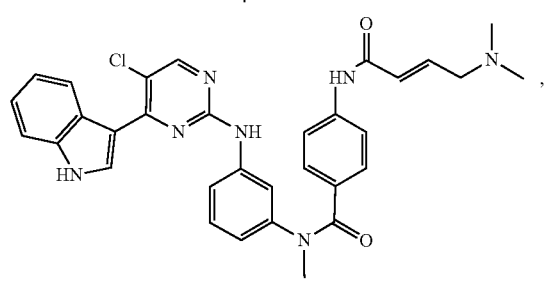
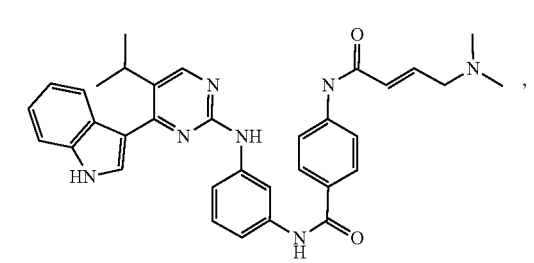
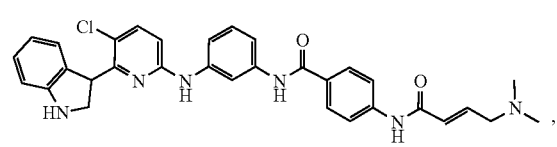
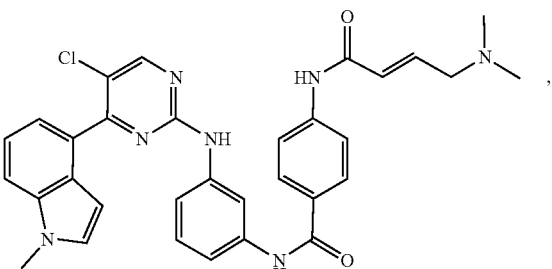
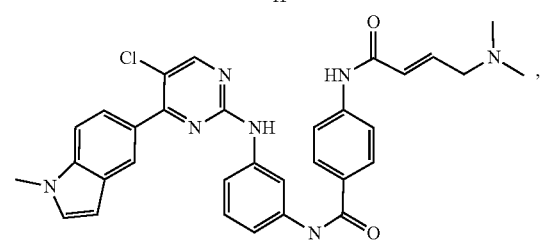
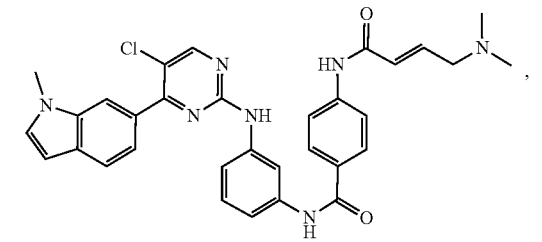
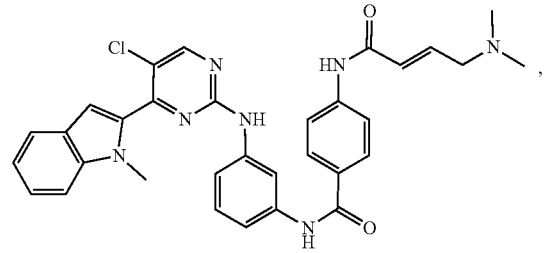
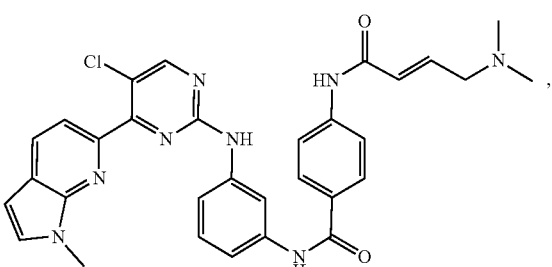
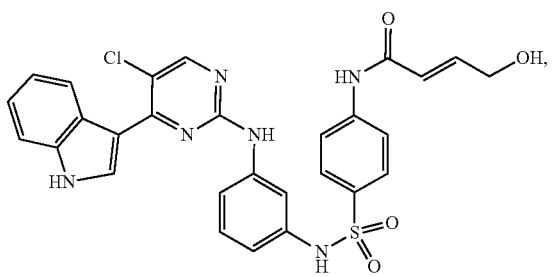

307
-continued

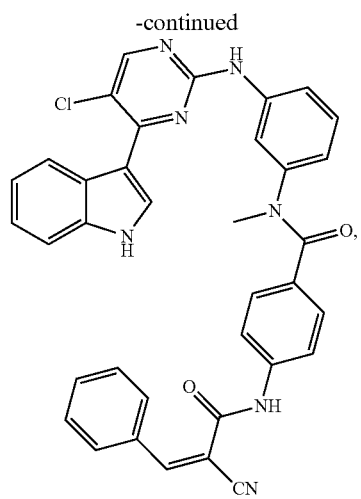

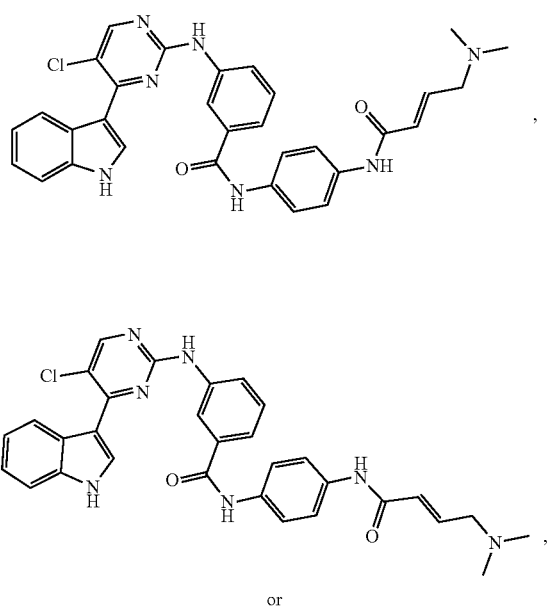

or

308
-continued

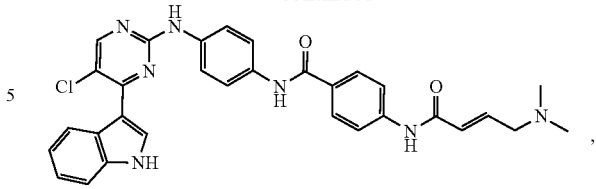

or a pharmaceutically acceptable salt, solvate, hydrate, polymorph, co-crystal, tautomer, or isotopically labeled compound thereof.

17. The method of claim 1, wherein the EGFR inhibitor is erlotinib, lapatinib, AZD8931, WZ4002, panitumumab, vandetanib, icotinib, afatinib, brigatinib, CO-1688, AZD-4769, poziotinib, CUDC-101, S-222611, AC-480, imgatuzumab, sapitinib, TAS-2913, theiiatinib, XGFR-2421, HM-61713B, epitinib, NRC-2694, MLBS-42, JRP-890, cetuximab, AL-6802, TAK-285, BGB-102, AEE788, gefitinib, DMS-3008, TX-2036, KI-6783, or KI-6896, or a pharmaceutically acceptable salt thereof.

18. The method of claim 1, wherein the EGFR inhibitor is erlotinib, or a pharmaceutically acceptable salt thereof.

19. The method of claim 1, wherein the EGFR inhibitor is afatinib, brigatinib, cetuximab, gefitinib, icotinib, lapatinib, panitumumab, or vandetanib, or a pharmaceutically acceptable salt thereof.

20. The method of claim 2, wherein the EGFR inhibitor is erlotinib, lapatinib, or WZ4002, or a pharmaceutically acceptable salt thereof.

21. The method of claim 2, wherein the EGFR inhibitor is afatinib, brigatinib, cetuximab, gefitinib, icotinib, lapatinib, panitumumab, vandetanib, or neratinib, or a pharmaceutically acceptable salt thereof.

22. The method of claim 1, wherein the solid tumor is lung cancer, esophageal cancer, or skin cancer.

23. The method of claim 1, wherein the solid tumor is associated with a mutation in an epidermal growth factor receptor (EGFR) gene.

24. The method of claim 23, wherein the mutation is a T790M mutation, L858R mutation, or exon 19 deletion mutation.

25. The method of claim 1, wherein the solid tumor is esophageal cancer.

26. The method of claim 1, wherein the solid tumor is skin cancer.

* * * * *